United States Patent [19]
Hoffberg et al.

[11] Patent Number: 5,903,454
[45] Date of Patent: May 11, 1999

[54] HUMAN-FACTORED INTERFACE CORPORATING ADAPTIVE PATTERN RECOGNITION BASED CONTROLLER APPARATUS

[76] Inventors: Linda Irene Hoffberg, 40 Jackson Dr., Acton, Mass. 01720; Steven M. Hoffberg, 29 Buckout Rd., West Harrison, N.Y. 10604

[21] Appl. No.: 07/812,805

[22] Filed: Dec. 23, 1991

[51] Int. Cl.⁶ .................................................. G05B 19/42
[52] U.S. Cl. ......................... 364/188; 364/150; 364/165; 364/191; 382/155
[58] Field of Search ........................... 364/146, 188–191, 364/148–150, 164, 165, 192; 395/156–160, 20; 382/155, 156–160

[56] References Cited

U.S. PATENT DOCUMENTS

| | | | |
|---|---|---|---|
| 4,789,933 | 12/1988 | Chen et al. ........................ | 364/413.13 |
| 4,841,575 | 6/1989 | Welsh et al. . | |
| 4,878,179 | 10/1989 | Larsen et al. ............................ | 364/490 |
| 5,038,390 | 8/1991 | Chandran .................................. | 382/56 |
| 5,060,277 | 10/1991 | Bokser . | |
| 5,076,662 | 12/1991 | Shih et al. ................................. | 359/36 |
| 5,089,978 | 2/1992 | Lipner et al. ........................... | 364/188 |
| 5,123,057 | 6/1992 | Verly et al. . | |
| 5,123,087 | 6/1992 | Newell et al. . | |
| 5,124,908 | 6/1992 | Broadbent ............................... | 364/188 |
| 5,136,659 | 8/1992 | Kaneko et al. . | |
| 5,148,522 | 9/1992 | Okazaki et al. . | |
| 5,187,797 | 2/1993 | Nielsen et al. ........................... | 364/180 |
| 5,239,617 | 8/1993 | Gardner et al. .......................... | 395/12 |
| 5,247,433 | 9/1993 | Kitaura et al. .......................... | 364/188 |
| 5,390,281 | 2/1995 | Luciw et al. .............................. | 395/12 |

OTHER PUBLICATIONS

Quinnell, Richard, "Image Compression, Part 3", EDN, May 13, 1993, pp. 114–120.

Shepard, Jeffrey, "Tapping the Potential of Data Compression", Military & Aerospace Electronics, May 17, 1993, pp. 25–28.

Siochi, Antonio C. and Hix, Deborah, "A Study of Computer–Supported User Interface Evaluation Using Maximal Repeating Pattern Analysis", *CHI '91 Proceedings*, (1991), ACM 0–89791–383–3/91/0004/0301, pp. 301–304.

Ueda, Hirotada et al, "Impact: An Interactive Natural–Motion–Picture Dedicated Multimedia Authoring System", *CHI '91 Proceedings*, (1991) ACM 0–89791–383–3/91/0004/0343, pp. 343–350.

Cypher, Allen, "Eager: Programming Repetitive Tasks by Example", *CHI '91 Proceedings*, (1991), ACM 0–89791–383–3/91/0004/0033, pp. 33–39.

Cypher, Allen, "Video Presentation Eager: Programming Repetitive Tasks by Example", *CHI '91 Proceedings*, (1991), pp. 445–446.

Smith, Sidney L. and Mosier, Jane N., "Guidelines for Designing User Interface Software", ESD–TR–86–278, MTR 10090, Mitre Corporation, Bedford, Massachusetts, (Aug., 1986), (pp. i–10, 401–418 provided) NTIS AD A177 198.

Fox, Jeffrey, A. and Smith, Sydney L., "Dynamic Rules for User Interface Design" (Druid), M89–22, Mitre Corporation, Bedford, Massachusetts, (May 1989), (pp. i–2, 40–42 provided).

Erickson, Thomas and Salomon, Gitta "Designing a Desktop Information System: Observations and Issues", *CHI '91 Proceedings*, (1991) ACM 0–89791–383–3/91/0004/0049, pp. 49–54.

*Primary Examiner*—Paul P. Gordon
*Assistant Examiner*—Thomas E. Brown
*Attorney, Agent, or Firm*—Steven M. Hoffberg

[57] ABSTRACT

The need for a more-readily usable interface for programmable devices is widely recognized. The present invention relates to programmable sequencing devices, or, more particularly, the remote controls for consumer electronic devices. The present invention provides an enhanced interface for facilitating human input of a desired control sequence in a programmable device by employing specialized visual feedback. The present invention also relates to a new interface and method of interfacing with a programmable device, which is usable as an interface for a programmable video cassette recorder.

37 Claims, 27 Drawing Sheets

Times for the Minimum, Theoretical and Actual Keypresses

Existing Interface

New Interface

HUMAN-FACTORED INTERFACE CORPORATING ADAPTIVE PATTERN RECOGNITION BASED CONTROLLER APPARATUS

A portion of the disclosure of this patent document and appendices contain material which is subject to copyright protection. The copyright owner has no objection to the facsimile reproduction by anyone of this patent document or the patent disclosure, as it appears in the patent and Trademark Office patent file or records, but otherwise reserves all copyright rights whatsoever.

FIELD OF THE INVENTION

The present invention relates to the field of programmable sequencing devices, or, more particularly, the field of remote controls for consumer electronic devices. The present invention provides an enhanced interface for facilitating human input of a desired control sequence in a programmable device by employing specialized visual feedback. Some of the most popular programmable products include VCRs, answering machines, microwave ovens, alarm clocks, thermostats, cameras, home security systems, lighting systems, and automobiles.

BACKGROUND OF THE INVENTION

Significant difficulties are experienced by users when programmable complex devices are infrequently used or programmed, or when a user attempts to use uncommon functions of these devices, such as, for example video cassette recorders (hereinafter "VCRs"). Studies have concluded that 80% of users cannot correctly program their VCRs. This has been due, in part, to the fact that manufacturers continue to add more features to existing devices, without simplifying those which already exist.

People learn most efficiently through the interactive experiences of doing, thinking, and knowing. For ease-of-use, efficiency, and lack of frustration of the user, utilizing the device should be intuitive. Users should be able to operate the device without referring to an instruction manual. Well-designed products should contain visual clues which prompt and convey their meanings, however, prior art devices do not always live up to this ideal. This problem is accentuated by various manufacturers and designers who focus on the production and design of feature-rich systems, rather than on ones which are also "User Friendly" and thus easier to use. Therefore, many products are extremely complex and thus difficult to use, thereby preventing all but the most technically advanced people from using them.

The act of programming, or determining a sequence of operations to be performed by, for example, a VCR, several steps are required. In addition to setting the clock, the user must assign a program number, set the current date and current time, select the start and stop times, choose the channel from which to record, and choose a tape speed. These actions require a minimum of four actuators ("Program", "+", "−", and "Enter"). Presently, some VCR controls contain up to 123 buttons, double function keys, and symbols which are not immediately recognized by the user.

In order to simplify commonly-used functions, a number of methods have been devised. Certain VCRs employ a bar-code reader in order to allow entry of programming steps from a menu of functions, or from an encoded description of an event to be programmed. However, this method suffers from the limitation that the channel, time and duration must be available in encoded form, otherwise the use of the device will not simplify the use or programming of the VCR. These machines come with a laminated sheet of bar codes. In order to program the VCR, the user must press a button on a wand, which lights its tip, and then run or pass the tip over a bar-code, to set each step separately. Finally, when all the information has been scanned in, the user must press the "Transmit" button. The "VCRplus+" is a device which allows the entry of a code representing a channel, time, date and duration of a program to be recorded, which when entered into the remote control device, is translated into commands for programming the VCR, and transmitted through an infrared link to the VCR, thus programming the VCR. This system has the limitations that the published codes must be available, and manually entered, which may be thus be erroneously entered, and the system does not allow for rescheduled programs, so that any variation in schedule will result in a defective recording. The time and date in the VCR device must also be set accurately for this system to operate.

On-screen programming systems exist; however, these generally require the user to scroll through menus and option choices without allowing direct entry of programming information. Direct-entry systems are available with, for example, programmable controllers with keypad entry. However, these do not generally have full information visual displays, meaning that all vital information is not or cannot be simultaneously displayed, and must be "multiplexed", meaning that data must share display space with other data, displayed at different times. In a VCR with on-screen programming, all programming information feedback is displayed on the television screen, and prompts are provided to guide the user through the necessary steps. Some VCRs have numeric keypads to enter the information, while others allow choices to be entered by the selection method, which depends on the use of "up" and "down" arrow keys to select a desired option.

The other major presently used method, which is available on most VCRs, as well as other types of programmable devices, is Display Panel Programming. This method is generally inadequate because full instructions are not normally available on the display panel, and the amount of information simultaneously displayed is limited. Users do not need a television set to see the displayed information, but they might have trouble reading the small, usually multi-functional multiplexed display and keypad. When programming the VCR, information may be entered on the display panel using the selection method, with either the "up" key or both "up" and "down" keys, or by direct entry in devices that support such a system.

The remote control device of a VCR is often the primary input device, and it sometimes has control functions not accessible from a keypad input present on the VCR itself. Remote controls often contain many buttons, which may be found overwhelming and confusing by the user. This results in under-utilization of the various actuators or buttons, and consequently, various useful features are unused or inaccessible, or the programming operation is inefficient. The extra clutter results in a greater "search time", the time needed to locate and execute a desired function, and thus it takes longer to program the VCR. The general structure of the search time in programming a VCR is shown diagrammatically in FIG. 1. Other problems arise from the layout and coding of the buttons. A study performed by Kamran Abedini and George Hadad in 1987 entitled "Guidelines for Designing Better VCRs", Report No. IME 462, Feb. 4, 1987, California State Polytechnic University, incorporated herein by reference, has shown that varying the shape of the remote control device is more effective than varying its size. In addition, they found that color coding and adequate contrast can effect a significant improvement in programming performance. Abedini and Kamran, in "An Ergonomically-improved Remote Control Unit Design", Interface '87 Proceedings, 375–380 (1987), incorporated herein by reference, found that 78% of the people surveyed favored direct entry numbers (0–9) in addition to labels, symbols, discrete volume switches, and channel up/down buttons for casual searching. In addition, the people surveyed preferred remote controls which fit comfortably into their hand.

Many techniques have been used to facilitate the programming of devices such as VCRs, including:

Display Panels (1982)—Programmed with the aid of an LED display panel on the front of the machine.

Programming Via Remote Control (1983)—Programmed using a remote control device with keys for input.

On-Screen Displays (1984)—Programmed by a series of menus on the television screen.

Bar Code Scanners (1987)—Programmed by a wand passing over a series of lines, which are decoded and then transmitted to the VCR.

Light Pens (1987)—Programmed by aiming a pointing device with a light beam sensor at the television screen, which allows timing signals to be extracted to determine the position of the device with respect to the screen, and hence, the intended instruction.

Video Program System Signal Transmitters (1988)—The VCR is programmed by entering the unique code number of a desired program to record, which is emitted by television stations in West Germany as videotext digital signals associated with each program.

Phone Lines (1989)—Programmed over a telephone line at from a remote location. The numeric keys on the phone are the input keys.

Video Memories (1989)—Programmed by a computer from a remote location. For example, a user contacts a service, who then records certain programs at a user's request. These can be characterized in a number of ways, e.g. comedies, movies, etc. and the service will then manually scan the broadcast schedules for these provided characterizations and record the desired programs.

Voice Coaches (1990)—Programmed by responding to voice instructions, e.g. speech prompts, from the remote control.

As the technology becomes more mature, and VCRs and other types of programmable consumer electronic devices become less expensive, a proportionally less-educated segment of society will be confronted with these devices. While education and ability to program a VCR are not necessarily correlated, the present invention is directed toward improving the interface to allow all segments of the population to effectively interface with these programmable devices. By making the user interface more intuitive, and facilitating program entry by all levels of users, the present method and apparatus allow a manufacturer to produce a single device, without regard to the ability of the user to learn the programming steps. It is also noted that, because of their previous inability to provide a programmable consumer electronic device with various user interface levels, manufacturers have had to compromise the programming power of their user interface to allow less than advanced users to program it, or to compromise the usability of the device in order to make the full programming power available.

TECHNOLOGY FOR IMPLEMENTING THE HUMAN INTERFACE, IMAGE PROCESSING AND DECISION MAKING METHODS OF THE PRESENT INVENTION

The following references are relevant to the interface aspects of the present invention, are contained in the appendix hereto, and are expressly incorporated herein by reference:

Hoffberg, Linda I, "AN IMPROVED HUMAN FACTORED INTERFACE FOR PROGRAMMABLE DEVICES: A CASE STUDY OF THE VCR" Master's Thesis, Tufts University (Master of Sciences in Engineering Design, November, 1990).

"Bar Code Programs VCR", Design News, Feb. 1, 1988, 26.

"The Highs and Lows of Nielsen Homevideo Index", Marketing & Media Decisions, November 1985, 84–86+.

"The Quest for 'User Friendly'", U.S. News & World Report, Jun. 13, 1988. 54–56.

"The Smart House: Human Factors in Home Automation", Human Factors in Practice, December 1990, 1–36.

"VCR, Camcorder Trends", Television Digest, Vol. 29:16 (Mar. 20, 1989).

Abedini, Kamran, "An Ergonomically-improved Remote Control Unit Design", Interface '87 Proceedings, 375–380.

Abedini, Kamran, and Hadad, George, "Guidelines For Designing Better VCRs", Report No. IME 462, Feb. 4, 1987.

Bensch, U., "VPV-VIDEOTEXT PROGRAMS VIDEORECORDER", IEEE Transactions on Consumer Electronics, 34(3):788–792.

Berger, Ivan, "Secrets of the Universals", Video, February 1989, 45–47+.

Beringer, D. B., "A Comparative Evaluation of Calculator Watch Data Entry Technologies: Keyboards to Chalkboards", Applied Ergonomics, December 1985, 275–278.

Bishop, Edward W., and Guinness, G. Victor Jr., "Human Factors Interaction with Industrial Design", Human Factors, 8(4):279–289 (August 1966).

Brown, Edward, "Human Factors Concepts For Management", Proceedings of the Human Factors Society, 1973, 372–375.

Bulkeley, Debra, "The Smartest House in America", Design News, Oct. 19, 1987, 56–61.

Card, Stuart K., "A Method for Calculating Performance times for Users of Interactive Computing Systems", IEEE, 1979, 653–658.

Carlson, Mark A., "Design Goals for an Effective User Interface", Electro/82 Proceedings, 3/1/1–3/1/4.

Carlson, Mark A., "Design Goals for an Effective User Interface", Human Interfacing with Instruments, Session 3.

Carroll, Paul B., "High Tech Gear Draws Cries of "Uncle"", Wall Street Journal, Apr. 27, 1988, 29.

Cobb, Nathan, "I don't get it", Boston Sunday Globe Magazine, Mar. 25, 1990, 23–29.

Davis, Fred, "The Great Look-and-Feel Debate", A+, 5:9–11 (July 1987).

Dehning, Waltraud, Essig Heidrun, and Maass, Susanne, The Adaptation of Virtual Man-Computer Interfaces to User Requirements in Dialogs, Germany: Springer-Verlag, 1981.

Ehrenreich, S. L., "Computer Abbreviations—Evidence and Synthesis", Human Factors, 27(2):143–155 (April 1985).

Friedman, M. B., "An Eye Gaze Controlled Keyboard", Proceedings of the 2nd International Conference on Rehabilitation Engineering, 1984, 446–447.

Gilfoil, D., and Mauro, C. L., "Integrating Human Factors and Design: Matching Human Factors Methods up to Product Development", C. L. Mauro Assoc., Inc., 1–7.

Gould, John D., Boies, Stephen J., Meluson, Antonia, Rasammy, Marwan, and Vosburgh, Ann Marie, "Entry and Selection Methods For Specifying Dates". Human Factors, 32(2):199–214 (April 1989).

Green, Lee, "Thermo Tech: Here's a common sense guide to the new thinking thermostats", Popular Mechanics, October 1985, 155–159.

Grudin, Jonathan, "The Case Against User Interface Consistency", MCC Technical Report Number ACA-HI-002-89, January 1989.

Harvey, Michael G., and Rothe, James T., "VideoCassette Recorders: Their Impact on Viewers and Advertisers", Journal of Advertising, 25:19–29 (December/January 1985).

Hawkins, William J., "Super Remotes", Popular Science, February 1989, 76–77.

Henke, Lucy L., and Donohue, Thomas R., "Functional Displacement of Traditional TV Viewing by VCR Owners", Journal of Advertising Research, 29:18–24 (April-May 1989).

Hoban, Phoebe, "Stacking the Decks", New York, Feb. 16, 1987, 20:14.

"How to find the best value in VCRs", Consumer Reports, March 1988, 135–141.

Howard, Bill, "Point and Shoot Devices", PC Magazine, 6:95–97 (August 1987).

Jane Pauley Special, NBC TV News Transcript, Jul. 17, 1990, 10:00 PM.

Kolson, Ann, "Computer wimps drown in a raging sea of technology", The Hartford Courant, May 24, 1989, B1.

Kreifeldt, J. G., "A Methodology For Consumer Product Safety Analysis", The 3rd National Symposium on Human Factors in Industrial Design in Consumer Products, August 1982, 175–184.

Kreifeldt, John, "Human Factors Approach to Medical Instrument Design", Electro/82 Proceedings, 3/3/1–3/3/6.

Kuocheng, Andy Poing, and Ellingstad, Vernon S., "Touch Tablet and Touch Input", Interface '87, 327.

Ledgard, Henry, Singer, Andrew, and Whiteside, John, Directions in Human Factors for Interactive Systems, New York, Springer-Verlag, 1981.

Lee, Eric, and MacGregor, James, "Minimizing User Search Time Menu Retrieval Systems", Human Factors, 27(2):157–162 (April 1986).

Leon, Carol Boyd, "Selling Through the VCR", American Demographics, December 1987, 40–43.

Long, John, "The Effect of Display Format on the Direct Entry of Numerical Information by Pointing", Human Factors, 26(1):3–17 (February 1984).

"Low-Cost VCRs: More For Less", Consumer Reports, March 1990, 168–172.

Mantei, Marilyn M., and Teorey, Toby J., "Cost/Benefit Analysis for Incorporating Human Factors in the Software Lifecycle", Association for Computing Machinery, 1988.

Meads, Jon A., "Friendly or Frivolous", Datamation, Apr. 1, 1988, 98–100.

Moore, T. G. and Dartnall, "Human Factors of a Microelectronic Product: The Central Heating Timer/Programmer", Applied Ergonomics, 1983, 13(1):15–23.

"Nielsen Views VCRs", Television Digest, Jun. 23, 1988, 15.

Norman, Donald A., "Infuriating By Design", Psychology Today, 22(3):52–56 (March 1988).

Norman, Donald A., The Psychology of Everyday Things, New York, Basic Book, Inc. 1988.

Platte, Hans-Joachim, Oberjatzas, Gunter, and Voessing, Walter, "A New Intelligent Remote Control Unit for Consumer Electronic Device", IEEE Transactions on Consumer Electronics, Vol. CE-31(1):59–68 (February 1985).

Rogus, John G. and Armstrong, Richard, "Use of Human Engineering Standards in Design", Human Factors, 19(1):15–23 (February 1977).

Rosch, Winn L., "Voice Recognition: Understanding the Master's Voice", PC Magazine, Oct. 27, 1987, 261–308.

Sarver, Carleton, "A Perfect Friendship", High Fidelity, 39:42–49 (May 1989).

Schmitt, Lee, "Let's Discuss Programmable Controllers", Modern Machine Shop, May 1987, 90–99.

Schniederman, Ben, Designing the User Interface: Strategies for Effective Human-Computer Interaction, Reading, Mass., Addison-Wesley, 1987.

Smith, Sidney J., and Mosier, Jane N., Guidelines for Designing User Interface Software, Bedford, Mass., MITRE, 1986.

Sperling, Barbara Bied, Tullis Thomas S., "Are You a Better 'Mouser' or 'Trackballer'? A Comparison of Cursor—Positioning Performance", An Interactive/Poster Session at the CHI+GI'87 Graphics Interface and Human Factors in Computing Systems Conference.

Streeter, L. A., Ackroff, J. M., and Taylor, G. A. "On Abbreviating Command Names", The Bell System Technical Journal, 62(6):1807–1826 (July/August 1983).

Swanson, David, and Klopfenstein, Bruce, "How to Forecast VCR Penetration", American Demographic, December 1987, 44–45.

Tello, Ernest R., "Between Man And Machine", Byte, September 1988, 288–293.

Thomas, John, C., and Schneider, Michael L., Human Factors in Computer Systems, New Jersey, Ablex Publ. Co., 1984.

Trachtenberg, Jeffrey A., "How do we confuse thee? Let us count the ways", Forbes, Mar. 21, 1988, 159–160.

Tyldesley, D. A., "Employing Usability Engineering in the Development of Office Products", The Computer Journal", 31(5):431–436 (1988).

"VCR's: A Look At The Top Of The Line", Consumer Reports, March 1989, 167–170.

Verplank, William L., "Graphics in Human-Computer Communication: Principles of Graphical User-Interface Design", Xerox Office Systems.

"VHS Videocassette Recorders", Consumer Guide, 1990, 17–20.

Voyt, Carlton F., "PLC's Learn New Languages", Design News, Jan. 2, 1989, 78.

Whitefield, A. "Human Factors Aspects of Pointing as an Input Technique in Interactive Computer Systems", Applied Ergonomics, June 1986, 97–104.

Wiedenbeck, Susan, Lambert, Robin, and Scholtz, Jean, "Using Protocol Analysis to Study the User Interface", Bulletin of the American Society for Information Science, June/July 1989, 25–26.

Wilke, William, "Easy Operation of Instruments by Both Man and Machine". Electro/82 Proceedings, 3/2/1–3/2/4.

Yoder, Stephen Kreider, "U.S. Inventors Thrive at Electronics Show", The Wall Street Journal, Jan. 10, 1990, B1.

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814–818.

The following cited patents and publications are relevant to pattern recognition and control aspects of the present invention, and are herein expressly incorporated by reference:

U.S. Pat. No. 5,067,163, incorporated herein by reference, discloses a method for determining a desired image signal range from an image having a single background, in particular a radiation image such as a medical X-ray. This reference teaches basic image enhancement techniques.

U.S. Pat. No. 5,068,664, incorporated herein by reference, discloses a method and device for recognizing a target among a plurality of known targets, by using a probability based recognition system. This patent document cites a number of other references, each incorporated herein by reference, which are relevant to the problem of image recognition:

Vannicola et al, "Applications of Knowledge based Systems to Surveillance", Proceedings of the 1988 IEEE National Radar Conference, 20–21 Apr. 1988, pp. 157–164;

Ksienski et al., "Low Frequency Approach to Target Identification", Proc. of the IEEE, 63(12):1651–1660 (December 1975);

Appriou, A., "Interet des theories de l'incertain en fusion de donnees", Colloque International sur le Radar Paris, 24–28 April 1989;

Appriou, A., "Procedure d'aide a la decision multi-informateurs. Applications a la classification multi-capteurs de cibles", Symposium de l'Avionics Panel (AGARD) Turquie, 25–29 April 1988;

Arrow, K. J., "Social choice and individual valves", John Wiley and Sons Inc. (1963);

Blair, D., R. Pollack, "La logique du choix collectif" Pour la Science (1983);

Scharlic, A., "Decider sur plusieurs criteres. Panorama de l'aide a la decision multicritere" Presses Polytechniques Romandes (1985);

Keeney, R. L., B. Raiffa, "Decisions with multiple objectives: Preferences and value tradeoffs", John Wiley and Sons, New York (1976);

Jeffrey, R. J., "The logic of decision", The University of Chicago Press, Ltd., London (1983)(2nd Ed.);

Roy, B., "Classements et choix en presence de points de vue multiples", R.I.R.O.-2eme annee-no. 8, pp. 57–75 (1968);

Roy, B., "Electre III: un algorithme de classements fonde sur une representation floue des preferences en presence de criteres multiples", Cahiers du CERO, 20(1):3–24 (1978);

Duda, R. O., P. E. Hart, M. J. Nilsson, "Subjective Bayesian methods for rule-based inference systems", Technical Note 124-Artificial Intelligence Center-SRI International;

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986);

Dempster, A. P., "Upper and lower probabilities induced by a multivalued mapping", Annals of mathematical Statistics, no. 38 (1967);

Dempster, A. P., "A generalization of Bayesian inference", Journal of the Royal Statistical Society, Vol. 30, Series B (1968);

Shafer, G., "A mathematical theory of evidence", Princeton University Press, Princeton, N.J. (1976);

Dubois, D., N. Prade, "Combination of uncertainty with belief functions: a reexamination", Proceedings 9th International Joint Conference on Artificial Intelligence, Los Angeles (1985);

Kyburg, H. E., "Bayesian and non Bayesian evidential updating", Artificial Intelligence 31:271–293 (1987);

Fua, P. V., "Using probability density functions in the framework of evidential reasoning Uncertainty in knowledge based systems", B. Bouchon, R. R. Yager, Eds. Springer Verlag (1987);

Chao, J. J., E. Drakopoulos, C. C. Lee, "An evidential reasoning approach to distributed multiple hypothesis detection", Proceedings of the 20th Conference on decision and control, Los Angeles, Calif., December 1987;

Yager, R. R., "Entropy and specificity in a mathematical theory of Evidence", Int. J. General Systems, 9:249–260 (1983);

Ishizuka, M., "Inference methods based on extended Dempster and Shafer's theory for problems with uncertainty/fuzziness", New Generation Computing, 1:159–168 (1983), Ohmsha, Ltd, and Springer Verlag;

Zadeh, L. A., "Fuzzy sets", Information and Control, 8:338–353 (1965);

Zadeh, L. A., "Probability measures of fuzzy events", Journal of Mathematical Analysis and Applications, 23:421–427 (1968);

Kaufmann, A., "Introduction a la theorie des sous-ensembles flous", Vol. 1, 2 et 3-Masson-Paris (1975);

Sugeno, M., "Theory of fuzzy integrals and its applications", Tokyo Institute of Technology (1974);

Bellman, R. E., L. A. Zadeh, "Decision making in a fuzzy environment", Management Science, 17(4) (December 1970);

Dubois, D., N. Prade, "Fuzzy sets and systems-Theory and applications", Academic Press, New York (1980);

Zadeh, L. A., "Fuzzy sets as a basis for a theory of possibility", Fuzzy sets and Systems 1:3–28 (1978);

Dubois, D., "Modeles mathematiques de l'imprecis et de l'incertain en vue d'applications aux techniques d'aide a la decision", Doctoral Thesis, University of Grenoble (1983);

Dubois, D., N. Prade, "Theorie des possibilites: application a la representation des connaissances en informatique", Masson, Paris (1985).

Thus, the image or object recognition feature of the present invention may be implemented in the manner of U.S. Pat. No. 5,068,664. Further, it is clear that this recognition feature may form an integral part of certain embodiments of the present invention. It is also clear that the various features of the present invention would be applicable as an adjunct to the various elements of the system disclosed in U.S. Pat. No. 5,068,664.

U.S. Pat. Nos. 5,065,447, and 4,941,193, both incorporated herein by reference, relate to the compression of image data by using fractal transforms. These are discussed in detail below. U.S. Pat. No. 5,065,447 cites a number of references, all incorporated herein by reference, relevant to the use of fractals in image processing:

U.S. Pat. No. 4,831,659;

Barnsley et al., "Hidden Variable Fractal Interpolation Functions", School of Mathematics, Georgia Institute of Technology, Atlanta, Ga. 30332, July 1986;

Barnsley, M. F., and Demko, S., "Iterated Function Systems and The Global Construction of Fractals", Proc. R. Soc. Lond., A399:243–275 (1985);

Barnsley, M. F., Ervin, V., Hardin, D., Lancaster, J., "Solution of an Inverse Problem for Fractals and Other Sets", Proc. Natl. Acad. Sci. U.S.A., 83:1975–1977 (April 1986);

"A New Class of Markov Processes for Image Encoding", School of Mathematics, Georgia Inst. of Technology (1988), pp. 14–32;

"Fractal Modelling of Biological Structures", Perspectives in Biological Dynamics and Theoretical Medicine, Koslow, Mandell, Shlesinger, eds., Annals of New York Academy of Sciences, vol. 504, 179–194 (date unknown);

Elton, J., "An Ergodic Theorem for Iterated Maps", Journal of Ergodic Theory and Dynamical Systems, 7 (1987);

"Construction of Fractal Objects with Iterated Function Systems", Siggraph '85 Proceedings, 19(3):271–278 (1985);

"Fractal Modelling of Real World Images, Lecture Notes for Fractals: Introduction, Basics and Perspectives", Siggraph (1987);

Peterson, Ivars, "Packing It In-Fractals . . . ", Science News, 131(18):283–285 (May 2, 1987);

"Fractal Geometry-Understanding Chaos", Georgia Tech Alumni Magazine, p. 16 (Spring 1986);

"Fractals-A Geometry of Nature", Georgia Institute of Technology Research Horizons, p. 9 (Spring 1986);

Fractal Modelling of Biological Structures, School of Mathematics, Georgia Institute of Technology (date unknown);

Barnsley et al., "A Better Way to Compress Images", Byte Magazine, January 1988, pp. 213–225;

Derra, Skip, "Researchers Use Fractal Geometry, . . . ", Research and Development Magazine, March 1988;

"Data Compression: Pntng by Numbrs", The Economist, May 21, 1988;

Baldwin, William, "Just the Bare Facts, Please", Forbes Magazine, Dec. 12, 1988;

Barnsley et al., "Harnessing Chaos For Images Synthesis", Computer Graphics, 22(4):131–140 (August, 1988);

Barnsley et al., "Chaotic Compression", Computer Graphics World, November 1987;

Gleick, James, "Making a New Science", pp. 215, 239, date unknown.

Byte Magazine, January 1988, supra, cites:

Mandelbrot, B., "The Fractal Geometry of Nature", W. H. Freeman & Co., San Francisco, Calif., 1982, 1977; and Barnsley, M. F., "Fractals Everywhere", Academic Press, Boston, Mass., 1988, both of which are also incorporated herein by reference.

U.S. Pat. No. 5,063,603, incorporated herein by reference, relates to a dynamic method for recognizing objects and image processing system therefor. This reference discloses a method of distinguishing between different members of a class of images, such as human beings. A time series of successive relatively high-resolution frames of image data, any frame of which may or may not include a graphical representation of one or more predetermined specific members (e.g., particular known persons) of a given generic class (e.g. human beings), is examined in order to recognize the identity of a specific member; if that member's image is included in the time series. The frames of image data may be examined in real time at various resolutions, starting with a relatively low resolution, to detect whether some earlier-occurring frame includes any of a group of image features possessed by an image of a member of the given class. The image location of a detected image feature is stored and then used in a later-occurring, higher resolution frame to direct the examination only to the image region of the stored location in order to (1) verify the detection of the aforesaid image feature, and (2) detect one or more other of the group of image features, if any is present in that image region of the frame being examined. By repeating this type of examination for later and later occurring frames, the accumulated detected features can first reliably recognize the detected image region to be an image of a generic object of the given class, and later can reliably recognize the detected image region to be an image of a certain specific member of the given class. Thus, the personae recognition feature of the present invention may be implemented in this manner. Further, it is clear that this recognition feature may form an integral part of certain embodiments of the present invention. It is also clear that the various features of the present invention would be applicable as an adjunct to the various elements of the system disclosed in U.S. Pat. No. 5,063,603.

U.S. Pat. No. 5,055,658, incorporated herein by reference, relates to a security system employing digitized personal characteristics, such as voice. The following cited references are incorporated herein by reference:

Naik et al., "High Performance Speaker Verification . . . ", ICASSP 86, Tokyo, CH2243-4/86/0000-0881, IEEE 1986, pp. 881–884;

"Voice Recognition and Speech Processing", Elektor Electronics, September 1985, pp. 56–57;

Shinan et al., "The Effects of Voice Disguise . . . ", ICASSP 86, Tokyo, CH2243-4/86/0000-0885, IEEE 1986, pp. 885–888.

Parts of this system relating to speaker recognition may be used to implement a voice recognition system of the present invention for determining an actor or performer in a broadcast.

U.S. Pat. No. 5,067,164, incorporated herein by reference, relates to a hierarchical constrained automatic learning neural network for character recognition, and thus represents an example of a trainable neural network for pattern recognition, which discloses methods which are useful for the present invention. This Patent cites various references of interest, which are incorporated herein by reference:

U.S. Pat. Nos. 4,760,604, 4,774,677 and 4,897,811;

Rumelhart, D. E., et al., Parallel Distr. Proc.: Explorations in Microstructure of Cognition, vol. 1, 1986, "Learning Internal Representations by Error Propagation", pp. 318–362;

Lippmann, R. P., "An Introduction to Computing with Neural Nets", IEEE ASSP Magazine, 4(2):4–22 (April 1987);

LeCun, Y., Connectionism in Perspective, R. Pfeifer, Z. Schreter, F. Fogelman, L. Steels, (Eds.), 1989, "Generalization and Network Design Strategies", pp. 143–55;

LeCun, Y., et al., "Handwritten Digit Recognition: Applications of Neural . . . ", IEEE Comm. Magazine, pp. 41–46 (November 1989).

U.S. Pat. Nos. 5,048,100, 5,063,601 and 5,060,278, all incorporated herein by reference, also relate to neural network adaptive pattern recognition methods and apparatuses. It is clear that the methods of U.S. Pat. Nos. 5,048,100, 5,060,278 and 5,063,601 may be used to perform the adaptive pattern recognition functions of the present invention. More general neural networks are disclosed in U.S. Pat. Nos. 5,040,134 and 5,058,184, both incorporated herein be reference, which provide background on the use of neural networks. In particular, U.S. Pat. No. 5,058,184 relates to the use of the apparatus in information processing and feature detection applications.

U.S. Pat. No. 5,058,180, incorporated herein by reference, relates to neural network apparatus and method for pattern recognition, and is thus relevant to the intelligent pattern recognition functions of the present invention. This patent cites the following documents of interest, which are incorporated herein by reference:

U.S. Pat. Nos. 4,876,731 and 4,914,708;

Computer Visions, Graphics, and Image Processing 1987, 37:54–115;

Jackel, L. D., H. P. Graf, J. S. Denker, D. Henderson and I. Guyon, "An Application of Neural Net Chips: Handwritten Digit Recognition," ICNN Proceeding, 1988, pp. II-107–15;

Carpenter, G. A., S. Grossberg, "The Art of Adaptive Pattern Recognition by a Self-Organizing Neural Network," IEEE Computer, March 1988, pp. 77–88;

Pawlicki, T. F., D. S. Lee, J. J. Hull and S. N. Srihari, "Neural Network Models and their Application to Handwritten Digit Recognition," ICNN Proceeding, 1988, pp. II-63–70;

Gullichsen E., E. Chang, "Pattern Classification by Neural Network: An Experiment System for Icon Recognition," ICNN Proceeding on Neural Networks, March 1987, pp. IV-725–32;

Grossberg, S., G. Carpenter, "A Massively Parallel Architecture for a Self-Organizing Neural Pattern Recognition Machine," Computer Vision, Graphics, and Image Processing (1987, 37, 54–115), pp. 252–315;

Lippman, R. P., "An Introduction to Computing with Neural Nets," IEEE ASSP Magazine, April 1987, pp. 4–22.

U.S. Pat. No. 5,067,161, incorporated herein by reference, relates to a video image pattern recognition system, which recognizes objects in near real time.

U.S. Pat. Nos. 4,817,176 and 4,802,230, both incorporated herein by reference, relate to harmonic transform methods of pattern matching of an undetermined pattern to known patterns, and are useful in the pattern recognition method of the present invention. U.S. Pat. No. 4,998,286, incorporated herein by reference, relates to a harmonic transform method for comparing multidimensional images, such as color images, and is useful in the present pattern recognition methods.

U.S. Pat. No. 5,060,282, incorporated herein by reference, relates to an optical pattern recognition architecture implementing the mean-square error correlation algorithm. This method allows an optical computing function to perform pattern recognition functions. U.S. Pat. No. 5,060,282 cites the following references, incorporated herein by reference, which are relevant to optical pattern recognition:

Psaltis, D., "Incoherent Electro-Optic Image Correlator", Optical Engineering, 23(1):12–15 (January/February 1984);

Kellman, P., "Time Integrating Optical Signal Processing", Ph. D. Dissertation, Stanford University, 1979, pp. 51–55;

Molley, P., "Implementing the Difference-Squared Error Algorithm Using An Acousto-Optic Processor", SPIE, 1098:232–239, (1989);

Rhodes, W., "Acousto-Optic Signal Processing: Convolution and Correlation", Proc. of the IEEE, 69(1):65–79 (January 1981);

Vander Lugt, A., "Signal Detection By Complex Spatial Filtering", IEEE Transactions On Information Theory, IT-10, 2:139–145 (April 1964);

Psaltis, D., "Two-Dimensional Optical Processing Using One-Dimensional Input Devices", Proceedings of the IEEE, 72(7):962–974 (July 1984);

Molley, P., et al., "A High Dynamic Range Acousto-Optic Image Correlator for Real-Time Pattern Recognition", SPIE, 938:55–65 (1988).

U.S. Pat. No. 5,063,602, incorporated herein by reference, also relates to an optical image correlators.

U.S. Pat. No. 5,067,160, incorporated herein by reference, relates to a motion-pattern recognition apparatus. The apparatus recognizes a motion of an object which is moving and is hidden in an image signal, and discriminates the object from the background within the signal. The apparatus has an image forming unit comprising non-linear oscillators, which forms an image of the motion of the object in accordance with an adjacent-mutual-interference-rule, on the basis of the image signal. A memory unit, comprising non-linear oscillators, stores conceptualized meanings of several motions. A retrieval unit retrieves a conceptualized meaning close to the motion image of the object. An altering unit alters the rule, on the basis of the conceptualized meaning. The image forming unit, memory unit, retrieval unit and altering unit form a holonic-loop. Successive alterations of the rules by the altering unit within the holonic loop change an ambiguous image formed in the image forming unit into a distinct image. U.S. Pat. No. 5,067,160 cites the following references, incorporated herein by reference, which are relevant to the task of discriminating a moving object in a background:

U.S. Pat. No. 4,710,964;

Shimizu et al, "Principle of Holonic Computer and Holovision", Journal of the Institute of Electronics, Information and Communication, 70(9):921–930 (1987);

Omata et al, "Holonic Model of Motion Perception", IEICE Technical Reports, Mar. 3, 1988, pp. 339–346;

Ohsuga et al, "Entrainment of Two Coupled van der Pol Oscillators by an External Oscillation", Biological Cybernetics, 51:225–239 (1985).

It is clear that U.S. Pat. No. 5,067,160 discloses an adaptive pattern recognition system that may be useful in various embodiments of the present invention. It is also clear that the interface and control systems of the present invention provide useful adjuncts to the elements disclosed in U.S. Pat. No. 5,067,160.

U.S. Pat. No. 5,065,440, incorporated herein by reference, relates to a pattern recognition apparatus, which compensates for, and is thus insensitive to pattern shifting, thus being useful for decomposing an image into its structural features and recognizing the features. U.S. Pat. No. 5,065,440 cites the following references, incorporated herein by reference, which are also relevant to the present invention: U.S. Pat. Nos. 4,543,660, 4,630,308, 4,677,680, 4,809,341, 4,864,629, 4,872,024 and 4,905,296.

U.S. Pat. No. 5,067,166, incorporated herein by reference, relates to a pattern recognition system, in which a local optimum match between subsets of candidate reference label sequences and candidate templates. It is clear that this method is useful in the pattern recognition aspects of the present invention. It is also clear that the interface and control system of the present invention are useful adjuncts to the method disclosed in U.S. Pat. No. 5,067,166.

U.S. Pat. No. 5,048,095, incorporated herein by reference, relates to the use of a genetic learning algorithm to adaptively segment images, which is an initial stage in image recognition. This patent has a software listing for this method. It is clear that this method is useful in the pattern recognition aspects of the present invention. It is also clear that the interface and control system of the present invention are useful adjuncts to the method disclosed in U.S. Pat. No. 5,048,095.

In addition, the following patents are considered relevant to the data compression and pattern recognition functions of the apparatus and interface of the present invention and are incorporated herein by reference: U.S. Pat. Nos. 3,950,733; 4,044,243; 4,254,474; 4,326,259; 4,442,544; 4,449,240; 4,468,704; 4,491,962; 4,501,016; 4,543,660; 4,547,811; 4,630,308; 4,656,665; 4,658,429; 4,660,166; 4,677,680; 4,682,365; 4,685,145; 4,710,822; 4,710,964; 4,719,591; 4,731,863; 4,736,439; 4,742,557; 4,752,890; 4,760,604; 4,764,971; 4,771,467; 4,773,099; 4,774,677; 4,790,025; 4,799,270; 4,803,736; 4,805,224; 4,805,255; 4,809,341; 4,817,171; 4,821,333; 4,823,194; 4,831,659; 4,833,637; 4,837,842; 4,845,610; 4,864,629; 4,872,024; 4,876,731; 4,887,304; 4,888,814; 4,891,762; 4,897,811; 4,905,296; 4,906,099; 4,914,708; 4,926,491; 4,932,065; 4,933,872; 4,941,193; 4,944,023; 4,958,375; 4,958,375; 4,965,725; 4,972,499; 4,979,222; 4,987,604; 4,989,258; 5,014,219; 5,014,327; 5,018,218; 5,018,219; 5,020,112; 5,022,062; 5,034,991; 5,038,379; 5,040,134; 5,046,121; 5,046,122; 5,046,179; 5,048,112; 5,050,223; 5,051,840; 5,052,043; 5,052,045; 5,052,046; 5,053,974; 5,054,093; 5,054,095; 5,054,101; 5,054,103; 5,055,658; 5,055,926; 5,056,147; 5,058,179; 5,058,180; 5,058,186; 5,059,126; 5,060,276; 5,060,277; 5,060,279; 5,060,282; 5,060,285; 5,061,063; 5,063,524; 5,063,525; 5,063,603; 5,063,605; 5,063,608; 5,065,439; 5,065,440; 5,065,447; 5,067,160; 5,067,161; 5,067,162; 5,067,163; 5,067,164; 5,068,664; 5,068,723; 5,068,724; 5,068,744; 5,068,909; 5,068,911; H 331; and Re. 33,316. The aforementioned patents, some of which are mentioned elsewhere in this disclosure, and which form a part of this disclosure, may be applied in known manner by those skilled in the art in order to practice various embodiments of the present invention.

The following scientific articles, some of which are discussed elsewhere herein, are incorporated by reference, and their relevance is understood by those skilled in the art and relate to the pattern recognition and image compression functions of the apparatus and interface of the present invention:

Liepins, G. E., M. R. Hilliard, "Genetic Algorithms: Foundations & Applications", Annals of Operations Research, 21:31–58 (1989).

Fitzpatrick, J. M., J. J. Grefenstette, D. Van Gucht, "Image Registration by Genetic Search", Conf. Proc., IEEE Southeastcon 1984, pp. 460–464.

McAulay, A. D., J. C. Oh, "Image Learning Classifier System Using Genetic Algorithms", IEEE Proc. of the National Aerospace & Electronics Conference, 2:705–710 (1989).

Wasserman, Philip D., "Neural Computing-Theory & Practice", 1989, pp. 128–129.

Nilsson, N. J., The Mathematical Foundations of Learning Machines ((c) 1990: Morgan Kaufmann Publishers, San Mateo, Calif.) and particularly section 2.6 "The Threshold Logic Unit (TLU)", pp. 21–23 and Chapter 6, "Layered Machines" pp. 95–114.

Martin, G. L. et al., "Recognizing Hand-Printed Letters and Digits Using Backpropagation Learning", Technical Report of the MCC, Human Interface Laboratory, Austin, Tex., January 1990, pp. 1–9.

Jean, J. S. N., et al., "Input Representation and Output Voting Considerations for Handwritten Numeral Recognition with Backpropagation", International Joint Conference on Neural Networks, Washington, D.C., January 1990, pp. I-408 to I-411.

Zhu, X., et al., "Feature Detector and Application to Handwritten Character Recognition", International Joint Conference on Neural Networks, Washington, D.C., January 1990, pp. II-457 to II-460.

Haruki, K. et al., "Pattern Recognition of Handwritten Phonetic Japanese Alphabet Characters", International Joint Conference on Neural Networks, Washington, D.C., January 1990, pp. II-515 to II-518.

Miller, R. K., Neural Networks ((c) 1989: Fairmont Press, Lilburn, Ga.), pp. 2–12 and Chapter 4, "Implementation of Neural Networks", pp. 4-1 to 4-26.

Hayashi, Y., et al., "Alphanumeric Character Recognition Using a Connectionist Model with the Pocket Algorithm", Proceedings of the International Joint Conference on Neural Networks, Washington, D.C. Jun. 18–22, 1989, vol. 2, pp. 606–613.

Caudill, M., "Neural Networks Primer-Part III", AI Expert, June 1988, pp. 53–59.

Burr, D. J., "A Neural Network Digit Recognizer", Proceedings of the 1986 IEEE International Conference of Systems, Man and Cybernetics, Atlanta, Ga., pp. 1621–1625.

Rumelhart, D. E., et al., Parallel Distributed Processing, ((c) 1986: MIT Press, Cambridge, Mass.), and specifically Chapter 8 thereof, "Learning Internal Representations by Error Propagation", pp. 318–362.

Danielsson, Erik, et al., "Computer Architectures for Pictorial Inf. Systems", IEEE Computer, November 1981, pp. 53–67.

Hopfield et al., "Computing with Neural Circuits: A Model", Science, 233:625–633 (Aug. 8, 1986).

Hinton et al., "Boltzmann Machines: Constraint Satisfaction Networks that Learn", Tech. Report CMU-CS-85-119, Carnegie-Mellon Univ, 5/84.

Hopfield, "Neurons with graded response have collective computational properties like those of two-state neurons", Proc. Natl. Acad. Sci. USA, 81:3088–3092 (May 1984).

Willshaw et al., "Non-Holographic Associative Memory", Nature, 222:960–962 (Jun. 7, 1969).

Cooper, L. N., "A PNssible Organization of Animal Memory and Learning", Nobel 24, (1973), Collective Properties of Physical Systems, pp. 252–264.

Hopfield, "Neural Networks and Physical Systems with Emergent Collective Computational Abilities", Proc. Natl. Acad. Sci. USA, 79:2554–2558 (April 1982).

Batchelor, B. G., "Practical Approach to Pattern Classification", Plenum Press, London and New York, (1974).

Batchelor, B. G., "Pattern Recognition, Ideas in Practice", Plenum Press, London and New York, (1978).

Udagawa, K., et al, "A Parallel Two-Stage Decision Method for Statistical Character Recognition . . . ", Electronics and Communications in Japan (1965).

Schurmann, J., "Zur Zeichen und Worterkennung beim Automatischen Anschriftenlesen", Wissenschaftlichl, Berichte, 52(1/2) (1979).

Computers and Biomedical Research 5, 388–410 (1972).

Proceedings, 6th International Conference on Pattern Recognition 1982, pp. 152–136.

Information Processing 71, North-Holland Publishing Company (1972) pp. 1530–1533.

Scientific American, "Not Just a Pretty Face", March 1990, pp. 77–78.

Farrelle, Paul M. and Jain, Anil K., "Recursive Block Coding-A New Approach to Transform Coding", IEEE Transactions on Communications, Com. 34(2) (February 1986).

Yamane et al., "An Image Data Compression Method Using Two-Dimensional Extrapolative Prediction-Discrete Sine Transform", Oct. 29–31, 1986, pp. 311–316.

Chen et al., "Adaptive Coding of Monochrome and Color Images", November 1977, pp. 1285–1292.

O'Neal et al., "Coding Isotropic Images", November 1977, pp. 697–707.

Anderson, F., W. Christiansen, B. Kortegaard, "Real Time, Video Image Centroid Tracker", Apr. 16–20, 1990.

Kortegaard, B. L., "PAC-MAN, a Precision Alignment Control System for Multiple Laser Beams Self-Adaptive Through the Use of Noise", Los Alamos National Laboratory, date unknown.

Kortegaard, B. L., "Superfine Laser Position Control Using Statistically Enhanced Resolution in Real Time", Los Alamos National Laboratory, SPIE-Los Angeles Technical Symposium, Jan. 23–25, 1985.

Aleksander, I., "Guide to Pattern Recognition Using Random-Access Memories", Computers and Digital Techniques, 2(1):29–40 (February 1979).

Rumelhart, D. E., et al., "Learning Internal Representations by Error Propagation", Parallel Distr. Proc.: Explorations in Microstructure of Cognition, 1:318–362 (1986).

Lippmann, R. P., "An Introduction to Computing with Neural Nets", IEEE ASSP Magazine, vol. 4(2):4–22 (April 1987).

LeCun, Y., "Connectionism in Perspective", in R. Pfeifer, Z. Schreter, F. Fogelman, L. Steels (Eds.), 1989, "Generalization and Network Design Strategies", pp. 143–155.

LeCun, Y. et al., "Handwritten Digit Recognition: Applications of Neural . . . ", IEEE Comm. Magazine, November 1989, pp. 41–46.

Denker, 1984 International Test Conf., October 1984, Philadelphia, Pa., pp. 558–563.

Gogoussis et al., Proc. SPIE Intl. Soc. Opt. Eng., November 1984, Cambridge, Mass., pp. 121–127.

Svetkoff et al., Hybrid Circuits (GB), No. May 13, 1987, pp. 5–8.

Kohonen, "Self-Organization & Memory", Second Ed., 1988, Springer-Verlag, pp. 199–209.

Specht, IEEE Internatl. Conf. Neural Networks, 1:1525–1532 (July 1988), San Diego, Calif.

Wald, Sequential Analysis, Dover Publications Inc., 1947, pp. 34–43.

Rosenfeld, Azriel and Avinash C. Kak, Digital Picture Processing, Second Edition, Volume 2, Academic Press, 1982.

Mori, "Towards the construction of a large-scale neural network", Electronics Information Communications Association Bulletin PRU 88-59, pp. 87–94.

Yamada et. al., "Character recognition system using a neural network", Electronics Information Communications Association Bulletin PRU 88-58, pp. 79–86.

Crawford et al., "Adaptive Pattern Recognition Applied To An Expert System For Fault Diagnosis In Telecommunications Equipment", pp. 10/1–8 (Inspec. Abstract No. 86C010699, Inspec IEE (London) & IEE Coll. on "Adaptive Filters", Digest No. 76, Oct. 10, 1985)

Rutter et al., "The Timed Lattice-A New Approach To Fast Converging Equalizer Design", pp.VIII/1–5 (Inspec. Abstract No. 84C044315, Inspec IEE (London) & IEE Saraga Colloquium on Electronic Filters, May 21, 1984)

Simpson, W. R., C. S. Dowling, "WRAPLE: The Weighted Repair Assistance Program Learning Extension", IEEE Design & Test, 2:66–73 (April 1986).

Dunning, B. B., "Self-Learning Data-Base For Automated Fault Localization", IEEE, 1979, pp. 155–157.

Stewart, R. M., "Expert Systems For Mechanical Fault Diagnosis", IEEE, 1985, pp. 295–300.

Lin, H. K., et al., "Real-Time Screen-Aided Multiple-image Optical Holographic Matched-Filter Correlator", Applied Optics, 21(18):3278–3286 (Sep. 15, 1982)

Vander Lugt, A., et al., "The Use of Film Nonlinearites in Optical Spatial Filtering", Applied Optics, 9(1) :215–222 (January 1970).

Vander Lugt, A., "Practical Considerations for the Use of Spatial Carrier-Frequency Filters", Applied Optics, 5(11):1760–1765 (November 1966).

Silverston et al., "Spectral Feature Classification and Spatial Pattern Rec.", SPIE 201:17–26, Optical Pattern Recognition (1979).

Perry et al., "Auto-indexing Storage Device", IBM Tech. Disc. Bulletin, 12(8):1219 (January 1970).

Vitols, "Hologram Memory for Storing Digital Data", IBM Tech. Disc. Bulletin 8(11):1581–1583 (April 1966).

Stanley R. Sternberg, "Biomedical Image Processing", IEEE Computer, 1983, pp. 22–34.

Rutherford, H. G., F. Taub and B. Williams, "Object Identification and Measurement from Images with Access to the Database to Select Specific Subpopulations of Special Interest", May 1986.

Ney, H., et al., "A Data Driven Organization of the Dynamic Programming Beam Search for Continuous Speech Recognition", Proc. ICASSP 87, pp. 833–836, 1987.

Sakoe, H., "A Generalization of Dynamic Programming Based Pattern Matching Algorithm Stack DP-Matching", Transactions of the Committee on Speech Research, The Acoustic Society of Japan, p. S83-23, 1983.

Sakoe, H., "A Generalized Two-Level DP-Matching Algorithm for Continuous Speech Recognition", Transactions of the IECE of Japan, E65(11):649–656 (November 1982).

Mahalanobis, A., et al., "Minimum Average Correlation Energy Filters", Applied Optics, 26(17):3633–40 (Sep. 1, 1987).

Sprageu, R. A., "A Review of Acousto-Optic Signal Correlators", Optical Engineering, 16(5):467–74 (September/October 1977)

Casasent, D., et al., "General I and Q Data Processing on a Multichannel AO System", Applied Optics, 25(18):3217–24 (Sep. 15, 1986).

Vannicola et al., "Applications of Knowledge Based Systems to Surveillance", Proceedings of the 1988 IEEE National Radar Conference, Apr. 20–21, 1988, pp. 157–164.

Ksienski et al., "Low Frequency Approach to Target Identification", Proc. of the IEEE, 63(12):1651–1660 (December 1975).

Appriou, A., "Interet des theories de l'incertain en fusion de donnees", Colloque International sur le Radar Paris, Apr. 24–28, 1989.

Appriou, A., "Procedure d'aide a la decision multi-informateurs.

Applications a la classification multi-capteurs de cibles", Symposium de l'Avionics Panel (AGARD) Turquie, Apr. 25–29, 1988.

Arrow, K. J., "Social choice and individual valves", John Wiley and Sons Inc. (1963).

Blair, D., R. Pollack, "La logique du choix collectif", Pour la Science (1983).

Scharlic, A., "Decider sur plusieurs criteres. Panorama de l'aide a la decision multicritere", Presses Polytechniques Romandes (1985).

Keeney, R. L., B. Raiffa, "Decisions with multiple objectives: Preferences and value tradeoffs", John Wiley and Sons, New York (1976).

Jeffrey, R. J., "The logic of decision", The University of Chicago Press, Ltd., London (1983)(2nd Ed.).

Roy, B., "Classements et choix en presence de points de vue multiples", R.I.R.O.-2eme annee-no. 8, pp. 57–75 (1968).

Roy, B., "Electre III: un algorithme de classements fonde sur une representation floue des preferences en presence de criteres multiples", Cahiers du CERO, 20(1):3–24 (1978).

Duda, R. O., P. E. Hart, M. J. Nilsson, "Subjective Bayesian methods for rule-based inference systems", Technical Note 124, Artificial Intelligence Center, SRI International.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Dempster, A. P., "Upper and lower probabilities induced by a multivalued mapping", Annals of mathematical Statistics, no. 38 (1967).

Dempster, A. P., "A generalization of Bayesian inference", Journal of the Royal Statistical Society, Vol. 30, Series B (1968).

Shafer, G., "A mathematical theory of evidence", Princeton University Press, Princeton, N.J. (1976).

Dubois, D., N. Prade, "Combination of uncertainty with belief functions: a reexamination", Proceedings 9th International Joint Conference on Artificial Intelligence, Los Angeles (1985).

Kyburg, H. E., "Bayesian and non Bayesian evidential updating", Artificial Intelligence 31:271–293 (1987).

Fua, P. V., "Using probability density functions in the framework of evidential reasoning Uncertainty in knowledge based systems", B. Bouchon, R. R. Yager, Eds. Springer Verlag (1987).

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Yager, R. R., "Entropy and specificity in a mathematical theory of Evidence", Int. J. General Systems, 9:249–260 (1983).

Ishizuka, M., "Inference methods based on extended Dempster and Shafer's theory for problems with uncertainty/fuzziness", New Generation Computing, Ohmsha, Ltd, and Springer Verlag, 1:159–168 (1983).

Zadeh, L. A., "Fuzzy sets", Information and Control, 8:338–353 (1965).

Zadeh, L. A., "Probability measures of fuzzy events", Journal of Mathematical Analysis and Applications, 23:421–427 (1968).

Kaufmann, A., "Introduction a la theorie des sous-ensembles flous", Vol. 1, 2 et 3, Masson, Paris (1975).

Sugeno, M., "Theory of fuzzy integrals and its applications", Tokyo Institute of Technology (1974).

Bellman, R. E., L. A. Zadeh, "Decision making in a fuzzy environment", Management Science, 17(4) (December 1970).

Dubois, D., N. Prade, "Fuzzy sets and systems-Theory and applications", Academic Press, New York (1980).

Zadeh, L. A., "Fuzzy sets as a basis for a theory of possibility", Fuzzy sets and Systems, 1:3–28 (1978).

Dubois, D., "Modeles mathematiques de l'imprecis et de l'incertain en vue d'applications aux techniques d'aide a la decision", Doctoral Thesis, University of Grenoble (1983).

Dubois, D., N. Prade, "Theorie des possibilites: application a la representation des connaissances en informatique", Masson, Paris (1985).

Barnsley et al., "Hidden Variable Fractal Interpolation Functions", School of Mathematics, Georgia Institute of Technology, Atlanta, Ga. 30332, July 1986.

Anson, L., M. Barnsley, "Graphics Compression Technology", SunWorld, pp. 43–52 (October 1991).

Caffery, B., "Fractal Compression Breakthrough for Multimedia Applications", Inside, Oct. 9, 1991.

"Fractal Modelling of Real World Images", Lecture Notes for Fractals: Introduction, Basics and Perspectives, Siggraph (1987).

"Fractal Geometry-Understanding Chaos", Georgia Tech Alumni Magazine, p. 16 (Spring 1986).

"Fractals Yield High Compression", Electronic Engineering Times, Sep. 30, 1991, p. 39.

"Fractals-A Geometry of Nature", Georgia Institute of Technology Research Horizons, p. 9 (Spring 1986).

"Fractal Modelling of Biological Structures", School of Mathematics, Georgia Institute of Technology (date unknown).

Peterson, Ivars, "Packing It In", Science News, 131(18):283–285 (May 2, 1987).

Barnsley et al., "A Better Way to Compress Images", Byte Magazine, January 1988.

Barnsley et al., "Harnessing Chaos For Images Systhesis", Computer Graphics, 22(4) (August 1988).

Naik et al., "High Performance Speaker Verification . . . ", ICASSP 86, Tokyo, CH2243-4/86/0000-0881, IEEE 1986, pp. 881–884.

"Voice Recognition and Speech Processing", Elektor Electronics, September 1985, pp. 56–57.

Shinan et al., "The Effects of Voice Disguise . . . ", ICASSP 86, Tokyo, CH2243-4/86/0000-0885, IEEE 1986, pp. 885–888.

Computer Visions, Graphics, and Image Processing, 1987, 37:54–115.

Jackel, L. D., H. P. Graf, J. S. Denker, D. Henderson and I. Guyon, "An Application of Neural Net Chips: Handwritten Digit Recognition", ICNN Proceeding, 1988, pp. II-107–15.

Carpenter, G. A., S. Grossberg, "The Art of Adaptive Pattern Recognition by a Self-Organizing Neural Network", IEEE Computer, March 1988, pp. 77–88.

Pawlicki, T. F., D. S. Lee, J. J. Hull and S. N. Srihari, "Neural Network Models and their Application to Handwritten Digit Recognition", ICNN Proceeding, 1988, pp. II-63–70.

Gullichsen, E., E. Chang, "Pattern Classification by Neural Network: An Experiment System for Icon Recognition", ICNN Proceeding on Neural Networks, March 1987, pp. IV-725–32.

Grossberg, S., G. Carpenter, "A Massively Parallel Architecture for a Self-Organizing Neural Pattern Recognition Machine", Computer Vision, Graphics, and Image Processing, 1987, 37, 54–115, 252–315.

Lippman, R. P., "An Introduction to Computing with Neural Nets", IEEE ASSP Magazine, April 1987, pp. 4–22.

Psaltis, D., "Incoherent Electro-Optic Image Correlator", Optical Engineering, 23(1):12–15 (January/February 1984).

Kellman, P., "Time Integrating Optical Signal Processing", Ph. D. Dissertation, Stanford University, 1979, pp. 51–55.

Molley, P., "Implementing the Difference-Squared Error Algorithm Using An Acousto-Optic Processor", SPIE, 1098:232–239 (1989).

Rhodes, W., "Acousto-Optic Signal Processing: Convolution and Correlation", Proc. of the IEEE, 69(1):65–79 (January 1981).

Vander Lugt, A., "Signal Detection By Complex Spatial Filtering", IEEE Transactions On Information Theory, IT-10, 2:139–145 (April 1964).

Psaltis, D., "Two-Dimensional Optical Processing Using One-Dimensional Input Devices", Proceedings of the IEEE, 72(7):962–974 (July 1984).

Molley, P., et al., "A High Dynamic Range Acousto-Optic Image Correlator for Real-Time Pattern Recognition", SPIE, 938:55–65 (1988).

Shimizu et al., "Principle of Holonic Computer and Holovision", Journal of the Institute of Electronics, Information and Communication, 70(9):921–930 (1987).

Omata et al., "Holonic Model of Motion Perception", IEICE Technical Reports, Mar. 26, 1988, pp. 339–346.

Ohsuga et al., "Entrainment of Two Coupled van der Pol Oscillators by an External Oscillation", Biological Cybernetics, 51:225–239 (1985).

The above-mentioned references are exemplary, and are not meant to be limiting in respect to the resources available to those skilled in the art. Of course it should be realized that the hardware available and the choice of specific method or software algorithm are interactive, and therefore must be specified together, however, it is noted that in view of the present disclosure, it is obvious to combine compatible technologies to achieve the advanced interface and control system of the present invention.

SUMMARY OF THE INVENTION

A new mechanism for easing the programming process is disclosed. The interface of the present invention serves to minimize the learning and searching times, better reflect users' expectations, provide better matching to human memory limits, be usable by both novices and experienced users, reduce intimidation of novice users by the device, and simplify the entering of programming data. The present invention optimizes the input scheme for programming an event-driven device, and can also be applied to many types of programmable devices. Thus, certain human factors design concepts, heretofore unexploited in the design of consumer electronics devices and industrial controls, have been incorporated. Background and theory of various aspects of the present invention is disclosed in "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November, 1990, publicly available January, 1991), by Linda I. Hoffberg, [an inventor of the present invention]. This thesis, and cited references, are incorporated herein by reference. (This thesis publication, and references cited therein, are attached as an appendix hereto.) Also incorporated by reference are: Hoffberg, Linda I., "Designing User Interface Guidelines For Time-Shift Programming of a Video Cassette Recorder (VCR)", Proc. of the Human Factors Soc. 35th Ann. Mtg. pp. 501–504 (1991); and Hoffberg, Linda I., "Designing a Programmable Interface for a Video Cassette Recorder (VCR) to Meet a User's Needs", Interface 91 pp. 346–351 (1991).

One aspect of the present invention relates to a programmable device that comprises a menu-driven interface in which the user enters information using a direct manipulation input device. Such a type of interface scheme is disclosed in Verplank, William L., "Graphics in Human-Computer Communication: Principles of Graphical User-interface Design", Xerox Office Systems, which is incorporated herein by reference; the references cited therein: Foley, J. D., Wallace, V. L., Chan, P., "The Human Factor of Computer Graphics Interaction Techniques", IEEE CG&A, November 1984, pp. 13–48; Koch, H., "Ergonomische Betrachtung von Schreibtastaturen", Humane Production, 1, pp. 12–15 (1985); Norman, D. A., Fisher, D., "Why Alphabetic Keyboards Are Not Easy To Use: Keyboard Layout Doesn't Much Matter", Human Factors 24(5), pp. 509–519 (1982); Perspectives: High Technology 2, 1985; Knowlton, K., "Virtual Pushbuttons as a Means of Person-Machine Interaction", Proc of Conf. Computer Graphics, Pattern Recognition and Data Structure, Beverly Hills, California, May 1975, pp. 350–352; "Machine Now Reads, enters Information 25 Times Faster Than Human Keyboard Operators", Information Display 9, p. 18 (1981); "Scanner Converts Materials to Electronic Files for PCs", IEEE CG&A, December 1984, p. 76; "New Beetle Cursor Director Escapes All Surface Constraints", Information Display 10, p. 12, 1984; Lu, C., "Computer Pointing Devices: Living With Mice", High Technology, January 1984, pp. 61–65; "Finger Painting", Information Display 12, p. 18, 1981; Kraiss, K. F., "Neuere Methoden der lnteraktion an der Schnittstelle Mensch-Maschine", Z. F. Arbeitswissenschaft, 2, pp. 65–70, 1978; Hirzinger, G., Landzettel, K., "Sensory Feedback Structures for Robots with Supervised Learning", IEEE Conf. on Robotics and Automation, St. Louis, March 1985; Horgan, H., "Medical Electronics", IEEE Spectrum, January 1984, pp. 90–93, are also incorporated herein by reference.

The apparatus typically involves a remote control entry device, and the interface of the present invention contains a displayed graphical interface for programming programmable devices. The present invention seeks more accurate programming through the use of program verification to ensure that the input program is both valid and executable. Thus, it has a mechanism to store and check to verify that there are no conflicting programs. An apparatus according to the present invention can be connected, for example, to any infrared programmable device in order to simplify the programming process. By way of example only, an improved video cassette recorder (VCR) interface forms the basis of a disclosed example. It is, of course, realized that the present method and apparatus may be applied to any programmable controller, i.e., any device which monitors an event or sensor and causes an event when certain conditions or parameters are met, and may also be used in other programming environments, which are not event driven.

A directional sensor based infrared remote control is disclosed in Zeisel, Tomas, Tomaszewski, "An Interactive Menu-Driven Remote Control Unit for TV-Receivers and VC-Recorders", IEEE Transactions on Consumer Electronics, Vol. 34, No. 3, 814–818, incorporated herein by reference, which relates to a control for programming with the West German Videotext system. This is a different implementation of the Videotext programming system than described in Bensch, U., "VPV—VIDEOTEXT PROGRAMS VIDEORECORDER", IEEE Transactions on Consumer Electronics, Vol. 34, No. 3, 788–792 (1988), incorporated herein by reference, which describes the system of Video Program System Signal Transmitters, in which the VCR is programmed by entering a code for the Video Program System signal, which is emitted by television stations in West Germany. Each separate program has a unique identifier code, transmitted at the beginning of the program, so that a user need only enter the code for the program, and the VCR will monitor the channel for the code transmission, and begin recording when the code is received. The VPV disclosed does not intelligently interpret the transmission, rather the system reads the transmitted code as a literal label, without any analysis or determination of a classification of the program type. The present invention incorporates an intelligent program recognition and characterization system, making use of any of the available cues, which allows an intelligent determination of the true nature of the broadcast and therefore is able to make a determination of whether parameters should be deemed met even with an inexact match to the specified parameters. Additionally, VPV also does not incorporate the interface of the present invention, and is much more like the "VCRPlus+" device.

The videotext signal of the prior art includes a digitally encoded text message which may be displayed in conjunction with the displayed image, similar to the closed caption system. The West German system demonstrates how the signal may be received by a computer and interpreted. However, the prior art does not disclose how this signal may be used to index and catalog the contents of a tape, nor does it disclose how this signal may be used to classify or interpret the character of the broadcast. In other words, in one embodiment of the present invention, the videotext or closed caption signal is not only interpreted as a literal label, as in the prior art, but is also further processed and analyzed to yield data about the content of the broadcast, other than merely the simultaneously broadcast information.

Beyond the visible region of an NTSC broadcast video frame ane a number of scan lines which are dedicated to presenting digital information, rather than analog picture information. These are normally coded as modulating the luminance signal only, with a bit timing which is far below the available bandwidth. It is therefore possible to use this area for transmitting additional information relating to the broadcast information, in particular, the characteristics of the video broadcast, and doing so could provide significant advantages, used in conjunction with the interface and intelligent pattern recognition controller of the present invention. If this information were directly available, there would be a significantly reduced need for advanced image recognition functions, which require costly hardware devices, while still maintaining the advantages of the present invention. It is noted, however, that this requires the cooperation of broadcasters, as well as possibly the FCC, which would be difficult to obtain. Further, governmental regulation of even private commercial broadcasting is likely, e.g. the Justice Department and the F.T.C., so that it remains likely that the implementation of the system of the present invention will require the user to maintain the image recognition and characterization system, rather than rely on a broadcast of the characterization along with the source material. It is nevertheless within the skill of the art to implement such a broadcast system. It should be noted that both are included within the scope of the present invention.

According to the present invention, if such characterizations are broadcast, they may, as stated above, make use of unused available spectrum bandwidth within the NTSC channel space, or other broadcast system channel space, or may be "simulcast" on a separate channel, such as an FM sideband or separate transmission channel. Use of a separate channel would allow a separate organization, other than the network broadcasters, to provide the characterization data for distribution to users of devices that make use of the present intelligent system for controlling a VCR. Thus, the characterization generating means need not be directly linked to the local user machine in order to fall within the scope of the present invention.

A menu based remote control-contained display device is disclosed in Platte, Oberjatzas, and Voessing, "A New Intelligent Remote Control Unit for Consumer Electronic Device", IEEE Transactions on Consumer Electronics, Vol.

CE-31, No. 1, Feb. 1985, 59–68, incorporated herein by reference. This system does not incorporate on-screen programming, nor various aspects of the display of the present invention.

Research has been performed on video cassette recorder ("VCR") usability, technology, implementation, programming steps, current technology, input devices, and human mental capacity. This research has resulted in a new paradigm for the entry of programming data into a sequential program execution device, such as a VCR, by casual users.

Four major problems in the interfaces of VCRs were found to exist. The first is that users spend far too much time searching for necessary information, which is necessary in order to complete the programming process. Second, people do not program the VCR to record at a later time (time-shift) frequently, and thus forget the programming steps in the interim. Third, the number of buttons on many remote control devices has become overwhelming. Fourth, people have become reluctant to operate or program VCRs because of their difficult operation. It was found that, by minimizing the learning and searching times, the user's programming time and frustration level can be greatly reduced. These concepts are easily applied to other special purpose programmable devices, and also to general purpose programmable devices wherein the programming paradigm is event-driven, as well as other programming systems. It should also be noted that it is within the scope of the present invention to provide an improved interface and programming environment for all types of programmable devices, and in this regard, the present invention incorporates adaptive features which optimize the programming environment for both the level of the user and the task to be programmed.

In optimizing the interface, four elements are most important: the input device, the display format, the sequence of the programming operation, and the ability of the device to properly interpret the input as the desired program sequence.

The present invention proceeds from an understanding that an absence of user frustration with respect to a programmable consumer or industrial device or interface, may be as important as the potential functionality thereof. The interface must be designed to minimize the user's frustration level. This can be accomplished by clearly furnishing the possible choices, presenting the data in a logical sequence, and leading the user through the steps necessary to program the device.

Research has indicated that survey respondents liked color coding and on-screen programming, while they disliked small print, blinking displays, confusing menus and too much information on the display. They also liked remote control access, with provisions for programming the VCR from the front panel, if desired, with large, well labelled single function buttons, keypad entry, natural layout of functions, "up" and "down" keys, an uncluttered display panel, a "help" key, simplified programming with fewer steps, one-touch recording, and an "OK" or "ready" indicator. Finally, they desired step-by-step instructions, the ability to backtrack to correct mistakes, a well ordered programming sequence, automatic completion of strings which must be entered, automatic compensation for lack of leading "0", and feedback of correct or erroneous inputs or status conditions.

Other objects and features of the present invention will become apparent from the following detailed description considered in conjunction with the accompanying drawings. It is to be understood, however, that the drawings are designed solely for the purposes of illustration and not as a definition of the limits of the invention, for which reference should be made to the appended claims.

OBJECTS OF THE PRESENT INVENTION

It is therefore an object of the present invention to provide a programmable apparatus for receiving instructions from a programmer and causing an action to occur on the happening of an event, comprising:

an input device, producing an input instruction signal;

a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event;

a display means for interactively displaying information related to the instructions to be received, and responsive thereto, controlled by said control means, so that the programmer is presented with feedback on a current state of the apparatus and said program instruction;

wherein said control means further comprises means for detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is displaying information in a suboptimal fashion, said control means controls said display means to display information in a more optimal fashion.

It is also an object of the present invention to provide a programmable apparatus for receiving instructions from a programmer and causing an action to occur on the happening of an event, comprising:

an input device, producing an input instruction signal;

a control means for receiving said input instruction signal, and storing a program instruction associated with said input instruction signal, said control means storing sufficient program instructions to perform an action on the occurrence of an event, said control means monitoring a status of said apparatus to determine the occurrence of various events, comparing the determined events with the program instructions, and performing said action on the occurrence of said event;

a display means for interactively displaying information related to the instructions to be received, and responsive thereto, controlled by said control means, so that the programmer is presented with feedback on a current state of the apparatus and said program instruction;

wherein said control means further comprises means for detecting a need by the programmer for more detailed information displayed on said display means, by detecting one or more characteristics of said input instruction signal independent of said program instruction selected from the group consisting of a velocity component, an efficiency of input, an accuracy of input, an interruption of input, a high frequency component of input and a past history of input by the programmer, whereby when said control means detects a characteristic indicating that said display means is insufficiently detailed information, said control means controls said display means to display more detailed information.

It is a further object of the present invention to provide a programmable apparatus having a data input, said apparatus receiving instructions from a programmer and causing an action to occur on the receipt of data indicating an event, comprising:

an input device, producing an input instruction signal;

a control means for receiving said input instruction signal, and storing a program instruction associated with said input instruction signal, said control means storing sufficient program instructions to perform an action on the receipt of data indicating an event, said control means monitoring the data input;

a display means for interactively displaying information related to the instructions to be received, and responsive thereto, controlled by said control means, so that the programmer is presented with feedback on a current state of the apparatus and said program instruction;

wherein said control means receives a programming preference indicating a desired event from said input device which does not unambiguously define said event, and said control means monitors said data and causes the occurrence of the action when a correlation between said programming preference and said monitored data is above a predetermined threshold, indicating a likely occurrence of said desired event.

It is also object of the present invention to provide the programmable aforementioned apparatus, wherein said input device is remote from said display means, and provides a direct manipulation of display information of said display means, further comprising means for verifying said program instructions so that said program instructions are executable by said control means. The control means may further comprise a calendar.

It is also an object of the present invention to provide a programmable apparatus, wherein said control means provides an option, selectable by said input means in conjunction with said display means, for changing an input program instruction prior to execution by said control means, so that said apparatus enters a state wherein a new program instruction may be input to substitute for said changed input step, wherein said control means verifies said program instructions so that said program instructions are executable by said control means.

It is still another object of the present invention to provide a programmable apparatus, wherein said control means further causes said display means to display a confirmation screen after said program instructions are input, so that the programmer may confirm said program instructions.

Another object of the present invention provides a programmable information storage apparatus having a data input, for receiving data to be stored, said apparatus receiving instructions from a programmer and causing an action to occur on the receipt of data indicating an event, comprising:

means for storing data from said data input;

an input device, producing an input instruction signal;

a control means for receiving said input instruction signal, and storing a program instruction associated with said input instruction signal, said control means storing sufficient program instructions to perform an action on the receipt of data from said data input indicating an event, said control means monitoring the data input to determine the occurrence of various events, comparing the determined events with the program instructions, and performing for storing the data said action on the occurrence of said event;

wherein said control means receives identifying data from at least one of said input device and the data input, said identifying data being stored separately from said input data on a storage medium. The programmable information storage apparatus may also include means for reading said identifying data stored separately on said storage medium, and may also receive as an input said identifying data.

Another object of the present invention is to provide a programmable information storage apparatus, wherein said control means further comprises means for recognizing character data present in a data stream of said input data, said identifying data comprising said recognized character data.

It is a still further object of the present invention to provide a video tape recording apparatus, comprising a video signal receiving device, a recording device for recording said video signal, wherein said control analyzes said video signal for the presence of a symbol, and recognizes said symbol as one of a group of recognized symbols, and said control stores said recognized symbol separately from said video signal.

Another object of the present invention is to provide a recording device for recording an analog signal sequentially on a recording medium, comprising means for characterizing the analog signal, wherein data representing said characterization and a location of the analog signal on the recording medium are stored in a directory location on the recording medium separately from the analog signal.

It is a further object of the present invention to provide an interface for a programmable control for input of a program for a controller to execute, which performs an action based on an external signal, comprising an input device, a controller for receiving data from said input device and from an external stimulus, a plant being controlled by said controller based on an input from said input device and said external stimulus, and a display device being controlled by said controller, for providing visual feedback to a user operating said input device, wherein:

a predetermined logical sequence of programming options is presented to the user on said display device, in a plurality of display screens, each of said display screens differing in available programming choices; said logical sequence including a correct sequence of choices to set an operable control program, so that no necessary steps are omitted;

said external stimulus comprises a timing device, and said display comprises a display option for programming said plant to perform an action at a time which is input through said input device as a relative position on said display device, said relative position including a means for displaying an absolute time entry and means for displaying a relative time entry, said display also comprising a display option means for performing an action at a time;

said control comprises means for presenting the user, on said display device, with a most probable action, which may be selected by the user through activation of said input device without entering data into said controller through said input device relating to both said action and said event;

said display also comprising means for indicating completion of a programming step after entry of data, which means will not allow the user to indicate to said controller that said programming step is completed if information necessary for execution of said step is not available to said controller; and said controller being capable of controlling said display device to present information to the user relating to the use of the apparatus if necessary for use of the device by the user.

Another object of the present invention provides a system for presenting a program to a viewer, comprising:
- a source of program material;
- means for determining a viewer preference;
- means for receiving the program material from said source;
- means for characterizing the program material based on its content;
- means for correlating said characterized content of the program material with said determined viewer preference to produce a correlation index; and
- means for presenting the program material to the viewer, if said correlation index indicates a probable high correlation between said characterization of the program material and said viewer preference.

Still another object of the present invention is to provide a system, wherein said program material is encrypted, further comprising:
- means for decrypting the program material to produce a decryption event; and
- means for charging an account of the viewer based on the occurrence of a decryption event.

Another object of the present invention ia to allow said means for characterizing the program material to operate without causing a decryption event. Further, the system may comprise a memory for storing the program material while said characterizing means produces characterized content and said correlating means produces said correlation index. The characterizing means may also characterize the program material stored in memory, and the program material stored in memory may be compressed.

Another object of the present invention is to provide a system for presenting a program to a viewer, comprising:
- a source of program material;
- means for determining a viewer preference;
- means for receiving the program material from said source;
- means for storing the program material;
- means for preprocessing the program material to produce a reduced data flow information signal retaining information relating to a character of the program material and eliminating data not necessary to characterize the program material;
- means for characterizing said information signal based on its content;
- means for correlating said characterized content of said information signal with said determined viewer preference to produce a correlation index; and
- means for presenting said stored program material to the viewer, if said correlation index indicates a probable high correlation between said characterization of said information signal and said viewer preference. The system may also include a means for storing said information signal, wherein said characterizing means characterizes said stored information signal, and also a memory for storing the program material while said characterizing means produces characterized content and said correlating means produces said correlation index.

It is a still further object of the present invention to provide a system, further comprising means for storing a characterization of the program material, further comprising feedback means for inputting a feedback signal from the viewer indicating a degree of agreement with said presented stored program material, wherein said feedback signal and said stored characterization are used by said viewer preference determining means to determine a new viewer preference.

Another object of the present invention is to provide a controller for controlling a plant, having a sensor for sensing an external event and producing a sensor signal, an actuator, responsive to an actuator signal, for influencing said external event, and a control means for receiving said sensor signal and producing an actuator signal, comprising:
- means for inputting a program;
- means for storing said program;
- means for characterizing said sensor signal to produce a characterized signal; and
- means for comparing said characterized signal with a pattern stored in a memory to produce a comparison index, wherein said actuator signal is produced on the basis of said comparison index and said program, wherein said characterization comprises an Affine transformation of said sensor signal. The characterization may comprise both an Affine transformation and a Fourier transformation.

It is another object of the present invention to provide a method for automatically recognizing digital image data consisting of image information, the method comprising the steps performed by a data processor of:
- storing a plurality of templates;
- storing the image data in the data processor;
- generating a plurality of addressable domains from the stored image data, each of the domains representing a portion of the image information;
- creating, from the stored image data, a plurality of addressable mapped ranges corresponding to different subsets of the stored image data, the creating step including the substep of:
  - executing, for each of the mapped ranges, a corresponding procedure upon the one of the subsets of the stored image data which corresponds to the mapped ranges;
  - assigning identifiers to corresponding ones of the mapped ranges, each of the identifiers specifying for the corresponding mapped range a procedure and a address of the corresponding subset of the stored image data;
  - optionally subjecting a domain to a transform selected from the group consisting of a predetermined rotation, an inversion, a predetermined scaling, and a predetermined frequency domain preprocessing;
  - selecting, for each of the domains or transformed domains, the one of the mapped ranges which most closely corresponds according to predetermined criteria;
  - representing the image information as a set of the identifiers of the selected mapped ranges; and
  - selecting, from the stored templates, a template which most closely corresponds to the set of identifiers representing the image information. The step of selecting the mapped ranges may also include the substep of selecting, for each domain, a most closely corresponding one of the mapped ranges.

It is another object of the present invention to provide a method wherein the step of selecting the most closely corresponding one of the mapped ranges includes the step of selecting, for each domain, the mapped range which is the most similar, by a method selected from one or more of the group consisting of selecting minimum Hausdorff distance from the domain, selecting the highest cross-correlation with the domain, selecting the highest fuzzy correlation with the domain and selecting the minimum mean square error with the domain.

Another object of the present invention provides a method wherein the step of selecting the most closely corresponding one of mapped ranges includes the step of selecting, for each domain, the mapped range with the minimum modified Hausdorff distance calculated as D[db,mrb]+D[1-db,1-mrb], where D is a distance calculated between a pair of sets of data each representative of an image, db is a domain, mrb is a mapped range, 1-db is the inverse of a domain, and 1-mrb is an inverse of a mapped range.

Another object of the present invention provides a method wherein the digital image data consists of a plurality of pixels each having one of a plurality of associated color map values, further comprising the steps of:

optionally transforming the color map values of the pixels of each domain by a function including at least one scaling function for each axis of the color map, each of which may be the same or different, and selected to maximize the correspondence between the domains and ranges to which they are to be matched;

selecting, for each of the domains, the one of the mapped ranges having color map pixel values which most closely correspond to the color map pixel values of the domain according to a predetermined criteria, wherein the step of representing the image color map information includes the substep of representing the image color map information as a set of values each including an identifier of the selected mapped range and the scaling functions; and selecting a most closely corresponding stored template, based on the identifier of the color map mapped range, the scaling functions and the set of identifiers representing the image information. The first criteria may comprise minimizing the Hausdorff distance between each domain and the selected range.

Another object of the present invention is to provide a method further comprising the steps of:

storing delayed image data, which represents an image of a moving object differing in time from the image data in the data processor;

generating a plurality of addressable further domains from the stored delayed image data, each of the further domains representing a portion of the delayed image information, and corresponding to a domain;

creating, from the stored delayed image data, a plurality of addressable mapped ranges corresponding to different subsets of the stored delayed image data;

matching the further domain and the domain by subjecting a further domain to one or both of a corresponding transform selected from the group consisting of a null transform, a predetermined rotation, an inversion, a predetermined scaling, and a predetermined frequency domain preprocessing, which corresponds to a transform applied to a corresponding domain, and a non-corresponding transform selected from the group consisting of a predetermined rotation, an inversion, a predetermined scaling, a translation and a predetermined frequency domain preprocessing, which does not correspond to a transform applied to a corresponding domain;

computing a motion vector between one of the domain and the further domain, or the set of identifiers representing the image information and the set of identifiers representing the delayed image information, and storing the motion vector;

compensating the further domain with the motion vector and computing a difference between the compensated further domain and the domain;

selecting, for each of the delayed domains, the one of the mapped ranges which most closely corresponds according to predetermined criteria;

representing the difference between the compensated further domain and the domain as a set of difference identifiers of a set of selected mapping ranges and an associated motion vector and representing the further domain as a set of identifiers of the selected mapping ranges;

determining a complexity of the difference based on a density of representation; and when the difference has a complexity below a predetermined threshold, selecting, from the stored templates, a template which most closely corresponds to the set of identifiers of the image data and the set of identifiers of the delayed image data.

Another object of the present invention provides an apparatus for automatically recognizing digital image data consisting of image information, comprising:

means for storing template data;

means for storing the image data;

means for generating a plurality of addressable domains from the stored image data, each of the domains representing a different portion of the image information;

means for creating, from the stored image data, a plurality of addressable mapped ranges corresponding to different subsets of the stored image data, the creating means including means for executing, for each of the mapped ranges, a procedure upon the one of the subsets of the stored image data which corresponds to the mapped range;

means for assigning identifiers to corresponding ones of the mapped ranges, each of the identifiers specifying for the corresponding mapped range an address of the corresponding subset of stored image data;

means for selecting, for each of the domains, the one of the mapped ranges which most closely corresponds according to predetermined criteria;

means for representing the image information as a set of the identifiers of the selected mapped ranges; and means for selecting, from the stored templates, a template which most closely corresponds to the set of identifiers representing the image information.

BRIEF DESCRIPTION OF THE DRAWINGS

Embodiments of the present invention are shown in the figures in the drawings, in which.

DETAILED DESCRIPTION OF THE PREFERRED EMBODIMENT

Figure 1:
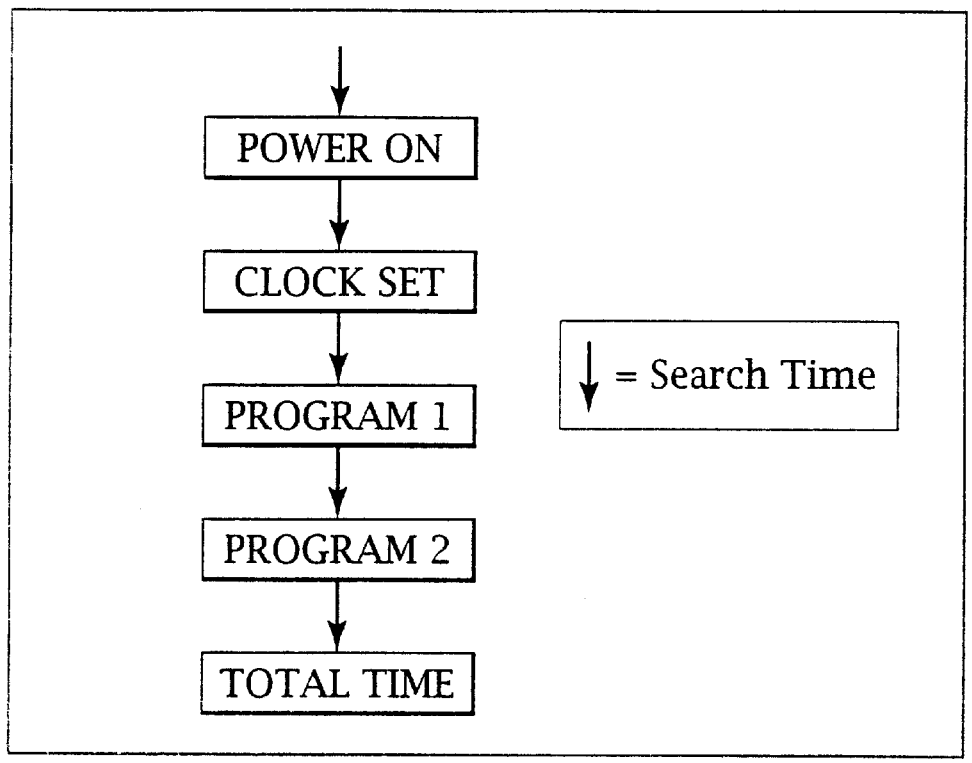
FIG. 1 is a flow chart of the steps required to set a VCR.

Many design considerations were found to be important in the improved interface of the present invention:

The interface should preferably employ only minimal amounts of abbreviations and the use of complete words is especially preferred. However, standard abbreviations and symbols are acceptable, and displayed character strings may be shortened or truncated in order to reduce the amount of information that is to be displayed, where necessary or desirable. An option may be provided to the user to allow full words, which may decrease the information which may be conveyed on each screen and increase the number of screens that must be displayed, or abbreviations and symbols, which may minimize the number of displayed screens of information, thus allowing the user to make the compromise. This aspect of the system may also be linked to the adaptive user level function of the present invention, wherein abstract symbols and abbreviations are presented to advanced users, while novices are presented with full words, based on an implicit indication of user level. These abstract symbols and abbreviations may be standard elements of the system, or user designated icons. Of course, the user could explicitly indicate his preference for the display type, thus deactivating the automatic adaptive user level function.

Some display systems have a higher available resolution than others, and the interface is preferably arranged to optimize the intended display for the resolution limits and display format of the intended or available display device. Further, even with sufficient resolution, certain displays are of small size, and thus the visibility of the information may also be optimized by taking into consideration the size, resolution, contrast, brightness of the display, ambient conditions, characteristics of the human visual system, factors specific for a known user, and the available options of the apparatus. Thus, the interface may employ a number of methods to optimize the visibility of the information for a variety of display devices, storage formats and transmission standards, which may include: NTSC, PAL, SECAM, CCIR-601, HDTV, MUSE, IDTV, VHS, S-VHS, Beta, SuperBeta, Hi-8 mm, videotel or picturephone (P×64), computer display standards (CGA, HGC, EGA, VGA, SVGA, XGA, Macintosh (TM), 8514, Private Eye (TM), LCD, etc.), etc., over a number of size ranges, e.g. about 1 $cm^2$ to about 10 $m^2$, with a resolution range including displays having about 16 dot matrix characters or about 16 by 64 dots to about 2,048 by 2,048 dots. Techniques such as antialiasing, fontsubstitution, hinting, precompensating forexpected distortion, etc., may all be employed to improve the readability of the display under various circumstances.

A preferred embodiment of the interface of the present invention, by automatic sequencing of steps, leads the user through the correct sequence of actions to set a program on the screen, so that no necessary steps are omitted, and no optional steps are accidentally omitted. These steps are shown diagrammatically in FIG. 15 of the present invention. In addition, such a system does not burden the user with the necessity of inputting superfluous information, nor overwhelm the user with the display of unnecessary data.

A built-in calendar menu screen is employed so that the user cannot set the device with a program step that relies on a non-existent date. Technology that will help eliminate the human problem of setting the wrong (yet existing) date may also be employed. Such technology might include accessing an on-line or other type of database containing media programming information, and prompting the user regarding the selected choice. In situations where it is applicable, the interface should prompt the user as to how many characters the interface is expecting, such as when entering the year.

Figure 16:
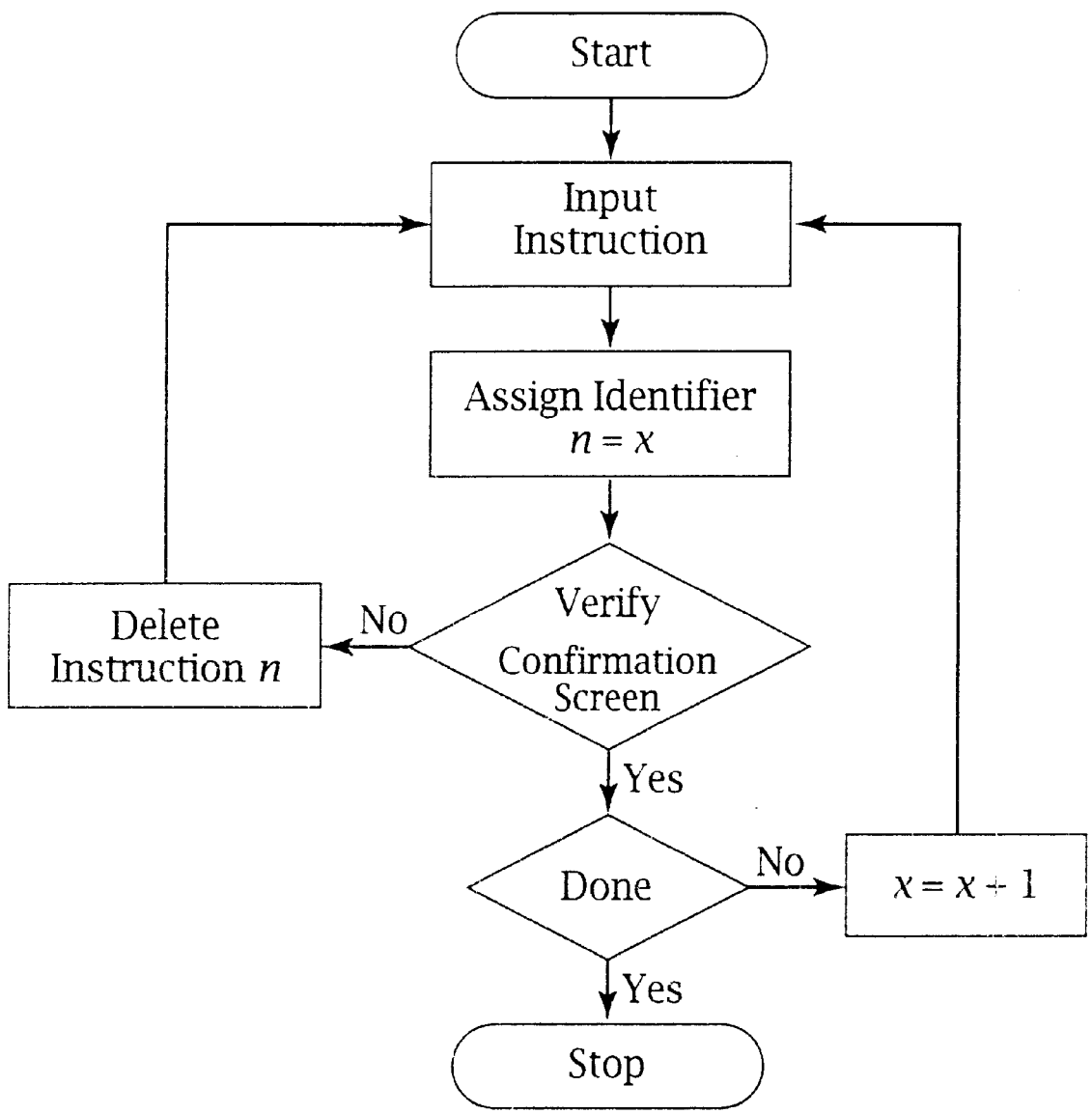
FIG. 16 is a flow diagram of the program input verification system of the present invention.

A preferred embodiment of the present invention has an easily accessible CHANGE or CANCEL feature, which facilitates backtracking or reprogramming the immediately previously entered information rather than forcing the user to repeat all or a substantial portion of the programming steps. A method of the type described is shown in FIG. 16 of the present invention. User input is also facilitated by the provision of frequently used settings as explicit choices, such as "Record today", "Record tomorrow", "Noon", and "Midnight", so that the user does not have to specify a date in these cases. This will eliminate extra keypresses, and reduce the programming time. In addition, this could eliminate user errors. Frequently used choices for program selections are also provided to the user to reduce the number of programming steps necessary and provide the user with all the frequently used selections. The especially preferred choices are "Once On . . . ", "Once a Week on . . . ", "Monday–Friday at . . . ", "Everyday at . . . ". These redundant, complex instructions reduce the number of keystrokes required for data entry, and reduce the amount of programming time required.

A preferred embodiment of the present invention provides, in the event that a color screen is available, conservatively used color coding, which allows the user to effectively and quickly acknowledge the function of each aspect of the screen. The preferred colors are royal blue for "help," red for mistakes, light blue for information previously entered, and yellow for current information being entered. Of course, other colors could be used, according to the user's or designer's preference, cultural differences, and display parameters.

Figure 15:
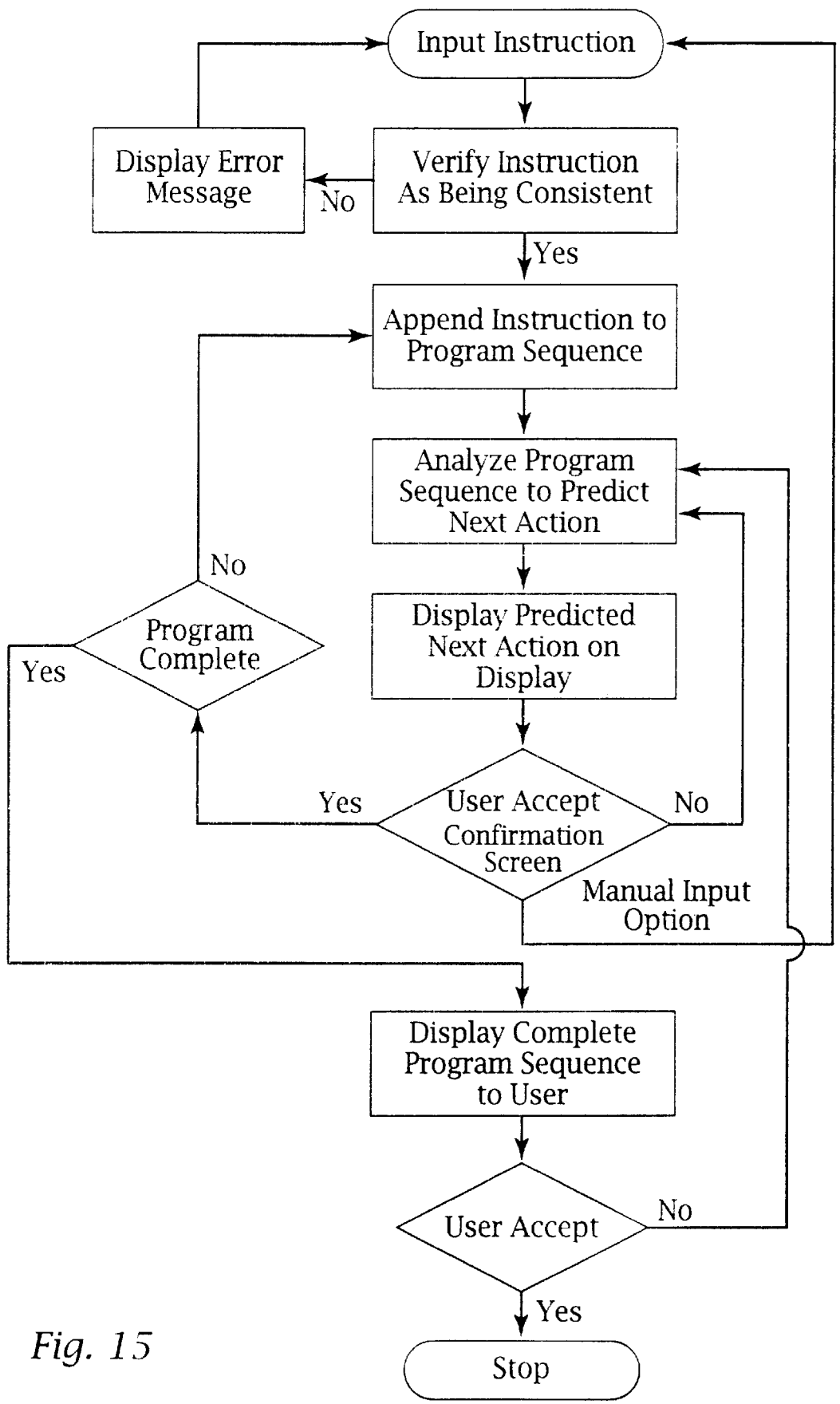
FIG. 15 is a flow diagram of a predictive user interface of the present invention.

A preferred embodiment of the interface contains a confirmation screen which displays to the user all of the categories and selections previously explicitly entered or otherwise inferred, and should be easily understandable. This is shown in FIG. 15 of the present invention. All of the necessary information is displayed on this screen, in addition to the change and cancel options, if possible.

The entering of information on each screen is preferably consistent throughout the program. All of the screens preferably have similar layouts. "Buttons" or screen locations which are keyed to a particular function, which appear on multiple screens, should appear in approximately the same location on all screens. However, in certain cases, relatively more important information on a given screen may be displayed more prominently, and possibly in a different screen location, in order to reduce the search time. Further, when other factors dictate, each screen may be independently optimized for the prescribed function. For example, a representation of an analog clock dial may be used to set time information. However, even if the format does change, a standard scheme should be maintained, such as the use of a particular color to indicate that a particular program aspect has been changed.

The interface should display data consistent with standards and conventions familiar to users. For, e.g., when entering dates, users are most familiar with calendars. However, this type of presentation of choices does not eliminate the human problem of entering incorrect information, e.g., setting a wrong, but existing, date. The problem of ensuring the accuracy of user input may be addressed by an intelligent interface which stores data concerning programming, user preferences, and by means of some logical method, such as Boolean logic, fuzzy logic, neural network theory, or any other predictive system, determines if an entry is likely in error. Of course, these predictive systems would also provide an initial default entry, so that the a priori most probably action or actions are initially presented to the user. In addition to following conventions of information presentation to the user, the interface of the present invention may also provide emulations of other user interfaces of which a particular user may be familiar, even if these are not optimized according to the presently preferred embodiments of the present invention, or not otherwise well known. These emulations need not be of the same type of device, so that a broad based standard for entry of information into a programmable controls, regardless of their type, may be implemented. By allowing emulation, the interface of the present invention could provide compatibility with a standard or proprietary interface, with enhanced functionality provided by the features of the present interface. These enhanced functional intelligent aspects of the controller may be implemented by means of software programming of a simple microcomputer, or by use of more specialized processors, such as a Fuzzy Set Processor (FSP) or Neural Network Processor. Of these, FSP's are preferred because they have the advantage of being easier to program through the use of presumptions or rules for making the fuzzy inferences, while Neural Networks are less easily programmed and their network weighing values are not easily understood in the abstract. Thus, Neural networks tend to require extensive "training", while Fuzzy Set Processors may be explicitly programmed without the need of duplicating or simulating actual operating conditions.

The most frequently used choices preferably should be displayed as the default setting. The screen cursor preferably appears at the "accept" screen button, when the screen is displayed. This default can either be set in advance, or acquired by the system. In the case of acquired defaults, these may be explicitly set by the user or adaptively acquired by the system through use. The interface of the present invention may be taught, in a "teach" mode, the preferences of the user, or may also acquire this information by analyzing the actual choices made by the user during operation of the interface and associated controller. This type of operation is shown schematically in FIG. 15 of the present invention. The options of "Midnight" (12:00 AM) and "Noon" (12:00 PM) should preferably be present, as some people often become confused when distinguishing between them. Icons, such as those indicative of the "sun" and the "moon", may also be used to facilitate data entry for AM and PM. The interface should preferably utilize an internal clock and calendar so that the user cannot set the time or program to record on a nonexistent date. Such a system could also compensate for daylight-savings time seasonal adjustments.

The cursor is preferably distinctive and readily distinguished from other parts of the screen. This may be by color, attribute (i.e. blinking), size, font change of underlying text, or by other means.

The user can preferably exit the programming sequence at any time by selecting a "Main Menu" button which may be on the lower left-hand corner of every screen. The user is preferably provided with an adequate amount of feedback, and error messages should be directive in nature. An acknowledgement is preferably displayed after each entry. The user should preferably not be able to go to the next programming step until the current step has been completed. A message to convey why the user can not continue should appear when an attempt to prematurely continue is recognized.

The "help" function is available for when the subject does not know what to do. The "help" screen(s) preferably explains the functions of each of the available buttons or functions, but may also be limited to those that are ambiguous. The "help" screen may also be used to indicate a current status of the interface and the controller. Further, the "help" function may also provide access to various other functions, such as advanced options and configurations, and thus need not be limited to merely providing information on the display. The help system may incorporate a hypertext-type system, wherein text or information relating to concepts that are conceptually linked may be easily accessed from one another, and in a logical sequence. To eliminate the possibility of the user trying to make selections on merely informative help screens, the cursor, in these cases, should be locked to a choice which returns the user to where they left off in the programming sequence, and this choice should be highlighted. The "help" function may also comprise "balloon help" similar to the system adopted by Apple Computer, Inc. in Macintosh Operating System 7.0 and later versions.

The interface preferably initiates the programming sequence where the user wants to be, so that the interface has so-called "smart screens". For example, when a VCR is first powered up, and the time and date are not stored in the machine, the "set date" and "set time" screens should appear. The sequence of screens may also vary depending on the system predicted requirements of the user and various aspects of the improved interface of the present invention. This is shown schematically in FIG. 17 of the present invention.

The preferable input device for the interface of the present invention provides as few buttons as possible to achieve the required functionality, thus reducing potential user intimidation, focusing the user's attention on the interactive display screen, where the available choices are minimized to that number necessary to efficiently allow the user to program the discrete task presented. A computer mouse with 1 to 3 buttons is the preferred input device, for use with a general purpose computer as a controller, while a trackball on a remote control device is especially preferred for limited purpose controllers because it does not require a flat surface for operation. Other stationary or movement sensitive input devices may, of course be used, such as joysticks, gyroscopes, sonic echo-location, magnetic or electrostatic location devices, RF phase location devices, etc. The present interface minimizes the number of necessary keys present on an input screen, while maintaining the functionality of the interface. It is noted that a strict minimization without consideration of functionality, might lead to inefficiency. For example, if the user wants to record a program which airs Monday–Friday, he would have to set five separate programs, rather than one program if a "weeknights" choice is made available.

Figure 17:
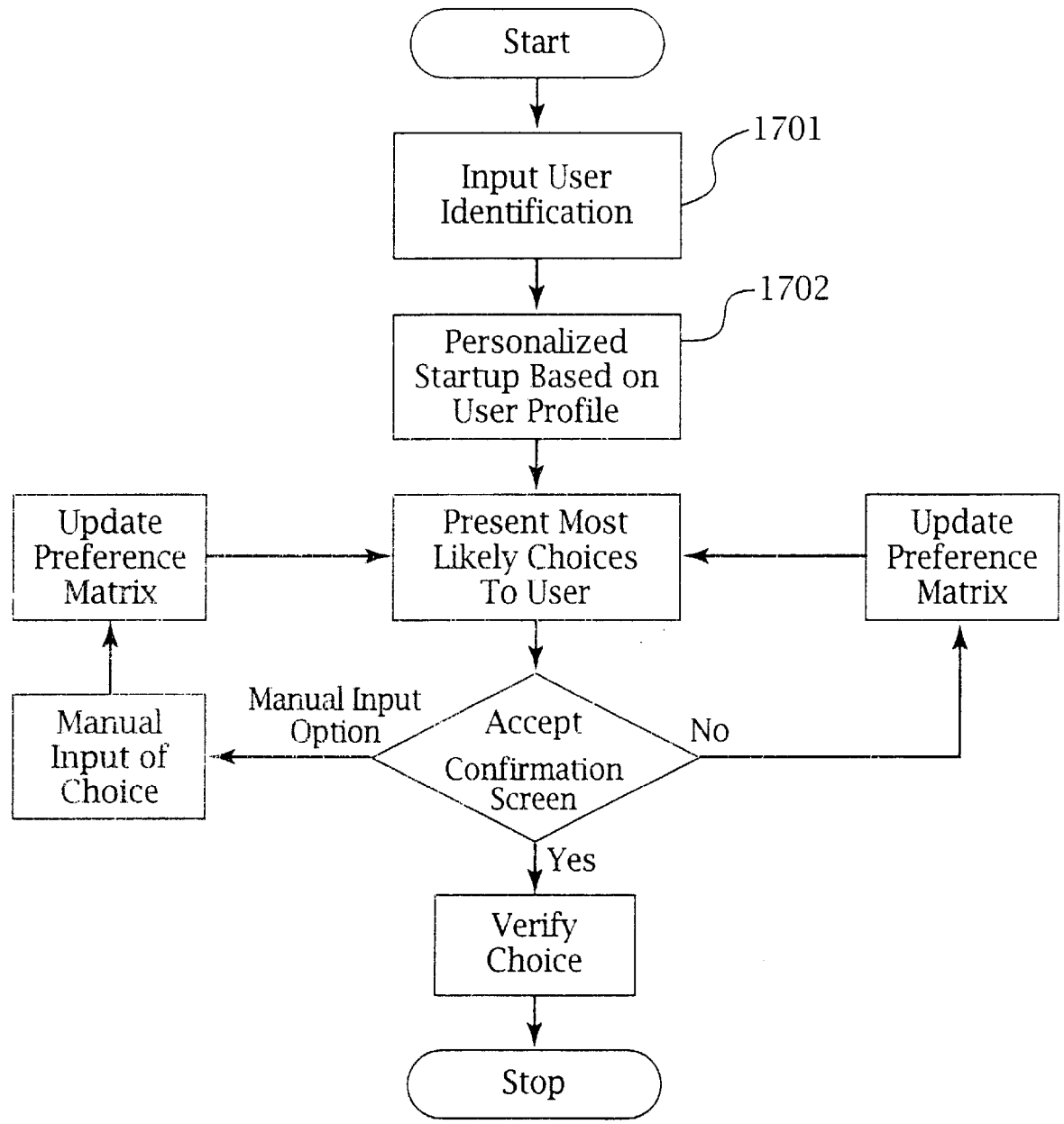
FIG. 17 is a flow diagram of a predictive user preference aware interface of the present inventions.

The interface preferably should be easy to learn and should not require that a user have prior knowledge of the interface in order to use it. An attempt has been made to minimize the learning curve, i.e., to minimize the time it takes to learn how to use the device. Research has shown that people do not program their VCRs often, and they often forget the sequence of steps between recording sessions. Thus, the present invention incorporates an adaptive user level interface, wherein a novice user is presented with a simpler interface with fewer advanced features initially available, so that there is less searching for the basic functions. A more advanced user is presented with more advanced choices and functions that are available initially. Thus, as shown in FIG. 17, the user identifies himself to the controller in block 1701. The controller 1806 of FIG. 18 thereafter uses a stored profile of the identified user in controlling the interaction with the user, as shown in block 1702 of FIG. 17, from information stored in the database 1807 of FIG. 18 of the present invention. It has been found that in the case of novice users, a greater number of simple instructions may be more quickly and easily input rather than a potentially fewer number of a larger set of more complex instructions. It has further been found that, even if presented with a set of instructions which will allow a program to be entered with a fewer number of inputs, a novice user may choose to input the program using the simple instructions exclusively, thus employing an increased number of instructions and being delayed by an increased search time for those instructions that are used, from the larger set.

Figure 19:
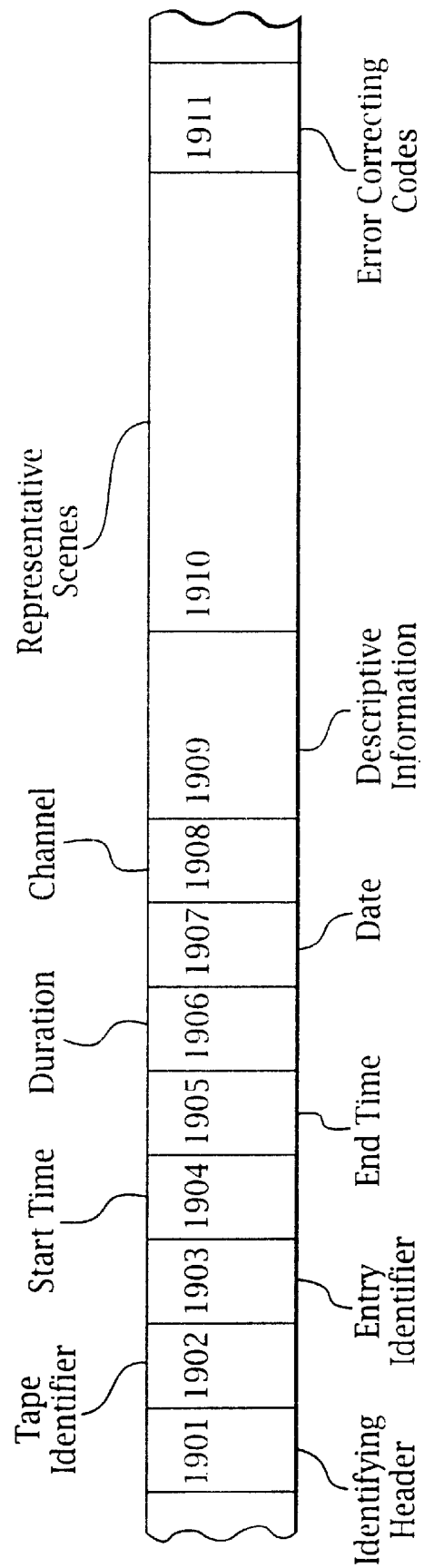
FIG. 19 is a diagram of a block of information for a catalog entry of the present invention.

In a preferred embodiment of the present invention, in a VCR, in order to track the content of the tape, a directory or a catalog is recorded, preferably digitally, containing the programming information, as well as additional information about the recorded programs, in a header, i.e., at the beginning of the tape, or in other locations on the tape. The device may also catalog the tape contents separately, and based on an identification of the tape, use a separately stored catalog. A format for storing information is shown in FIG. 19. Thus, if there are a number of selections on the tape, the entire contents of the tape could be accessible quickly, without the need for searching the entire tape. In a sequential access medium, the tape transport apparatus must still shuttle to the location of the desired material, but it may do so at increased speeds, because there is no need to read the tape once the location is determined; after the tape transport nears the desired spot, the tape may be slowed or precisely controlled to reach the exact location. The tape read and drive system is shown schematically in FIG. 20. The algorithm used in the final stage of approach may use fuzzy logic, mathematical formulae modeling the system (differential equations) to implement a Proportional-Differential-Integral (PID) controller, or a controller of higher order, or other known control methods. If a selection is to be recorded over, the start and stop locations would be automatically determined from the locations already indicated on the tape. Further, this information could be stored in memory device (which reads a catalog or index of the tape when a new tape is loaded) or non-volatile memory device (which stores information relating to known tapes within the device) or both types of memory in the VCR, so that an index function may be implemented in the VCR itself, without the need to read an entire tape. Optionally, a printer, such as a thermal label printer (available from, e.g. Seiko Instruments, Inc.), attached to the device, could be available to produce labels for the tapes, showing the index, so that the contents of a tape may be easily indicated. These contents may be derived from published data or database, transmitted data, and/or data determined by the control itself.

The present invention also allows encryption and decryption of material, much as the Videocipher series systems from General Instruments, and the fractal enciphering methods of $EMC^2$ and Iterated Systems, Inc. The present invention, however, is not limited to broadcasts, and instead could implement a system for both broadcasts and prerecorded materials. In the case of copying from one tape to another, such a system could not only provide the herein mentioned library functions of the present invention, it could also be used to aid in copy protection, serial copy management, and a pay-per-view royalty collection system. Such a system could be implemented by way of a telecommunication function incorporated in the device, shown as block 1808 of FIG. 18, or an electronic tag which records user activity relating to a tape or the like. A royalty fee, etc., could automatically be registered to the machine either by telecommunication or registry with the electronic tag, allowing new viewer options to be provided as compared with present VCR's. For example, an encrypted tape or other source material (so that special playback equipment need be used, and a usage registered), used with this device, could be decrypted by a decryption key available by telecommunication with a communication center, remote from the user, in a decryption unit, shown schematically as the decrypt unit 1806a of FIG. 18. During acquisition of the electronic key, a VCR device of an embodiment of the present invention would indicate its identity, and an account is charged a fee for such use. Such a system could also be used for controlled access software, for example for a computer, wherein a remote account is charged for use of the software. Such a system differs from the normal "key" or "dongle" because it requires on-line access for an encryption key, which may offer different levels of use. It also differs from a call-in registration, because of the automatic nature of the telecommunication. This presently described system differs from normal pay-per-view techniques because it allows, in certain instances, the user to schedule the viewing. Finally, with an encryption function implemented in the VCR, the device allows a user to create and distribute custom "software" or program material. In addition, the present controller could then act as the "telecommunication center" and authorize decryption of the material. The present invention is advantageous in this application because it provides an advanced user interface for creating a program (i.e. a sequence of instructions), and it assists the user in selecting from the available programs, without having presented the user with a detailed description of the programs, i.e., the user may select the choice based on characteristics rather than literal description. In the case of encrypted program source material, it is particularly advantageous if the characterization of the program occurs without charging the account of the user for such characterization, and only charging the account if the program is viewed by the user. The user may make a viewing decision based on the recommendation of the interface system, or may review the decision based on the title or description of the program.

The encryption may be of any type, but for sensitive material, i.e. where mere distortion of the material (e.g., loss of synchronization information and phase distortion) would be insufficient, an analog multiple subband transform, with spread spectrum band hopping and digital encryption of various control signals, would be particularly difficult for the user to view without authorization, and could be effectively implemented with conventionally available technology. The fractal compression and encryption of the $EMC^2$ and Iterated Systems, Inc. system is also particularly preferred. Of course, if a digital storage format is employed, a strict digital encryption system may be used. The implementation of these encryption systems is known to those skilled in the art. These may include the NBS, VSS and NSA encryption standards, as well as various proprietary standards.

Menu options are preferably displayed in logical order or in their expected frequencies. Research has shown that a menu-driven interface is best for applications involving new users and does not substantially hinder experienced users. Menu selection is preferably used for tasks which involve limited choices. They are most helpful for users with little or no training. Each menu should preferably allow only one selection at a time. Most of the information is preferably entered using a numeric keypad (entry method), rather than using up and down arrow keys (selection method). If there is more than one keystroke required, the user must then select an "OK" button to continue in the programming sequence. However, if the selection method is used, all of the choices are displayed on the screen at once. In addition, no leading zeros are required. The number of steps required to complete the task through a sequence of menus should be minimized. The choice of words used to convey information should not be specific computer terms, but rather normal, everyday terms which are easy to understand. In addition, very few abbreviations should be used. All necessary information which the user needs should preferably be displayed at once. A user preferably should not have to rely on his memory or his previous experience, in order to find the correct choice, at least at the lower user levels. If all selections cannot be displayed at once, a hierarchical sequence is preferably used. A main menu should preferably provide a top level to which the user can always return and start over.

Users of VCRs are concerned with the layouts of both the control panel on the VCR device and the remote control. The vast majority prefer on-screen programming, which utilizes the remote control rather than the control panel, and express a preference for entering the numbers over pressing the "up" and "down" arrow keys for selecting the time and channel. Some favor choosing the "start" and "stop" times over choosing the "start" time and duration. When using existing VCRs, users generally want more feedback, and they want to know when the VCR is ready to program. Subjective data indicates that it is preferable to reduce the amount of time required to set the clock and two programs on a VCR to a maximum of 7 minutes, wherein the reduction should focus on lessening the search time, which is the amount of time consumed because users do not know what to do next.

Searching and learning times should be kept to a minimum in order to obtain a subjectively better interface. The system's logic should reflect the users' expectations, offer visual clues and feedback, and stay within human memory limits. For example, the VCR should turn on not only with the "Power" button, but also by inserting a tape into the device. In addition, the sequence of steps for setting the machine to record, if the user does not indicate implicitly or explicitly that he knows how to use the device, should assume that the user is a novice. Nothing should be taken for granted. By developing an improved interface, an attempt is made to: Reduce the searching time; Reduce the learning time; Simplify the entering of data; and, Reduce the intimidation experienced by certain persons when using electronic devices.

In one embodiment of the present invention, the apparatus comprises a program entry device for a VCR. The human interface element has an infrared device to allow wireless communication between the human interface device and the VCR apparatus proper. The human interface device also includes a direct-manipulation type input device, such as a trackball or joystick. Of course it is understood that various alternatives can be employed, such as: the so-called "J-cursor" or "mousekey" which embeds a two (x,y) or three (x,y,p) axis pressure sensor in a button conformed to a finger, present in a general purpose keyboard; a keyboard joystick of the type described in Electronic Engineering Times, Oct. 28, 1991, p. 62, "IBM Points a New Way"; a so-called "isobar" which provides a two axis input by optical sensors (Θ,x), a two and one half axis (x,y,digital input) input device, such as a mouse or a "felix" device, infrared, acoustic, etc.; position sensors for determining the position of a finger or pointer on a display screen (touch-screen input); goniometer input (angle position, such as human joint position detector), etc. Thus, there are many available technologies which are adaptable for the present cursor positioning device. Many of these devices are summarized in Kraiss, K. F., "Alternative Input Devices For Human Computer Interaction", Forschunginstitut Fur Anthropotecahnik, Werthhoven, F. R. Germany, incorporated herein by reference. A new device, which may also be suitable is the GyroPoint, available from Gyration Inc., which provides 2-D or 3-D input information in up to six axes of motion: height, length, depth, roll, pitch and yaw. While such a device is generally considered too complex and costly for use with a VCR, the many degrees of freedom available may provide suitable input for other types of controllers, such as those based on "Artificial Reality" or which track a moving object, where many degrees of freedom and a high degree of input accuracy is required.

These input devices may be broken down into a number of categories: direct inputs, i.e. touch-screen and light pen; indirect inputs, i.e. trackball, joystick, mouse, touch-tablet, bar code scanner (see, e.g., Atkinson, Terry, "VCR Programming: Making Life Easier Using Bar Codes"), keyboard, and multi-function keys; and interactive input, i.e. Voice activation/instructions (see, e.g., Rosch, Winn L., "Voice Recognition: Understanding the Master's Voice", PC Magazine, Oct. 27, 1987, 261–308); and eye tracker and data suit/data glove (see, e.g. Tello, Ernest R., "Between Man And Machine", Byte, September 1988, 288–293; products of EXOS, Inc; Data Glove).

Each of the aforementioned input devices has advantages and disadvantages, which are summarized in the table below.

TABLE

| DEVICE | ADVANTAGES | DISADVANTAGES |
|---|---|---|
| Touch-Screen: a device which allows users to point directly to the screen to enter their choices. | accurate. fast. "natural" pointing device. Hand obscures view Difficult with curved screens. | Doesn't show location of the cursor on the screen. Requires an overlay. Requires frequent cleaning. Expensive. Must be within reach envelope. |
| Light Pen: a pen shaped device with which the users touch the screen to select their choices. | Points to the screen. | Inexpensive. Inaccurate. Awkward to use. Pen needs a storage location. Must be within reach envelope. |
| Trackball: a ball mounted on a stationary object; the ball's rolling motion controls the cursor. | Can be mounted and used anywhere. Does not require a horizontal surface Quick to use. | |
| Joystick: a stick mounted on a stationary object; the sticks movement controls the cursor. | Can be mounted and used anywhere. Does not require a horizontal surface. | Clumsy for cursor control. |
| Mouse: a ball mounted on the bottom of a movable object, which is rolled on a horizontal surface to control the cursor. | Most effective for pointing and selecting objects on the screen. Popular. | Requires a horizontal surface area. |
| Touch-Tablet: a pad which sits on a horizontal surface on which selections are made by using a finger or stylus. | Activated with fingers or stylus | Small interface. Remote from display. |
| Keyboard: a device which lies on a horizontal surface and which has alphanumeric keys on which to type information. | | Requires a horizontal surface. Large. Many keys. |
| Multi-Function Keys: buttons which serve more than one function. | Inexpensive. Space efficient. | Confusing. |
| Bar Code Scanner: a wand which must be wiped over a bar code to type enter information. Pressing a button then signals the controlling device. | Quick if Barcode is present in TV directory. | May require several tries to send data. Tedious if Barcode is not available in the TV directory. |
| Voice: the use of the human voice to give speech prompts or to accept commands. | Frees hands Enables disabled persons to use the device. | Requires training. Affected by surrounding noises. Low accuracy. Expensive. Has a limited vocabulary. Is sensitive to differences in languages, accents, and speech patterns. |
| Eye Tracker: an optical | Free hands. | Expensive. |

TABLE-continued

| DEVICE | ADVANTAGES | DISADVANTAGES |
| --- | --- | --- |
| scanner which is activated by the human eye. | Enables disabled persons to use the device. | Inaccurate. |
| Data Suit/Data Glove: a suit or glove which is controlled by manipulation of an on-screen "Virtual Image". It is controlled by optical fibers which measure the degree of bending. | Reacts to hand and body gestures. Gives a 3-D image. | Expensive. Computer insensitive. |

Recent studies suggest that a "direct manipulation" style of interface has advantages for menu selection tasks. This type of interface provides visual objects on the screen which can be manipulated by "pointing" and "clicking" on the them. For example, the popular Graphical User Interfaces ("GUIs"), known in the art, use a direct manipulation style interface. A device such as a touch-screen, with a more natural selection technique, is technically preferable to the direct manipulation method. However, its low accuracy and high cost make other inputs more commercially practical. In addition, the user must be within arms' length of the touch-screen display. In a cursor positioning task, Albert (1982) found the trackball to be the most accurate pointing device and the touch-screen to be the least accurate when compared with other input devices such as the light pen, joystick, data tablet, trackball, and keyboard. Epps (1986) found both the mouse and trackball to be somewhat faster than both the touch-pad and joystick, but he concluded that there were no significant performance differences between the mouse and trackball as compared with the touch-pad and joystick.

It is noted that many present devices, intended for use in computers having graphic interfaces, would advantageously make use of an input device which is accessible, without the necessity of moving the user's hands from the keyboard. Thus, for example, Electronic Engineering Times (EET), Oct. 28, 1991, p. 62, incorporated herein by reference, discloses a miniature joystick incorporated into the functional area of the keyboard. This technique is directed at a different aspect of user interaction with a programmable device than the preferred embodiment of the present invention, in that the input device does not have a minimal number of keys. While the device disclosed in EET is intended for use in a full function keyboard, the preferred embodiment of the present invention is directed towards the minimization of the number of keys and avoidance of superfluous keys by provision of a pointing device. Of course, the present invention could be used with a full function input device, where appropriate, and the joystick of EET (Oct. 28, 1991, p. 62) would be suitable in this case.

In a study of menu selection tasks comparing the mouse and the trackball, the accuracy data showed no significant difference between the two. The key finding shows that both mouse users and trackball users performed better with the trackball on the menu selection task. It should be noted that this was not the case for all tasks. However, the definition of the menu selection task used by Sperling, Bied, Tullis, in "Are You a Better 'Mouser' or 'Trackballer'? A Comparison of Cursor—Positioning Performance", An Interactive/Poster Session at the CHI+GI'87 Graphics Interface and Human Factors in Computing Systems Conference, incorporated herein by reference, which involved moving the cursor through a list of items and making a selection, is similar in nature to the selection tasks used in the present invention.

User dissatisfaction is generally proportionate to the length of "search time", the time necessary in order to locate and execute the next desired function or instruction. Search time may be minimized by the inclusion of up to a maximum of 4–8 choices per screen and by use of consistent wording and placement of items on the display.

The present invention proceeds from the understanding that there are a number of aspects of a programmable interface that are desirable:

1. Users should be able to operate the system successfully, without wide disparities in time. It should take, e.g., a normal person interacting with a VCR interface, less than seven minutes to set the time and two programs. Searching time spent in setting the clock, programming, getting into the correct mode, and checking whether or not the VCR is set correctly should be kept to a minimum through the appropriate choices of menu layout and the presentation of available choices.

2. Programming should be a stand-alone process, and not require an instruction manual. A help system should be incorporated in the interface. Word choices should be understandable, with a reduction in the use of confusing word terminology. Error messages should be understandable. The system should provide the ability to cancel, change or exit from any step.

3. The system should provide on-screen understandable information, with adequate visual feedback. The displays should be consistent. Color coding should be employed, where applicable, using, e.g. blue—new input; red—error condition; yellow—static, unchanged value. Layouts should be logical, and follow a predictable pattern. There should be a maximum of 4–8 choices per screen to minimize searching time. Keys should be labelled with text rather than with ambiguous graphics. However, a combination of both may be preferable in some cases.

4. Tasks should be simple, require a short amount of time and not create user frustration. The system should guide the user along a decision path, providing automatic sequencing of steps. The most frequently used choices should be provided as defaults, and smart screens may be employed. The learning curve should be minimized through the use of easily understandable choices. As a user becomes more sophisticated, the interface may present more advanced choices.

5. There should be a reminder to set the timer and to insert the tape once the programming information is entered. This reminder may also be automated, to eliminate the forgotten step of setting the timer, so that the VCR automatically sets the timer as soon as the necessary information is entered and a tape is inserted. Once the program is set in memory, a message should appear if a tape is not inserted. If the VCR is part of a "jukebox" (automatic changer), the tape may be automatically loaded. The VCR should preferably turn on when a tape is inserted. In addition, users should also be able to control the VCR with a Power button.

6. The VCR should be programmable from both the remote device and the control panel.

7. Each operation should require only one keypress, if possible, or otherwise reduce the number of keypresses required. There should be a 12 hour clock, not a 24 hour clock. There should be an on-screen keypad with entry keys, not "up" and "down" selector keys, allowing for the choice of specific day or time entry. There should be a "start" and a "stop" recording time, rather than "start" time and "length of program" or duration exclusively. The number of buttons on the remote control should be minimized so that as few buttons as are required are provided. The input device should provide for the direct manipulation of screen elements. A menu driven interface should be provided.

The interface of the present invention provides an automatic sequencing of steps which does not normally let the user continue until the previous step is complete. This is shown schematically in FIG. 16. In this manner, important steps will not be inadvertently omitted. Upon entering the programming sequence, if the current date or time is not set, the interface will prompt the user to enter this information. Thereafter, the interface will normally default to the main menu, the most frequently used first screen. Thus, the interface of the present invention is adaptive, in that its actions depend on the current state of the device, including prior programming or use of the device by the user. It can be appreciated that this adaptive behavior can be extended to include extended "intelligence". For example, if the device is similarly programmed on a number of occasions, then the default setup may be adapted to a new "normal" program mode. Further, the apparatus could provide multiple levels of user interface, e.g. beginner, intermediate, and advanced, which may differ for various functions, based on the behavior of the user. This user interface level determining feature extraction system is shown diagrammatically in FIG. 18. In contrast, prior art interfaces that have different user interface levels, allow the user to explicitly choose the interface level, which will then be used throughout the system until reset.

The interface of the present invention would study the initial behavior of the user to determine the expected user level of that user. An apparatus for performing this function is shown schematically in FIG. 18, and in more detain in FIG. 21. Thus, for example, if a user has an unsteady hand while using the cursor control device, producing a high frequency component, measured in the high frequency signal component detector 2112, and likely to also be detected by the path optimization detector 2105, the output could be adaptively filtered to increase the reliability, a function of the main control 1806, without unnecessarily limiting an advanced user who wishes to move the cursor quickly. Another example of the use of an adaptive user interface level is a user who repeatedly requests "help" or user instructions, through the explicit help request detector 2115, which causes an output from the current help level output 2102; such a user may benefit from an automatic context-sensitive help system, however such a system may interfere with an advanced user, and is unnecessary in that case and should be avoided. This adaptive user interface level concept is not limited to a particular embodiment of the present invention, such as a VCR, and in fact, may be broadly used wherever a system may be used by both experienced and inexperienced users. This differs from normal help systems which must be specifically requested, or "balloon help" (Apple Computer, Macintosh System 7.0) which is either engaged or disengaged, but not adaptive to the particular situation based on an implicit request or predicted need. In the case of a single user or group of users, the interface could maintain a history of feature usage for each user, as in the past user history block 2107, and provide a lower user interface level for those features which are rarely used, and therefore less familiar to the user, through the current user level output 2101.

The intelligence of the device of the present invention is not limited by the foregoing examples; the user could also input characteristics of the program material that are desired, and characteristics of that program material which is not desired. The device would then, over time, monitor various broadcast choices, and determine which most closely match the criterion, and thus be selected. For example, if the user prefers "talk-shows", and indicates a dislike for "situation comedies" ("sitcoms"), then the device could scan the various available choices for characteristics indicative of one or the other type of programming, and perform a correlation to determine the most appropriate choice(s). A sitcom, for example, usually has a "laugh track" during a pause in normal dialogue. The background of a sitcom is often a confined space, from different angles, which has a large number of props. A talk-show, on the other hand, more often relies on actual audience reaction (possibly in response to an "applause" sign), and not prerecorded or synthesized sounds. The set is simple, and the broadcast often shows a head and neck, or full body shot with a bland background. A signal processing computer, programmed for audio and/or video recognition, could differentiate between at least the two types with some degree of efficiency, and with a possibly extended sampling time, have excellent recognition accuracy. Further, with the aid of feedback, the search criterion would be improved. Thus, a user could teach the interface through trial and error to record the desired programs. Thus, the presently described recognition algorithms may be adaptive and learning, and need not apply a finite set of predetermined rules in operation. For such a learning task, a neural network processor may be implemented, as known in the art.

Figure 22:
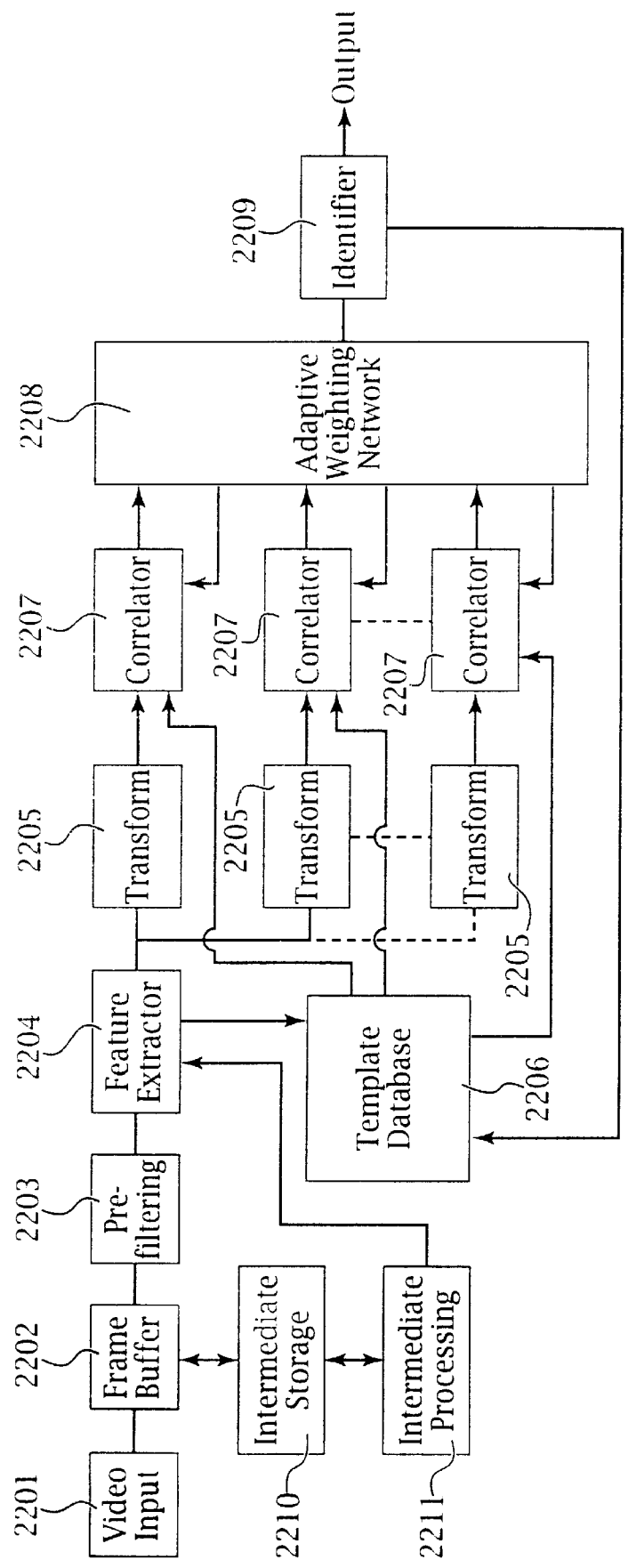
FIG. 22 is a block diagram of a template-based pattern recognition system of the present invention.

The feature extraction and correlation system of the present invention is shown in FIG. 22. In this figure, the video input, including the audio signal and all other available data, are input in the video input 2201. This is transferred to a frame buffer 2202, which temporarily stores all of the information. This frame buffer 2202 may have an integral or separate prefiltering component 2203. The filtered signal(s) are then passed to a feature extractor 2204, which divides the video frame into a number of features, including sound, movement, objects, correlated sound and object, background, etc. These features, are then passed to a transform engine or multiple engines in parallel, 2205. These transform engines 2205 serve to match the extracted features with the standard form of the templates in the template database 2206. The transformed extracted features and the templates are then correlated by a correlator or correlators 2207. The parallelism of the transforms and correlators serves to increase the recognition speed of the device. The outputs of the correlators are input into an adaptive weighing network 2208, to produce a probability of a match between a given feature and a given template. The recognition is completed in an identifier 2209, which produces a signal identifying one or more objects in the video frame input. The identifier 2209 also has an output to the template database 2206, which reinforces the recognition by providing feedback; therefore, if the same object appears again, it will be more easily recognized. The template database 2206 therefore also has an input from the feature extractor 2204, which provides it with information regarding the features recognized. It is also noted that, in addition to allowing recognition, the parallel transform engines 2205, correlators 2207, and adaptive weighing network 2208 also allows the system to ignore features that, though complex, do not aid in recognition. For example, during dialogue, the soundtrack voice will correlate with the mouth movements. Thus, the mouth movements aid little in recognition, and may be virtually ignored, except in the case where a particular person's mouth movements are unique, e.g., "Gomer Pyle". Thus, the complexity and parallelism in the intermediate recognition stages may actually simplify the later stages by allowing more abstract features to be emphasized in the analysis.

The pattern recognition function of the present invention could be used, in a VCR embodiment of the present invention to, e.g., to edit commercials out of a broadcast, either by recognition of characteristics present in commercials, in general, or by pattern recognition of specific commercials in particular, which are often repeated numerous times at various times of the day, and on various broadcast channels. Further, certain media present a recognizable audio or video cue when a commercial break has ended. (E.g. often sports events, such as the Olympic Games, will have theme music or distinctive video screens.) The present device need not respond immediately to such cues, and may incorporate a delay, which would store the information while a decision is being made. The temporary storage medium may be independent of the pattern recognition system. Thus, there may actually be two data streams: the first serving as the desired signal to be stored, and the second to the pattern recognition system. This system is advantageous because is allows a broadcast quality temporary storage, which may be analog in nature, to be separate from the digital signal processing and pattern recognition stage, which need only retain significant information for the pattern recognition, and therefore may be highly compressed, and devoid of various types of information which are irrelevant or of little importance to the pattern recognition functions. Further, the temporary storage may employ a different image compression algorithm, e.g. MPEG II or MPEG++, which is optimized for retention of visually important information, while the recognition system may use a compression system optimized for pattern recognition, which may retain information relevant to the recognition function which is lost in other compression systems, while discarding other information which would be visually important. Further, the compression algorithm is integral to the recognition function, preparing the data for the pattern matching and characterization, and therefore should be optimized for high throughput. In other words, the initial compression may include redundant information, if necessary in order to achieve real-time or near real-time recognition, and, thus may actually result in a larger intermediate data storage requirement than the instantaneous data presented to the recognition system; however, the term "compression", in this case, applies to the long term status of the device, and in a real-time recognition function, the amount of data stored for use in recognition will always be less than the cumulative amount of data presented, except during the very initial stages of data acquisition.

The image may be compressed using the so called "fractal transform", using the method of Barnsley and Sloan, which is implemented and available in product form from Iterated Systems, Inc., Norcross, Ga., as the FTC-II, which incorporates eight fractal transform integrated circuit chips, 1 MByte of RAM, and an Intel i80960CA-25 $\mu$P, and operates in conjunction with P.OEM software, which operates under MS-DOS. FTC-II hardware compression requires approximately 1 second per frame, while software decompression on an Intel 80486-25 based MS-DOS computer, using "Fractal Formatter" software, can be performed at about 30 frames per second, which allows approximately real time viewing. This is a non-symmetrical algorithm, requiring more processing to compress than to decompress the image. This method is advantageous because the transform allows compression up to about 2456:1, while still maintaining an aesthetically acceptable result. Further, since the method emphasizes the structure of the image, as opposed to the frequency decomposition used in DCT methods (JPEG, MPEG), the fractal method could be used as a part of the image recognition system. Further, the compression system might also be applicable to audio compression as well, so that a single hardware system could incorporate the basic functions of the device. It is noted that the audio compression and image recognition functions cannot be performed on the FTC-II board, and require a separate device. It should also be noted that an even more efficient compression-pattern recognition system could be constructed by using the fractal compression method in conjunction with other compression methods, which may be more efficient under certain circumstances, such as discrete cosine transform (DCT) or wavelet techniques.

Barnsley and Sloan's method for automatically processing digital image data consisting of image information, fully disclosed in U.S. Pat. Nos. 5,065,447 and 4,941,193, both expressly incorporated herein by reference, consists of the steps of storing the image data in the data processor, then generating a plurality of uniquely addressable domain blocks from the stored image data, each of the domain blocks representing a different portion of the image information such that all of the image information is contained in at least one of the domain blocks. A plurality of uniquely addressable mapped range blocks corresponding to different subsets of the stored image data are created, from the stored image data, with each of the subsets having a unique address. This step includes the substep of executing, for each of the mapped range blocks, a corresponding procedure upon the one of the subsets of the stored image data which corresponds to the mapped range block. Unique identifiers are then assigned to corresponding ones of the mapped range blocks, each of the identifiers specifying for the corresponding mapped range block a procedure and a address of the corresponding subset of the stored image data. For each of the domain blocks, the one of the mapped range blocks which most closely corresponds according to predetermined criteria is selected. Finally, the image information is represented as a set of the identifiers of the selected mapped range blocks. This method allows a fractal compression of image data. In particular, Drs. Barnsley and Sloan have optimized the match of the domain blocks with the mapping region by minimizing the Hausdorff distance. A decompression of the data precedes analogously in reverse order starting with the identifiers and the mapping regions to produce a facsimile of the original image. This system is highly asymmetric, and requires significantly more processing to compress than to decompress.

Basically, the fractal method proceeds from an understanding that real images are made up of a plurality of like subcomponents, varying in size, orientation, etc. Thus, a complex block of data may be described by reference to the subcomponent, the size, orientation, etc. of the block. The entire image may thus be described as the composite of the sub-images. This is what is meant by iterative function systems, where first a largest block is identified, and the pattern mapping is repetitively performed to describe the entire image.

The FTC-II board, as applied in the present invention, is used in conjunction with a frame-grabber board, such as Matrox, Quebec, Canada, Image-LC board, or a Data Translation DT1451, DT2651, DT2862, DT2867, DT2861 or DT2871, which may perform additional functions, such as preprocessing of the image signal, and may be further used in conjunction with an image processing system, such as the Data Translation DT2878.

A fractal-based system for real-time video compression, satellite broadcasting and decompression is also available from Iterated Systems, Inc. and Entertainment Made Convenient$^2$, Inc. (EMC$^2$). In such a system, since the compressed signal is transmitted, the remote receiving system need not apply decompression prior to the intelligent pattern recognition function of the present invention. This system also incorporates anti-copy encryption and royalty and accounting documentation systems. Thus, the interface of the present invention could interact with the standard accounting system to allow royalty-based recording, and possibly implement a serial-copy recording prevention system. It is noted that the EMC$^2$ system does not incorporate the intelligent features of the present invention. In particular, a user must still explicitly select a program, rather than allow an intelligent system to assist in selection and programming of the device. This system is described in "EMC$^2$ Pushes Video Rental By Satellite", Electronic Engineering Times, Dec. 2, 1991, p. 1, p. 98, which is incorporated herein by reference.

Thus, one embodiment of the device may incorporate a memory for storing a program, before being transferred to a permanent storage facility, such as tape. Such a memory may include a hard disk drive, magnetic tape loop, a rewritable optical disk drive, or semiconductor memories, including such devices as wafer scale memory devices. This is shown diagrammatically as the intermediate storage 2210 of FIG. 22. The capacity of such a device may be effectively increased through the use of image data compression, which may be proprietary or a standard format, i.e. MPEG, MPEG-II, MPEG++ (Motion Picture Experts Group), JPEG (Joint Photographic Experts Group), Px64 (CCITT H.261, video-conferencing transmission standard), DVI (Digital Video Interactive), CDI (Compact Disk Interactive), etc. Standard devices are available for processing such signals such as the IIT Vision Processor (VP) chip, Integrated Information Technology Inc., Santa Clara, Calif., the C-Cube CL550B (JPEG) and CL950 (MPEG decoding), SGS-Thompson ST13220, STV3200, STV3208 (JPEG, MPEG, Px64), LSI Logic L64735, L64745 and L64765 (JPEG) and Px64 chip sets, and the Intel Corp. i750B DVI processor sets (82750PB, 82750DB). These are available as single chips and chip sets; in board level products, such as the Super Motion Compression and Super Still-Frame Compression by New Media Graphics of Billerica, Mass., for the PC-AT bus; Optibase, Canoga Park, Calif. (Motorola DSP with dedicated processor for MPEG); NuVista+ from Truevision (Macintosh video capture and output); New Video Corp. (Venice, Calif,) EyeQ Delivery board for Macintosh NuBus systems (DVI); Intel Corp. ActionMedia II boards for Microsoft Windows and IBM OS/2 in ISA (AT bus); Micro Channel Architecture (MCA) (e.g., DVI, PLV 2.0, RTV 2.0) based machines; and as complete products, such as Media-Station by VideoLogic. The use and interfacing of chip sets and multimedia boards such as those described are known to those skilled in the art. It is noted that the present interface does not depend on a particular compression format or storage medium, so that any suitable format may be used. The following references describe various video compression hardware, and are incorporated herein by reference: Kim, Y., "Chips Deliver Multimedia", Byte, December 1991, pp. 163–173; and Donovan, J., "Intel/IBM's Audio-Video Kernel", Byte, December, 1991, pp. 177–202.

Various available DSP chips, exemplary board level signal processing products and available software are described in more detail in "32-bit Floating-Point DSP Processors", EDN, Nov. 7, 1991, pp. 127–146, incorporated herein by reference.

It should also be noted that the compression algorithm may be lossless or lossy, depending on the application. Various different methods and paradigms may be used. For example, DCT (discrete cosine transform), wavelets, fractals, and other known transform methods may be used. These may be implemented by various known means. A compressed image may also be advantageously used in conjunction with the image recognition system of the present invention, as described above. In such a case, the compression system would retain the information most important in the recognition function, and truncate the unimportant information.

A further method of performing pattern recognition, especially of two dimensional patterns, is optical pattern recognition, where an image is correlated with a set of known image patterns represented on a hologram, and the product is a pattern according to a correlation between the input pattern and the provided known patterns. Because this is an optical technique, it is performed nearly instantaneously, and the output information can be reentered into an electronic digital computer through optical transducers known in the art. Such a system is described in Casasent, D., Photonics Spectra, November 1991, pp. 134–140, which is incorporated herein by reference. The references cited therein provide further details of the theory and practice of such a system, and they are also incorporated herein by reference. Lendaris, G. G., and Stanely, G. L., "Diffraction Pattern Sampling for Automatic Target Recognition", Proc. IEEE 58:198–205 (1979); Ballard, D. H., and Brown, C. M., Computer Vision, Prentice Hall, Englewood Cliffs, N.J. (1982); Optical Engineering 28:5 (May 1988)(Special Issue on product inspection); Richards J., and Casasent, D., "Real Time Hough Transform for Industrial Inspection" Proc. SPIE Technical Symposium, Boston 1989 1192:2–21 (1989); Maragos, P., "Tutorial Advances in Morphological Image Processing" Optical Engineering 26:7:623–632 (1987); Casasent, D., and Tescher, A., Eds., "Hybrid Image and Signal Processing II", Proc. SPIE Technical Symposium, April 1990, Orlando Fla. 1297 (1990); Ravichandran, G. and Casasent, D., "Noise and Discrimination Performance of the MINACE Optical Correlation Filter", Proc. SPIE Technical Symposium, April 1990, Orlando Fla., 1471 (1990); Weshsler, H. Ed., "Neural Nets For Human and Machine Perception", Academic Press, New York (1991).

These optical recognition systems are best suited to applications where an uncharacterized input signal frame is to be compared to a finite number of visually different comparison frames (i.e., at least one), and where an optical correlation will provide useful information. Thus, if a user wished to detect one of, e.g., "Johnny Carson", "Dan Rather", "Willard Scott", or "Jane Pauley", a number of different views of these persons would be formed as a holographic correlation matrix, which could be superimposed as a multiple exposure, stacked in the width dimension, or placed in a planar matrix, side by side. The detection system produces, from the uncharacterized input image and the holographic matrix, a wavefront pattern that is detectable by photonic sensors. It is preferred that if multiple holographic images of a particular characterization are employed, that they each produce a more similar resulting wavefront pattern than the other characterizations, in order to enhance detection efficiency. The optical pattern recognition method is limited in that a holographic image must be prepared of the desired pattern to be detected, and that optically similar images might actually be of a different image, if the differences are subtle. However, this method may be used in conjunction with electronic digital pattern recognition methods, to obtain the advantages of both.

If image compression is used, once an image is compressed, it need not be decompressed and returned to NTSC or other standard transmission or format for storage on tape, and thus the compressed image information may be stored in the same format as is present in the temporary storage medium. Thus, the block labelled intermediate processing 2211 of FIG. 22 shows that the intermediate storage need not retain the information as received from the frame buffer 2202, and in fact, may prepare it for the feature extractor 2204. In addition, the storage medium itself need not be normal videotape (VHS, Beta, 8 mm) and may be an adapted analog storage technique or a digital storage technique.

Figure 23:
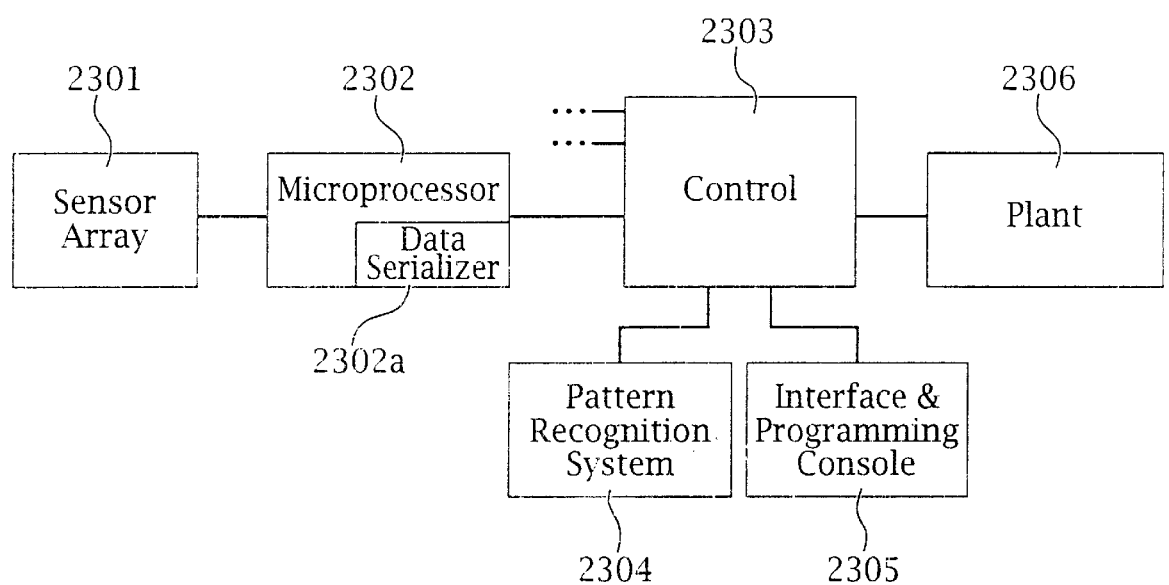
FIG. 23 is a block diagram of a control system of the present invention incorporating a pattern recognition element and an interface.

It is also noted that the interface of the present invention need not be limited to audio-visual and multimedia applications, as similar issues arise in various programmable controller environments. Such issues are disclosed in Carlson, Mark A., "Design Goals for an Effective User Interface", Electro/82 Proceedings, 3/1/1–3/1/4; Kreifeldt, John, "Human Factors Approach to Medical Instrument Design", Electro/82 Proceedings, 3/3/1–3/3/6; Wilke, William, "Easy Operation of Instruments by Both Man and Machine", Electro/82 Proceedings, 3/2/1–3/2/4; Green, Lee, "Thermo Tech: Here's a common sense guide to the new thinking thermostats", Popular Mechanics, October 1985, 155–159; Moore, T. G. and Dartnall, "Human Factors of a Microelectronic Product: The Central Heating Timer/Programmer", Applied Ergonomics, 1983, Vol. 13, No. 1, 15–23; and "The Smart House: Human Factors in Home Automation", Human Factors in Practice, December 1990, 1–36, all of which are incorporated herein by reference. In such a case, the pattern recognition function would be used to execute a contingent program. For example, in a programmable temperature controller application, a sensor or sensor array could be arranged to detect a "door opening". On the occurrence of the door opening, the system would recognize this pattern, i.e. a mass of air at a different temperature entering the environment from a single location, or a loss of climate controlled air through a single location. In either event, the system would take appropriate action, including: halt of normal climate control and impose a delay until the door is closed; after closure, set a time constant for assimilation of the replaced air with the climate controlled air; based on the actual climatic condition after assimilation, or a predicted climatic condition after assimilation, begin a climate compensation control; optionally, during the door opening, control a pressure or flow of air to counterbalance the normal flow through the door, by using a fan or other device. The climate may differ in temperature, humidity, pollutants, or the like, and appropriate sensors may be employed. This generalized system is shown in FIG. 23, in which the sensor array 2301 interfaces with a microprocessor 2302 with a serial data port 2302a, which transmits sensor data to a control 2303. The control 2303, further interfaces or includes a data pattern recognition system 2304 and an interface and programming console 2305 of the present invention, using the intelligent features and adaptive pattern recognition techniques. The control 2203 controls the plant 2306, which includes all the controlled actuators, etc.

It is also noted that the present technology could also be applied to any sort of mass storage, such as for a personal computer. In such a case, a characteristic of the computer file, which is analogous to the broadcast program in temporary storage of a VCR, is classified according to some criteria, which may be explicit, such as an explicit header or identifying information, or implicit, such as a document in letter format, or a memorandum, as well as by words and word proximity. In particular, such a recognition system could differentiate various clients or authors based on the content of the document, and these could be stored in different manner. The text analysis system of a text-based computer storage system is analogous to the program classification system of the VCR embodiment of the present invention. However, there is a further analogy, in that the VCR could incorporate optical character recognition of text displayed in the program material, or directly receive text information as a part of a closed caption or videotext system. Thus, the VCR device of the present invention could recognize and classify programs based on textual cues, and make decisions based on these cues. This might also provide a simple method of discriminating program material, for example, if a commercial does not include close caption or Second Audio Program (SAP), while the desired program does, or vice versa, then a commercial could be discriminated from a program with very little computational expenditure.

Other characteristics of this interface include color coding to help prompt the user as to which data he/she must enter. Red text signifies instructions or errors, yellow text represents data which must be entered or has not been changed, and blue text shows newly entered program data or status information. Blue buttons represent buttons which should normally be pressed during the programming sequence. Red buttons signify an erratic pattern in the data entry, such as the "cancel" and "return to main menu" buttons. Of course, these colors can be replaced by other display attributes, such as intensity, underline, reverse video, blinking and pixel dithering pattern, in addition to the use of various fonts. Such a situation would include a monochrome monitor or display.

The date may be entered in the form of a calendar rather than as numbers (i.e., Sep. 6, 1991). This calendar method is advantageous because users may wish to input date data in one of three ways: day of the week, day relative to the present, and day of the month. The present method allows the current date to be highlighted, so that the calendar may be used to easily enter the absolute day, absolute date, and relative day. Further, the choices "today" and "tomorrow", the most frequently used relative recording times, are included in addition to a month-by-month calendar. This information is provided to avoid an unnecessary waste of time and user frustration. Thus, another aspect of the present invention is to provide a partially redundant interactive display input system which allows, according to the highest probability, the choices to be prominently displayed and easily available, in addition to allowing random access to all choices.

The present device allows common user mistakes to be recognized and possibly addressed, such as the confusion between 12:00 PM and 12:00 AM with midnight and noon, respectively. Therefore, the options of "noon" and "midnight" are provided in addition to a direct numeric clock input. When entering time information, leading zeros need not be entered, and such information may be entered in either fashion.

The criteria for system acceptance of input depends on how many keystrokes are required on the screen. If only one keystroke is required to complete input of the information, upon depressing the key, the programming sequence will continue. If more than one keypress is required, the user must depress the "OK" button to continue programming. This context sensitive information entry serves to avoid unnecessary input.

An on-line "help" system and on-line feedback is preferably provided to the user throughout various aspects of the interface. Other features include minimizing the number of keypresses required to program the device. These features, together with other aspects of the present invention allow the user to achieve a greater efficiency with the input device than with prior art devices.

The interface of the present invention applied to a VCR control comprises a virtual keypad entry device, a directional input control for a cursor on a display screen, and a selection button. The input device has an input corresponding to a direction of movement relative to the cursor position. Thus, since the present input device seeks to minimize the physical control elements of the human interface device, the display elements for a preferred embodiment of the present interface include:

1. number keys 0–9
2. enter key
3. cancel key
4. status indicator
5. return to menu option button
6. program type indicator: program once, program once a week, program Monday-Friday, program everyday
7. Day indicators: 7 week days, today, tomorrow
8. Noon and midnight choices
9. Help button
10. Main menu options: Review, Enter new recording time, Set time, Set date
11. Timer button
12. Power button
13. AM/PM choices
14. 31 day calendar
15. 12 month Choices
16. 3 tape speed choices

EXAMPLE 1

The interface of the present invention includes an internal clock, 4 program memory, and the capability to display a graphical color interface. By providing the user with the aforementioned features, this design is a unique implementation for an instrument to be used for programming an event driven controller via an interactive display. All information that the user needs is displayed on the screen to avoid unnecessary searching for information. This information includes the current date and current time.

The simulation of the AKAI VCR VS303U (on-screen programming) and the interface of the present invention, were tested to evaluate users' performances. The AKAI interface of the prior art, hereinafter referred to as the prior art interface, was chosen because users made the fewest errors while using this machine, and no subject quit while programming, as compared to three other VCRs tested, a Panasonic PV4962 (Bar Coder), an RCA VKP950 (on-screen programming), Panasonic PV4700 (Display Panel).

The present embodiment was constructed and tested using HyperPAD™, a rapid prototyping package for an IBM-PC Compatible Computer. It is, of course obvious that the present embodiment could be incorporated in a commercial VCR machine by those skilled in the art, or be implemented on many types of general purpose computers with output screens which allow on-screen feedback for the programming operation. Further, the present embodiment can control an infrared remote controlled VCR or translate the programming information and program an infrared remote control through an interface to an infrared transmitter.

An IBM PC-AT compatible (MS-DOS, Intel 80286-10 MHz) computer was used to test the two simulations. In order to simulate the use of a remote control device in programming the VCR, an infrared device made by NView™ was attached to the computer. This device came with a keyboard that was used to "teach" a Memorex™ Universal Remote so that the desired actions could be obtained. By using a universal remote, the computer could be controlled by using a remote control.

The present embodiment incorporates a mouse input device. It is understood that a small trackball with a button for selection, mounted on a remote control would be preferred. However, a computer mouse is easily available, and the mouse and trackball data are essentially similar for the type of task used in this study, with trackball performance being slightly faster. For daily use on a VCR however, a trackball would be a more preferable input device because it does not require a hard, flat surface, which is not always available to a user, such as in the situation where a person is watching television while sitting in a chair or sofa.

A Genius™ Mouse was used as the input device in the prototype of the interface of the present invention. With the mouse, the user could view all of the choices at once on the display screen, and then make a selection from the items on the screen by moving the cursor and then pressing the left mouse button.

SIMULATIONS

Two simulations were prototyped. The first was a simulation of the existing AKAI On-Screen VCR, Model Number VS-303U, hereinafter referred to as the prior art interface. The second was the newly devised interface of the present invention. Data from each test was exported to data files on the computer so that specific actions, types of action, mouse clicks, number of times each screen is entered, and time spent on each screen may be compared.

Subjective data was also collected; it was verbally supplied by the subject during and after the testing. Usability tests were run, using the "Thinking-Aloud" technique. This method requires users to verbalize their thoughts as they interact with the system. This technique is especially useful in discovering strategies which users employ in approaching tasks, pin-pointing problems, and discovering the reasons why they occur. In addition, demographic data, such as each subject's age, occupation, and experience using VCRs and mice was also recorded.

The design was optimized according to the above-mentioned criteria through a procedure of testing, alteration of the simulation, and retesting. The alterations were maintained if they resulted in an improvement in subjective and/or objective criteria. Those alterations that did not result in improvement were reverted to a previous state. It is proposed that the interface be individually optimized for persons of various demographic groups, ages, education levels, etc., so that, in accordance with an object of the invention, the interface best matches a particular user's expectations. Simultaneous multivariate alterations were also implemented in order to demonstrate an interactive effect between various implementations. In such testing, subjective factors were weighted more heavily than objective factors because the purpose was to determine a qualitative effect, rather than a quantitative comparison. The resultant qualitative measurement of a multivariate alteration indicated whether the complex of changes displayed any advantage over the previous state. If an advantage was demonstrated, the multivariate alteration was decomposed into its quantum changes, full quantitative studies were performed, and statistical analysis completed. Thus, by incorporating subjective analysis, multivariate alterations in the interface could be quickly analyzed for their advantages as compared with a similar precursor.

EXPERIMENTAL TESTING

After an optimized design was obtained, the final testing was conducted as a repeated measures experiment of naive subjects. The tasks required were to set the clock and 3 programs to simulate a situation where the subject might go on vacation and, upon arrival home, have the desired programs on tape. Three programs were set so that the learning time between programs could be more accurately studied. The subjects did not know which interface was the experimental one.

The following directions were given to the subjects:

Set Time: 9:00 PM, Wednesday, Jun. 6, 1990

Program 1: 8:00 PM–11:00 PM, Sunday, Jun. 10, 1990, Channel 5

Program 2: 3:00 AM–3:30 AM, Monday–Friday, Channel 7

Program 3: Record your favorite television show

Each subject used both simulations, so as to eliminate the effect of between subject variability. The order in which the subjects used the interfaces was counterbalanced so as to offset the effect of learning. In all, 23 subjects were tested. However, data from only 16 subjects was used in the calculations because seven of the test participants quit while performing the programming tasks on the simulation of the prior art interface. Because these subjects were not able to complete all of the tasks, their data could not be validly compared with that of subjects who had fully completed the tasks.

DATA ANALYSIS

The objective data was analyzed according to Stuart Card's (1979) method, disclosed in Card, Stuart K., "A Method for Calculating Performance times for Users of Interactive Computing Systems", IEEE, 1979, 653–658, incorporated herein by reference, involving calculating performance times for users of interactive computing systems. He calculated the way in which the time to perform a task can be determined from the design phase by breaking the entire task into individual components. However, he focused his calculations on experienced users, not novices. This is a fundamental difference, in both theory and result, and this method has been herein validated by the present inventor.

Some of the interface factors affecting user performance include:

Time—How long it takes for a user to accomplish a task.

Errors—How many errors the user makes and how serious they are.

Learning—How long it takes a novice user to learn to use the system.

Functionality—The range of tasks that can be performed with the system.

Recall—How easy it is for a user to recall how to use the system after a period of non-use.

The optimized interface of the present invention sought to minimize the first three of these aspects. Recall and Learning were, for the present purpose, considered as identical since data collected has shown that most people perform the task being studied (time-shift programming) less than once a month and thus have to re-learn the task each time. Functionality was also disregarded because it was a negligible factor between tasks.

The most important factor considered in the present optimized interface focuses on time. Knowing the sequence of user actions and the response time of the system, the required user time can be predicted by application of the following equation:

$$T_{task} = T_{acquire} + T_{execute}$$

One goal of the interface of the present invention is to minimize $T_{acquire}$. By Card's model, the execution time is the time, $t_j$, for each of these operators j weighted by the frequency, $n_j$, with which they occur, plus the total system response time, $T_R$, to the steps performed by the user. The formula for the execution time is:

$$T_{execute} = \Sigma_j n_j t_j + T_R$$

Despite the endless number of possibilities that can be performed using a computer, according to Card's work, the steps necessary to perform the tasks required and their respective times can be divided into four categories:

1. The time required to use the mouse to point to the object and click:
   $t_P = 1.10$ seconds
2. The time to mentally prepare before pointing to a command:
   $t_M = 1.35$ seconds
3. The time to enter input:
   Prior Art interface:
   $t_K = 0.75$ seconds for typing complex codes
   Interface of the present invention:
   $t_K = 0.2$ seconds for an average typist or mouse user
4. The computer response time:
   $t_R = $ Variable The subjects' entry times, actions, and the computer response time were then subtracted from the total time required to perform the task in order to determine $T_{acquire}$. This technique gives estimates accurate to about 20% of actual times required by users.

RESULTS

Computer Response Time $T_R$, the average computer response time, was calculated individually for each subject. In order to attain a baseline, the researcher, an expert user of the systems, performed the tasks on both a 10 MHz (Intel 80286 based) and a 33 MHz (Intel 80386DX based) computer. The faster processor had a negligible computer response time, taken as $T_R=0$. The time using the faster computer was then subtracted from the time using the slower computer to achieve a measure of how much slower the 10 MHz computer was.

An additional time delay, due to the software used and dependent upon the number of screens accessed, was then subtracted from the change in time. This number was then divided by the number of keypresses required to complete the task to produce a number representing the number of seconds per keypress. The computer response times obtained were:

1.11 seconds per keypress for the prior art interface; and
 0.18 seconds per keypress for the interface of the present invention.

The large difference between these numbers was confirmed when many users commented that they had to wait for the outcome of their input on the prior art interface.

Errors

Errors are often made by the users and they can be classified as follows:

OMISSION—Failure to perform any task necessary to program the VCR.
 COMMISSION—Incorrectly performing a task without noticing the error.
 SEQUENTIAL EFFECTS—When judgment is affected by items that precede it.

In the interface of the present invention, the errors of omission are remedied by the fact that the user cannot continue programming if the current step is not completed. In the prior art interface, this is not the case and critical actions may be overlooked.

Figure 2:
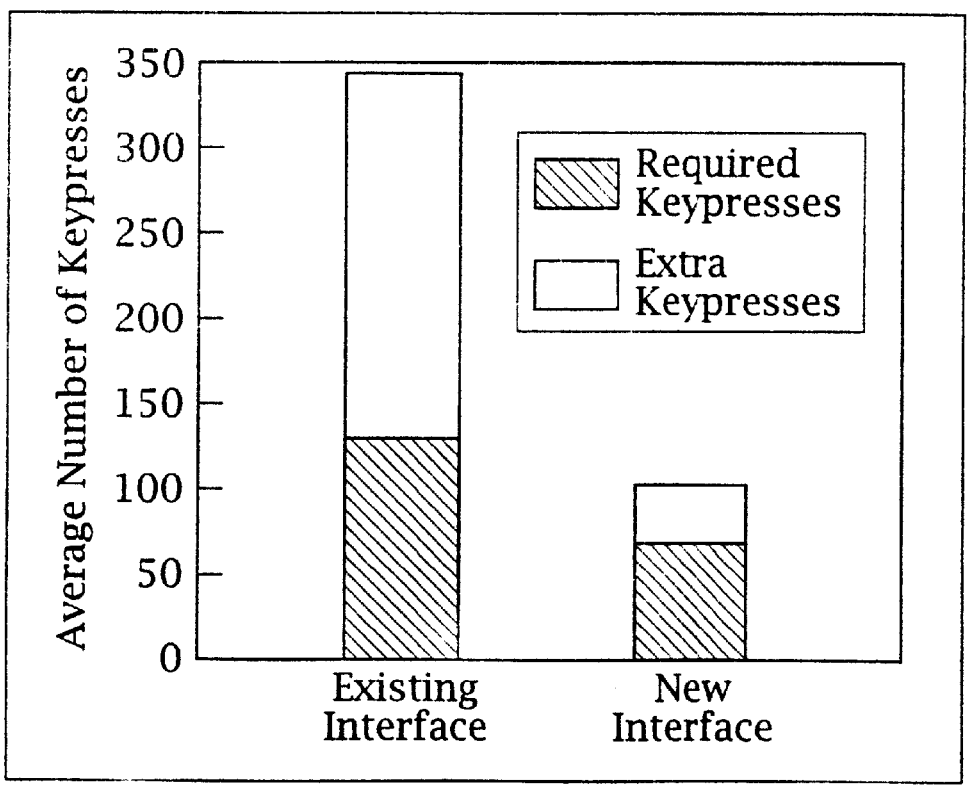
FIG. 2 shows a graphical comparison of required and extra keypresses for the prior art and the interface of the present invention.

Errors of commission seem inevitable. In the prior art interface, there were an average of 34.3 errors per subject, or 9% of the total number of buttons pressed. In the interface of the present invention, there were an average of 7.2 errors per subject, or 6% of the total number of keystrokes. In order to determine significance, a T-Test was applied and the difference between error rates of the two systems was found to be significant at $\alpha<0.10$. Sequential effects were eliminated by the testing procedure and did not affect the results obtained. FIG. 2 shows the required and the extra keypresses for each interface.

Simulation of the Prior Art Interface

Figure 3:
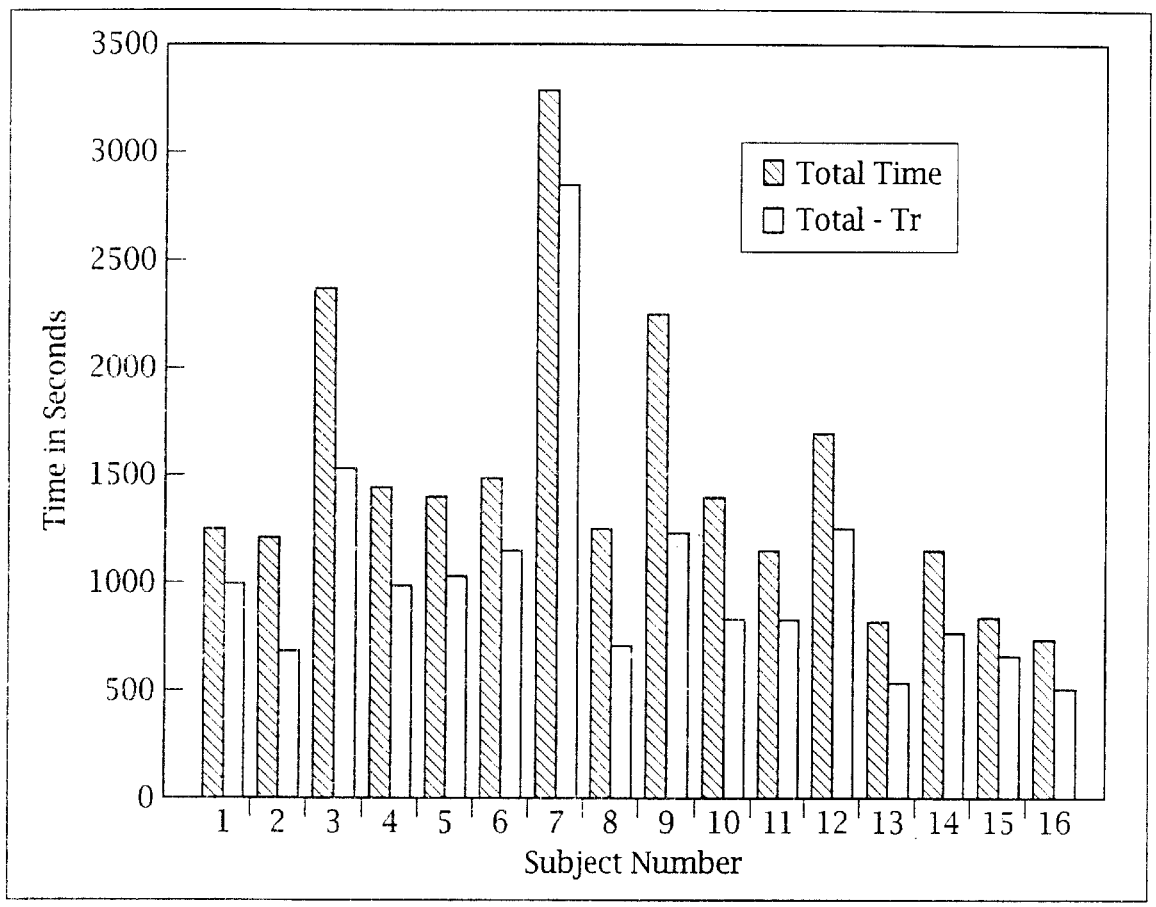
FIG. 3 graphically shows the differences in seconds between total time for the prior art for each subject.

In programming the simulation of the AKAI interface of the prior art, the average time that it took the 16 subjects to complete the setting of the clock and the recording of three programs was 1,476.9 seconds (24.6 minutes). An average of 451.4 seconds (7.5 minutes) of each trial, or 31% of the total time, can be attributed to computer response time (TR) using 1.11 seconds per keypress. This time can then be subtracted from the subjects' total time. Thus, the new average becomes 1,025.5 seconds (17.1 minutes). The fastest time recorded was 498 seconds (8.3 minutes) and the slowest time was 2,844.4 seconds (47.4 minutes). Table 1 shows the subjects and the time it took to complete the programming sequence for the prior art interface. FIG. 3 entitled "Differences In Seconds Between Total Time And (Total Time—Computer Time) For The prior art Interface" shows this data graphically.

TABLE 1

Total Time In Seconds And (Total Time - Computer Time)
For The Critical Steps Using The Prior Art Interface

| SUBJECT # | TOTAL | TOTAL-$T_R$ |
|---|---|---|
| 1 | 1228 | 981.9 |
| 2 | 1190 | 663.3 |
| 3 | 2358 | 1513.9 |
| 4 | 1425 | 976.2 |
| 5 | 1394 | 1022.5 |
| 6 | 1482 | 1144.6 |
| 7 | 3289 | 2844.4 |
| 8 | 1247 | 697.6 |
| 9 | 2248 | 1220.7 |
| 10 | 1389 | 825.8 |
| 11 | 1143 | 829.7 |
| 12 | 1697 | 1243.2 |
| 13 | 817 | 533.3 |
| 14 | 1146 | 764.3 |
| 15 | 841 | 648.2 |
| 16 | 737 | 498.0 |
| MEAN | 1477 | 1025.5 |

No subject was able to complete the programming tasks in the desirable mimimun time of seven minutes, and only eight subjects (50%) were able to finish in less than 14 minutes, double the ideal time goal established as a result of the previous testing. Two subjects (13%) required more than 21 minutes, triple the goal set, to perform these tasks. The seven minute time period was selected as a result of subjective data gathered earlier in research.

Only four subjects (25%) were able to correctly perform the tasks required. An additional six subjects (38%) did not select the timer button. Only one person realized his error (setting the wrong date). The problems encountered which led to incorrect recordings, and their frequency are as follows:

| Number of Subjects | Problem |
|---|---|
| 4 | Set the wrong date |
| 3 | Confused by the moving seconds field |
| 2 | Set the wrong time |
| 1 | Set the wrong channel |
| 1 | Didn't memorize a program |

Simulation of the Interface of the Present Invention

The average time required to complete the experimental tasks with the interface of the present invention was 560.1 seconds (9.3 minutes). The average computer response time, $T_R$, assuming it took 0.18 seconds per keypress, was 57.5, or 11% of the total time. When this is deducted from the total time, the new average is 502.7 seconds (8.4 minutes). The shortest length of time recorded for programming was 143.5 seconds (2.4 minutes) and the maximum was 1,187.7 seconds (19.8 minutes). Ten of the subjects (63%) took less than seven minutes to set the clock and three programs, thus meeting the original goal of a maximum of seven minutes, and 13 subjects (81%) took less than 14 minutes. Table 2 shows the subjects and the time it took each to successfully complete the tasks on the interface of the present invention. This table can be seen graphically in FIG. 4, entitled "Differences In Seconds Between Total Time And (Total Time—Computer Time) For The Interface of the Present Invention." Overall, 14 out of 16 of the test participants took less time using the interface of the present invention.

TABLE 2

Total Time In Seconds And (Total Time - Computer Time)
For The Programming Steps Using The Interface of the
present invention by subject.

| SUBJECT # | TOTAL | TOTAL-$T_R$ |
|---|---|---|
| 1 | 461 | 406.1 |
| 2 | 929 | 840.5 |
| 3 | 675 | 625.6 |
| 4 | 1151 | 1046.7 |
| 5 | 403 | 359.2 |
| 6 | 331 | 281.5 |
| 7 | 437 | 374.2 |
| 8 | 372 | 317.2 |
| 9 | 747 | 688.7 |
| 10 | 180 | 143.5 |
| 11 | 823 | 759.3 |
| 12 | 462 | 403.6 |
| 13 | 239 | 202.2 |
| 14 | 368 | 305.1 |
| 15 | 456 | 412.5 |
| 16 | 352 | 299.9 |
| MEAN | 560 | 502.7 |

Statistical Analysis

The data was analyzed using SPSS-X, a statistical package. The tasks can be divided into six programming steps:

1. CLOCK SET
2. PROGRAM 1
3. PROGRAM 2
4. PROGRAM 3
5. SEARCH TIME
6. TOTAL TIME

The average time for the 16 subjects, and their standard deviations can be seen in Table 3 The number of subjects and the tasks they could not accomplish can be seen in Table 4.

TABLE 3

Average Time In Seconds For The Six Programming Steps

| CRITICAL STEP | PRIOR ART INTERFACE | | INTERFACE OF THE PRESENT INVENTION | |
|---|---|---|---|---|
| | AVERAGE | STD | AVERAGE | STD |
| CLOCK SET | 332.0 | 266.7 | 105.9 | 67.8 |
| PROGRAM 1 | 431.7 | 316.7 | 167.6 | 142.7 |
| PROGRAM 2 | 283.3 | 135.0 | 85.6 | 52.6 |
| PROGRAM 3 | 189.7 | 97.4 | 55.3 | 16.5 |
| TOTAL | 1025.4 | 559.7 | 466.6 | 251.9 |
| SEARCH | 240.3 | 203.1 | 111.8 | 81.2 |

TABLE 4

Number Of Subjects Unable To Succeed In
Programming Both Interfaces

| CRITICAL STEPS | PRIOR ART INTERFACE | INTERFACE OF THE PRESENT INVENTION |
|---|---|---|
| MISTAKE | 8 | 4 |
| TIMER | 6 | 4 |

Figure 5:
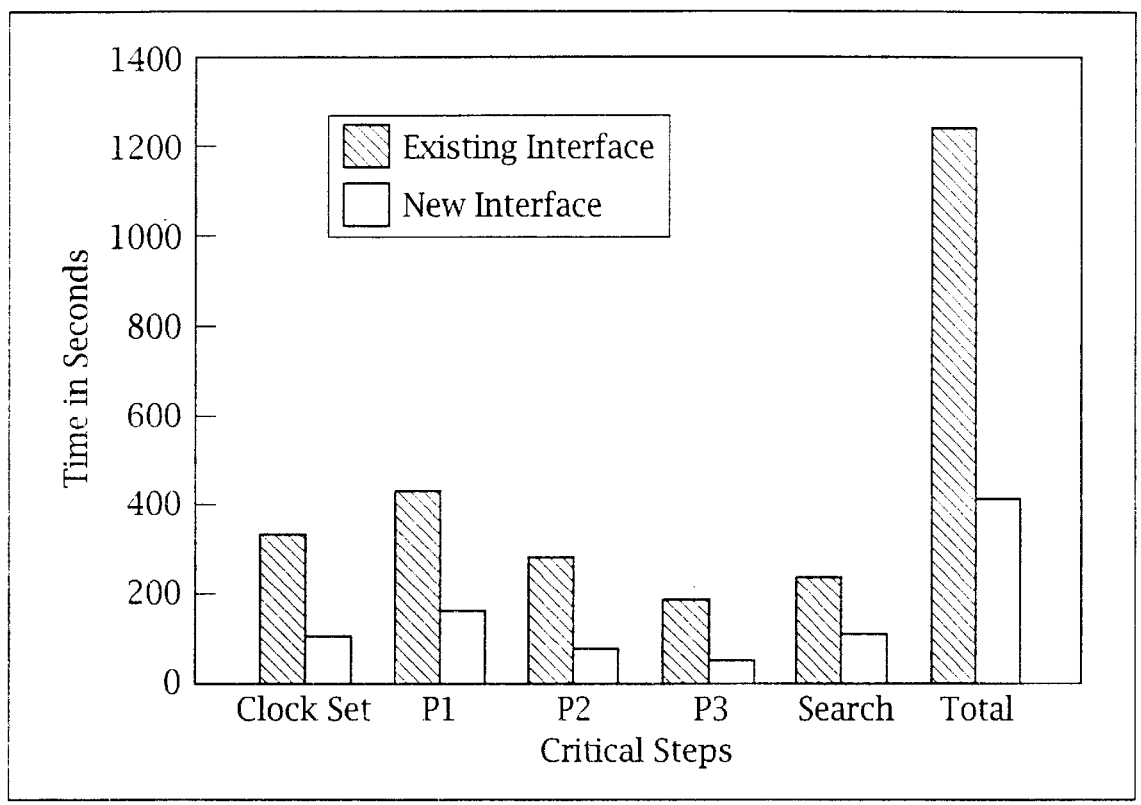
FIG. 5 graphically shows the programming steps for the comparison of the prior art and the interface of the present invention.
Figure 6:
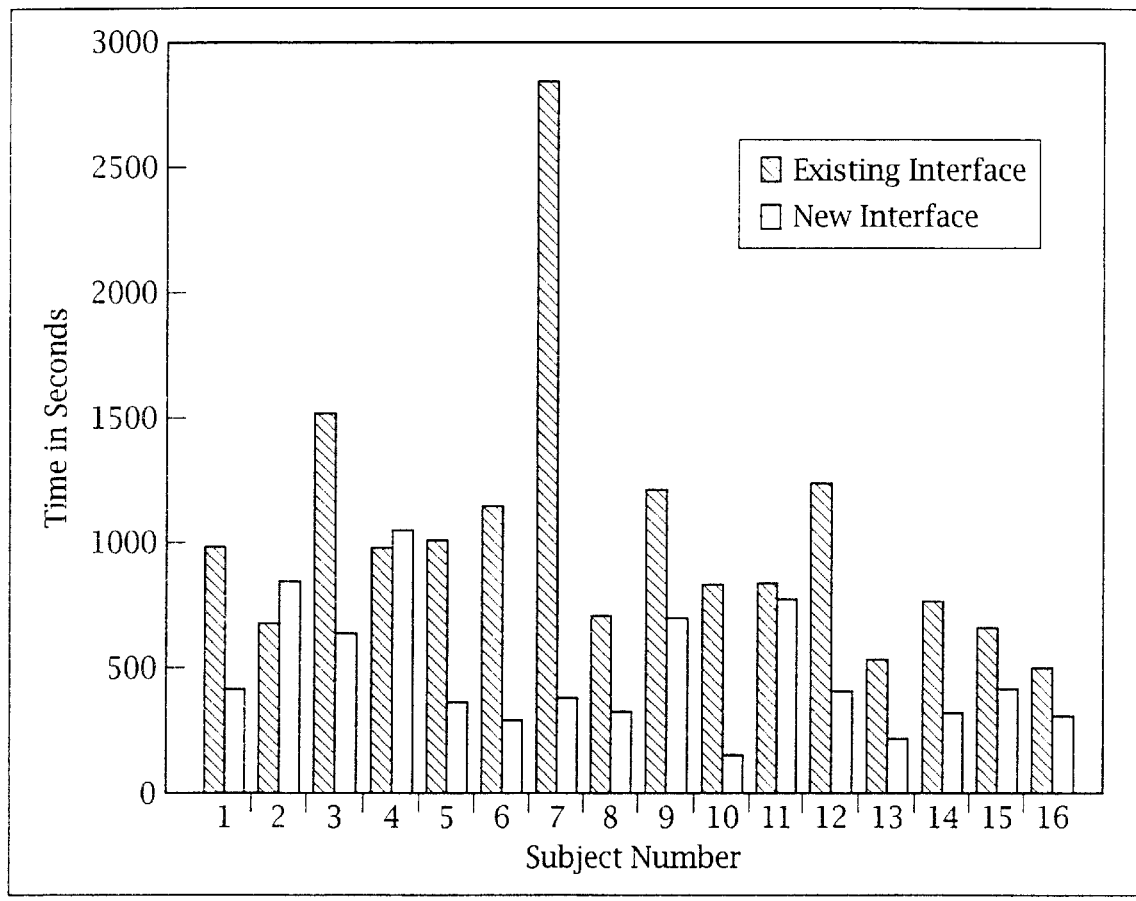
FIG. 6 graphically shows comparative statistics by subject comparing the prior art and the interface of the present invention.
Figure 7:
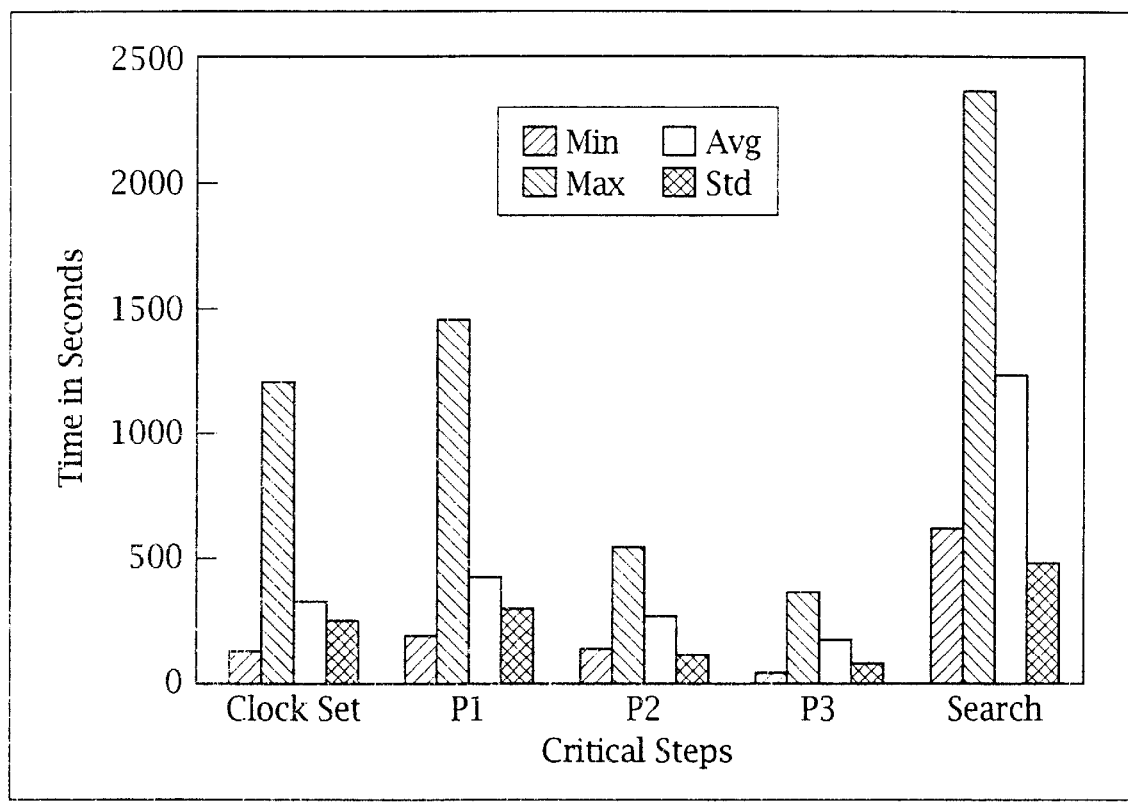
FIGS. 7 and 8 graphically show the critical steps in programming the prior art and the interface of the present invention.
Figure 8:
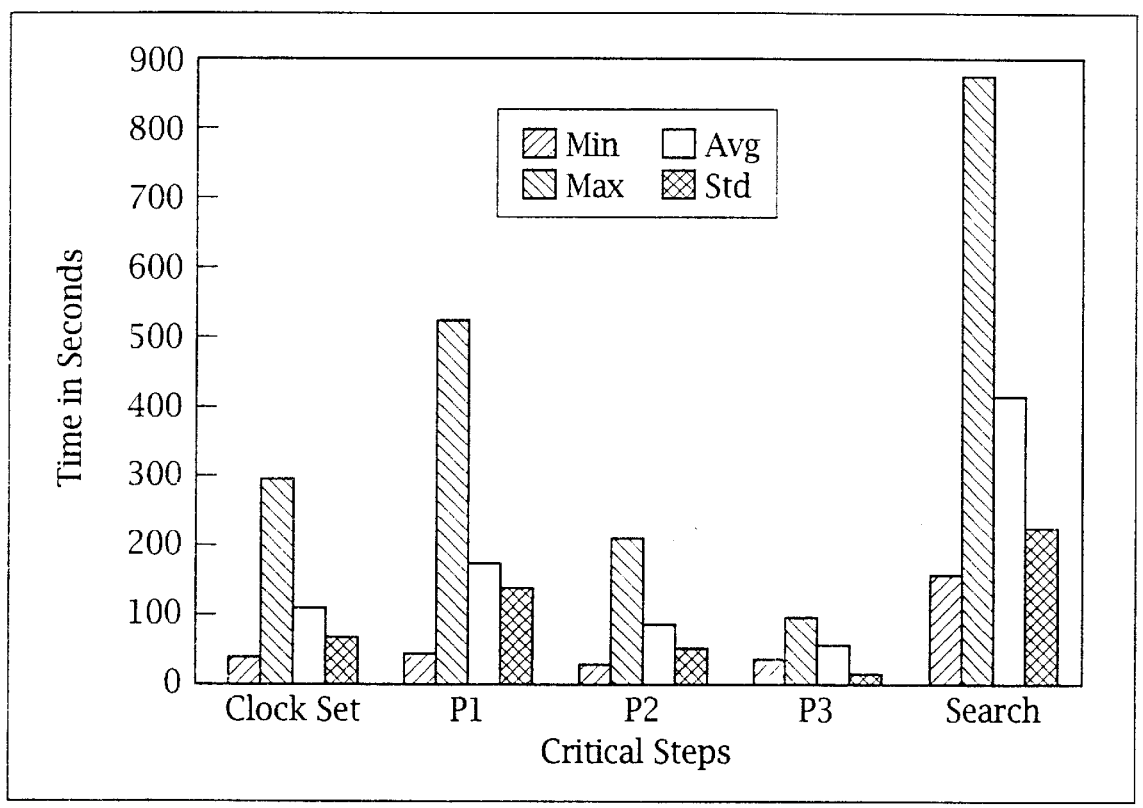

FIG. 5 graphically shows the critical steps for the two interfaces. FIG. 6 shows the total time by subject. In FIG. 6, subjects two and four took less time using the interface of the present invention in actuality, however, using adjusted times, the interface of the present invention took longer. In FIGS. 7 and 8 and show the minimum, maximum, average and standard deviations for both the prior art and the interface of the present inventions.

The interface of the present invention reduced the average programming time by 54%. However, the standard deviations are high for both cases, and equal slightly more than half of the total time. T-Tests for each of the six programming steps showed no significance. However, when subjected to the Pearson Correlation, some significance was found ($\alpha<0.10$).

Ten subjects (63%) were able to correctly perform the programming tasks using the interface of the present invention. Altogether, four users did not set the timer, and two of these did not set the timer on the prior art interface. Three subjects reported that they probably could have performed the tasks quicker if they were not using a mouse as the input device. None of the subjects who made mistakes using the interface of the present invention realized their errors. The problems encountered using the present invention and their frequencies are as follows:

| Number of Subjects | Error |
|---|---|
| 4 | Set the incorrect date |
| 4 | Did not set the timer |
| 3 | Set the incorrect time |
| 1 | Chose the wrong type of recording |

All measurements were subjected to separate Analysis of Variance tests. The differences between all measures were found to be statistically significant at $\alpha<0.01$ except search time, which was significant at $\alpha<0.05$.

The CHI Square test was performed to determine whether the probability of the times for each measurement is the same, or whether they are statistically different from one another. The results indicated that differences exist only between Clock Set, Program 2, and Program 3 and are significant at $\alpha<0.01$.

According to Stuart Card's theory, the total amount of time from the design stage can be calculated according to the following formula:

$$T_{EXECUTE} = \# \text{ OF KEYPRESSES} \times (T_M + T_K + T_P)$$

where $T_M$—Mentally Prepare $T_K$—Key in $T_P$—Point with mouse

Keypresses

THE PRIOR ART INTERFACE

To perform the necessary tasks on the prior art interface, a minimum of 130 keypresses was required for each of the 18 subjects. Using the formula above, an average of 273 seconds is calculated for $T_{EXECUTE}$. However, in the actual testing situation, an average of 342.1 keypresses were made per subject, 2.6 times the minimum number of keypresses required. According to Card's formula, it should have taken 718.4 seconds for 342.1 keypresses ($T_M=1.35$, $T_K=0.75$). It actually took an average of 1,025.5 seconds per subject, which is 1.4 times more than the theoretical time expected. Both the additional keypresses and the extra time can be attributed to $T_{ACQUIRE}$, which is dependent on the details of the task and whether it is given from without or generated from within the user.

Some of the extra keypresses can be attributed to the fact that all of the subjects had trouble deciphering the coded buttons and were confused by the week numbers and how to select the Mon-Fri option. Nine users thought that they had to "Memorize" the clock setting sequence after each step, and the subjects did not always mentally calculate whether using the "+" or "−" key would be faster, and if they realized their error, they commented that they had not selected the shortest route. One subject did not realize that there were "+" and "−" keys and therefore, when he missed setting the time by one minute, he had to cycle around 59 extra times, thus incurring 59 extra keypresses.

THE INTERFACE OF THE PRESENT INVENTION

The interface of the present invention required a theoretical minimum of 70 keypresses per subject, which was only 54% of the number of keypresses required by the simulation of the prior art interface. It can be noted that the time to perform the task of programming the interface of the present invention was also reduced by 54%. This results in a theoretical average of 185.5 seconds per subject, 87.5 seconds less than the prior art interface. The actual testing situation resulted in an average of 103.6 keypresses per subject, 68% more keypresses than the required minimum ($T_M$=1.35, $T_K$=0.2, $T_P$=1.10). Although the interface of the present invention required far fewer keypresses than the simulation of the prior art interface, by Card's calculations, it should have taken 274.5 seconds for 103.6 keypresses. However, it took an average of 502.7 seconds per subject, 1.8 times more than the predicted time. This can be attributed to $T_{ACQUIRE}$.

Some of the extra keypresses could be attributed to four subjects who originally entered the date as "90" rather than "1990", five subjects who tried to enter information on the help screens, five subjects who selected the places where the numbers are displayed on the screen before selecting from the numeric keypad, and six subjects who had trouble selecting AM/PM. All of these errors resulted in extra keypresses, and therefore consumed additional time.

Figure 9:
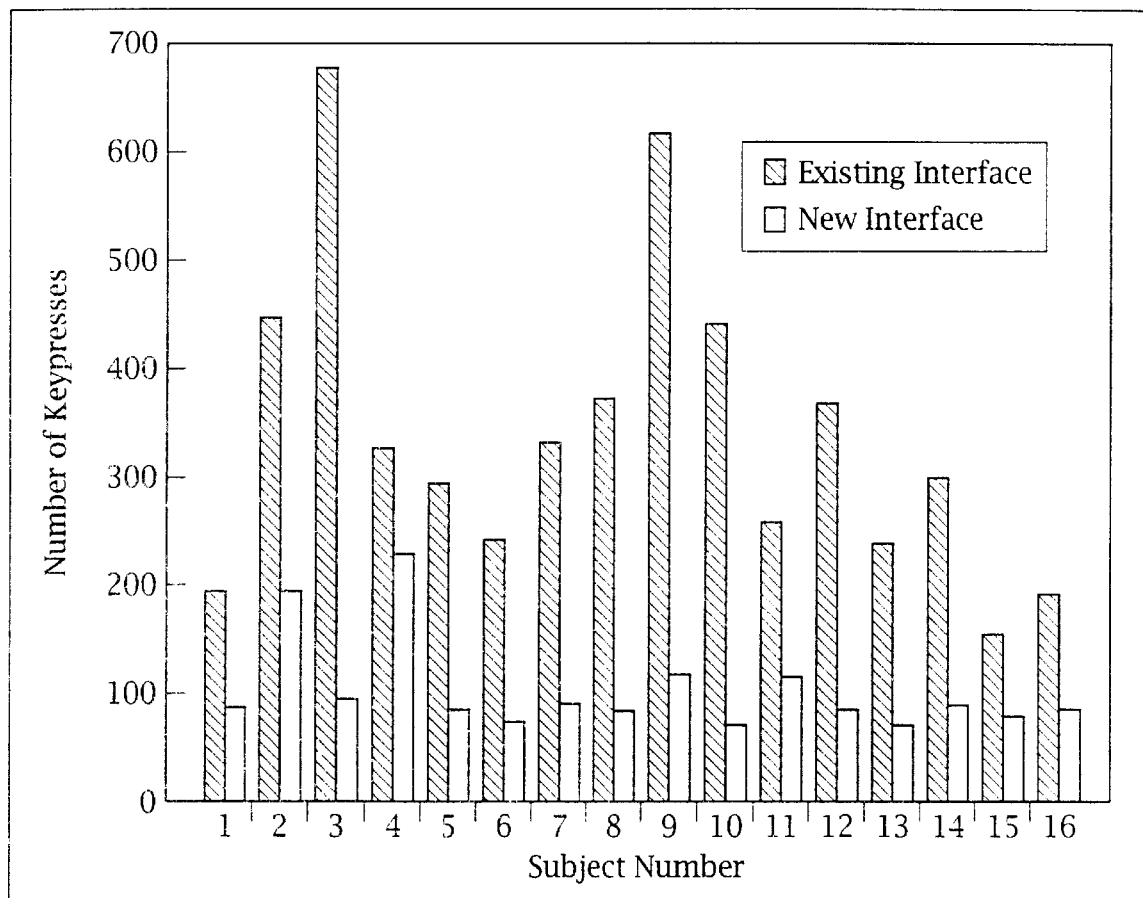
FIG. 9 graphically shows the number of keypresses made by test participants comparing the prior art and the interface of the present invention.
Figure 10:
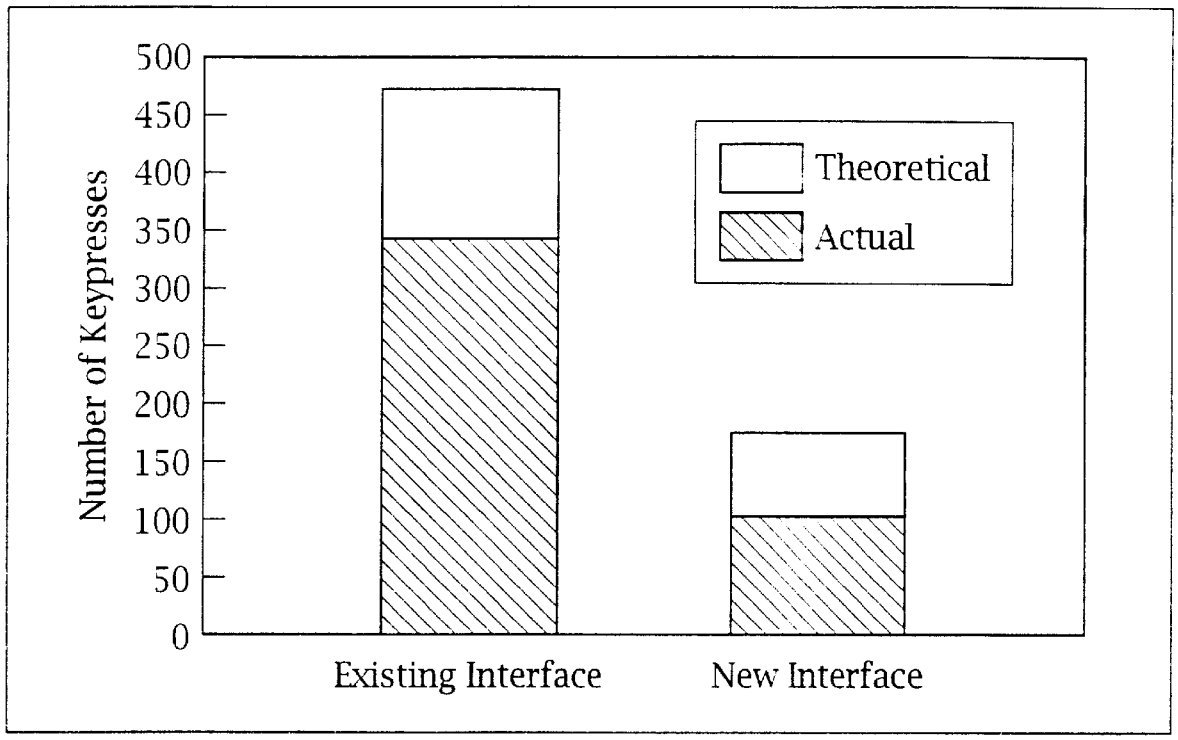
FIG. 10 graphically shows the comparison of the actual and theoretical number of keypresses necessary for programming the prior art and the interface of the present invention.

FIG. 9 shows keypresses per subject and FIG. 10 shows the differences between the theoretical and actual times for the keypresses, using Card's formulas, for each interface.

Several factors may account for the disparity between the times found in this study when compared with the formulas developed by Card. The major difference may be due to the fact that the formulas derived by Card are for experienced users, not novices. Thus, these numbers might indicate how well users might perform after a period of using the system. CHI Square tests, showed significance at $\alpha$<0.01 for both the theoretical and actual times for the keypresses and for the theoretical and actual number of keypresses. In designing the interface, an effort was made to reduce the learning time. Thus, Card's equations are appropriate since all users are considered to be experts. As can be seen in a comparison of the values between the two interfaces, the calculations of $T_{EXECUTE}$ for the interface of the present invention came much closer to that of the theoretical values than did the calculations for the prior art interface, thus proving that the interface of the present invention did reduce the learning time. The results for the theoretical time for minimum number of keypresses, theoretical time for the actual number of keypresses, and actual time can be seen in FIG. 11.

Searching Time

THE PRIOR ART INTERFACE

The prototypes can be divided into screens which represent the programming steps. In order to set the simulation of the prior art interface, a minimum of 13 screens must be entered by the user. The average for the trials of the 16 subjects was 36.8 screens per subject, almost three times more screens than were necessary. Table 5 shows the screens, the minimum number of times they must be accessed, the average number of times that each was accessed, the average amount of time spent on each screen, and the standard deviation of the number of screens opened.

TABLE 5

Screens Required For The Prior Art Interface

| SCREEN | MIN | # OF TIMES OPENED AVG | AVG TIME | S.D. |
| --- | --- | --- | --- | --- |
| CLOCK SET | 1 | 4.9 | 249.4 | 6.2 |
| GET TO CLOCK SET | 0 | 7.2 | 49.0 | 10.6 |
| DISPLAY CLOCK | 1 | 2.6 | 38.7 | 1.5 |
| SELECT PROGRAM | 4 | 8.4 | 99.7 | 3.9 |
| PROGRAM 1 | 3 | 5.5 | 446.6 | 2.1 |
| PROGRAM 2 | 2 | 2.9 | 207.3 | 1.2 |
| PROGRAM 3 | 1 | 1.5 | 172.2 | 0.7 |
| PROGRAM 4 | 0 | 0.9 | 14.4 | 1.0 |
| ON/OFF | 1 | 2.9 | 70.8 | 2.5 |
| TOTAL | 13 | 36.8 | 1476.9 | 21.7 |

Figure 12A:
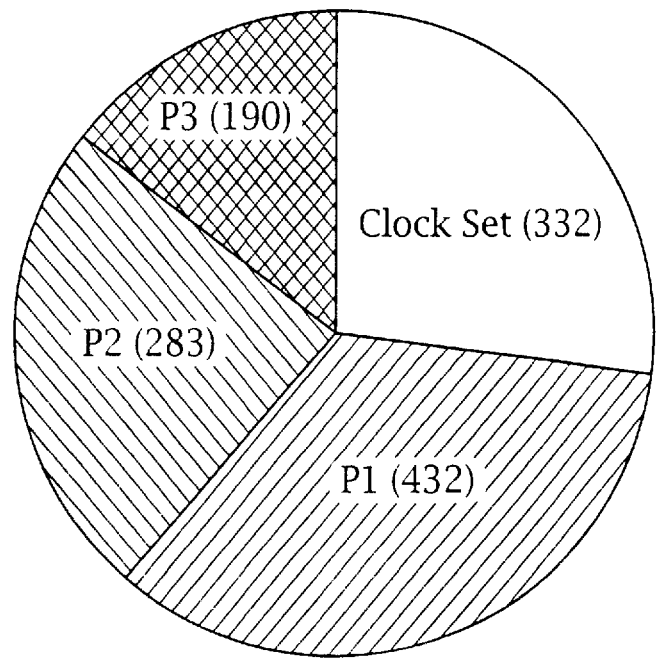
FIGS. 12a and 12b graphically compares the actual and theoretical time necessary for setting the programs in the prior art and the interface of the present invention.
Figure 12B:
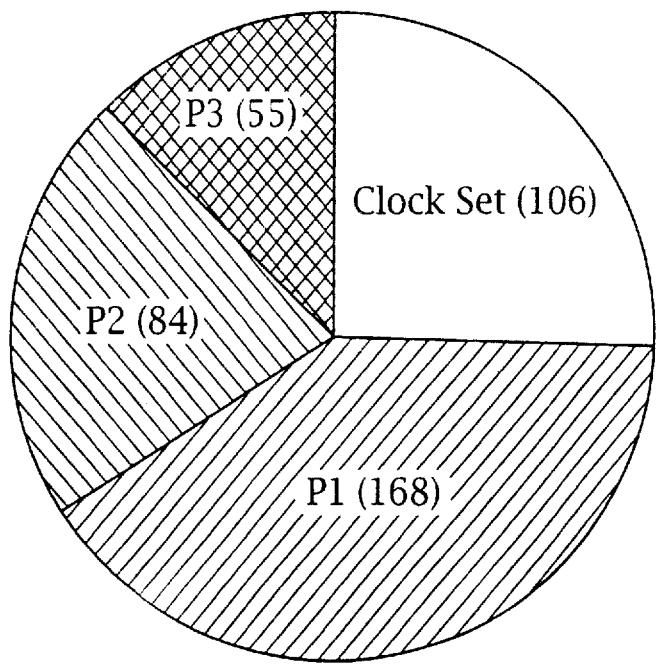

Subjects were confused when using the simulation of the prior art interface. The CLOCK ADJUST screen was displayed when the program began, and the subjects did not understand the directions on the screen. Fourteen out of the sixteen subjects pressed "CLOCK ADJUST" and then "C" which returned them to where they had started. Even if they were able to figure out that this was the correct screen on which to set the clock, 12 out of the 16 subjects wanted to "Memorize" after each step of setting the time and date, rather than after everything was set. This could account for the large number of times that the CLOCK SET, CLOCK ADJUST, and CLOCK screens were accessed. All subjects seemed to spend a great deal of time on the CLOCK SET page, trying to figure out which buttons to use. All subjects were extremely confused between "A+", "A−", "B+", and "B−". In fact, one subject never realized the difference between the "+" and "−" keys, and if, for example, he missed setting the channel, he cycled around another 98 times. In addition, users accidentally accessed Program 4 and turned on and off the VCR several times. The proportion of time spent setting the programs for the prior art interface and the interface of the present invention are shown in FIG. 12.

THE INTERFACE OF THE PRESENT INVENTION

To set the clock and three programs on the interface of the present invention, at least 32 screens must be opened. In testing, subjects opened an average of 42.9 screens, an average of 34% more screens than the minimum required. Although more screens are required to be opened in the interface of the present invention, the percentage of extra screens opened is much smaller than that of the prior art interface. Table 6 shows the screens which must be accessed, the minimum number of times they must be used, the average number of times subjects looked at them, the average amount of time subjects spent using them, and the standard deviation of the number of screens opened.

TABLE 6

Screens Required For The Interface of the present invention

| SCREEN | # OF TIMES OPENED MIN | AVG | AVG TIME | S.D. |
| --- | --- | --- | --- | --- |
| MAIN MENU: To make a selection | 5 | 6.6 | 70.1 | 3.4 |
| TIMER: To set the timer | 1 | 0.9 | 5.8 | 0.3 |
| MAIN MENU HELP: Help on Main Menu | 0 | 0.4 | 8.1 | 0.5 |
| HELP: Help on the Help Screen | 0 | 0.6 | 4.1 | 0.6 |
| CURRENT TIME: To set current time | 1 | 1.4 | 43.4 | 0.8 |
| CURRENT TIME HELP: To obtain help | 0 | 0.1 | 0.1 | 0.2 |
| SELECT THE PROGRAM: Select program | 3 | 4.0 | 26.9 | 1.7 |
| SPECIFIC DAY: To choose day type | 1 | 1.7 | 8.7 | 0.9 |
| SELECT THE PROGRAM HELP: Help | 0 | 0.1 | 0.1 | 0.2 |
| SELECT THE DAY: Choose specific day | 1 | 0.9 | 6.0 | 0.8 |
| SELECT THE MONTH: To choose month | 2 | 2.7 | 23.3 | 1.1 |
| YEAR SET: To set the current year | 1 | 1.4 | 41.4 | 0.5 |
| CHANNEL: To choose the channel | 3 | 3.6 | 24.9 | 1.4 |
| START TIME: To choose start time | 3 | 3.8 | 65.8 | 1.5 |
| STOP TIME: To choose stop time | 3 | 3.6 | 48.4 | 1.4 |
| TAPE SPEED: To choose tape speed | 3 | 3.6 | 17.3 | 1.4 |
| CONFIRMATION: To review programs | 3 | 4.8 | 114.9 | 2.6 |
| DAY OF MONTH: To choose the day | 2 | 2.6 | 16.6 | 1.1 |
| TOTAL | 32 | 42.9 | 560.1 | 15.9 |

When the VCR was first turned on, subjects viewed a prompt instructing them to set the time. Two subjects looked for a Main Menu at this point, and exited the screen before setting the time. The only occasion where the subjects had to enter the Main Menu screen was to set programs to record or to reset the current time or current date. This screen was accessed more times than necessary, possibly because several subjects selected the "Main Menu" button on the screen before setting the time, date, or pressing the "OK" button.

Help screens were accessed either when the user was confused as to what to do, or just for curiosity (from users' comments). The one "Help" button that provided the most assistance was MAIN MENU HELP. It told the users to "POWER OFF" and then to set the Timer to "ON" when programming was finished.

Only 34% more screens were opened when programming the interface of the present invention, whereas in the prior art interface, the additional number of screens opened approached 300%. This indicates that there was much more confusion when using the prior art interface. The two simulations showed significance at $\alpha<0.10$ for the number of screens opened when subjected to a CHI Square test of independence.

Mental Preparation Time

THE PRIOR ART INTERFACE

Both interfaces required that a confirmation button be pressed before proceeding to the next step. In the prior art interface, "C" represented this confirmation. At the end of each sub-task (setting the time, program 1, program 2, and program 3), it was necessary to press "C" after the instructions OK to Memorize appeared on the screen. Pressing this button would either advance the user to the CLOCK screen if he were on the CLOCK ADJUST screen, or the PROGRAM screen if he were on one of the programming screens. Theoretically, "C" on the prior art interface must be pressed a minimum of five times by each subject to complete the task, and 10.5 seconds is consumed in doing this. In testing, this button was pressed an average of 9.1 times by each the 16 subjects, which is almost double the number of keypresses required. Each keypress should theoretically have taken 2.1 seconds. However, in actuality, it took 12.1 seconds per "C" keypress, which is almost six times more than the theoretical value calculated using Card's formula.

The extra keypresses can be attributed to the fact that five users thought that they had to press the "C" button after each category they changed. The extra time can be attributed to the fact that, as many subjects commented, they were doing the tasks by trial and error and had to recheck all of the information carefully to make sure it was correct. While test participants were using the prior art interface, many made comments that the numbers seemed to be changing by themselves. What had really happened was that the test participants were not looking at the correct place on the screen to see the changes and were confused by the blinking numbers, or they had entered information faster than it could be displayed, and as a result, pressed too many buttons and passed the desired choice.

THE INTERFACE OF THE PRESENT INVENTION

The interface of the present invention used a blue "OK" button on the bottom of each screen that required more than one keypress. These screens included: the current year, current time, start time, stop time, channel, and the confirmation screen. Pressing "OK" either brought the user to the next step of the programming sequence or back to the Main Menu from the confirmation screen. It was necessary for each subject to press this button a minimum of 14 times to complete the task, which would theoretically have taken 37.1 seconds. In the testing situation, "OK" was pressed an average of 18.5 times per subject. This was only 33% more than the minimum number of keypresses required. The average time was 6.9 seconds per "OK" pressed, which was 2.6 times more than the theoretical 2.65 per keypress found by applying Card's formula.

COMPARISON OF INTERFACES

Comparing the results from the two interfaces on length of mental preparation time for pressing of the confirmation buttons, the interface of the present invention took considerably less time. If the user is confident about the information he enters, it takes less time to confirm the data entered. When subjected to a T-Test, there was no significance for the number of times that "C" or "OK" was pressed, or between the time that it took for the two buttons to be pressed.

THE PRIOR ART INTERFACE

Test participants were asked to rate each interface using the subjective ratings, including the Cooper-Harper Rating Scale. Using these ratings, the simulation of the prior art interface was rated and can be seen in Table 7.

TABLE 7

Averages And Standard Deviations Of The Subjective Ratings For The Prior Art Interface

| SCALE | AVERAGE | STANDARD DEVIATION |
|---|---|---|
| LIKE/DISLIKE | 5.47 | 1.58 |
| EASY/DIFFICULT | 5.41 | 1.40 |
| COOPER-HARPER | 6.66 | 2.61 |

Note: The Like/Dislike and Easy/Difficult ratings were based on a 7-point scale and the Cooper-Harper rating was based on a 10-point scale.

The results show that this interface is perceived to be almost at the unsatisfactory level according to the Cooper-Harper Scale and on the "dislike" and "difficult" ends of the other scales. A T-Test on the subjective data showed no significance.

The number of keystrokes required was found to directly affect the total time. When the selection method was used in the prior art interface, most subjects did not calculate whether going up or down would be faster, thus resulting in extra keypresses. The total time for each critical step and the errors made were proportional to the number of keypresses. Both interfaces took approximately the same percentage of the total time for the critical steps. The percentages for these critical steps can be seen in Table 8 and FIGS. 13 and 14.

The interface of the present invention was able to remedy all of the above mentioned problems. Results of the evaluations for the interface of the present invention can be seen in Table 9.

TABLE 8

Percentage Of Total Time For The Six Programming Steps

Prior Art Interface

| Critical Step | | Interface of the present invention |
|---|---|---|
| Clock Set | 22% | 20% |
| Program 1 | 30% | 32% |
| Program 2 | 19% | 16% |
| Program 3 | 13% | 11% |
| Search Time | 16% | 21% |

TABLE 9

Numerical Averages And Standard Deviations Of The Subjective Ratings For The Interface of the present invention

| SCALE | AVERAGE | STANDARD DEVIATION |
|---|---|---|
| LIKE/DISLIKE | 1.94 | 1.13 |
| EASY/DIFFICULT | 1.91 | 1.02 |
| COOPER-HARPER | 2.13 | 1.21 |

Note: The Like/Dislike and Easy/Difficult ratings were based on a 7-point scale and the Cooper-Harper rating was based on a 10-point scale.

The results show that the interface of the present invention was well-liked. It was rated at the "Good" level on the Cooper Harper rating scale and on the "like" and "easy" ends of the other two scales.

An analysis of users' comments regarding the interface of the present invention revealed the reasons for their evaluations. The frequency with which their likes and dislikes occurred confirms the fact that the newly developed interface clearly offers users what they want, and remedies problems perceived in the use of the prior art interfaces. Table 10 lists favorable comments made by the subjects.

TABLE 10

Comments Regarding The Interface of the Present Invention

| Number of Comments | Subjects |
|---|---|
| 8 | Easy to operate |
| 8 | Like it much better and would use it more often |
| 7 | No searching for choices was required |
| 6 | All choices were given at once |
| 6 | Like on-screen instructions |
| 5 | Like menu driven interface |
| 3 | Like entry method rather than selection method |
| 3 | Like single button keypress |
| 3 | Like to correct mistakes easily |
| 3 | Like "today", "tomorrow", "Monday-Friday" and "Days of Week" features |
| 2 | Like the use of a remote controlled device |
| 2 | Good confirmation screen |
| 2 | Like color coding |
| 1 | Like feedback |
| 1 | Like are no abbreviations |
| 1 | Like User-Friendliness |
| 1 | Like no leading zeros |
| 1 | Like "OK" buttons |
| 1 | Like the calendar and clock display |
| 1 | Like the quick interface |
| 1 | Like the good Help system |
| 1 | Like entering start and stop times, rather than duration |
| 1 | Thought it was even easier to use than the bar coder |

When subjects compared the simulation of the interface of the present invention with the simulation of the prior art interface, they unanimously preferred the interface of the present invention over any other VCR they had used. After the testing, some of the suggestions that subjects made for alternate input devices include: touch-screen, cursor control, voice, trackball, and automatic tracking of the remote.

Overall, the critical times for programming the interface of the present invention were at least half of those for the prior art interface. The new design reduced the programming time by 54% and reduced the errors by 500%.

The number of screens opened above the minimum number required had an effect on search time. In the prior art interface, 283% more screens were opened, whereas in the interface of the present invention, screens were opened only 34% more frequently. However, overall, the same percentage of time was spent searching on both interfaces.

Mental preparation time was measured in both simulations by pressing the confirmation buttons. The time delay in pressing "C" and "OK" respectively increases the times for the critical steps in the prior art and new simulations. The interface of the present invention took considerably less time. If the user is confident about the information entered, it takes less time to confirm the entry.

All measures remained in the same proportions to the total time in both interfaces. However these times were significantly reduced when 30% of the sample gave up while trying to program the prior art interface, therefore this data was excluded.

Attending to the user's needs is important in designing any interface, and must be modified for each application. By reducing the searching, learning times, and entry times, the mental load is also minimized. Some tradeoffs are necessary as a result of subjective and objective data. It is extremely difficult to design an interface for all levels of users. Thus, a menu system was used in an attempt to satisfy all users.

It must be noted that, in addition to reducing the programming time, the interface of the present invention reduced the number of incorrect recordings by 50%. The severity of the errors is unimportant here because one wrong entry will cause an irretrievable mistake and the user will not record the intended program. One study reported that faulty inputs, which lead to missing the program, can be reported by almost every present day owner of a VCR.

EXAMPLE 2

The "smart screen" aspect of the present invention is further explored in the present example. This aspect of the invention allows the interface to anticipate or predict the intent of the user, to provide, as a default user choice, the most likely action to be taken by the user of the programmable device as a default, which may be either accepted or rejected by the user, without delay to the user. The intelligent selection feature may also automatically choose an option and execute the selected option, without further intervention.

When a user regularly applies the VCR device, for example, to record a given television show which appears weekly on a given television channel, at a given time, on a given channel, such an action could be immediately presented to the user as a first option, without forcing him to explicitly program the entire sequence.

Further, if an entire television programming guide for a week or month is available as a database, the interface could actively determine whether the desired show is preempted, a repeat, changed in time or programming slot, etc. Thus, the interface could present information to the user, of which he might not be aware, and predict an action based on that information. Such a device could, if set in a mode of operation that allows such, automatically execute a sequence of instructions based on a predicted course of action. Thus, if a user is to be absent for a period, he could set the machine to automatically record a show, even if the recording parameters are not known at the time of setting. Of course, this depends on the availability of a database of current broadcast schedules, however, such a database may generally be available. An on-line database system of known type may be used and need not be described in detail herein.

The smart screens may be implemented as follows. The controller may be, for example, a Macintosh ci computer, operating under Macintosh 7.0 operating system. The Hypercard 2.0 software may be used to implement the screen interface, which incorporates the above-described features, which is generally compatible with the Hyperpad software described above. HyperCard is mentioned due to its capabilities to reference external programs, thus allowing interfacing to various software and hardware devices. A more global scripting language, such as Frontier by UserLand Software Inc., may also be used, especially where low level hardware control of interfaced devices, such as a VCR, multimedia adapter, or the like is desired. Other scripting languages include versions of REXX, by IBM, available on many platforms. The input device is an Apple ADB mouse, and the output display is an 8 bit or 24 bit graphics color adapter connected to, e.g., a 14" color monitor. In addition, various parameters concerning the use of the interface are stored in the computer's memory, and a non-volatile mass storage device, such as a hard disk drive, or EEPROM or EPROM, as well as battery backed RAM could also be used.

From the stored information regarding the prior use of the interface by the user, including prior sessions and the immediate session, and a current state of the machine, a predicted course of action or operation may be realized. This predicted operation is, in the context of the current user interface state, the most probable next action to be taken by the user.

The predicted operation is based on: the identity of the user, if more than one user operates the interface and machine, the information already entered into the interface during the present programming session, the presently available choices for data entry, settings for the use of the machine, which may be present as a result of a "isetup" operation, settings saved during a prior session, and a database of programming choices. In the case of a HyperCard script, the interface software calls another program which has access to the necessary data in the memory, as well as access to any remote database which may be necessary for the function. Using a predictive technology, such as Boolean logic, fuzzy logic, neural network logic, or other type of artificial intelligence, a most probable choice may be presented to the user for his approval, or another alternative choice may be selected. Further, a number of most probable choices may be presented simultaneously or in sequence, in order to improve the probability that the user will be immediately or quickly presented with an acceptable choice. If multiple choices are presented, and there is limited room on the display, two (or more) similar choices may be merged into a single menu selection, which may be resolved in a secondary menu screen.

Figure 24:
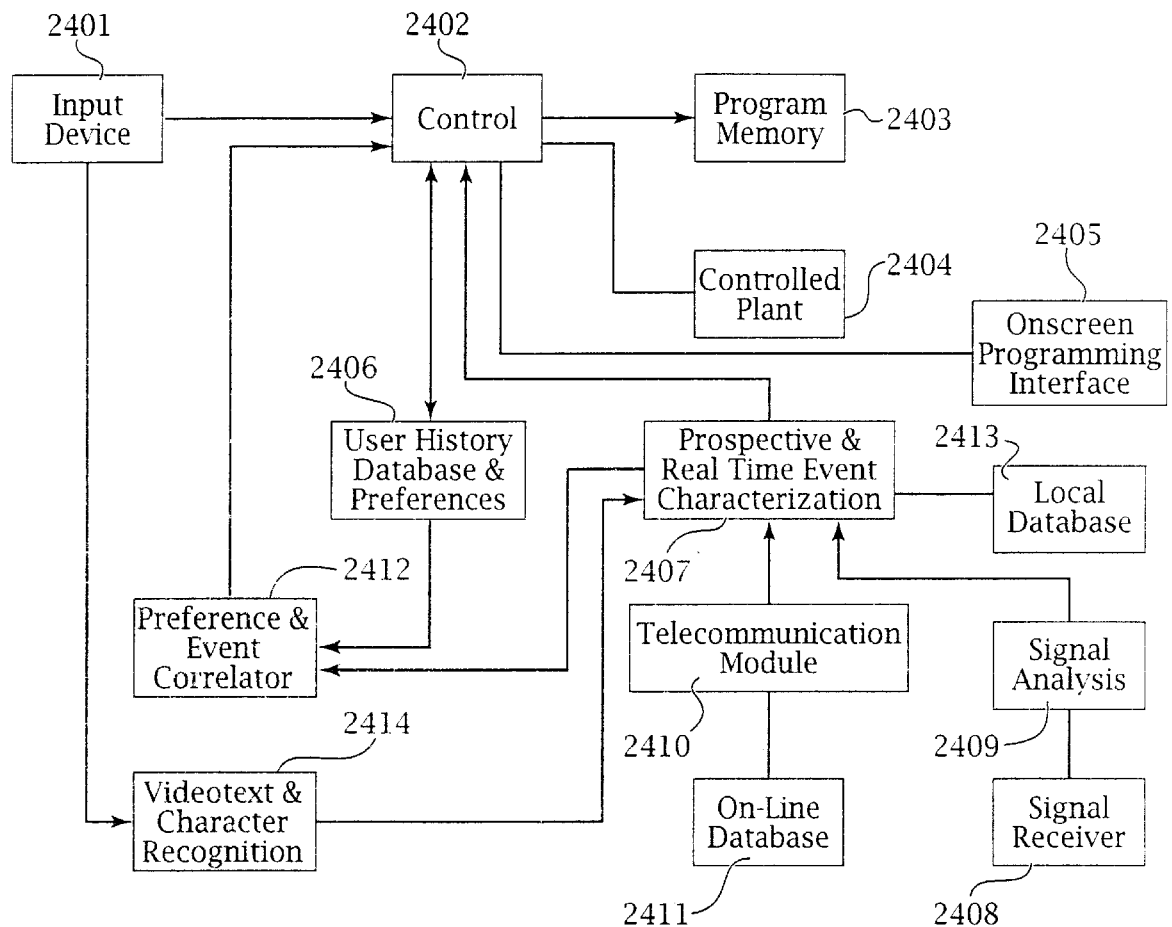
FIG. 24 is a block diagram of a control system for characterizing and correlating a signal pattern with a stored user preference of the present invention.

FIG. 24 shows a system for correlating a user's preferences with a prospective or real-time occurrence of an event. The input device 2401, which is a remote control with a pointing device, such as a trackball, provides the user's input to the control 2402. The program is stored in a program memory 2403, after it is entered. The control 2402 controls a plant 2404, which is a VCR. The control also controls an on-screen programming interface 2405, through which the user interactively enters the program information. Each program entry of the user is submitted to the user history database and preferences module 2406, which may also receive explicit preference information, input by the user through the input device 2401. The prospective and real time event characterization unit 2407 uses any and all information available in order to determine the character of a signal input, which is a video signal, from the signal receiver 2408. A signal analyzer 2409 provides a preliminary analysis and characterization of the signal, which is input to the prospective and real time event characterization unit 2407. The prospective and real time event characterization unit 2407 also interacts and receives an input from a telecommunication module 2410, which in turn interacts and receives information from an on-line database 2411. A user preference and event correlator 2412 produces an output relating to a relatedness of an event or prospective event and a user preference. In the event of a high correlation or relatedness, the control 2402 determines that the event or prospective event is a likely or most likely predicted action. The prospective event discussed above refers to a scheduled event, which is likely to occur in the future. The characterization unit also has a local database 2413 for storing schedule information and the like.

The following is an example of a user wishing to program the machine interface of a VCR to record, e.g., "Married With Children" (Fox, Sunday, 9:00 p.m.), every time it occurs. The interface would first perform a self diagnostic to determine whether the machine is set up and operating correctly. This would include a determination of whether the clock has been set and thereafter operating continuously. Of course, the clock could have, in practice, a battery to minimize the occurrence of problems relating to clock function. The interface would then, if the clock is not properly set, and if there is no telecommunication or other external means for automatically determining the exact time, present the user with a menu selection to set the proper time. If the user does not have access to a source of the exact time, the step may be deferred. If the machine has access to an external source of the exact time, it would then preferably access this source first. This could include a telephone connection to a voice line which repeats the time. The computer would then perform a speech recognition algorithm which would be used to determine the time. Such a speech recognition algorithm could also be used as a part of the user interface for other purposes. Alternatively, a modem could be used to obtain the time in digitally coded form, which would alleviate the need for speech recognition capabilities for this function. An on-line connection could also be used in order to obtain information concerning television scheduling. A further alternative would be to access a video signal which contains time information. For example, many cable broadcasting systems have a channel which continuously broadcasts the time. The interface could tune to this channel, acquire a representation of the screen image, and perform a character recognition algorithm to determine the time. This character recognition algorithm could also be used to decipher information regarding programming schedules, which may appear on certain cable broadcast channels. Thus, the interface determines a need for setting of the clock, and then takes measures to fulfill the necessary function, through any and all available resources, which may include speech recognition, character recognition, digital telecommunication means, radio wave reception and interpretation, and links to other devices.

The system next must determine what function the user wishes to perform. In this regard, if more than one user has access to the system, the user identifies himself to the interface, in a user identification step 1701 or an analogous action, which may be a coded entry, or a selection from the menu. If the interface has voice recognition capability, then the user may be recognized by his voice pattern, or merely by stating his name. The interface then accesses the memory for a profile of the past use of the machine by the user, which may include the entire prior history, relevant abstracts of the history, or derived user preferences, as shown in the personalized startup based on user profile step 1702, which information is also stored and used in the past user history determining element 2107. These choices differ in the amount of storage necessary in order to retain the desired information.

Thus, if the user has only used the VCR to record, e.g., the NBC 11 o'clock news, i.e., record all days from 11:00 p.m. to 11:30 p.m. on NBC, in the past, the most likely current predicted choice would be the NBC 11 o'clock news. If the interface were to present a number of choices, having lower probability, then it would interpret the recording history to be "news" based on a database of broadcast information. Therefore, a prediction of lower probability would be ABC or CBS news at, e.g., 11:00 p.m., and the NBC news at, e.g., 5:00 p.m. Thus, these three choices would be initially presented to the user, along with a menu selection to reject these predicted choices. In this case, the user would select the "reject" selection, and would be presented with a next predicted desired menu choice. Since the user history, in this case, does not provide for another choice of high probability, the user would be prompted to explicitly choose the program sequence by day, time, channel, and duration. The user would then enter the starting time for recording according to the methods described above. The interface would then search its databases regarding the user and broadcast listings to present a most likely choice, as well as all available alternatives. In this case, the user history is of little help, and is not used to predict. In other cases, the system would use its intelligence to "fill in the blanks", which could, of course, be rejected by the user. The most likely choices would then be those programs that begin at the selected time. If the user had input the channel, instead of starting time, then the presented choices would be the broadcast schedule of the channel, e.g. Fox, for the selected day. The user then selects one of the available choices, which would complete the programming sequence. If no database of broadcasts is available, then the user must then explicitly define all parameters of the broadcast. When the programming is completed, the interface must then update its user database, prompt the user to set the VCR to record, by, e.g., inserting a blank or recordable tape.

The user would then proceed to explicitly program the VCR interface to record "Married with Children" on Fox at 9:00 p.m. on Sunday evening. If a database is available, it might also show that "Married with Children" is also syndicated in reruns, and therefore may be available on other channels at other times. Thus, during the subsequent session, both the premier showing and re-run of "Married With Children" would be available predicted choices, along with the 11 o'clock News on NBC.

Having demonstrated a preference for "Married with Children", the interface would then characterize the program. This would include, for example, a characterization of the soundtrack, the background, foreground, actors and actresses present, credits, etc. The interface would then attempt to correlate the features present in the reference selection with other available selections. This comparison may be with a preformed database, providing immediate results, or prospectively, after entry of the reference selection. Of course, a number of correlation functions may proceed simultaneously, and various choices may be merged to form a compound reference selection. Further, as various "episodes" of the reference selection occur, the system appends and integrates the most recent occurrence with the stored reference information.

Returning to the programming process, if the user instead wishes to record weather reports on all channels, the interface may be of further help. The interface may control a plurality of tuner elements 2502 of a video signal reception device 2501, so that a plurality of broadcasts may be simultaneously received. Using the mass storage and possibly image data compression described above, a plurality of broadcasts may also be recorded simultaneously in the intermediate storage 2503. The mass storage may be multiple VCRs, optical storage, or magnetic storage, including disk and tape. The optical recording tape produced by ICI, Inc. might also be a useful storage medium for large volumes of data, as might be generated by recording multiple video signals. In this case, the interface 2506 would access its associated database 2413 to determine, at a given time, which channels have "news". The interface could also randomly or systematically monitor broadcasts for "special reports". The interface would then monitor these channels for indicia of a "weather" broadcast. For example, the newscaster who appears to report the weather on a given show is usually the same, so that a pattern recognition system 2505 of the video frame could indicate the presence of that newscaster. In addition, the satellite photographs, weather radar, computer generated weather forecast screens, etc. are often similar for each broadcast. Finally, news segments, such as "weather" often appear at the same relative time in the broadcast. Using this information, the interface could begin recording at a beginning of a news segment, such as "weather", stop recording during commercials, and continue recording after return from break, on all selected channels. It is noted that the system of the present invention is intelligent, and may therefore "learn" either explicitly, or through training. Therefore, if the system made an error during the process, the user would define the error to the system, e.g., a substitute newscaster or rearrangement of news segments, so that the system is less likely to make the same error again. Thus, while such a system is inherently complex, it poses significant advantages for an user. Further, while the system is complicated, the interface provides simplicity, with inductive reasoning and deductive reasoning.

It is noted that various algorithms and formulae for pattern recognition, correlation, data compression, transforms, etc., are known to those skilled in the art, and are available in compendiums, such as Netravali, Arun N., and Haskell, Barry G., "Digital Pictures Representation and Compression", Plenum Press, New York (1988); Baxes, Gregory A., "Digital Signal Processing, A Practical Primer", Prentice-Hall, Englewood Cliffs, N.J. (1984); Gonzalez, Rafael C., "Digital Image Processing", Addison-Wesley, Reading, Mass. (1987), and, of a more general nature, Press, William H. et al, "Numerical Recipes in C The Art of Scientific Computing", Cambridge University Press, 1988, which are incorporated herein by reference.

A further example of the use of the advanced intelligent features of the present invention would be the use of the system to record, e.g., "live" musical performances. These occur on many "talk" shows, such as "Tonight Show with Johnny Carson" (NBC, 11:30 p.m. to 12:30 p.m., weeknights), "Saturday Night Live" (NBC 11:30 p.m. to 1:00 a.m. Saturday-Sunday), and other shows such as the "Grammy Awards". The interface, if requested by the user to record such performances, would seek to determine their occurrence by, e.g.: analyzing a broadcast schedule; interacting with the on-line database 2411; and by reference to the local database 2413. When the interface determines with high probability that a broadcast will occur, it then monitors the channel(s) at the indicated time(s), through the plurality of tuners 2502. In the case of pay-per-view systems and the like, which incorporate encrypted signals, an encryption/decryption unit 2509 is provided for decrypting the transmitted signal for analysis and viewing. This unit also allows encryption of material in other modes of operation. During the monitoring, the interface system acquires the audio and video information being broadcast, through the signal receiver 2408, and correlates this information with a known profile of a "live musical performance", in the preference and event correlator 2412. This must be distinguished from music as a part of, e.g., a soundtrack, as well as "musicals" which are part of movies and recorded operas, if these are not desired. Further, music videos may also be undesirable. When the correlation is high between the broadcast and a reference profile of a "live musical performance", the system selects the broadcast for retention. In this case, the information in the intermediate storage 2503 is transferred to the plant 2507, which includes a permanent storage device 2508. The intermediate storage 2503 medium is used to record a "buffer" segment, so that none of the broadcast is lost while the system determines the nature of the broadcast. This, of course, allows an extended period for the determination of the type of broadcast, so that, while real-time recognition is preferred, it is not absolutely necessary in order to gain the advantages of the present invention.

Thus, while it is preferable to make a determination in real time, it is possible to make an ex post facto determination of the nature of the broadcast program. By using an available delay, e.g., about 5 to about 300 seconds, or longer, the reliability of the determination can be greatly increased as compared to an analysis of a few frames of video data, e.g., about 15 to about 300 mS. As stated above, the determination storage need not be uncompressed nor lossless, so long as features necessary to determine the character of the broadcast are present. However, it is preferred that for broadcast recording, the storage be as accurate as possible, so that if a compression algorithm is implemented, it be as lossless as possible. The MPEG II standard would be applicable in this situation. In a preferred situation, approximately 5 minutes of broadcast material is analyzed in order to make a determination of the content. This material is stored in two media. First, it is stored by normal means on video tape. Second, it is received in parallel by the computer control, where the data is subject to a number of recognition and characterization processes. These are performed in parallel and in series, to form an extracted feature storage matrix.

A preferred method incorporates one or more digital signal processor based coprocessor elements, which may be present on, e.g., Nubus cards in the Macintosh ci or other computer type. These elements may be based on C-Cube CL550 (JPEG compression), AT&T DSP32C, AT&T DSP3210, AMD 29000 series, Motorola DSP 96000ADS, Texas Instruments TMS 32050, etc, or a combination of types. A typical board containing a DSP is the MacDSP3210 by Spectral Innovations Inc., containing an AT&T digital signal processor and an MC68020 CISC processor, and uses Apple Real-time Operating System Executive (A/ROSE) and Visible Cache Operating System (VCOS). It is preferred that the processors employed be optimized for image processing, because of their higher throughput in the present applications, to process the video signals, and more general purpose signal processors to analyze the audio signals, because of the greater availability of software to analyze audio signals on these processors, as well as their particular strengths in this area. An array processor which may be interfaced with a Macintosh is the Superserver-C available from Pacific Parallel Research Inc., incorporating parallel Inmos Transputers. Such an array processor may be suitable for parallel analysis of the image segment and classification of its attributes. Pattern recognition, especially after preprocessing of the data signal by digital signal processors and image compression engines, may also be assisted by logical inference engines, such as FUTURE (Fuzzy Information Processing Turbo Engine) by The Laboratory for International Fuzzy Engineering (LIFE), which incorporates multiple Fuzzy Set Processors (FSP), which are single-instruction, multiple data path (SIMD) processors. Using a fuzzy logic paradigm, the processing system may provide a best fit output to a set of inputs more efficiently than standard computational techniques, and since the presently desired result requires a "best guess", rather than a very accurate determination, the present interface is an appropriate application of this technology. As noted above, these processors may also serve other functions such as voice recognition for the interface, or extracting text from video transmissions and interpreting it. It is also noted that, while these coprocessing engines are now costly, the present emergence of high levels of integration of functionality on semiconductor chips, as well as the development of optical computers will dramatically reduce the cost of implementing this aspect of the present invention; however, the present state of the art allows the basic functions to be performed.

It is noted that various methods are available for determining a relatedness of two sets of data, such as an image or a representation of an image. These include the determination of Hausdorff distance, fuzzy correlation, arithmetic correlation, mean square error, neural network "energy" minimization, covariance, cross correlation, and other known methods, which may be applied to the raw data or after a transformation process, such as an Affine transformation, a Fourier transformation, a warping transformation, a color map transformation, and the like. Further, it is emphasized that, in image or pattern recognition systems, there is no need that the entire image be correlated or even analyzed, nor that any correlation be based on the entirety of that image analyzed. Further, it is advantageous to allow redundancy, so that it is not necessary to have unique designations for the various aspects of the data to be recognized, nor the patterns to be identified as matching the uncharacterized input data.

The MSHELL from Applied Coherent Technology is a software system that runs on a Mercury MC3200 array processor, in conjunction with a Data Translation DT2861 or DT2862. The NDS1000 Development System from Nestor, Inc., provides image recognition software which runs on a PC compatible computer and a Data Translation DT2878. The above mentioned processing hardware and software, as known, is incorporated herein.

The C-Cube CL550 is fully disclosed in "C-Cube CL550 JPEG Image Compression Processor", Preliminary Data Book, August 1991, and addendum dated Nov. 20, 1991, incorporated herein by reference, and products incorporating the CL550 include the JPEG Video Development Kit (ISA bus card with Chips and Technologies PC video 82C9001A Video Window Controller), and the C-Cube CL550 Development Board/PC for ISA Bus (CL550, for use with Truevision TARGA-16 or ATVista cards) or for NuBus (Macintosh). The so-called C-Cube "CL950" (unofficially announced) is a MPEG decoder device. Such a device as the CL950 may be particularly useful for use in the present VCR for reproducing compressed program material, which may be compressed by the present apparatus, or may be used for decompressing pre-compressed program material.

It is noted that all functions of a VCR would also be simplified by the use of such powerful processors, and thus it is not only these advanced functions which are facilitated by the processors. It is also noted that these image recognition functions need not necessarily all be executed local to the user, and may in fact be centralized. This would be advantageous for two reasons: first, the user need not have an entire system of hardware in the VCR, and second, many of the operations which must be performed are common to a number of users, so that there is a net efficiency to be gained.

EXAMPLE 3

The interface of the present invention incorporates an intelligent user interface level determination. This function analyzes the quality of the user input, rather than its content. Thus, this differs from the normal interface user level determination which requires an explicit entry of the desired user level, which is maintained throughout the interface until explicitly changed. The present interface may incorporate the "smart screen" feature discussed above, which may, through its analysis of the past user interaction with the interface predict the most likely predicted user input function. Thus, the predictive aspects of Example 1 may be considered a species of the intelligent user level interface of Example 2. However, the following better serves to define this aspect of the invention.

The input device, in addition to defining a desired command, also provides certain information about the user which has heretofore been generally ignored or intentionally removed. With respect to a two-dimensional input device, such as a mouse, trackball, joystick, etc., this information includes a velocity component, an efficiency of input, an accuracy of input, an interruption of input, and a high frequency component of input. This system is shown schematically in FIG. 21, which has a speed detector 2104, a path optimization detector 2105, a selection quality detector 2106, a current programming status 2108, an error counter 2109, a cancel counter 2110, a high frequency signal component detector 2112, an accuracy detector 2113 and a physio-dynamic optimization detector 2114. In addition, FIG. 21 also shows that the interface also uses a past user history 2107, an explicit user level choice 2111 and an explicit help request 2115.

This list is not exclusive, and is somewhat dependent on the characteristics of the specific input device. For a mouse, trackball, or other like device, the velocity or speed component refers to the speed of movement of the sensing element, i.e. the rotating ball. This may also be direction sensitive, i.e., velocity vector. It is inferred that, all other things being equal, the higher the velocity, the more likely that the user "knows" what he is doing.

The efficiency of input refers to two aspects of the user interface. First, it refers to the selection of that choice which most simply leads to the selection of the desired selection. For example, if "noon" is an available choice along with direct entry of numbers, then the selection of "noon" instead of "12:00 p.m." would be more efficient. The second aspect of efficiency has to do with the path taken by the user in moving a menu selection cursor from a current position to a desired position. For example, a random curve or swiggle between locations is less efficient than a straight line. This effect is limited, and must be analyzed in conjunction with the amount of time it takes to move from one location of a cursor on the screen to another; if the speed of movement is very rapid, i.e. less than about 400 mS for a full screen length movement, then an inefficiency in path is likely due to the momentum of the mouse and hand, momentum of the rolling ball, or a physiological arc of a joint. This aspect is detected by the physio-dynamic optimization detector 2114. Thus, only if the movement is slow, deliberate, and inefficient, should this factor weigh heavily. It is noted that arcs of movement, as well as uncritical damping of movement around the terminal position may be more efficient, and a straight path actually inefficient, so that the interface may act accordingly where indicated. Thus, an "efficient" movement would indicate an user who may work at a high level, and conversely, an inefficient movement would indicate a user who should be presented with simpler choices.

Likewise, if a movement is abrupt or interrupted, yet follows an efficient path, this would indicate a probable need for a lower user interface level. This would be detected in a number of elements shown in FIG. 21, the speed detector 2104, a high frequency signal component detector 2112, an accuracy detector 2113 and a physio-dynamic optimization detector 2114. In addition, FIG. 21 also shows the use of a past user history 2107, an explicit user level choice 2111 and an explicit help request 2115.

While the interface may incorporate screen buttons which are smart, i.e. those which intelligently resolve ambiguous end locations, the accuracy of the endpoint is another factor in determining the probable level of the user. Thus, for example, if a 14" color monitor screen is used, having a resolution of 640 by 480 pixels, an accurate endpoint location would be within a central area of a screen button of size about 0.3" by about 1.0", would be an area of about 0.25" by about 0.75". A cursor location outside this location, but inside the screen button confines would indicate an average user, while a cursor location outside the screen button may be inferred to indicate the button, with an indication that the user is less experienced in using the pointing device.

Finally, in addition to the efficiency of the path of the cursor pointing device, a high frequency component may be extracted from the pointer signal by the high frequency signal component detector 2112, which would indicate a physical infirmity of the user (tremor), a distraction in using the interface, indecision in use, or environmental disturbance such as vibration. In this case, the presence of a large amount of high frequency signal indicates that, at least, the cursor movement is likely to be inaccurate, and possibly that the user desires a lower user level. While this is ambiguous based on the high frequency signal content alone, in conjunction with the other indicia, it may be interpreted. If, for example, the jitter is due to environmental vibrations, and the user is actually a high level user, then the response of the user level adjust system would be to provide a screen display with a lowered required accuracy of cursor placement, without necessarily qualitatively reducing the implied user level of the presented choices, thus, it would have an impact on the display simplification 2103, with only the necessary changes in the current user level 2101.

It is noted that, the adaptive user level interface is of use in uncontrolled environments, such as in a moving vehicle, especially for use by a driver. An intelligent system of the present invention would allow the driver of such a vehicle to execute control sequences, which may compensate for the limited ability to interact with an interface while driving. Thus, the driver need not explicitly control all individual elements, because the driver is assisted by an intelligent interface. Thus, for example, if it begins raining, the interface would predict the windshield wipers should be actuated, the windows and any roof opening closed, and possibly the headlights activated. Thus, the driver could immediately assent to these actions, without individually actuating each control. In such a case, the screen interface would provide a small number of choices, which may be simply selected. Further, under such conditions, there would likely be a large amount of jitter from the input device, which would be filtered to ease menu selection. Further, this jitter would indicate an unstable environment condition, which would cause the interface to present an appropriate display.

Likewise, the present interface could be used to control complex telecommunications functions of advanced telephone and telecommunications equipment. In such a case, the user display interface would be a video display, or a flat panel display, such as an LCD display. The interface would hierarchically present the available choices to the user, based on a probability of selection by the user. The input device would be, for example, a small track ball near the keypad. Thus, simple telephone dialing would not be substantially impeded, while complex functions, such as call diversion, automated telediction control, complex conferencing, caller identification-database interaction, and videotel systems, could easily be performed.

EXAMPLE 4

Another aspect of the present invention relates to the cataloging and indexing of the contents of a storage medium. While random access media normally incorporate a directory of entries on a disk, and devices such as optical juke boxes normally are used in conjunction with software that indexes the contents of the available disks, serial access mass storage devices, such as magnetic tape, do not usually employ an index; therefore, the entire tape must be searched in order to locate a specific selection.

In the present invention, an area of the tape, preferable at the beginning of the tape or at multiple locations therein, is encoded to hold information relating to the contents of the tape. This encoding is shown in FIG. 19, which shows a data format for the information. This format has an identifying header 1901, a unique tape identifier 1902, an entry identifier 1903, a start time 1904, an end time 1905 and/or a duration 1906, a date code 1907, a channel code 1908, descriptive information 1909 of the described entry, which may include recording parameters and actual recorded locations on the tape, as well as a title or episode identifying information, which may be a fixed or variable length entry, optionally representative scenes 1910, which may be analog, digital, compressed form, or in a form related to the abstract characterizations of the scenes formed in the operation of the device. Finally, there are error correcting codes 1911 for the catalog entry, which may also include advanced block encoding schemes to reduce the affect of non-Gaussian correlated errors which may occur on video tape, transmission media and the like. This information is preferably a modulated digital signal, recorded on, in the case of Hi-Fi VHS, one or more of the preexisting tracks on the tape, including the video, overscan area, Audio, Hi-Fi stereo audio, SAP or control tracks. It should be noted that an additional track could be added, in similar fashion to the overlay of Hi-Fi audio on the video tracks of Hi-Fi VHS. It is also noted that similar techniques could be used with Beta format, 8 mm, or other recording systems, to provide the necessary indexing functions.

The recording method is preferable a block encoding method with error correction within each block, block redundancy, and interleaving. Methods are known for reducing the error rate for digital signals recorded on unverified media, such as videotape, which are subject to burst errors and long term non-random errors. Such techniques reduce the effective error rate to acceptable levels. These are known to those skilled in the art and need not be discussed herein in detail. A standard reference related to this topic is *Digital Communications* by John G. Proakis, McGraw-Hill (1983), which is incorporated herein by reference. The digital data recording scheme is best determined according to the characteristics of the recording apparatus. Therefore, if an, e.g. Sony Corporation helical scan recording/reproducing apparatus was employed, one of ordinary skill in the art would initially reference methods of the Sony Corporation initially for an optimal error correcting recording scheme, which are available in the patent literature, in the U.S., Japan, and internationally, and the skilled artisan would also review the known methods used by other manufacturers of digital data recording equipment. Therefore, these methods need not be explained herein in detail.

The catalog of entries is also preferably stored in non-volatile memory, such as hard disk, associated with the VCR controller. This allows the random selection of a tape from a library, without need for manually scanning the contents of each tape. This also facilitates the random storage of recordings on tape, without the requirement of storing related entries in physical proximity with one another so that they may be easily located. This, in turn, allows more efficient use of tape, because of reduced empty space at the end of a tape.

Figure 20:
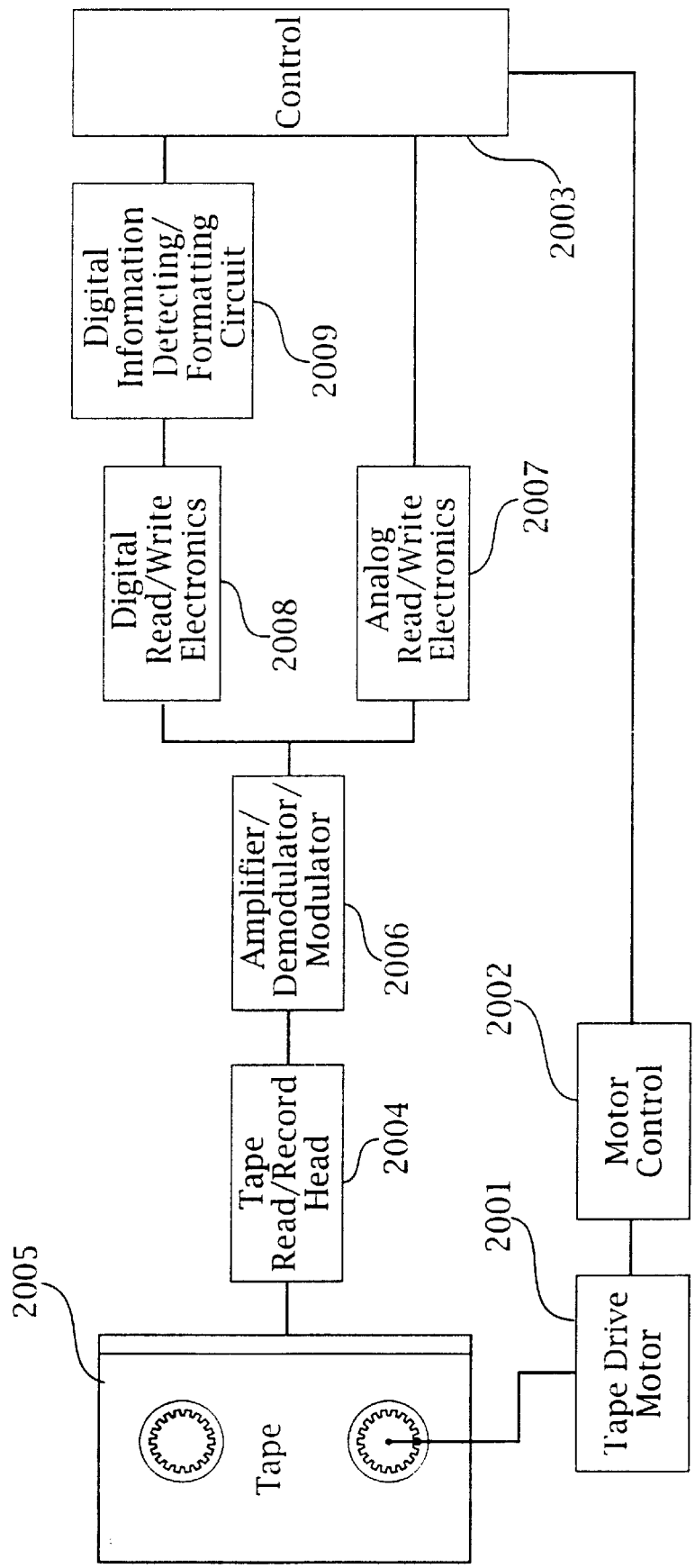
FIG. 20 is a block diagram of a digital information and analog signal reading/recording apparatus

The apparatus is shown schematically in FIG. 20, in which a tape drive motor 2001, controlled by a transport control 2002, which in turn is controlled by the control 2003, moves a tape 2005 past a reading head 2004. The output of the reading head 2004 is processed by the amplifier/demodulator 2006, which produces a split output signal. One part of the output signal comprises the analog signal path 2007, which is described elsewhere. A digital reading circuit 2008 transmits the digital information to a digital information detecting circuit 2009, which in turn decodes the information and provides it to the control 2003.

In order to retrieve an entry, the user interacts with the same interface that is used for programming the recorder functions; however, the user selects different menu selections, which guide him to the available selections. This function, instead of focusing mainly on the particular user's history in order to predict a selection, would analyze the entire library, regardless of which user instituted the recording. Further, there would likely be a bias against performing identically the most recently executed function, and rather the predicted function would be an analogous function, based on a programmed or inferred user preference. This is because it is unlikely that a user will perform an identical action repeatedly, but a pattern may still be derived.

It is noted that the present library functions differ from the prior art VHS tape index function, because the present index is intelligent, and does not require the user to mark an index location and explicitly program the VCR to shuttle to that location. Rather, the index is content based. Another advantage of the present library function is that it can automatically switch media. Such a system might be used, for example, if a user wishes to record, e.g., "The Tonight Show With Johnny Carson" in highly compressed form, e.g. MPEG at 200:1 compression, except during the performance of a musical guest, at which time the recording should be as lossless as possible. A normal VCR could hardly be used to implement such a function even manually, because the tape speed (the analogy of quality level) cannot be changed in mid recording. The present system could recognize the desired special segment, record it as desired, and indicate the specific parameters on the information directory. The recorded information may then be retrieved sequentially, as in a normal VCR, or the desired selection may be preferentially retrieved. If the interface of the present invention is set to automatically record such special requests, the catalog section would then be available for the user to indicate which selections were recorded based upon the implicit request of the user. Because the interface has the ability to characterize the input and record these characterizations in the index, the user may make an explicit request different from the recording criteria, after a selection has been recorded. The controller would then search the index for matching entries, which could then be retrieved based on the index, and without a manual search of the entire tape. Other advantages of the present system are obvious to those of ordinary skill in the art.

A library system is available from Open Eyes Video, called "Scene Locator", which implements a non-intelligent system for indexing the contents of a videotape. See NewMedia, November/December 1991, p. 69.

It is noted that, if the standard audio tracks are used to record the information, then standard audio frequency modems and recording/receiving methods are available. These standard modems range in speed from 300 baud to 19,200 baud, e.g. v.FAST, v.32bis, etc. While these systems are designed for dial-up telecommunications, and are therefore slower than necessary and incorporate features unnecessary for closed systems, they require a minimum of design effort and the same circuitry may be multiplexed and also be used for telecommunication with an on-line database, such as a database of broadcast listings, discussed above.

The Videotext standard may also be used to record the catalog or indexing information on the tape. This method, however, if used while desired material is on the screen, makes it difficult to change the information after it has been recorded, because the videotext uses the video channel, during non-visible scan periods thereof.

The use of on-line database listings may be used by the present interface to provide information to be downloaded and incorporated in the index entry of the library function, and may also be used as part of the intelligent determination of the content of a broadcast. This information may further be used for explicitly programming the interface by the user, in that the user may be explicitly presented with the available choices available from the database.

EXAMPLE 5

The present invention may incorporate character recognition from the video broadcast for automatic entry of this information. This is shown schematically in FIG. 24, with the inclusion of the videotext and character recognition module 2414. This information is shown to be transmitted to the event characterization unit 2407, where the detected information is correlated with the other available information. This information may also be returned to the control 2402. Examples of the types of information which would be recognized are titles of shows, cast and crew from programming material, broadcast special alerts, time (from digital display on special access channels), stock prices from "ticker tape" on special access channels, etc. Thus, this technology adds functionality to the interface. In addition, subtitled presentations could be recognized and presented through a voice synthesizer, to avoid the necessity of reading the subtitle. Further, foreign language subtitles could be translated into, e.g., English, and presented.

The character recognition is performed in known manner on a buffer memory containing a frame of video, from a device such as a Data Translation DT2851, DT2853, DT2855, DT2867, DT2861, DT2862 and DT2871. A contrast algorithm, run on, for example, a Data Translation DT2858, DT2868, or DT2878, first removes the background, leaving the characters. This works especially well where the characters are of a single color, e.g. white, so that all other colors are masked. After the "layer" containing the information to be recognized is masked, an algorithm similar to that used for optical character recognition (OCR) is employed. These methods are well known in the art. This may be specially tuned to the resolution of the video device, e.g. NTSC, S-VHS, IDTV, EDTV, MUSE, PAL, SECAM, etc. In addition, since the text normally lasts for a period in excess of one frame, a spatial-temporal image enhancement algorithm may be employed to improve the quality of the information to be recognized.

EXAMPLE 6

The present invention may also be incorporated into other types of programmable controls, for example those necessary or otherwise used in the control of a smart house. See, "The Smart House: Human Factors in Home Automation", Human Factors in Practice, December 1990, 1–36. The user interface in such a system is very important, because it must present the relevant data to the user for programming the control to perform the desired function. A smart house would likely have many rarely used functions, so that the presentation of both the data and the available program options must be done in the simplest manner consistent with the goal of allowing the user to make the desired program choice. For example, a smart house system might be used to execute the program "start dishwasher, if more than half full, at 9:00 p.m." A user who wishes to delay starting until 11:00 p.m. would be initially presented with the default time as an option, which would be simply modified by correcting the starting time. The next time the user wishes to program the device, an algorithm would change the predicted starting time to, e.g. 10:00 p.m., which is a compromise between the historical choices.

The smart house system also controls the climate control system. Thus, it could coordinate temperatures, air flow and other factors, based on learned complex behaviors, such as individual movement within the dwelling. Since the goal of the programming of the smart house is not based on the storage of discrete information, but rather the execution of control sequences at various times and under certain circumstances, the control would differ in various ways from that of a VCR. However, the user interface system, adaptive user level, help system, and the like would be common to both types of system. This differs from the Fuzzy Logic controlled air conditioner available (in Japan) from Mitsubishi in that that device does not have an intelligent interface of the present invention. It should also be noted that the control for the VCR could be the same control as that for the smart house, so that the common elements are not redundant. Therefore, by applying a single control to many tasks, a common user interface is used, and the cost is reduced.

EXAMPLE 7

The present Example relates to a programmable environmental controller application. In this case, a sensor or sensor array is arranged to detect a change in the environment which is related to a climatic condition, such as an open door. On the occurrence of the door opening, the system would apply a pattern recognition analysis to recognize this particular sensor pattern, i.e. a mass of air at a different temperature entering the environment from a single location, or a loss of climate controlled air to a single location. These sensor patterns must be distinguished from other events, such as the action of appliances, movement of individuals in the vicinity of the sensor, a shower and other such events. It is noted that in this instance, a neural network based adaptive controller may be more efficient, because the installation and design of such a system is custom, and therefore it would be difficult to program a priori. In this case, a learning system, such as a neural network, may be more efficient and produce a better result than other adaptive methods. The training procedure could be fully automated, so long as sufficient sensors are provided for controlling the system, and also that an initial presumption of the control strategy is workable during the training period. In this case, the initial strategy incorporated is the prior art "bang-bang" controller, which operates as a simple thermostat, or multi-zone thermostat. As a better starting point, a fuzzy logic temperature controller may be modeled and employed. Other known strategies which are not often used in environmental control include the proportional-integral-differential controller (PID).

In this example, which may be described with reference to FIG. 23, sufficient sensors in a sensor array 2301 are provided, being light, temperature, humidity, pressure, air flow and possibly a sensor for determining an event proximate to the sensor, such as door opening. While a single sensor array 2301 could provide input to the present control, a plurality of sensor arrays are preferably employed in complex installations, such as that described here. The sensors, with the possible exceptions of the flow sensor and event sensor, are housed in a single sensor head. Further, the temperature and pressure sensors may be combined in a single integrated circuit by known means. The light and temperature sensors are known to those skilled in the art, and need not be described herein. The pressure sensor may be a Sensym strain gage pressure transducer, a Motorola pressure transducer device, or the like, and may also be a derivative of the Analog Devices monolithic accelerometer. These devices are known in the art. The humidity sensor is preferably an electronic type, producing an electrical signal output. It need not be internally compensated for the other measured environmental factors. The air flow sensor may be based on pressure differentials, using the pressure sensor described above, or may be a mechanical vane type. In most applications, a single flow axis will be sufficient, however, in some circumstances, a two or greater axis sensor will be required. Further, in the case of large volume areas, complex turbulent flow patterns may be relevant, for which known sensors exist. The event sensor may be of any type, and depends particularly on the event being measured. In the present case, where a door opening is to be detected, it is preferred that the environmental control be interfaced with a perimeter intrusion alarm system, which, for example, provides a magnet embedded in the door and a magnetic reed switch in the door frame. Individual sensors are normally wired to the alarm control panel, thus providing central access to many or all of the desired event detection sensors while minimizing the added cost. The event detector may also be an ultrasonic, infrared, microwave-doppler, mechanical, or other type of sensor.

The preferred method of receiving sensor information is through a serial digital or multiplexed analog (i.e., 4–20 mA transmitter) data transmission scheme, with minimal local processing of the sensor data by the microprocessor 2302 with the serial link 2302a in the sensor head. This system allows the central control 2303 to incorporate the desired processing, e.g., by the pattern recognition system 2304, etc., while minimizing the installation expense. A simple microprocessor device 2302 in the sensor head interfaces the sensing elements, and may provide analog-to-digital conversion, or other conversion which may be necessary, of the sensor signal. In the case of a serial digital data transmission, the local microprocessor formats the sensor data, including a code indicating the sensor serial number and type, the sensor status (i.e., operative, defective, in need of maintenance or calibration, etc.), the sensor data, and an error correcting code. In the case that the data is transmitted on a local area network, the microprocessor also arbitrates for bus usage and the messaging protocol.

The control, it must be understood, has a number of available operative systems at its disposal, comprising the plant 2306. In this case, the system is a forced air heating and cooling system. This system has a heating unit, a humidifier, blowers, a cooling unit (which also dehumidifies), ducts, dampers, and possible control over various elements, such as automated door openers.

As described above, the system is installed with a complete array of sensors, some of which may be shared with other control systems in the environment, and begins operation with a basic acceptable initial control protocol. The system then receives data from the sensors, and correlates data from the various sensors, including the event sensors, with the operation of the systems being controlled. In such a case, a "door open" event may be correlated with a change in other measured variables. The system then correlates the control status with the effect on the interrelation of the measured variables. Thus, the system would detect that if the blower is operating while the door is open, then there is a high correlation that air will flow out of the door, unless a blower operates to recirculate air from a return near the door. Thus, the system will learn to operate the proximate return device while the door is open and the blower is on. Once this correlation is defined, the system may further interrelate the variables, such as a wind speed and direction outside the door, effects of other events such as other open doors, the absolute and relative speeds of the blowers and the return device, the effect of various damper devices, etc. It is further noted that, under some circumstances, an exchange of air through an open door is desired, and in such instance, the system may operate to facilitate the flow through such an open door. Finally, the system must be able to "learn" that conditions may exist which produce similar sensor patterns which should be handled differently. An example is a broken or inoperative sensor. In such a case, the system must be able to distinguish the type of condition, and not execute an aggressive control algorithm in an attempt to compensate for an erroneous reading or otherwise normal event. This requires the intelligent control of the present invention.

It is further noted that energy efficiency is a critical issue in climate control systems, and an absolute and continuous control over the internal environment may be very inefficient. Thus, the starting of large electrical motors may cause a large power draw, and simultaneous starting of such equipment may increase the peak power draw of a facility, causing an increase in the utility rates. Further, some facilities may operate on emergency or private power generation (co-generation) which may have different characteristics and efficiency criteria. These must all be considered in the intelligent control. It is also noted that a higher efficiency may also be achieved, in certain circumstances, by employing auxiliary elements of the climate control system which have a lower capacity and lower operating costs than the main elements. Thus, for example, if one side of a building is heated by the sun, it may be more efficient to employ an auxiliary device which suitably affects only a part of the building. Thus, if such equipment is installed, the aggregate efficiency of the system may be improved, even if the individual efficiency of an element is lower. The present intelligent control allows a fine degree of control, making use of all available control elements, in an adaptive and intelligent manner.

Returning to the situation of a door opening event, the system would take appropriate action, including: interruption of normal climate control until after the disturbance has subsided and normal conditions are achieved; based on the actual climatic conditions or predicted climatic conditions begin a climate compensation control, designed to maximize efficiency and also maintain climatic conditions during the disturbance, as well as return to normal after the disturbance; optionally, during the door opening disturbance, the system would control a pressure or flow of air to counterbalance a flow through the door, by using a fan, blower or other device, or halting such a device, if necessary. It is also noted that the climatic control system could also be outfitted with actuators for opening and closing doors and windows, or an interface with such other system, so that it could take direct action to correct the disturbance, e.g., by closing the door. The climate between the internal and external ambients may differ in temperature, humidity, pollutants, or the like, and appropriate sensors may be employed.

It is thus realized that the concepts of using all available resources to control an event, as well as using a predictive algorithm in order to determine a best course of action and a desired correction are a part of the present invention.

EXAMPLE 8

A remote control of the present invention may be constructed from, for example, a Micromint (Vernon, CT) RTC-LCD, RTC-V25 or RTC-HC11 or RTC180 or RTC31/52, and RTC-SIR, in conjunction with an infrared transmitter and receiver, input keys and a compatible trackball, which may provide raw encoder signals, or may employ a serial encoder and have a serial interface to the processor module. A power supply, such as a battery, is used. The use, interfacing and programming of such devices is known to those skilled in the art, and such information is generally available from the manufacturer of the boards and the individual circuit elements of the boards. The function of such a remote control is to receive inputs from the trackball and keys and to transmit an infrared signal to the controller. The processor and display, if present, may provide added functionality by providing a local screen, which would be useful for programming feedback and remote control status, as well as compressing the data stream from the trackball into a more efficient form. In this case, certain of the extracted information may be relevant to the determination of the user level, so that information related to the user level would be analyzed and transmitted separately to the controller by the infrared transmitter. If the local LCD screen is used in the programming process, then the main controller would transmit relevant information to the remote display, by a reverse infrared link. These components are known in the art, and many other types may also be used in known manner.

EXAMPLE 9

The interface and intelligent control of the present invention are applicable to control applications in medicine or surgery. This system may also be described with reference to the generic system drawings of FIGS. 23 and 24. In this case, an operator identifies himself and enters information regarding the patient, through the interface 2305. The interface 2305 automatically loads the profile 2406 of both the operator and the patient, if the device is used for more than one at a time, and is connected to a database containing such information, such as a hospital central records bureau. The interface may be connected to various sensors, of the input device 2401, such as ambient conditions (temperature, humidity, etc.), as well as data from the patient, such as EKC, EMG, EEG, Evoked Potentials, respirator, anesthesia, temperature, catheter status, arterial blood gas monitor, transcutaneous blood gas monitor, urinary output, IV solutions, pharmaceutical and chemotherapy administration data, mental status, movement, pacemaker, etc. as well as sensors and data sources separate from the patient such as lab results, radiology and medical scanner data, radiotherapy data and renal status, etc. Based on the available information, the interface 2405, using the simple input device and the display screen described above, presents the most important information to the operator, along with a most probable course of action. The user then may either review more parameters, investigate further treatment options, input new data, or accept the presented option(s). The system described has a large memory in the signal analysis module 2409 for recording available patient data from the signal receiver 2408, and thus assists in medical record keeping and data analysis, as well as diagnosis. While various systems are available for assisting in both controlling medical devices and for applying artificial intelligence to assist in diagnosis, the present system allows for individualization based on both the service provider and the patient. Further, the present invention provides the improved interface for interaction with the system. It is further noted that, analogously to the library function discussed above, medical events may be characterized in the characterization unit 2407 and recorded by the plant 2404, so that a recording of the data need not be reviewed in its entirety in order to locate a particular significant event, and the nature of this event need not be determined in advance. It is also noted that the compression feature of the recorder of the present invention could be advantageously employed with the large volume of medical data that is often generated. It is finally noted that, because of its ability to store and correlate various types of medical data in the characterization unit 2407, the system could be used by the operator to create notes and discharge summaries for patients, using the database stored in the local database 2413, as well as the user history and preferences 2406. Thus, in addition to saving time and effort during the use of the device, it would also perform an additional function, that of synthesizing the data, based on medical significance.

In addition to providing the aforementioned intelligence and ease of use, the present example also comprises a control 2402, and may interface with any of the sensors and devices, performing standard control and alarm functions. However, because the present control 2402 is intelligent and has pattern recognition capability, in addition to full data integration from all available data sources, it may execute advanced control functions. For example, if the present control 2402 is interfaced to a controlled infusion pump for, e.g., morphine solution, in e.g., a terminally ill patient, then certain parameters must be maintained, while others may be flexible. For example, a maximum flow rate is established as a matter of practice as a safety measure; too high a flow rate could result in patient death. However, a patient may not need a continuous infusion of a constant dose of narcotic. Further, as the patient's status changes, the level of infusion may be advantageously altered. In particular, if the renal status of the patient were to change, the excretion of the drug may be impaired. Therefore, if the controller had a urinary output monitor, it could immediately suppress the morphine infusion as soon as the renal output is recognized as being decreased, and further indicate an alarm condition. Further, it may be advantageous to provide a diurnal variation in the infusion rate, to provide a "sleep" period and a period of heightened consciousness with correspondingly lower levels of narcosis.

As another example of the use of the present device as a medical controller, the control 2402 could be interfaced with a cardiac catheter monitor, as a part of the signal receiver 2408. In such a case, normally, alarms are set based on outer ranges of each sensor measurement, and possibly a simple formula relating two sensor measurements, to provide a useful clinical index. However, by incorporating the advanced interface and pattern recognition function of the present invention, as well as its ability to interface with a variety of unrelated sensors, the present device, including the present control, may be more easily programmed to execute control and alarm functions, may provide a centralized source of patient information, including storage and retrieval, if diverse sources of such information are linked, and may execute advanced, adaptive control functions. The present control 2402 is equipped to recognize trends in the sensor data from the signal receiver 2408, which would allow earlier recognition and correction of various abnormal conditions, as well as recognizing improvements in conditions, which could allow a reduction in the treatment necessary. Further, by allowing a fine degree of control, parameters may be maintained within optimal limits for a greater percentage of the time. In addition, by monitoring various sensors, various false alarms may be avoided or reduced. In particular, false alarms may occur in prior art devices even when sensors do not indicate a dangerous condition, merely as a safety precaution when a particular parameter is out of a specified range. In such a case, if a cause of such abnormal condition may be identified, such as patient movement or the normal activities of the patient's caretakers, then such condition may be safely ignored, without indicating an alarm. Further, even if a sensor parameter does in and of itself indicate a dangerous condition, if a cause, other than a health risk, may be identified, then the alarm may be ignored, or at least signalled with a different level of priority. By providing an intelligent and active filter for false alarm events, the system may be designed to have a higher level of sensitivity to real health risks, and further to provide a finer level of control based on the sensor readings.

EXAMPLE 10

The present invention is also of use in automated securities, debt, variable yield and currency trading systems, where many complex functions are available, yet often a particular user under particular circumstances will use a small subset of the functionality available at a given time. Such a situation would benefit from the present interface, which provides adaptive user levels, prioritized screen information presentation, and pattern recognition and intelligent control. A securities trading system is disclosed in U.S. Pat. No. 5,034,916, for a mouse driven Fast Contact Conversational Video System, incorporated herein by reference. The present system relates primarily to the user terminal, wherein the user must rapidly respond to external events, in order to be successful. In such a case, the advantages of the interface aspects are obvious, and need not be detailed herein. However, the pattern recognition functions of the present invention may be applied to correspond to the desired actions of the trader, unlike in prior intelligent trading systems, where the terminal is not individually and adaptively responsive to the particular user. Thus, the system exploits the particular strengths of the user, facilitating his actions, including: providing the desired background information and trading histories, in the sequence most preferred by the user; following the various securities to determine when a user would execute a particular transaction, and notifying the user that such a condition exists; monitoring the success of the user's strategy, and providing suggestions for optimization to achieve greater gains, lower risk, or other parameters which may be defined by the user. Such a system, rather than attempting to provide a "level playing field", allows a user to use his own strategy, providing intelligent assistance.

EXAMPLE 11

The fractal method employing Affine transforms may be used to recognize images. This method proceeds as follows. A plurality of templates are stored in a memory device, which represent the images to be recognized. These templates may be preprocessed, or processed in parallel with the remainder of the procedure, in a corresponding manner.

Image data, which may be high contrast line image, greyscale, or having a full color map, the greyscale being a unidimensional color map, is stored in the data processor, provided for performing the recognition function. A plurality of addressable domains are generated from the stored image data, each of the domains representing a portion of the image information. It is noted that the entire image need not be represented, only those parts necessary for the recognition, which may be determined by known means. From the stored image data, a plurality of addressable mapped ranges are created, corresponding to different subsets of the stored image data. Creating these addressable mapped ranges, which should be uniquely addressable, also entails the step of executing, for each of the mapped ranges, a corresponding procedure upon the one of the subsets of the stored image data which corresponds to the mapped ranges. Identifiers are then assigned to corresponding ones of the mapped ranges, each of the identifiers specifying, for the corresponding mapped range, a procedure and a address of the corresponding subset of the stored image data. The treatment of the template and the image data is analogous, so that the resulting data is comparable. The domains are optionally each subjected to a transform, which may be a predetermined rotation, an inversion, a predetermined scaling, and a predetermined frequency domain preprocessing transform. This transform is used to optimize the procedure, and also to conform the presentation of the image data with the template, or vice versa. Each of the domains need not be transformed the same way. For each of the domains or transformed domains, as may be the case, the one of the mapped ranges which most closely corresponds according to predetermined criteria, is selected. The image is then represented as a set of the identifiers of the selected mapped ranges. Finally, from the stored templates, a template is selected which most closely corresponds to the set of identifiers representing the image information. It is preferred that, for each domain, a most closely corresponding one of the mapped ranges be selected. By performing analogous operations on a template and an unrecognized object in an image, a correspondence between the two may be determined.

In selecting the most closely corresponding one of the mapped ranges, for each domain, the mapped range is selected which is the most similar, by a method which is appropriate, and may be, for example, selecting minimum Hausdorff distance from the domain, selecting the highest cross-correlation with the domain, the minimum mean square error with the domain and selecting the highest fuzzy correlation with the domain. Neural network energy minimization may also yield the best fit, and other techniques may also be appropriate.

In particular, the step of selecting the most closely corresponding one of mapped ranges according to the minimum modified Hausdorff distance includes the step of selecting, for each domain, the mapped range with the minimum modified Hausdorff distance calculated as D[db,mrb]+D[1-db,1-mrb], where D is a distance calculated between a pair of sets of data each representative of an image, db is a domain, mrb is a mapped range, 1-db is the inverse of a domain, and 1-mrb is an inverse of a mapped range.

In the case where the digital image data consists of a plurality of pixels, each having one of a plurality of associated color map values, the method includes a matching of the color map, which as stated above, includes a simple grey scale. In such a case, the method is modified to optionally transform the color map values of the pixels of each domain by a function including at least one scaling function, for each axis of said color map, each of which may be the same or different, and selected to maximize the correspondence between the domains and ranges to which they are to be matched. For each of the domains, the one of the mapped ranges having color map pixel values is selected which most closely corresponds to the color map pixel values of the domain according to a predetermined criteria, wherein the step of representing the image color map information includes the substep of representing the image color map information as a set of values each including an identifier of the selected mapped range and the scaling functions. The correspondence method may be of any sort and, because of the added degree of complexity, may be a different method than that chosen for non-color images. The method of optimizing the correspondence may be minimizing the Hausdorff distance or other "relatedness" measurement between each domain and the selected range. The recognition method concludes by selecting a most closely corresponding stored template, based on the identifier of the color map mapped range and the scaling functions, which is the recognized image.

In the case of moving images, the method is further modified to accommodate time varying images. These images usually vary by small amounts between frames, and this allows a statistical improvement of the recognition function by compensating for a movement vector, as well as any other transformation of the image. This also allows a minimization of the processing necessary because redundant information between successive frames is not subject to the full degree of processing. Of course, if the image is substantially changed, then the statistical processing ceases, and a new recognition function may be begun, "flushing" the system of the old values. The basic method is thus modified by storing delayed image data information, i.e., a subsequent frame of a moving image. This represents an image of a moving object differing in time from the image data in the data processor. A plurality of addressable further domains are generated from the stored delayed image data, each of the further domains representing a portion of the delayed image information, and corresponding to a domain. Thus, an analogous transform is conducted so that the further domains each are corresponding to a domain. A plurality of addressable mapped ranges corresponding to different subsets of the stored delayed image data are created from the stored delayed image data. The further domain and the domain are optionally matched by subjecting a further domain to a corresponding transform selected from the group consisting of a predetermined rotation, an inversion, a predetermined scaling, and a predetermined frequency domain preprocessing transform, which corresponds to a transform applied to a corresponding domain, and a non-corresponding transform selected from the group consisting of a predetermined rotation, an inversion, a predetermined scaling, a translation and a predetermined frequency domain preprocessing transform, which does not correspond to a transform applied to a corresponding domain. For each of the further domains or transformed further domains, the one of the mapped ranges is selected which most closely corresponds according to predetermined criteria. A motion vector is then computed between one of the domain and the further domain, or the set of identifiers representing the image information and the set of identifiers representing the delayed image information, and the motion vector is stored. The further domain is compensated with the motion vector and a difference between the compensated further domain and the domain is computed. For each of the delayed domains, the one of the mapped ranges is selected which most closely corresponds according to predetermined criteria. The difference between the compensated further domain and the domain is represented as a set of difference identifiers of the selected mapping ranges and an associated motion vector.

Figure 27:
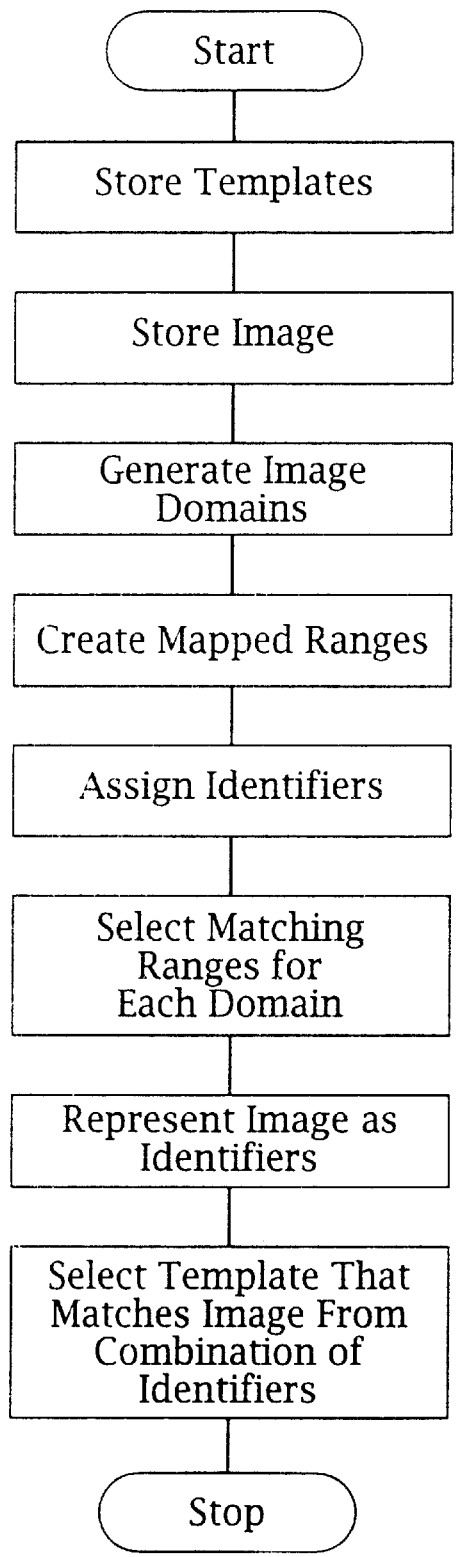
FIGS. 27, 28 and 29 are flow diagrams of an iterated function system method for recognizing a pattern according to the present invention.
Figure 28:
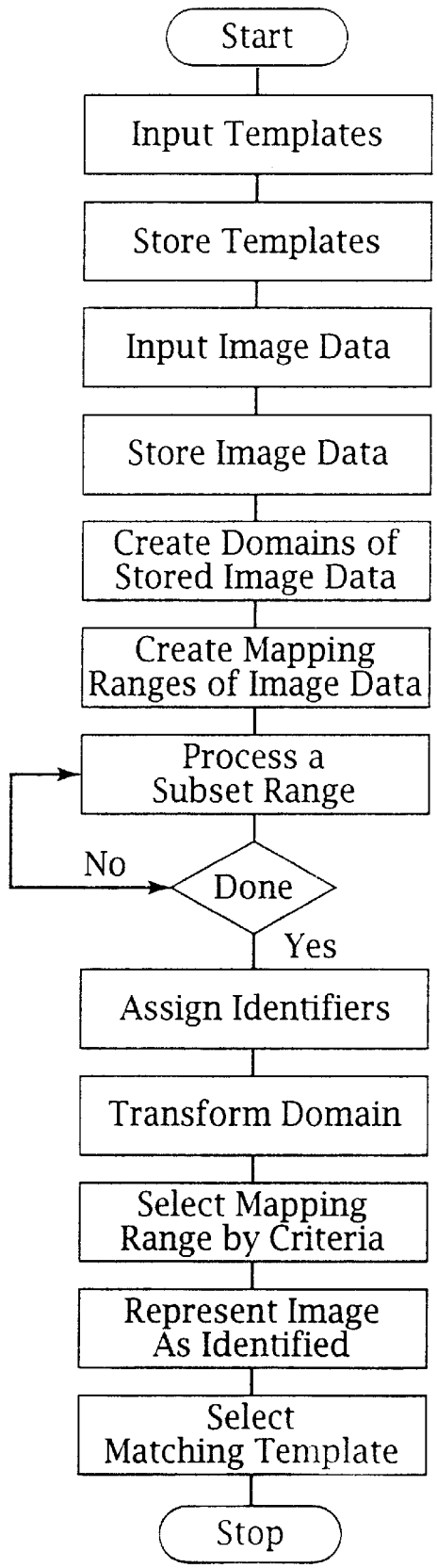
Figure 29:
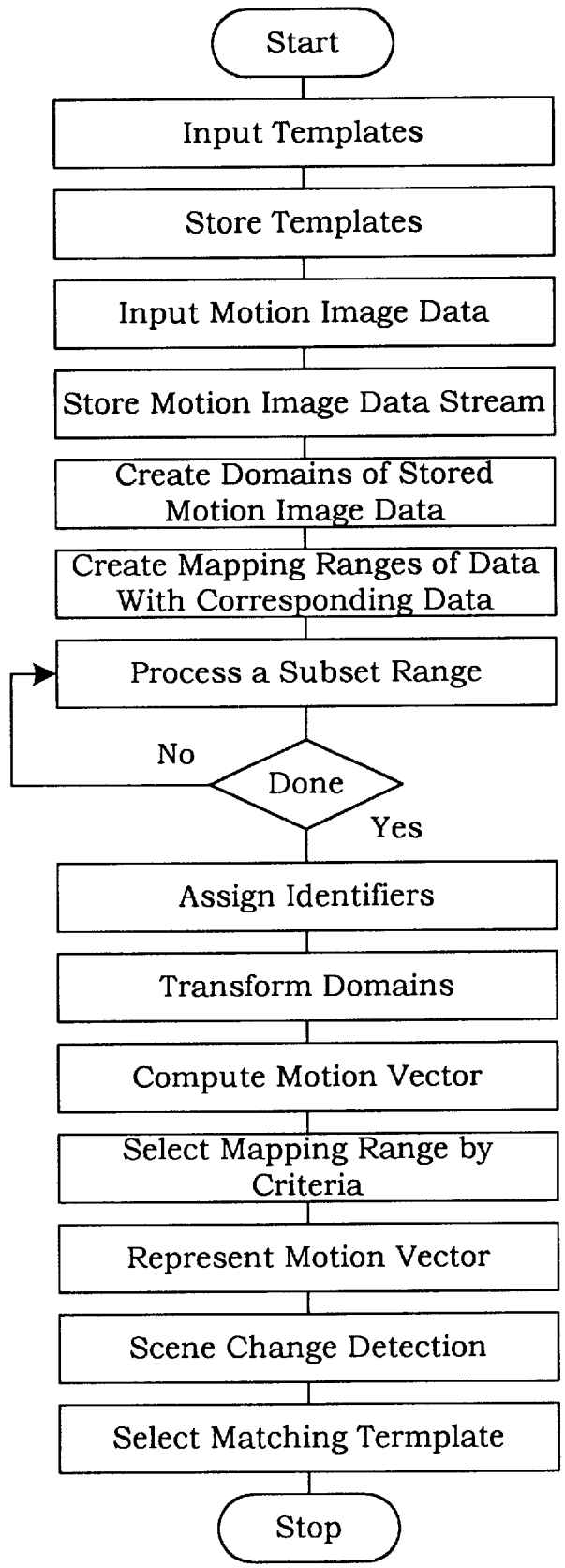

This method is described with respect to FIGS. 27, 28 and 29. FIG. 27 is a basic flow diagram of the recognition system of the present invention. FIG. 28 provides a more detailed description, including substeps, which are included in the major steps shown in FIG. 27. Basically, the image, or a part thereof, is decomposed into a compressed coded version of the scene, by a modified fractal-based compression method. In particular, this differs from the prior compression algorithms in that only a part, preferably that part containing objects of interest, need be processed. Thus, if a background is known (identified) or uninteresting, it may be ignored. Further, the emphasis is on matching the available templates to produce an image recognition, not achieving a high degree of compression. Therefore, the image, or domains thereof, may be transformed as required in order to facilitate the matching of the templates. As with respect to single images, the templates are represented in analogous form, having been processed similarly, so that a comparison of the relatedness of an object in an image and the templates may be performed. In particular, if an oblique view of an object is presented, then either the object may be transformed to achieve a predicted front view, or the template transformed or specially selected to correspond to the oblique view. Further, once a recognition has taken place with a high degree of certainty, the system need only ensure that the scene has not changed, and need not continually process the data. This has implications where multiple recognition processes are occurring simultaneously, either in a single scene or in different images, wherein the throughput for the recognition apparatus need not meet that required for de novo recognition of all aspects of all the objects or images.

Figure 30:
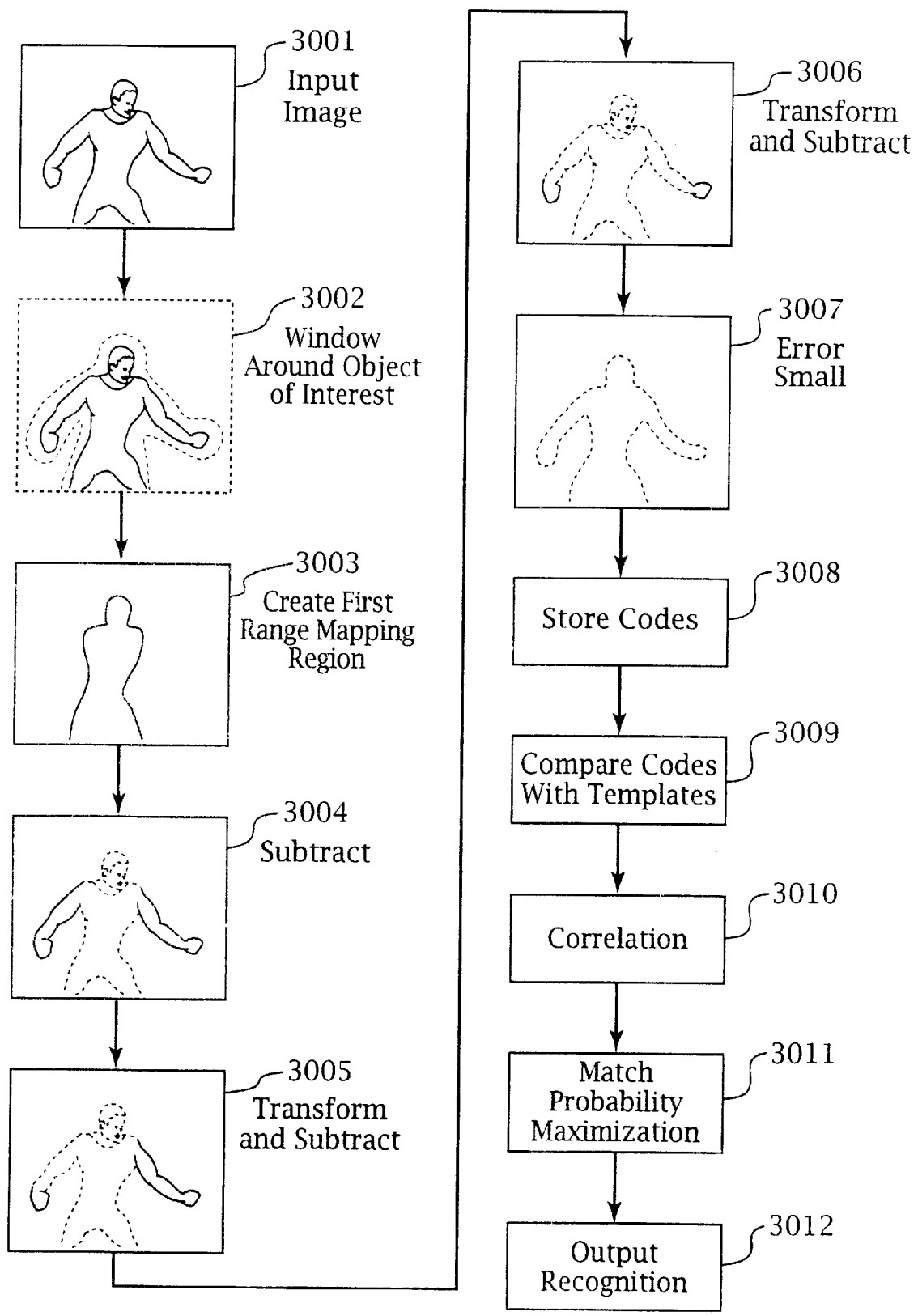
FIG. 30 is a semi-cartoon flow diagram of the object decomposition and recognition method of the present invention.

FIG. 30 shows a flow diagram of a cartoon-like representation of an image recognition method of the present invention. It shows initially, an input image 3001, having a degree of complexity. A windowing function 3002 isolates the object from the background. A first order approximation of the image is generated 3003, here called a mapping region. The first order approximation is then subtracted from the initial image to produce a difference 3004. The first order error is then subjected, iteratively, to successive transform and subtract operations 3005 and 3006, until the error is acceptably small, at which point the input image is characterized by a series of codes, representing the first order approximation and the successive transforms, which are stored 3008. These codes are then compared with stored templates 3009. The comparisons are then analyzed to determine which template produces the highest correlation 3010, and the match probability is maximized 3011. The recognized image is then indicated as an output 3012.

Figure 26:
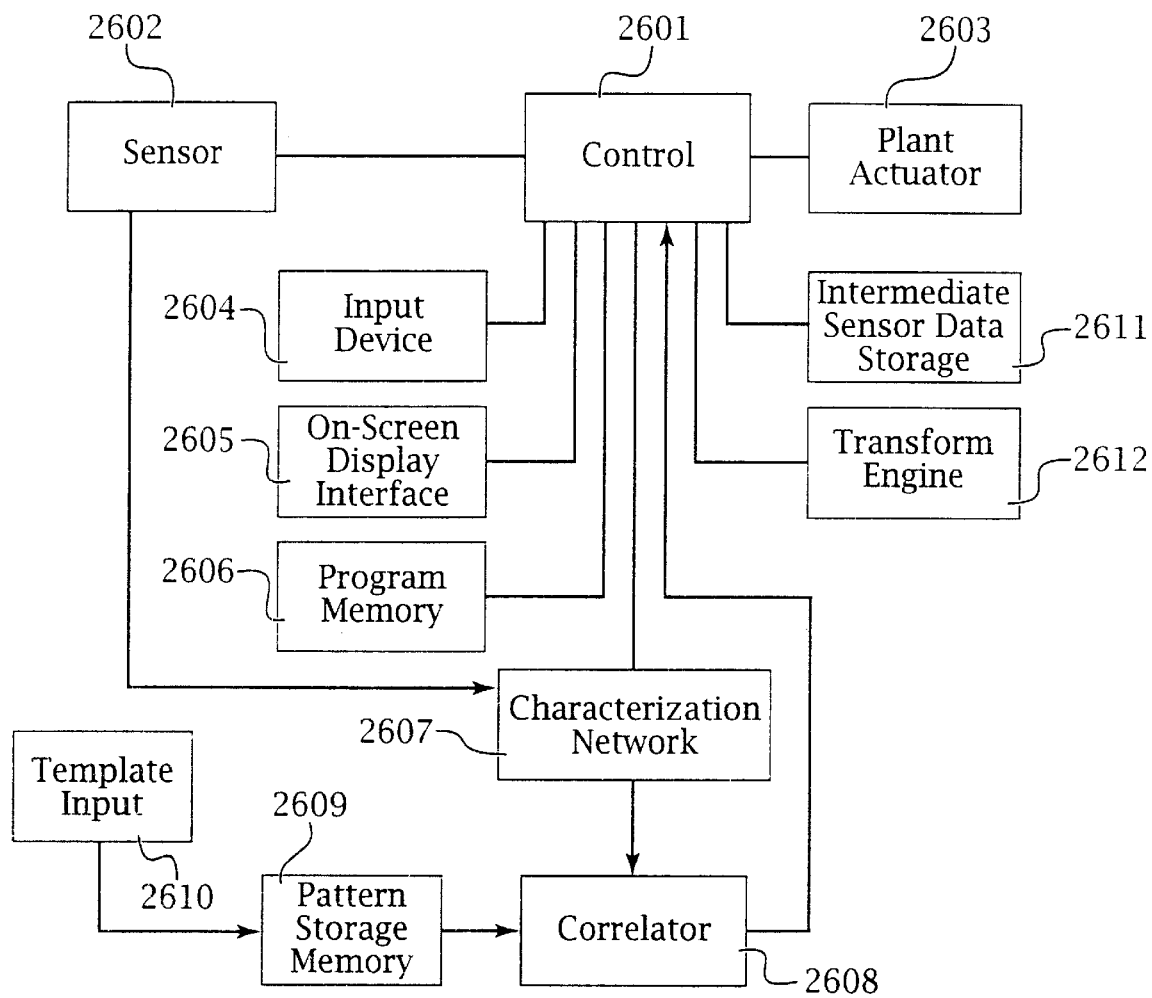
FIG. 26 is a block diagram of a control system for matching a template with a sensor input, of the present invention.

This system is shown in FIG. 26, wherein a sensor 2602 provides data, which may be image data, to a control 2601. The control 2601 serves to control the plant 2603, which has an actuator. The plant 2603 may be a VCR or the like. The control 2601 has associated with it an intermediate sensor data storage unit 2611, which may be, for example a frame buffer or the like. The control 2601 also has associated with it a transform engine 2612, which may perform a reversible or irreversible transform on the data or stored data.

The system also has a template input 2610, which may receive data from the sensor 2602, if accompanied by identifying information. Thus, the pattern storage memory 2609 stores a pattern, such as an image pattern, along with an identifier.

The control 2601 also has an input device 2604, an on-screen display interface 2605, and a program memory 2606, for inputting instructions from a user, providing feedback to the user, and recording the result of the user interaction, respectively. Finally, a characterization network 2607 characterizes the sensor 2602 data, which may be provided directly from the sensor 2602 or preprocessing circuitry, or through the control 2601. A correlator 2608 correlates the output of the characterization network with the stored patterns, representing the templates from the template input 2610. The system therefore operates to recognize sensor patterns, based on the correlator 2608 output to the control 2601.

A determination is made of the complexity of the difference based on a density of representation. In other words, the error between the movement and transform compensated delayed image and the image is quantified, to determine if the compensation is valid, or whether the scene is significantly changed. When the difference has a complexity below a predetermined threshold, a template is selected, from the stored templates, which most closely corresponds or correlates with both the set of identifiers of the image data and the set of identifiers of the delayed image data, thus improving recognition accuracy, by allowing a statistical correlation or other technique. For example, if the two images both have a high correlation with one template, while a first of the images has a slightly higher correlation with another template, while the second image has a much lower correlation with that other template, then the system would score the first template as a better match to the first image.

It should be understood that the preferred embodiments and examples described herein are for illustrative purposes only and are not to be construed as limiting the scope of the present invention, which is properly delineated only in the appended claims.

REFERENCES INCORPORATED BY REFERENCE

"32-bit Floating-Point DSP Processors", EDN, Nov. 7, 1991, pp. 127–146.

"A New Class of Markov Processes for Image Encoding", School of Mathematics, Georgia Inst. of Technology (1988), pp. 14–32.

"Bar Code Programs VCR", Design News, Feb. 1, 1988, 26.

"C-Cube CL550 JPEG Image Compression Processor", Preliminary Data Book, August 1991, and addendum dated Nov. 20, 1991.

"Construction of Fractal Objects with Iterated Function Systems", Siggraph '85 Proceedings, 19(3):271 –278 (1985).

"Data Compression: Pntng by Numbrs", The Economist, May 21, 1988.

"$EMC^2$ Pushes Video Rental By Satellite", Electronic Engineering Times, Dec. 2, 1991, p. 1, p. 98.

"Finger Painting", Information Display 12, p. 18, 1981.

"Fractal Modelling of Real World Images, Lecture Notes for Fractals: Introduction, Basics and Perspectives", Siggraph (1987).

"Fractal Geometry-Understanding Chaos"; Georgia Tech Alumni Magazine; p. 16 (Spring 1986).

"Fractal Modelling of Biological Structures", Perspectives in Biological Dynamics and Theoretical Medicine, Koslow, Mandell, Shlesinger, eds., Annals of New York Academy of Sciences, vol. 504, 179–194 (date unknown).

"Fractals Yield High Compression"; Electronic Engineering Times; Sep. 30, 1991; p. 39.

"Fractals-A Geometry of Nature", Georgia Institute of Technology Research Horizons; p. 9 (Spring 1986).

"How to find the best value in VCRs", Consumer Reports, March 1988, 135–141.

"Low-Cost VCRs: More For Less", Consumer Reports, March 1990, 168–172.

"Machine Now Reads, enters Information 25 Times Faster Than Human Keyboard Operators", Information Display 9, p. 18 (1981).

"New Beetle Cursor Director Escapes All Surface Constraints", Information Display 10, p. 12, 1984.

"Nielsen Views VCRs", Television Digest, Jun. 23, 1988, 15.

"Scanner Converts Materials to Electronic Files for PCs", IEEE CG&A, December 1984, p. 76.

"The Highs and Lows of Nielsen Homevideo Index", Marketing & Media Decisions, November 1985, 84–86+.

"The Smart House: Human Factors in Home Automation", Human Factors in Practice, December 1990, 1–36.

"The Quest for 'User Friendly'", U.S. News & World Report, Jun. 13, 1988. 54–56.

"VCR, Camcorder Trends", Television Digest, Vol. 29, Mar. 20, 1989, 16.

"VCR's: A Look At The Top Of The Line", Consumer Reports, March 1989, 167–170.

"VHS Videocassette Recorders", Consumer Guide, 1990, 17–20.

"Voice Recognition and Speech Processing", Elektor Electronics, September 1985, pp. 56–57.

Abedini, Kamran, and Hadad, George, "Guidelines For Designing Better VCRs", Report No. IME 462, Feb. 4, 1987.

Abedini, Kamran, "An Ergonomically-improved Remote Control Unit Design", Interface '87 Proceedings, 375–380.

Aleksander, I.; "Guide to Pattern Recognition Using Random-Access Memories"; Computers and Digital Techniques; 2(1):29–40 (February 1979).

Anderson, F., W. Christiansen, B. Kortegaard; "Real Time, Video Image Centroid Tracker"; Apr. 16–20, 1990.

Anson, L., M. Barnsley; "Graphics Compression Technology"; SunWorld; pp. 43–52 (October 1991).

Appriou, A., "Interet des theories de l'incertain en fusion de donnees", Colloque International sur le Radar Paris, Apr. 24–28 1989.

Appriou, A., "Procedure d'aide a la decision multi-informateurs. Applications a la classification multi-capteurs de cibles", Symposium de l'Avionics Panel (AGARD) Turquie, Apr. 25–29 1988.

Arrow, K. J., "Social choice and individual valves", John Wiley and Sons Inc. (1963).

Atkinson, Terry, "VCR Programming: Making Life Easier Using Bar Codes".

Baldwin, William, "Just the Bare Facts, Please", Forbes Magazine, Dec. 12, 1988.

Ballard, D. H., and Brown, C. M., Computer Vision, Prentice Hall, Englewood Cliffs, N.J. (1982).

Barnsley et al., "Harnessing Chaos For Images Systhesis", Computer Graphics, 22(4):131–140 (August, 1988).

Barnsley, M. F., Ervin, V., Hardin, D., Lancaster, J., "Solution of an Inverse Problem for Fractals and Other Sets", Proc. Natl. Acad. Sci. U.S.A., 83:1975–1977 (April 1986).

Barnsley, M. F., "Fractals Everywhere", Academic Press, Boston, Mass., 1988,

Barnsley, M. F., and Demko, S., "Iterated Function Systems and The Global Construction of Fractals", Proc. R. Soc. Lond., A399:243–275 (1985).

Barnsley et al., "Hidden Variable Fractal Interpolation Functions", School of Mathematics, Georgia Institute of Technology, Atlanta, Ga. 30332, July 1986.

Barnsley et al., "A Better Way to Compress Images", Byte Magazine, January 1988, pp. 213–225.

Barnsley et al., "Chaotic Compression", Computer Graphics World, November 1987.

Batchelor, B. G.; "Practical Approach to Pattern Classification"; Plenum Press, London and New York; (1974).

Batchelor, B. G.; "Pattern Recognition, Ideas in Practice"; Plenum Press, London and New York; (1978).

Baxes, Gregory A., "Digital Signal Processing, A Practical Primer", Prentice-Hall, Englewood Cliffs, N.J. (1984).

Bellman, R. E., L. A. Zadeh, "Decision making in a fuzzy environment", Management Science, 17(4) (December 1970).

Bensch, U., "VPV—VIDEOTEXT PROGRAMS VIDEORECORDER", IEEE Transactions on Consumer Electronics, 34(3):788–792 (1988).

Berger, Ivan, "Secrets of the Universals", Video, February 1989, 45–47+.

Beringer, D. B., "A Comparative Evaluation of Calculator Watch Data Entry Technologies: Keyboards to Chalkboards", Applied Ergonomics, December 1985, 275–278.

Bhatnagar, R. K., L. N. Kamal, "Handling uncertain information: a review of numeric and non-numeric methods", Uncertainty in Artificial Intelligence, L. N. Kamal and J. F. Lemmer, Eds. (1986).

Bishop, Edward W., and Guinness, G. Victor Jr., "Human Factors Interaction with Industrial Design", Human Factors, 8(4):279–289 (August 1966).

Blair, D., R. Pollack, "La logique du choix collectif" Pour la Science (1983).

Brown, Edward, "Human Factors Concepts For Management", Proceedings of the Human Factors Society, 1973, 372–375.

Bulkeley, Debra, "The Smartest House in America", Design News, Oct. 19, 1987, 56–61.

Burr, D. J.; "A Neural Network Digit Recognizer"; Proceedings of the 1986 IEEE International Conference of Systems, Man and Cybernetics, Atlanta, Ga.; pp. 1621–1625.

Caffery, B.; "Fractal Compression Breakthrough for Multimedia Applications"; Inside; Oct. 9, 1991.

Card, Stuart K., "A Method for Calculating Performance times for Users of Interactive Computing Systems", IEEE, 1979, 653–658.

Carlson, Mark A., "Design Goals for an Effective User Interface", Human Interfacing with Instruments, Electro/82 Proceedings, 3/1/1–3/1/4.

Carpenter, G. A., S. Grossberg, "The Art of Adaptive Pattern Recognition by a Self-Organizing Neural Network," IEEE Computer, March 1988, pp. 77–88.

Carroll, Paul B., "High Tech Gear Draws Cries of 'Uncle'", Wall Street Journal, Apr. 27, 1988, 29.

Casasent, D., et al.;, "General I and Q Data Processing on a Multichannel AO System"; Applied Optics; 25(18):3217–24 (Sep. 15, 1986).

Casasent, D., Photonics Spectra, November 1991, pp. 134–140.

Casasent, D., and Tescher, A., Eds., "Hybrid Image and Signal Processing II", Proc. SPIE Technical Symposium, April 1990, Orlando Fla. 1297 (1990).

Caudill, M.; "Neural Networks Primer-Part III"; AI Expert; June 1988; pp. 53–59.

Chao, J. J., E. Drakopoulos, C. C. Lee, "An evidential reasoning approach to distributed multiple hypothesis detection", Proceedings of the 20th Conference on decision and control, Los Angeles, Calif., December 1987.

Chen et al.; "Adaptive Coding of Monochrome and Color Images"; November 1977; pp. 1285–1292.

Cobb, Nathan, "I don't get it", Boston Sunday Globe Magazine, Mar, 25, 1990, 23–29.

Computer Visions, Graphics, and Image Processing 1987, 37:54–115.

Computers and Biomedical Research 5, 388–410 (1972).

Cooper, L. N.; "A Possible Organization of Animal Memory and Learning"; Nobel 24; (1973); Collective Properties of Physical Systems; pp. 252–264

Crawford et al.; "Adaptive Pattern Recognition Applied To An Expert System For Fault Diagnosis In Telecommunications Equipment"; pp. 10/1–8 (Inspec. Abstract No. 86C010699, Insepc IEE (London) & IEE Coll. on "Adaptive Filters", Digest No. 76, Oct. 10, 1985)

Danielsson, Erik, et al.; "Computer Architectures for Pictorial Inf. Systems"; IEEE Computer, November 1981; pp. 53–67.

Davis, Fred, "The Great Look-and-Feel Debate", A+, 5:9–11 (July 1987).

Dehning, Waltraud, Essig Heidrun, and Maass, Susanne, The Adaptation of Virtual Man-Computer Interfaces to User Requirements in Dialogs, Germany, Springer-Verlag, 1981.

Dempster, A. P., "A generalization of Bayesian inference", Journal of the Royal Statistical Society, Vol. 30, Series B (1968).

Dempster, A. P., "Upper and lower probabilities induced by a multivalued mapping", Annals of mathematical Statistics, no. 38 (1967).

Denker; 1984 International Test Conf., October 1984, Philadelphia, Pa.; pp. 558–563.

Derra, Skip, "Researchers Use Fractal Geometry, . . . ", Research and Development Magazine, March 1988.

Donovan, J., "Intel/IBM's Audio-Video Kernel", Byte, December, 1991, pp. 177–202.

Dubois, D., N. Prade, "Fuzzy sets and systems-Theory and applications", Academic Press, New York (1980).

Dubois, D.; "Modeles mathematiques de l'imprecis et de l'incertain en vue d'applications aux techniques d'aide a la decision"; Doctoral Thesis, University of Grenoble (1983).

Dubois, D., N. Prade, "Combination of uncertainty with belief functions: a reexamination", Proceedings 9th International Joint Conference on Artificial Intelligence, Los Angeles (1985).

Dubois, D., N. Prade, "Theorie des possibilites: application a la representation des connaissances en informatique", Masson, Paris (1985).

Duda, R. O., P. E. Hart, M. J. Nilsson, "Subjective Bayesian methods for rule-based inference systems", Technical Note 124-Artificial Intelligence Center-SRI International.

Dunning, B. B.; "Self-Learning Data-Base For Automated Fault Localization"; IEEE; 1979; pp. 155–157.

Ehrenreich, S. L., "Computer Abbreviations—Evidence and Synthesis", Human Factors, 27(2):143–155 (April 1985).

Electronic Engineering Times (EET), Oct. 28, 1991, p. 62.

Elton, J., "An Ergodic Theorem for Iterated Maps", Journal of Ergodic Theory and Dynamical Systems, 7 (1987).

Farrelle, Paul M. and Jain, Anil K.; "Recursive Block Coding-A New Approach to Transform Coding"; IEEE Transactions on Communications, Corn. 34(2) (February 1986).

Fitzpatrick, J. M., J. J. Grefenstette, D. Van Gucht; "Image Registration by Genetic Search"; Conf. Proc., IEEE Southeastcon 1984; pp. 460–464.

Foley, J. D., Wallace, V. L., Chan, P., "The Human Factor of Computer Graphics Interaction Techniques", IEEE CG&A, November 1984, pp. 13–48.

Friedman, M. B., "An Eye Gaze Controlled Keyboard", Proceedings of the 2nd International Conference on Rehabilitation Engineering, 1984, 446–447.

Fua, P. V., "Using probability density functions in the framework of evidential reasoning Uncertainty in knowledge based systems", B. Bouchon, R. R. Yager, Eds. Springer Verlag (1987).

Gilfoil, D., and Mauro, C. L., "Integrating Human Factors and Design: Matching Human Factors Methods up to Product Development", C. L. Mauro Assoc., Inc., 1–7.

Gleick, James, "Making a New Science", pp. 215, 239, date unknown.

Gogoussis et al.; Proc. SPIE Intl. Soc. Opt. Eng., November 1984, Cambridge, Mass.; pp. 121–127.

Gonzalez, Rafael C., "Digital Image Processing", Addison-Wesley, Reading, Mass. (1987).

Gould, John D., Boies, Stephen J., Meluson, Antonia, Rasammy, Marwan, and Vosburgh, Ann Marie, "Entry and Selection Methods For Specifying Dates". Human Factors, 32(2):199–214 (April 1989).

Green, Lee, "Thermo Tech: Here's a common sense guide to the new thinking thermostats", Popular Mechanics, October 1985, 155–159.

Grossberg, S., G. Carpenter, "A Massively Parallel Architecture for a Self-Organizing Neural Pattern Recognition Machine," Computer Vision, Graphics, and Image Processing (1987, 37, 54–115), pp. 252–315.

Grudin, Jonathan, "The Case Against User Interface Consistency", MCC Technical Report Number ACA-HI-002-89, January 1989.

Gullichsen, E., E. Chang, "Pattern Classification by Neural Network: An Experiment System for Icon Recognition," ICNN Proceeding on Neural Networks, March 1987, pp. IV-725–32.

Haruki, K. et al.; "Pattern Recognition of Handwritten Phonetic Japanese Alphabet Characters"; International Joint Conference on Neural Networks, Washington, D.C.; January 1990; pp. II-515 to II-518.

Harvey, Michael G., and Rothe, James T., "VideoCassette Recorders: Their Impact on Viewers and Advertisers", Journal of Advertising, 25:19–29 (December/January 1985).

Hawkins, William J., "Super Remotes", Popular Science, February 1989, 76–77.

Hayashi, Y., et al.; "Alphanumeric Character Recognition Using a Connectionist Model with the Pocket Algorithm"; Proceedings of the International Joint Conference on Neural Networks, Washington, D.C. Jun. 18–22; 1989; vol. 2, pp. 606–613.

Henke, Lucy L., and Donohue, Thomas R., "Functional Displacement of Traditional TV Viewing by VCR Owners", Journal of Advertising Research, 29:18–24 (April-May 1989).

Hinton et al.; "Boltzmann Machines: Constraint Satisfaction Networks that Learn"; Tech. Report CMU-CS-85-119; Carnegie-Mellon Univ; 5/84.

Hirzinger, G., Landzettel, K., "Sensory Feedback Structures for Robots with Supervised Learning", IEEE Conf. on Robotics and Automation, St. Louis, March 1985.

Hoban, Phoebe, "Stacking the Decks", New York, Feb. 16, 1987, 20:14.

Hoffberg, Linda I., "AN IMPROVED HUMAN FACTORED INTERFACE FOR PROGRAMMABLE DEVICES: A CASE STUDY OF THE VCR", Master's Thesis, Tufts University (Master of Sciences in Engineering Design, November).

Hoffberg, Linda I., "Designing User Interface Guidelines For Time-Shift Programming of a Video Cassette Recorder (VCR)", Proc. of the Human Factors Soc. 35th Ann. Mtg. pp. 501–504 (1991).

Hoffberg, Linda I., "Designing a Programmable Interface for a Video Cassette Recorder (VCR) to Meet a User's Needs", Interface 91 pp. 346–351 (1991).

Hopfield et al; "Computing with Neural Circuits: A Model"; Science; vol. 233:625–633 (Aug. 8, 1986).

Hopfield; "Neurons with graded response have collective computational properties like those of two-state neurons"; Proc. Natl. Acad. Sci. USA; 81:3088–3092 (May 1984).

Hopfield; "Neural Networks and Physical Systems with Emergent Collective Computational Abilities"; Proc. Natl. Acad. Sci. USA; 79:2554–2558 (April 1982).

Horgan, H., "Medical Electronics", IEEE Spectrum, January 1984, pp. 90–93.

Howard, Bill, "Point and Shoot Devices", PC Magazine, 6:95–97, August 1987.

Information Processing 71; North-Holland Publishing Company (1972) pp. 1530–1533.

Ishizuka, M., "Inference methods based on extended Dempster and Shafer's theory for problems with uncertainty/fuzziness", New Generation Computing, 1:159–168 (1983), Ohmsha, Ltd., and Springer Verlag.

Jackel, L. D., H. P. Graf, J. S. Denker, D. Henderson and I. Guyon, "An Application of Neural Net Chips: Handwritten Digit Recognition," ICNN Proceeding, 1988, pp. II-107–15.

Jane Pauley Special, NBC TV News Transcript, Jul. 17, 1990, 10:00 PM.

Jean, J. S. N., et al.; "Input Representation and Output Voting Considerations for Handwritten Numeral Recognition with Backpropagation"; International Joint Conference on Neural Networks, Washington, D.C., January 1990; pp. I-408 to I-411.

Jeffrey, R. J., "The logic of decision", The University of Chicago Press, Ltd., London (1983)(2nd Ed.).

Kaufmann, A., "Introduction a la theorie des sous-ensembles flous", Vol. 1, 2 et 3-Masson-Paris (1975).

Keeney, R. L., B. Raiffa, "Decisions with multiple objectives: Preferences and value tradeoffs", John Wiley and Sons, New York (1976).

Kellman, P., "Time Integrating Optical Signal Processing", Ph. D. Dissertation, Stanford University, 1979, pp. 51–55.

Kim, Y., "Chips Deliver Multimedia", Byte, December 1991, pp. 163–173.

Knowlton, K., "Virtual Pushbuttons as a Means of Person-Machine Interaction", Proc of Conf. Computer Graphics, Pattern Recognition and Data Structure, Beverly Hills, Calif., May 1975, pp. 350–352.

Koch, H., "Ergonomische Betrachtung von Schreibtastaturen", Humane Production, 1, pp. 12–15 (1985).

Kohonen; "Self-Organization & Memory", Second Ed., 1988; Springer-Verlag; pp. 199–209.

Kolson, Ann, "Computer wimps drown in a raging sea of technology", The Hartford Courant, May 24, 1989, B1.

Kortegaard, B. L.; "PAC-MAN, a Precision Alignment Control System for Multiple Laser Beams Self-Adaptive Through the Use of Noise"; Los Alamos National Laboratory; date unknown.

Kortegaard, B. L.; "Superfine Laser Position Control Using Statistically Enhanced Resolution in Real Time"; Los Alamos National Laboratory; SPIE-Los Angeles Technical Symposium; Jan. 23–25, 1985.

Kraiss, K. F., "Alternative Input Devices For Human Computer Interaction", Forschunginstitut Für Anthropotecahnik, Werthhoven, F. R. Germany.

Kraiss, K. F., "Neuere Methoden der Interaktion an der Schnittstelle Mensch-Maschine", Z. F. Arbeitswissenschaft, 2, pp. 65–70, 1978.

Kreifeldt, John, "Human Factors Approach to Medical Instrument Design", Electro/82 Proceedings, 3/3/1–3/3/6.

Kreifeldt, J. G., "A Methodology For Consumer Product Safety Analysis", The 3rd National Symposium on Human Factors in Industrial Design in Consumer Products, August 1982, 175–184.

Ksienski et al., "Low Frequency Approach to Target Identification", Proc. of the IEEE, 63(12):1651–1660 (December 1975).

Kuocheng, Andy Poing, and Ellingstad, Vernon S., "Touch Tablet and Touch Input", Interface '87, 327.

Kyburg, H. E., "Bayesian and non Bayesian evidential updating", Artificial Intelligence 31:271–293 (1987).

LeCun, Y., et al., "Handwritten Digit Recognition: Applications of Neural . . . ", IEEE Comm. Magazine, pp. 41–46 (November 1989).

LeCun, Y., "Connectionism in Perspective", in R. Pfeifer, Z. Schreter, F. Fogelman, L. Steels, (Eds.), 1989, "Generalization and Network Design Strategies", pp. 143–55.

Ledgard, Henry, Singer, Andrew, and Whiteside, John, Directions in Human Factors for Interactive Systems, New York, Springer-Verlag, 1981.

Lee, Eric, and MacGregor, James, "Minimizing User Search Time Menu Retrieval Systems", Human Factors, 27(2):157–162 (April 1986).

Lendaris, G. G., and Stanely, G. L., "Diffraction Pattern Sampling for Automatic Target Recognition", Proc. IEEE 58:198–205 (1979).

Leon, Carol Boyd, "Selling Through the VCR", American Demographics, December 1987, 40–43.

Liepins, G. E., M. R. Hilliard; "Genetic Algorithms: Foundations & Applications"; Annals of Operations Research, 21:31–58 (1989).

Lin, H. K., et al.; "Real-Time Screen-Aided Multiple-image Optical Holographic Matched-Filter Correlator"; Applied Optics; 21(18):3278–3286 (Sep. 15, 1982)

Lippmann, R. P., "An Introduction to Computing with Neural Nets", IEEE ASSP Magazine, 4(2):4–22 (April 1987).

Long, John, "The Effect of Display Format on the Direct Entry of Numerical Information by Pointing", Human Factors, 26(1):3–17 (February 1984).

Lu, C., "Computer Pointing Devices: Living With Mice", High Technology, January 1984, pp. 61–65.

Mahalanobis, A., et al.; "Minimum Average Correlation Energy Filters"; Applied Optics; 26(17):3633–40 (Sep. 1, 1987).

Mandelbrot, B., "The Fractal Geometry of Nature", W. H. Freeman & Co., San Francisco, Calif., 1982, 1977; and Mantei, Marilyn M., and Teorey, Toby J., "Cost/Benefit Analysis for Incorporating Human Factors in the Software Lifecycle", Association for Computing Machinery, 1988.

Maragos, P., "Tutorial Advances in Morphological Image Processing" Optical Engineering 26:7:623–632 (1987).

Martin, G. L. et al.; "Recognizing Hand-Printed Letters and Digits Using Backpropagation Learning"; Technical Report of the MCC, Human Interface Laboratory, Austin, Tex.; January 1990; pp. 1–9.

McAulay, A. D., J. C. Oh; "Image Learning Classifier System Using Genetic Algorithms"; IEEE Proc. of the National Aerospace & Electronics Conference; 2:705–710 (1989).

Meads, Jon A., "Friendly or Frivolous", Datamation, Apr. 1, 1988, 98–100.

Miller, R. K.; Neural Networks ((c) 1989: Fairmont Press; Lilburn, Ga.); pp. 2–12 and Chapter 4, "Implementation of Neural Networks"; pp. 4-1 to 4-26.

Molley, P., "Implementing the Difference-Squared Error Algorithm Using An Acousto-Optic Processor", SPIE, 1098:232–239,(1989).

Molley, P., et al., "A High Dynamic Range Acousto-Optic Image Correlator for Real-Time Pattern Recognition", SPIE, 938:55–65 (1988).

Moore, T.G. and Dartnall, "Human Factors of a Microelectronic Product: The Central Heating Timer/Programmer", Applied Ergonomics, 13(1):15–23 (1983).

Mori; "Towards the construction of a large-scale neural network"; Electronics Information Communications Association Bulletin PRU 88-59; pp. 87–94.

Naik et al., "High Performance Speaker Verification . . . ", ICASSP 86, Tokyo, CH2243-4/86/0000-0881, IEEE 1986, pp. 881–884.

Netravali, Arun N., and Haskell, Barry G., "Digital Pictures Representation and Compression", Plenum Press, New York (1988).

Ney, H., et al.; "A Data Driven Organization of the Dynamic Programming Beam Search for Continuous Speech Recognition"; Proc. ICASSP 87; pp. 833–836; 1987.

Nilsson, N. J.; The Mathematical Foundations of Learning Machines ((c) 1990: Morgan Kaufmann Publishers, San Mateo, Calif.) and particularly section 2.6 "The Threshold Logic Unit (TLU)", pp. 21–23 and Chapter 6, "Layered Machines" pp. 95–114.

Norman, Donald A., "Infuriating By Design", Psychology Today, 22(3):52–56 (March 1988).

Norman, Donald A., The Psychology of Everyday Things, New York: Basic Book, Inc. 1988.

Norman, D.A., Fisher, D., "Why Alphabetic Keyboards Are Not Easy To Use: Keyboard Layout Doesn't Much Matter", Human Factors 24(5), pp. 509–519 (1982).

O'Neal et al.; "Coding Isotropic Images"; November 1977; pp. 697–707.

Ohsuga et al, "Entrainment of Two Coupled van der Pol Oscillators by an External Oscillation", Biological Cybernetics, 51:225–239 (1985).

Omata et al, "Holonic Model of Motion Perception", IEICE Technical Reports, Mar. 26, 1988, pp. 339–346.

Optical Engineering 28:5 (May 1988)(Special Issue on product inspection).

Pawlicki, T. F., D. S. Lee, J. J. Hull and S. N. Srihari, "Neural Network Models and their Application to Handwritten Digit Recognition," ICNN Proceeding, 1988, pp. II-63–70.

Perry et al.; "Auto-Indexing Storage Device"; IBM Tech. Disc. Bulletin, 12(8):1219 (January 1970).

Perspectives: High Technology 2, 1985.

Peterson, Ivars, "Packing It In-Fractals . . . ", Science News, 131(18):283–285 (May 2, 1987).

Platte, Hans-Joachim, Oberjatzas, Gunter, and Voessing, Walter, "A New Intelligent Remote Control Unit for Consumer Electronic Device", IEEE Transactions on Consumer Electronics, Vol. CE-31(1):59–68 (February 1985).

Press, William H. et al, "Numerical Recipes in C The Art of Scientific Computing", Cambridge University Press, 1988.

Proakis, John G., *Digital Communications*, McGraw-Hill (1983)

Proceedings, 6th International Conference on Pattern Recognition 1982, pp. 152–136.

Psaltis, D., "Two-Dimensional Optical Processing Using One-Dimensional Input Devices", Proceedings of the IEEE, 72(7):962–974 (July 1984).

Psaltis, D., "Incoherent Electro-Optic Image Correlator", Optical Engineering, 23(1):12–15 (January/February 1984).

Ravichandran, G. and Casasent, D., "Noise and Discrimination Performance of the MINACE Optical Correlation Filter", Proc. SPIE Technical Symposium, April 1990, Orlando Fla., 1471 (1990).

Rhodes, W., "Acousto-Optic Signal Processing: Convolution and Correlation", Proc. of the IEEE, 69(1):65–79 (January 1981).

Richards J., and Casasent, D., "Real Time Hough Transform for Industrial Inspection" Proc. SPIE Technical Symposium, Boston 1989 1192:2–21 (1989).

Rogus, John G. and Armstrong, Richard, "Use of Human Engineering Standards in Design", Human Factors, 19(1) :15–23 (February 1977).

Rosch, Winn L., "Voice Recognition: Understanding the Master's Voice", PC Magazine, Oct. 27, 1987, 261–308.

Rosenfeld, Azriel and Avinash C. Kak; Digital Picture Processing, Second Edition, Volume 2, Academic Press, 1982.

Roy, B., "Classements et choix en presence de points de vue multiples", R.I.R.O.-2eme annee-no. 8; pp. 57–75 (1968).

Roy, B., "Electre III: un algorithme de classements fonde sur une representation floue des preferences en presence de criteres multiples" Cahiers du CERO, 20(1):3–24 (1978).

Rumelhart, D. E., et al.; Parallel Distributed Processing, ((c) 1986: MIT Press, Cambridge, Mass.), and specifically Chapter 8 thereof, "Learning Internal Representations by Error Propagation"; pp. 318–362.

Rumelhart, D. E., et al.; "Learning Internal Representations by Error Propagation"; Parallel Distr. Proc.: Explorations in Microstructure of Cognition, 1:318–362 (1986).

Rutherford, H. G., F. Taub and B. Williams; "Object Identification and Measurement from Images with Access to the Database to Select Specific Subpopulations of Special Interest"; May 1986.

Rutter et al.; "The Timed Lattice-A New Approach To Fast Converging Equalizer Design"; pp. VIII/1–5 (Inspec. Abstract No. 84C044315, Inspec IEE (London) & IEE Saraga Colloquium on Electronic Filters, May 21, 1984)

Sakoe, H.; "A Generalization of Dynamic Programming Based Pattern Matching Algorithm Stack DP-Matching"; Transactions of the Committee on Speech Research; The Acoustic Society of Japan; p. S83-23; 1983.

Sakoe, H.; "A Generalized Two-Level DP-Matching Algorithm for Continuous Speech Recognition"; Transactions of the IECE of Japan; E65(11):649–656 (November 1982).

Sarver, Carleton, "A Perfect Friendship", High Fidelity, 39:42–49 (May 1989).

Scharlic, A., "Decider sur plusieurs criteres. Panorama de l'aide a la decision multicritere" Presses Polytechniques Romandes (1985).

Schmitt, Lee, "Let's Discuss Programmable Controllers", Modern Machine Shop, May 1987, 90–99.

Schniederman, Ben, Designing the User Interface: Strategies for Effective Human-Computer Interaction, Reading, Mass., Addison-Wesley, 1987.

Schurmann, J.; "Zur Zeichen und Worterkennung beim Automatischen Anschriftenlesen"; Wissenschaftlichl, Berichte, 52(1/2) (1979).

Scientific American; "Not Just a Pretty Face"; March 1990, pp. 77–78.

Shafer, G., "A mathematical theory of evidence", Princeton University Press, Princeton, N.J. (1976).

Shimizu et al, "Principle of Holonic Computer and Holovision", Journal of the Institute of Electronics, Information and Communication, 70(9):921–930 (1987).

Shinan et al., "The Effects of Voice Disguise . . . ", ICASSP 86, Tokyo, CH2243-4/86/0000-0885, IEEE 1986, pp. 885–888.

Silverston et al.; "Spectral Feature Classification and Spatial Pattern Rec."; SPIE 201:17–26, Optical Pattern Recognition (1979).

Simpson, W. R., C. S. Dowling; "WRAPLE: The Weighted Repair Assistance Program Learning Extension"; IEEE Design & Test, 2:66–73 (April 1986).

Smith, Sidney J., and Mosier, Jane N., Guidelines for Designing User Interface Software, Bedford, Mass.; MITRE, 1986.

Specht; IEEE Internati. Conf. Neural Networks, 1:1525–1532 (July 1988); San Diego, Calif.

Sperling, Barbara Bied, Tullis Thomas S., "Are You a Better 'Mouser' or 'Trackballer'? AComparison of Cursor-Positioning Performance", An Interactive/Poster Session at the CHI+GI'87 Graphics Interface and Human Factors in Computing Systems Conference.

Sprageu, R. A.; "A Review of Acousto-Optic Signal Correlators"; Optical Engineering; 16(5):467–74 (September/October 1977)

Stanley R. Sternberg; "Biomedical Image Processing"; IEEE Computer; 1983; pp. 22–34.

Stewart, R. M.; "Expert Systems For Mechanical Fault Diagnosis"; IEEE; 1985; pp. 295–300.

Streeter, L. A., Ackroff, J. M., and Taylor, G. A. "On Abbreviating Command Names", The Bell System Technical Journal, 62(6):1807–1826 (July/August 1983).

Sugeno, M., "Theory of fuzzy integrals and its applications", Tokyo Institute of Technology (1974).

Svetkoff et al.; Hybrid Circuits (GB), No. 13, May 1987; pp. 5–8.

Swanson, David, and Klopfenstein, Bruce, "How to Forecast VCR Penetration", American Demographic, December 1987, 44–45.

Tello, Ernest R., "Between Man And Machine", Byte, September 1988, 288–293.

Thomas, John, C., and Schneider, Michael L., Human Factors in Computer Systems, New Jersey, Ablex Publ. Co., 1984.

Trachtenberg, Jeffrey A., "How do we confuse thee? Let us count the ways", Forbes, Mar. 21, 1988, 159–160.

Tyldesley, D. A., "Employing Usability Engineering in the Development of Office Products", The Computer Journal", 31(5):431–436 (1988).

Udagawa, K., et al; "A Parallel Two-Stage Decision Method for Statistical Character Recognition . . . "; Electronics and Communications in Japan (1965).

Vander Lugt, A., "Signal Detection By Complex Spatial Filtering", IEEE Transactions On Information Theory, IT-10, 2:139–145 (April 1964).

Vander Lugt, A., et al.; "The Use of Film Nonlinearites in Optical Spatial Filtering"; Applied Optics; 9(1):215–222 (January 1970).

Vander Lugt, A.; "Practical Considerations for the Use of Spatial Carrier-Frequency Filters"; Applied Optics; 5(11):1760–1765 (November 1966).

Vannicola et al, "Applications of Knowledge based Systems to Surveillance", Proceedings of the 1988 IEEE National Radar Conference, 20–21 April 1988, pp. 157–164.

Verplank, William L., "Graphics in Human-Computer Communication: Principles of Graphical User-interface Design", Xerox Office Systems.

Vitols; "Hologram Memory for Storing Digital Data"; IBM Tech. Disc. Bulletin 8(11):1581–1583 (April 1966).

Voyt, Carlton F., "PLC's Learn New Languages", Design News, Jan. 2, 1989, 78.

Wald; Sequential Analysis; Dover Publications Inc., 1947; pp. 34–43.

Wasserman, Philip D.; "Neural Computing-Theory & Practice"; 1989; pp. 128–129.

Weshsler, H. Ed., "Neural Nets For Human and Machine Perception", Academic Press, New York (1991).

Whitefield, A. "Human Factors Aspects of Pointing as an Input Technique in Interactive Computer Systems", Applied Ergonomics, June 1986, 97–104.

Wiedenbeck, Susan, Lambert, Robin, and Scholtz, Jean, "Using Protocol Analysis to Study the User Interface", Bulletin of the American Society for Information Science, June/July 1989, 25–26.

Wilke, William, "Easy Operation of Instruments by Both Man and Machine", Electro/82 Proceedings, 3/2/1–3/2/4.

Willshaw et al.; "Non-Holographic Associative Memory"; Nature; 222:960–962 (Jun. 7, 1969).

Yager, R. R., "Entropy and specificity in a mathematical theory of Evidence", lnt. J. General Systems, 9:249–260 (1983).

Yamada et. al.; "Character recognition system using a neural network"; Electronics Information Communications Association Bulletin PRU 88-58, pp. 79–86.

Yamane et al.; "An Image Data Compression Method Using Two-Dimensional Extrapolative Prediction-Discrete Sine Transform"; Oct. 29–31, 1986; pp. 311–316.

Yoder, Stephen Kreider, "U.S. Inventors Thrive at Electronics Show", The Wall Street Journal, Jan. 10, 1990, B1.

Zadeh, L. A., "Fuzzy sets", Information and Control, 8:338–353 (1965).

Zadeh, L. A., "Probability measures of fuzzy events", Journal of Mathematical Analysis and Applications, 23:421–427 (1968).

Zadeh, L. A., "Fuzzy sets as a basis for a theory of possibility", Fuzzy sets and Systems 1:3–28 (1978).

Zeisel, Gunter, Tomas, Philippe, Tomaszewski, Peter, "An Interactive Menu-Driven Remote Control Unit for TV-Receivers and VC-Recorders", IEEE Transactions on Consumer Electronics, 34(3):814–818.

Zhu, X., et al.; "Feature Detector and Application to Handwritten Character Recognition"; International Joint Conference on Neural Networks, Washington, D.C.; January 1990; pp. II-457 to II-460.

APPENDIX

AN IMPROVED HUMAN FACTORED INTERFACE FOR PROGRAMMABLE DEVICES:

A CASE STUDY OF THE VCR

A Thesis

Submitted by

Linda I. Hoffberg

In partial fulfillment of the requirements for the degree of

Master of Sciences in

Engineering Design

TUFTS UNIVERSITY

November, 1990

Copyright (C) 1990, by Linda I. Hoffberg

DEDICATION

In loving memory of Anne Elizabeth Borghesani (J'89)

ACKNOWLEDGEMENTS

There are many people to whom I would like to express appreciation for their contributions to this Thesis.

I would like to thank my advisory committee, Dr. Philip B. Sampson, Dr. Stephen Levine, and especially my principal adviser, Dr. John G. Kreifeldt, whose ideas initiated this project, and whose constant support were invaluable.

I greatly appreciate all of the volunteer subjects, friends, and the Engineering Design Department for making this research possible. I am also indebted to Tufts University Engineering Department, Digital Equipment Corporation, and the Mead family for financing this research, and to NVIEW™ who lent an infrared keyboard for the prototyping.

Finally, thank you Mom, Dad, and Phil for all your assistance, encouragement, and patience.

ABSTRACT

The need for a more usable interface for programmable devices is widely recognized. Research has been performed in the area of user interface design in order to produce a usable interface. The objective of this study is to propose guidelines for a "Human Factored" interface in a case study utilizing the Video Cassette Recorder (VCR).

Research and testing were performed in order to identify where problems exist and how to minimize them. From the results obtained, an interface was developed and implemented on HyperPAD™, a prototyping tool. An experiment was then devised to compare the new interface with the interface of an existing VCR. Improvements were made to reduce the time required to learn to use a VCR by 50%.

As a result of this work, guidelines are presented to help designers produce more usable interfaces, thus making VCRs and other programmable devices that people can use easily.

TABLE OF CONTENTS

LIST OF TABLES

LIST OF FIGURES

INTRODUCTION..........................................................1

CHAPTER 1  BACKGROUND.................................................3
        1.1  VCR Statistics...........................................4
        1.2  VCR Technology...........................................6
        1.3  VCR Usage................................................6
        1.4  Programming Steps........................................7
        1.5  Current Technology......................................10
        1.6  Input Devices...........................................12

CHAPTER 2  PROBLEM STATEMENT.........................................14
        2.1  Problem Definition......................................14
        2.2  Goal....................................................14

CHAPTER 3  TESTING OF EXISTING VCR INTERFACES........................16
        3.1  Methodology.............................................16
        3.2  Initialization..........................................16
        3.3  Directed Research.......................................17
        3.4  Design..................................................21
        3.5  Equipment...............................................26
            3.5.1  Bar Code Programming.............................27
            3.5.2  On Screen Programming............................29
            3.5.3  Display Panel Programming........................29
        3.6  Results.................................................29
            3.6.2  Subjective Analysis of Test 1....................38
            3.6.3  Statistical Analysis of Test 1...................40
        3.7  Discussion..............................................42

CHAPTER 4  DEVELOPMENT AND EVALUATION................................44
        4.1  Criteria for Developing the Interface...................44
        4.2  Constraints for Testing the Prototype (Test 2)..........45
        4.3  Interface Requirements..................................45
        4.4  Decision on the Input Device............................47

CHAPTER 5  CONCEPTUALIZATION OF THE IDEAL INTERFACE..................50

CHAPTER 6  TESTING OF THE NEW INTERFACE..............................51
        6.1  Methodology.............................................51
        6.2  Equipment...............................................51
        6.3  Programming.............................................51
        6.4  Revising the Interface..................................53
        6.5  Design..................................................53
        6.6  Card's Method for Calculating Performance Times for Users
             of Interactive Computing Systems......................54
        6.7 Results..................................................57
            6.7.1  Computer Response Time...........................57

```
         6.7.2  Errors..............................................58
         6.7.3  Simulation of the AKAI Interface....................59
         6.7.4  Simulation of the New Interface.....................62
    6.8  Statistical Analysis of Test 2 ..........................64
         6.8.1  Theory..............................................69
         6.8.2  Searching Time......................................73
         6.8.3  Mental Preparation Time.............................77
    6.9  Subjective Analysis of Test 2 ...........................79
    6.10 Discussion ..............................................85

CHAPTER 7  DEVELOPMENT OF AN INTERFACE FOR A VCR......................87

CHAPTER 8  SUMMARY....................................................90
         8.1  Recommendations for Improving the Prototype ............94
         8.2  Conclusion .............................................96
         8.3  Recommendations for Future Research ....................97

BIBLIOGRAPHY.........................................................100
```

LIST OF TABLES

Table 1 - Phases of the Design Process......................... 2
Table 2 - Advantages And Disadvantages Of Pointing Devices... 12
Table 3 - Frequency Of Playing Recordings On VCRs............ 19
Table 4 - Frequency Of Recording On VCRs..................... 19
Table 5 - Features The Respondents Liked And Disliked........ 21
Table 6 - VCRs Studied In Test 1............................. 22
Table 7 - The Steps Required To Set A VCR.................... 22
Table 8 - Critical Steps Necessary To Program A VCR.......... 26
Table 9 - Average Times In Seconds To Perform The Critical
    Steps................................................... 35
Table 10 - Critical Step Not Completed....................... 37
Table 11 - Like/Dislike And Easy/Difficult Scales............ 39
Table 12 - Cooper-Harper Rating Scale........................ 39
Table 13 - Averages Of The Subjective Ratings For The VCRs... 40
Table 14 - Total Time In Seconds And (Total Time - Computer
    Time) For The Critical Steps Using The AKAI Interface.. 60
Table 15 - Total Time In Seconds And (Total Time - Computer
    Time) For The Critical Steps Using The New Interface... 63
Table 16 - Average Time In Seconds For The Critical Steps.... 65
Table 17 - Number Of Subjects Unable To Succeed On The Critical
    Steps On Both Interfaces............................... 65
Table 18 - Screens Required For The AKAI Interface........... 74
Table 19 - Screens Required For The New Interface............ 76
Table 20 - Averages And Standard Deviations Of The Subjective
    Ratings For The AKAI Interface......................... 81
Table 21 - Comments Regarding The AKAI Interface............. 82
Table 22 - Numerical Averages And Standard Deviations Of The
    Subjective Ratings For The New Interface............... 82
Table 23- Comments Regarding The New Interface.............. 84
Table 24 - Guidelines For The Interface Of A VCR............. 87
Table 25 - Percentage Of Total Time For The Critical Steps... 91
Table 26 - Improvements For The New Interface................ 94
Table 27 - Dislikes Regarding The New Interface.............. 95

LIST OF FIGURES

Figure 4:
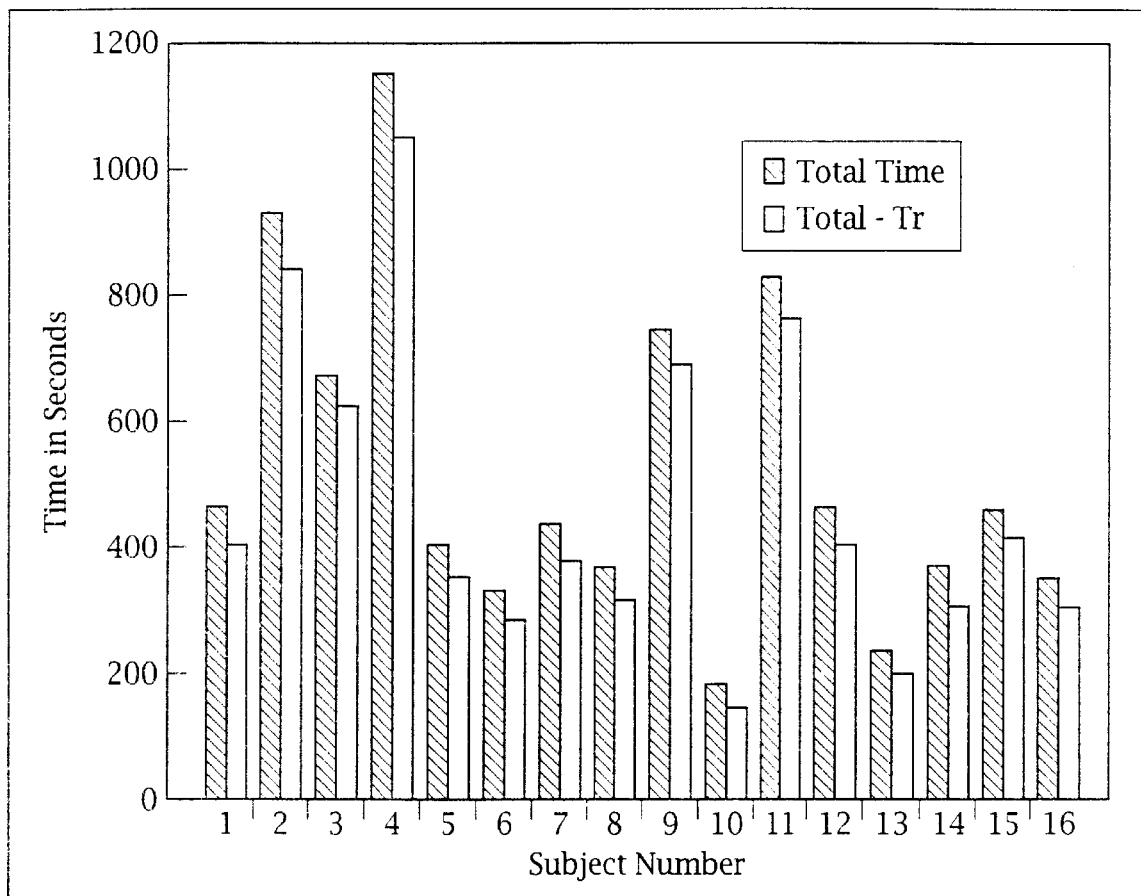
FIG. 4 graphically shows the differences in seconds between total time for the interface of the present invention for each subject.
Figure 11:
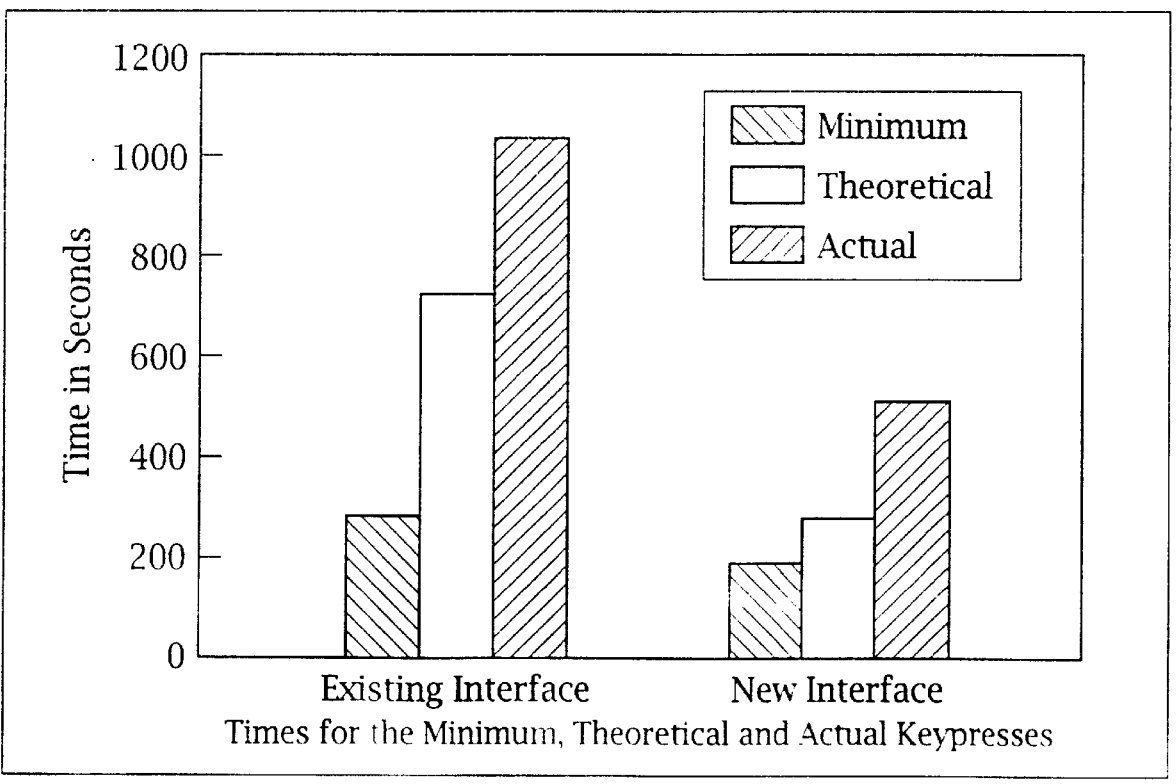
FIG. 11 graphically compares the actual and theoretical time necessary for programming the prior art and the interface of the present invention.
Figure 13:
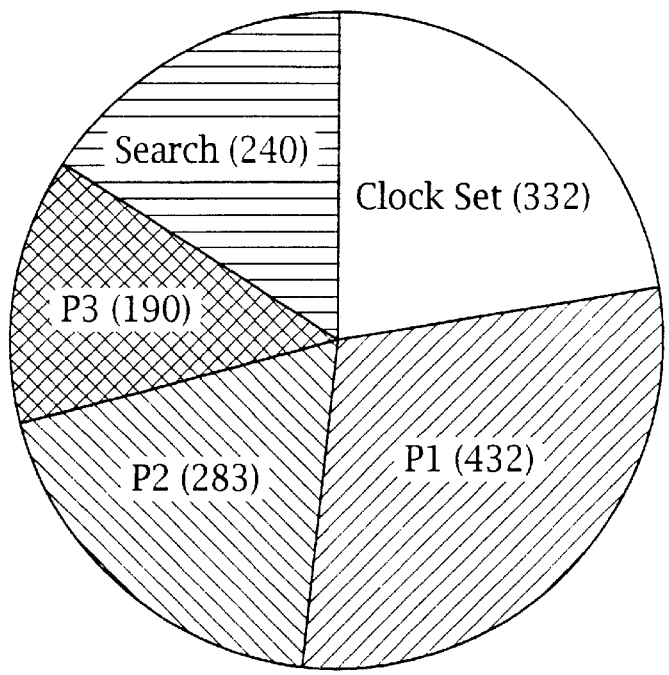
FIGS. 13 and 14 graphically show the percentage time for the critical steps in programming the prior art and the interface of the present invention.
Figure 14:
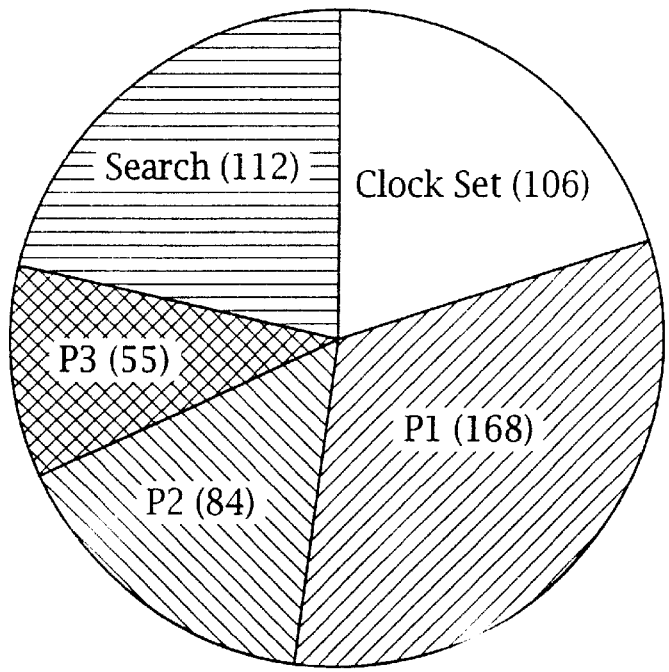
Figure 18:
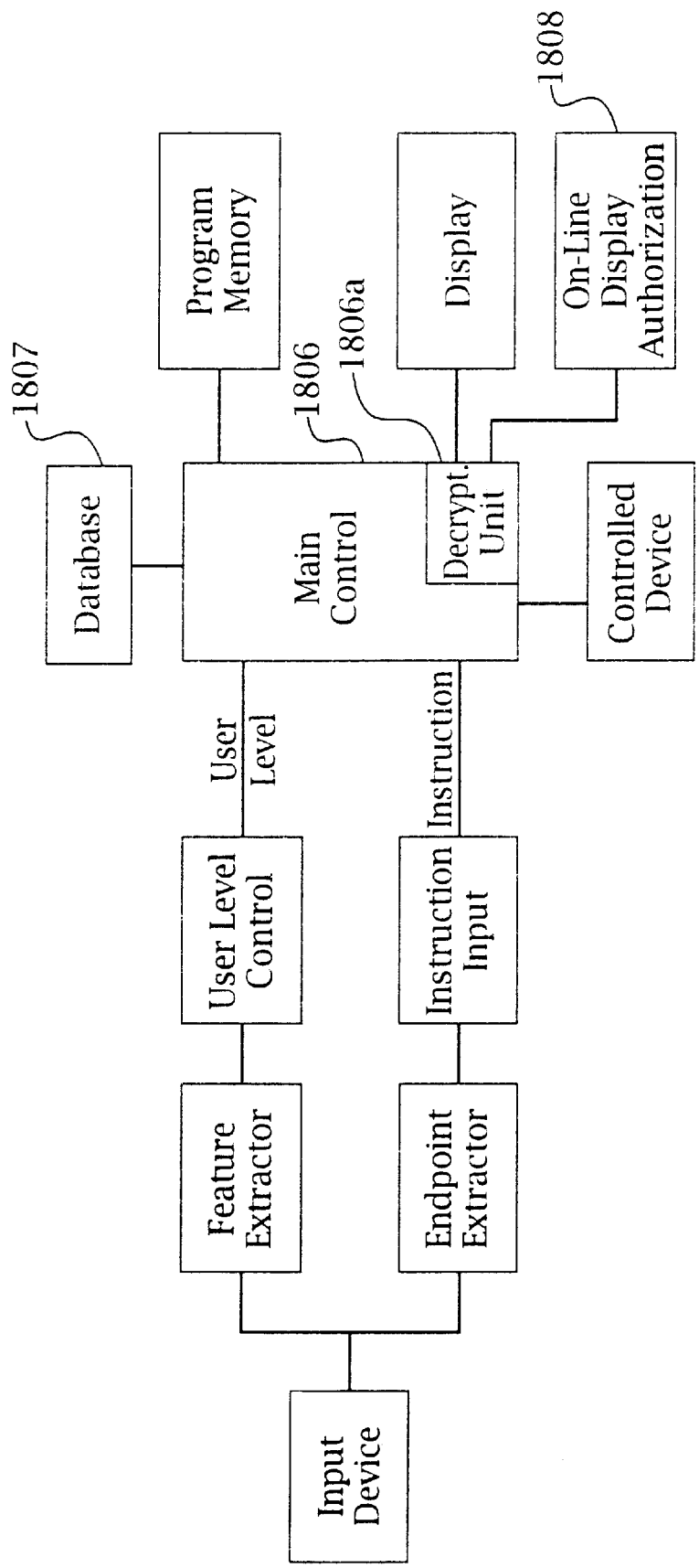
FIG. 18 is a block diagram of a non-program information feature extraction circuit of the present invention.
Figure 21:
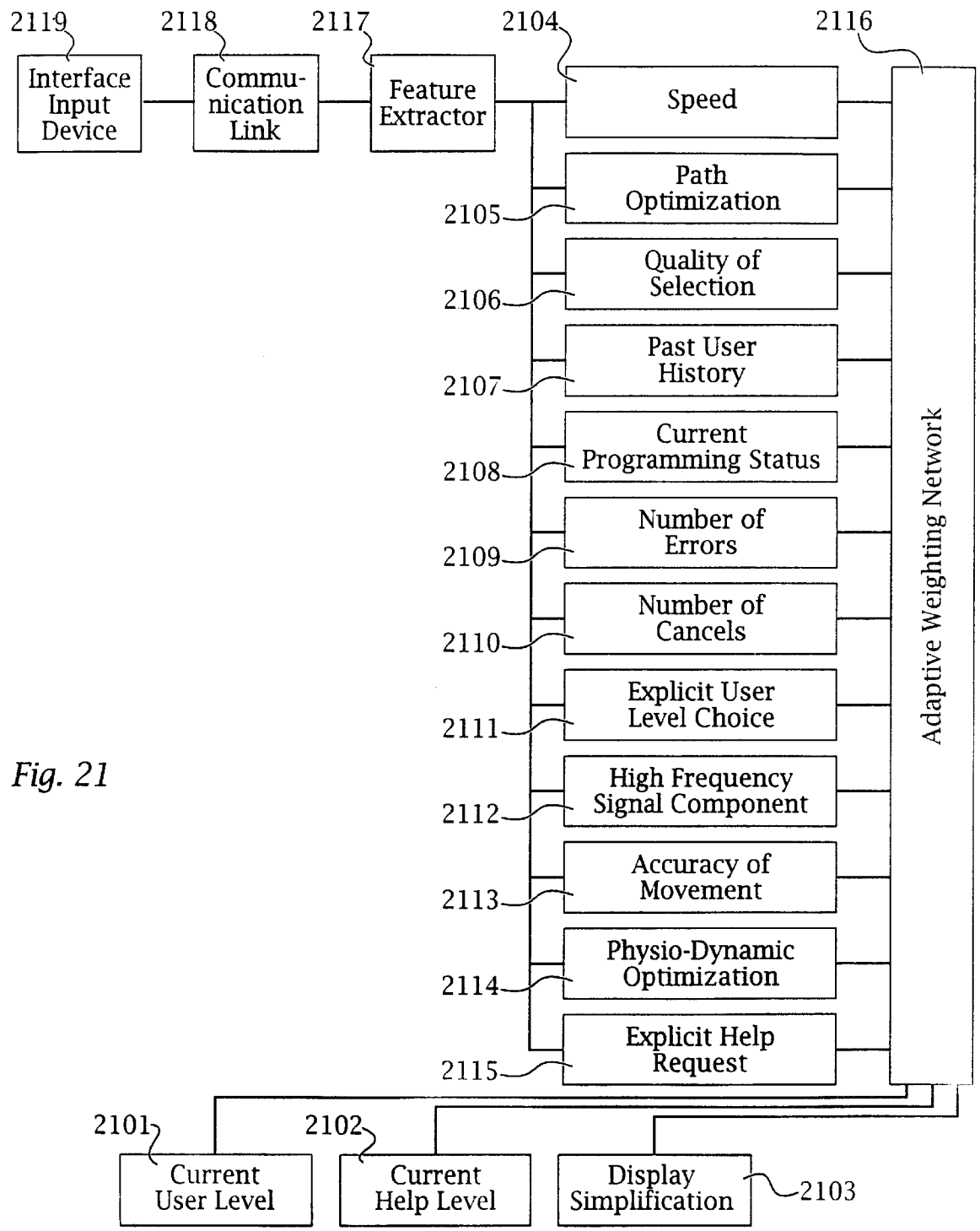
FIG. 21 is a block diagram of a user level determining system of the present invention.
Figure 25:
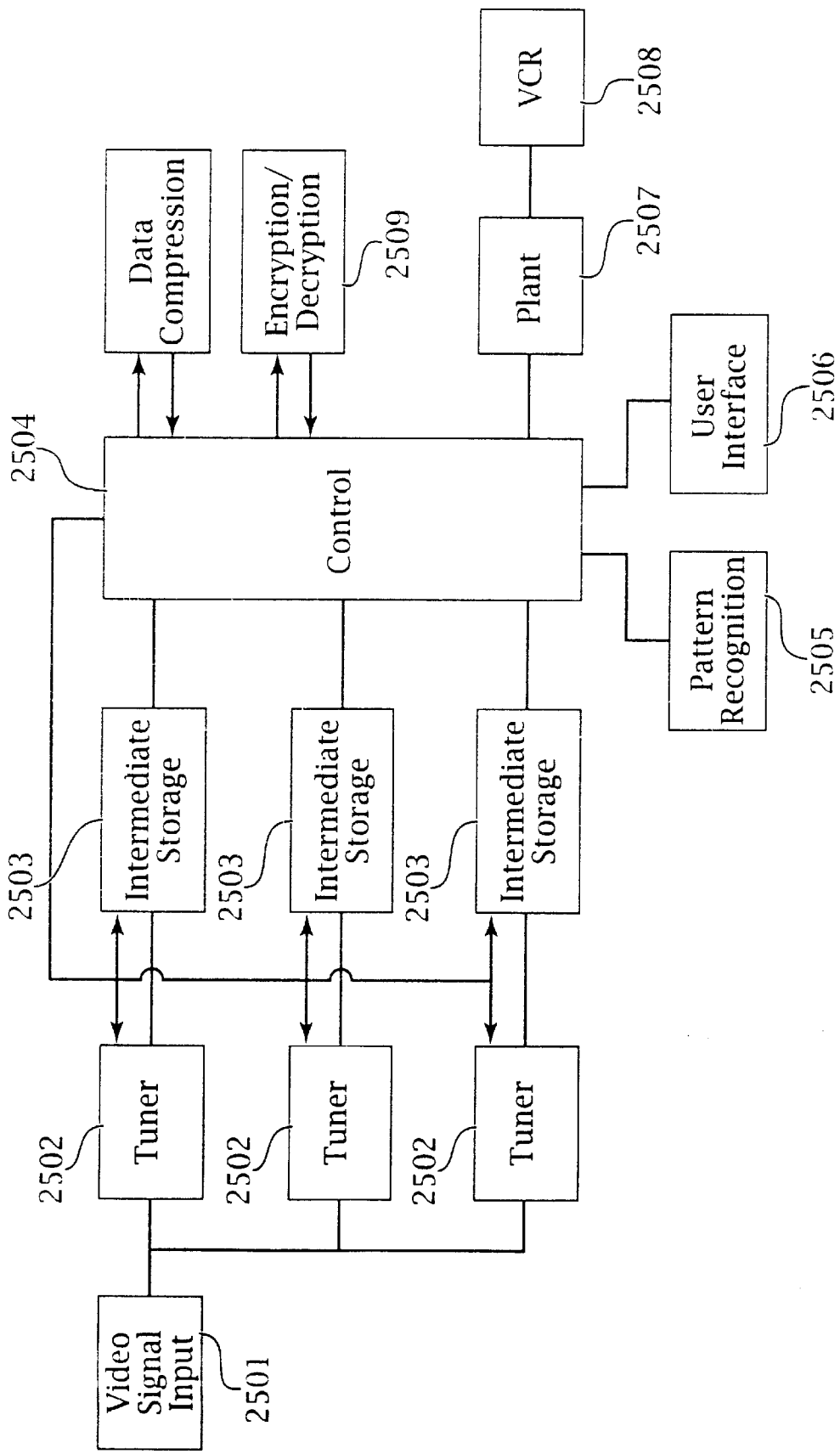
FIG. 25 is a block diagram of a multiple video signal input apparatus, with pattern recognition, data compression, data encryption, and a user interface of the present invention.

Figure 1 - Bloom County Cartoon................................ 3
Figure 2 - Questionnaire From Test 1.......................... 17
Figure 3 - Frequency Of Using The VCR......................... 20
Figure 4 - Flowchart Of The Steps Required To Set A VCR...... 23
Figure 5 - Briefing Statement................................. 23
Figure 6 - Instructions For Testing Phase 1. ................ 24
Figure 7 - Questionnaire/Interview For Test 1................. 25
Figure 8 - Panasonic Bar Code VCR............................. 28
Figure 9 - Critical Steps Required For Test 1................. 35
Figure 10 - The Minimum, Maximum, Average, And Standard
    Deviation Of The Total Times For The VCRs............... 36
Figure 11 - The Average Time In Seconds For Each Critical
    Step.................................................... 36
Figure 12 - Critical Steps Not Completed...................... 38
Figure 13 - Search Time vs. Total Time For Each VCR.......... 42
Figure 14 - Required And Average Extra Keypresses For Each
    Interface............................................... 59
Figure 15 - Differences In Seconds Between Total Time And
    (Total Time - Computer Time) For The AKAI Interface.... 60
Figure 16 - Differences In Seconds Between Total Time And
    (Total Time - Computer Time) For The New Interface..... 64
Figure 17 - The Critical Steps For Test 2..................... 66
Figure 18 - The Statistics By Subject For Test 2............. 66
Figure 19 - Statistics For The AKAI Interface................. 67
Figure 20 - Statistics For The New Interface.................. 67
Figure 21 - Number Of Keypresses Made By The Test
    Participants............................................ 71
Figure 22 - The Differences Between The Theoretical and Actual
    Times In Seconds For The Keypresses Of Both Interfaces. 72
Figure 23 - Theoretical Time In Seconds For Minimum Number Of
    Keypresses, Theoretical Time In Seconds For The Actual
    Number Of Keypresses, And Actual Time In Seconds....... 73
Figure 24 - Proportion Of Time Spent Setting The Programs.... 86
Figure 25 - Percentage Of The Total Time For The Critical Steps
    Using The AKAI Interface................................ 91
Figure 26 - Percentage Of The Total Time For The Critical Steps
    Using The New Interface................................. 92

INTRODUCTION

The programming of electronic devices has become a familiar everyday household challenge. Lifestyles are continually changing and people are extremely busy, so there is a distinct advantage to being able to preset appliances to perform their functions unattended. Although many industrial researchers are trying to improve electronic devices, they seem to focus on increasing the number of features, rather than on making the ones which already exist easier to use.[1] As a product becomes more "feature-rich," complexity also increases, and this makes the product difficult to use. Psychotherapist Craig Bro remarked, "I think we're gonna see more and more gadgets in our lives presented as these wonderful value-added items that are gonna make our lives richer."[2] Consumers are no longer satisfied with products that meet only technological criteria. They desire products they can use.[3]

Some of the most popular programmable products include VCRs, answering machines, microwave ovens, alarm clocks, thermostats, cameras, home security systems, lighting systems, and automobiles. The purpose of this research is to examine both existing technology and the human factors issues involved in programming electronic devices in order to develop a usable interface for one of the most frustrating products, the Video Cassette Recorder (VCR). The problems with programmable devices are described in an effort to develop interface guidelines for improving these devices. The design process was divided into the six phases shown in Table 1.

Table 1 − Phases of the Design Process

PHASE 1 − INITIALIZATION
1. Identification of Problem Statement and Goals
2. Background Research
   a. Programmable Devices
   b. Current Technology
   c. Human Factors
   d. Screen Display Design
   e. Patent Search
   f. Consumer Preferences Research
3. Market Research PHASE 2 − DIRECTED RESEARCH
1. Interviews
2. Questionnaires
3. Testing of Existing Interfaces (Test 1)

PHASE 3 − DEVELOPMENT AND EVALUATION
1. Development of Criteria
2. Definition of Interface Requirements
3. Evaluation of Input Devices PHASE 4 − CONCEPTUALIZATION OF THE IDEAL INTERFACE
1. Implementation of Information Gathered
2. Development of a Prototype PHASE 5 − FINAL EVALUATION
1. Testing of the Prototype (Test 2)
2. Data Analysis
3. Refinement of the Prototype PHASE 6 − FINAL SPECIFICATION AND REPORT
1. Documentation of Final Program
2. Documentation of Methodology
3. Production of a List of Recommended Techniques For Designing Programmable Devices
4. Writing of the Final Report

CHAPTER 1  BACKGROUND

Many guidelines for designing an interface for a computer screen have been developed.[4] However, few, if any, exist which are application-specific. People find it difficult to program devices and are thus intimidated by new technology. If there were adequate guidelines for manufacturers to follow while designing the interfaces, the problems that people are experiencing would be greatly reduced.

The term "Technodolts" has been coined, perhaps unfairly, to describe people who are baffled by VCRs and other complex electronic products.[5] These people are unable to even set the clock on the VCR, and many have covered the clock display with tape or have propped something in front of the blinking clock display in order to hide it so they won't be annoyed. Figure 1 shows a cartoon depicting a problem that many people face when trying to program their VCRs.

Figure 1 – Bloom County Cartoon
Copyright 1987 Washington Post Writers Group
Reprinted with Permission Psychologist Stephen Lande reported that he treats many patients who are computer and VCR phobic.[6] These people fear that they might harm the electronic system, invoking criticism or disapproval if they make mistakes. These consumers blame themselves, rather than the equipment, for their mistakes, and they often stay at home to manually record programs, even though they can set their equipment to record in advance. Perhaps the real fault lies in the complexity of the VCR, and efforts should be made to make it easier to use.

People learn most efficiently through the interactive experiences of doing, thinking, and knowing.[7] For ease-of-use, efficiency, and enjoyment, using the device should be intuitive. Users should be able to use the device without referring to the instruction manual.[8] Well-designed products contain visual clues which prompt and convey their meanings. Unfortunately, society has caused designers to become preoccupied with the mechanisms, rather than with the user. As a result, industry focuses on the production of feature-rich systems, rather than on ones that are also "User Friendly" and thus easier to use.[9] This conflict of interest creates a problem for many people. Therefore many products are extremely complex and thus difficult to use, preventing all but the most technically advanced people from using them.

1.1 VCR Statistics

Studies evaluating various aspects of VCRs and their users have revealed some interesting facts, the most important of which is that present users feel that the devices must be improved in such a way that the consumer can more readily benefit from their many features. During the past ten years, VCRs have become a popular household appliance. In 1982, five million VCRs were in use in American households.[10] In December 1987, a VCR could be found in more than 40 million homes, which constituted about 40% of all households, or 45% of all the households owning at least one TV.[11] Paul Kagan Associates predicted that this number will rise to 70% of all TV-owning households by 1992, and that 40% of these households will own at least two machines or two recorders in one machine by then.[12] Currently (1990) a VCR can be found in 68 million households and 80% of those who dwell therein cannot program them.[13]

Swanson and Klopfenstein (1977) predicted an increase in VCR ownership for the three years following their study. They foresaw that almost three quarters of the households in the United States would have a VCR by 1990. The authors reported that as of 1985, only 39% of the TV owning households possessed VCRs. Seventy percent of the owners were in their 20's, and the remainder were between the ages of 30-59. People younger than 20 or older than 60 were not represented in this study.[14]

According to an April, 1986 survey done by Link Resources of New York City. Sixty percent of VCR owners have household incomes greater than $30,000, and approximately 60% are college graduates.[15] One might think that this population could program their VCRs, but evidence to support this claim is lacking.

1.2 VCR Technology

All VCRs contain tuners, and the picture quality of most of the current VCRs is similar; however, VCRs differ greatly in their programmability. Users are often frustrated and have to first decipher an instruction manual before being able to operate the machine. The average consumer should ideally be able to operate the controls of a VCR without referring to the manual. David Horowitz, host of a syndicated television show on consumer products, said, "The level of frustration out there is incredible." He argues that companies are more likely to add features which would justify price increases than to make adaptations which would enable the consumer to easily use the features which are already built into the VCR.[16]

Dr. William Wilke, a project engineer at Textronix, observed that "For each increase in capability, there is at least a linear increase in unfriendliness - sometimes even more unless the manufacturer takes deliberate steps to include user-friendliness."[17] Psychologist Donald Norman, famous for his book entitled *The Psychology of Everyday Things*, developed the following generalization: "Whenever the number of possible actions exceeds the number of controls, there is apt to be difficulty in using the controls."[18] This case can be readily illustrated by an analysis of many of the programmable devices on the market, particularly the VCR.

1.3 VCR Usage

The Nielsen Homevideo Index (1984) found that women were the primary users of VCRs and that programming the VCR to record at a later time (time shifting) was the most common use in 1985.[19] In 1987, more than 70 models of VCRs were available and a study by Doyle Graf Ray revealed that affluent consumers considered a VCR the fourth most-important necessity.[20] In our society, the VCR is rapidly becoming an integral part of everyday life. However, a survey revealed that two-thirds of operators lack the ability to correctly program their VCRs.[21]

The present market consists primarily of people who are buying a second VCR or who are replacing their old one with a newer model which has updated features, such as on-screen programming.[22] A survey of 485 VCR owners or renters in Lexington, KY, showed that people who only use VCRs for playing tapes use VCRs significantly less than people who use VCRs for taping programs.[23]

Careful selection of components, consideration of the layout, and effective use of graphics can greatly improve the legibility, understandability, operability, and appearance of a product. Directions, color coding, and functional arrangement can only effect a small improvement in a poor design, but they cannot solve the problems which exist inherently in the device.[24] Steps must be taken to improve the interface, making it easier for people to use. One study found that many people feel that they stand a greater chance of winning their state lotteries than correctly setting their VCR to record.[25]

A review of current technology, patent searches, interviews, questionnaires, and consumer preferences, has shown the need for a "friendlier" user interface for programmable devices.

1.4 Programming Steps

The act of programming, or setting a sequence of operations to be performed by a mechanism,[26] requires several steps. Besides setting the clock, the user must assign a program number, set the current date and current time, select the start and stop times, choose the channel from which to record, and choose a tape speed. These actions require a minimum of four actuators ("Program", "+", "-", and "Enter"). Presently, some VCRs contain up to 123 buttons,[27] double function keys, and symbols which are not immediately recognized by the user. In order to provide for optimum usability, these VCRs should be simplified so that people can use them more easily and quickly.

The process of programming the VCR should be intuitive, as advocated in the introduction to this thesis. Ideally, the user should be able to operate the controls of a VCR without referencing an instruction booklet. Writer Stephen Yoder says "Americans want simple, straightforward machines without the 250 page instruction manuals."[28] The system's interface should focus the user's attention on the task, rather than on the interface, tool, computer, or himself. The scheme for programming should guide users through the sequence, and during this process, it should offer them some assurance that they are setting the system correctly.

Electronic consumer products must be adequately designed for first-time users, and for experienced users.[29] Research, and the analysis of questionnaires and interviews has shown that people generally do not program their VCRs often (less than once a month), and that most of those who have utilized the time-shift recording feature have forgotten the sequence of steps between uses.

Inconsistent terminology and the use of ambiguous abbreviations by the various manufacturers was one of the major problems which I encountered. Two examples of confusing terminology were:

1) To turn the machine on and off, different VCRs use terms such as: "Function", "Power", or "On/Off"

2) For selecting the day to record, VCRs use different terms, such as: "Weekday", "Everyday", "Normal", and "Daily".

Certain inherent problems exist because one guideline might be best for coding and another for decoding. Presently, no standards exist for abbreviations, and this makes it very difficult for users to understand what the captions on the buttons or the condensed prompts on the screen stand for.

Since the dissatisfaction of the user is proportionate to the length of search time,[30] some ways to minimize search time include using a maximum of 4-8 choices per screen and using consistent wording and placements. At present, in order to use an interface effectively, users must remember abbreviations. If there are no standards, this is much more difficult and confusing, especially when they own more than one brand or model of VCR.

Much of the success of the VCR can be attributed to the increasingly popular use of a remote control mechanism for programming. This device enables users to sit back in their chairs and program their VCRs using on-screen programming technology. However, the remote control device often contains many buttons, which users often find overwhelming and confusing, and thus often results in under-utilization of the actuators. The extra clutter necessitates in a greater search time, and thus it takes longer to program the VCR. Other problems arise from the layout and coding of the buttons. A study performed by Kamran Abedini and George Hadad in 1987 entitled "Guidelines for Designing Better VCRs" has shown that varying the shape of the remote control device is more effective than varying its size. In addition, they found that color coding and adequate contrast can effect a significant improvement in performance.[31]

Abedini found that 78% of the people surveyed favored entry numbers (0-9) in addition to labels, symbols, discrete volume switches, and channel up/down buttons for casual searching.[32] In addition, the people surveyed preferred remote controls which fit comfortably into their hand. Remote control technology has been both a blessing and a curse when applied to the VCR. The dream of being able to program a VCR while sitting on the couch is very desirable, but the existing systems are being under-utilized. In this thesis, a better way to utilize remote programming is proposed. The results are based on an understanding of how consumers typically use VCRs, and which aspects they find difficult.

1.5 Current Technology

Many devices which employ state-of-the-art technology could be adapted for programming the VCR. These can be broken down into three categories:

I. DIRECT INPUT DEVICES

Touch screen               Light pen

II. INDIRECT INPUT DEVICES

Trackball                 Joystick
    Mouse                     Touch tablet
    Bar Code Scanner       Keyboard
    Multi-Function Keys

III. INTERACTIVE INPUT DEVICES

Voice activation/ Instructions   Eye tracker
    Data Suit/ Data Glove

Each of these input devices has advantages and disadvantages, which are summarized in the section below. Over the past ten years, many techniques have been used. Some of the approaches developed to program VCRs include:

- Display Panels (1982) – Programmed on an LED panel on the front of the machine.

- Programming via remote control (1983) – Programmed using a remote control device with keys for input.

- On-Screen displays (1984) – Programmed by a series of menus on the television screen.

- Bar Code scanners (1987) – Programmed by a wand passing over a series of lines and then transmitted to the VCR.

- Light pens (1987) – Programmed by aiming a pointing device with a light beam at the television screen.

- Frequency signal Transmitters (1988) – Programmed by entering the number of frequency signals which are emitted by television stations in West Germany.

- Phone lines (1989) – Programmed over the telephone line at a remote location. The numeric keys on the phone are the input keys.

- Video memories (1989) – Programmed by a computer from a remote location.

- Voice coaches (1990) – Programmed by responding to voice instructions from the remote control.

1.6 Input Devices

To accomplish the task of programming the VCR, manufactures have tried various input technologies. Devices which enable the user to indicate his response by pointing either a part of the body or a hand-held object have become increasingly popular. Table 2 shows the advantages and disadvantages of some pointing devices which are currently available and could be adapted to control the VCR.

Table 2 – Advantages And Disadvantages Of Pointing Devices

| DEVICE | ADVANTAGES | DISADVANTAGES |
|---|---|---|
| Touch-Screen: a device which allows users to point directly to the screen to enter their choices. | accurate<br>fast<br>"natural" pointing device | Hand obscures view<br>  Difficult with curved<br>    screens<br>Doesn't show location of<br>    the cursor on the screen<br>Requires an overlay<br>Requires frequent cleaning<br>Expensive<br>Must be within reach<br>    envelope |
| Light Pen: a pen shaped device with which the users touch the screen to select their choices. | Points to the screen<br>Inexpensive | Inaccurate<br>Awkward to use<br>Pen needs a storage<br>    location<br>Must be within reach<br>    envelope |
| Trackball: a ball mounted on a stationary object; the ball's rolling motion controls the cursor. | Can be mounted and used<br>    anywhere<br>Does not require a<br>    horizontal surface<br>Quick to use | |
| Joystick: a stick mounted on a stationary object; the sticks movement controls the cursor. | Can be mounted and used<br>    anywhere<br>Does not require a<br>    horizontal surface | Clumsy for cursor control |

| | | |
|---|---|---|
| Mouse: a ball mounted on the bottom of a movable object, which is rolled on a horizontal surface to control the cursor. | Most effective for pointing and selecting objects on the screen Popular | Requires a horizontal surface area |
| Touch Tablet: a pad which sits on a horizontal surface on which selections are made by using a finger or stylus. | Activated with fingers or stylus | Small interface Remote from display |
| Keyboard: a device which lies on a horizontal surface and which has alphanumeric keys to type in information. | | Requires a horizontal surface Large Many keys |
| Multi-Function Keys: buttons which serve more than one function. | Inexpensive Space efficient | Confusing |
| Bar Code Scanner: a wand which must be wiped over a bar code to type enter information. Pressing a button then signals the controlling device. | Quick if Barcode is present in TV directory | May require several tries to send data Tedious if Barcode is not available in the TV directory |
| Voice: the use of the human voice to give speech prompts or to accept commands. | Frees hands Enables disabled persons to use the device | Requires training Affected by surrounding noises Low accuracy Expensive Has a limited vocabulary Is sensitive to differences in languages, accents, and speech patterns |
| Eye Tracker: an optical scanner which is activated by the human eye. | Frees hands Enables disabled persons to use the device | Expensive Inaccurate |
| Data Suit/Data Glove: a suit or glove which is controlled by manipulation of an on-screen "Virtual Image". It is controlled by optical fibers that measure the degree of bending. | Reacts to hand and body gestures Gives a 3-D image | Expensive Computer intensive |

CHAPTER 2 PROBLEM STATEMENT

2.1 Problem Definition

The previous sections indicate that four major problems in the interfaces of VCRs exist. The first is that users spend far too long searching for necessary information. Second, people do not program the VCR to record at a later time (time-shift) frequently, and thus forget the programming steps in the interim. Third, the number of buttons on the remote control device has become overwhelming. Fourth and as a result of the previously mentioned problems, people have become afraid of VCRs and shy away from using them.

The main objective of this research is to address the four issues mentioned above in order to develop guidelines to aid designers in developing better interfaces for VCRs. With this in mind, the following hypothesis was formulated: *By minimizing the learning and searching times, the user's programming time and frustration level can be greatly reduced.*

2.2 Goal

The goal of this research is to develop a usable interface for programming the VCR. In order to do this, the searching and learning times should be kept to a minimum. The system's logic should reflect the users' expectations, offer visual clues and feedback, and stay within human memory limits. For example, the VCR should turn on not only with the "Power" button, but also by inserting a tape. In addition, the sequence of steps for setting the machine to record should assume that the user is a novice. Nothing should be taken for granted. Research has shown that a menu-driven interface is best for applications involving new users and does not hinder experienced users.[33] By developing an improved interface, an attempt is made to:

1. Reduce the searching time
2. Reduce the learning time
3. Simplify the entering of data
4. Reduce the intimidation of using electronic devices

CHAPTER 3 TESTING OF EXISTING VCR INTERFACES

3.1 Methodology

A human factors approach was used in the development of the new interface. The techniques included an iterative loop of research, interviews, questionnaires, consultations with Human Factors and VCR experts, design reviews, prototyping, testing, redesigning, evaluating, and making recommendations.

3.2 Initialization

The underlying factor which motivated the focus of this research was the perceived need to establish guidelines for developing a user-friendly interface for programmable devices to facilitate their use.

The primary goals for directing direct the development of a new interface for a VCR were:

1. Familiarization with current technology.
2. Identification of problems.
3. Development of improvements to existing VCRs.
4. Reduction of the learning time.
5. Utilization of good screen design principles.

Before a new interface could be developed, existing devices had to be analyzed. An initial investigation of the current programming technology was conducted in order to gain a full understanding of what has been developed and what problems are present. This was accomplished by conducting extensive literature and patent searches, a morphological ordering of VCRs now on the market, and directed research involving consumers.

The literature search provided information on technology and VCR usage and formed the backbone for this thesis. The patent search revealed that the only parts of a VCR that are patented are the mechanical and electrical components, not the interface or "look-and-feel." In assessing the market, a morphological chart was made of the current devices sold in the United States within the past three years. The morphological chart can be seen in Appendix D.

3.3 Directed Research

From evaluating research, observing people using VCRs, conducting interviews, analyzing questionnaires, and testing existing technology, an understanding of when, why, and how often people use VCRs was established. Figure 2 shows the questionnaire used to collect relevant information.

Figure 2 - Questionnaire From Test 1

1. Sex:         Male      Female

2. Age:         Under 20      20-29      30-49      OVER 50

3. Highest level of education completed:
   HIGH SCHOOL  COLLEGE     GRADUATE SCHOOL 4. Occupation:

5. How technical would you consider yourself
   VERY TECHNICAL        MODERATELY TECHNICAL      NOT TECHNICAL 6. Do you own a VCR?   YES   NO
   If yes, for how many years?
   If you own more then 1 VCR, how many do you own?

7. What brand of VCR do you own?

8. Model number if possible

9. What features does your VCR have?
   ON-SCREEN PROGRAMMING   BAR CODE SCANNER
   14 + PRESET PROGRAMS    100+ CHANNEL PRESETS
   REMOTE                  OTHER 10. Do you personally operate your VCR?   YES   NO 11. If yes, how frequently?
    VERY FREQUENTLY   SOMETIMES   INFREQUENTLY 12. For what purposes and how often do you use each of the following features? Please check one or more of the following
    NEVER  <1X/MONTH  <1X/WEEK  >1X/WEEK
    Play a recording
    One-Touch recording
    Program recording
    Editing
    Other 13. How easy/difficult is the documentation?

| 1 | 2 | 3 | 4 | 5 | 6 | 7 |
|---|---|---|---|---|---|---|
| VERY EASY | MODERATELY EASY | SOMEWHAT EASY | NEITHER EASY NOR DIFFICULT | SOMEWHAT DIFFICULT | MODERATELY DIFFICULT | VERY DIFFICULT |

14. How often do you have to resort to using the documentation?
    EVERY TIME   SOMETIMES   NEVER   OTHER 15. How often do you use the remote control?
    ALWAYS   ONCE IN AWHILE   NEVER 16. How often do you use the control panel"
    ALWAYS   ONCE IN AWHILE   NEVER 17. How do you find the keyboard layout on each the control panel and remote control?

18. What features do you like most?

19. What features do you like least?

20. Please rate your VCR on the following 7-point scales

| 1 | 2 | 3 | 4 | 5 | 6 | 7 |
|---|---|---|---|---|---|---|
| VERY MUCH LIKE | MODERATELY LIKE | SOMEWHAT LIKE | NEITHER LIKE NOR DISLIKE | SOMEWHAT DISLIKE | MODERATELY DISLIKE | VERY MUCH DISLIKE |
| 1 | 2 | 3 | 4 | 5 | 6 | 7 |
| VERY EASY | MODERATELY EASY | SOMEWHAT EASY | NEITHER EASY NOR DIFFICULT | SOMEWHAT DIFFICULT | MODERATELY DIFFICULT | VERY DIFFICULT |

21. Can you suggest any ways to improve the programming of a VCR?

22. Can you suggest any ways to improve the VCR in general?

Of the 31 people surveyed, more than half play prerecorded VCR tapes than record their own tapes for viewing at a later date. Almost 60% of the respondents reported that they record less frequently than once per month. Tables 3 and 4 show how often participants in this study use their VCRs for playing and recording, respectively. These results can be seen graphically in Figure 3.

Table 3 — Frequency Of Playing Recordings On VCRs

| PERCENTAGE OF SUBJECTS | FREQUENCY OF USE |
|---|---|
| 43% | play > 1X/week |
| 35% | play < 1X/week |
| 22% | play < 2X/month |

Table 4 — Frequency Of Recording On VCRs

| PERCENTAGE OF SUBJECTS | FREQUENCY OF USE |
|---|---|
| 43% | play > 1X/week |
| 35% | play < 1X/week |
| 22% | play < 2X/month |
| 26% | never recorded |
| 33% | record < 1X/month |
| 17% | record < 1X/week |
| 21% | record > 1X/week |
| 3% | did not answer question |

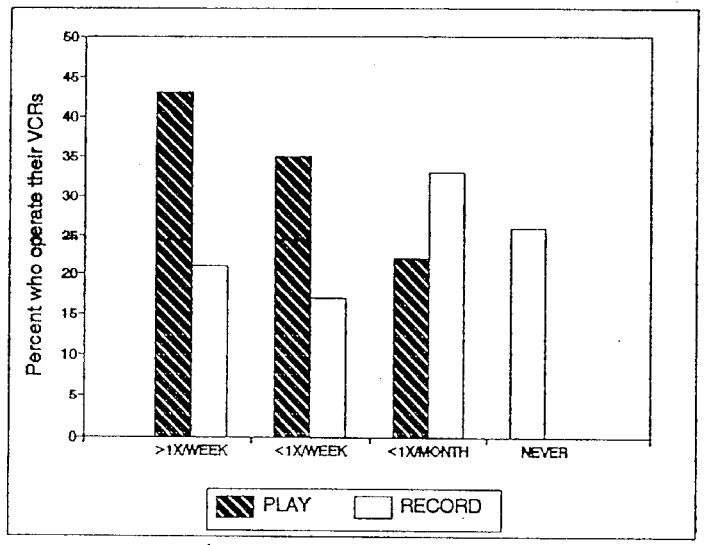

Figure 3 – Frequency Of Using The VCR

Gathering descriptive data about VCR users was helpful in designing the structure and focus of the new interface. Some of their comments can be seen in Table 5. Videotaping equipment was used during all Test 1 sessions to increase the experimenter's recall and to help aid in the analysis of the test sessions. In addition, observations noted and data obtained during the user tests led to conclusions about the development and design of the new interface. From this information, criteria for a more usable interface were developed.

Table 5 – Features The Respondents Liked And Disliked

| LIKES: | DISLIKES: |
|---|---|
| Color coding | Small print |
| On-Screen Programming | Small buttons |
| Remote Control | Complicated sequence for setting |
| Up & Down arrow keys | programs |
| Functional key arrangements, natural layouts (Left-Right, Top-Bottom) | Complex sequence to set the clock |
| | Blinking displays |
| Few buttons | Hidden buttons |
| Well-labelled buttons | Poor labelling |
| Uncluttered display panel | Lack of instructions or prompts for what to do next |
| Ability to backtrack | |
| One Touch Recording | Ambiguous coding of the keys |
| Large, clear print | Confusing menus |
| Large buttons | Too much information |
| Step-by-step instructions | Inappropriate remote controls |
| Keypad entry | Programmability only from the remote control |
| Help key | |
| Programming steps in which the order and tasks are obvious | Inability to backup and correct mistakes |
| Programming requiring few steps | Lack of feedback |
| Automatic completion of strings | Lack of "ready" or "OK" indicator |
| Ability to be used without referencing an instruction manual | Leading 0's must be entered |
| | Multiple function keys. |

3.4 Design

The first phase of testing was the evaluation of how some manufacturers have approached the problem of designing interfaces and determining which elements of the programming process gave people trouble. In order to accomplish this, four VCRs with differing interfaces were used in a same-users within subjects design experiment. The main criteria for selecting the tested VCRs were their interfaces. Each of the machines selected had a different technique for programming. These included differences such as word choice, layout, buttons, sequence, and displayed information. Each subject set the clock and the recording of two programs on all four VCRs to eliminate variability due to differences between subjects. In an attempt to find out where problems exist, the documentation was removed from all VCRs. The VCRs tested can be seen in Table 6.

Table 6 - VCRs Studied In Test 1

| Make | Model Number | Device |
|------|--------------|--------|
| A. Panasonic | PV4962 | Bar Coder |
| B. RCA | VKP950 | On Screen |
| C. Panasonic | PV4700 | Display Panel |
| D. AKAI | VS3030 | On Screen |

The subjects were 18 freshmen at Tufts University. The order of the VCRs was randomized so as to counterbalance the effect of learning. The individual settings required for completing these tasks can be seen in Table 7 and graphically in Figure 4.

Table 7 - The Steps Required To Set A VCR

CLOCK:
1. Set Current Hour
2. Set Current Minute
3. Set Current Day of Week
4. Set Current Day of Month
5. Set Current Month
6. Set Current Year PROGRAM
1. Type of Program
2. Program Number
3. Start Time Hour
4. Start Time Minute
5. Stop Time Hour
6. Stop Time Minute
7. Desired Day of Week
8. Desired Day of Month
9. Desired Month
10. Desired Year
11. Desired Channel
12. Desired Tape Speed
13. Repeat steps 1-12 for each additional program

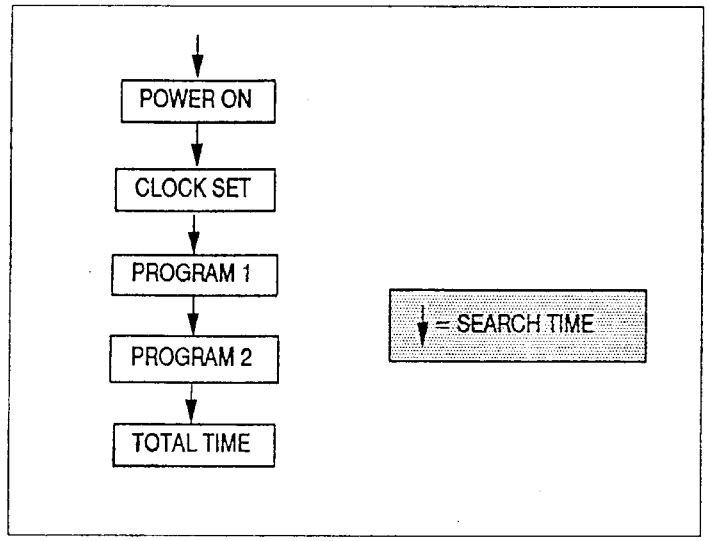

Figure 4 – Flowchart Of The Steps Required To Set A VCR

The testing scenario included briefing, instructions, and a questionnaire/interview, copies of which can be seen in Figures 5 through 6.

Figure 5 – Briefing Statement

The following experiment is part of a Master's Thesis to optimize programmable devices from a Human Factors perspective. There is no known deception involved. The tasks performed are those which I believe to be typical ones required of any VCR user. I am testing the VCRs, not YOU!

Figure 6 – Instructions For Testing Phase 1.

The purpose of this experiment is to compare four different VCRs. I am especially interested in the programming capabilities. I would like you to act as normal as possible and pretend that you are in your own family room at home, setting these VCRs to record programs which you would like to watch when you come home from vacation. There has just been a short power failure. I would like you to set the time on the clock to 9:00 PM on Wednesday, October 11, 1989.

Then, I would like you to program each VCR so that:
1) It will tape a movie that airs on channel 5 on Sunday, October 15, 1989 from 8:00 PM to 11:00 PM in program 1
2) tape a sitcom that airs Monday – Friday 3:00 am to 3:30 am on channel 7 in program 2.

I would like to videotape the sessions so that I can refer back to them to see where the difficult areas exist. Please talk aloud and let me know what you are doing and what problems you are encountering.

Remember, I am testing the VCRs, NOT you. I am interested in the design principles involved in programmable devices. At the end, I have a few short questions to ask you. If at any time during the test you would like to stop, please feel free to do so.

Thank you very much for you time and effort!

Figure 7 — Questionnaire/Interview For Test 1.

1. Sex: Male    Female
2. Age: Under 20    20-25    36-40    Over 40
3. Highest level of education completed: _____
5. Please describes your experiences using VCRs (i.e. how often do you use the VCR? Record? Play a tape? Do you own a VCR? What features of VCRs have you used?)
6. Please rate the VCRs on the following 7-point scales.

VCR A:   (like/dislike)_____
            (easy/difficult)_____
            Cooper-Harper Rating _____

3 Reasons:

VCR B:   (like/dislike)_____
            (easy/difficult)_____
            Cooper-Harper Rating _____

3 Reasons:
    VCR C:   (like/dislike) _____
            (easy/difficult) _____
            Cooper-Harper Rating _____

3 Reasons:
    VCR D:   (like/dislike) _____
            (easy/difficult) _____
            Cooper Harper Rating _____

3 Reasons:

7. Please rank the four VCRs according to preference
    #1 _____    #2 _____
    #3 _____    #4 _____
8. What features of the VCR do you like most?
9. What features of the VCR do you like least?
10. Can you list any suggestions for improving the programmability of a VCR? (other input technologies, Selection vs. Entry method, voice, remote, touch screen, light pen, trackball, mouse, abbreviation., layout, feedback, menus, etc.)
11. Would you like to participate in another VCR study? If yes, give name & number.

In order to pinpoint problem areas, the task was broken into critical steps. The steps and their definitions are summarized in Table 8.

Table 8 – Critical Steps Necessary To Program A VCR

1. PO: The time it took from the start of the test session to the time when the power was turned on.

2. CLOCK: The time it took from when the power was turned on until the subject set the clock.

3. P1 & P2: The time it took to set the first and second programs.

4. TOTAL: The time it took to set the clock and two programs during the test session.

5. SEARCH: The time which subjects spent while deciding what to do between programming steps.

6. GAVE UP: The number of subjects who gave up before they had set the VCR.

7. MISTAKE: The number of subjects who did not correctly set the clock and two programs.

8. TAPE: The number of subjects who did not insert a tape.

9. TIMER: The number of subjects who did not set the timer.

3.5 Equipment

Manufacturers are incorporating many newly designed input devices into their VCRs in attempt to make the programming process easier. Three methods of programming tested, were the Bar Code, On-Screen, and Display Panel. These input devices do not represent all of the technologies presently being used to program VCRs, but provide a representative sample.

3.5.1 Bar Code Programming

One device which was new to all the subjects was the bar coder. Panasonic (VCR "A") first introduced bar code programming in 1987, and they considered it to be "the most dramatic solution to programming" (Lechmere Advertisement, 1989). They eventually plan to run bar codes in *TV Guide* in an attempt to appeal to busy people who own VCRs but who might not be able see a particular show unless they time-shift. Presently, these machines come with a laminated sheet of bar codes. In order to program the VCR, the user must press a button on a wand which lights its tip, and then run the tip over a bar code to set each step separately. Finally, when all the information has been scanned in, users must press the "Transmit" button. A picture of the bar coder can be seen in Figure 8.

Figure 8 – Panasonic Bar Code VCR

Of the 18 participants in this study, over half reported that they did not enjoy using bar code programming. Six users found it to be confusing, and ten people were so intimidated by it that they never even tried it, preferring to use the remote control instead. The audio signals were confusing to the subjects, and there was no visual feedback. The only time the VCR provided noticeable feedback was after the subject had completed the entire task of programming and pressed the button to transmit the information: at this time, the VCR displayed a message on the screen which told the user whether the transmission had been completed.

3.5.2 On Screen Programming

VCR "A" and two of the other machines (VCR "B", an RCA recorder and VCR "D", an AKAI machine) contained on-screen programming. All information was displayed on the television screen and prompts were provided to guide the user through the necessary steps. VCRs "A" and "B" had numeric keypads to enter the information, while choices were entered into VCR "D" by the selection method, which depended on the use of up and down arrow keys.

3.5.3 Display Panel Programming

VCR "C" was a Panasonic machine which displayed all information on an LCD panel on the front of the device, but had no instructions on the panel. Users do not need a television set to see the displayed information, but they might have trouble reading the small display. Users enter information on the display panel when programming this VCR, using the selection method with either the up key or both up and down keys.

3.6 Results

3.6.1 Critical Steps

The critical steps necessary to program a VCR and the problems encountered during testing are as follows:

1. PO: The time it took from the start of the test session to the time when the power was turned on.

COMMENT: Optimally, this should take place immediately. In the testing situation, this was not the case. Several subjects did not realize that the power must be on in order to set the clock.

2. <u>CLOCK</u>: The time it took from when the power was turned on until the subject set the clock.

COMMENT: This should not be a cumbersome task. The date feature with an internal calendar proved very helpful in those situations where participants who accidentally set the wrong date and therefore could not get the correct day of the week for the show they wanted to record realized and corrected their mistake.

3. <u>P1 & P2</u>: The time it took to set the first and second programs, respectively.

COMMENT: Setting the programs should take more time than the other critical steps. In addition, setting subsequent programs should take no longer than the first one. There were several programming choices which could be selected. Choosing the frequency of the program to be recorded proved to be the most troublesome spot. The choices for day selection on the different VCRs used were as follows:

VCR A : "Everyday on ...", or "Day on"

VCR B : "Everyday", "Weekly", or "Normal"

VCR C : "Day of week" or "Everyday"

VCR D : "1st", "2nd", "3rd", "4th" or "Mon-Fri"

All subjects were confused by the options offered. None of the VCRs in this study offered the user all the options which were: Once on, Once a week on, Monday - Friday on, and Everyday on. In many cases, subjects had a difficult time setting the VCR to record Monday-Friday. The biggest problem that subjects complained about was that they could not see all the options at the same time, and thus did not know what the choices were. VCR "D" was especially confusing, with "1st", "2nd", "3rd", "4th" and "Mon-Fri" in the same field, with the numbers representing the number of the week, counting from the present day. These numbers were often confused with the program numbers, and the subjects did not notice that they were tied to the date. Incorporating numeric entry keys instead of using the selection method with up and down arrow keys (14 out of 18 subjects) and stop time instead of duration (7 out of 18 subjects) were two of the suggestions made by the users in an attempt to reduce the amount of time and keystrokes required to set the time.

4. TOTAL: The time it took to set the clock and two programs during the test session.

COMMENT: The average time that it took all 18 subjects to complete the task of setting the clock and two programs on all four VCRs was 11.8 minutes. 26 of 72 trials, or 36%, took more than ten minutes. The longest time that any subject took to successfully complete this task was 22.7 minutes, and the shortest was three minutes. For trials in which the subjects failed to complete this task, the time was recorded as 30 minutes. Subjective data from the subjects reveals that the maximum acceptable time to set the clock and two programs on a VCR is seven minutes, which is 40% less than the actual time recorded in this study.

5. SEARCH: The time which subjects spent while deciding what to do between programming steps.

COMMENT: The time should be minimal. The interface should guide the user so that he is never at a loss as to what to do next. Unfortunately, an average of 4.7 minutes, or 41% of the total time was lost in search time during the test sessions.

6. GAVE UP: The number of subjects who gave up before they had set the VCR.

COMMENT: In six out of the 72 trials subjects gave up. In all these trials, the users became frustrated and commented that they would never buy that VCR.

7. MISTAKE: The number of subjects who did not correctly set the clock and two programs.

COMMENT: In 31 out of 72 trials, excluding the six during which users gave up, subjects did not correctly program the VCR. In 27 of these cases, the users did not notice their mistakes and thought that they had set everything correctly. Some subjects made errors in more than one category. The mistakes and their frequency were:

- Choosing the wrong type of program (22)
- Incorrectly setting the date (9)
- Confusing AM and PM (5)
- Setting the wrong channel (3)
- Setting both programs in the same position, thus erasing the first program setting (1).

8. TAPE: The number of subjects who did not insert a tape.

COMMENT: The VCR will not record anything unless a tape is inserted. People who had previously used the time-shift capability (setting a program in advance) on VCRs cited this step as a crucial one that they often omitted. In this testing, 75% of the subjects omitted Inserting the Tape. There are several possible reasons for this error, such as that these subjects did not realize that this step was necessary for the test situation, and so they skipped it although they did answer "Yes" when asked "If you walked away from the VCR now, are you confident that it will record properly?"

Some suggestions to eliminate this problem are to have:

- An on-screen reminder to insert a tape
- An electronic indicator to tell whether the tape is write-protected and thus cannot be recorded on

- An electronic indicator to show if the steps for recording a program are incomplete.

9. <u>Timer</u>: The number of subjects who did not set the timer.

COMMENT: A VCR will not record anything unless the timer button is pressed. People who had previously used the time-shift capability (setting a program in advance) on VCRs cited this step as crucial and often omitted. In this testing, 58% omitted Setting the Timer. There are several possible reasons for these errors, such as the fact that these subjects did not realize that this step was necessary for the test situation, and so they skipped it. Curiously, they answered "Yes" when asked "If you walked away from the VCR now, are you confident that it will record properly?"

One suggestion to eliminate this problem is to have an on-screen reminder to set the timer and a button to set the timer that can only be pressed after a tape has been inserted.

Table 9 shows the average times in seconds for the critical steps and the standard deviation of the total time for each VCR for the 18 subjects. Figures 9 shows graphically each critical step listed in Table 9. Figure 10 shows the standard deviations, minimum, maximum, and average times to perform the critical steps for the four VCRs. Figure 11 shows the average percentage of the total time for each critical step.

Table 9 – Average Times In Seconds To Perform The Critical Steps
| STEP | VCR "A" | SD | VCR "B" | SD | VCR "C" | SD | VCR "D" | SD | AVG |
|---|---|---|---|---|---|---|---|---|---|
| PO | 64.3 | 56.1 | 67.3 | 67.3 | 69.3 | 73.6 | 127.1 | 67.6 | 82.0 |
| CLOCK | 71.3 | 122.2 | 27.2 | 46.0 | 64.7 | 77.1 | 72.6 | 64.7 | 59.0 |
| P1 | 113.0 | 98.0 | 110.0 | 113.5 | 118.1 | 78.3 | 210.5 | 137.9 | 137.9 |
| P2 | 155.0 | 137.5 | 178.9 | 150.2 | 104.6 | 34.9 | 141.1 | 98.5 | 144.9 |
| TOTAL | 856.1 | 500.1 | 616.7 | 381.6 | 568.9 | 371.6 | 787.1 | 285.9 | 707.2 |
| SEARCH | 444.1 | 465.7 | 233.3 | 138.1 | 218.2 | 315.7 | 255.5 | 180.5 | 287.8 |
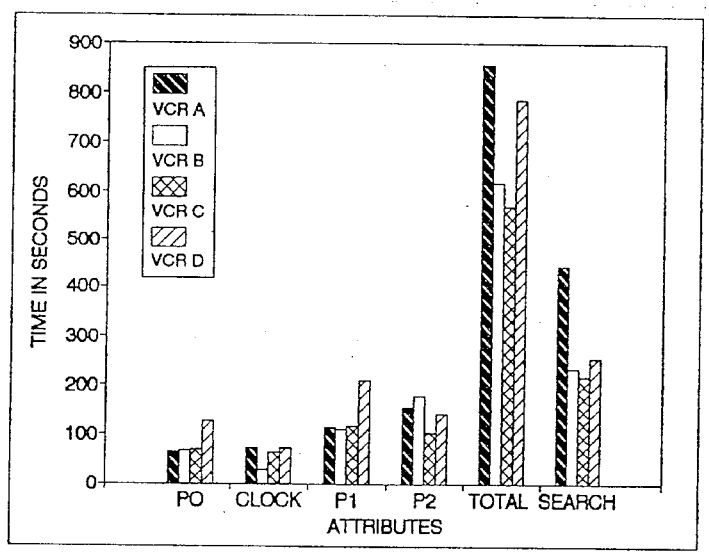
Figure 9 – Critical Steps Required For Test 1

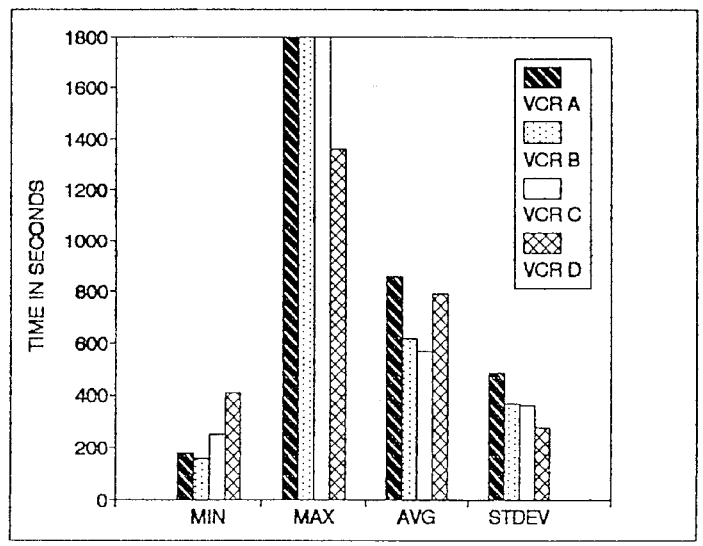
Figure 10 – The Minimum, Maximum, Average, And Standard Deviation Of The Total Times For The VCRs
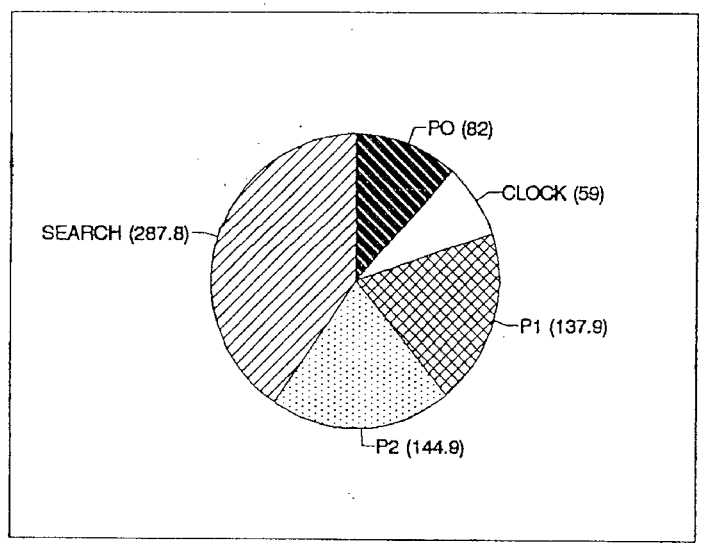
Figure 11 – The Average Time In Seconds For Each Critical Step During 6 of the 72 trials, subjects quit while trying to complete the task of setting the clock and two programs, and therefore a maximum time of 1,800 seconds (30 minutes) was assigned for these trials. In actuality, the longest time a subject spent programming any one VCR before giving up was 1,740 seconds (29 minutes). An average of 282.5 seconds, 40% of the total time, was expended in search time. Since many subjects revealed that they did not know what they should do next, concentration was placed on minimizing this unproductive time in the design of the new interface. Table 10 shows the number of subjects who could not complete the critical steps and Figure 12 shows the results graphically.

Table 10 – Critical Step Not Completed

| CRITICAL STEPS | VCR "A" | VCR "B" | VCR "C" | VCR "D" |
|---|---|---|---|---|
| GAVE UP | 3 | 1 | 1 | 1 |
| MISTAKE | 7 | 12 | 5 | 7 |
| TAPE | 14 | 13 | 14 | 13 |
| TIMER | 12 | 10 | 9 | 11 |

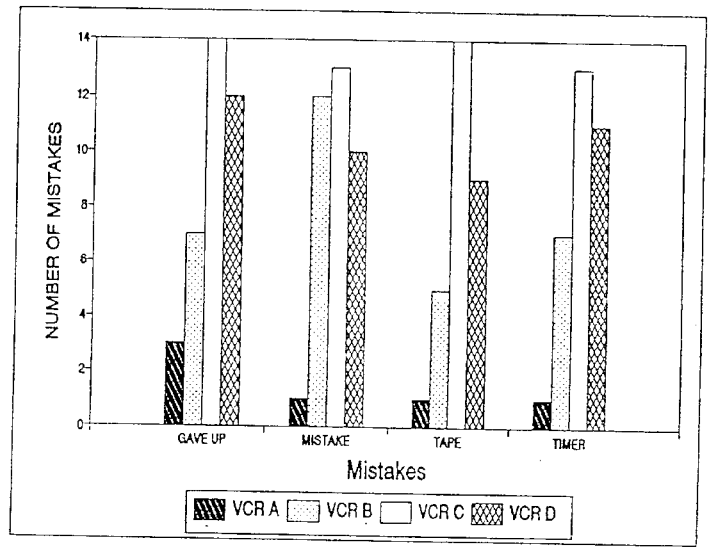

Figure 12 – Critical Steps Not Completed

3.6.2 Subjective Analysis of Test 1

The subjects were concerned with the layouts of both the control panel and the remote control on all the VCRs. All participants liked the on-screen programming which utilized the remote control rather than the control panel. Fourteen of the eighteen users expressed a preference for entering the numbers over pressing the up and down arrow keys for selecting the time and channel, and seven favored choosing the start and stop times over choosing the start time and duration. All subjects wanted more feedback, and they wanted to know when the VCR was ready to program. From subjective data, the goal set was reducing the amount of time required to set the clock and two programs on a VCR to a maximum of 7 minutes, concentrating on reducing the search time, wherein users do not know what to do next.

The questionnaire seen in Figure 2 was given to the subjects in order to collect subjective data.

Test participants were asked to rate each of the VCRs on three scales. The Like/Dislike and the Easy/Difficult Scales rank a task numerically from 1-7, and the Cooper-Harper Rating Scale ranks a task numerically on a scale from 1-9.[34] These can be seen in Tables 11 and 12.

Table 11 - Like/Dislike And Easy/Difficult Scales

| LIKE/DISLIKE | EASY/DIFFICULT | NUMERICAL RATING |
|---|---|---|
| VERY MUCH LIKE | VERY EASY | 1 |
| MODERATELY LIKE | MODERATELY EASY | 2 |
| SOMEWHAT LIKE | SOMEWHAT EASY | 3 |
| NEITHER LIKE NOR DISLIKE | NEITHER EASY NOR DIFFICULT | 4 |
| SOMEWHAT DISLIKE | SOMEWHAT DIFFICULT | 5 |
| MODERATELY DISLIKE | MODERATELY DIFFICULT | 6 |
| VERY DISLIKE | VERY DIFFICULT | 7 |

Table 12 - Cooper-Harper Rating Scale

| | | | |
|---|---|---|---|
| ACCEPTABLE | Satisfactory (OK as is) | 1 2 3 | Excellent Good Fair |
| UNSATISFACTORY | Improvements could be made | 4 5 6 | Fair Poor Bad |
| UNACCEPTABLE | Improvements must be made | 7 8 9 | Bad Very Bad Terrible |
| WOULD REFUSE TO USE AGAIN | | 10 | Awful |

Using the scales from Tables 11, and 12, the results for the four VCRs can be seen in Table 13.

Table 13 - Averages Of The Subjective Ratings For The VCRs

| SCALE | VCR "A" | VCR "B" | VCR "C" | VCR"D" |
|---|---|---|---|---|
| LIKE/DISLIKE | 3.7 | 3.1 | 4.0 | 4.1 |
| EASY/DIFFICULT | 4.2 | 3.4 | 4.2 | 4.5 |
| COOPER-HARPER | 4.0 | 3.2 | 4.2 | 4.1 |

Note: The Like/Dislike and Easy/Difficult scales were rated on a 7-point scale and the Cooper-Harper scale was rated on a 10-point scale.

The above data reveals that all VCRs were rated close to the center of the scales.

3.6.3 Statistical Analysis of Test 1

Using SPSS-X, All four VCRs were subjected to separate Analysis of Variance tests, six in all. The difference in total times between VCRs "A" & "B" was significant at the $\alpha < .05$ level. In a T-test, the total times for VCRs "A" & "D" and "B" & "C" proved significant at $\alpha < 0.05$ In a multiple comparison test using the Scheffe method, there were significant differences found between VCRs. The following VCRs showed significance at the $\alpha < .01$ level.

|   | A | B | C | D |
|---|---|---|---|---|
| B | X |   |   | X |
| C | X |   |   | X |
| D |   |   |   |   |

Thus, every VCR had a significant difference when compared with that of two other VCRs with respect to total time.

When subjected to an analysis of variance, there were no significant differences found between or within subjects. The actions were defined as follows:

1. Power On
2. Clock Set
3. Program 1
4. Program 2
5. Search Time
6. Total Time

The times to set Program 1 and the Total Time between VCRs were the only variables found to be significant at $\alpha < .05$. T-Tests were then conducted between the six possible pairs of means for the times for Program 1 and Total Time to determine the significance of the differences. The results indicate that:

1. For Program 1, VCRs "A" & "B", "A" & "C", and "B" & "C" were significant at the $\alpha < .05$ level. All other differences were not significant.
2. For Total Time, VCRs "A" & "D" were significant at $\alpha < .05$. All others were not significant.

Pearson correlation tests were carried out for Power, Clock Set, Program 1, Program 2, and Search Time. The results indicate that no correlation existed.

The fastest and slowest times to set the VCRs were between VCR "C" and VCR "A" respectively, with a difference of 287.2 seconds, or 34%. It is seen that searching time in general is at least double that for the average time required to perform any critical step. The results of these statistical tests can be found in Appendix A.

Figure 13 shows the search time with respect to the total time for each VCR.

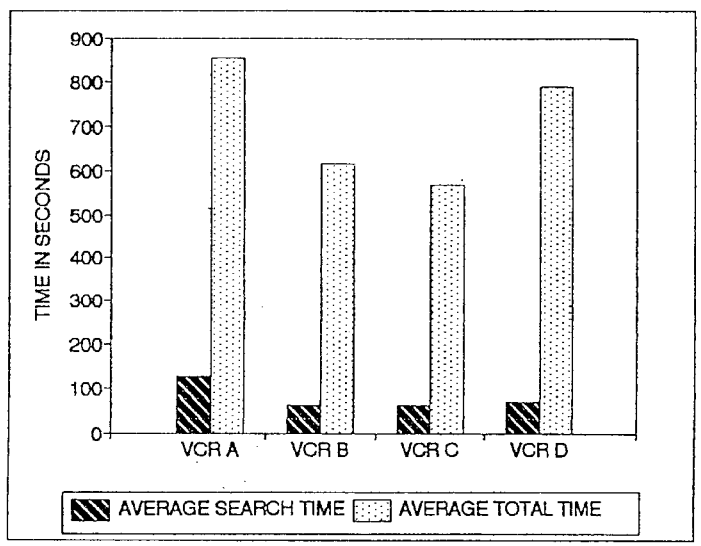

Figure 13 - Search Time vs. Total Time For Each VCR 3.7 Discussion

This experiment was designed in order to test four interfaces and to identify problem areas. The times measured represent an exact measure of the actual time that the process of programming took each subject. The amount of time required to program the on-screen VCRs was similar. However, VCR "C", containing display panel programming, took the shortest amount of time to program. This can be attributed to experience. All of the subjects who had used VCRs were familiar with some form of display panel programming, and only two were familiar with on-screen programming. The statistical analysis showed no correlation between the total times. However, the subjective data proved very helpful in designing the new interface.

CHAPTER 4 DEVELOPMENT AND EVALUATION

4.1 Criteria for Developing the Interface

The following usability goals for the design of a new interface to facilitate the tasks of setting the clock and programming to record were developed as a result of the research and testing described in Chapter 3.

1. Users should be able to operate the system successfully, without wide disparities in time.

2. Programming should be a stand-alone process, and not require an instruction manual.

3. The system should provide on screen understandable information

4. It should take less than seven minutes to set the time and two programs.

5. There should be adequate visual feedback.

6. The displays should be consistent.

7. Tasks should be simple and enjoyable.

8. Layouts should be logical.

9. Word choices should be understandable.

10. There should be a reminder to set the timer and to insert the tape.

11. The VCR should turn on when a tape is inserted. In addition, users should also be able to control the VCR with the Power button.

12. There should be a maximum of 4-8 choices per screen to minimize searching time.

13. Keys should be labelled with text rather than with ambiguous graphics. However, a combination of both would be preferable.

14. The system should guide the user along a decision path.

15. Each operation should require only one key press.

16. Error messages should be understandable.

17. The VCR should be programmable from both the remote and the control panel.

18. Searching time spent in setting the clock, programming, getting into the correct mode, and checking whether or not the VCR is set correctly should be kept to a minimum.

19. The design should minimize wasted time and frustration.

20. On-line assistance should be available when needed.

21. The learning curve should be minimized.

22. There should be 12 hour clock, not a 24 hour clock.

23. There should be entry keys, not up & down selector keys.

24. There should be a start and a stop recording time, rather than start time and length of program.

4.2 Constraints for Testing the Prototype (Test 2)

For practical considerations, the design was based on the following limiting factors.

- The use of a 286-10 MHz. Computer.
- The inherent Response Time of the computer.
- The use of existing hardware and software.
- The use of an existing Universal Remote.
- The use of a 14" computer screen.
- The availability of subjects.

4.3 Interface Requirements

The following are design considerations used in developing an improved interface:

- Automatic sequencing of steps – The VCR leads the user through the correct sequence of actions to set a program on the screen, so that no steps are skipped.

- Calendar – The VCR utilizes a built-in calendar screen so that the user cannot set the VCR for a non-existing date. However, this does not eliminate the human problem of setting the wrong date.

- Choice of Day – In order to eliminate extra keypresses, frequently-used settings, such as "Record today" or "Record tomorrow" are choices so that the user does not have to specify a date, thus saving keystrokes, and, ultimately, time. In addition, this could eliminate user errors.

- Choice of Program – Selections are given to the user to reduce the amount of programming necessary. The choices given are "Once On ...", "Once a Week on ...", "Monday – Friday at ...", "Everyday at ...". This reduces the number of keystrokes and the amount of programming time required.

- Color Coding – If a color screen is available, color can be used effectively so the user can quickly acknowledge the function of each aspect of the screen. For example, the normal selections are royal blue for help, red for mistakes, light blue for information previously entered, and yellow for information currently being entered.

- Confirmation Screen – This screen shows the user all of the categories and selections that he has made, in a format which is easy to understand.

- Consistency – The entering of information on each screen is consistent throughout the program. All of the screens have similar layouts.

- Exiting – The user can exit the programming sequence at any time by selecting the Main Menu button on the lower left-hand corner of every screen.

- Feedback – The user is provided with an adequate amount of feedback and descriptive error messages.

- Frustration – If people get frustrated with a device, they will not use it. This design attempts to minimize the user's frustration level by furnishing him with all possible choices, presenting the data in a logical sequence, and leading him through the steps necessary to program the VCR.

- Help – Help is provided for when the subject does not know what to do. The help screen explains the functions of each of the buttons. However, in the testing situation, the help utility was not available for every function.

- Initial smart screen – The VCR begins at the "set date" and "set time" screens if the time and date have not already been set.

- Input Device – The main criteria for selecting an input device was that it would require as few buttons as possible, thus reducing intimidation. For testing purposes, the mouse was used as an input device. Theoretically, a trackball on a remote control would be preferable because it does not require a flat surface.

- Learning Curve – The VCR should not require that a user have prior knowledge in order to use it. An attempt has been made to minimize the learning curve. Research has shown that people do not program their VCRs often, and they often forget the sequence of steps between recordings.[35] If the learning curve is flattened, no user is at a disadvantage, unless the curve is so high and flat that all users are at a disadvantage.

- Method of entering data – Most of the information is entered using a numeric keypad (entry method), rather than using up and down arrow keys (selection method). If there is more than one keystroke required, the user must then select an "OK" button. However, if the Selection method is used, all of the choices are displayed on the screen at once. In addition, no leading zeros are required.

- Setting the time – Since many people become confused when distinguishing between 12:00 AM and 12:00 PM, "Noon" and "Midnight" buttons were added for convenience.

- Thoroughness – The user cannot go on to the next programming step until the previous one has been completed.

- Word Choice – The words used are not specific computer terms, but rather are normal, everyday terms which are easy to understand. In addition, very few abbreviations are used.

4.4 Decision on the Input Device

Recent studies suggest that a "direct manipulation" style of interface has advantages for menu selection tasks.[36] This type of interface provides visual objects on the screen which can be manipulated by "pointing" and "clicking" on the them. For example, the popular Macintosh™ computer uses a direct manipulation style interface. Utilizing a device such as a touchscreen, with a more natural selection technique, would seem to be preferable to the direct manipulation method. However, its low accuracy and high cost make this impractical. In a cursor positioning task, Albert (1982) found the trackball to be the most accurate pointing device and the touchscreen to be the least accurate when compared with other input devices such as the light pen, joystick, data tablet, trackboard, and keyboard.[37] Epps (1986) found both the mouse and trackball to be somewhat faster than both the touchpad and joystick, but he concluded that there were no significant performance differences between the mouse and trackball as compared with the touchpad and joystick.[38]

The above-described research shows that both the mouse and the trackball appear to be insignificantly faster and more accurate as input devices when compared with other off-screen devices. In a study of menu selection tasks comparing the mouse and the trackball, the accuracy data showed no significant difference between the two.[39] The key finding shows that both mouse users and trackball users performed better with the trackball on the menu selection task. It should be noted that this was not the case for all tasks. However, the definition of the menu selection task used by Sperling & Tullis (1987), which involved moving the cursor through a list of items and making a selection, is similar to the selection tasks used in this experiment.

As discussed in Section 1.6, the ideal input device would be a small trackball with a button for selection, mounted on a remote control. However, a mouse was used for the testing because of its accessibility.

The mouse and trackball data are essentially similar for the type of task used in this study, with trackball performance being slightly faster. For daily use on a VCR however, a mouse would not be the most preferable input device because it requires a hard, flat surface, and this is not always available, such as in the situation where a person is watching television while sitting in a chair or sofa.

CHAPTER 5 CONCEPTUALIZATION OF THE IDEAL INTERFACE

As a result of the analytical study of the issues in the design of a VCR, a prototype was constructed and tested using HyperPAD™, a rapid prototyping package for an IBM-PC Compatible Computer. A prototyping tool was used because it was not feasible to actually construct a working model of a VCR. HyperPAD™ was selected over other prototyping tools because of its capabilities. In order to compare the new interface with that of an existing VCR, a simulation was made of the AKAI (VCR "D") interface. The results from prior testing showed that this interface fell in the middle of the range and had the fewest number of errors. In order to test the new interface (Test 2), which was devised to rectify the noted deficiencies, the previously mentioned information was implemented. To design the new interface, an iterative design process was used in order to improve the interface.

In doing this, answers to the following questions were sought.

- Which technology is most appropriate?
- Which format is best for the display?
- What feedback is required?
- What is the best sequence of operation?
- What instructions do users need to complete tasks successfully?
- What would be the best wording?
- What, if any, abbreviations should be used?
- What would be the best method of entering information?
- What selection choices should be available?

CHAPTER 6  TESTING OF THE NEW INTERFACE

6.1 Methodology

The working prototypes of the existing VCR "D" and the new interface, were tested to evaluate users' performances. The AKAI interface was chosen because users made the fewest errors while using this machine, and no subject quit while programming the AKAI VCR during Test 1.

6.2 Equipment

A 286-10 MHz. computer was used to test the two simulations. In order to simulate the use of a remote control device in programming the VCR, an infrared device made by NView™ was attached to the computer. This device came with a keyboard that was used to "teach" a Memorex Universal Remote so that the desired actions could be obtained. By using a universal remote, the computer could be controlled by using a remote control.

A Genius Mouse™ was used as the input device in the prototype of the new interface. With the mouse, the users could see all of the choices at once, and then make a selection from the items on the screen by moving the cursor and then pressing the left mouse button.

6.3 Programming

Two simulations were prototyped. One was a simulation of the existing AKAI On-Screen VCR, Model Number VS-303U. The other was the newly devised interface, which incorporated the previously mentioned design considerations in Section 4.3. The first step required for programming was to design the screen layouts which can be seen in Appendix C. The second stage was writing the scripts to define the outcome of the users' actions which can be seen in Appendix B. The third stage involved writing an analyzing program to record each subject's actions in such a way that the trials could be duplicated. The users' data is exported to data files so that specific actions, types of action, mouse clicks, number of times each screen is entered and time spent on each screen may be compared. This can be seen in Appendix E.

Two types of data were collected from the subjects. The first type was objective. A detailed explanation of how this was obtained is described in Chapter 3. The second type of data is subjective; it was verbally supplied by the subject during and after the testing. Usability tests were run, using the "Thinking-Aloud" technique.[40] This method requires users to verbalize their thoughts as they interact with the system. This technique is especially useful in discovering strategies which users employ in approaching tasks, pinpointing problems, and discovering the reasons why they occur.

Talking aloud while programming appeared to be easy and natural for most of the test participants. In fact, several subjects commented that they would undoubtedly be talking to their devices at home while programming them! It is crucial to capture the relationship between the actions of the users, the system's response, and the sequence of steps. Comments made during the test sessions were recorded for later analysis. In addition, demographic data, such as each subject's age, occupation, and experience using VCRs and mice was also recorded.

6.4 Revising the Interface

Debugging and revising the interface was a prodigious effort and required an enormous amount of time. The final version was developed after several modifications and improvements to the initial version through preliminary testing. The subjects from these preliminary trials did not serve as subjects for Test 2.

6.5 Design

The final testing was done as a repeated measures experiment. No subject had previously participated in any aspect of this study. Test participants were given the same briefing as in the earlier test. The tasks required in this test were to set the clock and 3 programs (the tasks of Test 1 were to set the clock and two programs) to simulate a situation where the subject might go on vacation and, upon arrival home, have the desired programs on tape. The same performance parameters were measured as in Test 1. Three programs were set so that the learning time between programs could be more accurately studied. The subjects did not know which interface was the experimental one.

The following directions were given to the test participants for Test 2:

Set Time: 9:00PM, Wednesday, June 6, 1990

Program 1: 8:00PM-11:00PM, Sunday, June 10, 1990, Channel 5

Program 2: 3:00AM-3:30AM, Monday-Friday, Channel 7

Program 3: Record your favorite television show

Each subject used both simulations, so as to eliminate the effect of between subject variability. The order in which the subjects used the interfaces was counterbalanced so as to offset the effect of learning. In all, 23 subjects were tested. However, data from only 16 subjects was used in the calculations because seven of the test participants quit while performing the programming tasks on the simulation of the AKAI interface. Because these subjects were not able to complete all of the tasks, their data could not be validly compared with that of subjects who had fully completed the tasks.

6.6 Card's Method for Calculating Performance Times for Users of Interactive Computing Systems Stuart Card's research in 1979 involved calculating performance times for users of interactive computing systems. He calculated the way in which the time to perform a task can be determined from the design phase by breaking the entire task into individual components. However, he focused his calculations on experienced users, not novices.

Some of the interface factors affecting user performance include:

- *Time* – How long it takes for a user to accomplish a task.
- *Errors* – How many errors the user makes and how serious they are.
- *Learning* – How long it takes a novice user to learn to use the system.
- *Functionality* – The range of tasks that can be performed with the system.
- *Recall* – How easy it is for a user to recall how to use the system after a period of non-use.

An attempt to minimize the first three of these aspects was addressed in this study. *Recall* and *Learning* were considered the same since data collected has shown that most people perform the task being studied (time-shift programming) less than once a month and thus have to re-learn the task each time. *Functionality* was also disregarded because it was negligible between tasks.

This study, like Card's, focuses on *Time*. Knowing the sequence of user actions and the response time of the system, the required user time can be predicted by application of the following equation:

$$T_{task} = T_{acquire} + T_{execute}$$

One goal of the new interface is to minimize $T_{acquire}$. By Card's model, the execution time is the time $t_j$ for each of these operators $j$ weighted by the frequency $n_j$ with which they occur, plus the total system response time, $T_R$ to the steps performed by the user. The formula for the execution time is:

$$T_{execute} = \Sigma_j\, n_j l_j + T_R$$

Despite the endless number of possibilities that can be performed using a computer, according to Card's work, the steps necessary to do the tasks required and their respective times can be divided into four categories:

1. The time required to use the mouse to point to the object and click:
$$t_P = 1.10 \text{ seconds}$$
2. The time to mentally prepare before pointing to a command:
$$t_M = 1.35 \text{ seconds}$$
3. The time to enter input:

Akai interface:
$$t_K = 0.75 \text{ seconds for typing complex codes}$$
    New interface:
$$t_K = 0.2 \text{ seconds for an average typist or mouse user}$$
4. The computer response time:
$$t_R = \text{Variable}$$

The subjects' entry times, actions, and the computer response time were then subtracted from the total time required to perform the task in order to determine $T_{acquire}$. This technique give estimates accurate to about 20% of actual times required by users. The use of Card's work enabled the researcher to estimate time needed for an experienced user to complete the task when the method is known.

6.7 Results

6.7.1 Computer Response Time $T_R$, the average computer response time, was calculated individually for each subject. In order to attain a baseline, the researcher, an expert user of the systems, performed the tasks on both a 10 MHz and a 33 MHz computer. The faster processor had a negligible computer response time, taken as $T_R=0$. The time using the faster computer was then subtracted from the time using the slower computer to achieve a measure of how much slower the 10 MHz computer was.

An additional time delay, due to the software used and dependent upon the number of screens accessed, was then subtracted from the change in time. This number was then divided by the number of keypresses required to complete the task to produce a number representing the number of seconds per keypress. The computer response times obtained were:

> 1.11 seconds per keypress for the AKAI interface
> 0.18 seconds per keypress for the new interface The large difference between these numbers was confirmed when many users commented that they had to wait for the outcome of their input on the AKAI interface.

6.7.2 Errors

Errors are often made by the users and they can be classified as follows:

- OMISSION – Failure to perform any task necessary to program the VCR.
- COMMISSION – Incorrectly performing a task without noticing the error.
- SEQUENTIAL EFFECTS – When judgment is affected by items that precede it.

In the new interface, the errors of omission are remedied by the fact that the user cannot continue programming if the current step is not completed. In the AKAI interface, this is not the case and critical actions may be overlooked.

Errors of commission seem inevitable. In the AKAI interface, there were an average of 34.3 errors per subject, or 9% of the total number of buttons pressed. In the new interface, there were an average of 7.2 errors per subject, or 6% of the total number of keystrokes. In order to determine significance, a T-Test was applied and the difference between error rates of the two systems is significant at $\alpha < .10$. Results of this test can be seen in Appendix A. Sequential effects were eliminated by the testing procedure and did not affect the results obtained. Figure 14 shows the required and the extra keypresses for each interface.

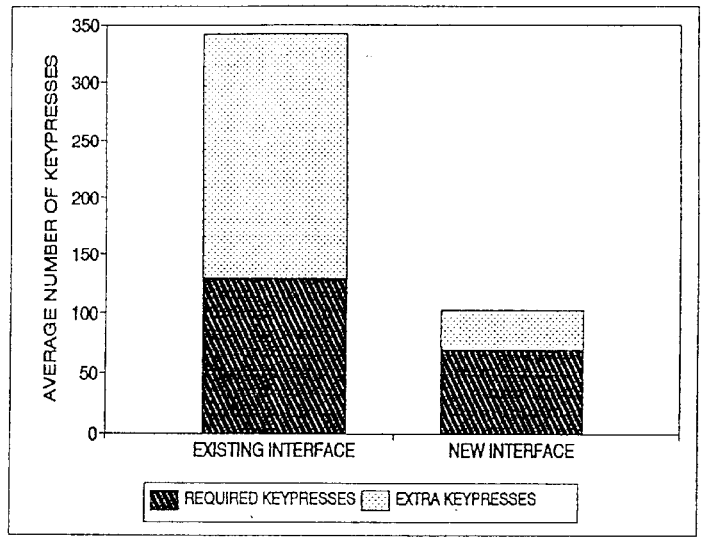

Figure 14 – Required And Average Extra Keypresses For Each Interface 6.7.3 Simulation of the AKAI Interface In programming the simulation of the AKAI interface, the average time that it took the 16 subjects to complete the setting of the clock and the recording of three programs was 1,476.9 seconds (24.6 minutes). An average of 451.4 seconds (7.5 minutes) of each trial, or 31% of the total time, can be attributed to computer response time ($T_R$) using 1.11 seconds per keypress. This time can then be subtracted from the subjects' total time.[41] Thus, the new average becomes 1,025.5 seconds (17.1 minutes). The fastest time recorded was 498 seconds (8.3 minutes) and the slowest time was 2,844.4 seconds (47.4 minutes). Table 14 shows the subjects and the time it took to complete the programming for the AKAI interface. Figure 15 shows this data graphically.

Table 14 – Total Time In Seconds And (Total Time – Computer Time) For The Critical Steps Using The AKAI Interface
| SUBJECT # | TOTAL | TOTAL-$T_R$ |
|---|---|---|
| 1 | 1228 | 981.9 |
| 2 | 1190 | 663.3 |
| 3 | 2358 | 1513.9 |
| 4 | 1425 | 976.2 |
| 5 | 1394 | 1022.5 |
| 6 | 1482 | 1144.6 |
| 7 | 3289 | 2844.4 |
| 8 | 1247 | 697.6 |
| 9 | 2248 | 1220.7 |
| 10 | 1389 | 825.8 |
| 11 | 1143 | 829.7 |
| 12 | 1697 | 1243.2 |
| 13 | 817 | 533.3 |
| 14 | 1146 | 764.3 |
| 15 | 841 | 648.2 |
| 16 | 737 | 498.0 |
| MEAN | 1477 | 1025.5 |
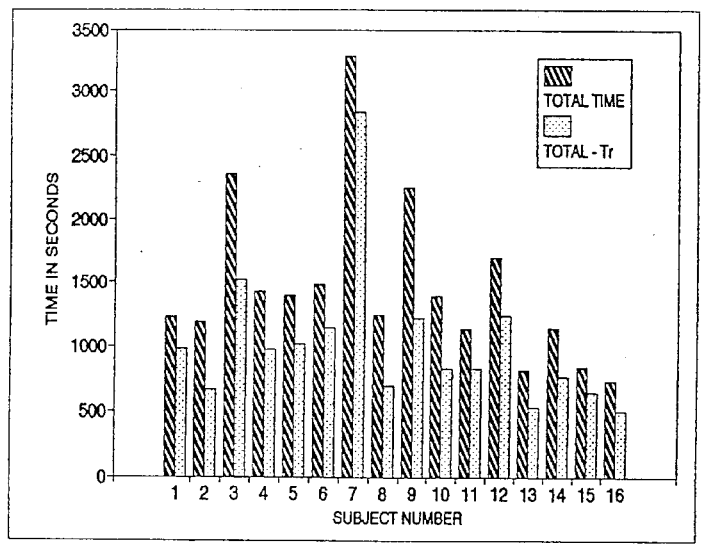
Figure 15 – Differences In Seconds Between Total Time And (Total Time – Computer Time) For The AKAI Interface.

No subjects were able to complete the task in the desirable minimum time of seven minutes and only eight subjects (50%) were able to set the clock and three programs in less than 14 minutes, double the ideal time goal established as a result of the previous testing. The seven minute time period was selected as a result of subjective data gathered earlier in research, which represents a 36% decrease compared with the average for the interface which took the least amount of time to program in Test 1. This is a significant time improvement. Two subjects (13%) required more than 21 minutes, triple the goal set, to perform these tasks.

Only four subjects (25%) were able to correctly perform the tasks required. An additional six subjects (38%) did not select the timer button. Only one person realized his error (setting the wrong date). The problems encountered which led to incorrect recordings, and their frequency are as follows:

| Number of Subjects | Problem |
| --- | --- |
| 4 | Set the wrong date |
| 3 | Confused by the moving seconds field |
| 2 | Set the wrong time |
| 1 | Set the wrong channel |
| 1 | Didn't memorize a program |

A summary of some of the problems which test participants encountered while using the simulation of the AKAI interface as follows:

- All subjects had difficulty figuring out the coded buttons "A", "B", "C", "+" and "-".

- All subjects were confused by the screen choices of "1st", "2nd", "3rd", "4th", and were surprised when they found "M-F". They did not understand why it was there. Several thought that it stood for program number. They expected the "M-F" option to be linked with the days of the week, not the week number.

- 16 out of the 18 subjects did not know what to do when the VCR was first turned on and the "Clock Set" mode appeared on the screen. They all pressed "Clock Adjust" and backtracked to set the clock during the testing rather than setting the clock when the screen first appeared.

- 11 subjects did not notice the changing instructions at the bottom of the screen.

- 9 subjects thought they had to memorize each step of setting the clock.

- 7 subjects quit before they had completed the entire programming task, and thus their data was unusable.

- 6 subjects did not press the timer button.

- 3 subjects were confused by the seconds field. They reasoned that "if I can't change it, it shouldn't be there".

- 1 subject never realized that there were "+" and "-" keys and thus circled around when overshooting a number, i.e. if he wanted to set the minutes to :30 and missed and set it at :31, he went around 59 more times in order to correctly set the time.

- 1 subject could not figure out how to get the minutes to :30. Instead, he recorded the station for an hour.

- 1 subject searched for a Main Menu.

6.7.4 Simulation of the New Interface

The average time required to complete the experimental tasks with the new interface was 560.1 seconds (9.3 minutes). The average computer response time, $T_R$, assuming it took 0.18 seconds per keypress, was 57.5, or 11% of the total time. When this is deducted from the total time, the new average is 502.7 seconds (8.4 minutes). The shortest length of time recorded for programming was 143.5 seconds (2.4 minutes) and the maximum was 1,187.7 seconds (19.8 minutes). Ten of the subjects (63%) took less than seven minutes to set the clock and three programs, thus meeting the original goal of a maximum of seven minutes, and 13 subjects (81%) took less than 14 minutes. Table 15 shows the subjects and the time it took each to successfully complete the tasks on the new interface. This table can be seen graphically in Figure 16. Overall, 14 out of 16 of the test participants took less time using the new interface.

Table 15 - Total Time In Seconds And (Total Time - Computer Time) For The Critical Steps Using The New Interface

| SUBJECT # | TOTAL | TOTAL-$T_R$ |
|---|---|---|
| 1 | 461 | 406.1 |
| 2 | 929 | 840.5 |
| 3 | 675 | 625.6 |
| 4 | 1151 | 1046.7 |
| 5 | 403 | 359.2 |
| 6 | 331 | 281.5 |
| 7 | 437 | 374.2 |
| 8 | 372 | 317.2 |
| 9 | 747 | 688.7 |
| 10 | 180 | 143.5 |
| 11 | 823 | 759.3 |
| 12 | 462 | 403.6 |
| 13 | 239 | 202.2 |
| 14 | 368 | 305.1 |
| 15 | 456 | 412.5 |
| 16 | 352 | 299.9 |
| MEAN | 560 | 502.7 |

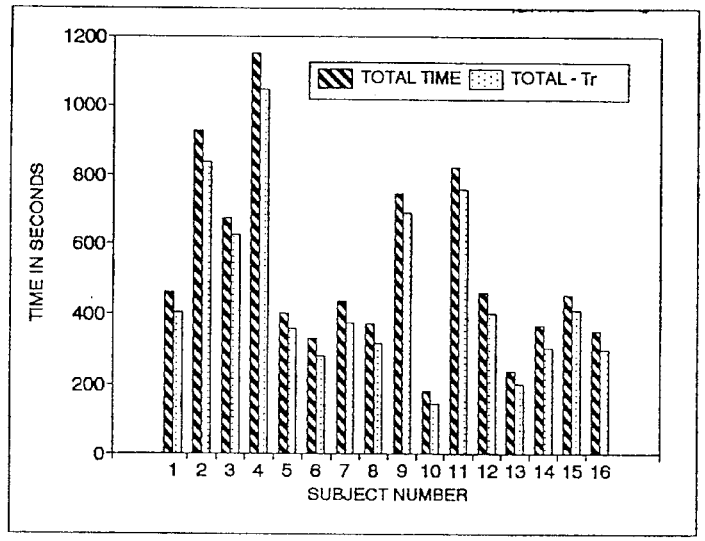

Figure 16 – Differences In Seconds Between Total Time And (Total Time – Computer Time) For The New Interface.

6.8  Statistical Analysis of Test 2

Similar parameters to that of Test 1 were used. The data was analyzed using the SPSS-X statistical package. The tasks can be divided into six steps.

1. CLOCK SET
2. PROGRAM 1
3. PROGRAM 2
4. PROGRAM 3
5. SEARCH TIME
6. TOTAL TIME

The average time for the 16 subjects, and their standard deviations can be seen in Table 16. The number of subjects and the tasks they could not accomplish can be seen in Table 17.

Table 16 — Average Time In Seconds For The Critical Steps

| CRITICAL STEP | AKAI INTERFACE | | NEW INTERFACE | |
|---|---|---|---|---|
| | AVERAGE | STD | AVERAGE | STD |
| CLOCK SET | 332.0 | 266.7 | 105.9 | 67.8 |
| PROGRAM 1 | 431.7 | 316.7 | 167.6 | 142.7 |
| PROGRAM 2 | 283.3 | 135.0 | 85.6 | 52.6 |
| PROGRAM 3 | 189.7 | 97.4 | 55.3 | 16.5 |
| TOTAL | 1025.4 | 559.7 | 466.6 | 251.9 |
| SEARCH | 240.3 | 203.1 | 111.8 | 81.2 |

Table 17 — Number Of Subjects Unable To Succeed On The Critical Steps On Both Interfaces

| CRITICAL STEPS | AKAI INTERFACE | NEW INTERFACE |
|---|---|---|
| MISTAKE | 8 | 4 |
| TIMER | 6 | 4 |

Figure 17 graphically shows the critical steps for the two interfaces. Figure 18 shows the total time by subject, and Figures 19 and 20 show the minimum, maximum, average and standard deviations for both the AKAI and the new interfaces. In Figure 18, subjects two and four took less time using the new interface in actuality, however, using adjusted times, the new interface took longer.

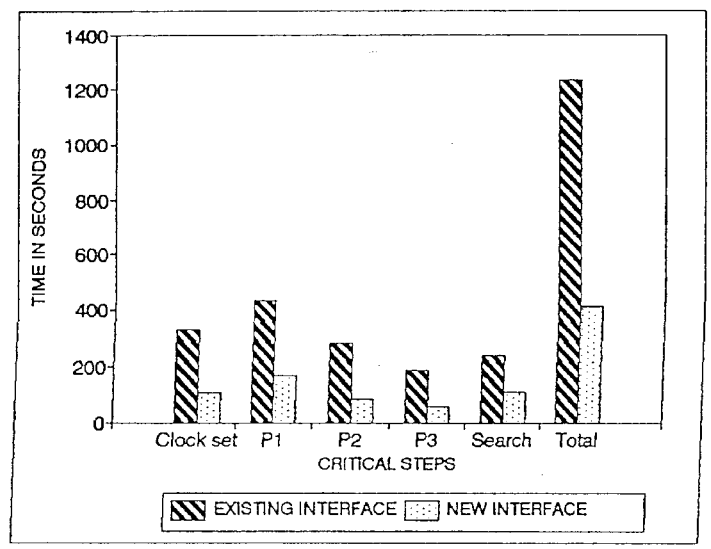
Figure 17 – The Critical Steps For Test 2
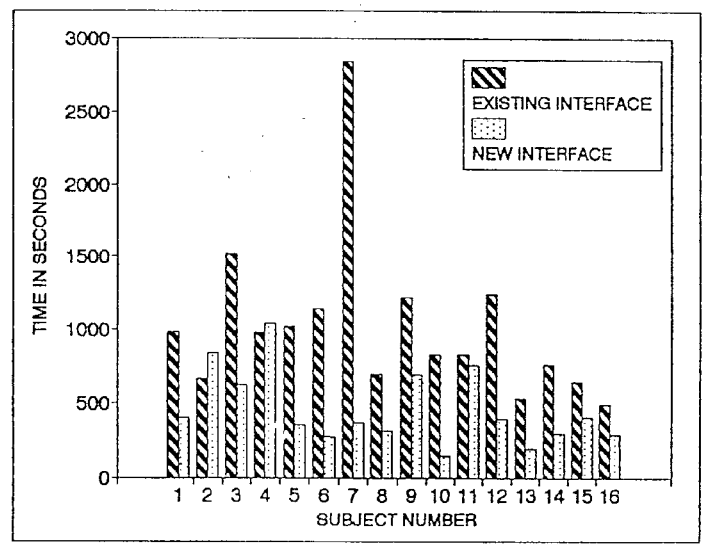
Figure 18 – The Statistics By Subject For Test 2

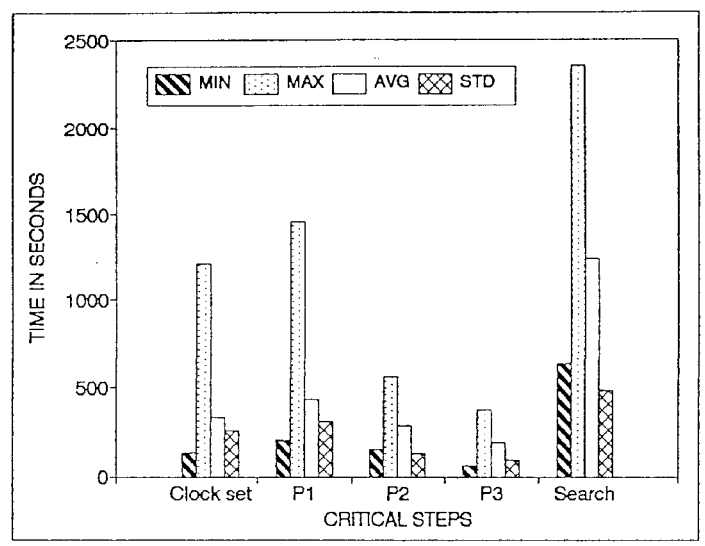
Figure 19 — Statistics For The AKAI Interface
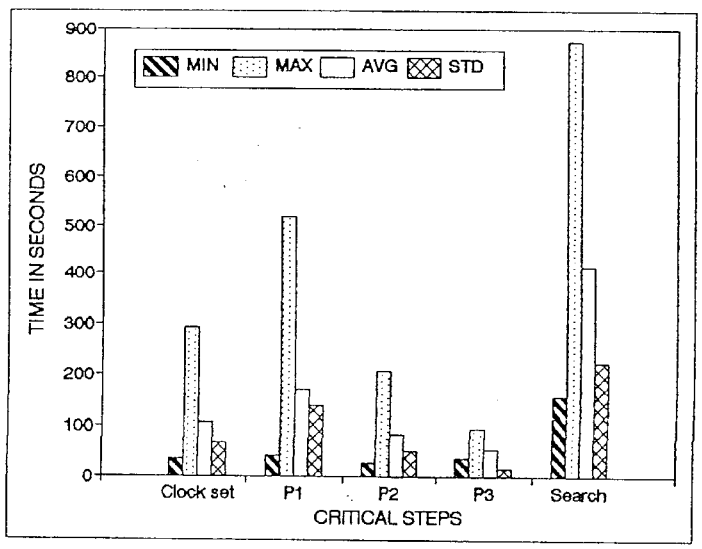
Figure 20 — Statistics for The New Interface The new interface reduced the average programming time by 54%! However, the standard deviations are high for both cases, and equal slightly more than half of the total time. T-Tests for each of the critical steps showed no significance. However, when subjected to the Pearson Correlation, some significance was found ($\alpha < .10$).

Ten subjects (63%) were able to correctly perform the programming tasks using the new interface. Altogether, four users did not set the timer, and two of these did not set the timer on the AKAI interface. Three subjects reported that they probably could have performed the tasks quicker if they were not using a mouse as the input device. None of the subjects who made mistakes using the new interface realized their errors. The problems encountered and their frequency are as follows:

| Number of Subjects | Error |
| --- | --- |
| 4 | Set the incorrect date |
| 4 | Did not set the timer |
| 3 | Set the incorrect time |
| 1 | Chose the wrong type of recording |

All measurements were subjected to separate Analysis of Variance tests. The differences between all measures were found to be statistically significant at $\alpha < .01$, except search time, which was significant at $\alpha < .05$.

The CHI Square test was performed to determine whether the probability of the times for each measurement is the same, or whether they are statistically different from one another. The results indicated that differences exist only between Clock Set, Program 2, and Program 3 and are significant at $\alpha < .01$. Results of the statistical tests can be seen in Appendix A.

6.8.1 Theory

According to Stuart Card's work, the total amount of time from the design stage can be calculated according to the following formula:

$$T_{EXECUTE} = \# \text{ OF KEYPRESSES} \times (T_M + T_K + T_P)$$

where  $T_M$ – Mentally Prepare $T_K$ – Key in $T_P$ – Point with mouse

THE AKAI INTERFACE

To perform the necessary tasks on the AKAI interface, a minimum of 130 keypresses was required for each of the 18 subjects. Using the formula above, an average of 273 seconds is calculated for $T_{EXECUTE}$. However, in the actual testing situation, an average of 342.1 keypresses were made per subject, 2.6 times the minimum number of keypresses required. According to Card's formula, it should have taken 718.4 seconds for 342.1 keypresses ($T_M=1.35$, $T_K=0.75$). It actually took an average of 1,025.5 seconds per subject, which is 1.4 times more than the theoretical time expected. Both the additional keypresses and the extra time can be attributed to $T_{ACQUIRE}$, which depends on the details of the task and whether it is given from without or generated from within the user.

Some of the extra keypresses can be attributed to the fact that all of the subjects had trouble deciphering the coded buttons and were confused by the week numbers and how to select the Mon-Fri option. Nine users thought that they had to "Memorize" the clock setting sequence after each step, and the subjects did not always mentally calculate whether using the "+" or "−" key would be faster, and if they realized their error, they commented that they had not selected the shortest route. One subject did not realize that there were "+" and "−" keys and therefore, when he missed setting the time by one minute, he had to cycle around 59 extra times, thus incurring 59 extra keypresses.

THE NEW INTERFACE

The new interface required a theoretical minimum of 70 keypresses per subject, which was only 54% of the number of keypresses required by the simulation of the AKAI interface. It can be noted that the time to perform the task of programming the new interface was also reduced by 54%. This results in a theoretical average of 185.5 seconds per subject, 87.5 seconds less than the other interface. The actual testing situation resulted in an average of 103.6 keypresses per subject, 68% more keypresses than the required minimum ($T_M=1.35$, $T_K=0.2$, $T_P=1.10$). Although the new interface required far fewer keypresses than the simulation of the AKAI interface, by Card's calculations, it should have taken 274.5 seconds for 103.6 keypresses. However, it took an average of 502.7 seconds per subject, 1.8 times more than the predicted time. This can be attributed to $T_{ACQUIRE}$.

Some of the extra keypresses could be attributed to four subjects who originally entered the date as "90" rather than "1990", five subjects who tried to enter information on the help screens, five subjects who selected the places where the numbers are displayed on the screen before selecting from the numeric keypad, and six subjects who had trouble selecting AM/PM. All of these errors resulted in extra keypresses, and therefore consumed additional time.

Figure 21 shows keypresses per subject and Figure 22 shows the differences between the theoretical and actual times for the keypresses, using Card's formulas, for each interface.

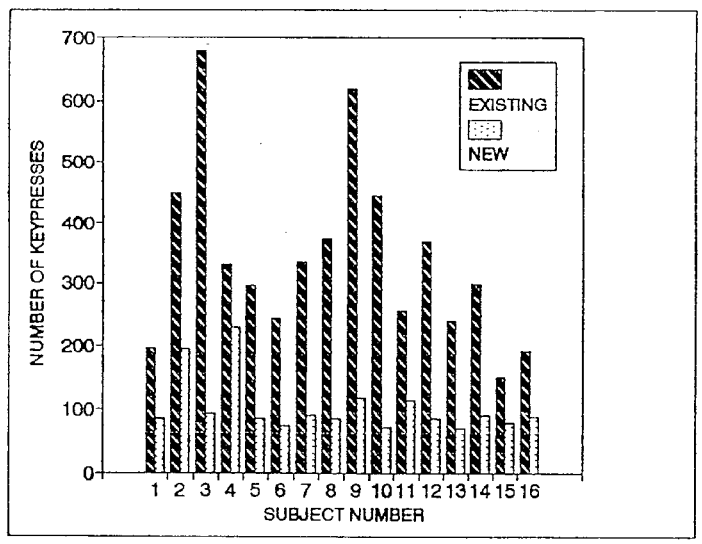

Figure 21 – Number Of Keypresses Made By The Test Participants

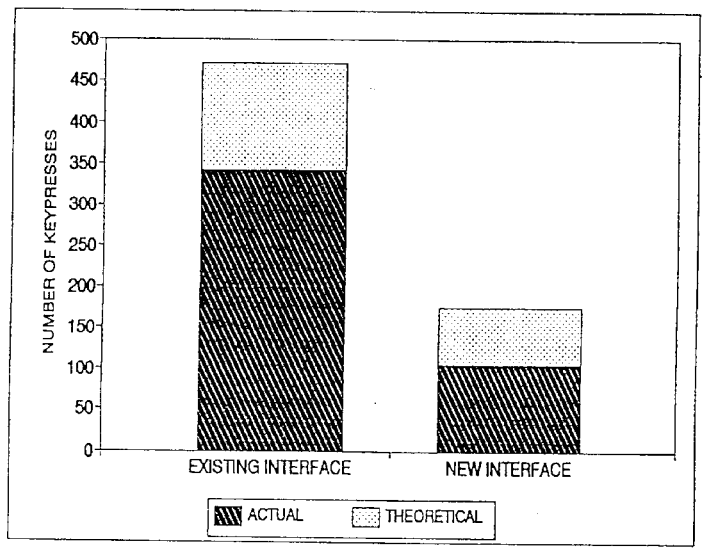

Figure 22 – The Differences Between The Theoretical and Actual Times In Seconds For The Keypresses Of Both Interfaces Several factors may account for the disparity between the times found in this study when compared with the formulas developed by Card. The major difference may be due to the fact that the formulas derived by Card are for experienced users, not novices. Thus, these numbers might indicate how well users might perform after a period of using the system. CHI Square tests, which are reproduced in Appendix A, showed significance at $\alpha < .01$ for both the theoretical and actual times for the keypresses and for the theoretical and actual number of keypresses. In designing the interface, an effort was made to reduce the learning time. Thus, Card's equations are appropriate since all users are considered to be experts. As can be seen in a comparison of the values between the two interfaces, the calculations of $T_{EXECUTE}$ for the new interface came much closer to that of the theoretical values than did the calculations for the AKAI interface, thus proving that the new interface did reduce the learning time. The results for the theoretical time for minimum number of keypresses, theoretical time for the actual number of keypresses, and actual time can be seen in Figure 23.

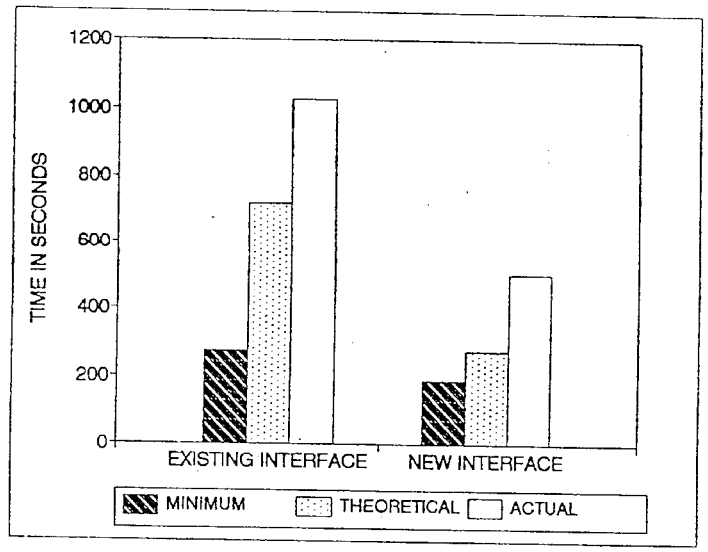

Figure 23 — Theoretical Time In Seconds For Minimum Number Of Keypresses, Theoretical Time In Seconds For The Actual Number Of Keypresses, And Actual Time In Seconds.

6.8.2 Searching Time

THE AKAI INTERFACE

The prototypes can be divided into screens which represent the programming steps. In order to set the simulation of the AKAI interface, a minimum of 13 screens must be entered by the user. The average for the trials of the 16 subjects was 36.8 screens per subject, almost three times more screens than were necessary. Table 18 shows the screens, the minimum number of times they must be accessed, the average number of times that each was accessed, the average amount of time spent on each screen, and the standard deviation of the number of screens opened. The first step of Test 1, to Power-On the VCR, was excluded in the interface. Screen layouts can be seen in Appendix C.

Table 18 - Screens Required For The AKAI Interface

| SCREEN | # OF TIMES OPENED | | AVG TIME | S.D. |
| --- | --- | --- | --- | --- |
| | MIN | AVG | | |
| CLOCK SET: To set the clock | 1 | 4.9 | 249.4 | 6.2 |
| CLOCK ADJUST: To get to CLOCK SET | 0 | 7.2 | 49.0 | 10.6 |
| CLOCK: Displays the clock | 1 | 2.6 | 38.7 | 1.5 |
| SELECT THE PROGRAM: To select a program | 4 | 8.4 | 99.7 | 3.9 |
| PROGRAM 1: To set program 1 | 3 | 5.5 | 446.6 | 2.1 |
| PROGRAM 2: To set program 2 | 2 | 2.9 | 207.3 | 1.2 |
| PROGRAM 3: To set program 3 | 1 | 1.5 | 172.2 | 0.7 |
| PROGRAM 4: To set program 4 | 0 | 0.9 | 14.4 | 1.0 |
| ON/OFF: To turn the on or off | 1 | 2.9 | 70.8 | 2.5 |
| TOTAL | 13 | 36.8 | 1476.9 | 21.7 |

Subjects were confused when using the simulation of the AKAI interface. The CLOCK ADJUST screen was displayed when the program began, and the subjects did not understand the directions on the screen. Fourteen out of the sixteen subjects pressed "CLOCK ADJUST" and then "C" which returned them to where they had started. Even if they were able to figure out that this was the correct screen on which to set the clock, 12 out of the 16 subjects wanted to "Memorize" after each step of setting the time and date, rather than after everything was set. This could account for the large number of times that the CLOCK SET, CLOCK ADJUST, and CLOCK screens were accessed. All subjects seemed to spend a great deal of time on the CLOCK SET page, trying to figure out which buttons to use. All subjects were extremely confused between "A+", "A−", "B+", and "B−". In fact, one subject never realized the difference between the "+" and "−" keys, and if, for example, he missed setting the channel, he cycled around another 98 times. In addition, users accidentally accessed Program 4 and turned on and off the VCR several times.

NEW INTERFACE

To set the clock and three programs on the new interface, at least 32 screens must be opened. In testing, subjects opened an average of 42.9 screens, an average of 34% more screens than the minimum required. Although more screens are required to be opened in the new interface, the percentage of extra screens opened is much smaller than that of the AKAI interface. Table 19 shows the screens which must be accessed, the minimum number of times they must be used, the average number of times subjects looked at them, the average amount of time subjects spent using them, and the standard deviation of the number of screens opened. Again, the initial step of turning on the VCR was excluded from this study.

Table 19 — Screens Required For The New Interface

| SCREEN | # OF TIMES OPENED MIN | AVG | AVG TIME | S.D. |
|---|---|---|---|---|
| MAIN MENU: To make a selection | 5 | 6.6 | 70.1 | 3.4 |
| TIMER: To set the timer | 1 | 0.9 | 5.8 | 0.3 |
| MAIN MENU HELP: Help on Main Menu | 0 | 0.4 | 8.1 | 0.5 |
| HELP: Help on the Help Screen | 0 | 0.6 | 4.1 | 0.6 |
| CURRENT TIME: To set the current time | 1 | 1.4 | 43.4 | 0.8 |
| CURRENT TIME HELP: To obtain help | 0 | 0.1 | 0.1 | 0.2 |
| SELECT THE PROGRAM: To select a program type | 3 | 4.0 | 26.9 | 1.7 |
| SPECIFIC DAY: To choose type of day | 1 | 1.7 | 8.7 | 0.9 |
| SELECT THE PROGRAM HELP: Help | 0 | 0.1 | 0.1 | 0.2 |
| SELECT THE DAY: To choose a specific day | 1 | 0.9 | 6.0 | 0.8 |
| SELECT THE MONTH: To choose a month | 2 | 2.7 | 23.3 | 1.1 |
| YEAR SET: To set the current year | 1 | 1.4 | 41.4 | 0.5 |
| CHANNEL: To choose the channel | 3 | 3.6 | 24.9 | 1.4 |
| START TIME: To choose the start time | 3 | 3.8 | 65.8 | 1.5 |
| STOP TIME: To choose the stop time | 3 | 3.6 | 48.4 | 1.4 |
| TAPE SPEED: To choose the tape speed | 3 | 3.6 | 17.3 | 1.4 |
| CONFIRMATION: To review programs | 3 | 4.8 | 114.9 | 2.6 |
| DAY OF MONTH: To choose the day | 2 | 2.6 | 16.6 | 1.1 |
| TOTAL | 32 | 42.9 | 560.1 | 15.9 |

When the VCR was first turned on, subjects viewed a prompt instructing them to set the time. Two subjects looked for a Main Menu at this point, and exited the screen before setting the time. The only occasion where the subjects had to enter the Main Menu screen was to set programs to record or to reset the current time or current date. This screen was accessed more times than necessary, possibly because several subjects selected the "Main Menu" button on the screen before setting the time, date, or pressing the "OK" button.

Help screens were accessed either when the user was confused as to what to do, or just for curiosity (from users' comments). The one "Help" button that provided the most assistance was MAIN MENU HELP. It told the users to "POWER OFF" and then to set the Timer to "ON" when programming was finished.

Only 34% more screens were opened when programming the new interface, whereas in the AKAI interface, the additional number of screens opened approached 300%. This indicates that there was much more confusion when using the AKAI interface. The two simulations showed significance at $\alpha < .10$ for the number of screens opened when subjected to a CHI Square test of independence. The results can be seen in Appendix A.

6.8.3 Mental Preparation Time

THE AKAI INTERFACE

Both interfaces required that a confirmation button be pressed before proceeding to the next step. In the AKAI interface, "C" represented this confirmation. At the end of each sub-task (setting the time, program 1, program 2, and program 3), it was necessary to press "C" after the instructions "OK to Memorize" appeared on the screen. Pressing this button would either advance the user to the CLOCK screen if he were on the CLOCK ADJUST screen, or the PROGRAM screen if he were on one of the programming screens. Theoretically, "C" on the AKAI interface must be pressed a minimum of five times by each subject to complete the task, and 10.5 seconds is consumed in doing this. In testing, this button was pressed an average of 9.1 times by each the 16 subjects, which is almost double the number of keypresses required. Each keypress should theoretically have taken 2.1 seconds. However, in actuality, it took 12.1 seconds per "C" keypress, which is almost six times more than the theoretical value calculated using Card's formula.

The extra keypresses can be attributed to the fact that five users thought that they had to press the "C" button after each category they changed. The extra time can be attributed to the fact that, as many subjects commented, they were doing the tasks by trial and error and had to recheck all of the information carefully to make sure it was correct. While test participants were using the AKAI interface, many made comments that the numbers seemed to be changing by themselves. What had really happened was that the test participants were not looking at the correct place on the screen to see the changes and were confused by the blinking numbers, or they had entered information faster than it could be displayed, and as a result, pressed too many buttons.

THE NEW INTERFACE

The new interface used a blue "OK" button on the bottom of each screen that required more than one keypress. These screens included the setting of the current year, current time, start time, stop time, channel, and the confirmation screen. Pressing "OK" brought the user to the next step of the programming sequence or back to the Main Menu from the confirmation screen. It was necessary for each subject to press this button a minimum of 14 times to complete the task, which would theoretically have taken 37.1 seconds. In the testing situation, "OK" was pressed an average of 18.5 times per subject. This was only 33% more than the minimum number of keypresses required. The average time was 6.9 seconds per "OK" pressed, which was 2.6 times more than the theoretical 2.65 per keypress found by applying Card's formula.

COMPARISON OF INTERFACES

Comparing the results from the two interfaces on length of mental preparation time for pressing of the confirmation buttons, the new interface took considerably less time. If the user is confident about the information he enters, it takes less time to confirm the data entered. When subjected to a T-Test, there was no significance for the number of times that "C" or "OK" was pressed, or between the time that it took for the two buttons to be pressed. The results can be seen in Appendix A.

6.9 Subjective Analysis of Test 2

6.9.1 Demographics

The population consisted of nine males and seven females chosen randomly. Their ages are as follows:

```
 2  <  20
10 between 20-29
 2 between 30-49
 2  >  50
```

The highest level of education completed is as follows:

```
6 Completed High School
7 Completed College
3 Completed Graduate School
```

Their experience in using VCRs is as follows:

5   Never Recorded

4   Have recorded, but not within the past two years.

4   Record less than once a month

2   Record twice a month

1   Records once a day

In addition, two subjects were familiar with on-screen programming, three had used the one-touch-record feature, two had used the remote to program, four reported that they referred to documentation whenever programming, and one had used a bar coder to program. Twelve of the 16 subjects were familiar with the use of a mouse. Although no subjects had too much difficulty using this device, inexperienced mouse users could not control the instrument as well as others. Therefore, it must be noted that the use of the input device is a variable which could affect the results.

THE AKAI INTERFACE

Test participants were asked to rate each interface using the same scales as in Test 1. The scales can be seen in Tables 11 and 12. Using these ratings, the simulation of the AKAI interface was rated and can be seen in Table 20.

Table 20 – Averages And Standard Deviations Of The Subjective
Ratings For The AKAI Interface

| SCALE | AVERAGE | STANDARD DEVIATION |
|---|---|---|
| LIKE/DISLIKE | 5.47 | 1.58 |
| EASY/DIFFICULT | 5.41 | 1.40 |
| COOPER-HARPER | 6.66 | 2.61 |

Note: The Like/Dislike and Easy/Difficult ratings were based on a 7-point scale and the Cooper-Harper rating was based on a 10-point scale.

The results show that this interface is perceived to be almost at the unsatisfactory level according to the Cooper-Harper Scale and on the "dislike" and "difficult" ends of the other scales. A T-Test on the subjective data showed no significance. The results can be seen in Appendix A.

An analysis of open-ended comments regarding this interface revealed some reasons for subject ratings and the frequency with which their dislikes occurred. Table 21 lists some of the comments made by the test participants.

Table 21 — Comments Regarding The AKAI Interface

| Number of Subjects | Comments |
|---|---|
| 10 | No directions |
| 7 | Want to enter the numbers, not select them with the arrow keys |
| 5 | Very difficult/ Hard to learn |
| 4 | Ambiguous |
| 4 | Desire a more user-friendly system |
| 3 | It seemed like trial and error |
| 3 | Forget the buttons and steps too easily |
| 2 | Too much searching |
| 2 | It was frustrating |
| 2 | Too many keys |
| 2 | Must look at the screen, then remote |
| 2 | I wasn't given enough information |
| 1 | Bad layout |
| 1 | Too little prompting |
| 1 | Too slow |
| 1 | No everyday selection |
| 1 | No help |
| 1 | Bad confirmation screen |
| 1 | Too many steps |

THE NEW INTERFACE

The new interface was able to remedy all of the above mentioned problems. Results of the evaluations for the new interface can be seen in Table 22.

Table 22 — Numerical Averages And Standard Deviations Of The Subjective Ratings For The New Interface

| SCALE | AVERAGE | STANDARD DEVIATION |
|---|---|---|
| LIKE/DISLIKE | 1.94 | 1.13 |
| EASY/DIFFICULT | 1.91 | 1.02 |
| COOPER-HARPER | 2.13 | 1.21 |

Note: The Like/Dislike and Easy/Difficult ratings were based on a 7-point scale and the Cooper-Harper rating was based on a 10-point scale.

The results show that the new interface was well-liked. It was at the "Good" level on the Cooper Harper rating scale and on the "like" and "easy" ends of the other two scales.

An analysis of users' comments regarding the new interface revealed the reasons for their evaluations. The frequency with which their likes and dislikes occurred confirms the fact that the newly developed interface clearly offers users what they want, and remedies problems perceived in the use of the AKAI interfaces. Table 23 lists favorable comments made by the subjects. Criticisms of the interface can be found in Tables 26 and 27.

Table 23— Comments Regarding The New Interface

| Number of Subjects | Comments |
|---|---|
| 8 | Easy to operate |
| 8 | Like it much better and would use it more often |
| 7 | No searching for choices was required |
| 6 | All choices were given at once |
| 6 | Like on-screen instructions |
| 5 | Like menu driven interface |
| 3 | Like entry method rather than selection method |
| 3 | Like single button keypress |
| 3 | Like to correct mistakes easily |
| 3 | Like "Today" and "tomorrow", "Monday-Friday", and "Days of Week" features |
| 2 | Like the use of a remote controlled device |
| 2 | Good confirmation screen |
| 2 | Like color coding |
| 1 | Like feedback |
| 1 | Like are no abbreviations |
| 1 | Like User-Friendliness |
| 1 | Like no leading zeros |
| 1 | Like "OK" buttons |
| 1 | Like the calendar and clock display |
| 1 | Like the quick interface |
| 1 | Like the good Help system |
| 1 | Like entering start and stop times, rather than duration |
| 1 | Thought it was even easier to use than the bar coder |

COMPARISON OF THE INTERFACES

When subjects compared the simulation of the new interface with the simulation of the AKAI one, they unanimously preferred the new interface over any other VCR they had used. After the testing, some of the suggestions that subjects made for alternate input devices include the touch screen, cursor control, voice, trackball, and automatic tracking of the remote.

6.10 Discussion

This experiment was designed to simulate programming a VCR as closely as possible. Although computer response time added to the programming times, efforts were made to correct this time delay. The errors were similar to those which would take place in the actual programming. The work performed by Card was used as a basis to attain the minimum times. However, subjects in this test were not considered "expert" users.

An attempt was made to reduce the searching and learning times in the new interface. In fact, the total search time in addition to the other critical steps was reduced by 50%. When the results of both interfaces are compared with the theoretical values, the results for the new interface more closely approximates the performance of an experienced user. Proportionally, the new interface showed the biggest difference between times for Program 1 and Program 3, thus showing that the learning time does play a major role. However, when subjected to a T-Test, neither interface showed a significant difference between the times required to set the first and third programs. See Appendix A for statistical results. Figure 24 shows the proportion of time that setting each program took for both the AKAI and new interfaces.

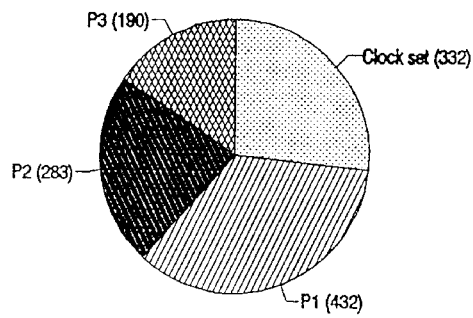 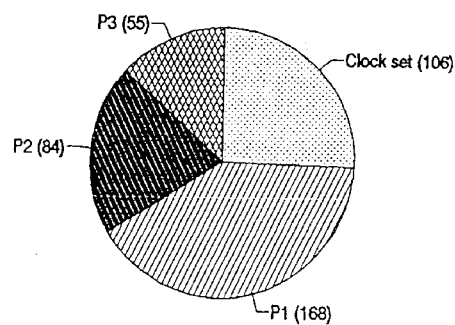

Figure 24 — Proportion Of Time Spent Setting The Programs

The final interface must reflect a compromise between both objective and subjective data. From a Human Factors standpoint, a design which takes a minimum amount of time, but is not well-liked, will not be successful. The results of this study show that performance, time, and subjective data were in favor of the new interface. However modifications can still be made.

The experiment described in Test 2 was developed and performed in order to test a new interface against that of an existing one. The results outlined previously gave quantitative measures of the interface performances. The times measured can be considered realistic estimates of the same performance expected on actual VCRs.

CHAPTER 7  DEVELOPMENT OF AN INTERFACE FOR A VCR

The new interface was designed to reduce the mental load on the user and to eliminate confusion. Throughout this paper, guidelines were established for designing an easy-to-use programmable interface with objective and subjective tradeoffs.

Using the initial list of criteria for developing the interface in Section 4.1 in conjunction with results obtained during Test 2, guidelines were formulated and can be seen in Table 24. It must be recognized that guidelines cannot tell a designer what the contents of the display should be, rather, it should help them decide how the contents should be presented.[42]

Table 24 - Guidelines For The Interface Of A VCR

- Abbreviations - The interface should use a minimal amount of abbreviations, if any. Complete words are preferred.

- Automatic sequencing of steps - The interface should lead the user through the correct sequence of actions required to set a program on the screen, so that no steps are accidentally skipped.

- Change/Cancel - This would allow users to change or cancel part of the displayed information, rather than forcing them to repeat all of the programming steps.

- Choice of specific day or time - To eliminate extra keypresses, frequently-used settings, such as "Record today", "Record tomorrow", "Noon" and "Midnight" should be provided for the user so that he does not have to specify a date or time, thus saving keystrokes, and ultimately, time. In addition, this could eliminate some user errors.

- Choice of Program - Selections should be given to the user to reduce the number of programming steps necessary and provide him with all the frequently used selections. The choices recommended are "Once On ...", "Once a Week on ...", "Monday - Friday at ...", "Everyday at ...". This reduces the number of keystrokes and the amount of programming time required.

- Color Coding – If a color screen is available, color should be used conservatively, but effectively so the user can quickly acknowledge the function of each aspect of the screen. For example, use royal blue for "help," red for mistakes, light blue for information previously entered, and yellow for current information being entered.

- Confirmation Screen – The interface should contain a confirmation screen which shows the user all of the categories and selections he has made, and is easy to understand. All of the necessary information should be displayed.

- Consistent information – Entering information on each screen should be consistent throughout the interface. A standard should be used to indicate that an entry is required, such as a color change.

- Consistent Layout – The screen should have a consistent layout throughout the interface. Buttons which appear on multiple screens should appear in the same location on all screens.

- Conventions – The interface should display data consistent with standards and conventions familiar to users. For entering dates, users are most familiar with calendars. However, this does not eliminate the human problem of setting the wrong date.

- Default settings – The most frequently-used choices should be displayed, as the defaults, and the cursor should appear here when the screen is displayed. This can either be set in advance, or acquired by the system.

- Distinctive cursor – The cursor should be readily distinguished from other parts of the screen.

- Exiting – The user should be able to exit the programming sequence at any time. One method is to place a Main Menu selection on the lower-left hand corner of every screen.

- Feedback – The user must be provided with an adequate amount of feedback, and error messages are directive. An acknowledgement should be displayed after each entry.

- Frustration – If people become frustrated with a device, they will not use it. The interface must minimize the user's frustration level. This can be accomplished by furnishing all possible choices, presenting the data in a logical sequence, and leading the user through the steps necessary to program the VCR.

- Help – A Help system should be provided. The screens should explain the functions of each of the buttons.

- Hierarchical menus – If all selections cannot be displayed at once, a hierarchical sequence should be used. A main menu should provide a top level to which the user can always return and start over.

- Initial smart screen – The interface should begin where the user wants to be. When the VCR is first powered up, and the time and date are not stored in the machine, the "set date" and "set time" screens should appear.

- Input Device – The input device should require as few buttons as possible, thus reducing intimidation. Theoretically, a trackball on a remote control would be preferable because it does not require a flat surface.

- Internal Clock – The interface should utilize an internal clock so that the user cannot set the time or program to record for a nonexistent date.

- Learning Curve – The VCR should not require that a user have prior knowledge in order to use it. If the learning time is minimized, or the learning curve is flattened, no user is at a disadvantage.

- Logical ordering – Menu options should be displayed in logical order or in their expected frequencies.

- Menu selection – Menu selection should be used for tasks which involve limited choices. They are most helpful for users with little training. Each menu should allow only one selection at a time.

- Method of entering data – Information should be entered by pointing using the entry method, rather than using the selection method. If there is more than one keystroke required, the user must then select an "OK" button. All choices should be displayed on the screen at once, and no leading zeros should be required.

- Minimal steps – The number of steps required to complete the task through a sequence of menus should be minimized.

- Necessary information – All information which the user needs should be displayed at once. A user should not have to rely on his memory or his previous experience in order to find the correct choice.

- Setting the time – The options of "Midnight" (12:00 AM) and "Noon" (12:00 PM) should be present, since many people become confused when distinguishing between them.

- Thoroughness – The user should not be able to go to the next programming step until the previous one has been completed. A message to convey why he cannot continue should appear when an attempt is made to continue.

- Word Choice – The words used should not be specific computer terms, but normal, everyday terms which are familiar and easy to understand. In addition, very few abbreviations should be used.

CHAPTER 8  SUMMARY

Redesigning interfaces is common in the software industry, but hasn't been widely recognized by the VCR manufacturers. There are numerous human factors issues involved in designing more usable systems. This research has attempted to investigate some of the issues associated with programming the VCR and understanding where problems exist. The focus was placed on reducing the searching and learning times in order to reduce the total time and user frustration level.

The first step was to become familiar with existing VCRs and some manufacturers' solutions. After critical programming steps were determined, and problems were classified, a prototype was developed and tested, and compared with a simulation of an existing interface.

The number of keystrokes required was found to directly affect the total time. When the selection method was used in the AKAI interface, most subjects did not calculate whether going up or down would be faster, thus resulting in extra keypresses. The total time for each critical step and the errors made were proportional to the number of keypresses. Both interfaces took approximately the same percentage of the total time for the critical steps. The percentages for these critical steps can be seen in Table 25 and Figures 25 and 26.

Table 25 – Percentage Of Total Time For The Critical Steps
| Critical Step | AKAI Interface | New Interface |
|---|---|---|
| Clock Set | 22% | 20% |
| Program 1 | 30% | 32% |
| Program 2 | 19% | 16% |
| Program 3 | 13% | 11% |
| Search Time | 16% | 21% |
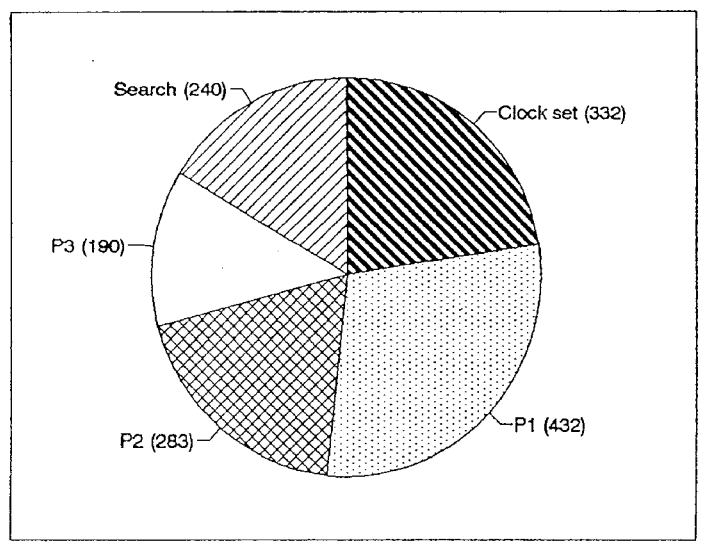
Figure 25 – Percentage Of The Total Time For The Critical Steps Using The AKAI Interface

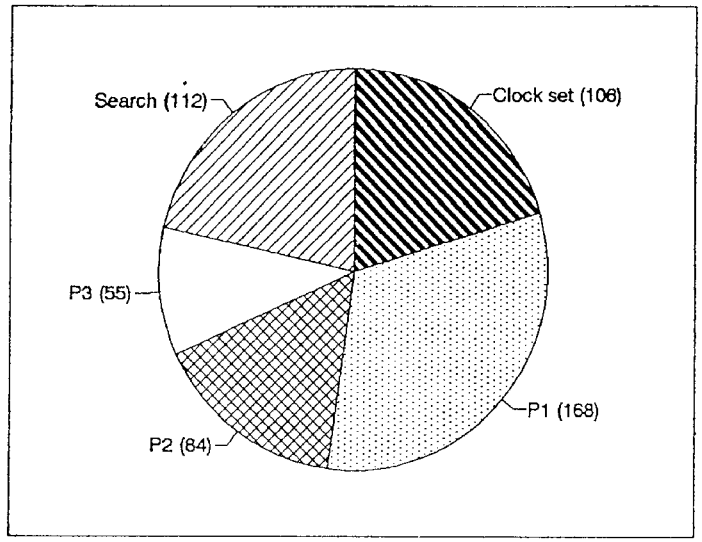

Figure 26 — Percentage Of The Total Time For The Critical Steps Using The New Interface Overall, the critical times for programming the new interface were at least half of those for the AKAI interface. The new design reduced the programming time by 54% and reduced the errors by 500%.

The number of screens opened above the minimum number required had an effect on search time. In the AKAI interface, 283% more screens were opened, whereas in the new interface, screens were opened only 34% more frequently. However, overall, the same percentage of time was spent searching on both interfaces.

Mental preparation time was measured in both simulations by pressing the confirmation buttons. The time delay in pressing "C" and "OK" respectively increases the times for the critical steps in the AKAI and new simulations. The new interface took considerably less time. If the user is confident about the information entered, it takes less time to confirm the entry.

All measures remained in the same proportions to the total time in both interfaces. However these times were significantly reduced when 30% of the sample who gave up while trying to program the AKAI interface were excluded.

Attending to the user's needs is important in designing any interface, and must be modified for each application. By reducing the searching, learning times, and entry times, the mental load is also minimized. Some tradeoffs are necessary as a result of subjective and objective data. It is extremely difficult to design an interface for all levels of users. Thus, a menu system was used in an attempt to satisfy all users.

It must be noted that, in addition to reducing the programming time, the new interface reduced the number of incorrect recordings by 50%. The severity of the errors is unimportant here because one wrong entry will cause an irretrievable mistake and the user will not record the intended program. One study reported that faulty inputs, which lead to missing the program, can be reported by almost every present day owner of a VCR.[43]

This research has aided in discovering some important variables involved in the design of the interface of a VCR. The interface guidelines enumerated in Table 24 can be applied to a VCR or any other programmable device which utilizes a screen.

8.1 Recommendations for Improving the Prototype

The results of this experiment have provided the foundation for developing interface guidelines. Some refinement following the testing and formation of the guidelines could be applied to the new interface. Table 26 lists some areas of the new interface with which users had trouble programming, and Table 27 lists dislikes expressed regarding the interface.

Table 26 – Improvements For The New Interface

| Number of Subjects | Problem |
|---|---|
| 13 | subjects consulted the help utility a total of 19 times. One subject accessed this function 5 times. The help system was operative only 9 of the 19 times. During the other times, a screen appeared that read "Sorry no help system available at this time." |
| 5 | subjects thought they had to select the places where the numbers are displayed on the screen before entering the numbers on the keypad. |
| 5 | subjects did not set the TIMER. |
| 5 | subjects had trouble selecting AM or PM; each time they tried to continue without completing the time, they received an error message. |
| 5 | subjects tried to enter information on the HELP screen. |
| 4 | subjects initially put in the year as "90" not "1990." |
| 3 | subjects were confused by the CANCEL and CHANGE buttons on the confirmation screen and the dialogue boxes which appeared as a message, such as: "OK to Return to the Main Menu?" |
| 2 | subjects looked for a Main Menu when first starting |

| | |
|---|---|
| 1 | subjects chose "Main Menu" before selecting "OK" and thus lost the information currently on the screen. |
| 1 | subjects were initially confused as to how to set the time. |
| 1 | subject tried to continue before entering all of the required information. When this occurred, the user received an error message prompting him to enter the required information. |

Table 27 – Dislikes Regarding The New Interface

| Number of Subjects | Comments |
|---|---|
| 3 | Disliked using the mouse as a selection device |
| 2 | Wanted "OK" on all screens |
| 1 | Cited bad word choices |
| 1 | Wants to be able to go to the last screen |
| 1 | Wants to enter duration time |
| 1 | Wants a 24 hour clock |
| 1 | Would like it better with a touch screen |
| 1 | Wants to be able to change some information but not all on the confirmation screen. |

To remedy some of the problems found during the testing, the following suggestions are made:

1. To help non-mouse users, include on-screen instructions or a video cassette explaining its use.

2. To eliminate the forgotten step of setting the timer, have the VCR automatically set the timer as soon as the necessary information is entered and a tape is inserted. Once the program is set in memory, a message should appear if a tape is not inserted.

3. To eliminate trying to make selections on the help screens, the cursor should be locked to the choice which returns the user to where they left off and the Exit Help choice should be highlighted.

4 In places where it is applicable, show the user how many characters the interface is expecting, such as when entering the year.

8.2 Conclusion

The advancement of technology has made electronic devices accessible to a large portion of the population. However, it has also caused people to become intimidated by the developments which science has made possible. Research has and is being performed continually with the goal of reducing human task load and error. In the case of the Video Cassette Recorder, only new technology is being added. When analyzed, the tasks of setting the clock and time-shift programming are not complex. Manufacturers are adding new devices, such as the remote control, light pen, bar code scanner, and voice activation, rather than improving their interfaces.

This research has showed that there are problems with existing interfaces of VCRs. By studying human performance the interfaces can be improved to reflect the users' behavior. By incorporating the guidelines presented in Chapter 7, the programming time was reduced 54%. However, it is interesting to note that the same percentage of time was spent performing each critical step.

Devices must be designed with consideration for the user. The basic features must be improved before adding new ones. Additionally, if the product is not well designed, it will not be used to its full potential as proven by this case study. Video Cassette Recorders are a wonderful enhancement to society, but their interfaces must be improved in order to satisfy the needs of the user.

8.3 Recommendations for Future Research

There are several studies which could be performed to further improve the interface. First, it is recommended that a VCR be built containing a similar interface to the one used in this study. Tests must be run under real conditions in a field test environment rather than under laboratory test conditions.

In addition, not all features of the experimental interface were used, and some were used only infrequently. In view of this, it is recommended that more trials utilizing these shortcuts be conducted. Testing should also be performed on individual parts of the interface, such as to determine a better way for the user to change or cancel a program or part of a program, whether or not to include dialogue boxes, and which is the best input device to use. One possibility for input devices not investigated here is a force position controller or cursor keys. These are cheap alternatives, but user studies need to be investigated.

An attempt was made to minimize the keypresses. However, there are tradeoffs between features and functionality. The case used in this research is only one possible arrangement. A different approach might be to minimize keypresses regardless of features. However, the disadvantage of this is that the user will not have as many options and if, for example, he wants to record a program which airs Monday – Friday, he would have to set five separate programs. Another possible improvement might be made in word choices. Additional testing of wording would help to clarify some of the confusions regarding users' comments.

The interface presented in this research is one possible way to help simplify programming the VCR, but it must not be assumed that it is the best way. The guidelines proposed should help designers to devise more usable interfaces which require less time to program and reduce the users' frustration level.

ENDNOTES

1. Abedini, 1987
2. Jane Pauley Special, July 17, 1990
3. Rogus & Armstrong, 1977
4. Smith and Mosier, 1986
5. Kolson, 1989, p.B1
6. Ibid
7. Thomas & Schneider, 1984
8. Bulkeley, October 19, 1987
9. Ledgard, et al., 1981, p.1
10. Leon, 1987
11. Loyd, 1987
12. Leon, 1987, p.41
13. Jane Pauley Special, July 17, 1990
14. Swanson and Klopfenstein, 1977
15. Leon, 1987, p.42
16. Carroll, 1988
17. Wilke, 1982, p.1
18. Norman, 1988, p.54
19. Marketing & Media Decisions, 1985
20. Television Digest, March 20, 1989, p.10
21. Jane Pauley Special, July 17, 1990
22. Television Digest, June 23, 1988, p.15
23. Henke & Donohue, 1989, p.18
24. Abedini, 1987, p.376
25. Cobb, 1989, p.26
26. Webster's New Collegiate Dictionary, 1977, p.920
27. Cobb, 1990, p.26
28. Yoder, 1990
29. Thomas & Schneider, 1984
30. Lee & MacGregor, 1986
31. Abedini & Hadad, 1987
32. Abedini, 1987, p.379
33. Lee & MacGregor, 1986, Thomas & Schneider, 1984, & Carlson, 1982, p.3
34. Kreifeldt, 1982
35. Mead, 1988
36. Hutchins, Hollan, & Norman, 1986
37. Albert, 1982
38. Epps, 1986
39. Sperling & Tullis, 1987
40. Connally & Tullis, 1986
41. Card, 1979
42. Smith and Mosier, 1986, p.91
43. Platate, Oberjatzas, and Voessing, 1985, p.60

BIBLIOGRAPHY

"Bar Code Programs VCR", *Design News*, February 1, 1988, 26.

"The Highs and Lows of Nielsen Homevideo Index", *Marketing & Media Decisions*, November 1985, 84-86+.

"The Quest for 'User Friendly'", *U.S. News & World Report*, June 13, 1988, 54-56.

"VCR, Camcorder Trends", *Television Digest*, Vol. 29, March 20, 1989, 16.

Abedini, Kamran, "An Ergonomically-improved Remote Control Unit Design", *Interface '87 Proceedings*, 375-380.

Abedini, Kamran, and Hadad, George, "Guidelines For Designing Better VCRs", Report No. IME 462, February 4, 1987.

Bensch, U., "VPV – VIDEOTEXT PROGRAMS VIDEORECORDER", *IEEE Transactions on Consumer Electronics*, Vol. 34, No. 3, 788-792.

Berger, Ivan, "Secrets of the Universals", *Video*, February 1989, 45-47+.

Beringer, D.B., "A Comparative Evaluation of Calculator Watch Data Entry Technologies: Keyboards to Chalkboards", *Applied Ergonomics*, December 1985, 275-278.

Bishop, Edward W., and Guinness, G. Victor Jr., "Human Factors Interaction with Industrial Design", *Human Factors*, Vol. 8, No. 4, August 1966, 279-289.

Brown, Edward, "Human Factors Concepts For Management", *Proceedings of the Human Factors Society*, 1973, 372-375.

Bulkeley, Debra, "The 'Smartest House in America", *Design News*, October 19, 1987, 56-61.

Card, Stuart K., "A Method for Calculating Performance times for Users of Interactive Computing Systems", *IEEE*, 1979, 653-658.

Carlson, Mark A., "Design Goals for an Effective User Interface", *Electro/82 Proceedings*, 3/1/1-3/1/4.

Carlson, Mark A., "Design Goals for an Effective User Interface", *Human Interfacing with Instruments*, Session 3.

Carroll, Paul B., "High Tech Gear Draws Cries of "Uncle", *Wall Street Journal*, April 27, 1988, 29.

Cobb, Nathan, "I don't get it", *Boston Sunday Globe Magazine*, March 25, 1990, 23-29.

Davis, Fred, "The Great Look-and-Feel Debate", *A+*, Vol. 5, July 1987, 9-11.

Dehning, Waltraud, Essig Heidrun, and Maass, Susanne, *The Adaptation of Virtual Man-Computer Interfaces to User Requirements in Dialogs*, Germany: Springe-Verlag, 1981.

Ehrenreich, S.L., "Computer Abbreviations - Evidence and Synthesis", *Human Factors*, Vol. 27, No. 2, April 1985, 143-155.

Freiedman, M.B., "An Eye Gaze Controlled Keyboard", *Proceedings of the 2nd International Conference on Rehabilitation Engineering*, 1984, 446-447.

Gilfoil, D., and Mauro, C.L., "Integrating Human Factors and Design: Matching Human Factors Methods up to Product Development", C.L. Mauro Assoc., Inc., 1-7.

Gould, John D., Boies, Stephen J., Meluson, Antonia, Rasammy, Marwan, and Vosburgh, Ann Marie, "Entry and Selection Methods For Specifying Dates". *Human Factors*, Vol. 32, No. 2, April 1989, 199-214.

Green, Lee, "Thermo Tech: Here's a common sense guide to the new thinking thermostats", *Popular Mechanics*, October 1985, 155-159.

Grudin, Jonathan, "The Case Against User Interface Consistency", MCC Technical Report Number ACA-HI-002-89, January 1989.

Harvey, Michael G., and Rothe, James T., "VideoCassette Recorders: Their Impact on Viewers and Advertisers", *Journal of Advertising*, Vol. 25, December/January 1985, 19-29.

Hawkins, William J., "Super Remotes", *Popular Science*, February 1989, 76-77.

Henke, Lucy L., and Donohue, Thomas R., "Functional Displacement of Tradiditonal TV Viewing by VCR Owners", *Journal of Advertising Research*, V29, April-May 1989, 18-24.

Hoban, Phoebe, "Stacking the Decks", *New York*, February 16,1987, Vol. 20, 14.

"How to find the best value in VCRs", *Consumer Reports*, March 1988, 135-141.

Howard, Bill, "Point and Shoot Devices", *PC Magazine*, Vol 6, August 1987, 95-97.

*Jane Pauley Special*, NBC TV News Transcript, July 17, 1990, 10:00 PM.

Kolson, Ann, "Computer wimps drown in a raging sea of technology", *The Hartford Courant*, May 24, 1989, B1.

Kreifeldt, J.G., "A Methodology For Consumer Product Safety Analysis", *The 3rd National Symposium on Human Factors in Industrial Design in Consumer Products*, August 1982, 175-184.

Kreifeldt, John, "Human Factors Approach to Medical Instrument Design". *Electro/82 Proceedings*, 3/3/1-3/3/6.

Kuocheng, Andy Poing, and Ellingstad, Vernon S., "Touch Tablet and Touch Input", *Interface '87*, 327.

Ledgard, Henry, Singer, Andrew, and Whiteside, John, *Directions in Human Factors for Interactive Systems*, New York: Springer-Verlag, 1981.

Lee, Eric, and MacGregor, James, "Minimizing User Search Time Menu Retrieval Systems", *Human Factors*, Vol. 27, No. 2, April 1986, 157-162.

Leon, Carol Boyd, "Selling Through the VCR", *American Demographics*, December 1987, 40-43.

Long, John, "The Effect of Display Format on the Direct Entry of Numerical Information by Pointing", *Human Factors*, Vol. 26, No. 1, February 1984, 3-17.

"Low-Cost VCRs: More For Less", *Consumer Reports*, March 1990, 168-172.

Mantei, Marilyn M., and Teorey, Toby J., "Cost/Benefit Analysis for Incorporating Human Factors in the Software Lifecycle", *Association for Computing Machinery*, 1988.

Meads, Jon A., "Friendly or Frivolous", *Datamation*, April 1, 1988, 98-100.

Moore, T.G. and Dartnall, "Human Factors of a Microelectronic Product: The Central Heating Timer/Programmer", *Applied Ergonomics*, 1983, Vol. 13, No.1, 15-23.

"Nielsen Views VCRs", *Television Digest*, June 23, 1988, 15.

Norman, Donald A., "Infuriating By Design", *Psychology Today*, Vol. 22, No. 3, March 1988, 52-56.

Norman, Donald A., *The Psychology of Everyday Things*, New York: Basic Book, Inc. 1988.

Platate, Hans-Joachim, Oberjatzas, Gunter, and Voessing, Walter, "A New Intelligent Remote Control Unit for Consumer Electronic Device", *IEEE Transactions on Consumer Electronics*, Vol. CE-31, No. 1, February 1985, 59-68.

Rogus, John G. and Armstrong, Richard, "Use of Human Engineering Standards in Design", *Human Factors*, Vol. 19, No. 1, February 1977, 15-23.

Rosch, Winn L., "Voice Recognition: Understanding the Master's Voice", *PC Magazine*, October 27, 1987, 261-308.

Sarver, Carleton, "A Perfect Friendship", *High Fidelity*, Vol. 39, May 1989, 42-49.

Schmitt, Lee, "Let's Discuss Programmable Controllers", *Modern Machine Shop*, May 1987, 90-99.

Schniederman, Ben, *Designing the User Interface: Strategies for Effective Human-Computer Interaction*, Reading, MA: Addison-Wesley, 1987.

Smith, Sidney J., and Mosier, Jane N., *Guidelines for Designing User Interface Software*, Bedford, MA: MITRE, 1986.

Sperling, Barbra Bied, & Tullis Thomas S., "Are You a Better 'Mouser' or 'Trackballer'? A Comparison of Cursor - Positioning Performance", *An Interactive/Poster Session at the CHI+GI'87 Graphics Interface and Human Factors in Computing Systems Conference.*

Streeter, L.A., Ackroff, J.M., and Taylor, G.A. "On Abbreviating Command Names", *The Bell System Technical Journal*, Vol. 62, No. 6, July/August 1983, 1807-1826.

Swanson, David, and Klopfenstein, Bruce, "How to Forecast VCR Penetration", *American Demographic*, December 1987, 44-45.

Tello, Ernest R., "Between Man And Machine", *Byte*, September 1988, 288-293.

Thomas, John, C., and Schneider, Michael L., *Human Factors in Computer Systems*, New Jersey: Ablex Publ. Co., 1984.

Trachtenberg, Jeffrey A., "How do we confuse thee? Let us count the ways", *Forbes*, March 21, 1988, 159-160.

Tyldesley, D.A., "Employing Usability Engineering in the Development of Office Products", *The Computer Journal*, Vol. 31, No. 5, 1988, 431-436.

"VCR's: A Look At The Top Of The Line", *Consumer Reports*, March 1989, 167-170.

Verplank, William L., "Graphics in Human-Computer Communication: Principles of Graphical User-Interface Design", *Xerox Office Systems.*

"VHS Videocassette Recorders", *Consumer Guide*, 1990, 17–20.

Voyt, Carlton F., "PLC's Learn New Languages", *Design News*, January 2, 1989, 78.

Whitefield, A. "Human Factors Aspects of Pointing as an Input Technique in Interactive Computer Systems", *Applied Ergonomics*, June 1986, 97–104.

Wiedenbeck, Susan, Lambert, Robin, and Scholtz, Jean, "Using Protocol Analysis to Study the User Interface", *Bulletin of the American Society for Information Science*, June/July 1989, 25–26.

Wilke, William, "Easy Operation of Instruments by Both Man and Machine". *Electro/82 Proceedings*, 3/2/1–3/2/4.

Yoder, Stephen Kreider, "U.S. Inventors Thrive at Electronics Show", *The Wall Street Journal*, January 10, 1990, B1.

Zeisel, Gunter & Tomas, Philippe & Tomaszewski, Peter, "An Interactive Menu-Driven Remote Control Unit for TV-Receivers and VC-Recorders", *IEEE Transactions on Consumer Electronics*, Vol. 34, No. 3, 814–818.

APPENDIX A • STATISTICAL RESULTS

ANALYSIS OF VARIANCE BETWEEN THE FOUR VCRS USED IN TEST 1
($\alpha < 0.05$)

VCRs A&B

| Source of Variation | Degrees of Freedom | Sum of Squares | Mean Squares | F | F(crit) |
|---|---|---|---|---|---|
| Between Columns | 1 | 142.670 | 142.670 | 5.457 | 4.45 |
| Residual | 17 | 444.441 | 26.144 | | |

VCRs A&C

| Source of Variation | Degrees of Freedom | Sum of Squares | Mean Squares | F | F(crit) |
|---|---|---|---|---|---|
| Between Columns | 1 | 206.242 | 206.242 | 3.933 | 4.45 |
| Residual | 17 | 891.383 | 52.434 | | |

VCRs A&D

| Source of Variation | Degrees of Freedom | Sum of Squares | Mean Squares | F | F(crit) |
|---|---|---|---|---|---|
| Between Columns | 1 | 25.000 | 25.000 | 0.975 | 4.45 |
| Residual | 17 | 435.722 | 25.631 | | |

VCRs B&C

| Source of Variation | Degrees of Freedom | Sum of Squares | Mean Squares | F | F(crit) |
|---|---|---|---|---|---|
| Between Columns | 1 | 5.840 | 5.840 | 0.202 | 4.45 |
| Residual | 17 | 491.396 | 28.906 | | |

A-1

VCRs B&D

| Source of Variation | Degrees of Freedom | Sum of Squares | Mean Squares | F | F(crit) |
|---|---|---|---|---|---|
| Between Columns | 1 | 48.225 | 48.225 | 2.796 | 4.45 |
| Residual | 17 | 293.191 | 17.247 | | |

VCRs C&D

| Source of Variation | Degrees of Freedom | Sum of Squares | Mean Squares | F | F(crit) |
|---|---|---|---|---|---|
| Between Columns | 1 | 87.630 | 87.630 | 3.678 | 4.45 |
| Residual | 17 | 405.050 | 23.826 | | |

T-TEST FOR THE TOTAL TIME FOR EACH VCR IN TEST 1 ($\alpha < .05$)

VCRS A&B

| | |
|---|---|
| The sample mean is | 736.400 |

The estimated population standard deviation is    169.281
The t-statistic is    6.152

The number of degrees of freedom is    1

---

VCRS A&C

| | |
|---|---|
| The sample mean is | 712.500 |

The estimated population standard deviation is    203.081
The t-statistic is    4.962

The number of degrees of freedom is    1

---

VCRS A&D

| | |
|---|---|
| The sample mean is | 821.600 |

The estimated population standard deviation is    48.790
The t-statistic is    23.814

The number of degrees of freedom is    1

---

VCRS B&C

| | |
|---|---|
| The sample mean is | 592.800 |

The estimated population standard deviation is    33.800
The t-statistic is    24.803

The number of degrees of freedom is    1

---

VCRS B&D

| | |
|---|---|
| The sample mean is | 701.900 |

The estimated population standard deviation is    120.491
The t-statistic is    8.238

The number of degrees of freedom is    1

```
VCRS C&D
─────────────────────────────────────────────────────────────
The sample mean is           678.000

The estimated population standard deviation is    154.291
The t-statistic is           6.214

The number of degrees of freedom is    1
─────────────────────────────────────────────────────────────
```

MULTIPLE COMPARISON TEST USING THE SCHEFFE METHOD (α < .01)
(A "*" Denotes Significance between the pair of VCRs at α < .01.

|  |  |  |  | A | B | C |
|---|---|---|---|---|---|---|
| VCRS A&B | = | 16.371 |  |  |  |  |
| VCRS A&C | = | 11.799 |  |  |  |  |
| VCRS A&D | = | 2.925 | B | * |  |  |
| VCRS B&C | = | 0.606 |  |  |  |  |
| VCRS B&D | = | 8.388 | C | * |  | * |
| VCRS C&D | = | 11.034 |  |  |  |  |
|  |  |  | D |  | * |  |

ANALYSIS OF VARIANCE BETWEEN THE CRITICAL STEPS IN TEST 1 ($\alpha < 0.05$)

POWER ON

| Source of Variation | Degrees of Freedom | Sum of Squares | Mean Squares | F | F(crit) |
|---|---|---|---|---|---|
| Between Columns | 3 | 2.112 | 0.704 | 0.822 | 2.79 |
| Residual | 51 | 43.684 | 0.857 | | |

CLOCK SET

| Source of Variation | Degrees of Freedom | Sum of Squares | Mean Squares | F | F(crit) |
|---|---|---|---|---|---|
| Between Columns | 3 | 13.114 | 4.371 | 2.150 | 2.79 |
| Residual | 51 | 103.203 | 2.033 | | |

PROGRAM 1

| Source of Variation | Degrees of Freedom | Sum of Squares | Mean Squares | F | F(crit) |
|---|---|---|---|---|---|
| Between Columns | 3 | 40.091 | 13.364 | 3.803 | 2.79 |
| Residual | 51 | 179.203 | 3.514 | | |

PROGRAM 2

| Source of Variation | Degrees of Freedom | Sum of Squares | Mean Squares | F | F(crit) |
|---|---|---|---|---|---|
| Between Columns | 3 | 22.135 | 7.378 | 2.140 | 2.79 |
| Residual | 51 | 175.869 | 3.448 | | |

SEARCH TIME

| Source of Variation | Degrees of Freedom | Sum of Squares | Mean Squares | F | F(crit) |
|---|---|---|---|---|---|
| Between Columns | 3 | 138.419 | 46.140 | 1.977 | 2.79 |
| Residual | 51 | 1190.436 | 23.342 | | |

TOTAL TIME

| Source of Variation | Degrees of Freedom | Sum of Squares | Mean Squares | F | F(crit) |
|---|---|---|---|---|---|
| Between Columns | 3 | 257.804 | 85.935 | 2.960 | 2.79 |
| Residual | 51 | 1480.592 | 29.031 | | |

T-TEST FOR THE CRITICAL STEP OF SETTING PROGRAM 1 FOR TEST 1 ($\alpha < .05$)

VCRS A&B

| | |
|---|---|
| The sample mean is | 111.500 |
| The estimated population standard deviation is | 2.121 |
| The t-statistic is | 74.333 |
| The number of degrees of freedom is | 1 |

VCRS A&C

| | |
|---|---|
| The sample mean is | 115.550 |
| The estimated population standard deviation is | 3.606 |
| The t-statistic is | 45.314 |
| The number of degrees of freedom is | 1 |

VCRS A&D

| | |
|---|---|
| The sample mean is | 161.700 |
| The estimated population standard deviation is | 68.872 |
| The t-statistic is | 3.320 |
| The number of degrees of freedom is | 1 |

VCRS B&C

| | |
|---|---|
| The sample mean is | 114.050 |
| The estimated population standard deviation is | 5.728 |
| The t-statistic is | 28.160 |
| The number of degrees of freedom is | 1 |

VCRS B&D

| | |
|---|---|
| The sample mean is | 160.250 |
| The estimated population standard deviation is | 71.064 |
| The t-statistic is | 3.189 |
| The number of degrees of freedom is | 1 |

VCRS C&D

| | |
|---|---|
| The sample mean is | 164.300 |
| The estimated population standard deviation is | 65.337 |
| The t-statistic is | 3.556 |
| The number of degrees of freedom is | 1 |

ANALYSIS OF VARIANCE FOR TEST 2 ($\alpha < .05$)

CLOCK SET

| Source of Variation | Degrees of Freedom | Sum of Squares | Mean Squares | F | F(crit) |
|---|---|---|---|---|---|
| Between Columns | 1 | 408834.031 | 408834.031 | 12.657 | 4.54 |
| Residual | 15 | 484510.469 | 32300.698 | | |

PROGRAM 1

| Source of Variation | Degrees of Freedom | Sum of Squares | Mean Squares | F | F(crit) |
|---|---|---|---|---|---|
| Between Columns | 1 | 558096.125 | 558096.125 | 8.912 | 4.54 |
| Residual | 15 | 939314.875 | 62620.992 | | |

PROGRAM 2

| Source of Variation | Degrees of Freedom | Sum of Squares | Mean Squares | F | F(crit) |
|---|---|---|---|---|---|
| Between Columns | 1 | 319200.500 | 319200.500 | 29.599 | 4.54 |
| Residual | 15 | 161764.500 | 10784.300 | | |

PROGRAM 3

| Source of Variation | Degrees of Freedom | Sum of Squares | Mean Squares | F | F(crit) |
|---|---|---|---|---|---|
| Between Columns | 1 | 144587.531 | 144587.531 | 34.247 | 4.54 |
| Residual | 15 | 63328.969 | 4221.931 | | |

SEARCH TIME

| Source of Variation | Degrees of Freedom | Sum of Squares | Mean Squares | F | F(crit) |
|---|---|---|---|---|---|
| Between Columns | 1 | 131969.531 | 131969.531 | 5.463 | 4.54 |
| Residual | 15 | 362383.969 | 24158.931 | | |

TOTAL TIME

| Source of Variation | Degrees of Freedom | Sum of Squares | Mean Squares | F | F(crit) |
|---|---|---|---|---|---|
| Between Columns | 1 | 2498607.174 | 2498607.17 | 13.716 | 4.54 |
| Residual | 15 | 2732443.001 | 182162.867 | | |

T-TEST OF THE CRITICAL STEPS FOR TEST 2

CLOCK SET

The sample mean is     218.950

The estimated population standard deviation is     159.877
The t-statistic is     1.937

The number of degrees of freedom is     1

PROGRAM 1

The sample mean is     299.650

The estimated population standard deviation is     186.747
    The t-statistic is     2.269

The number of degrees of freedom is     1

PROGRAM 2

The sample mean is     184.450

The estimated population standard deviation is     139.795
The t-statistic is     1.866

The number of degrees of freedom is     1

PROGRAM 3

The sample mean is     122.500

The estimated population standard deviation is     95.035
The t-statistic is     1.823

The number of degrees of freedom is     1

TOTAL TIME

The sample mean is     746.000

The estimated population standard deviation is     395.131
The t-statistic is     2.670

The number of degrees of freedom is     1

A-12

SEARCH TIME

| | |
|---|---|
| The sample mean is | 176.050 |
| The estimated population standard deviation is | 90.863 |
| The t-statistic is | 2.740 |
| The number of degrees of freedom is | 1 |

PEARSON CORRELATION FOR THE NEW INTERFACE
The regression equation is
Y =   2.019 X +   82.918
The correlation is   0.993
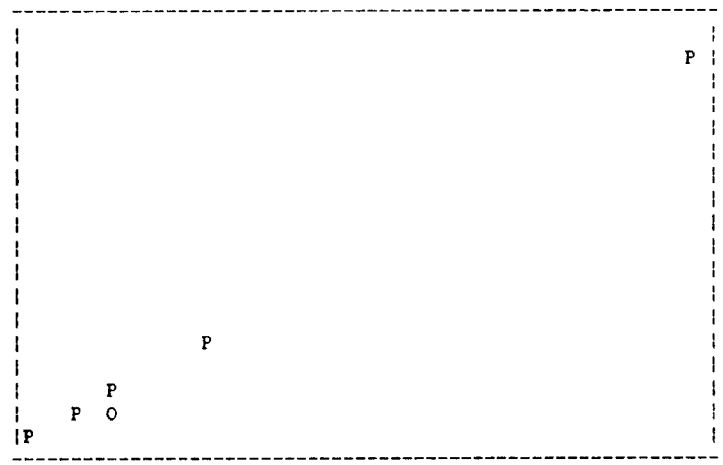
A-14

PEARSON CORRELATION FOR THE EXISTING INTERFACE
The regression equation is
Y =   0.488 X +   -38.122
The correlation is   0.993
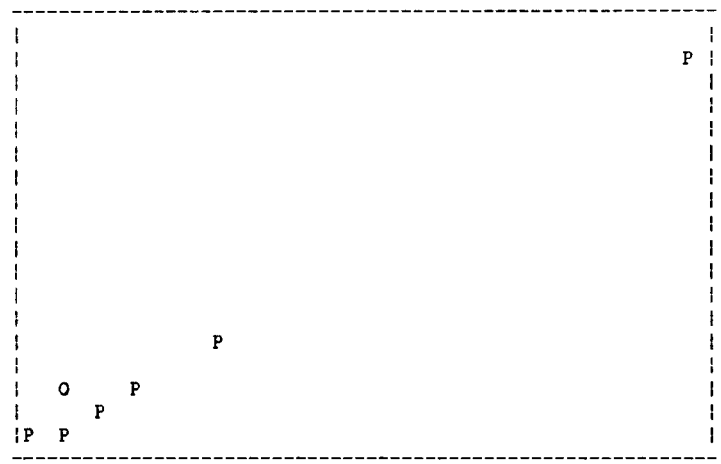
A-15

CHI SQUARE FOR THE CRITICAL STEPS OF TEST 2

CLOCK SET

| | |
|---|---|
| The value of Chi square is | 8.1559 |
| The value of Chi Square modified with the Yates correction factor is | 7.8196 |
| The value of the McNemar statistic is | 22.6862 |
| The value of the McNemar statistic with the Yates correction factor is | 22.3503 |
| The Coefficient of Contingency is | 0.0649 |

PROGRAM 1

| | |
|---|---|
| The value of Chi square is | 2.2137 |
| The value of Chi Square modified with the Yates correction factor is | 2.0599 |
| The value of the McNemar statistic is | 1.3559 |
| The value of the McNemar statistic with the Yates correction factor is | 1.2793 |
| The Coefficient of Contingency is | 0.0325 |

PROGRAM 2

| | |
|---|---|
| The value of Chi square is | 9.2287 |
| The value of Chi Square modified with the Yates correction factor is | 8.8461 |
| The value of the McNemar statistic is | 44.8045 |
| The value of the McNemar statistic with the Yates correction factor is | 44.3170 |
| The Coefficient of Contingency is | 0.0702 |

PROGRAM 3

| | |
|---|---|
| The value of Chi square is | 7.5819 |
| The value of Chi Square modified with the Yates correction factor is | 7.1735 |
| The value of the McNemar statistic is | 116.8271 |
| The value of the McNemar statistic with the Yates correction factor is | 115.9848 |
| The Coefficient of Contingency is | 0.0659 |

SEARCH TIME

| | |
|---|---|
| The value of Chi square is | 0.0303 |
| The value of Chi Square modified with the Yates correction factor is | 0.0122 |
| The value of the McNemar statistic is | 72.4455 |
| The value of the McNemar statistic with the Yates correction factor is | 71.8066 |
| The Coefficient of Contingency is | 0.0041 |

ACTUAL VS. THEORETICAL TIME FOR KEYPRESSES

| | |
|---|---|
| The value of Chi square is | 7.7752 |
| The value of Chi Square modified with the Yates correction factor is | 7.5310 |
| The value of the McNemar statistic is | 433.8469 |
| The value of the McNemar statistic with the Yates correction factor is | 432.6923 |
| The Coefficient of Contingency is | 0.0554 |

ACTUAL VS. THEORETICAL NUMBER OF KEYPRESSES

| | |
|---|---|
| The value of Chi square is | 9.7054 |
| The value of Chi Square modified with the Yates correction factor is | 9.1166 |
| The value of the McNemar statistic is | 179.6613 |
| The value of the McNemar statistic with the Yates correction factor is | 178.3431 |
| The Coefficient of Contingency is | 0.1217 |

CHI SQUARE TEST OF INDEPENDENCE FOR THE NUMBER OF SCREENS OPENED

| | |
|---|---|
| The value of Chi square is | 3.5820 |
| The value of Chi Square modified with the Yates correction factor is | 2.8977 |
| The value of the McNemar statistic is | 15.9930 |
| The value of the McNemar statistic with the Yates correction factor is | 14.9411 |

T-TEST OF P1 & P3 FOR THE EXISING INTERFACE

The sample mean is           310.700

The estimated population standard deviation is        171.120
The t-statistic is           2.568

The number of degrees of freedom is    1

T-TEST OF P1 & P3 FOR THE NEW INTEFACE

The sample mean is           111.450

The estimated population standard deviation is        79.408
The t-statistic is           1.985

The number of degrees of freedom is    1

T-TEST FOR THE NUMBER OF TIMES THE CONFIRMATION BUTTON WAS PRESSED

| | |
|---|---|
| The sample mean is | 1.570 |
| The estimated population standard deviation is | 0.354 |
| The t-statistic is | 6.280 |
| The number of degrees of freedom is | 1 |

T-TEST FOR THE TIME IT TOOK PER CONFIRMATION BUTTON

| | |
|---|---|
| The sample mean is | 4.182 |
| The estimated population standard deviation is | 2.234 |
| The t-statistic is | 2.647 |
| The number of degrees of freedom is | |

T-TEST OF SUBJECTIVE DATA FOR TEST 2

| | |
|---|---|
| The sample mean is | 3.915 |
| The estimated population standard deviation is | 2.722 |
| The t-statistic is | 2.034 |
| The number of degrees of freedom is | 1 |

APPENDIX B ● HYPERPAD SCRIPS

Script of Pad D:\HPAD\VCROLD.PAD

```
HANDLER OPENPAD;
  BEGIN;
    global CURRENTIME,TEST,POWER,DAYOFWEEK,
WEEKNSTORE,CURRENTPOSITION,VCRDELTA,CHANNEL,WEEKNUM,
STARTTIME, STOPTIME,START,STOP,TIMELOG,STARTSEC,NORUN;
    if norun then pass;
    hide the menu bar;
    set cursor to off;
    PUT "JANUARY 1, 1984 12:00 AM" INTO CURRENTIME;
    CONVERT CURRENTIME TO SECONDS;
    PUT CURRENTIME-SECONDS() INTO VCRDELTA;
    GO TO PG "CLOCK SET";
    PUT 1 INTO DAYOFWEEK;
    PUT 1 INTO CURRENTPOSITION;
    PUT 0 INTO POWER;
    put "0,0,0,0" into test;
    PUT "0,0,0,0" INTO WEEKNSTORE;
    SET THE VISIBLE OF PG BTN "TIMER" OF PG "ON/OFF" TO
FALSE;
    set the lockscreen to true;
    push this pg;
    for CURRENTPROGRAM = 1 to 4 do
      BEGIN
        go to pg ("program" & currentprogram);
        put "__" into pg fld "starthour";
        put "__" into pg fld "startminute";
        put "__" into pg fld "stophour";
        put "__" into pg fld "stopminute" ;
        put "__" into pg fld "date";
        put "__" into pg fld "PROG";
        put "CH__" into pg fld "channel"
      END;
    pop pg;
    set the lockscreen to true;
    PUT EMPTY INTO PG FLD "PROG1" OF PG "SELECT THE
PROGRAM";
    PUT EMPTY INTO PG FLD "PROG2" OF PG "SELECT THE
PROGRAM";
    PUT EMPTY INTO PG FLD "PROG3" OF PG "SELECT THE
PROGRAM";
    PUT EMPTY INTO PG FLD "PROG4" OF PG "SELECT THE
PROGRAM";
    add one to pg fld "subject info" of pg "status";
    put empty into timelog;
    put the seconds into startsec;
END;

HANDLER CLOSEPAD;
  BEGIN
    global norun;
    if norun then pass;
    SET THE LOCKSCREEN TO TRUE;
    GO TO PG "STATUS";
    GLOBAL TIMELOG;
    GET THE FIRST LINE OF PG FLD "FILENAME";
    PUT THE append OF IT INTO TEMP;
    get pg fld "subject info" of pg "status";
    Write "NS: Subject number " & it && the longdate && the
longtime & return to temp;
    WRITE TIMELOG TO TEMP;
    write return to temp;
    CLOSE TEMP;
  end;

handler mousedown;
  begin;
    global timelog, startsec;
    get the name of pg currentpage();
    put "MD: " & it && "(" & the name of the target & ")"
&& (seconds()-startsec) & return after timelog;
  end;

handler openpage;
  begin;
    global timelog, startsec;
    get the name of pg currentpage();
    put "OP: " & it && (seconds()-startsec) & return
after timelog;
  end;

handler closepage;
  begin;
    global timelog, startsec,norun;
    if norun then pass;
    put the name of pg currentpage() into temp;
    put "CP: " & temp && (seconds()-startsec) into temp;
    put temp & return after timelog;
  end;

handler logaction(x);
  begin;
    global timelog, startsec;
    put "LA: " & x && (seconds()-startsec) & return after
timelog;
  end;

HANDLER KEYPRESS(K);
  BEGIN
    CASE KEY(K) OF
      "6"     : GO TO PG "CLOCK ADJUST";
      "right" : GO TO PG "CLOCK ADJUST";
      "*"     : BEGIN
                GO TO PG "ON/OFF";
                SET THE VISIBLE OF PG BTN "TIMER" TO
TRUE;
                END;
      OTHERWISE : BEGIN
                  LOGACTION(KEY(K));
                  PASS;
                  END;
    END;
  END;

HANDLER LOGKEY(K);
  BEGIN
  GLOBAL TIMELOG,STARTSEC;
  CASE KEY(K) OF
    "6"     : put "LK: " & "(CLKADJ) " && (SECONDS()-
STARTSEC) & RETURN AFTER TIMELOG;
    "RIGHT" : put "LK: " & "(CLKADJ) " && (SECONDS()-
STARTSEC) & RETURN AFTER TIMELOG;
    "7"     : PUT "LK: " & "(A-) " && (SECONDS()-
STARTSEC) & RETURN AFTER TIMELOG;
    "HOME"  : PUT "LK: " & "(A-) " && (SECONDS()-
STARTSEC) & RETURN AFTER TIMELOG;
    "8"     : PUT "LK: " & "(A+) " && (SECONDS()-
STARTSEC) & RETURN AFTER TIMELOG;
    "UP"    : PUT "LK: " & "(A+) " && (SECONDS()-
STARTSEC) & RETURN AFTER TIMELOG;
    "4"     : PUT "LK: " & "(B-) " && (SECONDS()-
STARTSEC) & RETURN AFTER TIMELOG;
    "LEFT"  : PUT "LK: " & "(B-) " && (SECONDS()-
```

B-1

```
STARTSEC) & RETURN AFTER TIMELOG;
     "5"     : PUT "LK: " & "(B+) " && (SECONDS()-
STARTSEC) & RETURN AFTER TIMELOG;
     "CENTER" : PUT "LK: " & "(B+) " && (SECONDS()-
STARTSEC) & RETURN AFTER TIMELOG;
     "1"     : PUT "LK: " & "(C) " && (SECONDS()-
STARTSEC) & RETURN AFTER TIMELOG;
     "END"   : PUT "LK: " & "(C) " && (SECONDS()-
STARTSEC) & RETURN AFTER TIMELOG;
     "2"     : PUT "LK: " & "(D) " && (SECONDS()-
STARTSEC) & RETURN AFTER TIMELOG;
     "DOWN"  : PUT "LK: " & "(D) " && (SECONDS()-
STARTSEC) & RETURN AFTER TIMELOG;
     "/"     : PUT "LK: " & "(POWER) " && (SECONDS()-
STARTSEC) & RETURN AFTER TIMELOG;
     "SLASH" : PUT "LK: " & "(POWER) " && (SECONDS()-
STARTSEC) & RETURN AFTER TIMELOG;
     "*"     : PUT "LK: " & "(TIMER) " && (SECONDS()-
STARTSEC) & RETURN AFTER TIMELOG;
     "BIGMINUS" : PUT "LK: " & "(PRGM) " && (SECONDS()-
STARTSEC) & RETURN AFTER TIMELOG;
     OTHERWISE : PUT "LK: " && "(" & KEY(K) & ")" &&
(seconds()-startsec) & return after timelog;
     END;
END;

Script of bkgnd pg "CLOCK SET" of pad "D:\HPAD\VCROLD.PAD"

HANDLER UPDATETIME;
  BEGIN
  GLOBAL CURRENTIME,CURRENTPOSITION,DAYOFWEEK;
  PUT CURRENTIME INTO TEMP;
  CONVERT TEMP TO TIME;
  PUT THE LAST WORD OF TEMP & " " BEFORE TEMP;
  DELETE THE LAST WORD OF TEMP;
  PUT TEMP INTO BG FLD "CURRENT HOUR";
  put currentime into temp;
  convert temp to dateitems;
  put the third item of temp into bg fld "current date";
  get the first item of temp;
  put rightstring(it,2) into bg fld "current year";
  GET THE SECOND ITEM OF TEMP;
    CASE IT OF
      "1": PUT "JAN" INTO BG FLD "CURRENT MONTH";
      "2": PUT "FEB" INTO BG FLD "CURRENT MONTH";
      "3": PUT "MAR" INTO BG FLD "CURRENT MONTH";
      "4": PUT "APR" INTO BG FLD "CURRENT MONTH";
      "5": PUT "MAY" INTO BG FLD "CURRENT MONTH";
      "6": PUT "JUN" INTO BG FLD "CURRENT MONTH";
      "7": PUT "JUL" INTO BG FLD "CURRENT MONTH";
      "8": PUT "AUG" INTO BG FLD "CURRENT MONTH";
      "9": PUT "SEP" INTO BG FLD "CURRENT MONTH";
      "10": PUT "OCT" INTO BG FLD "CURRENT MONTH";
      "11": PUT "NOV" INTO BG FLD "CURRENT MONTH";
      "12": PUT "DEC" INTO BG FLD "CURRENT MONTH";
      OTHERWISE: PUT "LIN" INTO BG FLD "CURRENT MONTH";
    END;

CASE DAYOFWEEK OF
      "1": PUT "SUN" INTO BG FLD "CURRENT DAY";
      "2": PUT "MON" INTO BG FLD "CURRENT DAY";
      "3": PUT "TUE" INTO BG FLD "CURRENT DAY";
      "4": PUT "WED" INTO BG FLD "CURRENT DAY";
      "5": PUT "THU" INTO BG FLD "CURRENT DAY";
      "6": PUT "FRI" INTO BG FLD "CURRENT DAY";
      "7": PUT "SAT" INTO BG FLD "CURRENT DAY";
      OTHERWISE: PUT "LIN" INTO BG FLD "CURRENT DAY";
  END;

{ PUT "FLASH" & CURRENTPOSITION INTO TEMP;
  SET VISIBLE OF PG FLD TEMP TO true;
}
END;

Script of bkgnd pg "CLOCK SET" of pad "D:\HPAD\VCROLD.PAD"

HANDLER UPDATETIME;
  BEGIN
  GLOBAL CURRENTIME,CURRENTPOSITION,DAYOFWEEK;
  PUT CURRENTIME INTO TEMP;
  CONVERT TEMP TO TIME;
  PUT THE LAST WORD OF TEMP & " " BEFORE TEMP;
  DELETE THE LAST WORD OF TEMP;
  PUT TEMP INTO BG FLD "CURRENT HOUR";
  put currentime into temp;
  convert temp to dateitems;
  put the third item of temp into bg fld "current date";
  get the first item of temp;
  put rightstring(it,2) into bg fld "current year";
  GET THE SECOND ITEM OF TEMP;
    CASE IT OF
      "1": PUT "JAN" INTO BG FLD "CURRENT MONTH";
      "2": PUT "FEB" INTO BG FLD "CURRENT MONTH";
      "3": PUT "MAR" INTO BG FLD "CURRENT MONTH";
      "4": PUT "APR" INTO BG FLD "CURRENT MONTH";
      "5": PUT "MAY" INTO BG FLD "CURRENT MONTH";
      "6": PUT "JUN" INTO BG FLD "CURRENT MONTH";
      "7": PUT "JUL" INTO BG FLD "CURRENT MONTH";
      "8": PUT "AUG" INTO BG FLD "CURRENT MONTH";
      "9": PUT "SEP" INTO BG FLD "CURRENT MONTH";
      "10": PUT "OCT" INTO BG FLD "CURRENT MONTH";
      "11": PUT "NOV" INTO BG FLD "CURRENT MONTH";
      "12": PUT "DEC" INTO BG FLD "CURRENT MONTH";
      OTHERWISE: PUT "LIN" INTO BG FLD "CURRENT
MONTH";
    END;

CASE DAYOFWEEK OF
      "1": PUT "SUN" INTO BG FLD "CURRENT DAY";
      "2": PUT "MON" INTO BG FLD "CURRENT DAY";
      "3": PUT "TUE" INTO BG FLD "CURRENT DAY";
      "4": PUT "WED" INTO BG FLD "CURRENT DAY";
      "5": PUT "THU" INTO BG FLD "CURRENT DAY";
      "6": PUT "FRI" INTO BG FLD "CURRENT DAY";
      "7": PUT "SAT" INTO BG FLD "CURRENT DAY";

OTHERWISE: PUT "   " INTO BG FLD "CURRENT DAY";
  END;

END;

HANDLER KEYPRESS(K);
  BEGIN
    LOGKEY(K);
    CASE KEY(K) OF
      "7"      : SEND "SELECT" TO PG BTN ID 9;
      "HOME"   : SEND "SELECT" TO PG BTN ID 9;
      "8"      : SEND "SELECT" TO PG BTN ID 6;
      "UP"     : SEND "SELECT" TO PG BTN ID 6;
      "4"      : SEND "SELECT" TO PG BTN ID 10;
      "LEFT"   : SEND "SELECT" TO PG BTN ID 10;
      "5"      : SEND "SELECT" TO PG BTN ID 8;
      "CENTER" : SEND "SELECT" TO PG BTN ID 8;
```

```
    '1'       : SEND 'SELECT' TO PG BTN ID 11;
    'END'     : SEND 'SELECT' TO PG BTN ID 11;
    '/'       : GO TO PG 'ON/OFF';
    'SLASH'   : GO TO PG 'ON/OFF';
    '*'       : {THIS IS THE TIMER BTN}
    'BIGMINUS' : GO TO PG 'SELECT THE PROGRAM';
    OTHERWISE : BEGIN
        LOGACTION('WRONG KEY ' & KEY(K));
        PASS;
        END;
    END;
END;
```

Script of bkgnd btn "go to status" of bkgnd pg "CLOCK SET" of pad "D:\HPAD\VCROLD.PAD"

```
Handler Select;
Begin
  push this pg;
  go to pg 'status';
End;
```

Script of bkgnd pg "PROGRAM" of pad "D:\HPAD\VCROLD.PAD"

```
handler openpage;
  begin
    global
okdata,test,currentprogram,currentime,progtime,WEEKNUM,WEEKN
STORE,CURRENTPOSITION,START,STOP,CHANNEL;
    put 0 into currentposition;
    put currentprogram into BG fld 'program number';
    SEEALL;
  IF item currentprogram of test = 0 then
    begin
      put 0 into okdata;
      PUT '12:00 AM' INTO START;
      PUT '12:00 AM' INTO STOP;
      PUT 1 INTO CHANNEL;
      convert currentime to seconds;
      put currentime into progtime;
      PUT 2 INTO WEEKNUM;
      PUT EMPTY INTO BG FLD 'A';
    end else begin
      put 1 into okdata;
      PUT 'IF OK MEMORIZE       C' INTO BG FLD 'A';
      put item currentprogram of test into progtime;
      PUT RIGHTSTRING (PG FLD 'STARTHOUR',2) & ':' & PG FLD
'STARTMINUTE' & ' ' & LEFTSTRING (PG FLD 'STARTHOUR',2) INTO
START;
      PUT RIGHTSTRING (PG FLD 'STOPHOUR',2) & ':' & PG FLD
'STOPMINUTE' & ' ' & LEFTSTRING (PG FLD 'STOPHOUR',2) INTO
STOP;
      put PG fld 'channel' INTO CHANNEL;
      PUT ITEM CURRENTPROGRAM OF WEEKNSTORE INTO WEEKNUM;
      UGHH;
    end;
    put 'PROGRAM           B' INTO BG FLD 'D';
    PUT 'SELECT PROGRAM NO.  A' INTO BG FLD 'B';
    PASS;
end;

HANDLER UPDATETIME;
  BEGIN
    GLOBAL
CURRENTPOSITION,CURRENTIME,DAYOFWEEK,PROGTIME,START,START1,S
TART2,STOP,WEEKN,WEEKNUM,CHANNEL;
    case currentposition of
      1:begin
        IF THE LENGTH OF START ( 8 THEN PUT ' ' BEFORE START;
        PUT RIGHTSTRING(START,2) & LEFTSTRING(START,2) INTO
START1;
        PUT LEFTSTRING(START1,4) INTO PG FLD 'STARTHOUR';
        end;
      2:begin
        PUT THE RIGHTSTRING OF THE FIRST WORD OF START,2 INTO
START2;
        PUT START2 INTO PG FLD 'STARTMINUTE';
        end;
      3:begin
        IF THE LENGTH OF STOP ( 8 THEN PUT ' ' BEFORE STOP;
        PUT RIGHTSTRING(STOP,2) & LEFTSTRING(STOP,2) INTO PG
FLD 'STOPHOUR';
        end;
      4:begin
        PUT THE RIGHTSTRING OF THE FIRST WORD OF STOP,2 INTO
PG FLD 'STOPMINUTE';
        end;
      5:begin
        convert progtime to long date;
        put currentime into checkdate;
        convert checkdate to long date;
        CASE WEEKNUM OF
          1 : BEGIN
              PUT 'MON TO FRI.' INTO WEEKN;
              PUT ' ' INTO PG FLD 'PROG';
              END;
          2 : BEGIN
              PUT '1ST.' INTO WEEKN;
              END;
          3 : BEGIN
              PUT '2ND.' INTO WEEKN;
              END;
          4 : BEGIN
              PUT '3RD.' INTO WEEKN;
              END;
          5 : BEGIN
              PUT '4TH.' INTO WEEKN;
              END;
          OTHERWISE: PUT '1ST.' INTO WEEKN
        END;
        PUT WEEKN INTO PG FLD 'DATE';
        ughh;
        end;
      6: ughh;
      7: PUT CHANNEL INTO PG FLD 'CHANNEL';
      otherwise: begin end;
    end;

SEEALL;
END;

HANDLER UGHH;
  BEGIN
    GLOBAL PROGTIME,
PROGDISPLAY,WEEKNUM,CURRENTIME,STARTHOUR;
    IF PG FLD 'STARTHOUR' () '_' THEN
      BEGIN
      CONVERT PROGTIME TO LONG DATE;
      PUT PROGTIME INTO PROGDISPLAY;
      put LEFTstring(PROGDISPLAY,3) & '    ' INTO THE FIRST
WORD OF PROGDISPLAY;
      PUT '/'' & RIGHTSTRING (PROGDISPLAY,2) INTO THE LAST
WORD OF PROGDISPLAY;
      PUT LEFTSTRING (THE SECOND WORD OF PROGDISPLAY,3) INTO
```

B-3

```
            THE SECOND WORD OF PROGDISPLAY;
                 IF THE SECOND CHAR OF THE THIRD WORD OF PROGDISPLAY =
"," THEN
                     PUT LEFTSTRING (THE THIRD WORD OF PROGDISPLAY,1) &
"/" BEFORE THE SECOND WORD OF PROGDISPLAY
                 ELSE
                     PUT LEFTSTRING (THE THIRD WORD OF PROGDISPLAY,2) & "/"
BEFORE THE SECOND WORD OF PROGDISPLAY;
                 DELETE THE THIRD WORD OF PROGDISPLAY;
                 PUT THE THIRD WORD OF PROGDISPLAY INTO TEMP;
                 PUT THE SECOND WORD OF PROGDISPLAY BEFORE TEMP;
                 PUT TEMP INTO THE SECOND WORD OF PROGDISPLAY;
                 DELETE THE THIRD WORD OF PROGDISPLAY;
                 CASE WEEKNUM OF
                   1: begin
                      PUT " " INTO PG FLD "PROG";
                      END;
                   OTHERWISE:
                      PUT THE UPPER OF PROGDISPLAY INTO PG FLD "PROG";
             END;
           end;
          end;

HANDLER STOREINFO;
          {linda to make this routine work properly it must be based
          on progtime or
             the data in the fields on the pg}
                BEGIN
                GLOBAL
          CURRENTPROGRAM,test,progtime,WEEKNSTORE,WEEKNUM,timelog;
                   convert progtime to seconds;
                   put progtime into item currentprogram of test;
                   PUT WEEKNUM INTO ITEM CURRENTPROGRAM OF WEEKNSTORE;
                   IF PG fld "DATE" = "MON TO FRI." THEN
                     begin
                         PUT "M-F" & LEFTSTRING (PG fld "prog",3) && PG
          fld "STARTHOUR" & ":" & PG fld "STARTMINUTE" && PG fld
          "CHANNEL" INTO temp;
                         put temp into PG FLD ("PROG" & CURRENTPROGRAM) OF
          PG "SELECT THE PROGRAM";
                         put "CL: " & temp & return after timelog;
                     end
                     ELSE
                     begin
                         PUT LEFTSTRING (PG FLD "DATE",1) & "." &
          LEFTSTRING (PG FLD "PROG",3) && PG FLD "STARTHOUR" & ":" &
          PG FLD "STARTMINUTE" && PG FLD "CHANNEL" INTO temp;
                         put temp into PG FLD ("PROG" & CURRENTPROGRAM) OF
          PG "SELECT THE PROGRAM";
                         put "CL: " & temp & return after timelog;
                     END;
          end;
          HANDLER IDLE;
          BEGIN
          GLOBAL CURRENTPOSITION;
                 IF CURRENTPOSITION )=0 AND CURRENTPOSITION (8 THEN
                     SET VISIBLE OF PG FLD ("FLASH" & CURRENTPOSITION) TO
          (SECONDS() MOD 2 =1)
                     ELSE PUT CURRENTPOSITION & "IS INVALID" INTO MESSAGE
          BOX;
          END;

HANDLER SEEALL;
          BEGIN
               FOR X=0 TO 7 DO SET THE VISIBLE OF PG FLD ("FLASH" & X)
          TO FALSE;
          END;

HANDLER KEYPRESS(K);
             BEGIN
                logkey(k);
                CASE KEY(K) OF
                "7"       : SEND "SELECT" TO BTN ID 22;
                "HOME"    : SEND "SELECT" TO BTN ID 22;
                "8"       : SEND "SELECT" TO BTN ID 23;
                "UP"      : SEND "SELECT" TO BTN ID 23;
                "4"       : SEND "SELECT" TO BTN ID 25;
                "LEFT"    : SEND "SELECT" TO BTN ID 25;
                "5"       : SEND "SELECT" TO BTN ID 24;
                "CENTER"  : SEND "SELECT" TO BTN ID 24;
                "1"       : SEND "SELECT" TO BTN ID 26;
                "END"     : SEND "SELECT" TO BTN ID 26;
                "/"       : GO TO PG "ON/OFF";
                "SLASH"   : GO TO PG "ON/OFF";
          {     "*"       : {THIS IS THE TIMER BTN}
          }     "BIGMINUS" : GO TO PG "SELECT THE PROGRAM";
                OTHERWISE : pass;
             END;
          END;

Script of bkgnd btn "-" of bkgnd pg "PROGRAM" of pad
          "D:\HPND\WORLD.PND"

Handler Select;
             Begin
             GLOBAL
          CURRENTPOSITION,START,STOP,CURRENTIME,WEEKNUM,WEEKN,CHANNEL,
          PROGTIME,CURRENTPROGRAM;
             PUT "SHIFT          8" INTO BG FLD "D";

CASE CURRENTPOSITION OF
             0 : BEGIN
                    SUBTRACT 1 FROM currentprogram;
                    if currentprogram ( 1 then put 4 into currentprogram;
                    GO TO PG ("PROGRAM" & CURRENTPROGRAM);
                 END;

1 : BEGIN
                    CONVERT START TO DATEITEMS;
                    GET THE FOURTH ITEM OF START;
                    SUBTRACT 1 FROM IT;
                    IF IT = -1 THEN
                    PUT 23 INTO IT;
                    PUT IT INTO THE FOURTH ITEM OF START;
                    CONVERT START TO SHORT TIME;
                    IF THE LENGTH OF START ( 8 THEN PUT " " BEFORE START;
          {         PUT RIGHTSTRING(START,2) & LEFTSTRING(START,2) INTO
          PG FLD "STARTHOUR";
          }         END;
             2 : BEGIN
                    CONVERT START TO DATEITEMS;
                    GET THE FIFTH ITEM OF START;
                    SUBTRACT 1 FROM IT;
                    IF IT = -1 THEN
                    PUT 59 INTO IT;
                    PUT IT INTO THE FIFTH ITEM OF START;
                    CONVERT START TO SHORT TIME;
          {         PUT THE RIGHTSTRING OF THE FIRST WORD OF START,2
          INTO BG FLD "STARTMINUTE";
          }         END;
               3 : BEGIN
                    CONVERT STOP TO DATEITEMS;
                    GET THE FOURTH ITEM OF STOP;
                    SUBTRACT 1 FROM IT;
```

B-4

```
      IF IT = -1 THEN                                      CASE CURRENTPOSITION OF
        PUT 23 INTO IT;                                    0:  BEGIN
        PUT IT INTO THE FOURTH ITEM OF STOP;                       ADD 1 TO CURRENTPROGRAM;
        CONVERT STOP TO SHORT TIME;                                IF CURRENTPROGRAM > 4 THEN PUT 1 INTO
        IF THE LENGTH OF STOP < 8 THEN PUT " " BEFORE STOP;    CURRENTPROGRAM;
      END;                                                         GO TO PG ("PROGRAM" & CURRENTPROGRAM);
    4 : BEGIN                                                   END;
        CONVERT STOP TO DATEITEMS;                         1 : BEGIN
        GET THE FIFTH ITEM OF STOP;                                CONVERT START TO DATEITEMS;
        SUBTRACT 1 FROM IT;                                        GET THE FOURTH ITEM OF START;
        IF IT = -1 THEN                                            ADD 1 TO IT;
          PUT 59 INTO IT;                                          IF IT = 25 THEN
        PUT IT INTO THE FIFTH ITEM OF STOP;                        PUT 1 INTO IT;
        CONVERT STOP TO SHORT TIME;                                PUT IT INTO THE FOURTH ITEM OF START;
      END;                                                         CONVERT START TO SHORT TIME;
    5: BEGIN                                             {         PUT RIGHTSTRING(START,2) & LEFTSTRING(START,2) INTO
        GET THE FIRST ITEM OF WEEKNUM;                     BG FLD "STARTHOUR";
        SUBTRACT 1 FROM IT;                              }       END;
        CONVERT PROGTIME TO SECONDS;                       2 : BEGIN
          IF IT < 1 THEN BEGIN                                     CONVERT START TO DATEITEMS;
            PUT 5 INTO IT;                                         GET THE FIFTH ITEM OF START;
            ADD (3*24*3600*7) TO PROGTIME;                         ADD 1 TO IT;
          END ELSE IF IT >= 2 THEN                                 IF IT = 60 THEN
            SUBTRACT (24*3600*7) FROM PROGTIME;                      PUT 0 INTO IT;
          PUT IT INTO THE FIRST ITEM OF WEEKNUM;                   PUT IT INTO THE FIFTH ITEM OF START;
      END;                                                         CONVERT START TO SHORT TIME;
    6: BEGIN                                             {         PUT THE RIGHTSTRING OF THE FIRST WORD OF START,2
        global dayofweek;                                  INTO BG FLD "STARTMINUTE";
        SUBTRACT 1 FROM dayofweek;                       }       END;
        convert progtime to seconds;                       3 : BEGIN
        SUBTRACT (60*60*24) FROM PROGTIME;                         CONVERT STOP TO DATEITEMS;
        IF DAYOFWEEK <= 0 THEN                                     GET THE FOURTH ITEM OF STOP;
          BEGIN                                                    ADD 1 TO IT;
            ADD (60*60*24*7) TO PROGTIME;                          IF IT = 25 THEN
            PUT 7 INTO DAYOFWEEK;                                  PUT 1 INTO IT;
          end;                                                     PUT IT INTO THE FOURTH ITEM OF STOP;
      END;                                                         CONVERT STOP TO SHORT TIME;
    7 : BEGIN                                                      IF THE LENGTH OF STOP < 8 THEN PUT " " BEFORE STOP;
        GET THE FIRST ITEM OF CHANNEL;                           END;
        SUBTRACT 1 FROM IT;                                4 : BEGIN
        IF IT = 0 THEN                                             CONVERT STOP TO DATEITEMS;
          PUT 99 INTO IT;                                          GET THE FIFTH ITEM OF STOP;
          PUT IT INTO THE FIRST ITEM OF CHANNEL;                   ADD 1 TO IT;
      END;                                                         IF IT = 60 THEN
    otherwise:                                                       PUT 0 INTO IT;
        put 1 into currentposition;                                PUT IT INTO THE FIFTH ITEM OF STOP;
    END;                                                           CONVERT STOP TO SHORT TIME;
    UPDATETIME;                                                  END;
END;                                                       5: BEGIN
                                                                 GET THE FIRST ITEM OF WEEKNUM;
Script of bkgnd btn "A   +" of bkgnd pg "PROGRAM" of pad         ADD 1 TO IT;
"D:\VPAD\VCROLD.PAD"                                             CONVERT PROGTIME TO SECONDS;
                                                                 IF IT >= 6 THEN BEGIN
Handler Select;                                                    PUT 1 INTO IT;
  Begin                                                            SUBTRACT (3*24*3600*7) FROM PROGTIME;
    GLOBAL CURRENTPOSITION,                                      END ELSE IF IT > 1 THEN
  progtime,START,STOP,CURRENTIME,WEEKNUM,CHANNEL,CURRENTPROGRA     ADD (24*3600*7) TO PROGTIME;
  M;                                                             PUT IT INTO THE FIRST ITEM OF WEEKNUM;
    PUT "SHIFT        B" INTO BG FLD "D";
    IF PG FLD "STARTHOUR" = " _ " THEN                           END;
    BEGIN                                                    6 : BEGIN
      PUT "12:00 AM" INTO START;                                 GLOBAL DAYOFWEEK;
      PUT "12:00 AM" INTO STOP;                          {       put currentime into checkdate;
      PUT CURRENTIME INTO PROGTIME;                              convert checkdate to long date;
      PUT "1" INTO CHANNEL                               }       ADD 1 TO dayofweek;
    END;                                                         convert progtime to seconds;
                                                                 add (60*60*24) TO PROGTIME;
```

B-5

```
            IF DAYOFWEEK )= 8 THEN
                BEGIN
                    SUBTRACT (60*60*24*7) FROM PROGTIME;
                    PUT 1 INTO DAYOFWEEK;
                end;
            end;
        7 : BEGIN
            GET THE FIRST ITEM OF CHANNEL;
            ADD 1 TO IT;
            IF IT = 100 THEN
                PUT 1 INTO IT;
            PUT IT INTO THE FIRST ITEM OF CHANNEL;
            END;
        otherwise:
            put "linda" & currentposition into bg fld "D";
        END;
    UPDATETIME;
END;
```

Script of bkgnd btn "B    +" of bkgnd pg "PROGRAM" of pad
"D:\VPAD\VCRLD.PAD"

```
Handler Select;
Begin
    GLOBAL CURRENTPOSITION,weeknum,okdata;
    PUT          "SHIFT              B" INTO BG FLD "D";
{   PUT "FLASH" & CURRENTPOSITION INTO TEMP;
    SET VISIBLE OF PG FLD TEMP TO FALSE;}
    ADD 1 TO CURRENTPOSITION;
    if (weeknum = 1 and currentposition = 6) then
        put 7 into currentposition;
    IF CURRENTPOSITION = 8 THEN
        PUT 1 INTO CURRENTPOSITION;
--      PUT CURRENTPOSITION INTO pg fld "currentprogram";
    CASE CURRENTPOSITION OF
        "1": BEGIN
                PUT "SELECT START TIME    A" INTO BG FLD "B";
             END;
        "2": BEGIN
                PUT "SELECT START TIME    A" INTO BG FLD "B";
             END;
        "3": begin
                PUT "SELECT STOP TIME     A" INTO BG FLD "B";
             END;
        "4": BEGIN
                PUT "SELECT STOP TIME     A" INTO BG FLD "B";
             END;
        "5": BEGIN
                PUT "SELECT DAY           A" INTO BG FLD "B";
             END;
        "6": BEGIN
                PUT "SELECT DAY           A" INTO BG FLD "B";
             END;
        "7": BEGIN
                PUT "SELECT CHANNEL       A" INTO BG FLD "B";
                PUT "IF OK MEMORIZE       C" INTO BG FLD "A";
                put 1 into okdata;
             END;

OTHERWISE: PUT "LINDA" INTO BG FLD "A";
    END;
    updatetime;
END;
```

Script of bkgnd btn "-" of bkgnd pg "PROGRAM" of pad
"D:\VPAD\VCRLD.PAD"

```
Handler Select;
Begin
    GLOBAL CURRENTPOSITION,weeknum,okdata;
    PUT          "SHIFT              B" INTO BG FLD "D";
    SUBTRACT 1 FROM CURRENTPOSITION;
    if (weeknum = 1 and currentposition = 6) then
        put 5 into currentposition;
    IF CURRENTPOSITION <= 0 THEN
        if okdata = 0 then
            PUT 1 INTO CURRENTPOSITION
        else put 7 into currentposition;
--      PUT CURRENTPOSITION INTO pg fld "currentprogram";
    CASE CURRENTPOSITION OF
        0 : BEGIN
                PUT "SELECT PROGRAM NO.   A" INTO BG FLD "A";
                PUT "PROGRAM              B" INTO BG FLD "B";
             END;
        "1": BEGIN
                PUT "SELECT START TIME    A" INTO BG FLD "B";
             END;
        "2": BEGIN
                PUT "SELECT START TIME    A" INTO BG FLD "B";
             END;
        "3": begin
                PUT "SELECT STOP TIME     A" INTO BG FLD "B";
             END;
        "4": BEGIN
                PUT "SELECT STOP TIME     A" INTO BG FLD "B";
             END;
        "5": BEGIN
                PUT "SELECT DAY           A" INTO BG FLD "B";
             END;
        "6": BEGIN
                PUT "SELECT DAY           A" INTO BG FLD "B";
             END;
        "7": BEGIN
                PUT "SELECT CHANNEL       A" INTO BG FLD "B";
                PUT "IF OK MEMORIZE       C" INTO BG FLD "A";
                put 1 into okdata;
             END;

OTHERWISE: PUT "LINDA" INTO BG FLD "A";
    END;
    updatetime;
END;
```

Script of bkgnd btn "C" of bkgnd pg "PROGRAM" of pad
"D:\VPAD\VCRLD.PAD"

```
Handler Select;
Begin
    global okdata;
        IF okdata = 1 THEN
        BEGIN
            STOREINFO;
            GO TO PG "SELECT THE PROGRAM"
        END;
end;
```

Script of bkgnd btn "go to status" of bkgnd pg "PROGRAM" of
pad "D:\VPAD\VCRLD.PAD"

```
Handler Select;
Begin
    push this pg;
    go to pg "status";
End;
```

B-6

Script of bkgnd pg "on/off" of pad "D:\HPAD\VCROLD.PAD"

Script of bkgnd pg "CLOCK SET" of pad "D:\HPAD\VCROLD.PAD"

```
HANDLER UPDATETIME;
  BEGIN
  GLOBAL CURRENTIME,CURRENTPOSITION,DAYOFWEEK;
  PUT CURRENTIME INTO TEMP;
  CONVERT TEMP TO TIME;
  PUT THE LAST WORD OF TEMP & " " BEFORE TEMP;
  DELETE THE LAST WORD OF TEMP;
  PUT TEMP INTO BG FLD "CURRENT HOUR";
  put currentime into temp;
  convert temp to dateitems;
  put the third item of temp into bg fld "current date";
  get the first item of temp;
  put rightstring(it,2) into bg fld "current year";
  GET THE SECOND ITEM OF TEMP;
    CASE IT OF
      "1": PUT "JAN" INTO BG FLD "CURRENT MONTH";
      "2": PUT "FEB" INTO BG FLD "CURRENT MONTH";
      "3": PUT "MAR" INTO BG FLD "CURRENT MONTH";
      "4": PUT "APR" INTO BG FLD "CURRENT MONTH";
      "5": PUT "MAY" INTO BG FLD "CURRENT MONTH";
      "6": PUT "JUN" INTO BG FLD "CURRENT MONTH";
      "7": PUT "JUL" INTO BG FLD "CURRENT MONTH";
      "8": PUT "AUG" INTO BG FLD "CURRENT MONTH";
      "9": PUT "SEP" INTO BG FLD "CURRENT MONTH";
      "10": PUT "OCT" INTO BG FLD "CURRENT MONTH";
      "11": PUT "NOV" INTO BG FLD "CURRENT MONTH";
      "12": PUT "DEC" INTO BG FLD "CURRENT MONTH";
      OTHERWISE: PUT "LIN" INTO BG FLD "CURRENT
MONTH";}
    END;

CASE DAYOFWEEK OF
    "1": PUT "SUN" INTO BG FLD "CURRENT DAY";
    "2": PUT "MON" INTO BG FLD "CURRENT DAY";
    "3": PUT "TUE" INTO BG FLD "CURRENT DAY";
    "4": PUT "WED" INTO BG FLD "CURRENT DAY";
    "5": PUT "THU" INTO BG FLD "CURRENT DAY";
    "6": PUT "FRI" INTO BG FLD "CURRENT DAY";
    "7": PUT "SAT" INTO BG FLD "CURRENT DAY";

OTHERWISE: PUT " " INTO BG FLD "CURRENT DAY";
  END;

END;
```

Script of bkgnd btn "go to status" of bkgnd pg "CLOCK SET" of pad "D:\HPAD\VCROLD.PAD"

```
Handler Select;
Begin
  push this pg;
  go to pg "status";
End;
```

Script of pg "CLOCK SET" of pad "D:\HPAD\VCROLD.PAD"

```
HANDLER openPage;
  BEGIN;
  global CURRENTPOSITION,DAYOFWEEK,CURRENTIME,dayofmonth;
  PUT 1 INTO CURRENTPOSITION;
  PUT CURRENTIME INTO TEMP;
  CONVERT TEMP TO DATEITEMS;
  put the third item of temp into dayofmonth;
  PUT (THE LAST ITEM OF TEMP) INTO DAYOFWEEK;
  UPDATETIME;
  PUT "SELECT TIME" INTO PG FLD "SELECT";
  SET VISIBLE OF PG FLD "FLASH2" TO FALSE;
  SET VISIBLE OF PG FLD "FLASH3" TO FALSE;
  SET VISIBLE OF PG FLD "FLASH4" TO FALSE;
  SET VISIBLE OF PG FLD "FLASH5" TO FALSE;
  SET VISIBLE OF PG FLD "FLASH6" TO FALSE;
  PASS;
END;

HANDLER IDLE;
  BEGIN;
  GLOBAL CURRENTIME,CURRENTPOSITION;
  PUT SECONDS() mod 60 INTO TEMP;
  IF TEMP <10 THEN
    PUT "0" BEFORE TEMP;
  PUT TEMP INTO bg FLD "CURRENTSECONDS" ;
  PUT "FLASH" & CURRENTPOSITION INTO TEMP;
  SET VISIBLE OF PG FLD TEMP TO (SECONDS() MOD 2 =1) ;
END;

HANDLER CLOSEPAGE;
BEGIN
  GLOBAL VCRDELTA,CURRENTIME,TEST,WEEKNSTORE;
  PUT CURRENTIME-SECONDS() INTO VCRDELTA;
  FOR TEMP=1 TO 4 DO
    IF ITEM TEMP OF TEST()0 THEN
    BEGIN
    PUT CURRENTIME INTO ITEM TEMP OF TEST;
    PUT 2 INTO ITEM TEMP OF WEEKNSTORE;
    END;
  pass;
END;
```

Script of btn "A +" of pg "CLOCK SET" of pad "D:\HPAD\VCROLD.PAD"

```
Handler Select;
Begin
GLOBAL CURRENTIME,CURRENTPOSITION,DAYOFMONTH;
  CONVERT CURRENTIME TO DATEITEMS;
  CASE CURRENTPOSITION OF
  1 : BEGIN;
    GET THE FOURTH ITEM OF CURRENTIME;
    ADD 1 TO IT;
    IF IT = 25 THEN
      PUT 1 INTO IT;
    PUT IT INTO THE FOURTH ITEM OF CURRENTIME;
    END;
  2 : BEGIN;
    GET THE FIFTH ITEM OF CURRENTIME;
    ADD 1 TO IT;
    IF IT = 60 THEN
      PUT 0 INTO IT;
    PUT IT INTO THE FIFTH ITEM OF CURRENTIME;
    END;
  3 : BEGIN
    GLOBAL DAYOFWEEK;
    ADD 1 TO DAYOFWEEK;
    IF DAYOFWEEK = 8 THEN
      PUT 1 INTO DAYOFWEEK;
    end;
  4 : BEGIN
    GET THE THIRD ITEM OF CURRENTIME;
    ADD 1 TO IT;
```

```
            PUT CURRENTIME INTO TEMP;
            PUT IT INTO THE THIRD ITEM OF TEMP;
            CONVERT TEMP TO SECONDS;
            CONVERT TEMP TO DATEITEMS;
            IF THE THIRD ITEM OF TEMP () IT THEN
                PUT 1 INTO IT;
            PUT IT INTO THE THIRD ITEM OF CURRENTIME;
            PUT IT INTO DAYOFMONTH;
          END;
    5 : BEGIN
          GET THE SECOND ITEM OF CURRENTIME;
          add 1 to IT;
          PUT DAYOFMONTH INTO THE THIRD ITEM OF CURRENTIME;
          IF IT = 13 THEN
              PUT 1 INTO IT;
          PUT IT INTO THE SECOND ITEM OF currentime;
          REPEAT
            PUT CURRENTIME INTO TEMP;
            CONVERT TEMP TO SECONDS;
            CONVERT TEMP TO DATEITEMS;
            IF THE SECOND ITEM OF TEMP () IT THEN
                subtract 1 from THE THIRD ITEM OF currentime;
                put currentime into pg fld "currentime";
            UNTIL IT = THE SECOND ITEM OF TEMP;
          END;
    6 : BEGIN
          GET THE FIRST ITEM OF CURRENTIME;
          ADD 1 TO IT;
          IF IT = 2000 THEN
              PUT 1984 INTO IT;
          PUT IT INTO THE FIRST ITEM OF CURRENTIME;
          END;
  END;
  PUT CURRENTIME INTO PG FLD "CURRENTIME";
    CONVERT CURRENTIME TO SECONDS;
    UPDATETIME;

END;

Script of btn "A +" of pg "CLOCK SET" of pad
"D:\VPAD\VCWRLD.PAD"

Handler Select;
Begin
   GLOBAL CURRENTPOSITION;
   PUT "FLASH" & CURRENTPOSITION INTO TEMP;
   SET VISIBLE OF PG FLD TEMP TO FALSE;
   ADD 1 TO CURRENTPOSITION;
   IF CURRENTPOSITION = 7 THEN
   PUT 1 INTO CURRENTPOSITION;
   PUT CURRENTPOSITION INTO MESSAGE BOX;
   CASE CURRENTPOSITION OF
        "1": PUT "SELECT TIME" INTO PG FLD "SELECT";
        "2": PUT "SELECT TIME" INTO PG FLD "SELECT";
        "3": PUT "SELECT DAY" INTO PG FLD "SELECT";
        "4": PUT "SELECT DATE" INTO PG FLD "SELECT";
        "5": PUT "SELECT MONTH" INTO PG FLD "SELECT";
        "6": PUT "SELECT YEAR" INTO PG FLD "SELECT";
        OTHERWISE: PUT "SELECT TIME" INTO PG FLD "SELECT";
   END;

End;

Script of btn "-" of pg "CLOCK SET" of pad
"D:\VPAD\VCWRLD.PAD"

Handler Select;
Begin

GLOBAL CURRENTIME,CURRENTPOSITION,DAYOFMONTH;
    CONVERT CURRENTIME TO DATEITEMS;

CASE CURRENTPOSITION OF
    1 : BEGIN
          GET THE FOURTH ITEM OF CURRENTIME;
          SUBTRACT 1 FROM IT;
          IF IT = -1 THEN
              PUT 23 INTO IT;
          PUT IT INTO THE FOURTH ITEM OF CURRENTIME;
          END;
    2 : BEGIN
          GET THE FIFTH ITEM OF CURRENTIME;
          SUBTRACT 1 FROM IT;
          IF IT = -1 THEN
              PUT 59 INTO IT;
          PUT IT INTO THE FIFTH ITEM OF CURRENTIME;
          END;
    3 : BEGIN
          global dayofweek;
          SUBTRACT 1 FROM dayofweek;
          IF DAYOFWEEK = 0 THEN PUT 7 INTO DAYOFWEEK;
          END;
    4 : BEGIN
          REPEAT
          GET THE THIRD ITEM OF CURRENTIME;
          SUBTRACT 1 FROM IT;
          IF IT = 0 THEN
              PUT 31 INTO IT;
          PUT IT INTO THE THIRD ITEM OF CURRENTIME;
          PUT CURRENTIME INTO TEMP;
          CONVERT TEMP TO SECONDS;
          CONVERT TEMP TO DATEITEMS;
          UNTIL IT = THE THIRD ITEM OF TEMP;
          PUT IT INTO DAYOFMONTH;
          END;
    5 : BEGIN
          GET THE SECOND ITEM OF CURRENTIME;
          SUBTRACT 1 FROM IT;
          PUT DAYOFMONTH INTO THE THIRD ITEM OF CURRENTIME;
          IF IT = 0 THEN
              PUT 12 INTO IT;
          PUT IT INTO THE SECOND ITEM OF CURRENTIME;
          REPEAT
          PUT CURRENTIME INTO TEMP;
          CONVERT TEMP TO SECONDS;
          CONVERT TEMP TO DATEITEMS;
          IF THE SECOND ITEM OF TEMP () IT THEN
              SUBTRACT 1 FROM THE THIRD ITEM OF CURRENTIME;
          UNTIL IT = THE SECOND ITEM OF TEMP;
          END;
    6 : BEGIN
          GET THE FIRST ITEM OF CURRENTIME;
          SUBTRACT 1 FROM IT;
          IF IT = 1983 THEN
              PUT 1999 INTO IT;
          PUT IT INTO THE FIRST ITEM OF CURRENTIME;
          END;
    END;
    PUT CURRENTIME INTO PG FLD "CURRENTIME";
      CONVERT CURRENTIME TO SECONDS;
      UPDATETIME;

END;
```

```
Script of btn "C" of pg "CLOCK SET" of pad
"D:\VPAD\VCROLD.PAD"

Handler Select;
Begin
    go to pg "clock";
End;

Script of btn "-" of pg "CLOCK SET" of pad
"D:\VPAD\VCROLD.PAD"

Handler Select;
Begin
    GLOBAL CURRENTPOSITION;
    PUT "FLASH" & CURRENTPOSITION INTO TEMP;
    SET VISIBLE OF PG FLD TEMP TO FALSE;
    SUBTRACT 1 FROM CURRENTPOSITION;
    IF CURRENTPOSITION = 0 THEN
    PUT 6 INTO CURRENTPOSITION;
    PUT CURRENTPOSITION INTO MESSAGE BOX;
    CASE CURRENTPOSITION OF
        "1": PUT "SELECT TIME" INTO PG FLD "SELECT";
        "2": PUT "SELECT TIME" INTO PG FLD "SELECT";
        "3": PUT "SELECT DAY" INTO PG FLD "SELECT";
        "4": PUT "SELECT DATE" INTO PG FLD "SELECT";
        "5": PUT "SELECT MONTH" INTO PG FLD "SELECT";
        "6": PUT "SELECT YEAR" INTO PG FLD "SELECT";
        OTHERWISE: PUT "SELECT TIME" INTO PG FLD "SELECT";
        END;
END;

Script of pg "CLOCK ADJUST" of pad "D:\VPAD\VCROLD.PAD"

HANDLER openPage;
    BEGIN;
    global CURRENTPOSITION,DAYOFWEEK,CURRENTIME;
        PUT 1 INTO CURRENTPOSITION;
        PUT CURRENTIME INTO TEMP;
        CONVERT TEMP TO DATEITEMS;
        PUT (THE LAST ITEM OF TEMP) INTO DAYOFWEEK;
        SET VISIBLE OF PG FLD "FLASH2" TO FALSE;
        SET VISIBLE OF PG FLD "FLASH3" TO FALSE;
        SET VISIBLE OF PG FLD "FLASH4" TO FALSE;
        SET VISIBLE OF PG FLD "FLASH5" TO FALSE;
        SET VISIBLE OF PG FLD "FLASH6" TO FALSE;
        UPDATETIME;
        PASS;
    END;

HANDLER KEYPRESS(K);
    BEGIN
        LOGKEY(K);
        CASE KEY(K) OF
        "4"      : GO TO PG "CLOCK SET";
        "LEFT"   : GO TO PG "CLOCK SET";
        "5"      : GO TO PG "CLOCK SET";
        "CENTER" : GO TO PG "CLOCK SET";
        "/"      : GO TO PG "ON/OFF";
        "SLASH"  : GO TO PG "ON/OFF";
        "*"      : BEGIN
                    GO TO PG "ON/OFF";
                    SET THE VISIBLE OF PG BTN "TIMER" TO TRUE;
                   END;
        "BIGMINUS" : GO TO PG "SELECT THE PROGRAM";
        OTHERWISE : BEGIN
            LOGACTION("WRONG KEY " & KEY(K));
            PASS;
        END;
    END;
END;

Script of btn "B" of pg "CLOCK ADJUST" of pad
"D:\VPAD\VCROLD.PAD"

Handler Select;
Begin
    GO TO PG "CLOCK SET";
End;

Script of pg "CLOCK" of pad "D:\VPAD\VCROLD.PAD"

HANDLER openPage;
    BEGIN;
    global CURRENTPOSITION,CURRENTIME,DAYOFWEEK;
    PUT CURRENTIME INTO TEMP;
    CONVERT TEMP TO DATEITEMS;
    PUT THE LAST ITEM OF TEMP INTO DAYOFWEEK;
        PUT 1 INTO CURRENTPOSITION;
    SET VISIBLE OF PG FLD "BLANK" TO FALSE;
{   WAIT 3000;
    SET VISIBLE OF PG FLD "BLANK" TO TRUE;}
    PASS;

END;

HANDLER IDLE;
    BEGIN;
    GLOBAL CURRENTIME, VCRDELTA;
        PUT (SECONDS()+VCRDELTA) mod 60 INTO TEMP;
        IF TEMP <10 THEN
        PUT "0" BEFORE TEMP;
        PUT TEMP INTO bg FLD "CURRENTSECONDS" ;

put seconds()+vcrdelta into CURRENTIME;
        UPDATETIME;
    END;

HANDLER KEYPRESS(K);
    BEGIN
        CASE KEY(K) OF
        "/"      : GO TO PG "ON/OFF";
        "SLASH"  : GO TO PG "ON/OFF";
{       "*"      : (THIS IS THE TIMER BTN)
}       "BIGMINUS"  : GO TO PG "SELECT THE PROGRAM";
        OTHERWISE : Pass;
    END;
END;

Script of btn "+" of pg "CLOCK" of pad "D:\VPAD\VCROLD.PAD"

Handler Select;
Begin
GLOBAL CURRENTIME,CURRENTPOSITION;
    CONVERT CURRENTIME TO DATEITEMS;
    CASE CURRENTPOSITION OF
    1 : BEGIN;
        GET THE FOURTH ITEM OF CURRENTIME;
        ADD 1 TO IT;
        IF IT = 25 THEN
            PUT 1 INTO IT;
        PUT IT INTO THE FOURTH ITEM OF CURRENTIME;
        END;
    2 : BEGIN;
        GET THE FIFTH ITEM OF CURRENTIME;
```

```
    ADD 1 TO IT;
    IF IT = 60 THEN
      PUT 0 INTO IT;
    PUT IT INTO THE FIFTH ITEM OF CURRENTIME;
    END;
  3 : BEGIN
    GLOBAL DAYOFWEEK;
    ADD 1 TO DAYOFWEEK;
    IF DAYOFWEEK = 8 THEN
      PUT 1 INTO DAYOFWEEK;
    end;
  4 : BEGIN
    GET THE THIRD ITEM OF CURRENTIME;
    ADD 1 TO IT;
    IF IT = 32 THEN
      PUT 1 INTO IT;
    PUT IT INTO THE THIRD ITEM OF CURRENTIME;
    END;
  5 : BEGIN
    GET THE SECOND ITEM OF CURRENTIME;
    ADD 1 TO IT;
    IF IT = 13 THEN
      PUT 1 INTO IT;
    PUT IT INTO THE SECOND ITEM OF CURRENTIME;
    END;
  6 : BEGIN
    GET THE FIRST ITEM OF CURRENTIME;
    ADD 1 TO IT;
    IF IT = 2000 THEN
      PUT 1984 INTO IT;
    PUT IT INTO THE FIRST ITEM OF CURRENTIME;
    END;
  END;
  PUT CURRENTIME INTO PG FLD 'CURRENTIME';
    CONVERT CURRENTIME TO SECONDS;
    UPDATETIME;

END;

Script of btn "+" of pg "CLOCK" of pad "D:\WPAD\VCROLD.PAD"

Handler Select;
Begin
  GLOBAL CURRENTPOSITION;
  PUT "FLASH" & CURRENTPOSITION INTO TEMP;
  SET VISIBLE OF PG FLD TEMP TO FALSE;
  ADD 1 TO CURRENTPOSITION;
  IF CURRENTPOSITION = 7 THEN
  PUT 1 INTO CURRENTPOSITION;
  PUT CURRENTPOSITION INTO MESSAGE BOX;
  CASE CURRENTPOSITION OF
      '1': PUT "SELECT TIME" INTO PG FLD "SELECT";
      '2': PUT "SELECT TIME" INTO PG FLD "SELECT";
      '3': PUT "SELECT DAY" INTO PG FLD "SELECT";
      '4': PUT "SELECT DATE" INTO PG FLD "SELECT";
      '5': PUT "SELECT MONTH" INTO PG FLD "SELECT";
      '6': PUT "SELECT YEAR" INTO PG FLD "SELECT";
      OTHERWISE: PUT "SELECT TIME" INTO PG FLD "SELECT";
  END;

End;

Script of btn "-" of pg "CLOCK" of pad "D:\WPAD\VCROLD.PAD"

Handler Select;
Begin
  GLOBAL CURRENTIME,CURRENTPOSITION;
    CONVERT CURRENTIME TO DATEITEMS;

CASE CURRENTPOSITION OF
  1 : BEGIN
    GET THE FOURTH ITEM OF CURRENTIME;
    SUBTRACT 1 FROM IT;
    IF IT = -1 THEN
      PUT 23 INTO IT;
    PUT IT INTO THE FOURTH ITEM OF CURRENTIME;
    END;
  2 : BEGIN
    GET THE FIFTH ITEM OF CURRENTIME;
    SUBTRACT 1 FROM IT;
    IF IT = -1 THEN
      PUT 59 INTO IT;
    PUT IT INTO THE FIFTH ITEM OF CURRENTIME;
    END;
  3 : BEGIN
      global dayofweek;
      SUBTRACT 1 FROM dayofweek;
      IF DAYOFWEEK = 0 THEN PUT 7 INTO DAYOFWEEK;
    END;
  4 : BEGIN
    GET THE THIRD ITEM OF CURRENTIME;
    SUBTRACT 1 FROM IT;
    IF IT = 0 THEN
      PUT 31 INTO IT;
    PUT IT INTO THE THIRD ITEM OF CURRENTIME;
    END;
  5 : BEGIN
    GET THE SECOND ITEM OF CURRENTIME;
    SUBTRACT 1 FROM IT;
    IF IT = 0 THEN
      PUT 12 INTO IT;

PUT IT INTO THE SECOND ITEM OF CURRENTIME;
    END;
  6 : BEGIN
    GET THE FIRST ITEM OF CURRENTIME;
    SUBTRACT 1 FROM IT;
    IF IT = 1983 THEN
      PUT 1999 INTO IT;
    PUT IT INTO THE FIRST ITEM OF CURRENTIME;
    END;
  END;
  PUT CURRENTIME INTO PG FLD 'CURRENTIME';
    CONVERT CURRENTIME TO SECONDS;
    UPDATETIME;

END;

Script of btn "-" of pg "CLOCK" of pad "D:\WPAD\VCROLD.PAD"

Handler Select;
Begin
  GLOBAL CURRENTPOSITION;
  PUT "FLASH" & CURRENTPOSITION INTO TEMP;
  SET VISIBLE OF PG FLD TEMP TO FALSE;
  SUBTRACT 1 FROM CURRENTPOSITION;
  IF CURRENTPOSITION = 0 THEN
  PUT 6 INTO CURRENTPOSITION;
  PUT CURRENTPOSITION INTO MESSAGE BOX;
  CASE CURRENTPOSITION OF
      '1': PUT "SELECT TIME" INTO PG FLD "SELECT";
      '2': PUT "SELECT TIME" INTO PG FLD "SELECT";
      '3': PUT "SELECT DAY" INTO PG FLD "SELECT";
```

```
        "4": PUT "SELECT DATE" INTO PG FLD "SELECT";
        "5": PUT "SELECT MONTH" INTO PG FLD "SELECT";
        "6": PUT "SELECT YEAR" INTO PG FLD "SELECT";
        OTHERWISE: PUT "SELECT TIME" INTO PG FLD "SELECT";
        END;
    END;
```

Script of btn "PRGM" of pg "CLOCK" of pad
"D:\WPAD\VCWRLD.PAD"

```
Handler Select;
Begin
  go to pg "select the program";
End;
```

Script of pg "SELECT THE PROGRAM" of pad
"D:\WPAD\VCWRLD.PAD"

```
HANDLER OPENPAGE;
  BEGIN
    GLOBAL CURRENTPROGRAM;
    PUT 1 INTO CURRENTPROGRAM;
    SET FOCUS TO PG BTN "1        ";
    SET VISIBLE OF PG FLD "flashi" TO (SECONDS() MOD 2
=1) ;
    PASS;
  END;

HANDLER KEYPRESS(K);
  BEGIN
    CASE KEY(K) OF
      "7"      : SEND "SELECT" TO PG BTN ID 14;
      "HOME"   : SEND "SELECT" TO PG BTN ID 14;
      "8"      : SEND "SELECT" TO PG BTN ID 14;
      "UP"     : SEND "SELECT" TO PG BTN ID 14;
      "/"      : GO TO PG "ON/OFF";
      "SLASH"  : GO TO PG "ON/OFF";
      "*"      : {THIS IS THE TIMER BTN}
      "BIGMINUS" : GO TO PG "SELECT THE PROGRAM";
      OTHERWISE : PASS;
    END;
END;
```

Script of btn "- A +" of pg "SELECT THE PROGRAM" of pad
"D:\WPAD\VCWRLD.PAD"

```
Handler Select;
Begin
  GLOBAL CURRENTPROGRAM;
    PUT 1 INTO CURRENTPROGRAM;
    GO TO PG "PROGRAM1";
END;
```

Script of pg "PROGRAM1" of pad "D:\WPAD\VCWRLD.PAD"

Script of pg "PROGRAM2" of pad "D:\WPAD\VCWRLD.PAD"

Script of pg "PROGRAM3" of pad "D:\WPAD\VCWRLD.PAD"

Script of pg "PROGRAM4" of pad "D:\WPAD\VCWRLD.PAD"

Script of pg "STATUS" of pad "D:\WPAD\VCWRLD.PAD"

```
handler openpage;
begin
global timelog;
  put timelog into pg fld "log";
  set cursor to thin;
  show the menu bar;
  PASS;
end;

handler closepage;
begin
( set cursor to off;)
  put empty into pg fld "log";
  end;

handler pagetime(pagenum);
  Begin
  global timelog;
  put 1 into linenum;
  get line linenum of timelog;
  repeat
    if the first word of it="OP:" then
      if (the name of pg pagenum) is in it then
        begin
          put the last word of it into opentime;
          repeat
            add one to linenum;
            get line linenum of timelog;
          until the first word of it = "CP:";
          put the last word of it into closetime;
          put "entered: " & opentime & " exited: " & closetime
& " time: " &
          closetime-opentime & return after pg fld "log";
        end;
      add one to linenum;
      get line linenum of timelog;
    until it = the last line of timelog;
End;
```

Script of btn "RESET DATA FILE" of pg "STATUS" of pad
"D:\WPAD\VCWRLD.PAD"

```
Handler Select;
Begin
  GET THE FIRST LINE OF PG FLD "FILENAME";
  PUT THE CREATE OF IT INTO TEMP;
  write return to temp;
  CLOSE TEMP;
  PUT 1 INTO PG FLD "SUBJECT INFO";
End;
```

Script of btn "Page time" of pg "STATUS" of pad
"D:\WPAD\VCWRLD.PAD"

```
Handler Select;
Begin
  global timelog;
  put empty into pg fld "log";
  ask "Which pg?";
  put it into pagenum;
  pagetime(pagenum);
  beep(2);
End;
```

Script of btn "all pg times" of pg "STATUS" of pad
"D:\WPAD\VCWRLD.PAD"

```
Handler Select;
Begin
  put empty into pg fld "log";
  put the number of pages into lastpage;
```

```
for pagenum=1 to lastpage do
begin
    get the name of pg pagenum;
    put "Page " & it & return after pg fld "log";
    pagetime(pagenum);END;
    put return after pg fld "log";
end;
beep( 4);
End;
```

Script of btn "Return" of pg "STATUS" of pad "D:\VPAD\VCROLD.PAD"

```
Handler Select;
Begin
  pop pg;
End;
```

Script of btn "Page Data" of pg "STATUS" of pad "D:\VPAD\VCROLD.PAD"

```
Handler Select;
Begin
    put the create of "vcra.pag" into fl;
    go to pg 1;
    for x=1 to the number of pages do
    begin
        write the name of this pg & return to fl;
        go to the next pg;
    end;
    close fl;
End;
```

Script of pg "ON/OFF" of pad "D:\VPAD\VCROLD.PAD"

```
HANDLER OPENPAGE;
   BEGIN
       GLOBAL POWER;
           PUT 1 INTO POWER;
           PASS;
   END;

HANDLER KEYPRESS(K);
   BEGIN
       GLOBAL POWER;
       LOGKEY(K);
       CASE KEY(K) OF
       "/"     : BEGIN
                   PUT 0 INTO POWER;
                   GO TO PG "CLOCK";
                 END;
       "SLASH" : BEGIN
                   PUT 0 INTO POWER;
                   GO TO PG "CLOCK";
                 END;
       "*"     : BEGIN
                   IF THE VISIBLE OF PG BTN "TIMER" IS FALSE THEN
                       SET THE VISIBLE OF PG BTN "TIMER" TO TRUE
                   ELSE IF THE VISIBLE OF PG BTN "TIMER" IS TRUE THEN
                       SET THE VISIBLE OF PG BTN "TIMER" TO FALSE;
                 END;
       "1"     : GO TO PAD "HOME";
       "END"   : GO TO PAD "HOME";
```

```
OTHERWISE : BEGIN
              PASS;
            END;
END;
```

Script of Pad D:\HPAD\VCRPROTO.PAD

```
handler openpad;
  begin
  global timelog,
startsec,settime,vcrdelta,checkdate,norun;
  if norun then pass;
{ go to pg 1;}
  set the cursor to off;
    put 0 into checkdate;
    put 0 into settime;
    put "" into pg fld "date1" of pg "confirmation";
    put " : " into pg fld "startime1" of pg
"confirmation";
    put " : " into pg fld "stoptime1" of pg
"confirmation";
    put "  " into pg fld "channel1" of pg "confirmation";
    put "  " into pg fld "speed1" of pg "confirmation";
  put "" into pg fld "date2" of pg "confirmation";
    put " : " into pg fld "startime2" of pg
"confirmation";
    put " : " into pg fld "stoptime2" of pg
"confirmation";
    put "  " into pg fld "channel2" of pg "confirmation";
    put "  " into pg fld "speed2" of pg "confirmation";
  put "" into pg fld "date3" of pg "confirmation";
    put " : " into pg fld "startime3" of pg
"confirmation";
    put " : " into pg fld "stoptime3" of pg
"confirmation";
    put "  " into pg fld "channel3" of pg "confirmation";
    put "  " into pg fld "speed3" of pg "confirmation";
  put "" into pg fld "date4" of pg "confirmation";
    put " : " into pg fld "startime4" of pg
"confirmation";
    put " : " into pg fld "stoptime4" of pg
"confirmation";
    put "  " into pg fld "channel4" of pg "confirmation";
    put "  " into pg fld "speed4" of pg "confirmation";
    add one to pg fld "subject info" of pg "status";
    put empty into timelog;
    put the seconds into startsec;
    put "January 1, 1980" into vcrdelta;
    convert vcrdelta to seconds;
    put vcrdelta-seconds() into vcrdelta;
{   send "select" to pg btn "set current date";}
    go to pg "year set";
  end;

handler closepad;
begin
GLOBAL TIMELOG,norun;
  if norun then pass;
  for temp=1 to 4 do logconfline(temp);
  get the first line of pg fld "File Name" of pg "status";
  PUT THE append OF it INTO TEMP;
  get pg fld "subject info" of pg "status";
  Write "NS: Subject number " & it && the longdate && the
longtime & return to temp;
  WRITE TIMELOG TO TEMP;
  write return to temp;
  CLOSE TEMP;
end;

handler mousedown;
  begin;
  global timelog, startsec;
    get the name of pg currentpage();
    put "MD: " & it && the name of the target &&
(seconds()-startsec) & return after timelog;
  end;

handler openpage;
  begin;
  global timelog, startsec;
    get the name of pg currentpage();
    put "OP: " & it && (seconds()-startsec) & return
after timelog;
  end;

handler closepage;
  begin;
  global timelog, startsec;
    put the name of pg currentpage() into temp;
    put "CP: " & temp && (seconds()-startsec) into temp;
    put temp & return after timelog;
  end;

handler logaction(x);
  begin;
  global timelog, startsec;
    put "LA: " & x && (seconds()-startsec) & return after
timelog;
  end;

handler logconfline(prognum);
  begin
    global timelog;
    put "date" & prognum into temp;
    get pg fld temp of pg "confirmation";
    put "CL: " & prognum & " " before it;
    put it into hold;
    put "startime" & prognum into temp;
    get pg fld temp of pg "confirmation";
    put " " before it;
    put it after hold;
    put "stoptime" & prognum into temp;
    get pg fld temp of pg "confirmation";
    put " " before it;
    put it after hold;
    put "channel" & prognum into temp;
    get pg fld temp of pg "confirmation";
    put " " before it;
    put it after hold;
    put "speed" & prognum into temp;
    get pg fld temp of pg "confirmation";
    put " " before it;
    put it after hold;
    put hold & return after timelog;
end;
```

Script of bkgnd pg "VCRBKGND" of pad "D:\HPAD\VCRPROTO.PAD"

```
handler select;
 begin
   logaction("backround handler" && the name of the target);
end;

handler idle;

begin
  global vcrdelta;
    put seconds()+vcrdelta into temp;
```

B-13

```
convert temp to long date and long time:
PUT " " AFTER THE FOURTH WORD OF TEMP;
put temp into bg fld "Time Window";
end;

function checktime(ctime,ampm):
  begin;
    if ctime = "  :  " (THEN
      BEGIN
        IF CTIME > "12:59") OR CTIME < " 1:00" then
        BEGIN
          put "Enter a time" into pg fld "notfinished";
          logaction ("time not entered");
          return false
        end
      else if ampm = empty then
      begin
        put "Choose AM or PM" into pg fld "notfinished";
        logaction("Must choose am/pm");
        return false
      end
      else return true;
    END;
```

Script of bkgnd btn "Help" of bkgnd pg "VCRBKGRND" of pad "D:\VPAD\VCRPROTO.PAD"

```
handler select;
begin
  PUSH THIS PG;
  GO TO PG "HELP";
end;
```

Script of bkgnd btn "Main Menu" of bkgnd pg "VCRBKGRND" of pad "D:\VPAD\VCRPROTO.PAD"

```
handler select;

begin
  answer "Ok to return to main menu" WITH "YES","NO";
  if it = "YES" then go pg "main menu";
end;
```

Script of bkgnd btn "status" of bkgnd pg "VCRBKGRND" of pad "D:\VPAD\VCRPROTO.PAD"

```
Handler Select;
Begin
  push this pg;
  go to pg "status";
End;
```

Script of bkgnd pg "VCRBKGRND" of pad "D:\VPAD\VCRPROTO.PAD"

```
{HANDLER IDLE;
  BEGIN;
    PUT THE LONGTIME INTO BG FLD "TIME WINDOW";
    PUT THE LONGDATE INTO 3G FLD "DATE WINDOW";
  END;
}
handler select;
begin
  logaction("backround handler");
  { pass; }
end;

handler idle;

begin
  global vcrdelta;
  put seconds()+vcrdelta into temp;
  convert temp to long date and long time;
  PUT " " AFTER THE FOURTH WORD OF TEMP;
  put temp into bg fld "Time Window";
end;
```

Script of bkgnd btn "Help" of bkgnd pg "VCRBKGRND" of pad "D:\VPAD\VCRPROTO.PAD"

```
handler select;
begin
  PUSH THIS PG;
  GO TO PG "HELP";
end;
```

Script of bkgnd btn "Main Menu" of bkgnd pg "VCRBKGRND" of pad "D:\VPAD\VCRPROTO.PAD"

```
handler select;

begin
  ANSWER "Ok to return to Main Menu?" WITH "YES","NO";
  if it = "YES" then go to pg "main menu";
end;
```

Script of bkgnd pg "monthly" of pad "D:\VPAD\VCRPROTO.PAD"

```
handler dateitemmonth;

begin
  global convertedmonth,monthtocheck;
  put monthtocheck into thismonth;
  put word 1 of thismonth & " 1," & word 2 of thismonth
into monthname;
  convert monthname to dateitems;
  put monthname into convertedmonth;
end;

handler makemonth;

begin
  global convertedmonth,firstdayofthismonth,monthtocheck;
  put bg fld "month" into monthtocheck;
  dateitemmonth;
  put convertedmonth into firstdaythismonth;
  put item 2 of convertedmonth into monthnumber;
  put item 1 of convertedmonth into whatyear;
  put monthnumber + 1 into nextmonth;
  put nextmonth & "/1/" & whatyear into firstdaynextmonth;
  convert firstdaythismonth to seconds;
  convert firstdaynextmonth to seconds;
  put (firstdaynextmonth - firstdaythismonth) / (24 * 60 *
60)
      into daysinmonth;

convert firstdaythismonth to dateitems;
  put item 7 of firstdaythismonth into startday;

put 1 into dayone;
  while dayone < startday do
  begin
    put "day " & dayone into dayname;
    put "" into bg fld dayname;
    put dayone + 1 into dayone;
```

B-14

```
    end;
    put 1 into dayone;
    while dayone (= daysinmonth do
    begin
        put "day " & startday into dayname;
        put dayone into bg fld dayname;
        put dayone into i;
        put startday + 1 into startday;
        put dayone + 1 into dayone;
    end;
    put startday into daysinmonth;
    while startday (= 37 do
    begin
        put "day " & startday into dayname;
        put "" into bg fld dayname;
        put startday + 1 into startday;
    end;
end;

handler idle;

begin
    global vcrdelta;
    put seconds()+vcrdelta into temp;
    convert temp to long date and long time;
    PUT " " AFTER THE FOURTH WORD OF TEMP;
    put temp into bg fld "Time Window";
end;

handler select;
BEGIN
    GLOBAL daytorecord,settime,currentdate;

PUT THE TARGET INTO checkit;
    IF "BTN" IS IN CHECKIT THEN {SEE IF IT WAS A BTN}
        BEGIN
            {check for new interval}
            put the name of the target into temp;
            if "Day" is in temp then
            begin
                put bg fld temp into newdate;
                put newdate into pg fld "day of month";
                put first word of bg fld "month" & " " before
newdate;
                put ", " after newdate;
                put last word of bg fld "month" after newdate;
                if settime=1 then put newdate into daytorecord
                else put newdate into currentdate;
                global timelog, startsec;
                get the name of pg currentpage();
                put "MO: " & it && bg fld temp && (seconds()-
startsec) & return after timelog;
                Pagedone;
            end;
            END;
END;

Handler Pagedone;
Begin
GLOBAL SETTIME,VCRDELTA,currentdate,checkdate;
    if pg fld "day of month" = empty then
        put "Select a day" into pg fld "current"
    ELSE
        IF settime = 0 then
        BEGIN
            put currentdate into newdate;
            put seconds() + vcrdelta into temp;
```

```
            convert temp to time;
            put " " before temp;
            put newdate before temp;
            put temp into message box;
            convert temp to seconds;
            put temp - seconds() into vcrdelta;
{           put 1 into checkdate;}
            put 1 into settime;
            go to pg "main menu";
        end
        else
            go to pg "start time";
End;

handler mousedown;
    begin
        if "day" is not in the name of the target then
            pass;
    end;

Script of pg "main menu" of pad "D:\HPAD\VCRPROTO.PAD"

handler openpage;
begin
global checkdate;
if checkdate = 0 then
    begin
        put 1 into checkdate;
        send "select" to pg btn "set current time";
    end
else
    put empty into pg fld "full";
    set focus to bg fld "menu title";
    pass;
end;

Script of btn "SET CURRENT TIME" of pg "main menu" of pad "D:\HPAD\VCRPROTO.PAD"

Handler Select;
Begin
    GO TO PG "CURRENT TIME";
End;

Script of btn "ENTER NEW RECORDING TIME" of pg "main menu" of pad "D:\HPAD\VCRPROTO.PAD"

Handler Select;
Begin
    global settime,mode;
    begin;
    put "Program" into mode;
    put 1 into settime;
    put "PROGRAM" INTO PG FLD "status" OF PG "tape status";
    if "" () pg fld "date1" of pg "confirmation" then
    if "" () pg fld "date2" of pg "confirmation" then
    if "" () pg fld "date3" of pg "confirmation" then
    if "" () pg fld "date4" of pg "confirmation" then
        put "Program capacity is full. You must cancel one
of the existing programs to Continue." into pg fld "full"
    else
    go to pg "select the program"
    else
    go to pg "select the program"
    else
    go to pg "select the program"
    else
```

```
go to pg 'select the program';
End;
end;
```

Script of btn "REVIEW CURRENT RECORDING TIMES" of pg "main menu" of pad "D:\VPAD\VCRPROTO.PAD"

```
Handler Select;
Begin
global mode;
put 'Review' into mode;
 PUT "  PROGRAM REVIEW" INTO PG FLD 'status' OF PG 'tape status";
   go to pg 'confirmation';
End;
```

Script of btn "Power Off" of pg "main menu" of pad "D:\VPAD\VCRPROTO.PAD"

```
Handler Select;
Begin
   ANSWER 'OK to set the timer' WITH 'YES', 'NO';
   if it='YES' then
   begin
   go to pg 'timer';
   set the visible of pg fld 'timer on' to true;
   end
   ELSE
   IF IT='NO' THEN
   BEGIN
   ANSWER 'OK to turn off VCR?' with 'YES', 'NO';
   if it = 'NO' THEN GO TO PG 'MAIN MENU';
   IF IT='YES' THEN
   BEGIN
   GO TO PG 'TIMER';
   SET THE VISIBLE OF PG FLD 'TIMER ON' TO FALSE;
   QUIT;
   END;
   END;
End;
```

Script of btn "SET CURRENT DATE" of pg "main menu" of pad "D:\VPAD\VCRPROTO.PAD"

```
Handler Select;
Begin
global checkdate,settime;
   put 0 into settime;
   put 1 into checkdate;
   go to pg 'year set';
End;
```

Script of btn "Help" of pg "main menu" of pad "D:\VPAD\VCRPROTO.PAD"

```
handler select;
begin
   PUSH THIS PG;
   GO TO PG 'main menu HELP';
end;
```

Script of pg "timer" of pad "D:\VPAD\VCRPROTO.PAD"

Script of btn "FINISHED" of pg "timer" of pad "D:\VPAD\VCRPROTO.PAD"

```
Handler Select;
```

```
Begin
   GO TO PAD 'HOME';
End;
```

Script of pg "main menu help" of pad "D:\VPAD\VCRPROTO.PAD"

Script of btn "SET CURRENT TIME" of pg "main menu help" of pad "D:\VPAD\VCRPROTO.PAD"

```
Handler Select;
Begin
   GO TO PG 'CURRENT TIME';
End;
```

Script of btn "ENTER NEW RECORDING TIME" of pg "main menu help" of pad "D:\VPAD\VCRPROTO.PAD"

```
Handler Select;
Begin
   global settime,mode;
   begin;
put 'Program' into mode;
put 1 into settime;
   put 'PROGRAM' INTO PG FLD 'status' OF PG 'tape status';
   if '' () pg fld 'date1' of pg 'confirmation' then
   if '' () pg fld 'date2' of pg 'confirmation' then
   if '' () pg fld 'date3' of pg 'confirmation' then
   if '' () pg fld 'date4' of pg 'confirmation' then
      put 'Program capacity is full. You must cancel one
of the existing programs to Continue.' into pg fld 'full'
else
go to pg 'select the program'
else
go to pg 'select the program'
else
go to pg 'select the program'
else
go to pg 'select the program';
End;
end;
```

Script of btn "REVIEW CURRENT RECORDING TIMES" of pg "main menu help" of pad "D:\VPAD\VCRPROTO.PAD"

```
Handler Select;
Begin
global mode;
put 'Review' into mode;
 PUT "  PROGRAM REVIEW" INTO PG FLD 'status' OF PG 'tape status";
   go to pg 'confirmation';
End;
```

Script of btn "Quit" of pg "main menu help" of pad "D:\VPAD\VCRPROTO.PAD"

Script of btn "SET CURRENT DATE" of pg "main menu help" of pad "D:\VPAD\VCRPROTO.PAD"

```
Handler Select;
Begin
global setdate;
   put 0 into setdate;
   go to pg 'select the month';
End;
```

Script of btn "Exit Help" of pg "main menu help" of pad

```
"D:\VPAD\VCRPROTO.PAD"

handler select;
begin
   pop pg;
end;

Script of btn "Power Off" of pg "main menu help" of pad
"D:\VPAD\VCRPROTO.PAD"

Script of pg "HELP" of pad "D:\VPAD\VCRPROTO.PAD"

Script of btn "EXIT HELP" of pg "HELP" of pad
"D:\VPAD\VCRPROTO.PAD"

handler select;
begin
   POP PG;
end;

Script of pg "TAPE STATUS" of pad "D:\VPAD\VCRPROTO.PAD"

handler openpage;
   begin;
      set focus to bg fld "menu title";
      pass;
      end;

Script of btn "OK" of pg "TAPE STATUS" of pad
"D:\VPAD\VCRPROTO.PAD"

Handler Select;
Begin
   global mode;
   case mode of
   "Playing": go to pg "main menu";
   "Rewinding": go to pg "main menu";
   "Fast Forwarding": go to pg "main menu";
   "Stop": go to pg "main menu";
   "Pause": go to pg "main menu";
   "Eject": go to pg "main menu";
   "Program": go to pg "select the program";
End;
end;

Script of pg "Current Time" of pad "D:\VPAD\VCRPROTO.PAD"

Handler openpage;
begin
   global dstring;
   set focus to pg fld "enter the current time";
   put " " into pg fld "Display2";
   PUT " " INTO PG FLD "AM/PM";
   put "    " into dstring;
   put "         " into pg fld "notfinished";
   append(" ");
   pass;
   end;

handler append(x);
   begin;
   global dstring;
   put dstring & x into dstring;
   put the rightstring of dstring,4 into dstring;
   put dstring into pg fld "Display2";
   put ":" after second char of pg fld "display2";
end;

Script of btn "2" of pg "Current Time" of pad
"D:\VPAD\VCRPROTO.PAD"

handler select;

begin;
append (the name of me);
end;

Script of btn "OK" of pg "Current Time" of pad
"D:\VPAD\VCRPROTO.PAD"

Handler Select;
Begin
if pg fld "display2" = "  :  " then
   begin
      put "Enter the correct time" into pg fld "notfinished";
      logaction ("must choose correct time");
   end
   else if pg fld "AM/PM" = " " then
   begin
      put "Choose AM or PM" into pg fld "notfinished" of pg
   "current time";
      logaction("Must choose am/pm");
   end
   else
   begin
      global vcrdelta;
      put pg fld "display2"&& pg fld "am/pm" into newtime;
      put seconds() + vcrdelta into temp;
      convert temp to date;
      put " " after temp;
      put newtime after temp;
      convert temp to seconds;
      put temp - seconds() into vcrdelta;

go to pg "Main Menu";
      end;
End;

Script of btn "AM" of pg "Current Time" of pad
"D:\VPAD\VCRPROTO.PAD"

Handler Select;
Begin
   PUT "AM" INTO PG FLD "AM/PM";
   put "         " into pg fld "notfinished";
End;

Script of btn "PM" of pg "Current Time" of pad
"D:\VPAD\VCRPROTO.PAD"

Handler Select;
Begin
   PUT "PM" INTO PG FLD "AM/PM";
   put "         " into pg fld "notfinished";
End;

Script of btn "Clear" of pg "Current Time" of pad
"D:\VPAD\VCRPROTO.PAD"

Handler Select;
Begin
   global dstring;
   put " " into pg fld "am/pm";
   put "    " into dstring;
```

```
    append (" ");
End;

Script of btn "0" of pg "Current Time" of pad
"D:\HPAD\VCRPROTO.PAD"

handler select;

begin;
    append ("0");
end;

Script of btn "1" of pg "Current Time" of pad
"D:\HPAD\VCRPROTO.PAD"

handler select;

begin;
append (the name of me);
end;

Script of btn "3" of pg "Current Time" of pad
"D:\HPAD\VCRPROTO.PAD"

handler select;

begin;
append (the name of me);
end;

Script of btn "4" of pg "Current Time" of pad
"D:\HPAD\VCRPROTO.PAD"

handler select;

begin;
append (the name of me);
end;

Script of btn "5" of pg "Current Time" of pad
"D:\HPAD\VCRPROTO.PAD"

handler select;

begin;
append (the name of me);
end;

Script of btn "6" of pg "Current Time" of pad
"D:\HPAD\VCRPROTO.PAD"

handler select;

begin;
append (the name of me);
end;

Script of btn "7" of pg "Current Time" of pad
"D:\HPAD\VCRPROTO.PAD"

handler select;

begin;
append (the name of me);
end;

Script of btn "8" of pg "Current Time" of pad
"D:\HPAD\VCRPROTO.PAD"

handler select;

begin;
append (the name of me);
end;

Script of btn "9" of pg "Current Time" of pad
"D:\HPAD\VCRPROTO.PAD"

handler select;

begin;
append (the name of me);
end;

Script of btn "5" of pg "Current Time" of pad
"D:\HPAD\VCRPROTO.PAD"

handler select;

begin;
append (the name of me);
end;

Script of btn "Midnight" of pg "Current Time" of pad
"D:\HPAD\VCRPROTO.PAD"

handler select;

begin;
append ("1200");
put "AM" into pg fld "AM/PM";
end;

Script of btn "Noon" of pg "Current Time" of pad
"D:\HPAD\VCRPROTO.PAD"

handler select;

begin;
append ("1200");
put "PM" into pg fld "AM/PM";
end;

Script of btn "Help" of pg "Current Time" of pad
"D:\HPAD\VCRPROTO.PAD"

handler select;
begin
    PUSH THIS PG;
    GO TO PG "current time help";
end;

Script of pg "Current Time Help" of pad
"D:\HPAD\VCRPROTO.PAD"

Handler openpage;
begin
    global dstring;
    set focus to pg fld "enter the current time";
    put " " into pg fld "Display2";
    PUT " " INTO PG FLD "AM/PM";
    put " " into dstring;
    put "              " into pg fld "notfinished";
    append(" ");
```

B-18

```
       pass;
     end;

handler append(x);
  begin;
    global dstring;
    put dstring & x into dstring;
    put the rightstring of dstring,4 into dstring;
    put dstring into pg fld "Display2";
    put ":" after second char of pg fld "display2";
  end;

Script of btn "2" of pg "Current Time Help" of pad
"D:\HPAD\VCRPROTO.PAD"

handler select;

begin;
  append (the name of me);
end;

Script of btn "OK" of pg "Current Time Help" of pad
"D:\HPAD\VCRPROTO.PAD"

Handler Select;
Begin
if pg fld "display2" = "  :  " then
  begin
    put "Enter the correct time" into pg fld "notfinished";
    logaction ("must choose correct time");
  end
else if pg fld "AM/PM" = " " then
  begin
    put "Choose AM or PM" into pg fld "notfinished" of pg
"current time";
    logaction("Must choose am/pm");
  end
else
  begin
    global vcrdelta;
    put pg fld "display2"&& pg fld "am/pm" into newtime;
    put seconds() + vcrdelta into temp;
    convert temp to date;
    put " " after temp;
    put newtime after temp;
    convert temp to seconds;
    put temp - seconds() into vcrdelta;

go to pg "Main Menu";
  end;
End;

Script of btn "AM" of pg "Current Time Help" of pad
"D:\HPAD\VCRPROTO.PAD"

Handler Select;
Begin
  PUT "AM" INTO PG FLD "AM/PM";
  put "                    " into pg fld "notfinished";
End;

Script of btn "PM" of pg "Current Time Help" of pad
"D:\HPAD\VCRPROTO.PAD"

Handler Select;
Begin
  PUT "PM" INTO PG FLD "AM/PM";
```

```
  put "                    " into pg fld "notfinished";
End;

Script of btn "Clear" of pg "Current Time Help" of pad
"D:\HPAD\VCRPROTO.PAD"

Handler Select;
Begin
  global dstring;
  put " " into pg fld "am/pm";
  put "  " into dstring;
  append ("    ");
End;

Script of btn "0" of pg "Current Time Help" of pad
"D:\HPAD\VCRPROTO.PAD"

handler select;

begin;
  append ("0");
end;

Script of btn "1" of pg "Current Time Help" of pad
"D:\HPAD\VCRPROTO.PAD"

handler select;

begin;
  append (the name of me);
end;

Script of btn "3" of pg "Current Time Help" of pad
"D:\HPAD\VCRPROTO.PAD"

handler select;

begin;
  append (the name of me);
end;

Script of btn "4" of pg "Current Time Help" of pad
"D:\HPAD\VCRPROTO.PAD"

handler select;

begin;
  append (the name of me);
end;

Script of btn "5" of pg "Current Time Help" of pad
"D:\HPAD\VCRPROTO.PAD"

handler select;

begin;
  append (the name of me);
end;

Script of btn "6" of pg "Current Time Help" of pad
"D:\HPAD\VCRPROTO.PAD"

handler select;

begin;
  append (the name of me);
end;
```

Script of btn "7" of pg "Current Time Help" of pad
"D:\VPAD\VCRPROTO.PAD"

handler select;

begin;
append (the name of me);
end;

Script of btn "8" of pg "Current Time Help" of pad
"D:\VPAD\VCRPROTO.PAD"

handler select;

begin;
append (the name of me);
end;

Script of btn "9" of pg "Current Time Help" of pad
"D:\VPAD\VCRPROTO.PAD"

handler select;

begin;
append (the name of me);
end;

Script of btn "5" of pg "Current Time Help" of pad
"D:\VPAD\VCRPROTO.PAD"

handler select;

begin;
append (the name of me);
end;

Script of btn "Midnight" of pg "Current Time Help" of pad
"D:\VPAD\VCRPROTO.PAD"

handler select;

begin;
append ("1200");
put "AM" into pg fld "AM/PM";
end;

Script of btn "Noon" of pg "Current Time Help" of pad
"D:\VPAD\VCRPROTO.PAD"

handler select;

begin;
append ("1200");
put "PM" into pg fld "AM/PM";
end;

Script of btn "Exit Help" of pg "Current Time Help" of pad
"D:\VPAD\VCRPROTO.PAD"

Handler Select;
Begin
  go to pg "current time";
End;

Script of pg "Select the Program" of pad
"D:\VPAD\VCRPROTO.PAD"

handler openpage;
  begin;
    set focus to bg fld "menu title";
    PASS;
  end;

Script of btn "Program Once on ..." of pg "Select the
Program" of pad "D:\VPAD\VCRPROTO.PAD"

Handler Select;
Begin
  go to pg "specific day";
End;

Script of btn "Program Once a Week on ..." of pg "Select the
Program" of pad "D:\VPAD\VCRPROTO.PAD"

Handler Select;
Begin
GLOBAL DAYS,DAY;
PUT 0 INTO DAYs;

go to pg "select the day";
End;

Script of btn "Program Monday - Friday at ..." of pg "Select
the Program" of pad "D:\VPAD\VCRPROTO.PAD"

Handler Select;
Begin
global day,DAYS;
PUT 2 INTO DAYS;
  put "Monday-Friday" after day;
  go to pg "start time";
End;

Script of btn "Program EveryDay at ..." of pg "Select the
Program" of pad "D:\VPAD\VCRPROTO.PAD"

Handler Select;
Begin
  GLOBAL DAY,DAYS;
  PUT 3 INTO DAYS;
  put "Everyday" into day;
  go to pg "start time";
End;

Script of btn "Help" of pg "Select the Program" of pad
"D:\VPAD\VCRPROTO.PAD"

Handler Select;
Begin
  push this pg;
  go to pg "select the program help";
End;

Script of pg "specific day" of pad "D:\VPAD\VCRPROTO.PAD"

Script of btn "Today" of pg "specific day" of pad
"D:\VPAD\VCRPROTO.PAD"

Handler Select;
Begin
  global daytorecord,days;
  put 1 into days;
  put bg fld "time window" into temp;

```
    delete item 1 of temp;
    delete the first char of temp;
    put empty into daytorecord;
    put temp into daytorecord;
    go to pg "start time";

End;

Script of btn "Tomorrow" of pg "specific day" of pad
"D:\VPAD\VCRPROTO.PAD"

Handler Select;
Begin
    global daytorecord,days;
    put 1 into days;
    put bg fld "time window" into temp;
    convert temp to dateitems;
    add one to the third item of temp;
    convert temp to long date;
    delete the first word of temp;
    delete the first char of temp;
    put empty into daytorecord;
    put temp into daytorecord;
    go to pg "start time";

end;

Script of btn "Any other day" of pg "specific day" of pad
"D:\VPAD\VCRPROTO.PAD"

Handler Select;
Begin
    global daytorecord,days;
    put 1 into days;
    go to pg "select the month";

End;

Script of pg "Select the Program Help" of pad
"D:\VPAD\VCRPROTO.PAD"

Script of btn "Program Once on ..." of pg "Select the
Program Help" of pad "D:\VPAD\VCRPROTO.PAD"

Handler Select;
Begin
global daytorecord,days;
put 1 into days;
    go to pg "select the month";
End;

Script of btn "Program Once a Week on ..." of pg "Select the
Program Help" of pad "D:\VPAD\VCRPROTO.PAD"

Handler Select;
Begin
GLOBAL DAYS,DAY;
PUT 0 INTO DAYs;

go to pg "select the day";
End;

Script of btn "Program Monday - Friday at ..." of pg "Select
the Program Help" of pad "D:\VPAD\VCRPROTO.PAD"

Handler Select;
Begin
```

```
    global day,DAYS;
    PUT 2 INTO DAYS;
    put "Monday-Friday" into day;
    go to pg "start time";
End;

Script of btn "Program EveryDay at ..." of pg "Select the
Program Help" of pad "D:\VPAD\VCRPROTO.PAD"

Handler Select;
Begin
    GLOBAL DAY,DAYS;
    PUT 3 INTO DAYS;
    put "Everyday" into day;
    go to pg "start time";
End;

Script of btn "Exit Help" of pg "Select the Program Help" of
pad "D:\VPAD\VCRPROTO.PAD"

Handler Select;
Begin
    go to pg "select the program";
End;

Script of pg "Select the Day" of pad "D:\VPAD\VCRPROTO.PAD"

handler openpage;
    begin
    put empty into pg fld "day of week";
    put empty into pg fld "finished";
    pass;
end;

handler select;
    begin
{   global dayofweek;
}       PUT THE TARGET INTO dayofweek;
        IF "BTN" IS IN DAYOFWEEK THEN (SEE IF IT WAS A BTN)
        BEGIN
            (check for new interval)
            put the name of the target into temp;
            if "s" is the rightstring of temp,1 then
            begin
            put temp into pg fld "day of week";
            go to pg "start time";
            end;
end;
END;

Handler day;
Begin
if pg fld "day of week" () empty then
    go to pg "START TIME"
    else
    put "choose the day to record on" into pg fld "finished";
End;

Script of btn "Tuesdays" of pg "Select the Day" of pad
"D:\VPAD\VCRPROTO.PAD"

Handler Select;
Begin
    pass;
End;

Script of btn "Fridays" of pg "Select the Day" of pad
```

B-21

```
"D:\VPAD\VCRPROTO.PAD"

Handler Select;
Begin
    pass;
End;

Script of btn "Wednesdays" of pg "Select the Day" of pad
"D:\VPAD\VCRPROTO.PAD"

Handler Select;
Begin
    pass;
End;

Script of btn "Thursdays" of pg "Select the Day" of pad
"D:\VPAD\VCRPROTO.PAD"

Handler Select;
Begin
    pass;
End;

Script of btn "Mondays" of pg "Select the Day" of pad
"D:\VPAD\VCRPROTO.PAD"

Handler Select;
Begin
    pass;
End;

Script of btn "Saturdays" of pg "Select the Day" of pad
"D:\VPAD\VCRPROTO.PAD"

Handler Select;
Begin
    pass;
End;

Script of btn "Sundays" of pg "Select the Day" of pad
"D:\VPAD\VCRPROTO.PAD"

Handler Select;
Begin
    pass;
End;

Script of pg "select the month" of pad
"D:\VPAD\VCRPROTO.PAD"

handler openpage;
    begin
        global settime,linda;
        put empty into pg fld "notfinished";
        set focus to bg fld "menu title";
        put empty into linda;

if settime = 0 then
            put "Select the Current Month" into bg fld "Menu Title"
        else
            put "Select the Month to Record On" into bg fld "Menu Title";
        PASS;
    end;

Script of btn "January" of pg "select the month" of pad
"D:\VPAD\VCRPROTO.PAD"

Handler Select;
Begin
    global linda;
        put "January 1991" into bg fld "Month" of bg "monthly";
        put "date" into linda;
            go to pg "February 1990";
End;

Script of btn "February" of pg "select the month" of pad
"D:\VPAD\VCRPROTO.PAD"

Handler Select;
Begin
    global linda;
        put "February 1990" into bg fld "month" of bg "monthly";
    put "date" into linda;
    go to pg "february 1990";
    end;

Script of btn "June" of pg "select the month" of pad
"D:\VPAD\VCRPROTO.PAD"

Handler Select;
Begin
    global linda;
        put "June 1990" into bg fld "month" of bg "monthly";
        put "date" into linda;
            go to pg "february 1990";
End;

Script of btn "May" of pg "select the month" of pad
"D:\VPAD\VCRPROTO.PAD"

Handler Select;
Begin
    global linda;
        put "May 1990" into bg fld "month" of bg "monthly";
        put "date" into linda;
            go to pg "february 1990";
End;

Script of btn "April" of pg "select the month" of pad
"D:\VPAD\VCRPROTO.PAD"

Handler Select;
Begin
    global linda;
        put "April 1990" into bg fld "month" of bg "monthly";
        put "date" into linda;
            go to pg "february 1990";
End;

Script of btn "March" of pg "select the month" of pad
"D:\VPAD\VCRPROTO.PAD"

Handler Select;
Begin
    global linda;
        put "March 1990" into bg fld "month" of bg "monthly";
        put "date" into linda;
            go to pg "february 1990";
```

```
end;

Script of btn "August" of pg "select the month" of pad
"D:\VPAD\VCRPROTO.PAD"

Handler Select;
Begin
    global linda;
    put "August 1990" into bg fld "month" of bg "monthly";
    put "date" into linda;
        go to pg "february 1990";
End;

Script of btn "July" of pg "select the month" of pad
"D:\VPAD\VCRPROTO.PAD"

Handler Select;
Begin
    global linda;
    put "July 1990" into bg fld "month" of bg "monthly";
    put "date" into linda;
        go to pg "february 1990";

End;

Script of btn "September" of pg "select the month" of pad
"D:\VPAD\VCRPROTO.PAD"

Handler Select;
Begin
    global linda;
    put "September 1990" into bg fld "month" of bg "monthly";
    put "date" into linda;
        go to pg "february 1990";
End;

Script of btn "October" of pg "select the month" of pad
"D:\VPAD\VCRPROTO.PAD"

Handler Select;
Begin
    global linda;
    put "October 1990" into bg fld "month" of bg "monthly";
    put "date" into linda;
        go to pg "february 1990";
End;

Script of btn "November" of pg "select the month" of pad
"D:\VPAD\VCRPROTO.PAD"

Handler Select;
Begin
    global linda;
    put "November 1990" into bg fld "month" of bg "monthly";
    put "date" into linda;
        go to pg "february 1990";

End;

Script of btn "December" of pg "select the month" of pad
"D:\VPAD\VCRPROTO.PAD"

Handler Select;
Begin
    global linda;
    put "December 1990" into bg fld "month" of bg "monthly";
    put "date" into linda;
```

```
        go to pg "february 1990";
End;

Script of pg "year set" of pad "D:\VPAD\VCRPROTO.PAD"

Handler openpage;
begin
    global dstring;
    set focus to bg fld "menu title";
    put empty into dstring;
    put empty into pg fld "Display2";
    put empty into pg fld "notfinished";
    pass;
end;

handler append(x);
    begin;
        global dstring;

put dstring & x into dstring;
        put the rightstring of dstring,4 into dstring;
        put dstring into pg fld "Display2";
end;

Script of btn "OK" of pg "year set" of pad
"D:\VPAD\VCRPROTO.PAD"

Handler Select;
Begin
if pg fld "display2" < 1990 then
    begin
        put "Choose the correct year" into pg fld "notfinished"
of pg "year set";
        logaction("Must choose a year");
    end
else
    go to pg "select the month";
End;

Script of btn "Clear" of pg "year set" of pad
"D:\VPAD\VCRPROTO.PAD"

Handler Select;
Begin
global dstring;
put empty into dstring;
put empty into pg fld "notfinished";
    append empty;
End;

Script of btn "7" of pg "year set" of pad
"D:\VPAD\VCRPROTO.PAD"

handler select;

begin;
append (the name of me);
end;

Script of btn "8" of pg "year set" of pad
"D:\VPAD\VCRPROTO.PAD"

handler select;

begin;
append (the name of me);
end;
```

B-23

Script of btn "9" of pg "year set" of pad
"D:\HPAD\VCRPROTO.PAD"

handler select;

begin;
append (the name of me);
end;

Script of btn "4" of pg "year set" of pad
"D:\HPAD\VCRPROTO.PAD"

handler select;

begin;
append (the name of me);
end;

Script of btn "5" of pg "year set" of pad
"D:\HPAD\VCRPROTO.PAD"

handler select;

begin;
append (the name of me);
end;

Script of btn "6" of pg "year set" of pad
"D:\HPAD\VCRPROTO.PAD"

handler select;

begin;
append (the name of me);
end;

Script of btn "1" of pg "year set" of pad
"D:\HPAD\VCRPROTO.PAD"

handler select;

begin;
append (the name of me);
end;

Script of btn "2" of pg "year set" of pad
"D:\HPAD\VCRPROTO.PAD"

handler select;

begin;
append (the name of me);
end;

Script of btn "3" of pg "year set" of pad
"D:\HPAD\VCRPROTO.PAD"

handler select;

begin;
append (the name of me);
end;

Script of btn "0" of pg "year set" of pad
"D:\HPAD\VCRPROTO.PAD"

handler select;

begin;
append ("0");
end;

Script of pg "channel" of pad "D:\HPAD\VCRPROTO.PAD"

Handler openpage;
begin
    global dstring;
    set focus to bg fld "menu title";
    put empty into dstring;
    put empty into pg fld "Display2";
    put empty into pg fld "notfinished";
    pass;
    end;

handler append(x);
    begin;
    global dstring;

put dstring & x into dstring;
    put the rightstring of dstring,2 into dstring;
    put dstring into pg fld "Display2";
end;

Script of btn "OK" of pg "channel" of pad
"D:\HPAD\VCRPROTO.PAD"

Handler Select;
Begin
if pg fld "display2" = empty then
  begin
    put "Choose a Channel" into pg fld "notfinished" of pg "channel";
    logaction("Must choose a channel");
  end
else
  go to pg "tape speed";
End;

Script of btn "Clear" of pg "channel" of pad
"D:\HPAD\VCRPROTO.PAD"

Handler Select;
Begin
global dstring;
put empty into dstring;
put empty into pg fld "notfinished";
  append empty;
End;

Script of btn "7" of pg "channel" of pad
"D:\HPAD\VCRPROTO.PAD"

handler select;

begin;
append (the name of me);
end;

Script of btn "8" of pg "channel" of pad
"D:\HPAD\VCRPROTO.PAD"

handler select;

```
begin;
append (the name of me);
end;

Script of btn "9" of pg "channel" of pad
"D:\HPAD\VCRPROTO.PAD"

handler select;

begin;
append (the name of me);
end;

Script of btn "4" of pg "channel" of pad
"D:\HPAD\VCRPROTO.PAD"

handler select;

begin;
append (the name of me);
end;

Script of btn "5" of pg "channel" of pad
"D:\HPAD\VCRPROTO.PAD"

handler select;

begin;
append (the name of me);
end;

Script of btn "6" of pg "channel" of pad
"D:\HPAD\VCRPROTO.PAD"

handler select;

begin;
append (the name of me);
end;

Script of btn "1" of pg "channel" of pad
"D:\HPAD\VCRPROTO.PAD"

handler select;

begin;
append (the name of me);
end;

Script of btn "2" of pg "channel" of pad
"D:\HPAD\VCRPROTO.PAD"

handler select;

begin;
append (the name of me);
end;

Script of btn "3" of pg "channel" of pad
"D:\HPAD\VCRPROTO.PAD"

handler select;

begin;
append (the name of me);
end;
```

```
Script of btn "0" of pg "channel" of pad
"D:\HPAD\VCRPROTO.PAD"

handler select;

begin;
   append ('0');
end;

Script of pg "Start Time" of pad "D:\HPAD\VCRPROTO.PAD"

Handler openpage;
begin
   global dstring;
   set focus to bg fld "menu title";

put " " into pg fld "Display2";
   PUT empty INTO PG FLD "AM/PM";
   put " " into dstring;
   put EMPTY into pg fld "notfinished";
   append(" ");
   PASS;
   end;

handler append(x);
   begin;
   global dstring;
   put dstring & x into dstring;
   put the rightstring of dstring,4 into dstring;
   put dstring into pg fld "Display2";
   put ":" after second char of pg fld "display2";
end;

Script of btn "2" of pg "Start Time" of pad
"D:\HPAD\VCRPROTO.PAD"

handler select;

begin;
append (the name of me);
end;

Script of btn "OK" of pg "Start Time" of pad
"D:\HPAD\VCRPROTO.PAD"

handler select;
      begin;
         if checktime (pg fld "display2", pg fld "am/pm") then
   go to pg "stop time";
      end;

Script of btn "AM" of pg "Start Time" of pad
"D:\HPAD\VCRPROTO.PAD"

Handler Select;
Begin
      PUT "AM" INTO PG FLD "AM/PM";
      put "              " into pg fld "notfinished";
End;

Script of btn "PM" of pg "Start Time" of pad
"D:\HPAD\VCRPROTO.PAD"

Handler Select;
Begin
   PUT "PM" INTO PG FLD "AM/PM";
   put "              " into pg fld "notfinished";
```

End;

Script of btn "Clear" of pg "Start Time" of pad
"D:\HPAD\VCRPROTO.PAD"

Handler Select;
Begin
  global dstring;
  put empty into pg fld "am/pm";
  put empty into pg fld "notfinished";
  put "    " into dstring;
  append ("  ");
End;

Script of btn "0" of pg "Start Time" of pad
"D:\HPAD\VCRPROTO.PAD"

handler select;

begin;
  append ("0");
end;

Script of btn "1" of pg "Start Time" of pad
"D:\HPAD\VCRPROTO.PAD"

handler select;

begin;
append (the name of me);
end;

Script of btn "3" of pg "Start Time" of pad
"D:\HPAD\VCRPROTO.PAD"

handler select;

begin;
append (the name of me);
end;

Script of btn "4" of pg "Start Time" of pad
"D:\HPAD\VCRPROTO.PAD"

handler select;

begin;
append (the name of me);
end;

Script of btn "5" of pg "Start Time" of pad
"D:\HPAD\VCRPROTO.PAD"

handler select;

begin;
append (the name of me);
end;

Script of btn "6" of pg "Start Time" of pad
"D:\HPAD\VCRPROTO.PAD"

handler select;

begin;
append (the name of me);
end;

Script of btn "7" of pg "Start Time" of pad
"D:\HPAD\VCRPROTO.PAD"

handler select;

begin;
append (the name of me);
end;

Script of btn "8" of pg "Start Time" of pad
"D:\HPAD\VCRPROTO.PAD"

handler select;

begin;
append (the name of me);
end;

Script of btn "9" of pg "Start Time" of pad
"D:\HPAD\VCRPROTO.PAD"

handler select;

begin;
append (the name of me);
end;

Script of btn "Midnight" of pg "Start Time" of pad
"D:\HPAD\VCRPROTO.PAD"

handler select;

begin;
append ("1200");
put "AM" into pg fld "AM/PM";
end;

Script of btn "Noon" of pg "Start Time" of pad
"D:\HPAD\VCRPROTO.PAD"

handler select;

begin;
append ("1200");
put "PM" into pg fld "AM/PM";
end;

Script of pg "Stop Time" of pad "D:\HPAD\VCRPROTO.PAD"

Handler openpage;
begin
  global dstring;
  put "  " into pg fld "Display2a";
  put empty into pg fld "am/pm2";
  set focus to bg fld "menu title";
  put pg fld "display2" of pg "start time" into pg fld "display2";
  PUT PG FLD "AM/PM" OF PG "START TIME" INTO PG FLD "AM1/PM1";
  put "    " into dstring;
  put "    " into pg fld "notfinished";
  append("  ");
  pass;
end;

handler append(x);

```
begin;
    global dstring;

put dstring & x into dstring;
    put the rightstring of dstring,4 into dstring;
    put dstring into pg fld "Display2a";
    put ":" after second char of pg fld "display2a";

end;
```

Script of btn "OK" of pg "Stop Time" of pad
"D:\VPAD\VCRPROTO.PAD"

```
Handler Select;
Begin
    if checktime (pg fld "display2A", pg fld "am/pm2")
then go to pg "CHANNEL";
End;
```

Script of btn "AM" of pg "Stop Time" of pad
"D:\VPAD\VCRPROTO.PAD"

```
Handler Select;
Begin
    PUT "AM" INTO PG FLD "AM/PM2";
    put "                    " into pg fld "notfinished";
End;
```

Script of btn "PM" of pg "Stop Time" of pad
"D:\VPAD\VCRPROTO.PAD"

```
Handler Select;
Begin
    PUT "PM" INTO PG FLD "AM/PM2";
    put "                    " into pg fld
"notfinished";
End;
```

Script of btn "Clear" of pg "Stop Time" of pad
"D:\VPAD\VCRPROTO.PAD"

```
Handler Select;
Begin
    append ("     ");
    put empty into pg fld "am/pm2";
    put empty into pg fld "notfinished";
End;
```

Script of btn "0" of pg "Stop Time" of pad
"D:\VPAD\VCRPROTO.PAD"

```
handler select;

begin;
    append ("0");
end;
```

Script of btn "1" of pg "Stop Time" of pad
"D:\VPAD\VCRPROTO.PAD"

```
handler select;

begin;
append (the name of me);
end;
```

Script of btn "2" of pg "Stop Time" of pad
"D:\VPAD\VCRPROTO.PAD"

```
handler select;

begin;
append (the name of me);
end;
```

Script of btn "3" of pg "Stop Time" of pad
"D:\VPAD\VCRPROTO.PAD"

```
handler select;

begin;
append (the name of me);
end;
```

Script of btn "4" of pg "Stop Time" of pad
"D:\VPAD\VCRPROTO.PAD"

```
handler select;

begin;
append (the name of me);
end;
```

Script of btn "5" of pg "Stop Time" of pad
"D:\VPAD\VCRPROTO.PAD"

```
handler select;

begin;
append (the name of me);
end;
```

Script of btn "6" of pg "Stop Time" of pad
"D:\VPAD\VCRPROTO.PAD"

```
handler select;

begin;
append (the name of me);
end;
```

Script of btn "7" of pg "Stop Time" of pad
"D:\VPAD\VCRPROTO.PAD"

```
handler select;

begin;
append (the name of me);
end;
```

Script of btn "8" of pg "Stop Time" of pad
"D:\VPAD\VCRPROTO.PAD"

```
handler select;

begin;
append (the name of me);
end;
```

Script of btn "9" of pg "Stop Time" of pad
"D:\VPAD\VCRPROTO.PAD"

handler select;

```
begin;
append (the name of me);
end;
```

Script of btn "Midnight" of pg "Stop Time" of pad
"D:\VPAD\VCRPROTO.PAD"

handler select;

```
begin;
append ("1200");
put "AM" into pg fld "AM/PM2";
end;
```

Script of btn "Noon" of pg "Stop Time" of pad
"D:\VPAD\VCRPROTO.PAD"

handler select;

```
begin;
append ("1200");
put "PM" into pg fld "AM/PM2";
end;
```

Script of fld "notfinished" of pg "Stop Time" of pad
"D:\VPAD\VCRPROTO.PAD"

```
handler select();
begin
 logaction;
end;
```

Script of pg "tape speed" of pad "D:\VPAD\VCRPROTO.PAD"

```
handler openpage;
begin
    put empty into pg fld "speed";
    put empty into pg fld "notfinished";
    set the cursor to off;
    set focus to bg fld "menu title";
      pass;
    end;
```

Script of btn "Standard Play" of pg "tape speed" of pad
"D:\VPAD\VCRPROTO.PAD"

```
Handler Select;
Begin
    put " SP " into pg fld "speed";
    put empty into pg fld "notfinished";
    GO TO PG "CONFIRMATION";
End;
```

Script of btn "Long Play" of pg "tape speed" of pad
"D:\VPAD\VCRPROTO.PAD"

```
Handler Select;
Begin
    put " LP " into pg fld "speed";
    put empty into pg fld "notfinished";
    GO TO PG "CONFIRMATION";
End;
```

Script of btn "Extended Play" of pg "tape speed" of pad
"D:\VPAD\VCRPROTO.PAD"

Handler Select;

```
Begin
    put " EP " into pg fld "speed";
    put empty into pg fld "notfinished";
    GO TO PG "CONFIRMATION";

End;
```

Script of btn "Clear" of pg "tape speed" of pad
"D:\VPAD\VCRPROTO.PAD"

```
Handler Select;
Begin
    put empty into pg fld "speed";
    put empty into pg fld "notfinished";
End;
```

Script of btn "OK" of pg "tape speed" of pad
"D:\VPAD\VCRPROTO.PAD"

```
Handler Select;
Begin
if pg fld "speed" = empty then
begin
    put "Select the speed" into pg fld "notfinished";
    logaction ("must select speed");
    end
        else
    go to pg "confirmation";
End;
```

Script of pg "confirmation" of pad "D:\VPAD\VCRPROTO.PAD"

```
handler openpage;
    begin
    GLOBAL DAYS,mode,daytorecord;
        set the cursor to off;
        set focus to bg fld "menu title";

if mode()"review" then begin
                    put "1" into pg fld "number1";
                    PUT "2" INTO PG FLD "NUMBER2";
                    put "3" into pg fld "number3";
                    put "4" into pg fld "number4";

if pg fld "startime1" = " : " then
        begin
        IF DAYS =0 THEN
        PUT PG FLD "DAY OF WEEK" OF PG "SELECT THE DAY" INTO
PG FLD "DATE1" OF PG "CONFIRMATION"
        ELSE
        IF DAYS=2 THEN
        PUT "Monday-Friday" INTO PG FLD "DATE1"
        ELSE
        IF DAYS=3 THEN
        PUT "Everyday" INTO PG FLD "DATE1"
        ELSE
        if days=1 then
            put daytorecord into pg fld "date1";

put pg fld "display2" of pg "start time" into pg fld
"startime1" of pg "confirmation";
        put " " after pg fld "startime1";
        put pg fld "am/pm" of pg "start time" after pg fld
"startime1" of pg "confirmation";
        put pg fld "display2a" of pg "stop time" into pg fld
"stoptime1" of pg "confirmation";
        put " " after pg fld "stoptime1";
```

B-28

```
        put pg fld 'am/pm2' of pg 'stop time' after pg fld
'stoptime1' of pg 'confirmation';
        put pg fld 'display2' of pg 'channel' into pg fld
'channel1' of pg 'confirmation';
        put pg fld 'speed' of pg 'tape speed' into pg fld
'speed1' of pg 'confirmation'
        end
else
   if pg fld 'startime2' = ' : ' then
     begin
IF DAYS =0 THEN
        PUT PG FLD 'DAY OF WEEK' OF PG 'SELECT THE DAY' INTO
PG FLD 'DATE2' OF PG 'CONFIRMATION'
        ELSE
        IF DAYS=2 THEN
        PUT 'Monday-Friday' INTO PG FLD 'DATE2'
        ELSE
        IF DAYS=3 THEN
        PUT 'Everyday' INTO PG FLD 'DATE2'
        ELSE
        put daytorecord into pg fld 'date2' of pg
'confirmation';
        put pg fld 'display2' of pg 'start time' into pg fld
'startime2' of pg 'confirmation';
        put ' ' after pg fld 'startime2';
        put pg fld 'am/pm' of pg 'start time' after pg fld
'startime2' of pg 'confirmation';
        put pg fld 'display2a' of pg 'stop time' into pg fld
'stoptime2' of pg 'confirmation';
        put ' ' after pg fld 'stoptime2';
        put pg fld 'am/pm2' of pg 'stop time' after pg fld
'stoptime2' of pg 'confirmation';
        put pg fld 'display2' of pg 'channel' into pg fld
'channel2' of pg 'confirmation';
        put pg fld 'speed' of pg 'tape speed' into pg fld
'speed2' of pg 'confirmation'
        end
     else if pg fld 'startime3' = ' : ' then
     begin IF DAYS =0 THEN
        PUT PG FLD 'DAY OF WEEK' OF PG 'SELECT THE DAY' INTO
PG FLD 'DATE3' OF PG 'CONFIRMATION'
        ELSE
        IF DAYS=2 THEN
        PUT 'Monday-Friday' INTO PG FLD 'DATE3'
        ELSE
        IF DAYS=3 THEN
        PUT 'Everyday' INTO PG FLD 'DATE3'
        ELSE put daytorecord into pg fld 'date3' of pg
'confirmation';
        put pg fld 'display2' of pg 'start time' into pg fld
'startime3' of pg 'confirmation';
        put ' ' after pg fld 'startime3';
        put pg fld 'am/pm' of pg 'start time' after pg fld
'startime3' of pg 'confirmation';
        put pg fld 'display2a' of pg 'stop time' into pg fld
'stoptime3' of pg 'confirmation';
        put ' ' after pg fld 'stoptime3';
        put pg fld 'am/pm2' of pg 'stop time' after pg fld
'stoptime3' of pg 'confirmation';
        put pg fld 'display2' of pg 'channel' into pg fld
'channel3' of pg 'confirmation';
        put pg fld 'speed' of pg 'tape speed' into pg fld
'speed3' of pg 'confirmation' end
      else
         if pg fld 'startime4' = ' : ' then
         begin
IF DAYS =0 THEN
        PUT PG FLD 'DAY OF WEEK' OF PG 'select the day' INTO
PG FLD 'DATE4' OF PG 'CONFIRMATION'
        ELSE
        IF DAYS=2 THEN
        PUT 'Monday-Friday' INTO PG FLD 'DATE4'
        ELSE
        IF DAYS=3 THEN
        PUT 'Everyday' INTO PG FLD 'DATE4'
        ELSE put daytorecord into pg fld 'date4' of pg
'confirmation';
        put pg fld 'display2' of pg 'start time' into pg fld
'startime4' of pg 'confirmation';
        put ' ' after pg fld 'startime4';
        put pg fld 'am/pm' of pg 'start time' after pg fld
'startime4' of pg 'confirmation';
        put pg fld 'display2a' of pg 'stop time' into pg fld
'stoptime4' of pg 'confirmation';
        put ' ' after pg fld 'stoptime4';
        put pg fld 'am/pm2' of pg 'stop time' after pg fld
'stoptime4' of pg 'confirmation';
        put pg fld 'display2' of pg 'channel' into pg fld
'channel4' of pg 'confirmation';
        put pg fld 'speed' of pg 'tape speed' into pg fld
'speed4' of pg 'confirmation' end;
        end;
        pass;

end;

Script of btn 'Cancel' of pg 'confirmation' of pad
'D:\VPAD\VCRPROTO.PAD'

Handler Select;
Begin
    global cancelit,changeit;
    PUT 1 INTO CHANGEIT;
    answer 'Select the Program #' WITH 'OK', 'QUIT';
    if it = 'OK' then
       put 0 into cancelit
    ELSE PUT 1 INTO CANCELIT;

End;

Script of btn 'Change' of pg 'confirmation' of pad
'D:\VPAD\VCRPROTO.PAD'

Handler Select;
Begin
    global changeit,CANCELIT;
    PUT 1 INTO CANCELIT;
    answer 'Select the Program # to Change' WITH
'CHANGE','CANCEL CHANGE';
    if it = 'CHANGE' then
         put 0 into changeit
    ELSE PUT 1 INTO CHANGEIT;
END;

Script of btn 'OK' of pg 'confirmation' of pad
```

```
"D:\HPAD\VCRPROTO.PAD"

Handler Select;
Begin
    go to pg "main menu";
End;

Script of btn "clear 1" of pg "confirmation" of pad
"D:\HPAD\VCRPROTO.PAD"

Handler Select;
Begin
    global cancelit;
    if cancelit = 0 then
    begin
        logconfline(1);
        put "" into pg fld "date1";
        put " : " into pg fld "startime1";
        put " : " into pg fld "stoptime1";
        put "" into pg fld "channel1";
        put "" into pg fld "speed1";
        put 5 into cancelit
    End
    else begin
        global changeit;
        if changeit = 0 then
        begin
            logconfline(1);
            put "" into pg fld "date1";
            put " : " into pg fld "startime1";
            put " : " into pg fld "stoptime1";
            put "" into pg fld "channel1";
            put "" into pg fld "speed1";
            put 5 into changeit;
            go to pg "select the program";
        End;
    end;
end;

Script of btn "clear 2" of pg "confirmation" of pad
"D:\HPAD\VCRPROTO.PAD"

Handler Select;
Begin
    global cancelit;
    if cancelit = 0 then
    begin
        logconfline(2);
        put "" into pg fld "date2";
        put " : " into pg fld "startime2";
        put " : " into pg fld "stoptime2";
        put "" into pg fld "channel2";
        put "" into pg fld "speed2";
        put 5 into cancelit
    End
    else begin
        global changeit;
        if changeit = 0 then
        begin
            logconfline(2);
            put "" into pg fld "date2";
            put " : " into pg fld "startime2";
            put " : " into pg fld "stoptime2";
            put "" into pg fld "channel2";
            put "" into pg fld "speed2";
            put 5 into changeit;
            go to pg "select the program";
        End;
    end;
end;

Script of btn "New Button" of pg "confirmation" of pad
"D:\HPAD\VCRPROTO.PAD"

Handler Select;
Begin
    global cancelit;
    if cancelit = 0 then
    begin
        put "" into pg fld "date3";
        put " : " into pg fld "startime3";
        put "" into pg fld "stoptime3";
        put "" into pg fld "channel3";
        put "" into pg fld "speed3";
        put 5 into cancelit
    End
    else begin
        global changeit;
        if changeit = 0 then
        begin
            put "" into pg fld "date3";
            put " : " into pg fld "startime3";
            put "" into pg fld "stoptime6";
            put "" into pg fld "channel3";
            put "" into pg fld "speed3";
            put 5 into changeit;
            go to pg "select the program";
        End;
    end;
end;

Script of btn "clear 4" of pg "confirmation" of pad
"D:\HPAD\VCRPROTO.PAD"

Handler Select;
Begin
    global cancelit;
    if cancelit = 0 then
    begin
        logconfline(4);
        put "" into pg fld "date4";
        put " : " into pg fld "startime4";
        put " : " into pg fld "stoptime4";
        put "" into pg fld "channel4";
        put "" into pg fld "speed4";
        put 5 into cancelit
    End
    else begin
        global changeit;
        if changeit = 0 then
        begin
            logconfline(4);
            put "" into pg fld "date4";
            put " : " into pg fld "startime4";
            put " : " into pg fld "stoptime4";
            put "" into pg fld "channel4";
            put "" into pg fld "speed4";
            put 5 into changeit;
            go to pg "select the program";
        End;
    end;
end;
```

```
end;

Script of btn "New Button" of pg "confirmation" of pad
"D:\VPAD\VCRPROTO.PAD"

Handler Select;
Begin
    global cancelit;
    if cancelit = 0 then
    begin
        put "" into pg fld "date3";
        put " : " into pg fld "startime3";
        put "" into pg fld "stoptime3";
        put "" into pg fld "channel3";
        put "" into pg fld "speed3";
        put 5 into cancelit
    End
    else begin
        global changeit;
        if changeit = 0 then
        begin
            put "" into pg fld "date3";
            put " : " into pg fld "startime3";
            put "" into pg fld "stoptime3";
            put "" into pg fld "channel3";
            put "" into pg fld "speed3";
            put 5 into changeit;
            go to pg "select the program";
        End;
    end;
end;

Script of btn "New Button" of pg "confirmation" of pad
"D:\VPAD\VCRPROTO.PAD"

Handler Select;
Begin
    global cancelit;
    if cancelit = 0 then
    begin
        put "" into pg fld "date3";
        put " : " into pg fld "startime3";
        put "" into pg fld "stoptime3";
        put "" into pg fld "channel3";
        put "" into pg fld "speed3";
        put 5 into cancelit
    End
    else begin
        global changeit;
        if changeit = 0 then
        begin
            put "" into pg fld "date3";
            put " : " into pg fld "startime3";
            put "" into pg fld "stoptime3";
            put "" into pg fld "channel3";
            put "" into pg fld "speed3";
            put 5 into changeit;
            go to pg "select the program";
        End;
    end;
end;

Script of btn "clear 3" of pg "confirmation" of pad
"D:\VPAD\VCRPROTO.PAD"

Handler Select;
Begin
    global cancelit;
    if cancelit = 0 then
    begin
        logconfline(3);
        put "" into pg fld "date3";
        put " : " into pg fld "startime3";
        put " : " into pg fld "stoptime3";
        put "" into pg fld "channel3";
        put "" into pg fld "speed3";
        put 5 into cancelit
    End
    else begin
        global changeit;
        if changeit = 0 then
        begin
            logconfline(3);
            put "" into pg fld "date3";
            put " : " into pg fld "startime3";
            put " : " into pg fld "stoptime3";
            put "" into pg fld "channel3";
            put "" into pg fld "speed3";
            put 5 into changeit;
            go to pg "select the program";
        End;
    end;
end;

Script of btn "Help" of pg "confirmation" of pad
"D:\VPAD\VCRPROTO.PAD"

handler select;
begin
    global mode;
    put "Review" into mode;
    PUT "  PROGRAM REVIEW" INTO PG FLD "status" OF PG "tape status";
    PUSH THIS PG;
    GO TO PG "HELP";
end;

Script of pg "February 1990" of pad "D:\VPAD\VCRPROTO.PAD"

handler openpage;
begin
    global settime,checkit;
    put empty into pg fld "day of month";
    set focus to pg fld "day of month";
    if settime = 0 then
        put "Select today's date" into pg fld "Current"
    else
        put "Record on" into pg fld "current";
    put "" into pg fld "day of month";
        makemonth;
    pass;
end;

Script of btn "New Month" of pg "February 1990" of pad
"D:\VPAD\VCRPROTO.PAD"

Handler Select;
Begin
    go to pg "select the month";
End;
```

Script of btn "Help" of pg "February 1990" of pad
"D:\VPAD\VCRPROTO.PAD"

handler select;
begin
  PUSH THIS PG;
  GO TO PG "HELP";
end;

Script of pg "status" of pad "D:\VPAD\VCRPROTO.PAD"

handler openpage;
begin
global timelog;
 put timelog into pg fld "log";
 set cursor to thin;
end;

handler closepage;
begin
( set cursor to off;)
 put empty into pg fld "log";
 end;

handler pagetime(pagenum);
Begin
 global timelog;
 put 1 into linenum;
 get line linenum of timelog;
 repeat
   if the first word of it="OP:" then
     if (the name of pg pagenum) is in it then
     begin
       put the last word of it into opentime;
       repeat
         add one to linenum;
         get line linenum of timelog;
         until the first word of it = "CP:";
       put the last word of it into closetime;
       put "entered: " & opentime & " exited: " & closetime
& " time: " &
         closetime-opentime & return after pg fld "log";
     end;
     add one to linenum;
     get line linenum of timelog;End;
   until it = the last line of timelog;
End;

Script of btn "Return" of pg "status" of pad
"D:\VPAD\VCRPROTO.PAD"

Handler Select;
Begin
 pop pg;
End;

Script of btn "Page time" of pg "status" of pad
"D:\VPAD\VCRPROTO.PAD"

Handler Select;
Begin
 global timelog;
 put empty into pg fld "log";
 ask "Which pg?";
 put it into pagenum;
 pagetime(pagenum);
 beep(2);

End;

Script of btn "all pg times" of pg "status" of pad
"D:\VPAD\VCRPROTO.PAD"

Handler Select;
Begin
 put empty into pg fld "log";
 put the number of pages into lastpage;
 for pagenum=1 to lastpage do
 begin
   get the name of pg pagenum;
   put "Page "& it & return after pg fld "log";
   pagetime(pagenum);
   put return after pg fld "log";
 end;
  beep( 4);
End;

Script of btn "reset file" of pg "status" of pad
"D:\VPAD\VCRPROTO.PAD"

Handler Select;
Begin
 put 1 into pg fld "Subject info";
 get the first line of pg fld "File Name";
 put the create of it into temp;
 write return to temp;
 close temp;
End;

Script of btn "Page Data" of pg "status" of pad
"D:\VPAD\VCRPROTO.PAD"

Handler Select;
Begin
 put the create of "verb.pag" into fl;
 go to pg 1;
 for x=1 to the number of pages do
 begin
   write the name of this pg & return to fl;
   go to the next pg;
 end;
 close fl;

Script of Pad D:\HPAD\COMPUTE5.PAD

```
handler readfile;
begin
  global pagenames;
  if pagenames=empty then begin
    get the first line of pg fld "pagefilename" OF PG 2;
    put the open of it into fl;
    read from fl until end;
    put it into pagenames;
    close fl;
  end;
end;

function stats(dat);
  begin
    put the number of items of dat into numitems;
    put the first item of dat into tmin;
    put tmin into tmax;
    put tmin into tsum;
    for x=2 to numitems do begin
      get item x of dat;
      if it < tmin then put it into tmin;
      if it > tmax then put it into tmax;
      add it to tsum;
    end;
    put numitems && "NUMBER OF ITEMS" & return after temp;
    put tmin && "MIN" & return after temp;
    put tmax && "MAX" & return after temp;
    put tsum && "SUM" & return after temp;
    PUT tSUM/numitems && "AVG" & RETURN AFTER TEMP;
    do "put stdev(" & dat & ") into msg";
    put msg & " standard deviation" & return after temp;
    return temp
end;

handler openpad;
  begin
    global bold,normal,xypage;
    put "(" into xyleft;
    put ")" into xyright;
    put xyleft & "mdbo" & xyright into bold;
    put xyleft & "mdnm" & xyright into normal;
    put xyleft & "pg" & xyright into xypage;
end;

handler closepad;
  begin
    if the freesize > 5000 then domenu "compress";
end;
```

Script of bkgnd pg "subjects" of pad "D:\HPAD\COMPUTE5.PAD"

```
handler cleanup;
begin
  go to pg "base";
  go to the next pg;
  put the number of pages into temp;
  put currentpage() into x1;
  for x = x1 to temp do
    domenu "delete pg";
end;

handler printpage;

Begin
global bold,normal,xypage;
  print xypage & RETURN & bold & fld "user info" & normal & return;
  print return;
  print bold & "Page time log" &normal & return;
  PRINT (bg FLD "pagelog") ;
  print return;
  print bold & "Error log:"& normal & return;
  PRINT (bg FLD "ACTIONLOG");
  print return;
  print bold & "Users Actions:" & normal & return;
  PRINT (bg FLD "MOUSELOG");
  print return;
  print bold & "Programs set" & normal & return;
  PRINT (bg FLD "PROGRAMS");
  print return;
  print bold & "Page summary" & normal & return;
  print (bg fld "pg stats");
  print return;
  print bold & "COUNT:" & normal;
  print (bg fld "count");
  print return;
  print bold & "WASTED TIME:" & normal;
  print (bg fld "waste");
  print return;
  Print bold & "TOTAL TIME = Time - Waste=" & normal;
  print (bg fld "total") &return &return;
End;

handler breakup;
begin
  global timelog;
  PUT FALSE INTO DONE;
  get the first line of pg fld "filename" OF PG 2;
  put the open of it into fl;
  put 1 into count;
  REPEAT BEGIN
    READ ONE LINES FROM FL;
    put the first word of it into ltype;
    delete the first word of it;
    case ltype of
      "NS:" :begin
              if bg fld "mouselog" () empty then
              begin
                send "select" to bg btn "waste";
                send "select" to bg btn "count";
                send "select" to bg btn "pg stats";
                send "select" to bg fld "pgs opened";
              end;
              put it into subject;
              domenu "new pg";
              PUT SUBJECT INTO BG FLD "USER INFO";
              set the name of this pg to subject;
            end;
      "OP:" :put the last word of it into opentime;
      "CP:" :begin
              put it into temp;
              delete the last word of temp;
              put "," & opentime & "," & (the last word of it-opentime) & return        after temp;
              put temp after bg fld "pagelog" ;
            end;
      "MD:" :put it & return after bg fld "mouselog" ;
      "LK:" :put it & return after bg fld "mouselog";
      "LA:" :put it & return after bg fld "actionlog";
      "CL:" :put it & return after bg fld "programs";
      "END:" :PUT TRUE INTO DONE;
      "" : begin add 1 to count;
```

```
              put count )50 into done;
            end;
        otherwise: answer "not known :" & it;
    end; END;
    UNTIL DONE;
            send "select" to bg btn "waste";
            send "select" to bg btn "count";
            send "select" to bg btn "pg stats";
            send "select" to bg fld "pgs opened";
    beep 4;
end;
```

Script of bkgnd btn "PRINT" of bkgnd pg "subjects" of pad
"D:\VPAD\COMPUTE5.PAD"

```
Handler Select;
Begin
  SET THE PRINTER TO ON;
  printpage;
  SET THE PRINTER TO OFF;
End;
```

Script of bkgnd btn "COUNT" of bkgnd pg "subjects" of pad
"D:\VPAD\COMPUTE5.PAD"

```
Handler Select;
Begin
put empty into bg fld "total";
put empty into bg fld "count";
put the number of lines of bg fld "mouselog" into bg fld
"count";
put bg fld "count" into temp;
subtract 1 from temp;
get line temp of bg fld "mouselog";
put the last word of it into bg fld "total";
End;
```

Script of bkgnd btn "waste" of bkgnd pg "subjects" of pad
"D:\VPAD\COMPUTE5.PAD"

```
Handler Select;
Begin
  put empty into bg fld "waste";
  put 0 into waste;
  get line 1 of bg fld "pagelog";
  put item 2 of it into temp1;
  put item 3 of it into tot2;
  add item 3 of it to temp1;
    for x = 2 to the number of lines of bg fld "pagelog" do
  begin
  get line x of bg fld "pagelog";
  if item 2 of it () 0 then
      begin
          add item 2 of it to waste;
          subtract temp1 from waste
      end
      else
      begin
      end;
  put item 2 of it into temp1;
  add item 3 of it to temp1;
  add item 3 of it to tot2
  end;
  subtract item 2 of it from tot2;
  put waste after bg fld "waste";
End;
```

Script of bkgnd btn "pg Stats" of bkgnd pg "subjects" of pad
"D:\VPAD\COMPUTE5.PAD"

```
Handler Select;
Begin
  global pagenames;
  put empty into temp;
  put (the number of lines of pagenames)-1 into namelines;
  for x=1 to namelines do
     put "0,0" & return after temp;
  put (the number of lines of bg fld "pagelog")-1 into
pagelines;
  for x=1 to pagelines do
  begin
     get line x of bg fld "pagelog";
     put 1 into y;
     put false into found;
     put trim(the first item of it) into trimed;
     repeat
        if trimed=line y of pagenames then begin
           put line y of temp into temp2;
           add 1 to item 1 of temp2;
           add item 3 of it to item 2 of temp2;
           put temp2 into line y of temp;
           put true into found;
        end;
        add 1 to y;
     until found or y)namelines;
     if not found then begin
        answer "pg does not exist:" && trimed;
        if it () "OK" then exit;
     end;
  end;
  for x=1 to namelines do
     put line x of pagenames before item 1 of line x of temp;
  put temp into bg fld "pg stats";
  beep 1;
End;
```

Script of bkgnd fld "pgs opened" of bkgnd pg "subjects" of
pad "D:\VPAD\COMPUTE5.PAD"

```
handler select;
begin
  put (the number of lines of bg fld "pagelog") -1 & return
into me;
end;
```

Script of btn "Read from file" of pg "data" of pad
"D:\VPAD\COMPUTE5.PAD"

```
Handler Select;
Begin
  global pagenames;
  put empty into pagenames;
  readfile;
End;
```

Script of btn "Clean Up File" of pg "data" of pad
"D:\VPAD\COMPUTE5.PAD"

```
Handler Select;
begin
  PUT FALSE INTO DONE;
  get the first line of pg fld "filename";
  put the open of it into fl;
  put the create of "convert.dat" into outfile;
```

B-34

```
put 1 into count;
put 0 into phil;
put 0 into linda;
put 0 into hold;
put false into done;

REPEAT
  READ ONE LINES FROM FL;
  put the first word of it into ltype;
  case ltype of
    "NS:" :begin
             put 0 into phil;
             put 0 into linda;
           end;
    "" : begin add 1 to count;
             put count )50 into done;
         end;
    "CL:" : ;

otherwise: begin
      put the last word of it into hold;
      if hold ( phil then
        put phil into linda;
      put hold into phil;
      delete the last word of it;
      add linda to hold;
      put hold after it;
    END;
  end;
  write it & return to outfile;
UNTIL DONE;
beep 4;
close fl;
close outfile;
End;
```

Script of btn "Print all data" of pg "data" of pad "D:\HPAD\COMPUTES.PAD"

```
Handler Select;
Begin
  go to pg 3;
  set the printer to on;
  for x=3 to the number of pages do begin
    send "printpage" to this pg;
    go to the next pg;
  end ;
  set the printer to off;
  put "T255 01 L8 G 02 CEG P1 E L2 G" into trumpet;
  play trumpet;
End;
```

Script of btn "process data" of pg "data" of pad "D:\HPAD\COMPUTES.PAD"

```
Handler Select;
Begin
  readfile;
  go to pg "base";
  go to the next pg;
  send "cleanup" to this pg;
  go to pg "base";
  set lockscreen to true;
  send "breakup" to this pg;
  go to pg 3;
  send "select" to pg btn "total";
  send "select" to pg btn "statistics";
  go to the next pg;
  send "select" to pg btn "ok total";
  send "select" to pg btn "statistics";
  go to the next pg;
    send "select" to pg btn "count";
  send "select" to pg btn "statistics";
  send "select" to pg btn "errors";
  send "select" to pg btn "error stats";
  send "select" to pg btn "adjusted count";
  go to the next pg;
    send "select" to pg btn "wasted computer time";
  go to the next pg;
  send "select" to pg btn "pages opened";
  send "select" to pg btn "pg stats";
  go to pg 2;
  set lockscreen to false;
  send "select" to pg btn "print all data";
  put "T255 01 L8 G 02 CEG P1 E L2 G" into trumpet;
  play trumpet;
End;
```

Script of btn "Process Stats" of pg "data" of pad "D:\HPAD\COMPUTES.PAD"

```
Handler Select;
Begin
  go to pg 3;
  set lockscreen to true;
  send "select" to pg btn "total";
  send "select" to pg btn "statistics";
  go to the next pg;
  send "select" to pg btn "ok total";
  send "select" to pg btn "statistics";
  go to the next pg;
    send "select" to pg btn "count";
  send "select" to pg btn "statistics";
  send "select" to pg btn "errors";
  send "select" to pg btn "error stats";
  send "select" to pg btn "adjusted count";
  go to the next pg;
    send "select" to pg btn "wasted computer time";
  go to the next pg;
  send "select" to pg btn "pages opened";
  send "select" to pg btn "pg stats";
  go to pg 2;
  set lockscreen to false;
  put "T255 01 L8 G 02 CEG P1 E L2 G" into trumpet;
  play trumpet;
End;
```

Script of pg "analyzing" of pad "D:\HPAD\COMPUTES.PAD"

```
handler printpage;
Begin
GLOBAL BOLD,NORMAL;
  print BOLD & "Total time per user" & NORMAL &return;
  print return;
  print BOLD & "TOTAL Statistics" & NORMAL & return;
  PRINT (pg fld "TOTAL stats" of pg "ANALYZING");
  print return;
  print BOLD & "Total Time" & NORMAL & return;
  PRINT (pg FLD "total time");
  print return;
  PRINT BOLD & "TOTAL TIME - WASTED COMPUTER TIME" & NORMAL
  & RETURN;
  PRINT (PG FLD "TOTAL - WASTED TIME");
  PRINT RETURN;
```

```
     PRINT BOLD & "TOTAL - WASTED STATISTICS" & NORMAL &
RETURN;
     PRINT (PG FLD "TOTAL - WASTE STATS");
     PRINT RETURN;
     print return;
End;

Script of btn "Total" of pg "analyzing" of pad
"D:\VPAD\COMPUTES.PAD"

Handler Select;
Begin
     put empty into pg fld "total time";
     PUT EMPTY INTO PG FLD "TOTAL - WASTED TIME";
     put empty into pg fld "TOTAL stats";
     PUT EMPTY INTO PG FLD "TOTAL - WASTE STATS";
     go to pg "base";
     go to the next pg;
     put currentpage() into x1;
     for x=x1 to the number of pages do
     begin
     PUT the last word of bg fld "total" INTO TEMP1;
     PUT THE LAST WORD OF BG FLD "WASTE" INTO TEMP2;
     GET THE NAME OF THIS PG;
     PUT THE FIRST WORD OF IT && THE THIRD WORD OF IT INTO
TEMP;
     put TEMP && TEMP1 & return after pg fld "total time" of pg
"analyzing";
     SUBTRACT TEMP2 FROM TEMP1;
     PUT TEMP && TEMP2 & RETURN AFTER PG FLD "TOTAL - WASTED
TIME" OF PG "ANALYZING";
     go to the next pg;
     end;
     go to pg "analyzing";
     beep 4;
End;

Script of btn "Statistics" of pg "analyzing" of pad
"D:\VPAD\COMPUTES.PAD"

Handler Select;
Begin
     put empty into pg fld "TOTAL stats";
     PUT EMPTY INTO PG FLD "TOTAL - WASTE STATS";
     put empty into allnums;
          for x= 1 to (the number of lines of pg fld "total
time") - 1 do
          begin
               get line x of pg fld "total time";
               put the last word of it & "," after allnums;
               GET LINE X OF PG FLD "TOTAL - WASTED TIME";
               PUT THE LAST WORD OF IT & "," AFTER WASTENUMS;
          end;
          delete the last char of allnums;
          DELETE THE LAST CHAR OF WASTENUMS;
          put allnums && "allnums" & return after pg fld
"TOTAL stats";
          put stats(allnums) after pg fld "TOTAL stats";
          put WASTENUMS && "WASTENUMS" & return after pg fld
"TOTAL - WASTE STATS";
          put stats(WASTENUMS) after pg fld "TOTAL - WASTE
stats";
          beep 4;
     End;

Script of btn "PRINT" of pg "analyzing" of pad
"D:\VPAD\COMPUTES.PAD"

Handler Select;
Begin
     SET THE PRINTER TO ON;
     printpage;
     SET THE PRINTER TO OFF;
End;

Script of pg "ok" of pad "D:\VPAD\COMPUTES.PAD"

handler printpage;
begin
     global bold,normal;
     print bold & "OK total"& normal & return;
     print (pg fld "stats");
     print return& return;
end;

Script of btn "ok total" of pg "ok" of pad
"D:\VPAD\COMPUTES.PAD"

Handler Select;
Begin
     { MENTAL OK TIME }
     if (the fourth char of pg fld "pagefilename" of pg 2)
="a" then
          put "(C)" into test
     else put "OK" into test;
     put empty into pg fld "temp";
     put empty into pg fld "stats";
     go to pg "base";
     go to the next pg;
     put currentpage() into x1;
     for y=x1 to the number of pages do
          begin
               put (the number of lines of bg fld "mouselog") into
loops;
          for x=1 to loops do
          begin
               get line x of bg fld "mouselog";
               if it contains test then
               begin
                    put the name of this pg into temp1;
                    put line (x-1) of bg fld "mouselog" into
temp2a;
                    put the last word of temp2a into temp2;
                    put it into temp3a;
                    put the last word of temp3a into temp3;
                    subtract temp2 from temp3;
                    put the third word of temp1 && temp2a & ";" &&
                         temp3a & ";" && temp3 & return after pg fld
"temp" of pg "ok";
               end;
          end;
          go to the next pg;
     end;
     go to pg "ok";
     beep 4;
End;

Script of btn "statistics" of pg "ok" of pad
"D:\VPAD\COMPUTES.PAD"

Handler Select;
Begin
     put empty into pg fld "stats";
     put empty into allnums;
```

```
put (the number of lines of pg fld "temp") - 1 into nl;
for x= 1 to nl do
    begin
        get line x of pg fld "temp";
        put the last word of it & "," after allnums;
    end;
    delete the last char of allnums;
    put allnums && "allnums" & return after pg fld
"stats";
    put stats(allnums) after pg fld "stats";
    beep 4;
End;
```

Script of pg "count" of pad "D:\VPAD\COMPUTES.PAD"

```
handler printpage;
begin
    global bold,normal;
    print bold & "Mouse /key pressed data" &normal &return;
    print (pg fld "stats");
    print return;
    print bold & "# of Errors Made Per Subject" & normal &
return;
    print (pg fld "errors");
    print return;
    print bold & "Error Statistics" & normal & return;
    print (pg fld "error stats");
    print return;
    print bold & "Adjusted Count (Count + Errors)" & normal &
return;
    print (pg fld "Adjusted Count");
    print return;
end;
```

Script of btn "COUNT" of pg "count" of pad "D:\VPAD\COMPUTES.PAD"

```
Handler Select;
Begin
put empty into pg fld "count";
put empty into pg fld "stats";
go to pg "base";
go to next pg;
put currentpage() into x1;
for x=x1 to the number of pages do
begin
    get the number of lines of bg fld "mouselog";
    put the last word of it & return after pg fld "count" of
pg "count";
    go to the next pg;
end;
go to pg "count";
beep 4;
End;
```

Script of btn "Statistics" of pg "count" of pad "D:\VPAD\COMPUTES.PAD"

```
Handler Select;
Begin
    put empty into pg fld "stats";
    put 0 into mean;
    put 0 into temp1;
    put 0 into temp2;
    put empty into allnums;
    for x= 1 to (the number of lines of pg fld "count") - 1
do
```

```
begin
    get line x of pg fld "count";
    put the last word of it into temp1;
    put the last word of it & "," after allnums;
    add temp1 to mean;
end;
delete the last char of allnums;
put allnums && "allnums" & return after pg fld
"stats";
    put stats(allnums) after pg fld "stats";
        beep 4;
End;
```

Script of btn "Errors" of pg "count" of pad "D:\VPAD\COMPUTES.PAD"

```
Handler Select;
Begin
    put empty into pg fld "errors";
    put empty into pg fld "error stats";
    put empty into pg fld "adjusted count";
    go to pg "base";
    go to next pg;
    put currentpage() into x1;
    for x=x1 to the number of pages do
begin
    get the number of lines of bg fld "actionlog";
    subtract 1 from the last word of it;
    put the last word of it & return after pg fld "errors" of
pg "count";
    go to the next pg;
end;
go to pg "count";
beep 4;
End;
```

Script of btn "Error Stats" of pg "count" of pad "D:\VPAD\COMPUTES.PAD"

```
Handler Select;
Begin
    put empty into pg fld "error stats";
    put 0 into mean;
    put 0 into temp1;
    put 0 into temp2;
    put empty into allnums;
    for x= 1 to (the number of lines of pg fld "errors") -
1 do
        begin
            get line x of pg fld "errors";
            put the last word of it into temp1;
            put the last word of it & "," after allnums;
            add temp1 to mean;
        end;
        delete the last char of allnums;
        put allnums && "allnums" & return after pg fld
"error stats";
        put stats(allnums) after pg fld "error stats";
        beep 4;
End;
```

Script of btn "Adjusted Count" of pg "count" of pad "D:\VPAD\COMPUTES.PAD"

```
Handler Select;
Begin
    put empty into pg fld "adjusted count";
```

```
for x=1 to (the number of lines of pg fld "count")-1 do
begin
    get line x of pg fld "count";
    put the last item of it into temp;
    get line x of pg fld "errors";
    add the last item of it to temp;
    put temp & "," after pg fld "adjusted count";
end;
delete the last char of pg fld "adjusted count";
get pg fld "adjusted count";
put return & stats(it) after pg fld "adjusted count";
beep 4;
End;
```

Script of pg "waste stats" of pad "D:\HPAD\COMPUTES.PAD"

```
handler printpage;
begin
    global bold,normal;
    print bold & "Wasted time data"& normal &return;
    print (pg fld "stats");
    print return & return;
end;
```

Script of btn "wasted computer time" of pg "waste stats" of pad "D:\HPAD\COMPUTES.PAD"

```
Handler Select;
Begin
    put empty into pg fld "waste";
    put empty into pg fld "stats";
    put empty into temp1;
    put empty into allnums;
    go to pg "base";
    go to next pg;
    put currentpage() into x1;
    for x=x1 to the number of pages do
    begin
        get bg fld "waste";
        put the name of this pg into temp10;
        put the third word of temp10 && it & return after pg fld "waste" of pg "waste stats";
        go to the next pg;
    End;
    go to pg "waste stats";
    for x= 1 to (the number of lines of pg fld "waste") - 1 do
        begin
            get line x of pg fld "waste";
            put the last word of it into temp1;
            put the last word of it & "," after allnums;
            add temp1 to mean;
        end;
            delete the last char of allnums;
            put allnums && "allnums" & return after pg fld "stats";
    put stats(allnums) after pg fld "stats";
    go to pg "waste stats";
beep 4;
End;
```

Script of pg "pg times" of pad "D:\HPAD\COMPUTES.PAD"

```
handler printpage;
begin
    global bold,normal;
    print bold & "total pg stats (# number of pages opened)"& normal & return;
    print (pg fld "pg stats");
    print return & return;
end;
```

Script of btn "pages opened" of pg "pg times" of pad "D:\HPAD\COMPUTES.PAD"

```
Handler Select;
Begin
    put empty into pg fld "pages opened";
    put empty into pg fld "pg stats";
    go to pg "base";
    go to next pg;
    put currentpage() into x1;
    for x=x1 to the number of pages do
    begin
        get the name of this pg;
        put the third word of it into temp10;
        get bg fld "pgs opened";
        put temp10 & "," && it after temp;
        go to the next pg;
    end;
    go to pg "pg times";
    put temp into pg fld "pages opened";
    beep 4;
End;
```

Script of btn "pg stats" of pg "pg times" of pad "D:\HPAD\COMPUTES.PAD"

```
Handler Select;
Begin
    put empty into pg fld "pg stats";
    put empty into allnums;
        for x= 1 to (the number of lines of pg fld "pages opened") - 1 do
            begin
                get line x of pg fld "pages opened";
                put the last word of it & "," after allnums;
            end;
            delete the last char of allnums;
            put allnums && "allnums" & return after pg fld "pg stats";
            put stats(allnums) after pg fld "pg stats";
beep 4;
End;
```

Script of pg "individual pages" of pad "D:\HPAD\COMPUTES.PAD"

```
handler printpage;
begin
    global bold,normal;
    print bold & "pg stats by pg" & normal & return;
    print bold & "stats on number of times pg entered"& normal & return & return;
    send "select" to pg btn "pg entered";
    send "select" to pg btn "stats";
    print (pg fld "stats");
    print return;
    print bold & "stats on the amount of time spent in each pg" & normal & return &return;
    send "select" to pg btn "pg seconds";
    send "select" to pg btn "stats";
    print (pg fld "stats");
    print return;
    print bold & "average time spent in each pg per pg" &
```

```
normal & return & return;
  send "select" to pg btn "seconds per entry";
  send "select" to pg btn "stats";
  print (pg fld "stats");
  print return;
end;
```

Script of btn "get data" of pg "individual pages" of pad "D:\WPAD\COMPUTES.PAD"

```
Handler Select;
Begin
readfile;
global pagenames;
put empty into pg fld "individual pages";
put empty into pg fld "stats";
put empty into temp;
put (the number of lines of pagenames)-1 into namelines;
put namelines into temp;
  for x=1 to namelines do
    put "0,0" & return after temp;
go to pg "base";
go to next pg;
put currentpage() into pg1;
  for ps=pg1 to the number of pages do
  begin
    for x=1 to namelines do
    begin
      get line x of bg fld "pg stats";
      add the second item of it to the first item of line x
of temp;
      add the third item of it to the second item of line x
of temp;
    end;
    go to the next pg;
end;
go to pg "individual pages";
  for x=1 to namelines do
    put line x of pagenames before item 1 of line x of temp;
  put temp into pg fld "individual pages";
beep 4;
End;
```

Script of btn "stats" of pg "individual pages" of pad "D:\WPAD\COMPUTES.PAD"

```
Handler Select;
Begin
global normal,bold;
  put empty into pg fld "stats";
  put (the number of lines of pg fld "individual pages")-1
into nl;
  for x=1 to nl do
  begin
    put line x of pg fld "individual pages" into dat;
    get the first item of dat;
    put "Page name: " & bold & it & normal & return after pg
fld "stats";
    delete the first item of dat;
    put dat & return after pg fld "stats";
    if (the number of items of dat))1 then
      put stats(dat) after pg fld "stats";
    put return after pg fld "stats";
  end;
  beep 4;
End;
```

Script of btn "pg seconds" of pg "individual pages" of pad "D:\WPAD\COMPUTES.PAD"

```
Handler Select;
Begin
readfile;
global pagenames;
put empty into pg fld "individual pages";
put empty into pg fld "stats";
put empty into temp;
put (the number of lines of pagenames)-1 into namelines;
put empty into temp;
  for x=1 to namelines do
    put "0,0" & return after temp;
go to pg "base";
go to next pg;
put currentpage()-1 into pg1;
  for ps=1 to (the number of pages)-pg1 do
  begin
    for x=1 to namelines do
    begin
      get line x of bg fld "pg stats";
      put the third item of it into item ps of line x of
temp;
    end;
    go to the next pg;
end;
go to pg "individual pages";
  for x=1 to namelines do
    put line x of pagenames & " " before item 1 of line x of
temp;
  put temp into pg fld "individual pages";
beep 4;
End;
```

Script of btn "pg entered" of pg "individual pages" of pad "D:\WPAD\COMPUTES.PAD"

```
Handler Select;
Begin
readfile;
global pagenames;
put empty into pg fld "individual pages";
put empty into pg fld "stats";
put empty into temp;
put (the number of lines of pagenames)-1 into namelines;
put empty into temp;
  for x=1 to namelines do
    put "0,0" & return after temp;
go to pg "base";
go to next pg;
put currentpage()-1 into pg1;
  for ps=1 to (the number of pages)-pg1 do
  begin
    for x=1 to namelines do
    begin
      get line x of bg fld "pg stats";
      put the second item of it into item ps of line x of
temp;
    end;
    go to the next pg;
end;
go to pg "individual pages";
  for x=1 to namelines do
    put line x of pagenames& " " before item 1 of line x of
temp;
    put temp into pg fld "individual pages";
```

```
beep 4;
End;
```

Script of btn "seconds per entry" of pg "individual pages"
of pad "D:\VPAD\COMPUTES.PAD"

```
Handler Select;
Begin
readfile;
global pagenames;
put empty into pg fld "individual pages";
put empty into pg fld "stats";
put empty into temp;
put (the number of lines of pagenames)-1 into namelines;
put empty into temp;
  for x=1 to namelines do
    put "," & return after temp;
go to pg "base";
go to next pg;
put currentpage()-1 into pg1;
  for ps=1 to (the number of pages)-pg1 do
  begin
    for x=1 to namelines do
      begin
        get line x of bg fld "pg stats";
        if the second item of it () 0 then begin
          put line x of temp into temp2;
          put the third item of it/the second item of it
after the last item of temp2;
          put temp2 into line x of temp;
        end;
      end;
    go to the next pg;
  end;
go to pg "individual pages";
  for x=1 to namelines do
    put line x of pagenames & " " before item 1 of line x of
temp;
  put temp into pg fld "individual pages";
beep 4;
End;
```

Script of btn "cleanup" of pg "base" of pad
"D:\VPAD\COMPUTES.PAD"

```
Handler Select;
Begin
  cleanup;
End;
```

Script of btn "process data" of pg "base" of pad
"D:\VPAD\COMPUTES.PAD"

```
Handler Select;
Begin
  readfile;
  go to pg "base";
  go to the next pg;
  cleanup;
  go to pg "base";
  set lockscreen to true;
  breakup;
  go to pg 3;
  send "select" to pg btn "total";
  send "select" to pg btn "statistics";
  go to the next pg;
  send "select" to pg btn "ok total";
  send "select" to pg btn "statistics";
  go to the next pg;
   send "select" to pg btn "count";
  send "select" to pg btn "statistics";
  go to the next pg;
   send "select" to pg btn "wasted computer time";
  go to the next pg;
  send "select" to pg btn "pages opened";
  send "select" to pg btn "pg stats";
  go to pg 2;
  set lockscreen to false;
  send "select" to pg btn "print all data";
  put "T255 O1 L8 G O2 CEG P1 E L2 G" into trumpet;
  play trumpet;
End;
```

APPENDIX C ● PICTURES OF THE INTERFACES

SCREENS FROM THE EXISTING VCR
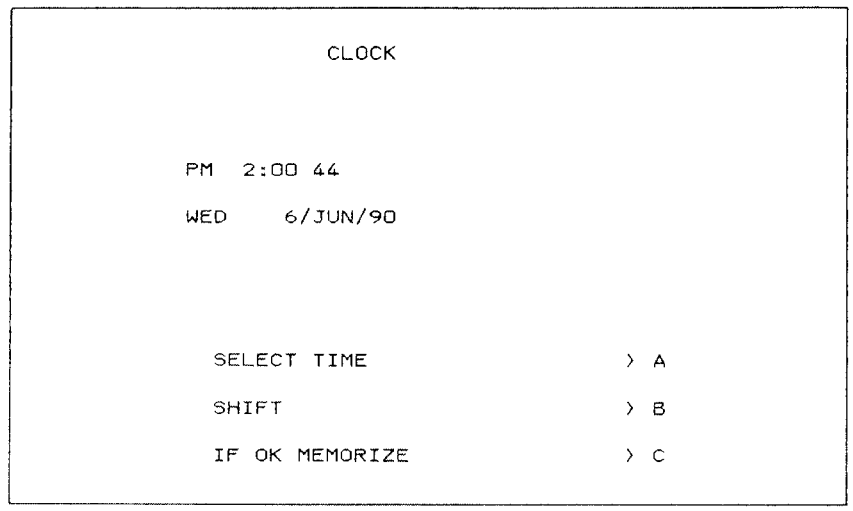
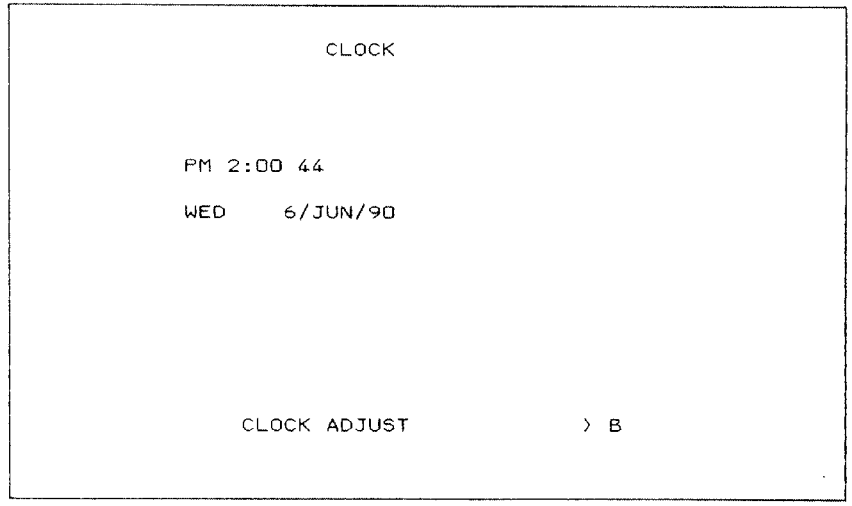
C-1

```
1   M-F      AM 3:00    4
2   2.SUN    PM8:00     5
3   4.TUE    PM9:30     8
4

SELECT PROGRAM NO.             > A
```

```
            PROGRAM  2

PM11:00        AM12:00
   2ND. TUE       10/JUN/90
   8

SELECT CHANNEL              > A
   SHIFT                       > B
   IF OK MEMORIZE              > C
```

C-2

```
                    TIMER

FINISHED              > C
```

C-3

THE NEW INTERFACE
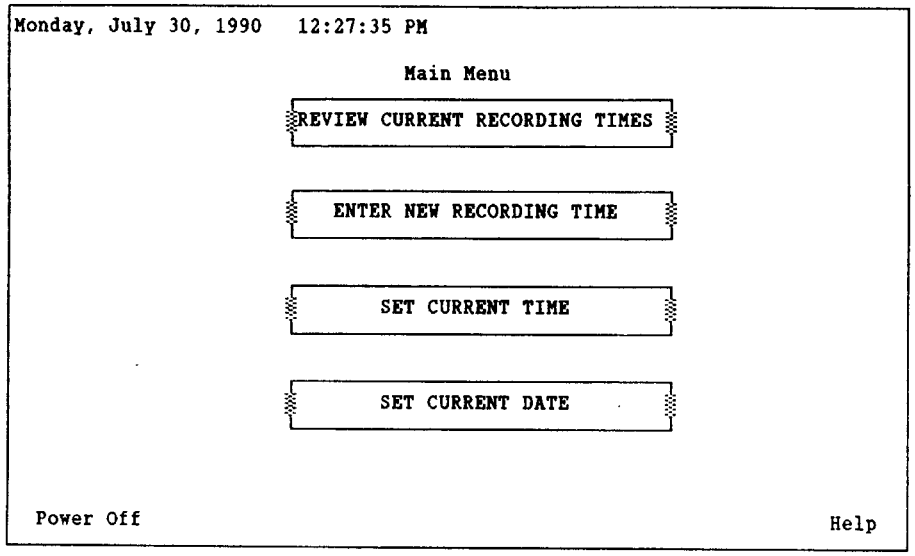
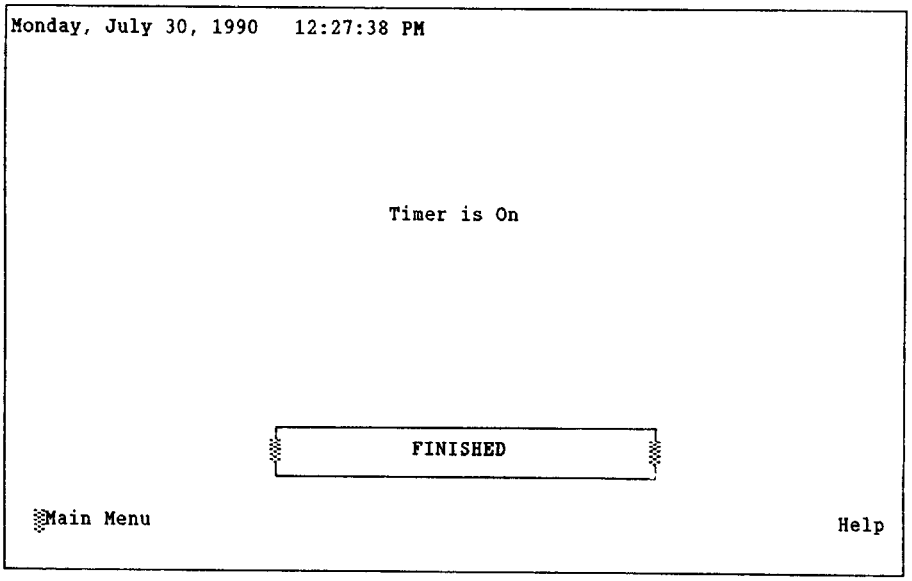

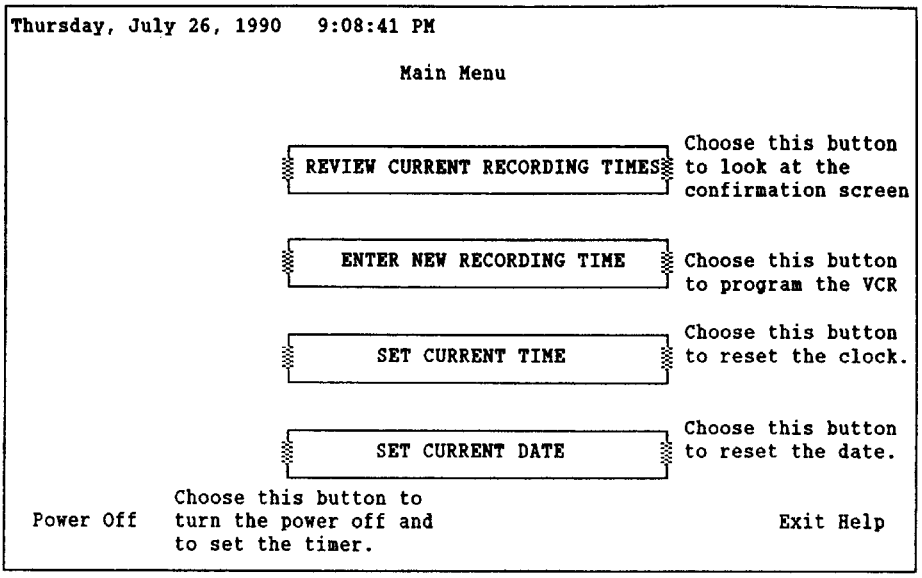
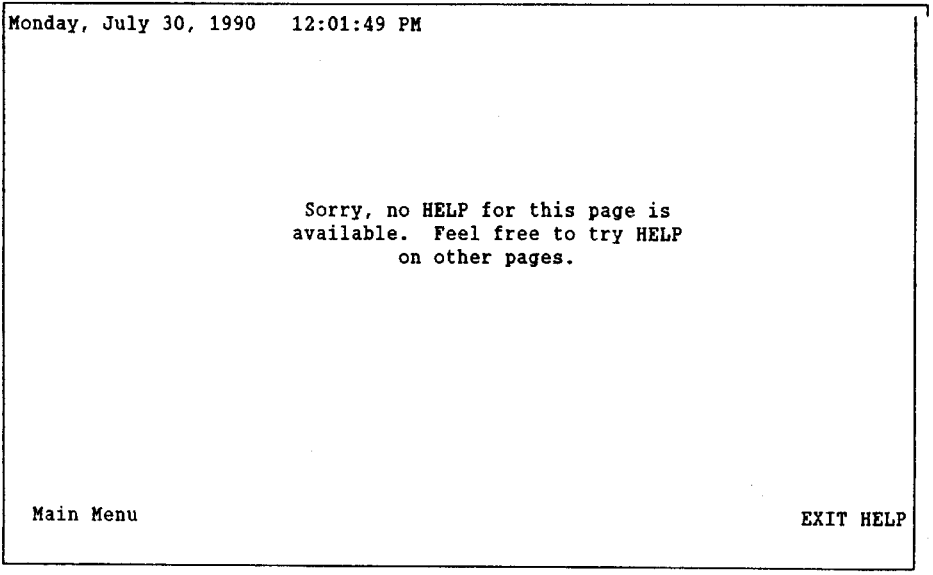
C-5

```
Monday, July 30, 1990    12:27:32 PM

Enter the Current Time:
                                    ┌─────┬─────┬─────┐
                      AM            │  7  │  8  │  9  │
          ┌───────┐                 ├─────┼─────┼─────┤
          │   :   │                 │  4  │  5  │  6  │
          └───────┘   PM            ├─────┼─────┼─────┤
                                    │  1  │  2  │  3  │
                                    ├─────┼─────┼─────┤
                                    │Noon │  0  │Midnight│
                                    └─────┴─────┴─────┘

Clear

Main Menu                    OK                    Help
```

```
Monday, July 30, 1990    12:27:31 PM   This line shows the current date & tim Enter the Current Time:
                                    ┌─────┬─────┬─────┐  To enter
                      AM            │  7  │  8  │  9  │  the time,
          ┌───────┐                 ├─────┼─────┼─────┤  press the
          │   :   │   PM            │  4  │  5  │  6  │  numbers.
          └───────┘                 ├─────┼─────┼─────┤
  When entering the numbers they    │  1  │  2  │  3  │
  scroll to the left.  For          ├─────┼─────┼─────┤
  example when setting for 2 AM     │Noon │  0  │Midnight│
  it will look like 2:00 AM.        └─────┴─────┴─────┘

Clear

Main Menu                    OK                    Exit Help
```

```
Monday, July 30, 1990    12:00:16 PM

Program Once on ...

Program Once a Week on ...

Program Monday - Friday at ...

Program EveryDay at ...

Main Menu                                        Help
```

```
Monday, July 30, 1990    12:00:43 PM

Today

Tomorrow

Any other day

Main Menu                                        Help
```

```
Thursday, July 26, 1990    9:09:30 PM

EX.  May 22, 1990
                     Program Once on ...           8:00pm-11:00pm EX.  Mondays
                Program Once a Week on ...         8:00pm-9:00pm EX.  Monday-Friday
              Program Monday - Friday at ...       3:00pm-4:00pm EX.  Everyday
                     Program EveryDay at ...       11:00pm-11:30p Main Menu                                                Exit Help
```

```
Thursday, July 26, 1990    9:03:21 PM
        Day to Record On ...     Wednesdays Mondays
                                             Fridays
                         Tuesdays
                                             Saturdays
                         Wednesdays
                                             Sundays
                         Thursdays Main Menu                                                     Help
```

```
Tuesday, January 1, 1980    12:00:10 PM
                    Setting the Date Select the Current Month January          February          March April            May               June July             August            September October          November          December Main Menu                                                Help
```

```
Tuesday, January 1, 1980    12:00:18 AM

Set the Current Year:            ┌─────┬─────┬─────┐
                                 │  7  │  8  │  9  │
                                 ├─────┼─────┼─────┤
         ┌─────┐                 │  4  │  5  │  6  │
         │     │                 ├─────┼─────┼─────┤
         └─────┘                 │  1  │  2  │  3  │
                                 └─────┼─────┼─────┘
                                       │  0  │
                                       └─────┘

Clear

Main Menu              OK                                Help
```

```
Monday, July 30, 1990    12:01:56 PM

Select the Channel:
                              ┌─────┐ ┌─────┐ ┌─────┐
                              │  7  │ │  8  │ │  9  │
                              └─────┘ └─────┘ └─────┘
         ┌─────┐
         │  2  │              ┌─────┐ ┌─────┐ ┌─────┐
         └─────┘              │  4  │ │  5  │ │  6  │
                              └─────┘ └─────┘ └─────┘

┌─────┐ ┌─────┐ ┌─────┐
                              │  1  │ │  2  │ │  3  │
                              └─────┘ └─────┘ └─────┘

┌─────┐
                                      │  0  │
                                      └─────┘
         Clear Main Menu                   OK                            Help
```

```
Monday, July 30, 1990    12:00:53 PM

Select the Start Time:
                              ┌─────┐ ┌─────┐ ┌─────┐
                       AM     │  7  │ │  8  │ │  9  │
      ┌────────────┐          └─────┘ └─────┘ └─────┘
      │  8:00 PM   │
      └────────────┘   PM     ┌─────┐ ┌─────┐ ┌─────┐
                              │  4  │ │  5  │ │  6  │
                              └─────┘ └─────┘ └─────┘

┌─────┐ ┌─────┐ ┌─────┐
                              │  1  │ │  2  │ │  3  │
                              └─────┘ └─────┘ └─────┘

┌─────┐ ┌─────┐ ┌────────┐
                              │Noon │ │  0  │ │Midnight│
                              └─────┘ └─────┘ └────────┘
         Clear Main Menu                   OK                            Help
```

C-10

```
Monday, July 30, 1990    12:01:53 PM

Select the Start Time:           ┌─────────────────────────┐
                                    │  ┌───┐  ┌───┐  ┌───┐    │
        ┌─────────┐                 │  │ 7 │  │ 8 │  │ 9 │    │
        │ 8:00 PM │                 │  └───┘  └───┘  └───┘    │
        └─────────┘                 │                         │
                                    │  ┌───┐  ┌───┐  ┌───┐    │
                                    │  │ 4 │  │ 5 │  │ 6 │    │
   Select the Stop Time:            │  └───┘  └───┘  └───┘    │
                              AM    │                         │
        ┌─────────┐                 │  ┌───┐  ┌───┐  ┌───┐    │
        │12:00 AM │                 │  │ 1 │  │ 2 │  │ 3 │    │
        └─────────┘           PM    │  └───┘  └───┘  └───┘    │
                                    │  ┌──────┐ ┌───┐ ┌────────┐ │
                                    │  │ Noon │ │ 0 │ │Midnight│ │
             Clear                  │  └──────┘ └───┘ └────────┘ │
                                    └─────────────────────────┘

Main Menu                   OK                              Help
```

```
Monday, July 30, 1990    12:01:58 PM

Select the Tape Speed:
                                    Standard Play
         LP Long Play Extended Play Main Menu                                                    Help
```

C-11

```
Monday, July 30, 1990    12:02:04 PM

Confirmation Screen

Program #    Date      Start Time    Stop Time    Channel    Speed

1                      :             :

2                      :             :

3                      :             :

4                      :             :

Cancel                                      Change

Main Menu                       OK                             Help
```

|  | | | July 1990 | | | |
|---|---|---|---|---|---|---|
| SUN | MON | TUE | WED | THUR | FRI | SAT |
| 1 | 2 | 3 | 4 | 5 | 6 | 7 |
| 8 | 9 | 10 | 11 | 12 | 13 | 14 |
| 15 | 16 | 17 | 18 | 19 | 20 | 21 |
| 22 | 23 | 24 | 25 | 26 | 27 | 28 |
| 29 | 30 | 31 | | | | |

New Month

Help

C-12

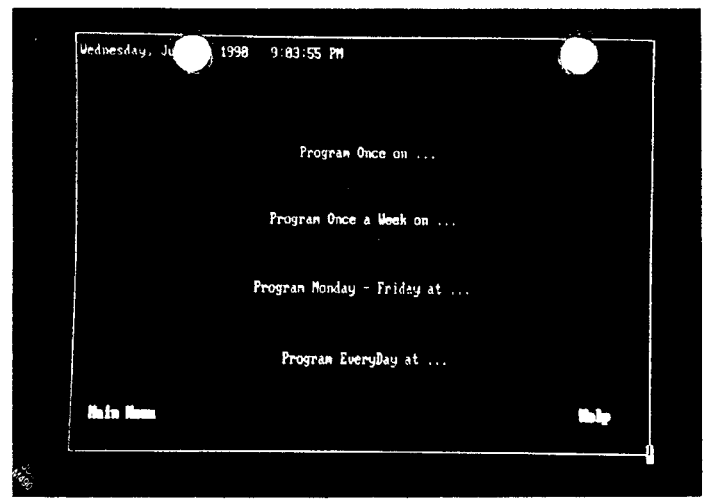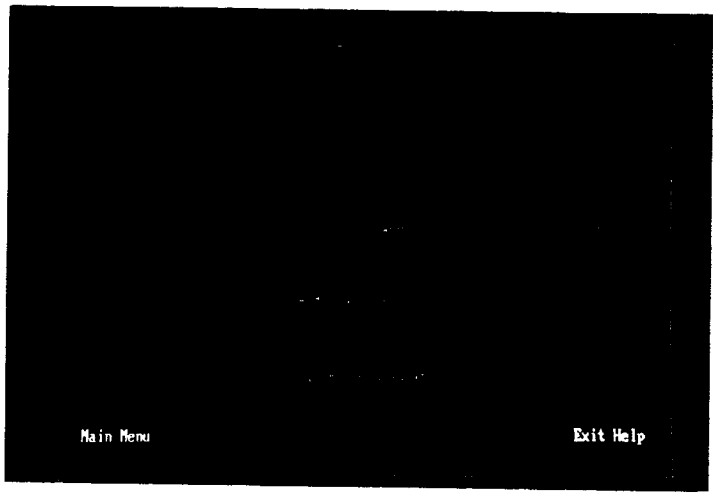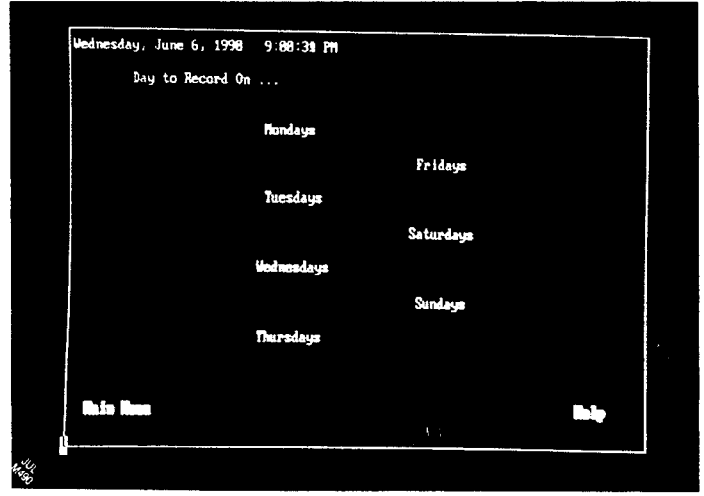

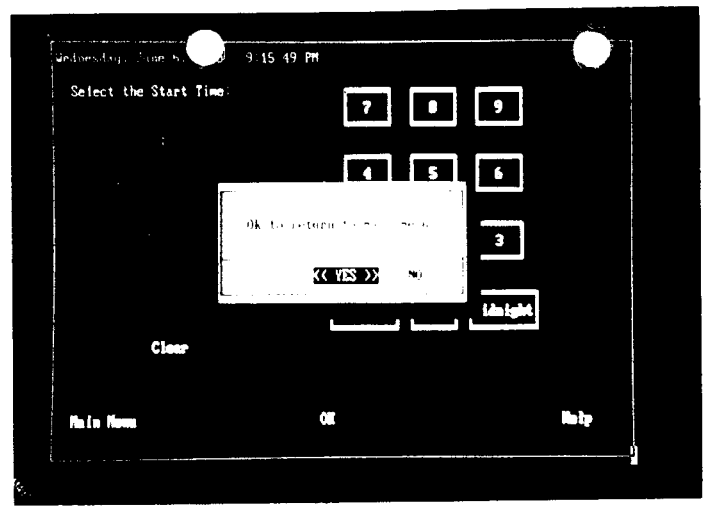
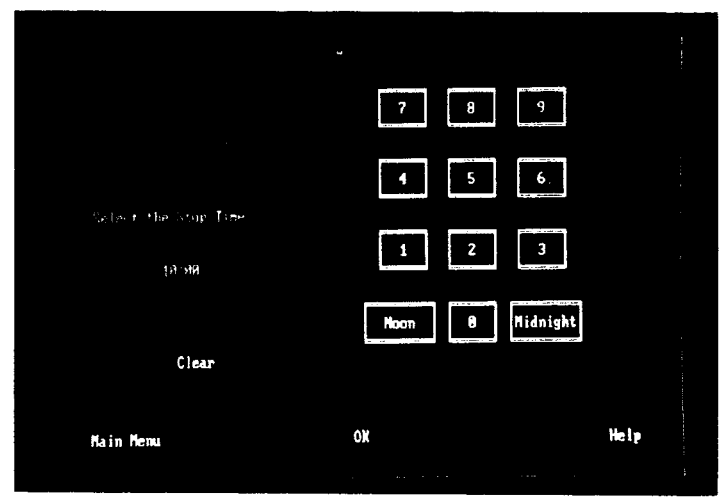
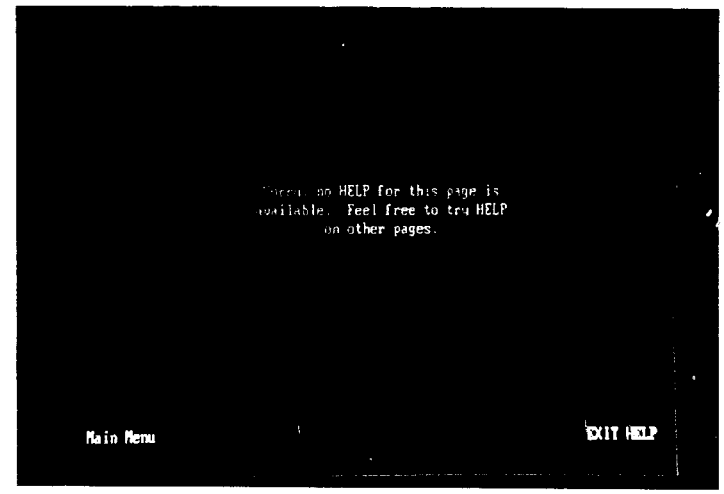

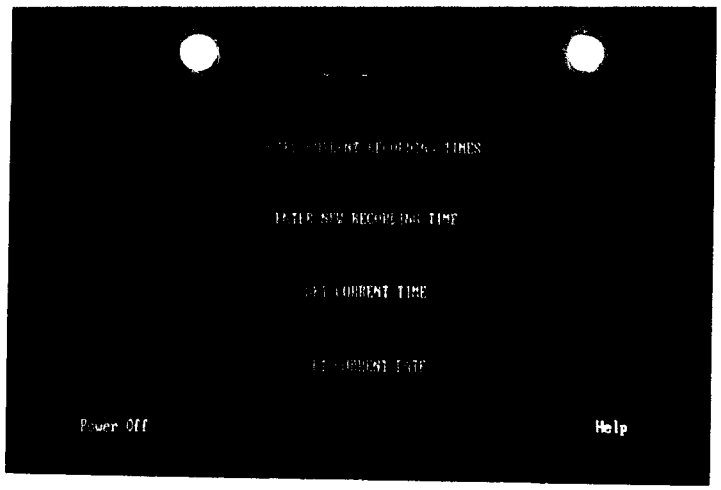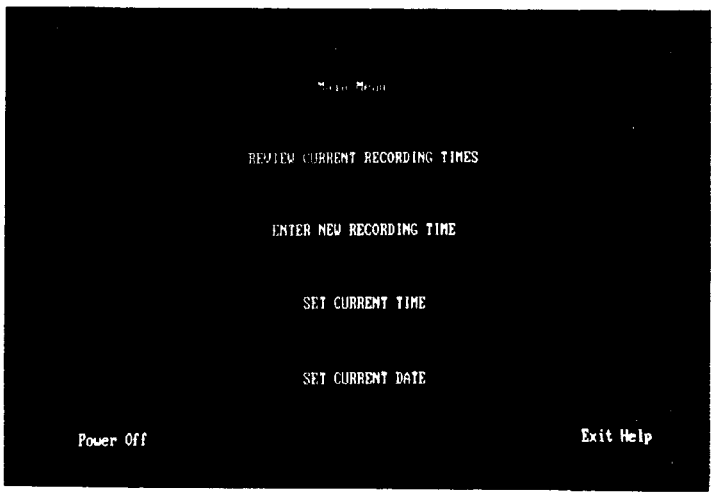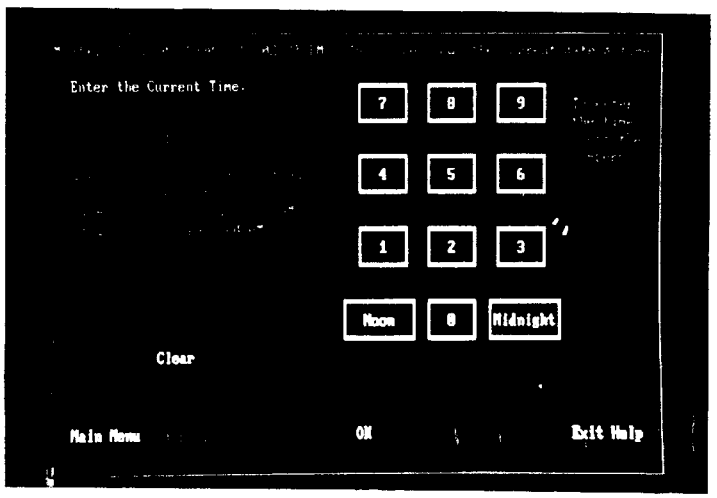

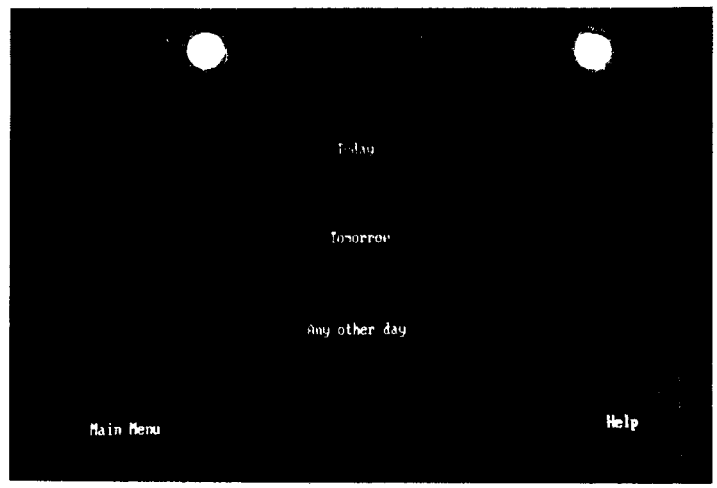
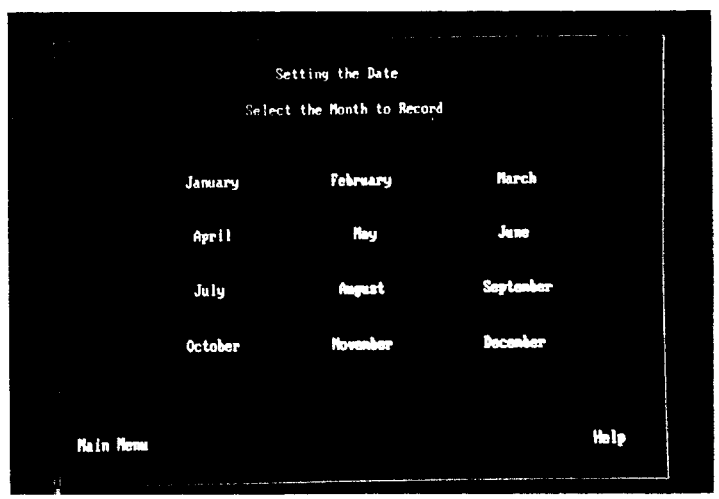
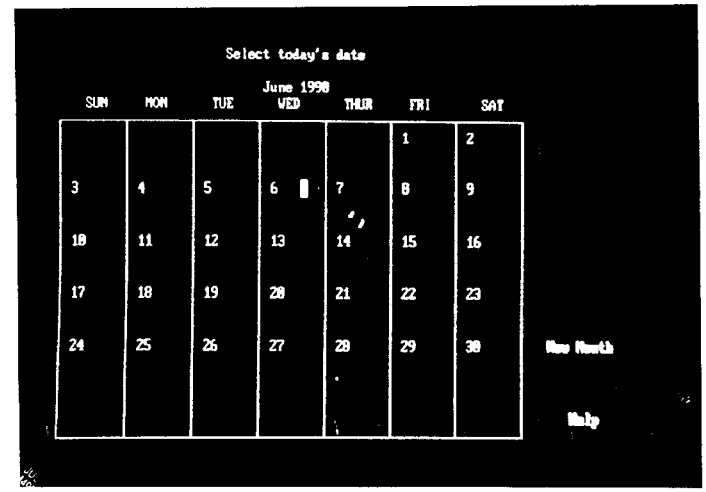

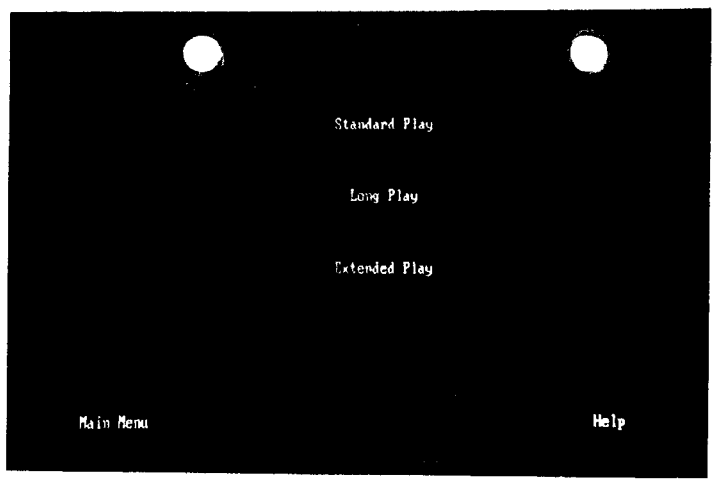
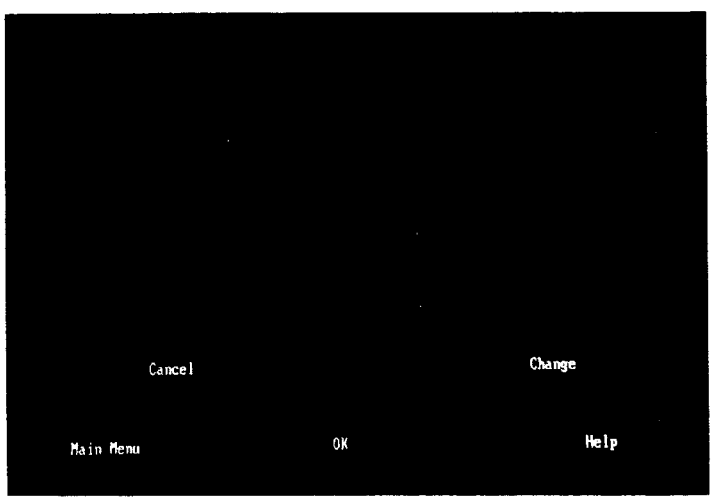
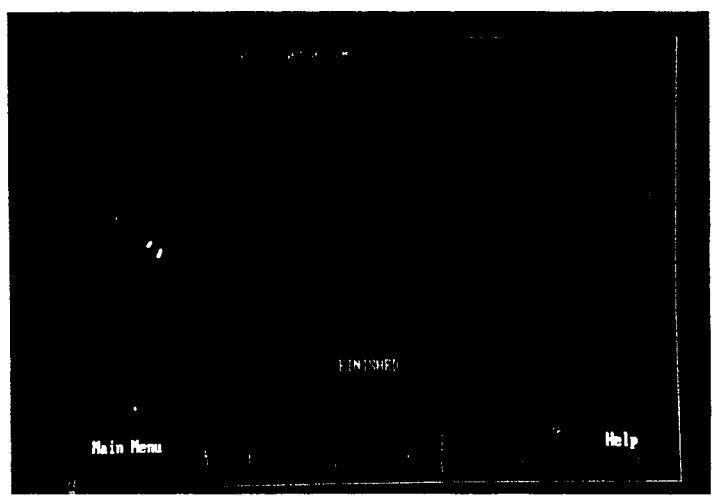

APPENDIX D • MORPHOLOGICAL ORDERING

Morphological Chart

| VCR Model | List Price | Ease of Use | On Screen | Prgms | Number Pad | Remote Display | Instr. Tape | Bar Coder |
|---|---|---|---|---|---|---|---|---|
| Akai VS-626U | 1050 | 5 | Y | | N | N | N | N |
| Emerson VCR870 | -- | 2 | N | | N | | N | N |
| Emerson VCR873 | 287 | 2 | N | 8/28 | | N | N | N |
| Emerson VCR875 | 243 | 2 | Y | | Y | N | N | N |
| Emerson VCS966 | 730 | 4 | Y | | Y | N | N | N |
| Fisher FVH-6200 | 289 | 3 | Y | | Y | N | N | N |
| Fisher FVH-905 | 500 | 4 | N | | Y | | N | N |
| Fisher FVH-960 | 850 | 3 | Y | | Y | N | N | N |
| Fisher FVH-D5600 | 850 | 3 | Y | 4/14 | | N | N | N |
| Fisher FVH4100 | 299 | 3 | Y | 4/14 | | N | N | N |
| GE 9-7145 | 399 | 2 | N | | Y | N | N | N |
| GE 9-7400 | 1250 | 5 | N | | Y | N | N | N |
| GE 97620 | 330 | 3 | Y | 8/21 | | N | N | N |
| GE VG-7620 | 285 | 3 | Y | | Y | N | N | N |
| GE VG7785 | 699 | 3 | Y | 8/31 | | N | N | N |
| Goldstar GHV-1700M | 288 | 2 | Y | | Y | N | N | N |
| Hitachi HPX VT2600A | 799 | 3 | N | 8/365 | | Y | N | N |
| Hitachi VT-1100A | 495 | 3 | N | | N | | N | N |
| Hitachi VT-M121A | 295 | 3 | Y | | Y | N | N | N |
| Hitachi VT2000A | 279 | 2 | N | 4/14 | | N | N | N |
| J.C. Penney 855-8918 | 290 | 4 | Y | | Y | N | N | Y |
| JVC HR-D180U | 499 | 5 | Y | | Y | N | N | N |
| JVC HR-D520U | 315 | 3 | Y | | Y | N | N | N |
| JVC HR-D566U | 899 | 4 | Y | | Y | N | N | N |
| JVC HRD217U | 330 | 3 | Y | 4/14 | | N | N | N |
| Kenwood DV-917HF | 1000 | 4 | Y | | Y | N | N | N |
| Magnavox VR-1820 AT | 285 | 4 | Y | | Y | N | N | N |
| Magnavox VR9530AT | 355 | 2 | N | | Y | N | N | N |
| Magnavox VR9565AT | 855 | 5 | Y | | Y | N | N | N |
| Magnavox VR9622AT | 350 | 3 | Y | 8/21 | | N | N | N |
| Magnovox VR967OAT | 1000 | 3 | N | 8/21 | | Y | N | N |
| Mitsubishi HS-339UR | 480 | 3 | Y | | Y | N | N | N |
| Mitsubishi HS-430UR | 1000 | 2 | Y | | Y | N | N | N |
| Mitsubishi HS-U51 | 699 | | Y | 8/28 | Y | N | N | N |
| Mitsubishi HS348UR | 300 | 2 | N | 5/14 | | N | N | N |
| NEC N-915 | 449 | 5 | N | | Y | | N | N |
| NEC N916U | 330 | 3 | Y | 4/21 | | N | N | N |
| Panasonic PV-1364 | 500 | 2 | N | | Y | N | N | N |
| Panasonic PV-1742 | 1290 | 5 | Y | | Y | N | N | N |
| Panasonic PV-2912 | 303 | 3 | Y | | Y | N | N | Y |
| Panasonic PV-4862 | 660 | 4 | Y | 8/31 | | N | N | Y |
| Panasonic PV3720 | 330 | 3 | Y | | | N | N | N |
| Panasonic PVB-4924 | 449 | | Y | 8/28 | Y | N | N | N |
| Pansonic PV-4962 | 649 | | Y | 8/31 | Y | N | N | Y |
| Pansonic PV3720 | 330 | 3 | Y | 8/21 | | | N | N |

D-1

Morphological Chart

| VCR Model | List Price | Ease of Use | On Screen | Prgms | Number Pad | Remote Display | Instr. Tape | Bar Coder |
|---|---|---|---|---|---|---|---|---|
| Quasar VH-5163 | 450 | 2 | N | | N | N | N | N |
| Quasar VH-5865 | 949 | 5 | Y | | Y | N | N | N |
| Quasar VH5371 | 310 | 3 | Y | 8/21 | | N | N | N |
| RCA VMT295 | 399 | 3 | N | | N | | N | N |
| RCA VMT670HF | 899 | 5 | Y | | Y | N | N | N |
| RCA VPT391 | 330 | 4 | Y | 6/365 | | N | N | N |
| RCA VPT595 | 799 | 3 | Y | 6/365 | | N | N | N |
| RCA VR 270 | 349 | 5 | Y | 4/365 | Y | N | N | N |
| RCA VR-270 | 276 | 4 | Y | | Y | N | N | N |
| RCA VR-295 | 399 | | Y | 4/365 | N | N | N | N |
| Realistic 14 | 330 | 4 | N | | N | | N | N |
| Realistic 21 | 319 | 2 | Y | | N | N | N | N |
| Realistic 23 | 420 | 3 | Y | 4/14 | | N | N | N |
| Realistic 40 | 700 | 4 | Y | | Y | N | N | N |
| Samsung VR-3509 | 230 | 3 | Y | | Y | N | N | N |
| Samsung VR2410 | 250 | 2 | N | 4/14 | | N | N | N |
| Sanyo VHR-9200 | 269 | 3 | Y | | Y | Y | N | N |
| Sanyo VHR2950 | 750 | 3 | Y | 4/14 | | N | N | N |
| Sanyo VHR3350 | 315 | 4 | Y | 4/365 | | N | N | N |
| Sears 53324 | 250 | 3 | Y | | Y | N | N | N |
| Sears 53350 | 370 | 3 | N | | N | | N | N |
| Sears 5343 | 350 | 2 | N | 4/365 | | N | N | N |
| Sears 53521 | 640 | 4 | Y | 4/365 | | N | N | N |
| Sharp VC-6846UB | 550 | 4 | N | | N | | N | N |
| Sharp VC-A210U | 281 | 3 | Y | | Y | N | N | N |
| Sharp VCA201U | 280 | 3 | Y | 4/14 | | N | N | N |
| Sony SLV-50 | 600 | | Y | 8/28 | | N | N | N |
| Sylvania VC8942AT | 379 | 3 | Y | 8/21 | | N | N | N |
| Symphonic 7400A | 235 | 2 | Y | | Y | N | N | N |
| Toshiba M-220 | 280 | 3 | Y | | Y | N | N | N |
| Toshiba M-2430 | 680 | 3 | Y | | N | | N | N |
| Toshiba M-5900 | 1000 | 5 | Y | | Y | N | N | N |
| Toshiba M-HF845 | 770 | | Y | 4/14 | | N | N | N |
| Toshiba M6230 | 270 | 2 | N | 4/14 | | N | N | N |
| Zenith VCR200 | 290 | 2 | Y | | | N | Y | N |
| Zenith VR1810 | 459 | 5 | Y | | Y | N | N | N |
| Zenith VR4100 | 1099 | 4 | Y | | Y | N | Y | N |
| Zenith VRD200 | 290 | 2 | N | 4/14 | | N | Y | N |
| Zenith VRD600HF | -- | 2 | Y | 8/14 | Y | N | Y | N |
| Zenith VRF-160 | 275 | 2 | Y | | Y | N | N | N |

D-2

Morphological Chart

KEY:
VCR Model:        Make and Model Number
List Price:       Manufacturers List Price
Ease of Use:      Rating on a 1-5 Scale with 1= Worse and 5= Better
On Screen:        Whether or not the VCR contains on screen programming
Prgms:            Program capability (number of programs/time in days)
Number Pad:       Whether or not the VCR contains an numeric enty keypad
Remote Display:   Whether or not the Remote control contains a display pane
Instr. Tape:      Whether or not the VCR comes with an instruction tape
Bar Coder:        Whether or not the VCR comes with a bar coder References:
Consumer Reports, March 1988
Consumer Reports, 1989
Consumer Reports, March 1989
Consumer Guide, 1990
Consumer Reports, March 1990

D-3

APPENDIX E • RAW DATA

VCR A Raw Data

TOTAL Time Statistics
1228,1190,2358,1425,1394,148
2,3289,1247,2248,1389,11
43,1697,817,1146,841,737
allnums
16 NUMBER OF ITEMS
737 MIN
3289 MAX
23631 SUM
1476.9375 AVG
659.585271 standard
  deviation

Total Time
Subject 1 1228
Subject 2 1190
Subject 4 2358
Subject 5 1425
Subject 9 1394
Subject 10 1482
Subject 11 3289
Subject 15 1247
Subject 16 2248
Subject 17 1389
Subject 18 1143
Subject 19 1697
Subject 20 817
Subject 21 1146
Subject 22 841
Subject 23 737

TOTAL TIME - WASTED COMPUTER TIME
Subject 1 28
Subject 2 23
Subject 4 46
Subject 5 47
Subject 9 35
Subject 10 33
Subject 11 45
Subject 15 38
Subject 16 72
Subject 17 44
Subject 18 21
Subject 19 32
Subject 20 18
Subject 21 33
Subject 22 19
Subject 23 22

TOTAL - WASTED STATISTICS
28,23,46,47,35,33,45,38,72,4
4,21,32,18,33,19,22
WASTENUMS
16 NUMBER OF ITEMS
18 MIN
72 MAX
556 SUM
34.75 AVG
14.007141 standard deviation

OK total
24,13,14,5,35,9,5,3,5,8,3,4,
 3,6,4,20,13,13,8,19,43,9
 ,12,2,1,63,1,4,3,1,3,1,2

,1,10,8,5,2,4,26,9,8,10,
6,42,12,8,8,1,11,8,16,33
,2,12,63,9,2,5,27,1,8,11
,22,2,24,9,9,274,3,5,0,5
,4,5,4,7,2,39,2,6,4,2,2,
2,4,2,2,2,3,2,3,2,2,8,2,
8,5,4,10,9,6,5,5,3,14,9,
6,5,16,31,35,64,11,3,10,
27,12,9,4,6,4,19,2,4,8,2
,8,18,17,10,7,2,5,42,20,
13,26,7,5,60,3,7,3,2,26
allnums
146 NUMBER OF ITEMS
0 MIN
274 MAX
1828 SUM
12.520548 AVG
25.225663 standard deviation

Mouse /key pressed data
195,448,679,330,297,244,334,
  375,619,444,257,370,239,
  299,152,192 allnums
16 NUMBER OF ITEMS
152 MIN
679 MAX
5474 SUM
342.125 AVG
147.318193 standard
  deviation

Error Statistics
2,7,42,33,7,31,27,87,244,25,
  7,11,1,16,5,4 allnums
16 NUMBER OF ITEMS
1 MIN
244 MAX
549 SUM
34.3125 AVG
60.003021 standard deviation

Adjusted Count (Count + Errors)
197,455,721,363,304,275,361,
  462,863,469,264,381,240,
  315,157,196
16 NUMBER OF ITEMS
157 MIN
863 MAX
6023 SUM
376.4375 AVG
189.990164 standard
  deviation

Wasted time data
28,23,46,47,35,33,45,38,72,4
  4,21,32,18,33,19,22
 allnums
16 NUMBER OF ITEMS
18 MIN
72 MAX
556 SUM
34.75 AVG
14.007141 standard deviation total page stats (# number of pages opened)
21,26,47,51,33,46,55,39,102, 38,19,35,15,27,17,17
 allnums
16 NUMBER OF ITEMS
15 MIN
102 MAX
588 SUM
36.75 AVG
21.656408 standard deviation page stats by page stats on number of times page entered

Page name: CLOCK SET
2,5,3,7,2,5,6,7,27,2,2,3,1,3
 ,2,1
16 NUMBER OF ITEMS
1 MIN
27 MAX
78 SUM
4.875 AVG
6.227627 standard deviation Page name: CLOCK ADJUST
1,4,11,5,2,11,11,8,44,4,1,8,
 0,4,1,0
16 NUMBER OF ITEMS
0 MIN
44 MAX
115 SUM
7.1875 AVG
10.584383 standard deviation Page name: CLOCK
1,4,2,2,3,5,4,6,3,2,2,3,1,1,
 2,1
16 NUMBER OF ITEMS
1 MIN
6 MAX
42 SUM
2.625 AVG
1.5 standard deviation Page name: SELECT THE PROGRAM
4,5,11,18,11,10,15,7,8,8,5,6
 ,6,10,5,6
16 NUMBER OF ITEMS
4 MIN
18 MAX
135 SUM
8.4375 AVG
3.898183 standard deviation Page name: PROGRAM1
5,4,9,8,7,5,9,4,5,8,4,6,3,4,
 3,4
16 NUMBER OF ITEMS
3 MIN
9 MAX
88 SUM
5.5 AVG
2.065591 standard deviation Page name: PROGRAM2
3,2,3,4,4,3,4,2,2,6,2,3,1,3,
 2,2
16 NUMBER OF ITEMS 1 MIN
6 MAX
46 SUM
2.875 AVG
1.204159 standard deviation Page name: PROGRAM3
2,1,3,2,1,1,1,2,1,3,1,2,1,1,
 1,1
16 NUMBER OF ITEMS
1 MIN
3 MAX
24 SUM
1.5 AVG
0.730297 standard deviation Page name: PROGRAM4
2,0,3,1,0,0,0,2,2,1,0,1,1,0,
 0,1
16 NUMBER OF ITEMS
0 MIN
3 MAX
14 SUM
0.875 AVG
0.957427 standard deviation Page name: ON/OFF
1,1,2,4,3,6,5,1,10,4,2,3,1,1
 ,1,1
16 NUMBER OF ITEMS
1 MIN
10 MAX
46 SUM
2.875 AVG
2.5 standard deviation stats on the amount of time spent in each page

Page name: CLOCK SET
221,357,368,272,135,327,236,
  343,721,122,83,211,157,1
  18,174,146
16 NUMBER OF ITEMS
83 MIN
721 MAX
3991 SUM
249.4375 AVG
155.98973 standard deviation Page name: CLOCK ADJUST
53,15,57,35,7,91,67,52,279,2
  2,5,86,0,10,5,0
16 NUMBER OF ITEMS
0 MIN
279 MAX
784 SUM
49 AVG
83.542732 standard deviation Page name: CLOCK
31,41,74,55,19,43,41,46,125,
  9,24,38,10,6,30,16
16 NUMBER OF ITEMS
6 MIN
125 MAX
619 SUM
38.6875 AVG

E-1

29.758402 standard deviation

Page name: SELECT THE PROGRAM
78,53,169,83,102,202,200,64, 79,52,56,210,39,65,100,4 3
16 NUMBER OF ITEMS
39 MIN
210 MAX
1595 SUM
99.6875 AVG
60.233677 standard deviation Page name: PROGRAM1
320,335,733,338,311,410,1451 ,274,178,664,432,683,301 ,275,232,212
16 NUMBER OF ITEMS
178 MIN
1451 MAX
7149 SUM
446.8125 AVG
317.057349 standard deviation Page name: PROGRAM2
240,196,562,214,548,183,421, 319.647,273,245,156,172, 460,217,164
16 NUMBER OF ITEMS
156 MIN
562 MAX
4917 SUM
307.3125 AVG
148.92133 standard deviation Page name: PROGRAM3
247,173,380,333,150,121,289, 102,4,85,172,254,93,174, 59,119
16 NUMBER OF ITEMS
4 MIN
380 MAX
2755 SUM
172.1875 AVG
103.5453 standard deviation Page name: PROGRAM4
5,0,26,7,0,0,0,4,163,6,0,9,2 ,0,0,9
16 NUMBER OF ITEMS
0 MIN
163 MAX
231 SUM
14.4375 AVG
40.167929 standard deviation Page name: ON/OFF
6,14,16,40,96,66,544,5,80,11 4,105,29,25,4,4,5
16 NUMBER OF ITEMS
4 MIN
544 MAX
1133 SUM
70.8125 AVG
131.237763 standard deviation average time spent in each page per page Page name: CLOCK SET
110.5,71.4,122.666667,38.857 143,67.5,65.4,39.333333, 49,26.703704,61,41.5,70. 333333,157,39.333333,87, 146
16 NUMBER OF ITEMS
26.703704 MIN
157 MAX
1193.527513 SUM
74.59547 AVG
39.832316 standard deviation Page name: CLOCK ADJUST
53,3.75,5.181818,7,3.5,8.272 727,6.090909,6.5,6.34090 9,5.5,5,10.75,2.5,5
14 NUMBER OF ITEMS
2.5 MIN
53 MAX
128.386363 SUM
9.170455 AVG
12.781776 standard deviation Page name: CLOCK
31,11.75,37,27.5,6.333333,9. 8,10.25,7.666667,41.6666 67,4.12,12.566667,10,6,1 5,16
16 NUMBER OF ITEMS
4 MIN
41.666667 MAX
258.633334 SUM
16.164583 AVG
11.596434 standard deviation Page name: SELECT THE PROGRAM
19.5,10.6,15.363636,4.611111 ,9.272727,20.2,13.333333 ,9.142857,9.875,6.5,11.2 ,35,6.5,6.5,20,7.166667
16 NUMBER OF ITEMS
4.611111 MIN
35 MAX
204.765331 SUM
12.797833 AVG
7.792393 standard deviation Page name: PROGRAM1
64,83,75,81.444444,42.25,44. 428571,82,161.222222,68. 5,35,6,83,108,113.833333 ,100.333333,68.75,77.333 333,53
16 NUMBER OF ITEMS
35.6 MIN
161.222222 MAX
1267.445236 SUM
79.215327 AVG
31.486673 standard deviation Page name: PROGRAM2
80.98,187.333333,53.5,137.61 ,105.25,159.5,273.5,45.5 ,122.5,52,172,153.333333 ,108.5,82
16 NUMBER OF ITEMS
45.5 MIN
273.5 MAX
1890.916666 SUM
118.182292 AVG
60.920214 standard deviation Page name: PROGRAM3
123.5,173,126.666667,166.5,1 50,121,289,51,4,28.33333 3,172,127,93,174,59,119
16 NUMBER OF ITEMS
4 MIN
289 MAX
1977 SUM
123.5625 AVG
68.81214 standard deviation Page name: PROGRAM4
2.5,8.666667,7,2,81.5,6,9,2, 9
9 NUMBER OF ITEMS
2 MIN
81.5 MAX
127.666667 SUM
14.185185 AVG
25.415634 standard deviation Page name: ON/OFF
6,14,8,10,28.666667,11,108.8 ,5.8,28.5,52.5,6.333333, 25,4,4,5
16 NUMBER OF ITEMS
4 MIN
108.8 MAX
324.8 SUM
20.3 AVG
27.033792 standard deviation

**Subject number 1 Friday,
   June 1, 1990 3:00 pm**

Page time log
CLOCK SET ,1,22
CLOCK ADJUST ,25,53
CLOCK SET ,79,199
CLOCK ,280,31
SELECT THE PROGRAM ,311,19
PROGRAM1 ,332,19
PROGRAM4 ,352,4
PROGRAM1 ,357,287
SELECT THE PROGRAM ,645,9
PROGRAM1 ,656,10
PROGRAM2 ,667,8
PROGRAM3 ,677,2
PROGRAM4 ,681,1
PROGRAM1 ,684,3
PROGRAM2 ,688,228
SELECT THE PROGRAM ,917,21
PROGRAM1 ,940,1
PROGRAM2 ,943,4
PROGRAM3 ,949,245
SELECT THE PROGRAM ,1194,29
ON/OFF ,1224,6

Error log:
WRONG KEY 6 22
SETS TIMER 1220

Users Actions:
(CLKADJ) 22
(B+) 78
(A+) 94
(A+) 100
(A+) 103
(A+) 104
(A+) 105
(A+) 106
(A+) 106
(A+) 108
(A+) 109
(A+) 114
(A-) 115
(A+) 117
(A+) 118
(A+) 122
(A+) 122
(A+) 124
(A+) 125
(A+) 127
(A+) 129
(A+) 132
(A+) 133
(B+) 149
(B+) 152
(B+) 164
(B+) 166
(B-) 170
(B+) 173
(B+) 176
(B+) 177
(A-) 197
(A+) 200
(A+) 201
(B+) 203
(A+) 214

(A+) 215
(A+) 217
(A+) 218
(A+) 220
(B+) 230
(A+) 233
(A+) 236
(A+) 238
(A+) 239
(A+) 241
(B+) 245
(A+) 248
(A+) 249
(A+) 250
(A+) 252
(A+) 253
(A+) 254
(C) 278
(A-) 350
(A+) 355
(B+) 390
(A-) 410
(A-) 416
(A-) 417
(A-) 419
(B+) 423
(B+) 425
(B-) 429
(B+) 433
(A-) 457
(B+) 463
(B+) 465
(B+) 503
(A-) 518
(A-) 522
(A+) 528
(A+) 531
(A+) 533
(A+) 535
(A+) 537
(A+) 539
(A-) 545
(A+) 548
(B+) 557
(B+) 559
(B+) 562
(B+) 568
(B+) 571
(B+) 575
(A+) 590
(B+) 609
(B+) 611
(A+) 618
(A+) 620
(A+) 622
(A+) 625
(C) 643
(A+) 665
(A+) 675
(A+) 679
(A+) 682
(A+) 687
(B+) 701
(A+) 721
(A+) 722
(A+) 724
(B-) 727
(B+) 729

(A+) 732
(A+) 734
(A+) 736
(B+) 739
(A+) 740
(A+) 742
(A+) 743
(A+) 745
(A+) 747
(A+) 748
(A+) 750
(A+) 751
(A+) 753
(A+) 754
(A+) 756
(A+) 757
(A+) 759
(A+) 760
(A+) 762
(A+) 763
(B+) 765
(B+) 766
(A+) 768
(A+) 770
(A+) 771
(A+) 773
(A+) 775
(A-) 776
(A+) 778
(A-) 779
(A+) 781
(A+) 782
(A+) 784
(A+) 785
(B+) 792
(A+) 839
(A-) 855
(A-) 857
(B+) 881
(A+) 888
(A+) 892
(A+) 894
(B+) 895
(A+) 897
(A+) 902
(C) 916
(A+) 940
(A+) 947
(B+) 960
(A+) 965
(A-) 967
(A-) 969
(A-) 970
(B+) 978
(B+) 980
(A-) 983
(B+) 987
(B+) 988
(B+) 999
(A-) 1004
(B+) 1012
(A-) 1017
(B-) 1026
(B-) 1041
(B-) 1043
(A-) 1057
(A-) 1060
(A+) 1066

(A-) 1071
(A-) 1073
(A+) 1079
(A-) 1083
(A-) 1085
(A+) 1092
(A+) 1096
(A-) 1107
(A-) 1109
(A-) 1111
(A-) 1113
(A-) 1116
(A-) 1118
(A-) 1121
(B+) 1161
(B+) 1164
(A+) 1179
(A+) 1182
(A+) 1184
(A+) 1188
(C) 1193
(C) 1228

Programs set
2.SUN PM 8:00 5
M-F  AM 3:00 7
4.TUE PM10:00 5

Page summary
CLOCK SET,2,221
CLOCK ADJUST,1,53
CLOCK,1,31
SELECT THE PROGRAM,4,78
PROGRAM1,5,320
PROGRAM2,3,240
PROGRAM3,2,247
PROGRAM4,2,5
ON/OFF,1,6

**COUNT:195
WASTED TIME:28
TOTAL TIME = Time -
    Waste=1228**

Subject number 2 Friday,
June 1, 1990 4:00 pm

Page time log
CLOCK SET ,1,22
CLOCK ADJUST ,25,0
CLOCK ADJUST ,26,7
CLOCK SET ,34,167
CLOCK ,203,11
CLOCK ADJUST ,215,6
CLOCK SET ,222,14
CLOCK ,237,7
CLOCK ADJUST ,245,2
CLOCK SET ,248,15
CLOCK ,263,10
SELECT THE PROGRAM ,273,6
PROGRAM1 ,280,138
ON/OFF ,419,14
CLOCK SET ,433,139
CLOCK ,572,19
SELECT THE PROGRAM ,591,5
PROGRAM1 ,597,193
SELECT THE PROGRAM ,791,14
PROGRAM1 ,806,3
PROGRAM2 ,810,195
SELECT THE PROGRAM ,1005,5
PROGRAM1 ,1012,1
PROGRAM2 ,1015,1
PROGRAM3 ,1018,173
SELECT THE PROGRAM ,1191,23

Error log:
WRONG KEY 6 23
WRONG KEY 6 25
BIGMINUS 426
SUBJECT NUMBER 2 CONTINUED 433
Subject number 2 Friday, June 1, 1990 433
9 683
  Subject stopped here, didn't set the timer 1214

Users Actions:
(CLKADJ) 23
(CLKADJ) 25
(B+) 33
(B-) 41
(B-) 43
(B+) 45
(B+) 46
(B+) 47
(B+) 47
(B+) 49
(B+) 49
(B+) 52
(A+) 50
(A+) 61
(A+) 62
(A+) 63
(A+) 64
(A+) 55
(A+) 56
(A-) 63
(B+) 79
(A-) 85

(A-) 87
(A-) 88
(A-) 92
(A-) 95
(A-) 96
(A-) 97
(A-) 97
(A-) 98
(A-) 99
(A-) 100
(A-) 101
(A-) 101
(A-) 102
(A-) 103
(A-) 104
(A-) 104
(A-) 105
(A-) 106
(A-) 107
(A-) 108
(A-) 109
(A-) 110
(A-) 110
(A-) 111
(B+) 113
(B+) 119
(A-) 126
(A-) 128
(A-) 130
(A-) 133
(B+) 136
(A+) 141
(A+) 142
(A+) 144
(A+) 146
(A+) 147
(B+) 155
(B+) 157
(B+) 158
(B+) 160
(B+) 166
(B+) 167
(B+) 169
(A+) 171
(A+) 172
(A+) 173
(A+) 175
(A+) 176
(A+) 177
(B+) 184
(B+) 186
(A-) 190
(A-) 192
(C) 201
(B-) 220
(B+) 223
(B+) 224
(A-) 229
(A-) 231
(C) 236
(B+) 247
(B+) 249
(B+) 252
(B+) 254
(B+) 255
(B+) 256
(B-) 257
(A-) 259

(C) 262
(B+) 289
(A+) 297
(A+) 299
(A+) 300
(A-) 302
(A-) 304
(A-) 305
(A-) 307
(A-) 308
(A-) 310
(A-) 312
(A-) 314
(A-) 315
(A-) 317
(B+) 320
(B-) 325
(A-) 328
(A+) 330
(A+) 331
(A+) 333
(A+) 334
(B+) 338
(B+) 342
(A+) 349
(A-) 350
(A-) 352
(A-) 353
(A-) 355
(A-) 356
(A-) 358
(A+) 359
(A+) 361
(A-) 363
(A-) 364
(A-) 366
(A-) 367
(A+) 369
(A+) 370
(A-) 372
(A-) 373
(A-) 376
(A-) 377
(A-) 379
(A+) 380
(A+) 382
(A+) 383
(A+) 385
(A+) 387
(A+) 388
(A+) 390
(A+) 391
(A+) 393
(A+) 395
(A+) 396
(A+) 398
(B+) 399
(A+) 402
(A-) 405
(A-) 407
(A-) 408
(A-) 410
(A-) 411
(B+) 413
(B-) 415
(TIMER) 418
(PRGM) 426
(C) 431

(A+) 439
(A+) 441
(B+) 445
(A+) 449
(A-) 451
(A+) 452
(A+) 453
(B+) 455
(B+) 458
(B+) 460
(B+) 462
(B+) 463
(A-) 468
(A-) 469
(A-) 470
(A-) 470
(A-) 471
(A-) 472
(A-) 473
(A-) 473
(A+) 474
(A+) 476
(A+) 477
(B+) 484
(B+) 487
(B-) 492
(B-) 493
(A+) 500
(A-) 503
(B+) 505
(B+) 511
(A+) 515
(A+) 517
(A+) 518
(B+) 521
(A+) 524
(A+) 525
(A+) 526
(A+) 527
(A+) 528
(B+) 531
(A+) 533
(A+) 534
(A+) 536
(A+) 537
(A+) 539
(B+) 550
(A+) 552
(A+) 553
(A+) 554
(A+) 555
(A+) 556
(A+) 557
(A+) 558
(B-) 560
(B+) 561
(A-) 563
(C) 571
(B+) 577
(A+) 617
(A+) 618
(A+) 620
(A-) 621
(A-) 623
(A-) 625
(A-) 626
(A-) 628
(A-) 629

E-4

| | | | | |
|---|---|---|---|---|
| (A-) 631 | (A+) 837 | (B-) 955 | (B+) 1152 | |
| (A-) 632 | (A-) 838 | (A-) 958 | (B+) 1154 | |
| (A-) 634 | (A+) 841 | (A+) 961 | (B-) 1158 | |
| (A-) 635 | (B+) 844 | (A-) 963 | (B-) 1159 | |
| (A-) 637 | (A+) 845 | (B+) 966 | (B-) 1161 | |
| (A-) 638 | (A+) 847 | (A+) 971 | (B+) 1167 | |
| (B+) 640 | (A+) 848 | (A+) 973 | (B-) 1170 | |
| (A+) 642 | (A+) 850 | (A+) 974 | (A-) 1173 | |
| (A+) 644 | (A+) 851 | (A+) 976 | (A-) 1175 | |
| (A+) 645 | (A+) 853 | (A+) 978 | (A+) 1177 | |
| (A+) 647 | (A+) 855 | (A+) 979 | (A+) 1179 | |
| (B-) 648 | (A+) 856 | (A+) 981 | (A+) 1181 | |
| (B-) 650 | (A+) 858 | (A+) 982 | (A+) 1182 | |
| (A+) 651 | (A+) 859 | (A+) 983 | (A+) 1183 | |
| (A+) 653 | (A+) 861 | (A+) 985 | (A+) 1185 | |
| (A+) 654 | (A+) 862 | (A+) 986 | (A+) 1187 | |
| (A+) 656 | (A+) 864 | (A+) 988 | (C) 1190 | |
| (A+) 658 | (A+) 865 | (B-) 989 | | |
| (B+) 661 | (A+) 866 | (B+) 993 | Programs set | |
| (A-) 667 | (A+) 868 | (A-) 995 | 2.SUN PM 8:00 6 (wrong | |
| (A-) 668 | (A-) 869 | (A-) 997 | channel) 356 | |
| (A-) 670 | (A+) 871 | (A-) 999 | M-F AM 3:00 7 | |
| (A-) 672 | (A-) 872 | (A-) 1000 | 2.THU PM 8:00 5 | |
| (B+) 673 | (A+) 874 | (C) 1004 | | |
| (A-) 676 | (A+) 875 | (A+) 1013 | Page summary | |
| (A-) 678 | (A+) 877 | (A+) 1016 | CLOCK SET,5,357 | |
| (A+) 679 | (A+) 878 | (B+) 1019 | CLOCK ADJUST,4,15 | |
| (B+) 681 | (A+) 880 | (A+) 1023 | CLOCK,4,47 | |
| (A-) 683 | (A+) 881 | (A-) 1025 | SELECT THE PROGRAM,5,53 | |
| (B+) 685 | (A+) 883 | (A-) 1027 | PROGRAM1,4,335 | |
| (B+) 691 | (A+) 885 | (A-) 1028 | PROGRAM2,2,196 | |
| (B+) 694 | (A+) 886 | (A-) 1030 | PROGRAM3,1,173 | |
| (B-) 696 | (A+) 888 | (A-) 1031 | PROGRAM4,0,0 | |
| (B-) 697 | (A+) 889 | (B+) 1035 | ON/OFF,1,14 | |
| (B-) 700 | (A+) 891 | (B+) 1037 | | |
| (B+) 704 | (A+) 892 | (A-) 1042 | COUNT:448 | |
| (A+) 715 | (A+) 894 | (A-) 1044 | WASTED TIME:23 | |
| (A-) 721 | (A+) 895 | (A+) 1045 | TOTAL TIME = Time - | |
| (B+) 725 | (A+) 897 | (B+) 1047 | Waste=1190 | |
| (A+) 729 | (A+) 898 | (B+) 1048 | | |
| (A+) 731 | (A+) 900 | (B-) 1058 | | |
| (A+) 734 | (A+) 901 | (B+) 1062 | | |
| (A+) 736 | (A+) 903 | (A-) 1065 | | |
| (B+) 740 | (A+) 904 | (A-) 1069 | | |
| (B-) 743 | (A+) 906 | (A-) 1072 | | |
| (B-) 747 | (A+) 907 | (A-) 1074 | | |
| (B+) 756 | (A+) 909 | (A-) 1077 | | |
| (B-) 758 | (A+) 910 | (A-) 1079 | | |
| (A+) 764 | (A+) 912 | (A-) 1084 | | |
| (B+) 772 | (A+) 913 | (A+) 1088 | | |
| (B+) 776 | (A-) 915 | (A-) 1092 | | |
| (A+) 780 | (A-) 917 | (A+) 1094 | | |
| (A+) 782 | (A-) 918 | (B+) 1099 | | |
| (A+) 783 | (A-) 920 | (A-) 1107 | | |
| (A+) 785 | (A-) 921 | (B+) 1109 | | |
| (A+) 786 | (A-) 923 | (B-) 1113 | | |
| (C) 789 | (A-) 924 | (B-) 1115 | | |
| (A-) 809 | (A-) 926 | (B-) 1117 | | |
| (B+) 812 | (A-) 927 | (A-) 1119 | | |
| (A-) 817 | (A-) 928 | (B-) 1121 | | |
| (A-) 819 | (A-) 930 | (B+) 1123 | | |
| (A+) 820 | (A-) 935 | (B+) 1125 | | |
| (A+) 822 | (A-) 936 | (A+) 1132 | | |
| (A+) 823 | (A-) 938 | (A+) 1136 | | |
| (A+) 825 | (A-) 939 | (B+) 1140 | | |
| (A-) 829 | (A-) 941 | (A+) 1145 | | |
| (B-) 831 | (B+) 943 | (B+) 1147 | | |
| (B-) 833 | (B+) 952 | (B+) 1149 | | |

E-5

Subject number 4 Tuesday, June 5, 1990 5:54:14 PM

Page time log
| | |
|---|---|
| CLOCK SET | ,1,18 |
| SELECT THE PROGRAM | ,19,3 |
| PROGRAM1 | ,23,30 |
| PROGRAM2 | ,54,3 |
| PROGRAM3 | ,58,5 |
| PROGRAM2 | ,64,2 |
| PROGRAM1 | ,68,1 |
| PROGRAM4 | ,70,19 |
| CLOCK ADJUST | ,90,7 |
| ON/OFF | ,98,12 |
| CLOCK ADJUST | ,111,34 |
| CLOCK ADJUST | ,145,1 |
| CLOCK ADJUST | ,147,0 |
| CLOCK ADJUST | ,148,1 |
| CLOCK ADJUST | ,150,1 |
| ON/OFF | ,151,4 |
| CLOCK ADJUST | ,156,2 |
| SELECT THE PROGRAM | ,158,7 |
| CLOCK ADJUST | ,166,7 |
| CLOCK SET | ,174,121 |
| CLOCK | ,295,55 |
| CLOCK ADJUST | ,351,2 |
| CLOCK ADJUST | ,354,0 |
| CLOCK ADJUST | ,355,2 |
| CLOCK SET | ,358,229 |
| CLOCK | ,588,19 |
| SELECT THE PROGRAM | ,608,7 |
| PROGRAM1 | ,616,677 |
| SELECT THE PROGRAM | ,1294,5 |
| PROGRAM1 | ,1301,5 |
| SELECT THE PROGRAM | ,1306,4 |
| PROGRAM1 | ,1312,2 |
| SELECT THE PROGRAM | ,1315,14 |
| PROGRAM1 | ,1331,2 |
| SELECT THE PROGRAM | ,1334,32 |
| SELECT THE PROGRAM | ,1367,2 |
| PROGRAM1 | ,1371,6 |
| SELECT THE PROGRAM | ,1377,9 |
| PROGRAM1 | ,1388,3 |
| PROGRAM4 | ,1392,2 |
| PROGRAM3 | ,1395,1 |
| PROGRAM2 | ,1398,557 |
| SELECT THE PROGRAM | ,1955,14 |
| PROGRAM1 | ,1971,7 |
| PROGRAM4 | ,1979,5 |
| PROGRAM3 | ,1985,374 |
| SELECT THE PROGRAM | ,2360,72 |

Error log:
WRONG KEY RIGHT 144
WRONG KEY RIGHT 146
WRONG KEY RIGHT 147
WRONG KEY RIGHT 149
WRONG KEY HOME 163
HOME 168
WRONG KEY HOME 170
HOME 170
WRONG KEY UP 171
UP 171
END 297
END 298
END 302
CENTER 304
CENTER 305
CENTER 306
LEFT 308
LEFT 309
LEFT 309
LEFT 310
LEFT 310
LEFT 311
END 312
END 312
END 313
CENTER 314
CENTER 315
END 316
END 316
END 317
CENTER 319
CENTER 320
WRONG KEY RIGHT 353
WRONG KEY RIGHT 354
DOWN 846
DOWN 847
DOWN 852
LEFT 1338
LEFT 1343
CENTER 1358
END 1363
subject did not turn power off or set timer 2432

Users Actions:
| | | | | | | |
|---|---|---|---|---|---|---|
| (PRGM) | 19 | (A-) | 205 | (B-) | 480 | |
| (A+) | 53 | (A-) | 207 | (B-) | 482 | |
| (A+) | 56 | (A-) | 208 | (B-) | 485 | |
| (A-) | 63 | (A-) | 210 | (B-) | 486 | |
| (A-) | 66 | (A-) | 211 | (B-) | 489 | |
| (A-) | 69 | (A-) | 213 | (B-) | 490 | |
| (B-) | 73 | (A-) | 214 | (B-) | 491 | |
| (B+) | 76 | (A-) | 215 | (B-) | 494 | |
| (B+) | 81 | (A-) | 215 | (B-) | 500 | |
| (B-) | 82 | (A-) | 216 | (B-) | 505 | |
| (B+) | 85 | (A-) | 217 | (B-) | 509 | |
| (C) | 87 | (A-) | 218 | (A-) | 512 | |
| (CLKADJ) | 89 | (A-) | 219 | (A-) | 516 | |
| (TIMER) | 97 | (A-) | 221 | (A-) | 517 | |
| (TIMER) | 103 | (A-) | 223 | (A-) | 519 | |
| (CLKADJ) | 110 | (A-) | 227 | (A-) | 520 | |
| (CLKADJ) | 144 | (A-) | 229 | (A-) | 522 | |
| (CLKADJ) | 146 | (A-) | 231 | (A-) | 524 | |
| (CLKADJ) | 147 | (A+) | 250 | (A-) | 526 | |
| (CLKADJ) | 149 | (A-) | 253 | (A-) | 527 | |
| (TIMER) | 151 | (B-) | 256 | (A-) | 529 | |
| (TIMER) | 153 | (B-) | 264 | (A-) | 532 | |
| (CLKADJ) | 155 | (B-) | 265 | (A-) | 537 | |
| (PRGM) | 158 | (B-) | 277 | (A-) | 539 | |
| (A-) | 168 | (B-) | 278 | (A-) | 541 | |
| (A+) | 170 | (B-) | 280 | (A-) | 543 | |
| (A+) | 170 | (B-) | 284 | (A-) | 544 | |
| (B-) | 173 | (B-) | 284 | (A-) | 549 | |
| (A-) | 188 | (B+) | 288 | (A-) | 551 | |
| (A-) | 194 | (B+) | 289 | (A-) | 553 | |
| (A-) | 195 | (B+) | 290 | (A-) | 556 | |
| (A-) | 196 | (C) | 294 | (A-) | 558 | |
| (A-) | 198 | (CLKADJ) | 353 | (A-) | 559 | |
| (A-) | 199 | (CLKADJ) | 354 | (A-) | 562 | |
| (A-) | 199 | (B-) | 357 | (A-) | 564 | |
| (A-) | 201 | (B-) | 358 | (A-) | 567 | |
| (A-) | 202 | (A+) | 363 | (C) | 587 | |
| | | (A-) | 373 | (B-) | 625 | |
| | | (A-) | 374 | (A-) | 633 | |
| | | (A-) | 375 | (A-) | 635 | |
| | | (A-) | 377 | (A-) | 636 | |
| | | (A-) | 378 | (A-) | 648 | |
| | | (A-) | 381 | (B-) | 652 | |
| | | (A-) | 383 | (B-) | 656 | |
| | | (A-) | 384 | (B-) | 659 | |
| | | (A-) | 386 | (B-) | 662 | |
| | | (A-) | 388 | (B-) | 667 | |
| | | (A-) | 390 | (B-) | 675 | |
| | | (B+) | 395 | (B+) | 676 | |
| | | (B+) | 399 | (B-) | 686 | |
| | | (B+) | 401 | (B-) | 694 | |
| | | (A-) | 407 | (B-) | 707 | |
| | | (A-) | 409 | (B-) | 711 | |
| | | (A-) | 411 | (B+) | 715 | |
| | | (A-) | 413 | (B+) | 721 | |
| | | (B-) | 421 | (A-) | 734 | |
| | | (B-) | 427 | (B+) | 741 | |
| | | (B-) | 429 | (B+) | 747 | |
| | | (B-) | 430 | (A-) | 770 | |
| | | (A-) | 438 | (A-) | 773 | |
| | | (A-) | 440 | (A-) | 780 | |
| | | (A-) | 442 | (A-) | 783 | |
| | | (A-) | 444 | (A-) | 785 | |
| | | (A-) | 445 | (A-) | 790 | |
| | | (A-) | 446 | (A-) | 794 | |
| | | (A-) | 456 | (A-) | 797 | |
| | | (B-) | 475 | (A-) | 800 | |
| | | (B-) | 476 | (B-) | 809 | |

E-6

| | | | | | | | |
|---|---|---|---|---|---|---|---|
| (B+) | 814 | (A-) | 972 | (A-) | 1110 | (A-) | 1279 |
| (B+) | 819 | (A-) | 973 | (A-) | 1119 | (C) | 1292 |
| (A-) | 827 | (A-) | 975 | (A-) | 1122 | (C) | 1305 |
| (A-) | 829 | (A-) | 976 | (A-) | 1124 | (C) | 1313 |
| (A-) | 832 | (A-) | 978 | (A-) | 1125 | (C) | 1332 |
| (D) | 845 | (A-) | 980 | (A-) | 1129 | (C) | 1375 |
| (D) | 846 | (A-) | 981 | (A-) | 1131 | (A-) | 1391 |
| (D) | 852 | (A-) | 983 | (A-) | 1133 | (A-) | 1394 |
| (B-) | 859 | (A-) | 984 | (A-) | 1135 | (A-) | 1396 |
| (B+) | 864 | (A-) | 986 | (A-) | 1136 | (B-) | 1401 |
| (B+) | 870 | (A-) | 987 | (A-) | 1138 | (A-) | 1429 |
| (A-) | 876 | (A-) | 989 | (A-) | 1139 | (A-) | 1431 |
| (A-) | 878 | (A-) | 990 | (A-) | 1141 | (A-) | 1432 |
| (A-) | 880 | (A-) | 992 | (A-) | 1142 | (A-) | 1434 |
| (A-) | 885 | (A-) | 993 | (A-) | 1144 | (A-) | 1435 |
| (A-) | 888 | (A-) | 994 | (A-) | 1151 | (A-) | 1437 |
| (A-) | 890 | (A-) | 996 | (A-) | 1153 | (A-) | 1445 |
| (A-) | 892 | (A-) | 997 | (A-) | 1154 | (A-) | 1447 |
| (A-) | 894 | (A-) | 999 | (A-) | 1156 | (A-) | 1448 |
| (A-) | 895 | (A-) | 1000 | (A-) | 1157 | (A-) | 1452 |
| (A-) | 898 | (A-) | 1002 | (A-) | 1168 | (A-) | 1454 |
| (A-) | 899 | (A-) | 1003 | (A-) | 1170 | (A-) | 1455 |
| (A-) | 901 | (A-) | 1005 | (A-) | 1171 | (A-) | 1458 |
| (A-) | 903 | (A-) | 1006 | (A-) | 1173 | (A-) | 1462 |
| (A-) | 905 | (A-) | 1008 | (A-) | 1174 | (A-) | 1464 |
| (A-) | 907 | (A-) | 1010 | (A-) | 1176 | (A-) | 1466 |
| (A-) | 909 | (A-) | 1011 | (A-) | 1177 | (A-) | 1467 |
| (A-) | 910 | (A-) | 1013 | (A-) | 1179 | (A-) | 1474 |
| (A-) | 912 | (A-) | 1014 | (A-) | 1180 | (A-) | 1480 |
| (A-) | 913 | (A-) | 1016 | (A-) | 1182 | (A-) | 1485 |
| (A-) | 915 | (A-) | 1017 | (A-) | 1183 | (A-) | 1490 |
| (A-) | 917 | (A-) | 1019 | (A-) | 1185 | (B-) | 1496 |
| (A-) | 918 | (A-) | 1020 | (A-) | 1186 | (B-) | 1501 |
| (A-) | 920 | (A-) | 1022 | (A-) | 1188 | (B+) | 1503 |
| (A-) | 921 | (A-) | 1023 | (A-) | 1189 | (B+) | 1509 |
| (A-) | 923 | (A-) | 1025 | (A-) | 1191 | (B+) | 1514 |
| (A-) | 924 | (A-) | 1026 | (A-) | 1192 | (A-) | 1522 |
| (A-) | 926 | (A-) | 1027 | (A-) | 1193 | (A-) | 1524 |
| (A-) | 927 | (A-) | 1029 | (A-) | 1195 | (A-) | 1526 |
| (A-) | 929 | (A-) | 1030 | (A-) | 1203 | (A-) | 1527 |
| (A-) | 930 | (A-) | 1032 | (A-) | 1205 | (A-) | 1529 |
| (A-) | 931 | (A-) | 1033 | (A-) | 1206 | (A-) | 1530 |
| (A-) | 933 | (A-) | 1035 | (A-) | 1208 | (A-) | 1532 |
| (A-) | 934 | (A-) | 1036 | (A-) | 1209 | (A-) | 1534 |
| (A-) | 936 | (A-) | 1038 | (A-) | 1211 | (A-) | 1535 |
| (A-) | 937 | (A-) | 1039 | (A-) | 1212 | (A-) | 1537 |
| (A-) | 939 | (A-) | 1041 | (A-) | 1214 | (B-) | 1538 |
| (A-) | 940 | (A-) | 1043 | (A-) | 1215 | (A-) | 1543 |
| (A-) | 942 | (A-) | 1044 | (A-) | 1217 | (A-) | 1545 |
| (A-) | 943 | (A-) | 1046 | (A-) | 1218 | (A-) | 1549 |
| (A-) | 945 | (A-) | 1047 | (A-) | 1220 | (A-) | 1551 |
| (A-) | 947 | (A-) | 1049 | (A-) | 1221 | (A-) | 1552 |
| (A-) | 948 | (A-) | 1059 | (A-) | 1223 | (A-) | 1556 |
| (A-) | 950 | (A-) | 1062 | (A-) | 1224 | (A-) | 1564 |
| (A-) | 951 | (A-) | 1066 | (A-) | 1226 | (A-) | 1566 |
| (A-) | 953 | (A-) | 1070 | (A-) | 1228 | (A-) | 1567 |
| (A-) | 954 | (A-) | 1072 | (A-) | 1229 | (A-) | 1569 |
| (A-) | 956 | (A-) | 1079 | (A-) | 1231 | (A-) | 1570 |
| (A-) | 957 | (A-) | 1081 | (A-) | 1232 | (A-) | 1572 |
| (A-) | 959 | (A-) | 1082 | (A-) | 1237 | (A-) | 1578 |
| (A-) | 960 | (A-) | 1085 | (A-) | 1240 | (A-) | 1580 |
| (A-) | 961 | (A-) | 1086 | (A-) | 1244 | (A-) | 1581 |
| (A-) | 963 | (A-) | 1088 | (A-) | 1248 | (A-) | 1589 |
| (A-) | 964 | (A-) | 1093 | (A-) | 1252 | (A-) | 1595 |
| (A-) | 966 | (A-) | 1095 | (A-) | 1256 | (A-) | 1602 |
| (A-) | 967 | (A-) | 1096 | (A-) | 1258 | (A-) | 1607 |
| (A-) | 969 | (A-) | 1104 | (A-) | 1263 | (A-) | 1612 |
| (A-) | 970 | (A-) | 1107 | (A-) | 1265 | (A-) | 1614 |

E-7

| | | | |
|---|---|---|---|
| (B-) 1620 | (A-) 1835 | (A-) 2040 | (A-) 2307 |
| (B+) 1624 | (A-) 1837 | (A-) 2041 | (A-) 2308 |
| (B+) 1626 | (A-) 1838 | (A-) 2042 | (A-) 2310 |
| (A-) 1640 | (A-) 1840 | (A-) 2044 | (A-) 2311 |
| (A-) 1644 | (A-) 1842 | (A-) 2051 | (A-) 2313 |
| (A-) 1648 | (A-) 1843 | (A-) 2053 | (A-) 2314 |
| (A-) 1650 | (A-) 1844 | (A-) 2054 | (A-) 2315 |
| (A-) 1651 | (A-) 1846 | (A-) 2056 | (A-) 2317 |
| (A-) 1657 | (A-) 1847 | (A-) 2058 | (A-) 2318 |
| (A-) 1658 | (A-) 1849 | (A-) 2059 | (A-) 2320 |
| (A-) 1660 | (A-) 1850 | (A-) 2060 | (A-) 2321 |
| (A-) 1663 | (A-) 1852 | (A-) 2062 | (A-) 2323 |
| (A-) 1670 | (A-) 1853 | (A-) 2063 | (A-) 2324 |
| (A-) 1671 | (A-) 1854 | (A-) 2065 | (A-) 2325 |
| (A-) 1672 | (A-) 1856 | (A-) 2066 | (A-) 2327 |
| (A-) 1677 | (A-) 1857 | (A-) 2068 | (A-) 2328 |
| (A-) 1678 | (A-) 1859 | (A-) 2069 | (A-) 2330 |
| (A-) 1680 | (A-) 1860 | (A-) 2071 | (A-) 2331 |
| (A-) 1682 | (A-) 1862 | (A-) 2072 | (A-) 2333 |
| (A-) 1687 | (A-) 1863 | (A-) 2076 | (A-) 2335 |
| (A-) 1691 | (A-) 1864 | (A-) 2078 | (A-) 2336 |
| (A-) 1694 | (A-) 1866 | (A-) 2079 | (A-) 2337 |
| (A-) 1698 | (A-) 1867 | (B+) 2082 | (A-) 2339 |
| (B+) 1702 | (A-) 1869 | (A-) 2087 | (A-) 2340 |
| (A-) 1720 | (A-) 1870 | (A-) 2089 | (A-) 2342 |
| (B+) 1729 | (A-) 1872 | (A-) 2090 | (A-) 2343 |
| (A-) 1734 | (A-) 1892 | (A-) 2092 | (A-) 2345 |
| (A-) 1736 | (A-) 1893 | (A-) 2093 | (A-) 2346 |
| (A-) 1740 | (A-) 1895 | (A-) 2095 | (C) 2358 |
| (A-) 1742 | (A-) 1896 | (A-) 2096 | |
| (A-) 1750 | (A-) 1898 | (A-) 2098 | Programs set |
| (A-) 1754 | (A-) 1899 | (A-) 2099 | 2.SUN PM 8:00 5 |
| (A-) 1756 | (A-) 1900 | (A-) 2101 | 2.SUN PM 8:00 5 |
| (A-) 1757 | (A-) 1902 | (A-) 2102 | 2.SUN PM 8:00 5 |
| (A-) 1759 | (A-) 1904 | (A-) 2104 | 2.SUN PM 8:00 5 |
| (A-) 1760 | (A-) 1905 | (A-) 2105 | 2.SUN PM 8:00 5 |
| (A-) 1761 | (A-) 1914 | (A-) 2107 | M-F AM 3:00 7 |
| (A-) 1763 | (A-) 1916 | (A-) 2108 | 1.TUE PM 8:30 66 |
| (A-) 1764 | (A-) 1917 | (A-) 2118 | |
| (A-) 1766 | (A-) 1918 | (A-) 2120 | Page summary |
| (A-) 1767 | (A-) 1920 | (A-) 2121 | CLOCK SET,3,368 |
| (A-) 1776 | (A-) 1921 | (A-) 2123 | CLOCK ADJUST,11,57 |
| (A-) 1778 | (A-) 1923 | (A-) 2124 | CLOCK,2,74 |
| (A-) 1780 | (A-) 1924 | (A-) 2126 | SELECT THE PROGRAM,11,169 |
| (A-) 1781 | (A-) 1926 | (A-) 2132 | PROGRAM1,9,733 |
| (A-) 1782 | (A-) 1927 | (A-) 2134 | PROGRAM2,3,562 |
| (A-) 1784 | (A-) 1934 | (A-) 2135 | PROGRAM3,3,380 |
| (A-) 1785 | (A-) 1936 | (A-) 2137 | PROGRAM4,3,26 |
| (A-) 1787 | (A-) 1937 | (A-) 2138 | ON/OFF,2,16 |
| (A-) 1788 | (A-) 1939 | (A-) 2144 | |
| (A-) 1789 | (A-) 1945 | (B+) 2148 | COUNT:679 |
| (A-) 1811 | (C) 1954 | (B+) 2151 | WASTED TIME:46 |
| (A-) 1813 | (A-) 1978 | (A-) 2161 | TOTAL TIME = Time - |
| (A-) 1814 | (A-) 1983 | (A-) 2164 | Waste=2358 |
| (A-) 1815 | (B-) 2006 | (A-) 2166 | |
| (A-) 1817 | (A-) 2010 | (A-) 2168 | |
| (A-) 1818 | (A-) 2011 | (A-) 2171 | |
| (A-) 1820 | (A-) 2013 | (B+) 2173 | |
| (A-) 1821 | (A-) 2015 | (A-) 2177 | |
| (A-) 1823 | (B+) 2021 | (B+) 2188 | |
| (A-) 1824 | (A-) 2028 | (B-) 2199 | |
| (A-) 1825 | (A-) 2030 | (B+) 2272 | |
| (A-) 1827 | (A-) 2031 | (A-) 2290 | |
| (A-) 1829 | (A-) 2032 | (A-) 2298 | |
| (A-) 1830 | (A-) 2034 | (A-) 2300 | |
| (A-) 1831 | (A-) 2035 | (A-) 2302 | |
| (A-) 1832 | (A-) 2037 | (A-) 2304 | |
| (A-) 1834 | (A-) 2038 | (A-) 2305 | |

E-8

Subject number 5 Tuesday,
June 5, 1990 9:54:04 PM

Page time log
CLOCK SET ,1,7
SELECT THE PROGRAM ,8,12
PROGRAM1 ,22,33
SELECT THE PROGRAM ,55,0
SELECT THE PROGRAM ,56,5
CLOCK ADJUST ,63,11
CLOCK SET ,75,59
CLOCK ADJUST ,135,4
CLOCK SET ,140,13
CLOCK SET ,165,45
CLOCK ,211,48
SELECT THE PROGRAM ,259,0
SELECT THE PROGRAM ,260,1
SELECT THE PROGRAM ,261,1
SELECT THE PROGRAM ,262,1
SELECT THE PROGRAM ,263,3
CLOCK ADJUST ,267,7
CLOCK SET ,275,21
SELECT THE PROGRAM ,297,4
SELECT THE PROGRAM ,301,3
CLOCK ADJUST ,305,8
SELECT THE PROGRAM ,313,11
PROGRAM1 ,325,14
ON/OFF ,339,13
ON/OFF ,339,13
CLOCK SET ,354,1
SELECT THE PROGRAM ,355,1
SELECT THE PROGRAM ,356,0
SELECT THE PROGRAM ,357,3
PROGRAM1 ,362,40
PROGRAM4 ,404,7
PROGRAM3 ,412,2
PROGRAM2 ,416,1
PROGRAM1 ,419,2
PROGRAM2 ,422,3
PROGRAM1 ,427,229
SELECT THE PROGRAM ,657,16
PROGRAM1 ,676,6
PROGRAM2 ,684,208
SELECT THE PROGRAM ,892,8
PROGRAM1 ,902,3
PROGRAM2 ,907,2
PROGRAM3 ,911,331
SELECT THE PROGRAM ,1242,4
PROGRAM1 ,1249,11
ON/OFF ,1260,6
CLOCK ADJUST ,1267,5
CLOCK SET ,1273,126
CLOCK ,1400,7
SELECT THE PROGRAM ,1407,10
ON/OFF ,1417,8

Error log:
WRONG KEY RIGHT 133
WRONG KEY SPACE 153
SPACE 153
SPACE 154
SPACE 154
SPACE 155
SPACE 155
SPACE 155
SPACE 155
LEFT 156

WRONG KEY ALT+SPACE 171
ALT+SPACE 171
END 213
END 213
LEFT 249
LEFT 250
LEFT 251
CENTER 252
CENTER 253
END 255
END 256
END 257
WRONG KEY END 272
END 273
WRONG KEY END 273
END 274
BIGMINUS 344
BIGMINUS 346
BIGMINUS 348
BIGMINUS 349
 subject 5 continued 353
Subject number 5 continue
    Tuesday, June 5, 1990
    10:12:20 PM MARION 353
SETS TIMER 1425

Users Actions:
(PRGM) 7
(B-) 34
(A-) 41
(A+) 43
(A-) 45
(A+) 47
(B-) 49
(B+) 51
(C) 53
(PRGM) 54
(B+) 74
(A-) 82
(A-) 88
(A+) 91
(B-) 98
(B+) 102
(B-) 104
(B+) 105
(A+) 106
(A-) 108
(CLKADJ) 133
(B+) 139
(A-) 142
(SPACE) 152
STATUS (Return) 164
(ALT+SPACE) 170
(B+) 176
(B-) 178
(B-) 180
(B-) 181
(B-) 182
(B-) 184
(B-) 185
(B-) 186
(B-) 187
(B-) 188
(B-) 189
(B-) 190
(B-) 191
(B-) 192
(B-) 194

(B+) 204
(B+) 206
(B+) 207
(B+) 208
(C) 209
(C) 272
(C) 273
(B-) 274
(B-) 276
(B+) 281
(B+) 282
(B+) 283
(B-) 284
(A-) 287
(A+) 292
(A+) 293
(PRGM) 295
(PRGM) 312
(TIMER) 339
(PRGM) 344
(PRGM) 346
(PRGM) 347
(PRGM) 348
(C) 352
(PRGM) 354
(A-) 402
(A-) 410
(A-) 414
(A-) 417
(A-) 421
(A-) 425
(B-) 429
(B+) 437
(B+) 440
(B-) 445
(B-) 449
(B-) 451
(C) 454
(C) 455
(C) 457
(C) 458
(C) 460
(C) 461
(B-) 462
(B-) 464
(B+) 466
(B-) 468
(A-) 471
(A-) 475
(A-) 478
(A-) 480
(B-) 486
(B+) 493
(B+) 497
(A-) 506
(A-) 510
(A-) 512
(A+) 515
(A-) 518
(A-) 520
(B-) 529
(B-) 541
(B-) 545
(B-) 548
(B-) 550
(B-) 552
(B+) 554
(B-) 560

(B+) 564
(B+) 566
(A-) 572
(A+) 579
(A+) 581
(C) 591
(B+) 599
(B+) 604
(A+) 616
(A+) 619
(A+) 622
(A+) 625
(B+) 636
(A+) 642
(A+) 644
(A+) 647
(C) 655
(A+) 682
(B+) 711
(A+) 720
(A+) 723
(A+) 725
(A+) 727
(A+) 729
(A+) 731
(A+) 733
(A+) 735
(A+) 737
(A+) 740
(A+) 742
(A+) 744
(A+) 746
(A+) 748
(A+) 750
(A+) 752
(A+) 758
(A+) 761
(A+) 763
(A+) 765
(B+) 769
(B+) 773
(A+) 782
(A+) 785
(A+) 787
(A+) 789
(A+) 791
(A+) 793
(A+) 795
(A+) 797
(A+) 799
(A+) 802
(A+) 807
(A+) 810
(A+) 812
(A+) 814
(A+) 816
(A+) 820
(A+) 823
(A+) 825
(A+) 827
(A+) 829
(A+) 831
(A+) 834
(A+) 836
(B+) 842
(B+) 856
(B+) 864
(B+) 869

| | | | |
|---|---|---|---|
| (A+) 879 | (A+) 1090 | (B+) 1360 | Subject number 9 Thursday, |
| (A+) 881 | (A+) 1093 | (B+) 1362 | June 7, 1990 10:36:47 AM |
| (A+) 883 | (A+) 1096 | (B+) 1365 | |
| (A+) 885 | (A+) 1098 | (A+) 1371 | |
| (C) 890 | (A+) 1101 | (A+) 1372 | Page time log |
| (A+) 904 | (A+) 1104 | (A+) 1374 | CLOCK SET ,1,1 |
| (A+) 909 | (A+) 1106 | (A+) 1375 | CLOCK ADJUST ,4,2 |
| (B+) 916 | (A+) 1109 | (B+) 1378 | CLOCK ADJUST ,7,5 |
| (A+) 924 | (A+) 1112 | (A+) 1385 | CLOCK SET ,13,134 |
| (A+) 927 | (A+) 1115 | (A+) 1386 | CLOCK ,148,8 |
| (A+) 929 | (A+) 1117 | (A+) 1388 | SELECT THE PROGRAM ,156,9 |
| (B+) 931 | (A+) 1123 | (A+) 1390 | PROGRAM1 ,167,234 |
| (B+) 934 | (A+) 1130 | (B+) 1393 | SELECT THE PROGRAM ,402,6 |
| (A+) 939 | (A-) 1135 | (A+) 1395 | PROGRAM1 ,410,4 |
| (A+) 941 | (A-) 1150 | (C) 1399 | PROGRAM2 ,416,233 |
| (A+) 943 | (A-) 1157 | (C) 1425 | SELECT THE PROGRAM ,649,4 |
| (B+) 945 | (A-) 1159 | | SELECT THE PROGRAM ,654,13 |
| (A+) 947 | (A-) 1162 | Programs set | ON/OFF ,667,52 |
| (A+) 951 | (A-) 1164 | M-F PM 8:00 4 (subject | CLOCK ,719,5 |
| (A+) 953 | (A-) 1167 | knows this is wrong) 302 | ON/OFF ,724,3 |
| (A+) 955 | (A-) 1170 | 1.SUN PM 8:00 5 | CLOCK ,727,6 |
| (A+) 957 | (A-) 1172 | 1.FRI AM 3:00 7 (wrong | SELECT THE PROGRAM ,733,31 |
| (A+) 959 | (A-) 1175 | date) 887 | SELECT THE PROGRAM ,764,9 |
| (A+) 961 | (A-) 1178 | | SELECT THE PROGRAM ,773,4 |
| (A+) 963 | (A-) 1180 | Page summary | PROGRAM1 ,779,21 |
| (A+) 965 | (A-) 1183 | CLOCK SET,7,272 | SELECT THE PROGRAM ,800,3 |
| (A+) 968 | (A-) 1186 | CLOCK ADJUST,5,35 | PROGRAM1 ,806,7 |
| (A+) 970 | (A-) 1189 | CLOCK,2,55 | PROGRAM2 ,815,311 |
| (A+) 972 | (A-) 1191 | SELECT THE PROGRAM,18,83 | SELECT THE PROGRAM ,1127,10 |
| (A+) 977 | (A-) 1194 | PROGRAM1,8,338 | PROGRAM1 ,1139,4 |
| (A+) 979 | (B+) 1220 | PROGRAM2,4,214 | PROGRAM2 ,1145,2 |
| (A+) 981 | (A+) 1228 | PROGRAM3,2,333 | PROGRAM1 ,1150,36 |
| (A+) 983 | (A+) 1230 | PROGRAM4,1,7 | SELECT THE PROGRAM ,1187,4 |
| (A+) 985 | (A+) 1232 | ON/OFF,4,40 | PROGRAM1 ,1193,5 |
| (A+) 987 | (A+) 1234 | | PROGRAM2 ,1200,2 |
| (A+) 989 | (A+) 1236 | COUNT:330 | PROGRAM3 ,1204,150 |
| (A+) 992 | (A+) 1238 | WASTED TIME:47 | SELECT THE PROGRAM ,1354,9 |
| (A+) 994 | (C) 1240 | TOTAL TIME = Time - | ON/OFF ,1363,31 |
| (A+) 1001 | (TIMER) 1260 | Waste=1425 | |
| (A+) 1003 | (CLKADJ) 1266 | | Error log: |
| (A+) 1005 | (B+) 1272 | | WRONG KEY RIGHT 2 |
| (A+) 1007 | (A+) 1276 | | WRONG KEY RIGHT 5 |
| (A+) 1009 | (A+) 1279 | | (SUBJECT SET TIME FOR 9:00 |
| (A+) 1012 | (A-) 1286 | | AM) 146 |
| (A+) 1014 | (A-) 1287 | | BIGMINUS 675 |
| (A+) 1019 | (A-) 1289 | | BIGMINUS 682 |
| (A+) 1021 | (A-) 1290 | | DOWN 920 |
| (B+) 1025 | (A-) 1291 | | TURNS POWER OFF AND SETS |
| (A+) 1032 | (A-) 1292 | | TIMER 1394 |
| (A+) 1036 | (A-) 1294 | | |
| (A+) 1038 | (A+) 1299 | | Users Actions: |
| (A+) 1041 | (A+) 1300 | | (CLKADJ) 1 |
| (A+) 1044 | (B+) 1306 | | (CLKADJ) 5 |
| (B+) 1047 | (B+) 1309 | | (B+) 11 |
| (A+) 1050 | (B+) 1313 | | (A+) 20 |
| (A+) 1053 | (A+) 1320 | | (A+) 23 |
| (A+) 1056 | (B+) 1329 | | (A+) 24 |
| (A+) 1059 | (A+) 1335 | | (A+) 25 |
| (A-) 1061 | (A+) 1337 | | (A+) 26 |
| (A-) 1064 | (A+) 1338 | | (A+) 28 |
| (A-) 1067 | (A+) 1340 | | (A+) 29 |
| (A-) 1069 | (B+) 1344 | | (A+) 31 |
| (A-) 1072 | (A+) 1349 | | (A+) 32 |
| (A-) 1074 | (A+) 1350 | | (A+) 34 |
| (A+) 1079 | (A+) 1352 | | (A+) 35 |
| (A+) 1082 | (A+) 1353 | | (A-) 40 |
| (A-) 1084 | (A+) 1355 | | (A-) 43 |
| (A+) 1088 | (A+) 1356 | | (B+) 55 |

E-10

| | | | | | | | |
|---|---|---|---|---|---|---|---|
| (B+) | 63 | (A+) | 318 | (B+) | 606 | (A+) | 1049 |
| (A+) | 70 | (A-) | 324 | (B+) | 610 | (A+) | 1057 |
| (A+) | 72 | (B+) | 338 | (B+) | 617 | (A+) | 1063 |
| (A+) | 74 | (A+) | 347 | (B+) | 622 | (A+) | 1070 |
| (B+) | 82 | (A+) | 350 | (B+) | 625 | (A+) | 1072 |
| (A+) | 87 | (A+) | 352 | (PRGM) | 648 | (A+) | 1077 |
| (A+) | 90 | (A+) | 355 | (PRGM) | 674 | (A+) | 1082 |
| (A+) | 92 | (B-) | 363 | (PRGM) | 682 | (A+) | 1084 |
| (A+) | 94 | (A+) | 368 | (POWER) | 719 | (A+) | 1087 |
| (A+) | 96 | (B+) | 374 | (POWER) | 727 | (A+) | 1090 |
| (B+) | 101 | (B+) | 377 | (B+) | 786 | (A+) | 1103 |
| (A+) | 105 | (A+) | 384 | (B-) | 793 | (A+) | 1107 |
| (A+) | 107 | (A+) | 386 | (B-) | 797 | (A+) | 1111 |
| (A+) | 108 | (A+) | 388 | (PRGM) | 800 | (A+) | 1115 |
| (A+) | 110 | (A+) | 392 | (A+) | 813 | (C) | 1125 |
| (A+) | 114 | (C) | 400 | (B+) | 824 | (A+) | 1142 |
| (B+) | 123 | (A+) | 413 | (B-) | 842 | (A-) | 1147 |
| (A+) | 126 | (B+) | 421 | (B-) | 844 | (B+) | 1151 |
| (A+) | 128 | (A+) | 428 | (B-) | 846 | (B+) | 1153 |
| (A+) | 130 | (A+) | 431 | (B+) | 848 | (B-) | 1161 |
| (A+) | 131 | (A+) | 433 | (B-) | 850 | (B-) | 1166 |
| (A+) | 133 | (B+) | 436 | (B-) | 856 | (B-) | 1170 |
| (A+) | 137 | (B+) | 444 | (B-) | 863 | (B+) | 1173 |
| (C) | 146 | (A+) | 447 | (A+) | 867 | (B+) | 1179 |
| (B+) | 171 | (A+) | 449 | (A+) | 869 | (PRGM) | 1186 |
| (A+) | 181 | (A+) | 451 | (A+) | 883 | (A+) | 1197 |
| (A+) | 183 | (B+) | 458 | (B+) | 887 | (A+) | 1202 |
| (A+) | 185 | (A+) | 467 | (B+) | 890 | (B+) | 1211 |
| (A+) | 187 | (A+) | 469 | (A+) | 896 | (A+) | 1220 |
| (A+) | 190 | (A+) | 471 | (A+) | 901 | (A+) | 1222 |
| (A+) | 192 | (A+) | 473 | (A+) | 904 | (A+) | 1224 |
| (A+) | 194 | (A+) | 475 | (B+) | 909 | (A+) | 1226 |
| (A+) | 196 | (A+) | 477 | (B+) | 913 | (A+) | 1228 |
| (A+) | 198 | (A+) | 479 | (D) | 919 | (A+) | 1230 |
| (A+) | 201 | (A+) | 481 | (B+) | 925 | (A+) | 1232 |
| (A+) | 203 | (A+) | 484 | (A+) | 930 | (A+) | 1234 |
| (A+) | 205 | (A+) | 486 | (B+) | 936 | (A+) | 1236 |
| (A+) | 207 | (A+) | 489 | (B-) | 944 | (A+) | 1238 |
| (A+) | 210 | (A+) | 491 | (B-) | 947 | (A+) | 1240 |
| (A+) | 212 | (A+) | 493 | (B-) | 952 | (A+) | 1242 |
| (A+) | 214 | (A+) | 495 | (B+) | 957 | (A+) | 1244 |
| (A+) | 216 | (A+) | 497 | (A-) | 962 | (B+) | 1252 |
| (A+) | 219 | (A+) | 499 | (B+) | 972 | (B+) | 1254 |
| (A+) | 221 | (A+) | 501 | (A+) | 978 | (A-) | 1262 |
| (A+) | 223 | (A+) | 503 | (A+) | 980 | (A-) | 1264 |
| (A+) | 225 | (A+) | 506 | (A+) | 982 | (A-) | 1266 |
| (A+) | 227 | (A+) | 508 | (A+) | 984 | (A-) | 1268 |
| (A+) | 230 | (A+) | 510 | (A+) | 986 | (A-) | 1270 |
| (A+) | 232 | (A+) | 512 | (A+) | 988 | (A-) | 1272 |
| (A+) | 234 | (A+) | 514 | (A-) | 999 | (A-) | 1274 |
| (A-) | 236 | (A+) | 516 | (B-) | 1005 | (A-) | 1276 |
| (A-) | 241 | (A+) | 518 | (B-) | 1007 | (A-) | 1278 |
| (A-) | 249 | (A+) | 520 | (A+) | 1012 | (A-) | 1280 |
| (A-) | 254 | (A+) | 522 | (A+) | 1014 | (A-) | 1282 |
| (B+) | 261 | (A+) | 524 | (A+) | 1016 | (A-) | 1284 |
| (B-) | 267 | (A+) | 531 | (A+) | 1018 | (A-) | 1286 |
| (A-) | 272 | (A+) | 533 | (A+) | 1020 | (A-) | 1288 |
| (B+) | 278 | (B+) | 540 | (A+) | 1022 | (A-) | 1290 |
| (B+) | 283 | (B-) | 565 | (A+) | 1024 | (A-) | 1292 |
| (A-) | 285 | (B-) | 567 | (A+) | 1026 | (A+) | 1296 |
| (A-) | 288 | (B-) | 571 | (A+) | 1028 | (A+) | 1299 |
| (A-) | 290 | (B-) | 572 | (A+) | 1030 | (A-) | 1301 |
| (A-) | 292 | (B-) | 576 | (A+) | 1033 | (A+) | 1303 |
| (A-) | 295 | (B-) | 584 | (A+) | 1035 | (A+) | 1305 |
| (A+) | 297 | (B-) | 589 | (A+) | 1037 | (A-) | 1307 |
| (B+) | 299 | (B+) | 595 | (A+) | 1042 | (B+) | 1315 |
| (B+) | 305 | (B+) | 598 | (A+) | 1045 | (B+) | 1320 |
| (B+) | 310 | (B+) | 602 | (A+) | 1047 | (B+) | 1329 |

E-11

```
(A+) 1334              Subject number 10 Tuesday,   WRONG KEY HOME 261      (A-) 323
(B+) 1338                June 12, 1990 6:01:51 PM   HOME 261                (A-) 325
(A+) 1341                                           END 274                 (B+) 337
(A+) 1344              Page time log                WRONG KEY RIGHT 279     (B+) 339
(A+) 1346              CLOCK SET ,0,30              WRONG KEY RIGHT 281     (B+) 341
(C)  1352              ON/OFF ,31,25                WRONG KEY RIGHT 283     (B+) 343
(C)  1394              CLOCK ,57,8                  HOME 310                (B+) 345
                       CLOCK ADJUST ,66,5           HOME 311                (B+) 347
Programs set           SELECT THE PROGRAM ,72,19    LEFT 313                (B+) 350
2.SUN PM 8:00 5        SELECT THE PROGRAM ,91,3     LEFT 314                (B+) 352
M-F  AM 3:00 6 (WRONG  SELECT THE PROGRAM ,94,2     SUBJECT 10 RESTARTS 315 (B+) 354
    CHANNEL) 1125      ON/OFF ,96,3                 Subject number 10 CONT. (A+) 363
1.THU PM 1:00 4        CLOCK ADJUST ,99,6             Tuesday, June 12, 1990(A+) 368
                       CLOCK SET ,106,53              6:21:46 PM GIMMY 315  (A-) 373
Page summary           CLOCK ,160,13                BIGMINUS 570            (A-) 376
CLOCK SET,2,135        CLOCK ADJUST ,173,7          BIGMINUS 572            (A+) 379
CLOCK ADJUST,2,7       CLOCK ADJUST ,180,32         END 1168                (A+) 380
CLOCK,3,19             ON/OFF ,212,9                NO TIMER NO POWER OFF - (A+) 382
SELECT THE PROGRAM,11,102 CLOCK ADJUST ,222,9         THINKS POWER SHOULD STAY (A+) 383
PROGRAM1,7,311         CLOCK SET ,231,15              ON 1482               (B+) 387
PROGRAM2,4,548         CLOCK ,246,4                                         (A+) 409
PROGRAM3,1,150         CLOCK ADJUST ,251,13         Users Actions:          (A+) 410
PROGRAM4,0,0           CLOCK SET ,265,7             (POWER) 30              (A+) 412
ON/OFF,3,86            CLOCK ,273,3                 (POWER) 56              (A+) 413
                       CLOCK ADJUST ,277,2          (PRGM) 71               (A+) 415
COUNT:297              CLOCK ADJUST ,279,2          (CLKADJ) 99             (B+) 420
WASTED TIME:35         CLOCK ADJUST ,282,1          (A-) 102                (A+) 424
TOTAL TIME = Time -    CLOCK ADJUST ,284,12         (B-) 105                (A+) 426
    Waste=1394         SELECT THE PROGRAM ,296,10   (A-) 112                (A+) 427
                       ON/OFF ,306,9                (A-) 115                (A+) 429
                       CLOCK SET ,316,222           (A-) 120                (A+) 432
                       CLOCK ,538,21                (B-) 132                (A+) 433
                       ON/OFF ,559,18               (B-) 134                (B+) 436
                       CLOCK ADJUST ,577,2          (B-) 134                (A-) 451
                       SELECT THE PROGRAM ,579,5    (B-) 135                (A+) 453
                       PROGRAM1 ,586,396            (B-) 137                (B+) 463
                       SELECT THE PROGRAM ,982,8    (B+) 140                (B-) 474
                       PROGRAM1 ,992,3              (B+) 142                (B+) 479
                       PROGRAM2 ,996,171            (B+) 144                (B-) 494
                       SELECT THE PROGRAM ,1167,24  (B+) 145                (B+) 496
                       PROGRAM1 ,1193,8             (B+) 147                (B+) 499
                       SELECT THE PROGRAM ,1201,6   (C)  159                (B+) 502
                       PROGRAM1 ,1209,2             (CLKADJ) 180            (B+) 508
                       PROGRAM2 ,1213,1             (A-) 187                (B+) 509
                       PROGRAM3 ,1216,121           (A-) 188                (B+) 511
                       SELECT THE PROGRAM ,1338,66  (TIMER) 212             (B+) 513
                       PROGRAM1 ,1406,1             (TIMER) 218             (B+) 518
                       PROGRAM2 ,1409,11            (CLKADJ) 221            (A+) 522
                       SELECT THE PROGRAM ,1420,59  (A-) 226                (A+) 524
                       ON/OFF ,1480,2               (A+) 228                (A+) 526
                                                    (B-) 231                (C)  537
                       Error log:                   (B+) 237                (PRGM) 569
                       WRONG KEY HOME 102           (C)  245                (PRGM) 572
                       HOME 103                     (A-) 261                (CLKADJ) 576
                       END 162                      (B-) 264                (PRGM) 579
                       CENTER 165                   (C)  272                (B+) 602
                       LEFT 169                     (CLKADJ) 279            (B+) 608
                       WRONG KEY RIGHT 180          (CLKADJ) 281            (B+) 610
                       WRONG KEY HOME 187           (CLKADJ) 283            (B-) 615
                       HOME 187                     (PRGM) 295              (B-) 617
                       WRONG KEY HOME 188           (A-) 310                (B-) 619
                       HOME 189                     (A-) 311                (A-) 627
                       WRONG KEY HOME 226           (B-) 313                (A-) 629
                       HOME 226                     (B-) 314                (A-) 630
                       WRONG KEY UP 228             (C)  315                (A-) 634
                       UP 228                       (A-) 316                (B+) 639
                       END 247                      (A+) 319                (B+) 645
                                                    (A-) 321                (A-) 652
```

E-12

```
(B+)  657       (B+) 1025      M-F  PM 6:00 4        Subject number 11
(B+)  661       (A+) 1031      M-F  AM 3:00 1        Wednesday, May 30, 1990
(B+)  685       (A+) 1033
(B+)  688       (A+) 1035      Page summary          Page time log
(B-)  706       (A+) 1036      CLOCK SET,5,327       CLOCK SET ,1,9
(A+)  715       (A-) 1038      CLOCK ADJUST,11,91    CLOCK ADJUST ,12,10
(A+)  718       (A+) 1040      CLOCK,5,49            CLOCK SET ,23,33
(A+)  720       (A+) 1042      SELECT THE PROGRAM,10,202  CLOCK ADJUST ,57,5
(A+)  722       (A-) 1044      PROGRAM1,5,410        CLOCK SET ,63,58
(A+)  731       (A-) 1046      PROGRAM2,3,183        CLOCK ADJUST ,122,4
(A+)  734       (B+) 1052      PROGRAM3,1,121        CLOCK SET ,127,12
(A+)  736       (B-) 1056      PROGRAM4,0,0          CLOCK ADJUST ,140,15
(A+)  740       (A-) 1065      ON/OFF,6,66           ON/OFF ,155,9
(A+)  743       (A+) 1069                            CLOCK ADJUST ,165,0
(A+)  745       (A+) 1098      COUNT:244             CLOCK ADJUST ,166,3
(A+)  747       (A+) 1104      WASTED TIME:33        CLOCK ADJUST ,170,36
(A-)  758       (A-) 1112      TOTAL TIME = Time -   CLOCK ,207,7
(A+)  774       (A-) 1115             Waste=1482     SELECT THE PROGRAM ,214,8
(A+)  776       (A+) 1121                            PROGRAM1 ,223,20
(A+)  779       (B+) 1127                            PROGRAM2 ,244,5
(A+)  783       (B+) 1130                            PROGRAM1 ,250,24
(A+)  786       (A-) 1144                            SELECT THE PROGRAM ,275,7
(A+)  790       (B+) 1150                            PROGRAM1 ,284,3
(A+)  800       (C)  1166                            PROGRAM2 ,288,2
(A+)  804       (C)  1199                            PROGRAM1 ,291,730
(A-)  809       (A+) 1211                            SELECT THE PROGRAM ,1022,22
(B+)  814       (A+) 1214                            CLOCK ADJUST ,1045,8
(A+)  824       (B+) 1217                            CLOCK SET ,1054,88
(A+)  827       (A+) 1233                            CLOCK ,1142,2
(A+)  829       (A-) 1237                            SELECT THE PROGRAM ,1145,4
(A+)  831       (A-) 1239                            PROGRAM1 ,1150,343
(B+)  833       (A-) 1240                            SELECT THE PROGRAM ,1494,3
(B+)  838       (A-) 1242                            CLOCK ADJUST ,1498,9
(B+)  842       (A-) 1243                            SELECT THE PROGRAM ,1507,3
(B+)  846       (A-) 1244                            PROGRAM1 ,1512,197
(B+)  850       (A-) 1246                            SELECT THE PROGRAM ,1710,4
(A-)  857       (A-) 1247                            PROGRAM1 ,1716,4
(A-)  877       (A+) 1249                            PROGRAM2 ,1721,412
(A-)  882       (B+) 1251                            SELECT THE PROGRAM ,2133,10
(A-)  886       (B+) 1256                            PROGRAM1 ,2145,2
(A-)  896       (A-) 1270                            PROGRAM2 ,2148,2
(A+)  901       (A-) 1272                            PROGRAM3 ,2152,289
(A+)  925       (A-) 1274                            SELECT THE PROGRAM ,2441,67
(A+)  928       (A-) 1276                            SELECT THE PROGRAM ,2508,4
(A+)  931       (A-) 1278                            SELECT THE PROGRAM ,2512,25
(A+)  935       (A+) 1285                            SELECT THE PROGRAM ,2537,14
(A-)  938       (A-) 1288                            PROGRAM1 ,2553,128
(A-)  940       (B-) 1292                            SELECT THE PROGRAM ,2681,14
(A-)  944       (B+) 1299                            CLOCK ADJUST ,2696,4
(A-)  946       (B+) 1300                            ON/OFF ,2700,8
(A-)  949       (B+) 1303                            CLOCK ADJUST ,2709,3
(A-)  954       (A-) 1309                            SELECT THE PROGRAM ,2713,0
(A+)  961       (B+) 1316                            SELECT THE PROGRAM ,2713,15
(A+)  964       (A+) 1328                            ON/OFF ,2728,466
(A+)  966       (A+) 1330                            CLOCK ,3194,29
(A-)  971       (A+) 1332                            ON/OFF ,3224,1
(A-)  973       (B+) 1334                            CLOCK ,3225,3
(C)   985       (C)  1336                            CLOCK ADJUST ,3229,6
(A+)  995       (A+) 1407                            ON/OFF ,3235,60
(B+)  999       (C)  1419
(A-) 1005       (C)  1482                            Error log:
(A-) 1008                                            WRONG KEY 6 10
(A+) 1010       Programs set                         WRONG KEY 3 35
(A+) 1011       1.SAT PM 8:00 5                      3 35
(A+) 1013       M-F  AM 3:00 1 (WRONG                WRONG KEY 3 36
(A+) 1015              CHANNEL AND STOP TIME)        3 36
(A+) 1016              851                           WRONG KEY 6 59
(B+) 1021       1.SAT PM 8:00 5
```

E-13

```
WRONG KEY 6 121          (A+)  197        (C)   510       (A+) 1568
WRONG KEY 6 139          (A+)  198        (B+) 1053       (A+) 1576
WRONG KEY 1 147          (A+)  199        (A+) 1064       (C)  1600
1 147                    (A+)  200        (A-) 1066       (A+) 1720
WRONG KEY 1 150          (C)   205        (A-) 1068       (B+) 1725
1 150                    (C)   232        (A-) 1071       (A+) 1732
WRONG KEY 2 151          (C)   233        (B+) 1078       (A+) 1734
2 151                    (A+)  242        (A+) 1083       (A+) 1736
WRONG KEY 6 165          (A-)  249        (A+) 1084       (B+) 1737
2 259                    (C)   257        (A+) 1086       (9)  1740
9 1740                   (D)   259        (B+) 1090       (B+) 1745
2 2524                   (PRGM) 274       (A+) 1094       (A+) 1748
2 2526                   (A+)  287        (A+) 1095       (A+) 1749
4 2548                   (A-)  290        (A+) 1098       (A+) 1751
5 2684                   (B-)  294        (A+) 1100       (B+) 1753
5 2685                   (B-)  297        (B+) 1103       (A+) 1756
1 2689                   (B+)  299        (B+) 1105       (A+) 1757
2 2693                   (B-)  301        (A+) 1106       (A+) 1759
8 3252                   (B-)  305        (A-) 1108       (A+) 1761
ALT+SPACE 3289           (A+)  324        (B+) 1110       (A+) 1762
TURNS POWER OFF AND SETS (A+)  326        (A+) 1113       (A+) 1764
  TIMER, HAS NO IDEA IF IT (A+) 328       (A+) 1114       (A+) 1766
  WILL WORK 3295         (A+)  330        (A+) 1115       (A+) 1767
                         (A+)  332        (A+) 1117       (A+) 1769
Users Actions:           (A-)  334        (A+) 1118       (A+) 1771
(A+)     8               (A-)  335        (A+) 1120       (A+) 1773
(CLKADJ) 10              (A+)  337        (C)  1142       (A+) 1774
(B+)    22               (A-)  339        (B+) 1157       (A+) 1776
(B+)    32               (A-)  340        (B+) 1162       (A+) 1778
(3)     34               (A-)  342        (B+) 1164       (A+) 1779
(3)     35               (A-)  344        (B+) 1165       (A+) 1781
(A+)    45               (A-)  345        (B+) 1169       (A+) 1783
(B+)    48               (B+)  347        (A+) 1177       (A+) 1785
(CLKADJ) 56              (B+)  349        (B-) 1182       (A+) 1787
(B-)    62               (B+)  350        (B+) 1186       (A+) 1788
(B+)    79               (A+)  355        (A+) 1193       (A+) 1790
(B+)    81               (A+)  358        (A+) 1196       (A+) 1792
(B+)    97               (A+)  365        (A+) 1201       (A+) 1793
(B+)    99               (A-)  370        (A+) 1209       (A+) 1795
(A+)   114               (A-)  373        (A-) 1212       (A+) 1797
(A+)   115               (A-)  376        (A+) 1216       (A+) 1799
(A+)   118               (A-)  378        (A+) 1219       (A+) 1800
(CLKADJ) 121             (A-)  389        (B+) 1221       (A+) 1802
(B+)   126               (B+)  401        (B-) 1225       (A+) 1804
(CLKADJ) 138             (B+)  403        (B-) 1242       (A+) 1811
(C)    147               (B+)  409        (B-) 1247       (B+) 1813
(C)    149               (A-)  418        (B-) 1249       (A+) 1827
(D)    151               (A+)  422        (B-) 1253       (A-) 1831
(TIMER) 155              (A-)  424        (B-) 1254       (B+) 1833
(CLKADJ) 164             (A-)  425        (C)  1256       (A+) 1836
(CLKADJ) 165             (A-)  427        (PRGM) 1506     (A+) 1839
(B+)   169               (A-)  432        (B-) 1515       (A+) 1841
(A+)   176               (A-)  434        (B+) 1518       (A+) 1843
(A+)   178               (A+)  438        (B+) 1520       (B-) 1848
(A+)   179               (A+)  443        (B+) 1524       (A+) 1851
(A+)   180               (B+)  447        (B+) 1526       (B+) 1856
(A-)   181               (B-)  462        (B+) 1530       (B+) 1859
(A+)   182               (B-)  464        (A+) 1533       (A+) 1864
(A+)   183               (B-)  466        (A-) 1536       (A+) 1866
(A+)   184               (B-)  471        (A-) 1539       (A+) 1868
(A-)   185               (B-)  474        (B-) 1541       (A+) 1869
(A-)   186               (B+)  477        (B-) 1546       (B-) 1885
(A+)   189               (B+)  482        (B-) 1553       (B-) 1887
(A+)   190               (B-)  485        (B-) 1558       (A+) 1893
(A+)   191               (A-)  489        (A+) 1562       (A+) 1896
(A+)   192               (B+)  493        (A-) 1564       (A+) 1898
(A+)   193               (B+)  495                        (B+) 1902
(A+)   194               (A-)  499                        (A+) 1909
```

E-14

| | | | |
|---|---|---|---|
| (A+) 1911 | ON/OFF (ON/OFF) 3091 | Subject # 15 Wednesday, | 7 12 |
| (C) 1920 | ON/OFF (ON/OFF) 3092 | June 20, 1990 7:06:37 PM | WRONG KEY 7 12 |
| (A+) 2146 | ON/OFF (ON/OFF) 3092 | | 7 13 |
| (A+) 2150 | ON/OFF (ON/OFF) 3093 | | WRONG KEY 7 13 |
| (B+) 2156 | ON/OFF (ON/OFF) 3095 | Page time log | 7 13 |
| (A+) 2161 | ON/OFF (ON/OFF) 3095 | CLOCK SET ,1,3 | WRONG KEY 7 13 |
| (A+) 2163 | ON/OFF (ON/OFF) 3095 | CLOCK ADJUST ,5,9 | 7 14 |
| (A+) 2164 | ON/OFF (ON/OFF) 3096 | CLOCK SET ,15,34 | 8 56 |
| (A+) 2166 | ON/OFF (ON/OFF) 3116 | CLOCK ,50,9 | 8 57 |
| (A+) 2168 | ON/OFF (ON/OFF) 3116 | CLOCK ADJUST ,60,0 | 8 57 |
| (A+) 2169 | ON/OFF (ON/OFF) 3117 | CLOCK ADJUST ,61,8 | WRONG KEY 6 60 |
| (A+) 2171 | ON/OFF (ON/OFF) 3117 | CLOCK SET ,70,25 | WRONG KEY 8 65 |
| (A+) 2173 | ON/OFF (ON/OFF) 3117 | CLOCK ,95,8 | 8 65 |
| (A+) 2174 | (POWER) 3194 | CLOCK ADJUST ,104,0 | WRONG KEY 8 68 |
| (A+) 2176 | (POWER) 3224 | CLOCK ADJUST ,105,2 | 8 68 |
| (A+) 2178 | (TIMER) 3235 | CLOCK SET ,108,2 | WRONG KEY 8 68 |
| (A+) 2180 | (A+) 3252 | CLOCK ,110,6 | 8 68 |
| (A+) 2182 | (ALT+SPACE) 3289 | CLOCK ADJUST ,117,27 | 5 100 |
| (A+) 2183 | | CLOCK SET ,145,94 | 5 101 |
| (A+) 2185 | Programs set | CLOCK ,240,5 | WRONG KEY 6 104 |
| (A+) 2187 | 4.SUN PM 8:00 511 | CLOCK ADJUST ,246,2 | WRONG KEY 8 107 |
| (B+) 2188 | 2.SUN PM 8:00 747 | CLOCK SET ,249,41 | 8 107 |
| (B+) 2194 | 3.WED PM 8:00 859 | CLOCK ,290,9 | 1 111 |
| (A+) 2197 | M-F AM 3:00 1073 | CLOCK ADJUST ,300,4 | 1 112 |
| (A+) 2199 | M-F PM 4:00 1225 | CLOCK SET ,305,144 | WRONG KEY 7 123 |
| (A+) 2201 | 3.WED PM 8:00 1345 | CLOCK ,450,9 | 7 123 |
| (A+) 2202 | | SELECT THE PROGRAM ,459,7 | WRONG KEY 7 125 |
| (A+) 2204 | Page summary | PROGRAM1 ,467,266 | 7 125 |
| (A+) 2206 | CLOCK SET,6,236 | SELECT THE PROGRAM ,734,3 | WRONG KEY 7 125 |
| (A+) 2207 | CLOCK ADJUST,11,67 | PROGRAM1 ,745,3 | 7 126 |
| (A+) 2210 | CLOCK,4,41 | PROGRAM4 ,749,3 | WRONG KEY 8 128 |
| (A+) 2212 | SELECT THE PROGRAM,15,200 | PROGRAM1 ,754,1 | 8 128 |
| (A+) 2213 | PROGRAM1,9,1451 | PROGRAM2 ,757,317 | WRONG KEY 8 129 |
| (A+) 2215 | PROGRAM2,4,421 | SELECT THE PROGRAM ,1075,16 | 8 129 |
| (A+) 2217 | PROGRAM3,1,289 | PROGRAM1 ,1093,4 | WRONG KEY 8 130 |
| (A+) 2218 | PROGRAM4,0,0 | PROGRAM2 ,1099,2 | 8 130 |
| (A+) 2220 | ON/OFF,5,544 | PROGRAM3 ,1102,1 | WRONG KEY 8 131 |
| (A+) 2222 | | PROGRAM4 ,1105,1 | 8 131 |
| (A+) 2224 | COUNT:334 | PROGRAM3 ,1108,101 | WRONG KEY 8 131 |
| (A+) 2225 | WASTED TIME:45 | SELECT THE PROGRAM ,1209,17 | 8 132 |
| (B+) 2229 | TOTAL TIME = Time - | SELECT THE PROGRAM ,1226,4 | WRONG KEY 8 134 |
| (B+) 2231 | Waste=3289 | SELECT THE PROGRAM ,1231,7 | 8 134 |
| (B+) 2233 | | SELECT THE PROGRAM ,1238,5 | WRONG KEY 8 135 |
| (B-) 2235 | | ON/OFF ,1243,5 | 8 135 |
| (A+) 2240 | | | WRONG KEY 8 136 |
| (A+) 2242 | | Error log: | 8 136 |
| (A+) 2244 | | WRONG KEY 6 3 | WRONG KEY 8 136 |
| (A+) 2247 | | WRONG KEY 8 6 | 8 136 |
| (A+) 2249 | | 8 6 | WRONG KEY 8 137 |
| (B+) 2251 | | WRONG KEY 8 7 | 8 137 |
| (B-) 2254 | | 8 7 | WRONG KEY 8 137 |
| (B-) 2256 | | WRONG KEY 8 7 | 8 138 |
| (B+) 2260 | | 8 7 | WRONG KEY 8 138 |
| (A-) 2264 | | WRONG KEY 8 8 | 8 138 |
| (B+) 2267 | | 8 8 | WRONG KEY 8 138 |
| (A+) 2272 | | WRONG KEY 7 8 | 8 139 |
| (A-) 2273 | | 7 8 | WRONG KEY 8 139 |
| (A+) 2275 | | WRONG KEY 7 9 | 8 139 |
| (A+) 2277 | | 7 9 | WRONG KEY 8 140 |
| (C) 2285 | | WRONG KEY 7 10 | 8 140 |
| (C) 2560 | | 7 10 | 1 1235 |
| (TIMER) 2700 | | WRONG KEY 7 10 | 1 1236 |
| (TIMER) 2702 | | 7 10 | 1 1236 |
| (CLEAR) 2708 | | WRONG KEY 7 11 | 1 1237 |
| PRGM 2712 | | 7 11 | SETS TIMER AND TURNS POWER |
| ON/OFF (ON/OFF) 3090 | | WRONG KEY 7 12 | OFF 1248 |
| ON/OFF (ON/OFF) 3091 | | 7 12 | |
| ON/OFF (ON/OFF) 3091 | | WRONG KEY 7 12 | Users Actions: |

| | | | |
|---|---|---|---|
| (CLKADJ) 3 | (A+) 137 | (B+) 280 | (A+) 495 |
| (A+) 6 | (A+) 137 | (B-) 285 | (A+) 497 |
| (A+) 6 | (A+) 138 | (C) 289 | (A+) 498 |
| (A+) 7 | (A+) 138 | (B+) 304 | (A+) 500 |
| (A+) 8 | (A+) 139 | (A+) 315 | (A+) 502 |
| (A-) 8 | (A+) 139 | (B-) 320 | (A+) 503 |
| (A-) 9 | (B+) 144 | (B-) 320 | (A+) 505 |
| (A-) 10 | (A+) 153 | (B-) 321 | (A+) 507 |
| (A-) 10 | (A+) 154 | (B-) 323 | (A+) 508 |
| (A-) 11 | (A+) 155 | (A+) 331 | (A+) 510 |
| (A-) 11 | (A+) 156 | (A+) 332 | (A+) 518 |
| (A-) 12 | (A+) 157 | (A+) 336 | (A+) 520 |
| (A-) 12 | (A+) 157 | (A+) 338 | (A+) 522 |
| (A-) 13 | (A+) 158 | (A+) 340 | (A+) 523 |
| (A-) 13 | (A+) 160 | (A+) 341 | (A+) 525 |
| (B+) 14 | (A+) 161 | (B-) 347 | (A+) 527 |
| (B+) 16 | (A+) 163 | (A+) 352 | (B-) 532 |
| (B+) 16 | (A+) 164 | (A+) 353 | (B+) 543 |
| (B+) 17 | (A+) 165 | (A+) 354 | (B+) 546 |
| (B+) 18 | (A+) 165 | (A+) 355 | (A-) 551 |
| (B+) 19 | (A+) 166 | (A+) 356 | (A-) 553 |
| (B+) 20 | (A+) 167 | (A+) 357 | (A+) 554 |
| (B+) 20 | (A+) 168 | (A+) 358 | (B+) 559 |
| (B+) 21 | (A+) 169 | (A+) 359 | (B+) 561 |
| (B+) 22 | (A+) 170 | (A+) 359 | (A+) 571 |
| (B+) 22 | (A+) 171 | (A+) 360 | (A-) 575 |
| (B-) 23 | (A+) 172 | (A+) 361 | (B-) 587 |
| (A+) 38 | (A+) 173 | (A+) 362 | (B+) 595 |
| (A+) 39 | (A+) 174 | (A+) 363 | (B+) 599 |
| (A+) 40 | (A+) 175 | (A+) 364 | (A+) 605 |
| (A+) 41 | (A+) 176 | (A-) 365 | (A+) 608 |
| (A+) 42 | (A+) 177 | (A-) 366 | (A+) 610 |
| (A+) 43 | (A+) 178 | (A-) 367 | (A+) 615 |
| (A+) 44 | (A+) 179 | (A-) 370 | (B+) 623 |
| (A+) 45 | (A+) 180 | (A-) 371 | (B-) 630 |
| (C) 48 | (A+) 181 | (A-) 373 | (A+) 641 |
| (CLKADJ) 50 | (A+) 182 | (A-) 374 | (A+) 646 |
| (A+) 55 | (A+) 183 | (B-) 379 | (A+) 648 |
| (A+) 57 | (A+) 184 | (B-) 381 | (A+) 650 |
| (A+) 58 | (A+) 184 | (B-) 383 | (A+) 652 |
| (B+) 69 | (A+) 185 | (B-) 388 | (A+) 655 |
| (B+) 70 | (A+) 186 | (A-) 393 | (A+) 657 |
| (A-) 81 | (A-) 187 | (A+) 395 | (A+) 659 |
| (A-) 81 | (A-) 188 | (A+) 396 | (A+) 672 |
| (A-) 82 | (A+) 189 | (A+) 398 | (A+) 677 |
| (A-) 83 | (A+) 210 | (A+) 400 | (A+) 681 |
| (A-) 84 | (A+) 211 | (A+) 402 | (A+) 684 |
| (A-) 85 | (A+) 213 | (B-) 404 | (A+) 686 |
| (A-) 86 | (A+) 215 | (B+) 412 | (A+) 689 |
| (B-) 90 | (A+) 217 | (B+) 413 | (B-) 702 |
| (C) 95 | (A+) 220 | (A+) 419 | (A+) 707 |
| (CLKADJ) 104 | (A+) 222 | (A+) 421 | (B+) 713 |
| (A+) 106 | (A+) 223 | (A+) 422 | (B+) 717 |
| (B+) 107 | (A+) 227 | (A+) 424 | (A+) 722 |
| (B+) 109 | (A+) 229 | (A+) 425 | (A+) 724 |
| (C) 109 | (A+) 234 | (B-) 429 | (A+) 726 |
| (A-) 123 | (C) 239 | (B+) 437 | (A+) 728 |
| (A-) 125 | (B-) 248 | (B+) 438 | (C) 732 |
| (A-) 125 | (A-) 263 | (A-) 441 | (A-) 742 |
| (A+) 128 | (A+) 265 | (A-) 442 | (A+) 751 |
| (A+) 129 | (A-) 266 | (A-) 443 | (A+) 755 |
| (A+) 130 | (B+) 270 | (A+) 444 | (B+) 766 |
| (A-) 131 | (B+) 271 | (C) 449 | (A-) 774 |
| (A+) 131 | (B+) 272 | (B+) 482 | (A+) 776 |
| (A+) 134 | (B-) 273 | (A+) 488 | (A-) 778 |
| (A+) 135 | (B-) 274 | (A-) 490 | (B+) 779 |
| (A-) 135 | (B-) 275 | (A+) 492 | (B+) 781 |
| (A-) 136 | (B+) 278 | (A+) 493 | (A+) 783 |

E-16

```
(A+) 795        (A+) 1051       Subject # 16 Saturday, June    CLOCK ADJUST ,955,18
(A+) 797        (A+) 1053         23, 1990 10:03:39 PM         CLOCK SET ,973,6
(B+) 798        (A-) 1057                                      CLOCK ADJUST ,980,1
(A+) 801        (A-) 1059                                      CLOCK SET ,982,6
(A+) 804        (A-) 1060       Page time log                  CLOCK ADJUST ,989,15
(A+) 806        (B+) 1066       CLOCK SET ,1,112               CLOCK SET ,1005,19
(A+) 808        (C)  1073       CLOCK ,113,89                  CLOCK ,1024,28
(A+) 809        (A+) 1096       CLOCK ADJUST ,203,6            CLOCK ADJUST ,1053,1
(A+) 811        (A+) 1100       CLOCK ADJUST ,210,8            CLOCK SET ,1055,37
(A+) 812        (A+) 1103       ON/OFF ,218,57                 CLOCK ADJUST ,1093,3
(A+) 814        (A-) 1106       CLOCK ADJUST ,276,5            CLOCK SET ,1097,11
(A+) 816        (B+) 1137       ON/OFF ,281,2                  CLOCK ADJUST ,1109,2
(A+) 817        (A-) 1149       CLOCK ADJUST ,284,12           CLOCK SET ,1112,17
(A+) 819        (A-) 1151       CLOCK SET ,297,44              CLOCK ADJUST ,1130,6
(A+) 821        (A-) 1152       ON/OFF ,341,2                  CLOCK SET ,1136,29
(A+) 822        (A+) 1157       CLOCK ADJUST ,343,3            CLOCK ADJUST ,1166,8
(A+) 824        (B+) 1159       CLOCK SET ,347,7               CLOCK SET ,1175,24
(A+) 826        (B+) 1161       ON/OFF ,355,2                  CLOCK ADJUST ,1200,4
(A+) 827        (A-) 1165       CLOCK ADJUST ,357,4            CLOCK SET ,1205,17
(A+) 829        (B+) 1167       CLOCK SET ,361,39              CLOCK ADJUST ,1223,34
(A+) 830        (B+) 1170       CLOCK ADJUST ,400,1            SELECT THE PROGRAM ,1258,16
(A+) 832        (A+) 1178       CLOCK ADJUST ,402,1            PROGRAM1 ,1276,54
(A+) 845        (B+) 1180       CLOCK SET ,404,4               CLOCK ADJUST ,1330,6
(A+) 847        (B+) 1185       ON/OFF ,408,2                  SELECT THE PROGRAM ,1337,3
(A+) 854        (A+) 1192       CLOCK ADJUST ,410,24           PROGRAM1 ,1341,5
(A+) 856        (A+) 1193       CLOCK ADJUST ,435,4            PROGRAM4 ,1347,158
(A+) 858        (A+) 1195       CLOCK SET ,440,38              SELECT THE PROGRAM ,1505,14
(A+) 860        (A+) 1196       CLOCK ,478,8                   PROGRAM1 ,1520,2
(A+) 867        (A+) 1198       ON/OFF ,486,3                  PROGRAM2 ,1523,243
(A+) 868        (A-) 1200       CLOCK ADJUST ,489,10           SELECT THE PROGRAM ,1766,7
(A+) 870        (A-) 1202       CLOCK SET ,500,13              PROGRAM1 ,1775,12
(A+) 871        (B+) 1206       ON/OFF ,513,3                  PROGRAM4 ,1788,5
(A+) 873        (C)  1208       CLOCK ADJUST ,517,2            PROGRAM3 ,1795,4
(B+) 877        (C)  1247       CLOCK SET ,520,29              PROGRAM2 ,1801,304
(A+) 919                        CLOCK ADJUST ,550,1            SELECT THE PROGRAM ,2106,21
(B+) 930        Programs set    CLOCK ADJUST ,551,1            SELECT THE PROGRAM ,2127,7
(A-) 935        2.SUN PM 8:00 5 CLOCK ADJUST ,553,0            SELECT THE PROGRAM ,2135,3
(A-) 937        M-F AM 3:00 7   CLOCK ADJUST ,554,0            PROGRAM1 ,2139,105
(A-) 949        2.WED PM10:00 4 CLOCK ADJUST ,555,1            ON/OFF ,2244,5
(A-) 951                        CLOCK ADJUST ,556,1
(A-) 957        Page summary    CLOCK ADJUST ,558,0            Error log:
(A-) 959        CLOCK SET,7,343 SELECT THE PROGRAM ,559,8      HOME 115
(A-) 961        CLOCK ADJUST,8,52 CLOCK ADJUST ,567,4          HOME 115
(A-) 963        CLOCK,6,46      CLOCK SET ,572,43              HOME 116
(A-) 966        SELECT THE PROGRAM,7,64 ON/OFF ,615,2          HOME 117
(A-) 968        PROGRAM1,4,274  CLOCK ADJUST ,618,7            HOME 118
(A-) 970        PROGRAM2,2,319  CLOCK SET ,625,17              HOME 120
(A-) 972        PROGRAM3,2,102  CLOCK ADJUST ,642,1            HOME 121
(A-) 974        PROGRAM4,2,4    CLOCK ADJUST ,644,0            HOME 122
(A-) 976        ON/OFF,1,5      CLOCK ADJUST ,645,0            LEFT 123
(A-) 978                        CLOCK ADJUST ,646,1            LEFT 124
(A-) 980        COUNT:375       CLOCK ADJUST ,648,0            END 125
(A-) 982        WASTED TIME:38  CLOCK SET ,649,62              END 125
(A-) 984        TOTAL TIME = Time - ON/OFF ,711,2              END 126
(A-) 986           Waste=1247   CLOCK ADJUST ,714,15           END 128
(B-) 1001                       CLOCK SET ,730,96              END 129
(A+) 1008                       CLOCK ADJUST ,826,9            END 129
(A-) 1010                       CLOCK SET ,836,5               END 130
(A-) 1012                       CLOCK ADJUST ,842,21           END 130
(A-) 1014                       CLOCK SET ,864,6               END 131
(B+) 1028                       CLOCK ADJUST ,871,9            END 131
(A+) 1040                       CLOCK SET ,880,12              END 132
(A+) 1042                       CLOCK ADJUST ,892,4            END 132
(A+) 1043                       CLOCK SET ,897,10              END 133
(A+) 1045                       CLOCK ADJUST ,908,3            END 133
(A+) 1046                       CLOCK SET ,912,5               END 134
(A-) 1048                       CLOCK ADJUST ,918,23           END 134
(A-) 1049                       CLOCK SET ,942,13              CENTER 135
```

```
CENTER 136              WRONG KEY RIGHT 401      WRONG KEY RIGHT 825     HOME 1044
UP 148                  WRONG KEY * 408          WRONG KEY RIGHT 841     UP 1046
UP 150                  WRONG KEY HOME 413       WRONG KEY UP 844        END 1048
UP 151                  HOME 413                 UP 844                  END 1049
UP 152                  WRONG KEY HOME 415       WRONG KEY UP 847        WRONG KEY RIGHT 1092
UP 152                  HOME 415                 UP 847                  WRONG KEY RIGHT 1108
UP 153                  WRONG KEY HOME 416       WRONG KEY HOME 849      WRONG KEY RIGHT 1129
UP 160                  HOME 416                 HOME 849                WRONG KEY RIGHT 1165
UP 161                  WRONG KEY HOME 419       WRONG KEY HOME 851      WRONG KEY RIGHT 1199
UP 161                  HOME 419                 HOME 851                WRONG KEY RIGHT 1222
HOME 162                WRONG KEY HOME 421       WRONG KEY END 854       CENTER 1514
HOME 163                HOME 421                 END 854                 CENTER 1516
HOME 163                WRONG KEY HOME 423       WRONG KEY END 856       TURNS TIMER ON AND POWER OFF
HOME 164                HOME 423                 END 857                   2249
HOME 164                WRONG KEY HOME 425       WRONG KEY END 858
HOME 165                HOME 425                 END 859                 Users Actions:
HOME 165                WRONG KEY UP 426         WRONG KEY END 860       (A-)  21
HOME 166                UP 427                   END 861                 (A-)  36
HOME 166                WRONG KEY UP 428         WRONG KEY RIGHT 870     (A-)  39
HOME 167                UP 428                   WRONG KEY END 875       (A+)  54
HOME 167                WRONG KEY UP 429         END 875                 (A+)  57
HOME 168                UP 429                   WRONG KEY END 876       (A+)  59
HOME 168                WRONG KEY UP 430         END 876                 (A+)  61
HOME 169                UP 430                   WRONG KEY END 878       (A+)  63
HOME 169                WRONG KEY UP 431         END 878                 (B-)  65
HOME 170                UP 431                   WRONG KEY RIGHT 891     (B-)  67
HOME 170                WRONG KEY RIGHT 434      WRONG KEY RIGHT 907     (B-)  68
HOME 171                WRONG KEY UP 437         WRONG KEY RIGHT 917     (B-)  69
HOME 171                UP 437                   WRONG KEY UP 920        (B-)  70
HOME 172                END 481                  UP 920                  (A+)  77
HOME 172                END 482                  WRONG KEY UP 924        (A+)  79
HOME 172                END 484                  UP 924                  (A+)  80
WRONG KEY RIGHT 209     WRONG KEY UP 493         WRONG KEY HOME 929      (A+)  81
WRONG KEY HOME 210      UP 493                   HOME 930                (A+)  84
HOME 210                WRONG KEY UP 494         WRONG KEY END 932       (A+)  88
WRONG KEY HOME 211      UP 494                   END 932                 (A+)  88
HOME 211                WRONG KEY RIGHT 549      WRONG KEY END 934       (A+)  89
HOME 222                WRONG KEY RIGHT 551      END 934                 (A+)  90
LEFT 237                WRONG KEY RIGHT 552      WRONG KEY END 937       (A+)  90
LEFT 238                WRONG KEY RIGHT 553      END 937                 (A+)  91
UP 245                  WRONG KEY RIGHT 554      WRONG KEY RIGHT 954     (A+)  92
UP 246                  WRONG KEY RIGHT 556      WRONG KEY RIGHT 979     (A+)  92
UP 247                  WRONG KEY RIGHT 557      WRONG KEY RIGHT 988     (A+)  93
UP 248                  WRONG KEY * 615          WRONG KEY END 990       (A+)  94
UP 250                  WRONG KEY UP 619         END 990                 (A+)  94
UP 251                  UP 620                   WRONG KEY END 993       (A+)  95
HOME 252                WRONG KEY UP 622         END 993                 (A+)  96
HOME 254                UP 622                   WRONG KEY END 994       (A+)  96
UP 256                  WRONG KEY HOME 624       END 994                 (A+)  97
UP 258                  HOME 624                 WRONG KEY UP 996        (A+)  98
LEFT 261                WRONG KEY RIGHT 641      UP 996                  (A+)  99
HOME 265                WRONG KEY RIGHT 643      WRONG KEY HOME 998      (A+)  99
CENTER 267              WRONG KEY RIGHT 644      HOME 998                (A+)  100
CENTER 272              WRONG KEY RIGHT 645      WRONG KEY HOME 1000     (A+)  101
CENTER 274              WRONG KEY RIGHT 647      HOME 1000               (A+)  101
WRONG KEY HOME 288      WRONG KEY * 710          WRONG KEY HOME 1002     (A+)  102
HOME 288                WRONG KEY HOME 720       HOME 1002               (A+)  103
WRONG KEY UP 291        HOME 720                 WRONG KEY UP 1003       (A+)  103
UP 291                  WRONG KEY UP 723         UP 1003                 (A+)  104
WRONG KEY UP 294        UP 723                   END 1027                (A+)  105
UP 294                  WRONG KEY UP 724         END 1028                (A+)  105
WRONG KEY UP 294        UP 724                   END 1030                (A+)  106
UP 294                  WRONG KEY UP 725         CENTER 1032             (A+)  107
WRONG KEY UP 295        UP 725                   CENTER 1034             (A+)  107
UP 295                  WRONG KEY UP 726         CENTER 1035             (A-)  109
WRONG KEY * 340         UP 726                   LEFT 1037               (A-)  109
WRONG KEY * 354         WRONG KEY HOME 727       LEFT 1041               (A-)  110
WRONG KEY RIGHT 399     HOME 727                 CENTER 1042             (C)   112
```

E-18

| Col1 | Col2 | Col3 | Col4 |
|---|---|---|---|
| (CLKADJ) 208 | (B+) 380 | (B+) 468 | (B-) 640 |
| (A-) 210 | (B+) 382 | (B+) 469 | (CLKADJ) 641 |
| (A-) 211 | (B+) 383 | (B+) 469 | (CLKADJ) 643 |
| (TIMER) 218 | (B+) 384 | (B+) 470 | (CLKADJ) 644 |
| (A-) 222 | (B-) 387 | (B+) 470 | (CLKADJ) 645 |
| (TIMER) 223 | (B-) 389 | (B+) 471 | (CLKADJ) 646 |
| (B-) 237 | (B-) 390 | (B+) 472 | (B-) 648 |
| (B-) 238 | (B-) 391 | (C) 478 | (B-) 649 |
| (TIMER) 240 | (B-) 391 | (CLKADJ) 489 | (B+) 650 |
| (A+) 245 | (B-) 392 | (A+) 492 | (A+) 656 |
| (A+) 246 | (B-) 392 | (A+) 494 | (A-) 660 |
| (A+) 247 | (B-) 393 | (B-) 499 | (B+) 666 |
| (A+) 248 | (B-) 393 | (B+) 502 | (B+) 668 |
| (A+) 250 | (B-) 394 | (B+) 503 | (B+) 670 |
| (A+) 251 | (B-) 395 | (B+) 506 | (B+) 671 |
| (A-) 252 | (B-) 395 | (POWER) 512 | (B+) 672 |
| (A-) 253 | (B-) 396 | (CLKADJ) 516 | (B-) 675 |
| (A+) 256 | (B-) 396 | (B+) 519 | (B-) 676 |
| (A+) 258 | (B-) 397 | (B+) 523 | (A+) 702 |
| (B-) 260 | (B-) 398 | (B+) 524 | (A+) 703 |
| (A-) 265 | (B-) 398 | (B+) 525 | (A+) 705 |
| (B+) 267 | (B-) 399 | (B+) 526 | (TIMER) 710 |
| (TIMER) 270 | (CLKADJ) 399 | (B+) 527 | (CLKADJ) 713 |
| (B+) 272 | (CLKADJ) 401 | (B-) 529 | (A-) 720 |
| (B+) 274 | (B+) 403 | (A+) 540 | (A+) 723 |
| (CLKADJ) 275 | (TIMER) 407 | (B-) 545 | (A+) 724 |
| (TIMER) 280 | (CLKADJ) 409 | (CLKADJ) 549 | (A+) 725 |
| (TIMER) 281 | (A-) 413 | (CLKADJ) 550 | (A+) 725 |
| (CLKADJ) 283 | (A-) 415 | (CLKADJ) 552 | (A-) 727 |
| (A-) 288 | (A-) 416 | (CLKADJ) 553 | (B-) 728 |
| (A+) 290 | (A-) 419 | (CLKADJ) 554 | (B+) 738 |
| (A+) 293 | (A-) 421 | (CLKADJ) 555 | (B+) 741 |
| (A+) 294 | (A-) 423 | (CLKADJ) 557 | (B+) 742 |
| (A+) 295 | (A-) 424 | (PRGM) 558 | (B-) 746 |
| (B+) 296 | (A+) 426 | (B+) 571 | (B-) 748 |
| (A+) 303 | (A+) 428 | (B-) 578 | (A-) 771 |
| (A+) 307 | (A+) 429 | (B-) 581 | (A-) 773 |
| (A+) 308 | (A+) 430 | (B-) 582 | (A-) 775 |
| (A+) 310 | (A+) 431 | (B-) 582 | (A-) 777 |
| (A+) 311 | (CLKADJ) 433 | (B+) 590 | (A-) 778 |
| (A+) 312 | (A+) 437 | (B+) 603 | (A-) 780 |
| (A+) 312 | (B+) 439 | (B-) 606 | (A-) 782 |
| (A-) 315 | (B+) 440 | (A+) 611 | (A-) 783 |
| (A+) 316 | (B+) 441 | (TIMER) 615 | (A-) 784 |
| (A+) 317 | (B+) 443 | (CLKADJ) 617 | (A-) 786 |
| (A+) 318 | (B+) 444 | (A+) 619 | (A-) 788 |
| (A+) 319 | (B+) 447 | (A+) 621 | (A-) 789 |
| (A+) 320 | (B+) 448 | (A-) 624 | (A-) 790 |
| (A+) 324 | (B+) 452 | (B-) 624 | (A-) 792 |
| (A+) 325 | (B+) 452 | (B-) 626 | (A-) 793 |
| (A+) 327 | (B+) 454 | (B-) 626 | (A-) 795 |
| (A+) 329 | (B+) 455 | (B-) 627 | (A-) 797 |
| (A+) 331 | (B+) 456 | (B-) 628 | (A-) 798 |
| (A+) 333 | (B+) 457 | (B-) 628 | (A-) 804 |
| (TIMER) 340 | (B+) 458 | (B-) 629 | (A-) 806 |
| (CLKADJ) 343 | (B+) 459 | (B-) 629 | (A-) 807 |
| (B-) 346 | (B+) 460 | (B-) 630 | (A-) 808 |
| (TIMER) 354 | (B+) 461 | (B-) 631 | (A-) 809 |
| (CLKADJ) 356 | (B+) 461 | (B-) 633 | (A-) 811 |
| (B+) 360 | (B+) 462 | (B-) 635 | (A-) 812 |
| (B+) 363 | (B+) 463 | (B-) 635 | (A-) 813 |
| (B+) 365 | (B+) 463 | (B-) 636 | (A-) 814 |
| (B+) 368 | (B+) 464 | (B-) 637 | (A-) 815 |
| (B+) 369 | (B+) 465 | (B-) 637 | (A-) 816 |
| (B-) 371 | (B+) 465 | (B-) 638 | (A-) 817 |
| (B+) 373 | (B+) 466 | (B-) 639 | (A-) 819 |
| (B+) 375 | (B+) 467 | (B-) 639 | (A-) 820 |
| (B+) 377 | (B+) 467 | (B-) 640 | (A-) 821 |

```
(CLKADJ) 825      (B-)  1135      (A-)  1557      (A-)  1857
(B-)    835       (B-)  1140      (A-)  1559      (A+)  1860
(CLKADJ) 841      (A+)  1147      (B+)  1564      (B+)  1862
(A+)    844       (A+)  1149      (B+)  1568      (A+)  1869
(A+)    847       (A+)  1151      (B+)  1571      (A+)  1871
(A-)    848       (A+)  1153      (A+)  1576      (A+)  1874
(A-)    850       (A+)  1155      (A+)  1578      (A+)  1875
(C)     854       (A+)  1157      (A+)  1581      (A+)  1877
(C)     856       (CLKADJ) 1164   (A+)  1583      (A+)  1878
(C)     858       (B-)  1174      (B+)  1587      (A+)  1880
(C)     860       (B-)  1177      (B+)  1590      (A+)  1881
(B+)    863       (B-)  1179      (B+)  1592      (A+)  1883
(CLKADJ) 870      (A+)  1183      (A-)  1598      (A+)  1884
(C)     874       (CLKADJ) 1198   (A+)  1601      (A+)  1886
(C)     876       (B-)  1204      (B+)  1603      (A+)  1887
(C)     878       (CLKADJ) 1221   (B+)  1605      (A+)  1889
(B-)    879       (PRGM) 1257     (B+)  1607      (A+)  1890
(A-)    885       (B-)  1297      (B+)  1610      (A+)  1892
(A+)    888       (A-)  1309      (B+)  1612      (A+)  1893
(CLKADJ) 891      (A-)  1312      (B+)  1615      (A+)  1896
(B+)    896       (A-)  1321      (A-)  1621      (A+)  1897
(CLKADJ) 906      (A-)  1324      (A-)  1623      (A+)  1899
(B-)    911       (CLKADJ) 1329   (A-)  1624      (A+)  1900
(CLKADJ) 916      (PRGM) 1336     (A-)  1626      (A+)  1902
(A+)    920       (A-)  1345      (A+)  1628      (A+)  1903
(A+)    924       (B-)  1356      (B+)  1632      (A+)  1905
(A-)    929       (A-)  1360      (B+)  1635      (A+)  1907
(C)     931       (A-)  1361      (A-)  1642      (A+)  1908
(C)     934       (A-)  1363      (A+)  1644      (A+)  1911
(C)     936       (A-)  1364      (B+)  1647      (A+)  1913
(B-)    941       (B+)  1373      (B+)  1651      (A+)  1915
(CLKADJ) 954      (B+)  1382      (B+)  1655      (A+)  1916
(B-)    972       (A-)  1388      (B+)  1660      (A+)  1918
(CLKADJ) 978      (B+)  1394      (B+)  1662      (B+)  1921
(B+)    981       (B+)  1399      (B+)  1664      (A+)  1933
(CLKADJ) 987      (B+)  1413      (A+)  1672      (B+)  1938
(C)     990       (A+)  1420      (B+)  1675      (A-)  1953
(C)     992       (A+)  1423      (B+)  1679      (A-)  1955
(C)     994       (A+)  1430      (B+)  1682      (B+)  1963
(A+)    996       (A+)  1432      (B+)  1685      (A+)  1974
(A-)    998       (B+)  1439      (A+)  1723      (A+)  1978
(A-)    999       (B+)  1450      (A+)  1724      (A+)  1980
(A-)    1001      (B+)  1454      (A+)  1726      (A+)  1982
(A+)    1003      (B+)  1456      (A+)  1728      (A+)  1983
(B-)    1004      (B+)  1459      (B+)  1732      (A+)  1985
(B+)    1013      (B+)  1461      (PRGM) 1765     (A+)  1986
(B+)    1015      (B+)  1465      (A-)  1786      (A-)  1989
(C)     1023      (B+)  1467      (A-)  1793      (B+)  1993
(B-)    1054      (B-)  1482      (A-)  1799      (B+)  1997
(B+)    1057      (B-)  1485      (B+)  1804      (B+)  1999
(B+)    1063      (B-)  1487      (A+)  1813      (B+)  2001
(A+)    1065      (B+)  1490      (A+)  1815      (B+)  2003
(B+)    1069      (B+)  1492      (A+)  1816      (A-)  2010
(B+)    1071      (B+)  1494      (B+)  1819      (A-)  2017
(A+)    1078      (B+)  1496      (B+)  1823      (B+)  2024
(A+)    1080      (B+)  1499      (B-)  1829      (B+)  2028
(A+)    1082      (B+)  1502      (B-)  1830      (B+)  2050
(CLKADJ) 1092     (C)   1504      (B+)  1836      (B+)  2053
(B-)    1096      (A+)  1522      (B+)  1839      (A-)  2060
(A-)    1099      (B+)  1530      (A-)  1843      (A-)  2062
(A-)    1104      (B-)  1537      (A-)  1845      (A-)  2067
(CLKADJ) 1108     (A-)  1541      (A-)  1846      (A-)  2069
(B+)    1111      (A-)  1542      (A-)  1848      (A-)  2071
(B-)    1113      (A-)  1545      (A-)  1849      (A-)  2072
(A+)    1117      (A+)  1547      (A-)  1851      (A-)  2074
(A-)    1119      (A+)  1548      (A-)  1852      (A-)  2076
(A-)    1126      (A+)  1550      (A-)  1854      (A-)  2077
(CLKADJ) 1129     (B+)  1553      (A-)  1855      (A-)  2079
```

```
(A-) 2081           Subject number 17           7 235                        (PRGM) 204
(A-) 2082             Wednesday, June 27, 1990  5 919                        (TIMER) 205
(B+) 2086                5:51:36 PM             NO TIMER, DOES TURN POWER    (TIMER) 208
(B+) 2096                                              OFF 1391              (TIMER) 213
(C)  2104                                                                    (CLKADJ) 218
(B+) 2153           Page time log              Users Actions:                (A-) 233
(A-) 2158           CLOCK SET ,0,108            (A-)  7                      (A-) 234
(A-) 2159           ON/OFF ,109,61              (A-) 13                      (A-) 234
(B+) 2163           CLOCK ADJUST ,172,0         (A+) 22                      (B-) 236
(B+) 2166           CLOCK ADJUST ,173,0         (A-) 23                      (B-) 246
(A-) 2172           ON/OFF ,173,45              (A-) 24                      (C)  250
(B+) 2174           CLOCK ADJUST ,219,17        (B-) 28                      (A-) 269
(B+) 2177           CLOCK SET ,237,14           (B+) 34                      (A-) 276
(B+) 2185           CLOCK ,251,4                (B+) 37                      (A-) 282
(A+) 2192           SELECT THE PROGRAM ,255,5   (B+) 39                      (A-) 287
(B+) 2197           PROGRAM1 ,262,7             (B+) 40                      (B-) 290
(A+) 2206           PROGRAM4 ,270,6             (B-) 43                      (B+) 297
(A+) 2209           PROGRAM3 ,277,5             (B+) 48                      (B+) 300
(A+) 2211           PROGRAM2 ,284,4             (B-) 49                      (B+) 301
(B+) 2214           PROGRAM1 ,289,619           (A+) 51                      (B-) 303
(TIMER) 2243        SELECT THE PROGRAM ,909,4   (A+) 53                      (B-) 305
(C) 2248            PROGRAM1 ,915,2             (A+) 55                      (B-) 309
                    SELECT THE PROGRAM ,918,7   (B+) 58                      (A+) 314
Programs set        PROGRAM1 ,927,1             (A+) 61                      (A+) 316
1.SUN PM 8:00 1     PROGRAM2 ,929,8             (A+) 62                      (A+) 318
M-? AM 3:00 7       PROGRAM3 ,938,1             (A+) 63                      (A+) 319
                    PROGRAM2 ,941,245           (A+) 64                      (A+) 321
Page summary        SELECT THE PROGRAM ,1186,2  (A+) 66                      (A+) 323
CLOCK SET,27,721    PROGRAM1 ,1191,4            (B+) 71                      (A+) 325
CLOCK ADJUST,44,279 PROGRAM2 ,1197,2            (A+) 74                      (A+) 326
CLOCK,3,125         PROGRAM1 ,1202,28           (A+) 75                      (A+) 328
SELECT THE PROGRAM,8,79 SELECT THE PROGRAM ,1231,3 (A+) 76                   (A+) 330
PROGRAM1,5,178      PROGRAM1 ,1236,1            (A+) 78                      (A+) 331
PROGRAM2,2,547      PROGRAM2 ,1239,13           (A+) 79                      (A+) 333
PROGRAM3,1,4        SELECT THE PROGRAM ,1252,3  (B+) 83                      (A+) 335
PROGRAM4,2,163      PROGRAM1 ,1257,2            (A+) 84                      (A+) 336
ON/OFF,10,80        PROGRAM2 ,1261,1            (A+) 85                      (A+) 338
                    PROGRAM3 ,1263,79           (A+) 86                      (A+) 340
COUNT:619           SELECT THE PROGRAM ,1342,19 (A+) 87                      (A+) 342
WASTED TIME:72      ON/OFF ,1361,4              (A+) 88                      (A+) 344
TOTAL TIME = Time - CLOCK ,1366,4               (A+) 89                      (A+) 346
     Waste=2248     CLOCK ADJUST ,1371,5        (A+) 90                      (A+) 347
                    SELECT THE PROGRAM ,1376,9  (A+) 91                      (A+) 349
                    ON/OFF ,1386,4              (B-) 93                      (A+) 351
                                                (B+) 99                      (A+) 352
                    Error log:                  (A-) 101                     (A+) 354
                    WRONG KEY * 108             (A-) 102                     (A+) 356
                    BIGMINUS 131                (TIMER) 108                  (A+) 357
                    BIGMINUS 132                (PRGM) 131                   (A+) 359
                    BIGMINUS 133                (PRGM) 132                   (A+) 361
                    BIGMINUS 143                (PRGM) 133                   (A+) 363
                    BIGMINUS 151                (PRGM) 143                   (A+) 364
                    7 158                       (PRGM) 150                   (A+) 366
                    BIGMINUS 161                (A-) 157                     (A+) 368
                    BIGMINUS 164                (PRGM) 161                   (A+) 369
                    4 168                       (PRGM) 163                   (A+) 371
                    WRONG KEY 6 172             (B-) 168                     (A+) 373
                    BIGMINUS 188                (CLKADJ) 170                 (A+) 375
                    BIGMINUS 189                (CLKADJ) 172                 (A+) 377
                    BIGMINUS 191                (TIMER) 173                  (A+) 378
                    BIGMINUS 199                (TIMER) 175                  (A+) 380
                    BIGMINUS 203                (TIMER) 178                  (A+) 382
                    BIGMINUS 204                (TIMER) 183                  (A+) 383
                    WRONG KEY 7 233             (PRGM) 187                   (A+) 385
                    7 233                       (PRGM) 189                   (A+) 387
                    WRONG KEY 7 234             (PRGM) 191                   (A+) 389
                    7 234                       (PRGM) 199                   (A+) 390
                    WRONG KEY 7 234             (PRGM) 203                   (A+) 392
```

| | | | | | | | |
|---|---|---|---|---|---|---|---|
| (B-) | 394 | (A+) | 653 | (A+) | 928 | (A+) | 1055 |
| (B-) | 395 | (A+) | 655 | (A+) | 936 | (B+) | 1057 |
| (B-) | 397 | (A+) | 691 | (A-) | 939 | (A-) | 1059 |
| (B-) | 405 | (A-) | 695 | (B+) | 942 | (A-) | 1061 |
| (B-) | 411 | (B+) | 697 | (A+) | 945 | (B-) | 1064 |
| (B-) | 417 | (B+) | 702 | (A+) | 947 | (A-) | 1070 |
| (A-) | 421 | (A+) | 710 | (A+) | 949 | (A-) | 1072 |
| (A-) | 423 | (B-) | 717 | (B+) | 951 | (A-) | 1073 |
| (A+) | 426 | (A-) | 724 | (B+) | 953 | (A-) | 1075 |
| (A+) | 429 | (B+) | 730 | (A+) | 957 | (A-) | 1077 |
| (A-) | 433 | (B+) | 733 | (A+) | 959 | (A-) | 1078 |
| (A-) | 435 | (A-) | 736 | (A+) | 961 | (A-) | 1080 |
| (B+) | 437 | (A+) | 739 | (B+) | 962 | (A-) | 1081 |
| (B+) | 440 | (A+) | 741 | (A+) | 964 | (A-) | 1083 |
| (B+) | 442 | (A-) | 743 | (A+) | 966 | (A-) | 1084 |
| (B-) | 447 | (A+) | 745 | (A+) | 967 | (A-) | 1086 |
| (A+) | 450 | (A+) | 747 | (A+) | 969 | (A-) | 1087 |
| (A-) | 452 | (A+) | 749 | (A+) | 971 | (A-) | 1089 |
| (A-) | 454 | (A-) | 751 | (A+) | 972 | (A-) | 1091 |
| (A-) | 456 | (B-) | 753 | (A+) | 974 | (A-) | 1092 |
| (A+) | 457 | (A+) | 758 | (A+) | 975 | (A-) | 1094 |
| (B+) | 463 | (A+) | 759 | (A+) | 977 | (A-) | 1095 |
| (B+) | 466 | (A+) | 761 | (A+) | 979 | (A-) | 1097 |
| (B+) | 476 | (A-) | 763 | (A+) | 981 | (A-) | 1098 |
| (A+) | 479 | (A-) | 764 | (A+) | 982 | (A-) | 1100 |
| (A+) | 481 | (A-) | 766 | (A+) | 984 | (A-) | 1101 |
| (A+) | 484 | (A-) | 768 | (A+) | 986 | (A-) | 1103 |
| (A+) | 486 | (B+) | 770 | (A+) | 987 | (A-) | 1105 |
| (B+) | 491 | (B+) | 771 | (A+) | 989 | (A-) | 1107 |
| (B-) | 495 | (B+) | 775 | (A+) | 991 | (A-) | 1108 |
| (A+) | 502 | (B+) | 779 | (A+) | 992 | (A-) | 1110 |
| (A+) | 508 | (B+) | 784 | (A+) | 994 | (A-) | 1111 |
| (A+) | 510 | (B+) | 787 | (A+) | 995 | (A-) | 1113 |
| (A+) | 512 | (B-) | 791 | (A+) | 997 | (A-) | 1114 |
| (A+) | 514 | (B+) | 795 | (A+) | 999 | (A-) | 1116 |
| (A+) | 517 | (A+) | 800 | (A+) | 1000 | (A-) | 1117 |
| (A+) | 519 | (A+) | 803 | (A+) | 1002 | (A-) | 1119 |
| (A+) | 521 | (A+) | 805 | (A+) | 1004 | (A-) | 1120 |
| (A+) | 525 | (A+) | 806 | (A+) | 1005 | (A+) | 1122 |
| (A+) | 527 | (A+) | 808 | (A+) | 1007 | (A+) | 1124 |
| (A+) | 529 | (B-) | 815 | (A+) | 1008 | (A+) | 1125 |
| (A+) | 532 | (B+) | 821 | (A+) | 1011 | (A+) | 1127 |
| (A+) | 534 | (B-) | 823 | (A+) | 1012 | (A+) | 1129 |
| (A+) | 537 | (A+) | 827 | (A+) | 1014 | (A+) | 1130 |
| (A+) | 547 | (A-) | 830 | (A+) | 1015 | (A+) | 1132 |
| (A+) | 549 | (B+) | 833 | (A+) | 1017 | (B+) | 1133 |
| (A+) | 551 | (B+) | 839 | (A+) | 1019 | (B+) | 1139 |
| (A+) | 554 | (B+) | 845 | (A+) | 1020 | (B-) | 1144 |
| (A+) | 556 | (B+) | 847 | (A+) | 1022 | (A+) | 1147 |
| (A+) | 558 | (B+) | 848 | (A+) | 1024 | (B+) | 1151 |
| (A+) | 566 | (B+) | 850 | (A+) | 1025 | (A+) | 1155 |
| (A+) | 585 | (B+) | 852 | (A+) | 1027 | (A+) | 1157 |
| (A-) | 589 | (B+) | 855 | (A+) | 1028 | (A+) | 1158 |
| (A+) | 593 | (B+) | 856 | (A+) | 1030 | (A+) | 1160 |
| (B+) | 595 | (B-) | 858 | (A+) | 1032 | (A+) | 1162 |
| (B-) | 600 | (B-) | 863 | (A+) | 1033 | (A+) | 1164 |
| (B+) | 606 | (A+) | 868 | (A+) | 1035 | (B+) | 1166 |
| (B-) | 609 | (A+) | 870 | (A+) | 1037 | (B+) | 1169 |
| (A+) | 614 | (A+) | 872 | (A+) | 1038 | (B+) | 1172 |
| (B+) | 616 | (A+) | 874 | (A+) | 1040 | (B+) | 1175 |
| (B-) | 624 | (A+) | 876 | (A+) | 1042 | (B+) | 1176 |
| (B+) | 628 | (A-) | 878 | (A+) | 1044 | (B+) | 1179 |
| (B-) | 631 | (A+) | 881 | (A+) | 1045 | (C) | 1185 |
| (B+) | 637 | (A+) | 886 | (A+) | 1047 | (A+) | 1195 |
| (B-) | 642 | (A+) | 892 | (A+) | 1049 | (A-) | 1199 |
| (A+) | 646 | (B+) | 897 | (A+) | 1050 | (B+) | 1203 |
| (A+) | 649 | (C) | 907 | (A+) | 1052 | (B+) | 1205 |
| (A+) | 651 | (C) | 916 | (A+) | 1053 | (B+) | 1209 |

| | | | |
|---|---|---|---|
| (B+) 1212 | Subject number 18 | (B+) 131 | (C) 436 |
| (B+) 1215 | Wednesday, June 27, 1990 | (A-) 133 | (A+) 451 |
| (B+) 1217 | 8:08:48 PM | (B-) 134 | (B+) 455 |
| (B-) 1221 | | (CLKADJ) 148 | (B+) 459 |
| (A+) 1224 | Page time log | (B+) 154 | (B+) 463 |
| (C) 1229 | CLOCK SET ,1,77 | (C) 160 | (B+) 468 |
| (A+) 1236 | CLOCK ,80,12 | (B+) 196 | (B+) 472 |
| (B+) 1241 | ON/OFF ,92,56 | (A+) 203 | (B+) 476 |
| (B-) 1246 | CLOCK ADJUST ,149,5 | (A+) 209 | (B-) 481 |
| (C) 1251 | CLOCK SET ,154,6 | (A+) 210 | (A+) 489 |
| (A+) 1258 | CLOCK ,161,12 | (A+) 212 | (A+) 491 |
| (A+) 1262 | SELECT THE PROGRAM ,173,12 | (A+) 214 | (A+) 493 |
| (B+) 1274 | PROGRAM1 ,186,251 | (A+) 216 | (A+) 495 |
| (A-) 1279 | SELECT THE PROGRAM ,437,11 | (A+) 217 | (A+) 497 |
| (A-) 1281 | PROGRAM1 ,450,176 | (A+) 219 | (A+) 500 |
| (A+) 1285 | SELECT THE PROGRAM ,627,5 | (A+) 221 | (A+) 502 |
| (A-) 1287 | PROGRAM1 ,634,5 | (A+) 222 | (A+) 504 |
| (B+) 1288 | PROGRAM2 ,641,244 | (A+) 224 | (A-) 510 |
| (B+) 1290 | SELECT THE PROGRAM ,885,13 | (A+) 226 | (A+) 516 |
| (A-) 1293 | PROGRAM1 ,901,0 | (A+) 227 | (A+) 519 |
| (B+) 1295 | PROGRAM2 ,905,1 | (A+) 229 | (A+) 521 |
| (B+) 1297 | PROGRAM3 ,908,172 | (A+) 231 | (A+) 524 |
| (A+) 1301 | SELECT THE PROGRAM ,1080,15 | (A+) 232 | (A+) 526 |
| (A+) 1303 | ON/OFF ,1095,49 | (A+) 235 | (A+) 528 |
| (A+) 1306 | | (A+) 236 | (A+) 530 |
| (A-) 1309 | Error log: | (A+) 238 | (A-) 536 |
| (A-) 1312 | BIGMINUS 97 | (A+) 240 | (B+) 543 |
| (A-) 1314 | BIGMINUS 118 | (A+) 242 | (B-) 556 |
| (A+) 1317 | 8 130 | (A+) 243 | (B-) 573 |
| (A-) 1319 | 5 131 | (A-) 249 | (A+) 580 |
| (B+) 1321 | 7 133 | (A-) 251 | (B+) 589 |
| (A+) 1325 | 4 134 | (B+) 258 | (A-) 598 |
| (B+) 1329 | SETS TIMER AND POWER OFF | (B+) 265 | (A-) 600 |
| (A+) 1333 | 1145 | (A+) 283 | (A-) 602 |
| (A+) 1334 | | (A+) 284 | (A-) 605 |
| (A+) 1336 | Users Actions: | (A+) 286 | (A-) 607 |
| (B+) 1338 | (A-) 10 | (A+) 288 | (A-) 609 |
| (C) 1341 | (A-) 10 | (A+) 290 | (C) 625 |
| (POWER) 1365 | (A-) 13 | (A+) 291 | (A+) 639 |
| (PRGM) 1375 | (B+) 19 | (A+) 293 | (B+) 653 |
| (C) 1389 | (B+) 20 | (A+) 295 | (A+) 656 |
| | (A+) 27 | (A+) 297 | (A+) 658 |
| Programs set | (A+) 28 | (A+) 299 | (A+) 660 |
| 1.SUN PM 8:00 5 | (A+) 29 | (A+) 301 | (B+) 663 |
| 1.SUN PM 8:00 5 | (B+) 35 | (A+) 302 | (B+) 665 |
| M-F AM 3:00 7 | (A+) 37 | (A+) 304 | (A+) 666 |
| 2.SUN PM 8:00 5 | (A+) 38 | (A+) 306 | (A+) 668 |
| M-F AM 3:00 7 | (A+) 40 | (A+) 308 | (A+) 670 |
| 1.THU PM10:00 4 | (A+) 41 | (A+) 310 | (B+) 672 |
| | (A+) 43 | (A+) 311 | (A+) 675 |
| Page summary | (B+) 46 | (A+) 320 | (A+) 676 |
| CLOCK SET,2,122 | (A+) 49 | (A+) 322 | (A+) 678 |
| CLOCK ADJUST,4,22 | (A+) 50 | (A+) 324 | (A+) 679 |
| CLOCK,2,8 | (A+) 51 | (A+) 326 | (A+) 681 |
| SELECT THE PROGRAM,8,52 | (A+) 53 | (A+) 328 | (A+) 683 |
| PROGRAM1,8,664 | (A+) 55 | (A+) 332 | (A+) 684 |
| PROGRAM2,6,273 | (B+) 60 | (B+) 340 | (A+) 686 |
| PROGRAM3,3,85 | (A+) 63 | (B+) 341 | (A+) 688 |
| PROGRAM4,1,6 | (A+) 64 | (B+) 354 | (A+) 689 |
| ON/OFF,4,114 | (A+) 65 | (A+) 372 | (A+) 691 |
| | (A+) 66 | (A+) 374 | (A+) 693 |
| COUNT:444 | (A+) 58 | (A+) 380 | (A+) 695 |
| WASTED TIME:44 | (A+) 69 | (A+) 383 | (A+) 696 |
| TOTAL TIME = Time - | (C) 78 | (B+) 388 | (A+) 698 |
| Waste=1389 | (PRGM) 97 | (A+) 425 | (B+) 700 |
| | (TIMER) 114 | (A+) 426 | (A+) 701 |
| | (PRGM) 117 | (A+) 428 | (A+) 703 |
| | (A+) 130 | (A+) 431 | (A+) 704 |

E-23

```
(A+)  706        (B+)  974        Subject number 19           (C)      135
(A+)  708        (A+)  976          Wednesday, June 27, 1990  (CLKADJ)  153
(A+)  709        (A+)  977              11:06:46 PM           (CLKADJ)  160
(A+)  711        (A+)  979                                    (TIMER)   166
(A+)  713        (B-)  985        Page time log               (CLKADJ)  177
(A+)  714        (B+)  993        CLOCK SET ,0,33             (A-)     202
(A+)  716        (B-)  996        CLOCK ,34,16                (A+)     203
(A+)  718        (A+)  999        CLOCK ADJUST ,51,32         (CLKADJ)  208
(A+)  719        (A+)  1008       CLOCK SET ,84,52            (CLKADJ)  211
(A+)  721        (A-)  1011       CLOCK ,136,15               (TIMER)   216
(A+)  723        (B-)  1014       CLOCK ADJUST ,152,2         (CLKADJ)  220
(A+)  725        (B-)  1019       CLOCK ADJUST ,154,7         (B-)     225
(A+)  726        (B+)  1024       CLOCK ADJUST ,161,5         (B+)     249
(A+)  728        (A-)  1029       ON/OFF ,166,11              (B+)     256
(A+)  729        (A-)  1031       CLOCK ADJUST ,178,30        (A-)     262
(A+)  731        (A-)  1037       CLOCK ADJUST ,209,2         (A-)     264
(A+)  733        (A-)  1039       CLOCK ADJUST ,212,4         (A-)     265
(A+)  734        (A-)  1044       ON/OFF ,216,4               (A-)     266
(A+)  736        (C)   1079       CLOCK ADJUST ,221,4         (B+)     272
(A-)  738        (C)   1143       CLOCK SET ,226,126          (A+)     285
(A-)  739                         CLOCK ,352,7                (A+)     286
(A-)  741        Programs set     SELECT THE PROGRAM ,359,8   (A+)     288
(A-)  742        1.SUN PM 8:00 5  PROGRAM1 ,368,666           (A+)     289
(A-)  744        2.SUN PM 8:00 5  SELECT THE PROGRAM ,1035,5  (A+)     290
(A-)  745        M-F  AM 3:00 7   PROGRAM1 ,1042,1            (A+)     291
(A-)  747        1.THU PM10:00 4  PROGRAM2 ,1044,150          (A-)     293
(A-)  749                         SELECT THE PROGRAM ,1194,6  (B+)     298
(A-)  750        Page summary     PROGRAM1 ,1202,1            (A-)     310
(A-)  752        CLOCK SET,2,83   PROGRAM2 ,1205,1            (A-)     312
(A+)  754        CLOCK ADJUST,1,5 PROGRAM3 ,1207,251          (A-)     314
(A+)  760        CLOCK,2,24       SELECT THE PROGRAM ,1458,13 (A-)     315
(B+)  763        SELECT THE PROGRAM,5,56  PROGRAM1 ,1473,5    (A-)     316
(B+)  769        PROGRAM1,4,432   PROGRAM2 ,1480,5            (A-)     318
(B+)  773        PROGRAM2,2,245   PROGRAM3 ,1487,3            (A-)     320
(A+)  784        PROGRAM3,1,172   PROGRAM4 ,1492,9            (B+)     325
(A+)  786        PROGRAM4,0,0     PROGRAM1 ,1503,4            (A+)     328
(A+)  787        ON/OFF,2,105     SELECT THE PROGRAM ,1507,10 (A+)     329
(A+)  789                         PROGRAM1 ,1519,6            (A+)     330
(A+)  791        COUNT:257        SELECT THE PROGRAM ,1525,168 (A+)    331
(A+)  794        WASTED TIME:21   ON/OFF ,1694,4              (A+)     332
(B-)  798        TOTAL TIME = Time -                          (A+)     335
(B-)  801           Waste=1143    Error log:                  (B+)     341
(A+)  827                         WRONG KEY 6 154             (C)      351
(A-)  831                         WRONG KEY 6 160             (C)      378
(A+)  834                         WRONG KEY 7 202             (B+)     388
(A+)  837                         7 202                       (A-)     404
(A+)  850                         WRONG KEY 8 203             (A-)     406
(A-)  853                         8 203                       (A-)     408
(C)   884                         WRONG KEY 6 208             (A-)     409
(A+)  901                         WRONG KEY 6 211             (B+)     415
(A+)  906                         2 877                       (A+)     427
(B+)  912                         DATE WRONG-NOT SUBJECTS     (A-)     433
(A-)  940                             FAULT 1699              (B+)     435
(A-)  941                         NO TIMER 1699               (A-)     443
(A-)  943                                                     (B+)     448
(A-)  945                         Users Actions:              (B+)     452
(A+)  946                         (A-)  17                    (A+)     461
(A+)  948                         (A-)  20                    (A+)     463
(A+)  949                         (A-)  21                    (A+)     466
(B+)  951                         (C)   32                    (A+)     468
(B-)  953                         (B+)  83                    (A+)     471
(A-)  955                         (B+)  118                   (A+)     473
(B+)  957                         (B+)  121                   (A+)     475
(B+)  959                         (A-)  128                   (A+)     479
(A-)  961                         (A-)  130                   (A+)     482
(B+)  963                         (A-)  131                   (A+)     498
(B+)  966                         (A-)  132                   (A+)     511
(B+)  969                                                     (A+)     515
```

| | | | | | | | |
|---|---|---|---|---|---|---|---|
| (A-) | 521 | (A-) | 800 | (A+) | 985 | (A+) | 1206 |
| (A-) | 531 | (A-) | 802 | (A+) | 988 | (B+) | 1219 |
| (A-) | 537 | (A-) | 804 | (A+) | 990 | (A+) | 1223 |
| (A+) | 539 | (A-) | 806 | (A+) | 993 | (A-) | 1226 |
| (B-) | 549 | (A-) | 808 | (A+) | 995 | (A-) | 1227 |
| (B+) | 553 | (A-) | 810 | (A+) | 997 | (A-) | 1229 |
| (A+) | 567 | (A-) | 812 | (B+) | 1013 | (A-) | 1231 |
| (A-) | 578 | (A-) | 814 | (A+) | 1016 | (A-) | 1233 |
| (A+) | 581 | (A-) | 817 | (A+) | 1018 | (A-) | 1234 |
| (A+) | 584 | (A-) | 819 | (A+) | 1019 | (A-) | 1236 |
| (A-) | 592 | (A-) | 821 | (A+) | 1021 | (A-) | 1237 |
| (A-) | 606 | (A-) | 823 | (C) | 1033 | (A-) | 1239 |
| (A+) | 613 | (A-) | 825 | (A+) | 1042 | (B+) | 1241 |
| (A-) | 615 | (A-) | 827 | (B+) | 1054 | (B-) | 1243 |
| (A-) | 618 | (A-) | 829 | (A+) | 1067 | (A+) | 1245 |
| (A+) | 624 | (A-) | 831 | (A+) | 1068 | (B+) | 1248 |
| (A-) | 627 | (A-) | 834 | (A+) | 1070 | (B+) | 1250 |
| (A-) | 629 | (A-) | 836 | (B+) | 1072 | (A-) | 1253 |
| (A-) | 631 | (A-) | 838 | (B+) | 1074 | (A-) | 1255 |
| (A-) | 634 | (A-) | 840 | (A+) | 1079 | (A-) | 1256 |
| (A-) | 636 | (A-) | 842 | (A+) | 1080 | (A-) | 1258 |
| (A-) | 645 | (A-) | 844 | (A+) | 1082 | (A-) | 1260 |
| (B-) | 648 | (A-) | 846 | (B+) | 1084 | (A-) | 1263 |
| (B+) | 651 | (A-) | 848 | (A+) | 1086 | (B+) | 1265 |
| (A+) | 655 | (A-) | 850 | (A+) | 1087 | (B+) | 1267 |
| (A+) | 657 | (A-) | 852 | (A+) | 1089 | (A-) | 1277 |
| (A+) | 667 | (A-) | 854 | (A+) | 1090 | (A-) | 1279 |
| (A+) | 669 | (A-) | 856 | (A+) | 1092 | (A-) | 1281 |
| (A+) | 672 | (A-) | 859 | (A+) | 1094 | (A-) | 1283 |
| (A+) | 674 | (A-) | 861 | (A+) | 1095 | (A-) | 1285 |
| (A+) | 676 | (A-) | 863 | (A+) | 1097 | (A-) | 1287 |
| (A-) | 679 | (B-) | 865 | (A+) | 1098 | (A-) | 1300 |
| (B+) | 688 | (A-) | 868 | (A+) | 1100 | (A-) | 1302 |
| (B+) | 690 | (A-) | 870 | (A+) | 1102 | (A+) | 1305 |
| (B-) | 698 | (A-) | 872 | (A+) | 1103 | (A+) | 1307 |
| (A+) | 704 | (A-) | 874 | (A+) | 1105 | (A-) | 1310 |
| (A+) | 709 | (D) | 877 | (A+) | 1107 | (A+) | 1312 |
| (A+) | 714 | (B-) | 877 | (A+) | 1109 | (A+) | 1317 |
| (A+) | 718 | (B-) | 879 | (A+) | 1110 | (A+) | 1319 |
| (B+) | 728 | (B+) | 881 | (A+) | 1112 | (A+) | 1327 |
| (B-) | 732 | (B+) | 883 | (A+) | 1113 | (A+) | 1330 |
| (B+) | 741 | (A+) | 888 | (A+) | 1115 | (A+) | 1332 |
| (B-) | 743 | (A-) | 890 | (A+) | 1117 | (A-) | 1335 |
| (A-) | 745 | (A+) | 893 | (A+) | 1119 | (A+) | 1337 |
| (A+) | 747 | (A+) | 895 | (A+) | 1121 | (A+) | 1339 |
| (A+) | 750 | (A+) | 898 | (A+) | 1123 | (A+) | 1341 |
| (A+) | 753 | (A+) | 900 | (A+) | 1124 | (A+) | 1350 |
| (A+) | 756 | (A+) | 902 | (A+) | 1126 | (A+) | 1355 |
| (A-) | 758 | (A+) | 905 | (A+) | 1127 | (A+) | 1357 |
| (A-) | 760 | (A+) | 907 | (A+) | 1129 | (A+) | 1360 |
| (A-) | 762 | (B-) | 917 | (A+) | 1131 | (A+) | 1362 |
| (A-) | 764 | (B+) | 919 | (A+) | 1132 | (A+) | 1368 |
| (A-) | 766 | (A-) | 921 | (A+) | 1134 | (A+) | 1370 |
| (A-) | 768 | (A+) | 927 | (B+) | 1135 | (A+) | 1372 |
| (A-) | 771 | (A-) | 930 | (A-) | 1144 | (A-) | 1374 |
| (A-) | 773 | (A-) | 933 | (B+) | 1149 | (A+) | 1376 |
| (A-) | 775 | (A+) | 935 | (B-) | 1155 | (A+) | 1379 |
| (A-) | 777 | (A+) | 937 | (A+) | 1157 | (A-) | 1381 |
| (A-) | 779 | (A+) | 947 | (A-) | 1165 | (A-) | 1384 |
| (A-) | 781 | (A+) | 950 | (B+) | 1168 | (A-) | 1386 |
| (A-) | 783 | (A-) | 952 | (A+) | 1170 | (A-) | 1392 |
| (A-) | 785 | (A-) | 956 | (A+) | 1172 | (A-) | 1396 |
| (A-) | 787 | (A+) | 959 | (A+) | 1173 | (A-) | 1401 |
| (A-) | 789 | (A+) | 963 | (A+) | 1175 | (A-) | 1407 |
| (A-) | 791 | (A+) | 966 | (A+) | 1183 | (A-) | 1409 |
| (A-) | 793 | (B+) | 974 | (A+) | 1184 | (A-) | 1414 |
| (A-) | 795 | (B+) | 977 | (C) | 1193 | (A-) | 1416 |
| (A-) | 797 | (B-) | 981 | (A+) | 1202 | (B-) | 1417 |

E-25

```
(A+) 1425           Subject number 20 Sunday,      (A+) 100        (B-) 312
(A+) 1427               July 1, 1990 1:47:40 PM    (B+) 102        (B-) 314
(A+) 1429                                          (B+) 104        (B-) 317
(B+) 1441                                          (A+) 113        (A-) 321
(A+) 1448           Page time log                  (A+) 116        (B+) 325
(A+) 1449           CLOCK SET ,1,157               (A+) 118        (B+) 329
(A+) 1451           CLOCK ,160,10                  (B+) 120        (A-) 332
(A+) 1453           SELECT THE PROGRAM ,171,3      (A+) 123        (B+) 335
(C)  1457           PROGRAM1 ,176,296              (A+) 125        (B+) 339
(A+) 1478           SELECT THE PROGRAM ,473,3      (A+) 127        (B+) 347
(A+) 1484           PROGRAM1 ,479,1                (A+) 129        (A+) 356
(A+) 1490           PROGRAM2 ,481,172              (A+) 131        (A+) 360
(C)  1496           SELECT THE PROGRAM ,653,2      (A+) 132        (A+) 363
(A+) 1501           PROGRAM1 ,658,4                (A-) 136        (A+) 366
(C)  1505           PROGRAM4 ,664,2                (B+) 138        (A+) 369
(C)  1524           PROGRAM3 ,668,93               (A+) 142        (B+) 372
<TIMER> 1695        SELECT THE PROGRAM ,761,11     (A+) 143        (A-) 375
(C)  1697           SELECT THE PROGRAM ,773,14     (A+) 145        (A-) 380
                    SELECT THE PROGRAM ,787,6      (A+) 147        (B-) 382
Programs set        ON/OFF ,793,25                 (A+) 148        (A-) 389
2.SUN PM 8:00 5                                    (A+) 150        (B+) 394
M-F  AM 3:00 7      Error log:                     (B+) 153        (A-) 400
2.SAT PM 5:00 5     POWERS OFF, SETS TIMER 818     (C)  157        (A-) 405
2.SUN PM 8:00 5                                    (B+) 181        (B-) 407
2.SUN PM 8:00 5     Users Actions:                 (A+) 188        (B-) 413
                    (A+)  5                        (A+) 200        (A+) 417
Page summary        (A+) 15                        (A+) 202        (B+) 422
CLOCK SET,3,211     (A+) 16                        (A+) 205        (B+) 425
CLOCK ADJUST,8,86   (A+) 17                        (A+) 207        (A+) 428
CLOCK,3,38          (A+) 19                        (A+) 209        (A+) 430
SELECT THE PROGRAM,5,210  (A+) 20                  (A+) 211        (A+) 432
PROGRAM1,6,683      (A+) 21                        (A+) 214        (A+) 434
PROGRAM2,3,156      (A+) 23                        (A+) 216        (A+) 436
PROGRAM3,2,254      (A+) 24                        (A+) 218        (A+) 438
PROGRAM4,1,9        (A+) 25                        (A+) 220        (A+) 440
ON/OFF,3,19         (A+) 27                        (A+) 223        (A+) 443
                    (A+) 28                        (A+) 225        (A+) 445
COUNT:370           (A+) 30                        (A+) 227        (A+) 447
WASTED TIME:32      (A+) 31                        (A+) 230        (A+) 450
TOTAL TIME = Time - (A+) 33                        (A+) 232        (A-) 458
    Waste=1697     (A+) 34                         (A+) 234        (A-) 461
                    (A+) 35                        (A+) 236        (A-) 463
                    (A+) 37                        (A+) 238        (C)  471
                    (A+) 38                        (B+) 241        (A+) 479
                    (A+) 39                        (A+) 243        (B+) 489
                    (A+) 41                        (A+) 245        (A+) 494
                    (A+) 42                        (A-) 247        (A+) 496
                    (A+) 43                        (A+) 249        (A+) 498
                    (A+) 45                        (A+) 252        (B+) 502
                    (A+) 46                        (A+) 254        (B+) 504
                    (A+) 48                        (A+) 257        (A+) 506
                    (A+) 49                        (A+) 259        (A+) 509
                    (A+) 50                        (A+) 261        (A+) 511
                    (A+) 52                        (A+) 263        (B+) 514
                    (A+) 53                        (A-) 266        (A+) 516
                    (A-) 54                        (A-) 268        (A+) 518
                    (A-) 56                        (A-) 270        (A+) 520
                    (A-) 67                        (A-) 272        (A+) 522
                    (A-) 68                        (A-) 274        (A+) 524
                    (A-) 70                        (A-) 276        (A+) 526
                    (A-) 71                        (A-) 278        (A+) 529
                    (A-) 73                        (A-) 282        (A+) 531
                    (A-) 74                        (A-) 285        (A+) 533
                    (A-) 83                        (B-) 287        (A+) 536
                    (B+) 91                        (B+) 295        (A-) 538
                    (B+) 93                        (B+) 304        (A-) 540
                    (A+) 97                        (B-) 306        (A+) 542
                    (A+) 98                        (B-) 309        (A+) 544
```

```
(A+)  546          CLOCK,1,10              Subject number 21 Sunday,   (B-) 37
(A+)  548          SELECT THE PROGRAM,6,39    July 1, 1990 2:23:54 PM  (B-) 39
(A+)  551          PROGRAM1,3,301                                      (B+) 40
(A+)  553          PROGRAM2,1,172                                      (A-) 44
(A+)  555          PROGRAM3,1,93           Page time log               (A-) 46
(A+)  557          PROGRAM4,1,2            CLOCK SET ,1,10             (A+) 48
(A+)  559          ON/OFF,1,25             CLOCK ADJUST ,13,1          (B+) 59
(A+)  561                                  CLOCK ADJUST ,15,4          (B+) 62
(A+)  564          COUNT:239               CLOCK ADJUST ,20,0          (B+) 64
(A+)  566          WASTED TIME:18          CLOCK SET ,21,3             (A+) 69
(A+)  573          TOTAL TIME = Time -     SELECT THE PROGRAM ,24,1    (A+) 71
(A+)  577              Waste=817           SELECT THE PROGRAM ,26,2    (A+) 73
(A+)  580                                  SELECT THE PROGRAM ,29,2    (A+) 75
(A+)  582                                  CLOCK ADJUST ,32,5          (A+) 80
(A+)  584                                  CLOCK SET ,38,105           (B+) 89
(A+)  587                                  CLOCK ,143,6                (A+) 92
(B+)  592                                  SELECT THE PROGRAM ,149,4   (A+) 94
(A+)  599                                  PROGRAM1 ,154,269           (A+) 96
(A+)  602                                  SELECT THE PROGRAM ,424,5   (A+) 98
(A+)  606                                  PROGRAM1 ,432,0             (A+) 106
(A+)  609                                  PROGRAM2 ,434,238           (B+) 111
(B+)  612                                  SELECT THE PROGRAM ,673,5   (B+) 113
(A+)  618                                  SELECT THE PROGRAM ,679,5   (A+) 115
(A+)  620                                  PROGRAM1 ,687,5             (A+) 116
(A+)  622                                  PROGRAM2 ,693,220           (A+) 118
(A+)  624                                  SELECT THE PROGRAM ,914,6   (A+) 119
(A+)  626                                  PROGRAM1 ,923,1             (A+) 121
(A+)  629                                  PROGRAM2 ,927,2             (A+) 122
(B-)  638                                  PROGRAM3 ,931,174           (A-) 125
(B-)  641                                  SELECT THE PROGRAM ,1105,30 (C)  142
(B+)  646                                  SELECT THE PROGRAM ,1136,5  (B+) 176
(B+)  649                                  ON/OFF ,1142,4              (A+) 179
(C)   651                                                              (A+) 181
(A-)  652                                  Error log:                  (A+) 183
(A-)  666                                  WRONG KEY RIGHT 10          (A+) 186
(B+)  669                                  WRONG KEY UP 13             (A+) 188
(A-)  673                                  UP 13                       (A+) 190
(A-)  675                                  WRONG KEY RIGHT 14          (A+) 192
(A-)  677                                  WRONG KEY RIGHT 19          (A+) 194
(A+)  679                                  WRONG KEY UP 34             (A+) 196
(B+)  683                                  UP 35                       (A+) 198
(B+)  685                                  WRONG KEY HOME 35           (A+) 200
(A-)  688                                  HOME 35                     (A+) 203
(B+)  690                                  WRONG KEY UP 36             (A+) 205
(B+)  693                                  UP 36                       (A+) 207
(B+)  703                                  WRONG KEY HOME 37           (A+) 209
(B-)  709                                  HOME 37                     (A-) 212
(A-)  713                                  CENTER 427                  (A-) 214
(A+)  716                                  SETS CURRENT DATE FOR WRONG (A+) 216
(B+)  719                                     DAY AND SETS P3 FOR A    (A+) 218
(A+)  724                                     DATE IN THE PAST 1146    (A+) 220
(A+)  727                                  SETS TIMER 1146             (A+) 222
(B+)  740                                                              (A+) 224
(A+)  747                                  Users Actions:              (A+) 226
(A+)  749                                  (A+)  7                     (A+) 230
(A+)  751                                  (A-)  8                     (B+) 237
(C)   759                                  (A-)  9                     (B+) 239
(TIMER) 799                                (CLKADJ) 10                 (A-) 242
(C)   817                                  (A+)  13                    (A-) 244
                                           (CLKADJ) 13                 (A+) 246
Programs set                               (CLKADJ) 19                 (B+) 249
2.SUN PM 8:00 5                            (B-)  20                    (B+) 251
M-F    AM 5:00 7                           (A-)  22                    (B+) 260
1.FRI PM10:30 4                            (PRGM) 23                   (A+) 265
                                           (A+)  34                    (A+) 268
Page summary                               (A-)  35                    (A+) 271
CLOCK SET,1,157                            (A+)  35                    (A+) 274
CLOCK ADJUST,0,0                           (A-)  36                    (B+) 276
```

E-27

(A+) 279
(A+) 281
(B+) 283
(B+) 285
(B+) 289
(B+) 294
(B+) 298
(B+) 305
(B+) 310
(A+) 315
(B-) 319
(B+) 328
(A+) 336
(B-) 339
(A+) 349
(A+) 352
(A+) 355
(A+) 359
(A+) 363
(A+) 366
(A+) 370
(A-) 381
(A+) 388
(B-) 405
(A+) 412
(C) 422
(A+) 432
(B+) 441
(A+) 445
(A+) 447
(A+) 449
(B+) 453
(B+) 458
(A+) 461
(A+) 463
(A+) 465
(B+) 469
(A+) 471
(A+) 473
(A+) 475
(A+) 478
(A+) 480
(A+) 483
(A+) 485
(A+) 487
(A-) 489
(A+) 491
(A+) 493
(A+) 495
(A+) 497
(A+) 499
(A+) 501
(A+) 503
(A+) 506
(A+) 508
(A+) 510
(A+) 512
(A+) 514
(A+) 516
(A+) 518
(A+) 521
(A+) 531
(A+) 534
(A+) 536
(A+) 538
(A-) 540
(A+) 542
(B+) 557

(B-) 579
(B+) 583
(B+) 589
(A-) 594
(A-) 599
(B+) 610
(A+) 613
(A+) 615
(A+) 617
(A+) 619
(A+) 621
(A+) 623
(B+) 638
(B+) 647
(B+) 651
(B+) 658
(B+) 668
(PRGM) 672
(A+) 691
(B+) 703
(A+) 709
(A+) 711
(A+) 713
(B+) 729
(A+) 732
(B+) 735
(B-) 739
(A+) 744
(A+) 746
(A+) 748
(B+) 755
(A+) 759
(A+) 762
(A+) 764
(B+) 769
(B+) 774
(B-) 780
(A+) 785
(A+) 789
(A+) 796
(A+) 799
(B-) 817
(A+) 820
(A+) 823
(A+) 825
(A+) 827
(A+) 829
(A+) 831
(A+) 833
(A+) 836
(A+) 838
(A+) 840
(A+) 842
(A+) 844
(A+) 846
(A+) 848
(A+) 850
(A+) 852
(A+) 855
(A+) 857
(A+) 859
(A-) 861
(A+) 863
(A+) 865
(A+) 867
(A+) 869
(A+) 871
(A+) 874

(A+) 876
(B+) 878
(C) 885
(B+) 892
(A+) 896
(A+) 898
(A+) 900
(A+) 902
(A+) 907
(A+) 910
(C) 912
(A+) 924
(A+) 929
(B+) 948
(A-) 953
(A-) 955
(A-) 957
(A-) 959
(B+) 961
(A+) 963
(A+) 965
(A+) 967
(A+) 969
(A+) 972
(A+) 974
(A+) 975
(A+) 978
(A+) 980
(A+) 982
(A+) 984
(A+) 987
(A+) 989
(A+) 991
(A+) 993
(A+) 995
(A+) 997
(A+) 999
(A+) 1001
(A+) 1003
(A+) 1005
(A+) 1007
(A+) 1010
(A+) 1012
(A+) 1014
(A+) 1016
(A+) 1018
(A+) 1020
(A+) 1022
(A+) 1025
(B+) 1027
(A-) 1029
(A-) 1031
(A-) 1033
(A-) 1035
(A+) 1037
(B+) 1041
(B+) 1044
(B+) 1050
(B+) 1054
(B-) 1056
(A+) 1061
(A+) 1064
(A+) 1066
(A+) 1069
(B+) 1073
(A+) 1075
(A+) 1077
(A+) 1079

(A+) 1081
(A+) 1083
(A+) 1085
(A+) 1087
(A+) 1089
(A+) 1091
(A+) 1093
(A+) 1095
(A+) 1097
(A+) 1099
(C) 1104
(C) 1146

Programs set
2.SUN PM 8:00 5
M-F AM 3:00 7
1.SUN PM 8:30 14

Page summary
CLOCK SET,3,118
CLOCK ADJUST,4,10
CLOCK,1,6
SELECT THE PROGRAM,10,65
PROGRAM1,4,275
PROGRAM2,3,460
PROGRAM3,1,174
PROGRAM4,0,0
ON/OFF,1,4

COUNT:299
WASTED TIME:33
**TOTAL TIME = Time -
    Waste=1146**

Subject number 22 Sunday,
July 1, 1990 4:24:19 PM

Page time log
CLOCK SET ,1,77
CLOCK ,80,14
CLOCK ADJUST ,96,5
CLOCK SET ,102,97
CLOCK ,199,16
SELECT THE PROGRAM ,216,6
PROGRAM1 ,224,225
SELECT THE PROGRAM ,449,10
PROGRAM1 ,462,3
PROGRAM2 ,466,214
SELECT THE PROGRAM ,681,30
PROGRAM1 ,713,4
PROGRAM2 ,719,3
PROGRAM3 ,723,59
SELECT THE PROGRAM ,783,45
SELECT THE PROGRAM ,828,9
ON/OFF ,837,4

Error log:
CENTER 313
CENTER 816
LEFT 818
END 821
POWERS OFF, NO TIMER 841

Users Actions:
(A+) 35
(A+) 39
(A+) 45
(A+) 46
(A+) 48
(A-) 49
(A-) 50
(A-) 51
(A-) 53
(A-) 54
(A-) 55
(A-) 57
(A-) 58
(C) 78
(B+) 101
(B+) 106
(B+) 110
(A+) 122
(A+) 123
(A+) 126
(B+) 136
(A+) 143
(A+) 144
(A-) 146
(A+) 148
(A+) 149
(B+) 156
(A-) 161
(A+) 163
(A+) 164
(A+) 166
(A+) 168
(B+) 173
(A+) 178
(A+) 181
(A+) 182
(A+) 184
(A+) 185
(C) 198
(B+) 234
(B+) 240
(B-) 245
(B-) 248
(A-) 263
(A-) 265
(A-) 267
(A-) 269
(B+) 282
(B+) 286
(A-) 291
(B+) 296
(B+) 299
(B+) 327
(A-) 333
(A-) 336
(A-) 339
(B+) 343
(B-) 355
(B+) 360
(B+) 362
(B+) 365
(B+) 367
(B+) 369
(B+) 374
(B+) 378
(B-) 383
(A+) 387
(B+) 403
(B+) 408
(A+) 416
(A+) 418
(A+) 420
(A+) 422
(C) 448
(A+) 464
(B+) 470
(A+) 493
(A+) 495
(A+) 497
(B+) 499
(B+) 502
(A+) 504
(A+) 507
(A+) 509
(B+) 511
(A+) 514
(A+) 516
(A+) 519
(A+) 521
(A+) 523
(A+) 525
(A+) 527
(A+) 529
(A+) 531
(A+) 533
(A+) 535
(A+) 537
(A+) 539
(A+) 541
(A+) 543
(A+) 545
(A+) 547
(A+) 550
(A+) 552
(A+) 554
(A+) 556
(A+) 558
(A+) 560
(A+) 562
(A+) 564
(A+) 566
(A+) 571
(A+) 573
(A+) 575
(A+) 577
(B+) 582
(B+) 603
(A-) 608
(A-) 611
(B-) 626
(A+) 631
(A+) 634
(A+) 637
(A+) 640
(B+) 655
(A+) 662
(A+) 664
(A+) 666
(A+) 668
(A+) 670
(A+) 672
(C) 679
(A+) 716
(A+) 722
(B+) 729
(A-) 731
(A-) 733
(B+) 736
(B+) 738
(A-) 740
(B+) 743
(B+) 745
(B+) 755
(A+) 759
(B+) 766
(A+) 772
(A+) 774
(A+) 776
(C) 781
(C) 841

Programs set
2.SUN PM 8:00 5
M-F AM 3:00 7
1.THU PM10:00 4

Page summary
CLOCK SET,2,174
CLOCK ADJUST,1,5
CLOCK,2,30
SELECT THE PROGRAM,5,100
PROGRAM1,3,232
PROGRAM2,2,217
PROGRAM3,1,59
PROGRAM4,0,0
ON/OFF,1,4

COUNT:152
WASTED TIME:19
TOTAL TIME = Time −
    Waste=841

Subject number 23 Sunday,
July 1, 1990 4:52:08 PM

Page time log
CLOCK SET ,1,146
CLOCK ,147,16
SELECT THE PROGRAM ,163,6
PROGRAM1 ,171,3
PROGRAM4 ,176,9
SELECT THE PROGRAM ,185,1
SELECT THE PROGRAM ,187,5
PROGRAM1 ,194,205
SELECT THE PROGRAM ,400,5
PROGRAM1 ,408,3
PROGRAM2 ,413,162
SELECT THE PROGRAM ,576,8
PROGRAM1 ,586,1
PROGRAM2 ,590,2
PROGRAM3 ,593,119
SELECT THE PROGRAM ,713,18
ON/OFF ,732,5

Error log:
WRONG KEY DOWN 72
DOWN 72
END 576
TIMER ON 737

Users Actions:
(A-)  9
(A-) 11
(A-) 13
(A-) 14
(A+) 15
(A-) 16
(B+) 18
(B-) 22
(A+) 29
(B+) 33
(A-) 39
(A+) 43
(B+) 46
(A-) 50
(A-) 52
(A-) 54
(A-) 56
(A-) 57
(A+) 59
(B+) 61
(B-) 68
(D)  71
(B+) 74
(A+) 77
(A+) 78
(A+) 80
(A+) 82
(A+) 83
(B+) 85
(A+) 87
(A+) 91
(A+) 93
(A+) 94
(A+) 96
(B+) 97
(B+) 99
(A-) 101
(A-) 105

(B+) 109
(B+) 112
(B+) 114
(B+) 116
(B+) 117
(B+) 122
(A+) 123
(A+) 125
(A+) 126
(A+) 128
(A+) 129
(B+) 133
(A+) 137
(B-) 141
(B+) 143
(C)  146
(A-) 174
(PRGM) 184
(B+) 197
(A+) 207
(A+) 210
(A-) 212
(A-) 214
(A-) 216
(A-) 218
(A-) 220
(A-) 223
(A-) 225
(A-) 227
(A-) 229
(A-) 231
(A+) 234
(A-) 236
(A-) 238
(A+) 240
(B+) 242
(B+) 245
(A+) 253
(A-) 257
(A-) 260
(B+) 262
(B+) 265
(A+) 272
(A+) 275
(A+) 278
(A+) 281
(A+) 284
(B+) 303
(A+) 310
(A+) 313
(A+) 315
(A+) 318
(A+) 321
(B+) 323
(A-) 326
(A+) 333
(A+) 335
(A+) 337
(A+) 341
(A+) 343
(B+) 345
(B+) 354
(B+) 356
(B+) 358
(B+) 360
(B+) 367
(A-) 373
(B+) 377

(B+) 391
(C)  398
(A+) 411
(B+) 416
(A+) 420
(A+) 422
(A+) 424
(B+) 427
(B+) 429
(A+) 435
(A+) 437
(A+) 439
(B+) 441
(A+) 443
(A+) 445
(A+) 447
(A+) 449
(A+) 452
(A+) 454
(A+) 456
(A+) 458
(A+) 460
(A+) 462
(A+) 464
(A+) 466
(A+) 468
(A+) 470
(A+) 472
(A+) 474
(A+) 476
(A+) 478
(A+) 480
(A+) 482
(A+) 489
(A+) 491
(A+) 493
(A+) 495
(A+) 497
(A+) 499
(A+) 501
(A+) 503
(A+) 505
(A+) 507
(B+) 509
(A-) 545
(B+) 552
(A+) 558
(A+) 560
(A+) 562
(A+) 564
(A+) 565
(A+) 567
(B+) 571
(C)  574
(A+) 587
(A+) 591
(B+) 595
(A+) 611
(A-) 615
(A-) 617
(A-) 619
(A-) 621
(A-) 623
(A-) 625
(B+) 630
(B+) 632
(A-) 636
(A-) 638

(A-) 640
(A-) 642
(B+) 647
(B+) 649
(A-) 666
(A-) 669
(A-) 674
(A-) 677
(A-) 680
(B+) 683
(A+) 686
(A+) 689
(A+) 691
(B+) 694
(B+) 709
(C)  711
(C)  737

Programs set
1.SUN PM 8:00 5
M-F AM 3:00 7
1.SAT PM 7:00 1

Page summary
CLOCK SET,1,146
CLOCK ADJUST,0,0
CLOCK,1,16
SELECT THE PROGRAM,6,43
PROGRAM1,4,212
PROGRAM2,2,164
PROGRAM3,1,119
PROGRAM4,1,9
ON/OFF,1,5

COUNT:192
WASTED TIME:22
TOTAL TIME = Time -
      Waste=737

E-30

VCR B Raw Data

TOTAL Time Statistics
461,929,675,1151,403,331,437
,372,747,180,823,461,239
,368,456,352 allnums
16 NUMBER OF ITEMS
180 MIN
1151 MAX
8385 SUM
524.0625 AVG
266.79467 standard deviation

Total Time
Subject 1 461
Subject 2 929
Subject 4 675
Subject 5 1151
Subject 9 403
Subject 10 331
Subject 11 437
Subject 15 372
Subject 16 747
Subject 17 180
Subject 18 823
Subject 19 461
Subject 20 239
Subject 21 368
Subject 22 456
Subject 23 352

WASTED COMPUTER TIME
Subject 1 39
Subject 2 51
Subject 4 31
Subject 5 63
Subject 9 28
Subject 10 36
Subject 11 46
Subject 15 39
Subject 16 31
Subject 17 23
Subject 18 43
Subject 19 42
Subject 20 24
Subject 21 47
Subject 22 19
Subject 23 36

WASTED STATISTICS
39,51,31,63,28,36,46,39,31,2
3,43,42,24,47,19,36
WASTENUMS
16 NUMBER OF ITEMS
19 MIN
63 MAX
598 SUM
37.375 AVG
11.441882 standard deviation

OK total
6,3,1,16,2,2,36,3,1,3,10,2,1
,2,15,15,,2,4,3,9,3,2,1,
5,6,1,2,2,13,4,2,3,5,3,2
,1,3,45,2,1,2,9,16,7,1,2
,42,23,3,7,,2,,1,7,6,6,3
9,5,3,4,5,20,4,6,3,8,5,2
1,5,2,4,4,3,4,4,3,2,8,5, 3,2,8,4,3,2,10,9,10,2,1,
1,25,3,2,2,7,3,22,2,1,6,
1,2,1,3,39,1,2,9,7,11,3,
2,4,1,4,9,3,2,5,2,3,2,
12,4,4,1,1,0,2,11,4,0,1,
4,1,1,1,5,15,3,2,7,2,2,3
,2,4,1,1,2,2,2,2,7,8,4,4
,5,3,3,6,3,2,2,5,2,2,2,6
,12,19,7,13,6,7,4,17,12,
22,8,4,4,14,3,2,2,2,3,1,
3,4,1,1,4,2,0,1,3,1,1,2,
3,21,8,6,2,2,2,2,2,7,2,3
,1,1,27,1,2,1,5,3,6,2,4,
4,3,13,3,4,3,12,1,1,2,6,
16,2,2,1,4,1,8,3,1,1,6,3
,1,1,5,2,4,10,3,3,5,3,1,
2,8,1,1,2,3,2,5,4,5,2,2,
1,19,6,5,1,1,2,2,2,10,1,
2,2,0,1,6,2,2,1,9,1,1,2,
4 allnums
295 NUMBER OF ITEMS
0 MIN
45 MAX
1541 SUM
5.223729 AVG
6.583641 standard deviation

Mouse /key pressed data (w/errors)
86,194,94,229,86,74,91,86,11
8,72,114,86,71,90,79,88
allnums
16 NUMBER OF ITEMS
71 MIN
229 MAX
1658 SUM
103.625 AVG
44.477522 standard deviation

Error Statistics
5,20,11,7,4,3,5,4,35,5,4,2,2
,1,3,4 allnums
16 NUMBER OF ITEMS
1 MIN
35 MAX
115 SUM
7.1875 AVG
8.696503 standard deviation

Wasted time data
39,51,31,63,28,36,46,39,31,2
3,43,42,24,47,19,36
allnums
16 NUMBER OF ITEMS
19 MIN
63 MAX
598 SUM
37.375 AVG
11.441882 standard deviation total page stats (# number of pages opened)
35,63,33,97,35,35,41,37,40,2
8,42,43,31,39,33,34
allnums
16 NUMBER OF ITEMS
28 MIN
97 MAX
667 SUM
41.6875 AVG
16.696182 standard deviation page stats by page stats on number of times page entered

Page name: main menu
6,9,4,18,5,6,6,6,8,4,5,7,4,6
,5,6
16 NUMBER OF ITEMS
4 MIN
18 MAX
105 SUM
6.5625 AVG
3.346018 standard deviation Page name: timer
1,1,0,1,1,1,0,1,0,1,1,1,1,1,
1,1
16 NUMBER OF ITEMS
0 MIN
1 MAX
13 SUM
0.8125 AVG
0.403113 standard deviation Page name: main menu help
0,0,0,1,0,0,0,1,1,0,1,0,0,1,
0,1
16 NUMBER OF ITEMS
0 MIN
1 MAX
6 SUM
0.375 AVG
0.5 standard deviation Page name: HELP
0,1,1,1,1,0,1,0,2,0,3,1,0,1,
0,0
16 NUMBER OF ITEMS
0 MIN
2 MAX
9 SUM
0.5625 AVG
0.629153 standard deviation Page name: TAPE STATUS
0,0,0,0,0,0,0,0,3,0,0,0,0,0,
0,0
16 NUMBER OF ITEMS
0 MIN
0 MAX
0 SUM
0 AVG
0 standard deviation Page name: Current Time
1,1,2,4,1,1,1,1,2,1,1,1,1,1,
1.1
16 NUMBER OF ITEMS
1 MIN
4 MAX
21 SUM
1.3125 AVG
0.7932 standard deviation Page name: Current Time Help
0,0,0,0,0,0,0,0,0,0,0,0,0,
0,0
16 NUMBER OF ITEMS
0 MIN
0 MAX
0 SUM
0 AVG
0 standard deviation Page name: Select the Program
3,7,3,9,4,4,4,3,3,3,4,4,3,3,
3,3
16 NUMBER OF ITEMS
3 MIN
9 MAX
63 SUM
3.9375 AVG
1.691892 standard deviation Page name: specific day
1,3,2,3,3,1,2,2,0,1,2,2,1,1,
1,1
16 NUMBER OF ITEMS
0 MIN
3 MAX
26 SUM
1.625 AVG
0.885061 standard deviation Page name: Select the Program Help
0,0,0,0,0,0,0,0,0,0,0,0,0,0,
0,0
16 NUMBER OF ITEMS
0 MIN
0 MAX
0 SUM
0 AVG
0 standard deviation Page name: Select the Day
1,2,0,2,0,1,1,0,2,0,1,1,1,1,
1,0
16 NUMBER OF ITEMS
0 MIN
2 MAX
14 SUM
0.875 AVG
0.718795 standard deviation Page name: select the month
2,4,2,5,2,2,4,3,1,1,3,4,2,3,
2,2
16 NUMBER OF ITEMS
1 MIN
5 MAX
42 SUM
2.625 AVG
1.147461 standard deviation Page name: year set
2,1,2,2,2,1,1,2,2,1,1,2,1,2,
1,1
16 NUMBER OF ITEMS
1 MIN 2 MAX
22 SUM
1.375 AVG
0.5 standard deviation Page name: channel
3,6,3,8,3,3,3,3,3,4,3,3,3,
3,3
16 NUMBER OF ITEMS
3 MIN
8 MAX
57 SUM
3.5625 AVG
1.41274 standard deviation Page name: Start Time
3,7,3,8,3,3,4,3,3,3,4,3,3,3,
3,3
16 NUMBER OF ITEMS
3 MIN
8 MAX
59 SUM
3.6875 AVG
1.537043 standard deviation Page name: Stop Time
3,6,3,8,3,3,3,3,3,3,4,3,3,3,
3,3
16 NUMBER OF ITEMS
3 MIN
8 MAX
57 SUM
3.5625 AVG
1.41274 standard deviation Page name: tape speed
3,6,3,8,3,3,3,3,3,3,4,3,3,3,
3,3
16 NUMBER OF ITEMS
3 MIN
8 MAX
57 SUM
3.5625 AVG
1.41274 standard deviation Page name: confirmation
4,6,4,14,3,4,4,4,6,3,4,4,3,4
,4,4
16 NUMBER OF ITEMS
3 MIN
14 MAX
75 SUM
4.6875 AVG
2.625992 standard deviation Page name: February 1990
2,3,2,5,2,2,4,3,1,1,3,4,2,3,
2,2
16 NUMBER OF ITEMS
1 MIN
5 MAX
41 SUM
2.5625 AVG
1.093542 standard deviation stats on the amount of time spent in each page Page name: main menu
60,89,31,113,47,46,62,37,97,
27,133,74,56,56,105,54
16 NUMBER OF ITEMS
27 MIN
133 MAX
1087 SUM
67.9375 AVG
31.045061 standard deviation Page name: timer
25,0,0,4,9,28,0,3,0,0,2,5,5,
3,2,3
16 NUMBER OF ITEMS
0 MIN
28 MAX
89 SUM
5.5625 AVG
8.54766 standard deviation Page name: main menu help
0,0,0,10,0,0,0,45,36,0,21,0,
0,9,0,7
16 NUMBER OF ITEMS
0 MIN
45 MAX
128 SUM
8 AVG
14.066509 standard deviation Page name: HELP
0,9,3,4,5,0,9,0,18,0,0,0,12,0,
5,0,0
16 NUMBER OF ITEMS
0 MIN
18 MAX
65 SUM
4.0625 AVG
5.421792 standard deviation Page name: TAPE STATUS
0,0,0,0,0,0,0,0,0,0,0,0,0,0,
0,0
16 NUMBER OF ITEMS
0 MIN
0 MAX
0 SUM
0 AVG
0 standard deviation Page name: Current Time
25,101,167,64,27,15,17,20,81
,16,51,27,8,31,23,21
16 NUMBER OF ITEMS
8 MIN
167 MAX
694 SUM
43.375 AVG
42.026777 standard deviation Page name: Current Time Help
0,0,0,0,0,0,0,0,0,0,0,0,0,0,
0,0
16 NUMBER OF ITEMS
0 MIN
0 MAX
0 SUM 0 AVG
0 standard deviation Page name: Select the Program
31,59,31,46,22,25,17,28,18,1
3,27,20,19,16,33,26
16 NUMBER OF ITEMS
13 MIN
59 MAX
431 SUM
26.9375 AVG
11.817889 standard deviation Page name: specific day
7,14,7,17,22,7,8,8,0,6,6,9,4
,5,7,11
16 NUMBER OF ITEMS
0 MIN
22 MAX
138 SUM
8.625 AVG
5.27731 standard deviation Page name: Select the Program Help
0,0,0,0,0,0,0,0,0,0,0,0,0,0,
0,0
16 NUMBER OF ITEMS
0 MIN
0 MAX
0 SUM
0 AVG
0 standard deviation Page name: Select the Day
5,20,0,21,0,14,3,0,10,0,5,3,
7,5,2,0
16 NUMBER OF ITEMS
0 MIN
21 MAX
95 SUM
5.9375 AVG
6.923089 standard deviation Page name: select the month
14,31,22,25,15,14,22,22,26,8
,53,39,10,22,30,19
16 NUMBER OF ITEMS
8 MIN
53 MAX
372 SUM
23.25 AVG
11.316654 standard deviation Page name: year set
44,28,104,24,79,18,16,20,82,
23,55,33,15,31,54,36
16 NUMBER OF ITEMS
15 MIN
104 MAX
662 SUM
41.375 AVG
26.717971 standard deviation Page name: channel
20,53,33,41,21,14,16,20,34,1
1,28,23,11,20,19,15

16 NUMBER OF ITEMS
11 MIN
53 MAX
381 SUM
23.8125 AVG
11.385481 standard deviation Page name: Start Time
63,120,95,158,49,50,56,53,75
,31,74,43,31,63,46,45
16 NUMBER OF ITEMS
31 MIN
158 MAX
1052 SUM
65.75 AVG
33.681845 standard deviation Page name: Stop Time
24,89,52,155,41,24,42,31,69,
23,79,33,18,23,50,20
16 NUMBER OF ITEMS
18 MIN
155 MAX
773 SUM
48.3125 AVG
35.910089 standard deviation Page name: tape speed
25,40,12,13,8,10,25,15,9,8,5
7,8,12,10,13,10
16 NUMBER OF ITEMS
8 MIN
57 MAX
275 SUM
17.1875 AVG
13.653907 standard deviation Page name: confirmation
66,245,76,368,20,26,95,22,15
7,3,123,37,11,15,42,43
16 NUMBER OF ITEMS
3 MIN
368 MAX
1349 SUM
84.3125 AVG
99.177765 standard deviation Page name: February 1990
14,8,12,24,10,5,24,9,9,2,66,
53,6,7,10,5
16 NUMBER OF ITEMS
2 MIN
66 MAX
264 SUM
16.5 AVG
18.011108 standard deviation average time spent in each page per page Page name: main menu
10,9.888889,7.75,6.277778,9.
4,7.666667,10.333333,6.1
56667,12.125,6.75,26.6,1
0.571429,14,9.333333,21,
9
16 NUMBER OF ITEMS
5.166667 MIN

E-32

26.6 MAX
176.863096 SUM
11.053944 AVG
5.484379 standard deviation

Page name: timer
25,0,4,9,28,3,0,2,5,5,3,2,3
13 NUMBER OF ITEMS
0 MIN
28 MAX
89 SUM
6.846154 AVG
9.04476 standard deviation Page name: main menu help
10,45,36,21,9,7
6 NUMBER OF ITEMS
7 MIN
45 MAX
128 SUM
21.333333 AVG
15.882905 standard deviation Page name: HELP
9,3,4,5,9,9,12,5
8 NUMBER OF ITEMS
3 MIN
12 MAX
56 SUM
7 AVG
3.162278 standard deviation Page name: Current Time
25,101,83.5,16,27,15,17,20,4
0.5,16,51,27,8,31,23,21
16 NUMBER OF ITEMS
8 MIN
101 MAX
522 SUM
32.625 AVG
25.675215 standard deviation Page name: Current Time Help

Page name: Select the Program
10.333333,8.428571,10.333333
,5.1111111,5.5,6.25,4.25,
9.333333,6,4.333333,6.75
,5,6.333333,5.333333,11,
8.666667
16 NUMBER OF ITEMS
4.25 MIN
11 MAX
112.956347 SUM
7.059772 AVG
2.27694 standard deviation Page name: specific day
7,4.666667,3.5,5.666667,7.33
3333,7,4,4,6,3,4.5,4,5,7
,11
15 NUMBER OF ITEMS
3 MIN
11 MAX
83.666667 SUM
5.577778 AVG 2.061424 standard deviation Page name: Select the Program Help

Page name: Select the Day
5,10,10.5,14,3,5,5,3,7,5,2
11 NUMBER OF ITEMS
2 MIN
14 MAX
69.5 SUM
6.318182 AVG
3.71667 standard deviation Page name: select the month
7,7,7.75,11.5,7.5,7,5.5,7.3333
33,26,8,17.666667,9.75,5
,7.333333,15,9.5
16 NUMBER OF ITEMS
5 MIN
26 MAX
156.333333 SUM
9.770833 AVG
5.525907 standard deviation Page name: year set
22.28,104.12,39.5,18,16,20,4
1,23.55,16.5,15,15.5,54,
36
16 NUMBER OF ITEMS
12 MIN
104 MAX
515.5 SUM
32.21875 AVG
23.585284 standard deviation Page name: channel
6.666667,8.833333,11,5.125,7
,4.666667,5.333333,6.666
667,11.333333,3.666667,7
.7.666667,4.333333,6.666
667,6.333333,5
16 NUMBER OF ITEMS
3.666667 MIN
11.333333 MAX
107.291667 SUM
6.705729 AVG
2.189911 standard deviation Page name: Start Time
21,17.142857,31.666667,19.75
,16.333333,16.666667,14,
17.666667,25,10.333333,1
8.5,14.333333,10.333333,
21,15.333333,15
16 NUMBER OF ITEMS
10.333333 MIN
31.666667 MAX
284.059523 SUM
17.75372 AVG
5.320603 standard deviation Page name: Stop Time
8,14.833333,17.333333,19.375
,13.666667,8,14,10.33333
3,23,7.666667,19.75,11,6
,7.666667,16.666667,6.66
6667

16 NUMBER OF ITEMS
6 MIN
23 MAX
203.958334 SUM
11.747396 AVG
5.349898 standard deviation Page name: tape speed
8.333333,6.666667,4,1.625,2.
666667,3.333333,8.333333
,5,3,2.666667,14.25,2.66
6667,4,3.333333,4.333333
,3.333333
16 NUMBER OF ITEMS
1.625 MIN
14.25 MAX
77.541666 SUM
4.846354 AVG
3.19047 standard deviation Page name: confirmation
16.5,40.833333,19,26.285714,
6.666667,6.5,23.75,5.5,2
6.166667,1,30.75,9.25,3.
666667,3.75,10.5,10.75
16 NUMBER OF ITEMS
1 MIN
40.833333 MAX
240.869048 SUM
15.054316 AVG
11.59476 standard deviation Page name: February 1990
7,2.666667,6,4.8,5,2.5,6.3,9
,2,22,13.25,3,2.333333,5
,2.5
16 NUMBER OF ITEMS
2 MIN
22 MAX
96.05 SUM
6.003125 AVG
5.196524 standard deviation

E-33

Subject number 1 Friday,
June 1, 1990 3:30 PM

Page time log
year set ,1,15
Current Time ,19,25
main menu ,44,11
year set ,55,28
select the month ,84,8
February 1990 ,96,12
main menu ,108,14
Select the Program ,122,22
specific day ,144,7
select the month ,151,6
February 1990 ,160,2
Start Time ,164,40
Stop Time ,206,11
channel ,218,8
tape speed ,227,14
confirmation ,245,33
main menu ,278,10
Select the Program ,289,4
Start Time ,294,10
Stop Time ,305,7
channel ,312,7
tape speed ,321,8
confirmation ,332,7
main menu ,340,7
Select the Program ,348,5
Select the Day ,351,5
Start Time ,358,13
Stop Time ,373,6
channel ,380,5
tape speed ,385,3
confirmation ,390,12
main menu ,403,6
confirmation ,410,14
main menu ,425,12
timer ,438,25

Error log:
backround handler Display2 24
backround handler Display2 51
Must choose a year 67
backround handler Missed 312
TURNS POWER OFF AND SETS THE TIMER 463

Users Actions:
year set Main Menu 11
Current Time Display2 24
Current Time PM 29
Current Time 9 34
Current Time 0 37
Current Time 0 38
Current Time OK 44
main menu SET CURRENT DATE 54
year set Display2 57
year set 9 63
year set 0 64
year set OK 67
year set 1 71
year set 9 73
year set Clear 76 year set 1 78
year set 9 79
year set 9 80
year set 0 81
year set OK 83
select the month June 89
February 1990 6 108
main menu ENTER NEW RECORDING TIME 121
Select the Program Program Once on ... 144
specific day Any other day 151
select the month June 156
February 1990 10 162
Start Time 8 170
Start Time 0 172
Start Time 0 173
Start Time PM 179
Start Time PM 181
Start Time AM 187
Start Time PM 188
Start Time OK 204
Stop Time PM 209
Stop Time 1 212
Stop Time 1 213
Stop Time 0 215
Stop Time 0 215
Stop Time OK 217
channel 5 224
channel OK 226
tape speed Standard Play 241
confirmation OK 277
main menu ENTER NEW RECORDING TIME 287
Select the Program Program Monday - Friday at ... 293
Start Time AM 297
Start Time 3 300
Start Time 0 301
Start Time 0 301
Start Time OK 304
Stop Time AM 307
Stop Time 3 309
Stop Time 3 310
Stop Time 0 310
Stop Time Missed 311
Stop Time OK 312
channel 7 316
channel OK 319
tape speed Extended Play 329
confirmation OK 339
main menu ENTER NEW RECORDING TIME 346
Select the Program Program Once a Week on ... 353
Select the Day Tuesdays 357
Start Time 1 361
Start Time 0 362
Start Time 0 363
Start Time 0 367
Start Time PM 369
Start Time OK 371
Stop Time PM 374
Stop Time 1 375
Stop Time 1 375
Stop Time 0 377

Stop Time 0 378
Stop Time OK 379
channel 5 384
channel OK 385
tape speed Extended Play 397
confirmation OK 402
main menu REVIEW CURRENT RECORDING TIMES 409
confirmation OK 424
main menu Power Off 433
timer FINISHED 461

Programs set
1 June 10, 1990 8:00 PM 11:00 PM 5 SP
2 Monday-Friday 3:00 AM 3:30 AM 7 EP
3 Tuesdays 10:00 PM 11:00 PM 5 EP
4 : :

Page summary
main menu,6,60
timer,1,25
main menu help,0,0
HELP,0,0
TAPE STATUS,0,0
Current Time,1,25
Current Time Help,0,0
Select the Program,3,31
specific day,1,7
Select the Program Help,0,0
Select the Day,1,5
select the month,2,14
year set,2,44
channel,3,20
Start Time,3,63
Stop Time,3,24
tape speed,3,25
confirmation,4,66
February 1990,2,14

COUNT:36
WASTED TIME:39
TOTAL TIME = Time - Waste=461

Subject number 2 Friday,
June 1, 1990 4:00 PM

Page time log
year set ,1,28
select the month ,30,7
February 1990 ,39,4
Current Time ,45,101
main menu ,146,5
confirmation ,151,8
main menu ,159,9
Select the Program ,168,20
specific day ,189,6
select the month ,195,8
February 1990 ,206,2
Start Time ,210,24
HELP ,234,9
Start Time ,244,19
Stop Time ,266,12
channel ,279,12
tape speed ,292,19
main menu ,311,13
Select the Program ,324,3
specific day ,327,3
select the month ,330,11
main menu ,341,4
Select the Program ,346,8
Start Time ,355,16
Stop Time ,372,33
channel ,406,5
tape speed ,412,8
confirmation ,422,10
main menu ,432,7
Select the Program ,440,12
Select the Day ,452,7
Start Time ,459,19
Stop Time ,479,11
channel ,491,9
tape speed ,500,7
confirmation ,510,2
main menu ,512,5
Select the Program ,517,4
specific day ,521,5
select the month ,526,5
February 1990 ,535,2
Start Time ,539,13
Stop Time ,553,9
channel ,562,8
tape speed ,571,2
confirmation ,575,99
main menu ,674,9
Select the Program ,683,4
Select the Day ,687,13
Start Time ,701,11
Stop Time ,713,10
channel ,724,12
tape speed ,736,3
confirmation ,741,87
main menu ,828,4
Select the Program ,832,8
Start Time ,841,18
Stop Time ,860,14
channel ,874,7
tape speed ,882,2
confirmation ,886,39
main menu ,925,33
timer ,958,0

Error log:
backround handler Display2 78
backround handler Display2 84
backround handler Missed 94
backround handler Missed 94
backround handler Display2 95
backround handler Display2 100
backround handler Missed 105
backround handler Missed 106
backround handler Missed 107
backround handler Display2 108
backround handler Display2 127
Must choose am/pm 256
Must choose am/pm 382
Must choose am/pm 559
backround handler 620
backround handler 621
backround handler 623
backround handler Missed 716
Must choose am/pm 721
SUBJECT TURNS POWER OFF BUT SET TIMER 958

Users Actions:
year set 1 10
year set 9 13
year set 9 14
year set 0 17
year set OK 29
select the month June 35
February 1990 6 43
Current Time 9 54
Current Time PM 56
Current Time OK 60
Current Time PM 74
Current Time 9 75
Current Time Display2 78
Current Time 9 79
Current Time Display2 83
Current Time 0 84
Current Time Clear 88
Current Time 9 91
Current Time Missed 93
Current Time Missed 94
Current Time Display2 95
Current Time 9 97
Current Time Clear 98
Current Time Display2 100
Current Time 9 101
Current Time Missed 105
Current Time Missed 106
Current Time Missed 107
Current Time Display2 108
Current Time 9 110
Current Time 9 112
Current Time Clear 114
Current Time 9 123
Current Time Display2 127
Current Time 0 130
Current Time 0 131
Current Time PM 143

Current Time OK 146
main menu REVIEW CURRENT RECORDING TIMES 150
confirmation OK 159
main menu ENTER NEW RECORDING TIME 167
Select the Program Program Once on ... 188
specific day Any other day 195
select the month June 202
February 1990 10 208
Start Time 8 217
Start Time 0 218
Start Time 0 218
Start Time PM 222
Start Time Help 234
HELP EXIT HELP 243
Start Time 8 252
Start Time 0 253
Start Time 0 253
Start Time OK 256
Start Time PM 261
Start Time OK 263
Stop Time 1 269
Stop Time 1 269
Stop Time 0 271
Stop Time 0 271
Stop Time PM 276
Stop Time OK 277
channel 5 286
channel OK 291
tape speed Main Menu 301
main menu ENTER NEW RECORDING TIME 323
Select the Program Program Once on ... 327
specific day Any other day 330
select the month Main Menu 339
main menu ENTER NEW RECORDING TIME 345
Select the Program Program Monday - Friday at ... 354
Start Time 3 358
Start Time 0 362
Start Time 0 362
Start Time AM 365
Start Time OK 371
Stop Time 3 375
Stop Time 3 378
Stop Time 0 380
Stop Time OK 381
Stop Time PM 386
Stop Time Clear 390
Stop Time 3 399
Stop Time 3 401
Stop Time 0 402
Stop Time AM 403
Stop Time OK 405
channel 7 409
channel OK 411
tape speed Standard Play 419
confirmation OK 432
main menu ENTER NEW RECORDING TIME 438

Select the Program Program Once a Week on ... 451
Select the Day Tuesdays 458
Start Time 9 464
Start Time 0 465
Start Time 0 466
Start Time 0 466
Start Time Clear 468
Start Time 9 470
Start Time 0 471
Start Time 0 472
Start Time PM 474
Start Time OK 478
Stop Time 1 484
Stop Time 1 485
Stop Time 0 486
Stop Time 0 486
Stop Time PM 488
Stop Time OK 490
channel 4 493
channel Clear 494
channel 5 496
channel OK 499
tape speed Long Play 507
confirmation OK 512
main menu ENTER NEW RECORDING TIME 516
Select the Program Program Once on ... 520
specific day Any other day 526
select the month June 530
February 1990 10 537
Start Time 8 543
Start Time 0 544
Start Time 0 544
Start Time PM 549
Start Time OK 552
Stop Time 1 555
Stop Time 1 555
Stop Time 0 556
Stop Time 0 557
Stop Time 0 557
Stop Time OK 559
Stop Time PM 561
Stop Time OK 562
channel 5 567
channel OK 570
tape speed Standard Play 573
confirmation Change 593
confirmation Change 604
confirmation startime2 619
confirmation startime2 621
confirmation stoptime2 623
confirmation Change 629
confirmation OK 674
main menu ENTER NEW RECORDING TIME 682
Select the Program Program Once a Week on ... 687
Select the Day Thursdays 700
Start Time 9 705
Start Time 0 707
Start Time 0 707
Start Time PM 710
Start Time OK 712
Stop Time 1 713
Stop Time 1 713

Stop Time 1 714
Stop Time Missed 716
Stop Time Clear 717
Stop Time 1 718
Stop Time 1 719
Stop Time 0 719
Stop Time 0 723
Stop Time OK 721
Stop Time PM 722
Stop Time OK 723
channel 7 727
channel OK 736
tape speed Standard Play 739
confirmation Cancel 748
confirmation Cancel 756
confirmation clear 2 784
confirmation Cancel 791
confirmation Cancel 803
confirmation clear 3 808
confirmation Change 812
confirmation OK 828
main menu ENTER NEW RECORDING TIME 831
Select the Program Program Monday - Friday at ... 840
Start Time 3 844
Start Time 0 846
Start Time 0 846
Start Time AM 852
Start Time OK 859
Stop Time 3 865
Stop Time 3 866
Stop Time 0 868
Stop Time AM 872
Stop Time OK 873
channel 7 879
channel OK 881
tape speed Standard Play 883
confirmation OK 925
main menu Power Off 929

Programs set
2 Tuesdays   9:00 PM 11:00 PM
             5 LP
3 June 10, 1990  8:00 PM
             10:00 PM 5 SP
1 Monday-Friday  3:00 AM
             3:30 AM 7 SP
2 Monday-Friday  3:00 AM
             3:30 AM 7 SP
3    :      :
4 Thursdays  9:00 PM 11:00
             PM 7 SP

Page summary
main menu,9,89
timer,1,0
main menu help,0,0
HELP,1,9
TAPE STATUS,0,0
Current Time,1,101
Current Time Help,0,0
Select the Program,7,59
specific day,3,14
Select the Program Help,0,0
Select the Day,2,20
select the month,4,31 year set,1,28
channel,6,53
Start Time,7,120
Stop Time,6,89
tape speed,6,40
confirmation,6,245
February 1990,3,8

COUNT:194
WASTED TIME:51
TOTAL TIME = Time -
Waste=929

Subject number 4 Tuesday,
June 5, 1990 6:15:44 PM

Page time log
year set ,0,134
select the month ,104,14
February 1990 ,122,5
Current Time ,129,123
HELP ,253,3
Current Time ,257,44
main menu ,301,16
Select the Program ,317,17
specific day ,335,4
select the month ,340,8
February 1990 ,352,7
Start Time ,360,33
Stop Time ,394,19
channel ,413,13
tape speed ,426,5
confirmation ,434,36
main menu ,471,5
Select the Program ,476,9
Start Time ,486,41
Stop Time ,528,17
channel ,545,11
tape speed ,556,2
confirmation ,561,17
main menu ,578,7
Select the Program ,585,5
specific day ,591,3
Start Time ,594,21
Stop Time ,616,16
channel ,632,9
tape speed ,641,5
confirmation ,649,18
main menu ,667,3
confirmation ,671,5

Error log:
backround handler Missed 28
backround handler Display2 30
backround handler Display2 34
Must choose a year 70
Must choose am/pm 172
backround handler Missed 248
Must choose am/pm 280
Must choose am/pm 537
Must choose am/pm 605
Must choose am/pm 623
SUBJECT DID NOT TURN POWER
  OFF OR SET THE TIMER 676

Users Actions:
year set Missed 28
year set Display2 30
year set Display2 34
year set 9 40
year set 0 46
year set OK 69
year set 1 93
year set 9 96
year set 9 98
year set 0 100
year set OK 103
select the month June 114

February 1990 6 126
Current Time 9 155
Current Time 0 163
Current Time 0 165
Current Time OK 172
Current Time 1 193
Current Time Clear 212
Current Time 9 219
Current Time 0 224
Current Time 0 226
Current Time Missed 248
Current Time Help 252
HELP EXIT HELP? 256
Current Time 9 263
Current Time 0 265
Current Time 0 266
Current Time OK 279
Current Time PM 290
Current Time OK 301
main menu ENTER KEY
  RECORDING TIME 316
Select the Program Program
  Once on ... 334
specific day Any other day
  339
select the month June 347
February 1990 10 359
Start Time 8 374
Start Time 0 378
Start Time 0 379
Start Time PM 385
Start Time OK 392
Stop Time 1 400
Stop Time 1 400
Stop Time 0 402
Stop Time 0 402
Stop Time PM 406
Stop Time OK 412
channel 5 419
channel OK 425
tape speed Standard Play 431
confirmation OK 470
main menu ENTER KEY
  RECORDING TIME 475
Select the Program Program
  Monday - Friday at ...
  485
Start Time 3 491
Start Time 3 492
Start Time 0 496
Start Time Clear 506
Start Time 3 512
Start Time 0 516
Start Time 0 517
Start Time AM 522
Start Time OK 527
Stop Time 3 531
Stop Time 3 532
Stop Time 0 533
Stop Time OK 536
Stop Time AM 540
Stop Time OK 544
channel 7 550
channel OK 555
tape speed Standard Play 558
confirmation OK 578
main menu ENTER KEY
  RECORDING TIME 583

Select the Program Program
  Once on ... 590
specific day Today 593
Start Time 8 598
Start Time 3 600
Start Time 9 601
Start Time OK 605
Start Time PM 609
Start Time OK 615
Stop Time 9 618
Stop Time 0 619
Stop Time 0 619
Stop Time OK 622
Stop Time PM 626
Stop Time OK 632
channel 5 636
channel OK 641
tape speed Standard Play 646
confirmation OK 667
main menu REVIEW CURRENT
  RECORDING TIMES 670
confirmation OK 675

Programs set
1 June 10, 1990  8:00 PM
  11:00 PM 5  SP
2 Monday-Friday  3:00 AM
  3:30 AM 7  SP
3 June 6, 1990  9:04:52 PM
  8:30 PM  9:00 PM 5  SP
4   :    :

Page summary
main menu,4,31
timer,0,0
main menu help,0,0
HELP,1,3
TAPE STATUS,0,0
Current Time,2,167
Current Time Help,0,0
Select the Program,3,31
specific day,2,7
Select the Program Help,0,0
Select the Day,0,0
select the month,2,22
year set,1,104
channel,3,33
Start Time,3,95
Stop Time,3,52
tape speed,3,12
confirmation,4,76
February 1990,2,12

COUNT:94
WASTED TIME:31
TOTAL TIME = Time -
Waste=675

Subject number 5 Tuesday,
June 5, 1990 9:45:09 PM

Page time log
year set ,1.16
select the month ,27,7
February 1990 ,26,7
Current Time ,34,35
main menu ,69.24
Select the Program ,93,9
specific day ,103,10
select the month ,114,9
February 1990 ,126,4
Start Time ,131,36
Stop Time ,168,13
channel ,181,6
tape speed ,188,4
confirmation ,194,69
Select the Program ,263,3
specific day ,265,3
select the month ,269.3
February 1990 ,275,5
Start Time ,281,38
Stop Time ,319.13
channel ,332,6
tape speed ,339,2
confirmation ,343,5
main menu ,348,13
Select the Program ,361,10
Start Time ,371,14
Stop Time ,386,35
channel ,422,7
tape speed ,430,2
confirmation ,434,30
main menu ,464,2
Select the Program ,467,0
Select the Day ,468,6
Start Time ,474,14
Stop Time ,489,14
channel ,503,6
tape speed ,509,1
confirmation ,513,46
main menu ,560,3
confirmation ,563,11
main menu ,574,10
Select the Program ,584,1
Select the Day ,585,15
main menu ,600,3
confirmation ,603,23
main menu ,626,3
Select the Program ,629,8
Start Time ,637,11
Stop Time ,649,6
channel ,655,4
tape speed ,660,1
confirmation ,663,57
HELP ,721,4
confirmation ,725,34
main menu ,759,3
confirmation ,763,35
Select the Program ,798,5
Start Time ,803,16
Stop Time ,820,10
channel ,830,4
tape speed ,835,1
confirmation ,837,6
main menu ,844,3

Select the Program ,847,5
Start Time ,850,18
Stop Time ,869,55
channel ,923,4
tape speed ,927,1
confirmation ,930,4
main menu ,935,3
Select the Program ,939,7
specific day ,946,4
select the month ,951,4
February 1990 ,959,6
Start Time ,966,11
Stop Time ,977,9
channel ,986,4
tape speed ,990,1
confirmation ,993,1
main menu ,994,3
confirmation ,998,38
main menu ,1036,6
Current Time ,1043,10
main menu ,1053,7
Current Time ,1060,6
main menu ,1066,3
Current Time ,1069,15
main menu ,1083,4
year set ,1088,8
select the month ,1097,2
February 1990 ,1103,1
main menu ,1105,8
confirmation ,1113,9
main menu ,1122,10
main menu help ,1132,10
main menu ,1142,5
timer ,1147,4

Error log:
backround handler
  notfinished 474
time not entered 891
time not entered 898
backround handler Missed 973
  984
SUBJECT RESETS DATE WRONG
  1151
TURNS POWER OFF AND SETS
  TIMER 1151

Users Actions:
year set 1 8
year set 9 10
year set 9 12
year set 0 14
year set OK 16
select the month June 22
February 1990 6 33
Current Time 9 44
Current Time 0 48
Current Time 0 49
Current Time Noon 65
Current Time OK 69
main menu ENTER NEW
  RECORDING TIME 92
Select the Program Program
  Once on ... 102
specific day Any other day
  113
select the month June 123
February 1990 10 130

Start Time 8 157
Start Time 0 159
Start Time 0 160
Start Time Noon 162
Start Time OK 166
Stop Time 1 172
Stop Time 1 173
Stop Time 0 174
Stop Time 0 175
Stop Time Noon 177
Stop Time OK 180
channel 5 183
channel OK 187
tape speed Extended Play 192
confirmation Change 214
confirmation Change 225
confirmation Change 231
confirmation clear 1 263
Select the Program Program
  Once on ... 265
specific day Any other day
  268
select the month June 271
February 1990 10 281
Start Time 8 288
Start Time 0 290
Start Time 0 290
Start Time Noon 292
Start Time 8 303
Start Time Clear 307
Start Time 8 309
Start Time 0 311
Start Time 0 312
Start Time PM 314
Start Time OK 318
Stop Time 1 323
Stop Time 1 324
Stop Time 0 326
Stop Time 0 327
Stop Time PM 329
Stop Time OK 332
channel 5 336
channel OK 338
tape speed Extended Play 340
confirmation OK 348
main menu ENTER NEW
  RECORDING TIME 360
Select the Program Program
  Monday - Friday at ...
  370
Start Time 3 377
Start Time 0 378
Start Time 0 379
Start Time PM 380
Start Time OK 385
Stop Time Clear 391
Stop Time Clear 393
Stop Time Clear 395
Stop Time 3 413
Stop Time 3 415
Stop Time 0 417
Stop Time AM 418
Stop Time OK 421
channel 7 427
channel OK 429
tape speed Extended Play 431
confirmation Change 435
confirmation Change 456 confirmation OK 464
main menu ENTER NEW
  RECORDING TIME 465
Select the Program Program
  Once a Week on ... 467
Select the Day Mondays 473
Start Time notfinished 474
Start Time 3 481
Start Time 0 482
Start Time 0 482
Start Time AM 484
Start Time OK 488
Stop Time 3 494
Stop Time 3 495
Stop Time 0 497
Stop Time AM 500
Stop Time OK 503
channel 7 506
channel OK 508
tape speed Extended Play 510
confirmation Change 528
confirmation Change 543
confirmation Change 549
confirmation OK 559
main menu REVIEW CURRENT
  RECORDING TIMES 563
confirmation Change 565
confirmation OK 574
main menu ENTER NEW
  RECORDING TIME 583
Select the Program Program
  Once a Week on ... 585
Select the Day Main Menu 598
main menu REVIEW CURRENT
  RECORDING TIMES 602
confirmation Change 615
confirmation OK 625
main menu ENTER NEW
  RECORDING TIME 628
Select the Program Program
  Monday - Friday at ...
  637
Start Time 3 642
Start Time 0 643
Start Time 0 644
Start Time AM 646
Start Time OK 648
Stop Time 3 650
Stop Time 3 651
Stop Time 0 652
Stop Time AM 654
Stop Time 0 655
channel 7 658
channel OK 659
tape speed Extended Play 661
confirmation Cancel 672
confirmation Cancel 693
confirmation Help 720
HELP EXIT HELP 725
confirmation Change 734
confirmation OK 759
main menu REVIEW CURRENT
  RECORDING TIMES 762
confirmation Cancel 767
confirmation clear 2 772
confirmation Cancel 776
confirmation clear 3 783
confirmation Change 788

```
confirmation clear 4 798        channel 4 989                    year set,2,24              Subject number 9 Thursday,
Select the Program Program      channel OK 989                   channel,8,41                 June 7, 1990 10:08:19 AM
    Monday - Friday at ...      tape speed Extended Play 991     Start Time,8,158
    803                         confirmation OK 994              Stop Time,8,155           Page time log
Start Time 3 807                main menu REVIEW CURRENT         tape speed,8,13           year set ,0,49
Start Time 0 809                    RECORDING TIMES 997          confirmation,14,368       HELP ,49,5
Start Time 0 810                confirmation OK 1036             February 1990,5,24        year set ,54,30
Start Time PM 812               main menu SET CURRENT TIME                                 select the month ,85,10
Start Time AM 816                   1042                         COUNT:229                 February 1990 ,97,6
Start Time OK 819               Current Time Main Menu 1050      WASTED TIME:63            Current Time ,104,27
Stop Time 3 822                 main menu SET CURRENT TIME       TOTAL TIME = Time -       main menu ,131,11
Stop Time 3 823                     1060                            Waste=1151             Select the Program ,142,11
Stop Time 0 825                 Current Time Main Menu 1064                                specific day ,154,2
Stop Time AM 827                main menu SET CURRENT TIME                                 select the month ,158,5
Stop Time OK 829                    1069                                                   February 1990 ,166,4
channel 7 832                   Current Time 9 1077                                        Start Time ,171,19
channel OK 834                  Current Time 0 1078                                        Stop Time ,191,14
tape speed Extended Play 836    Current Time 0 1079                                        channel ,206,7
confirmation OK 843             Current Time PM 1081                                       tape speed ,214,3
main menu ENTER NEW             Current Time OK 1082                                       confirmation ,219,7
    RECORDING TIME 846          main menu SET CURRENT DATE                                 main menu ,227,9
Select the Program Program          1087                                                   Select the Program ,236,3
    Monday - Friday at ...      year set 1 1090                                            specific day ,239,17
    849                         year set 9 1091                                            main menu ,256,7
Start Time 3 853                year set 9 1092                                            Select the Program ,264,6
Start Time 0 855                year set 0 1094                                            Start Time ,271,17
Start Time 0 856                year set OK 1096                                           Stop Time ,289,15
Start Time AM 857               select the month June 1098                                 channel ,305,6
Start Time 3 859                February 1990 16 1104                                      tape speed ,311,3
Start Time 3 861                main menu REVIEW CURRENT                                   confirmation ,316,3
Start Time 0 862                    RECORDING TIMES 1113                                   main menu ,320,5
Start Time AM 864               confirmation OK 1122                                       Select the Program ,326,2
Start Time OK 867               main menu Help 1132                                        specific day ,328,2
Stop Time 7 869                 main menu help Exit Help                                   Start Time ,330,13
Stop Time OK 891                    1141                                                   Stop Time ,344,12
Stop Time 3 904                 main menu Power Off 1144                                   channel ,356,8
Stop Time 3 909                 timer FINISHED 1151                                        tape speed ,365,2
Stop Time 0 911                                                                            confirmation ,369,10
Stop Time Clear 915             Programs set                                               main menu ,379,15
Stop Time 3 917                 1 June 10, 1990 12:00 PM                                   timer ,394,9
Stop Time 3 918                     12:00 PM 5  EP
Stop Time 0 920                 2 Monday-Friday  3:00 PM                                   Error log:
Stop Time AM 921                    3:30 AM 7  EP                                          Must choose a year 29
Stop Time OK 923                3 Mondays  3:00 AM  3:30 AM                                Must choose a year 40
channel 7 925                       7  EP                                                  backround handler Missed 204
channel OK 926                  4 Monday-Friday  3:00 AM                                   TURNS POWER OFF AND SETS
tape speed Extended Play 928        3:30 AM 7  EP                                              TIMER 403
confirmation OK 934             1 June 10, 1990  8:00 PM
main menu ENTER NEW                 11:00 PM 5  EP                                         Users Actions:
    RECORDING TIME 937          2 Monday-Friday 03:30 AM                                   year set 9 15
Select the Program Program          3:30 AM 7  EP                                          year set 0 22
    Once on ... 946             3 June 9, 1990  9:00 PM                                    year set OK 29
specific day Any other day          9:30 PM 4  EP                                          year set OK 40
    950                         4     :    :                                               year set Help 49
select the month June 954                                                                  HELP EXIT HELP 54
February 1990 9 965             Page summary                                               year set Clear 62
Start Time 9 969                main menu,18,113                                           year set 1 72
Start Time 0 971                timer,1,4                                                  year set 9 77
Start Time 0 972                main menu help,1,10                                        year set 9 77
Start Time Missed 973           HELP,1,4                                                   year set 0 81
Start Time PM 975               TAPE STATUS,0,0                                            year set OK 84
Start Time OK 976               Current Time,4,64                                          select the month June 93
Stop Time 9 979                 Current Time Help,0,0                                      February 1990 6 102
Stop Time 3 981                 Select the Program,9,46                                    Current Time 0 112
Stop Time 0 982                 specific day,3,17                                          Current Time 9 117
Stop Time notfinished 983       Select the Program Help,0,0                                Current Time 0 121
Stop Time PM 984                Select the Day,2,21                                        Current Time 0 121
Stop Time OK 986                select the month,5,25
```

```
Current Time PM 129              Stop Time PM 353              Subject number 10 Tuesday,       Start Time 8 107
Current Time OK 131              Stop Time OK 356                June 12, 1990 6:34:05 PM       Start Time 0 108
main menu ENTER NEW              channel 0 359                                                  Start Time 0 109
  RECORDING TIME 141             channel 4 362                                                  Start Time 0 110
Select the Program Program       channel OK 364                Page time log                    Start Time PM 113
  Once on ... 151                tape speed Long Play 367      year set ,0,18                   Start Time OK 114
specific day Any other day       confirmation OK 379           select the month ,18,11          Stop Time 1 120
  157                            main menu Power Off 389       February 1990 ,33,2              Stop Time 1 120
select the month June 162        timer FINISHED 403            Current Time ,37,15              Stop Time 0 121
February 1990 10 170                                           main menu ,53,10                 Stop Time 0 122
Start Time 0 176                 Programs set                  Select the Program ,64,15        Stop Time PM 123
Start Time 8 180                 1 June 10, 1990 08:00 PM      specific day ,80,7               Stop Time OK 123
Start Time 0 183                   11:00 PM 5 LP               select the month ,88,3           channel 5 128
Start Time 0 183                 2 Monday-Friday 03:00 AM      February 1990 ,95,3              channel OK 130
Start Time PM 186                  03:30 AM 7 SP               Start Time ,99,15                tape speed Standard Play 134
Start Time OK 190                3 June 6, 1990  9:03:19 PM    Stop Time ,116,8                 confirmation OK 145
Stop Time 1 196                    01:00 PM 02:00 PM 04 LP     channel ,125,5                   main menu ENTER NEW
Stop Time 1 197                  4   :     :                   tape speed ,131,4                  RECORDING TIME 153
Stop Time 0 198                                                confirmation ,137,9              Select the Program Program
Stop Time 0 199                  Page summary                  main menu ,146,8                   Once a Week on ... 156
Stop Time PM 202                 main menu,5,47                Select the Program ,154,2        Select the Day Main Menu 160
Stop Time Missed 204             timer,1,9                     Select the Day ,157,14           main menu ENTER NEW
Stop Time OK 205                 main menu help,0,0            main menu ,171,4                   RECORDING TIME 174
channel 5 209                    HELP,1,5                      Select the Program ,175,3        Select the Program Program
channel OK 213                   TAPE STATUS,0,0               Start Time ,179,11                 Monday - Friday at ...
tape speed Long Play 217         Current Time,1,27             Stop Time ,191,10                  178
confirmation OK 226              Current Time Help,0,0         channel ,201,6                   Start Time 3 183
main menu ENTER NEW              Select the Program,4,22       tape speed ,207,4                Start Time 0 184
  RECORDING TIME 235             specific day,3,22             confirmation ,214,1              Start Time 0 185
Select the Program Program       Select the Program Help,0,0   main menu ,215,7                 Start Time AM 186
  Once on ... 238                Select the Day,0,0            Select the Program ,222,5        Start Time OK 190
specific day Main Menu 250       select the month,2.15         Start Time ,227,24               Stop Time 3 194
main menu ENTER NEW              year set,2,79                 Stop Time ,252,6                 Stop Time 3 196
  RECORDING TIME 262             channel,3,21                  channel ,259,3                   Stop Time 0 197
Select the Program Program       Start Time,3,49               tape speed ,263,2                Stop Time AM 200
  Monday - Friday at ...         Stop Time,3,41                confirmation ,268,2              Stop Time OK 200
  270                            tape speed,3,8                main menu ,270,2                 channel 7 205
Start Time 0 276                 confirmation,3,20             confirmation ,273,14             channel Missed 206
Start Time 3 279                 February 1990,2,10            main menu ,288,15                channel OK 207
Start Time 0 280                                               timer ,304,28                    tape speed Long Play 211
Start Time 0 281                 COUNT:86                                                       confirmation OK 215
Start Time AM 285                WASTED TIME:28                Error log:                       main menu ENTER NEW
Start Time OK 288                TOTAL TIME = Time -           Must choose am/pm 111              RECORDING TIME 221
Stop Time 0 293                    Waste=403                   backround handler Missed 206     Select the Program Program
Stop Time 3 295                                                TURNS POWER OFF AND SETS THE       EveryDay at ... 226
Stop Time 3 296                                                  TIMER 332                      Start Time 6 247
Stop Time 0 298                                                                                 Start Time 0 248
Stop Time AM 302                                               Users Actions:                   Start Time 0 249
Stop Time OK 304                                               year set 1 10                    Start Time PM 250
channel 7 309                                                  year set 9 12                    Start Time OK 251
channel OK 311                                                 year set 9 13                    Stop Time 7 254
tape speed Standard Play 314                                   year set 0 14                    Stop Time 3 255
confirmation OK 319                                            year set OK 18                   Stop Time 0 256
main menu ENTER NEW                                            select the month June 26         Stop Time PM 257
  RECORDING TIME 324                                           February 1990 6 35               Stop Time OK 258
Select the Program Program                                     Current Time 9 43                channel 4 261
  Once on ... 328                                              Current Time 0 44                channel OK 262
specific day Today 330                                         Current Time 0 45                tape speed Long Play 265
Start Time 0 333                                               Current Time PM 48               confirmation OK 270
Start Time 1 336                                               Current Time OK 52               main menu REVIEW CURRENT
Start Time 0 338                                               main menu ENTER NEW                RECORDING TIMES 272
Start Time 0 338                                                 RECORDING TIME 62              confirmation OK 287
Start Time PM 340                                              Select the Program Program       main menu Power Off 293
Start Time OK 342                                                Once on ... 79                 timer FINISHED 331
Stop Time 0 344                                                specific day Any other day
Stop Time 2 346                                                  87                             Programs set
Stop Time 0 348                                                select the month June 89         1 June 10, 1990  8:00 PM
Stop Time 0 349                                                February 1990 10 98                11:00 PM 5 SP
```

E-39

```
2 Monday-Friday 3:00 AM
   3:30 AM 7 LP
3 Everyday 6:00 PM 7:00 PM
   4 LP
4 : :

Page summary
main menu,6,46
timer,1.28
main menu help,0,0
HELP,0,0
TAPE STATUS,0,0
Current Time,1.15
Current Time Help,0,0
Select the Program,4,25
specific day,1,7
Select the Program Help,0,0
Select the Day,1,14
select the month,2,14
year set,1,18
channel,3,14
Start Time,3,50
Stop Time,3,24
tape speed,3,10
confirmation,4,26
February 1990,2,9

COUNT:74
WASTED TIME:36
TOTAL TIME = Time -
    Waste=331
```

Subject number 11

Page time log
year set ...16
select the month ,19,9
February 1990 ,31,19
select the month ,51,4
February 1990 ,59,2
Current Time ,63,17
main menu ,80,9
confirmation ,89,7
main menu ,96,2
Select the Program ,99,5
specific day ,104,5
select the month ,109,5
February 1990 ,117,2
Start Time ,120,12
HELP ,132,9
main menu ,141,3
Select the Program ,146,5
specific day ,151,3
select the month ,155,4
February 1990 ,163,1
Start Time ,164,15
Stop Time ,181,21
channel ,204,7
tape speed ,212,10
confirmation ,224,30
main menu ,254,4
Select the Program ,258,5
Start Time ,264,15
Stop Time ,280,12
channel ,292,5
tape speed ,297,5
confirmation ,305,20
main menu ,326,14
Select the Program ,342,2
Select the Day ,345,3
Start Time ,349,14
Stop Time ,364,9
channel ,373,4
tape speed ,378,10
confirmation ,391,38
main menu ,429,30

Error log:
backround handler Missed 185
backround handler Missed 188
backround handler Missed 361
SETS THE DATE FOR TODAY, NOT
   6/6/90 459
TURNS POWER OFF BUT DOES NOT
   SET TIMER 459

Users Actions:
year set 1 9
year set 9 11
year set 9 12
year set 0 14
year set OK 17
select the month May 24
February 1990 New Month 50
select the month June 54
February 1990 6 60
Current Time 9 69
Current Time 0 71
Current Time 0 72

Current Time PM 77
Current Time OK 79
main menu REVIEW CURRENT
   RECORDING TIMES 86
confirmation OK 95
main menu ENTER NEW
   RECORDING TIME 97
Select the Program Program
   Once on ... 103
specific day Any other day
   108
select the month June 113
February 1990 1 119
Start Time Clear 122
Start Time Clear 126
Start Time Help 131
HELP Main Menu 137
main menu ENTER NEW
   RECORDING TIME 143
Select the Program Program
   Once on ... 150
specific day Any other day
   154
select the month June 158
February 1990 10 164
Start Time 8 171
Start Time 0 173
Start Time 0 173
Start Time PM 177
Start Time OK 179
Stop Time Missed 185
Stop Time 1 187
Stop Time Missed 188
Stop Time 1 190
Stop Time 0 193
Stop Time 0 194
Stop Time PM 199
Stop Time OK 201
channel 5 208
channel OK 211
tape speed Long Play 219
tape speed OK 221
confirmation Main Menu 228
main menu ENTER NEW
   RECORDING TIME 257
Select the Program Program
   Monday - Friday at ...
   263
Start Time 3 269
Start Time 0 272
Start Time 0 272
Start Time AM 275
Start Time OK 279
Stop Time 3 283
Stop Time 3 284
Stop Time 0 287
Stop Time AM 290
Stop Time OK 291
channel 7 295
channel OK 296
tape speed Standard Play 300
tape speed OK 302
confirmation Main Menu 320
main menu ENTER NEW
   RECORDING TIME 339
Select the Program Program
   Once a Week on ... 344
Select the Day Thursdays 348

Start Time 1 352
Start Time 0 354
Start Time 0 355
Start Time 0 355
Start Time PM 353
Start Time Missed 360
Start Time OK 362
Stop Time 1 366
Stop Time 1 366
Stop Time 0 368
Stop Time 0 369
Stop Time PM 370
Stop Time OK 372
channel 4 375
channel OK 377
tape speed Standard Play 381
tape speed OK 388
confirmation Main Menu 401
confirmation Main Menu 412
confirmation Main Menu 420
confirmation OK 428
main menu Power Off 437

Programs set
1 June 10, 1990  8:00 PM
   11:00 PM 5  LP
2 Monday-Friday 3:00 AM
   3:30 AM 7 SP
3 Thursdays 10:00 PM 11:00
   PM 4  SP
4 : :

```
Page summary
main menu,6,62
timer,0,0
main menu help,0,0
HELP,1,9
TAPE STATUS,0,0
Current Time,1.17
Current Time Help,0,0
Select the Program,4,17
specific day,2,8
Select the Program Help,0,0
Select the Day,1,3
select the month,4,22
year set,1,16
channel,3,16
Start Time,4,56
Stop Time,3,42
tape speed,3,25
confirmation,4,95
February 1990,4,24

COUNT:91
WASTED TIME:46
TOTAL TIME = Time -
    Waste=437
```

E-40

Subject NUMBER 15
Wednesday, June 20, 1990
7:17:01 PM

Page time log
year set ,1,20
select the month ,22,15
February 1990 ,40,3
Current Time ,46,20
main menu ,66,7
Select the Program ,74,14
specific day ,89,6
select the month ,95,4
February 1990 ,102,4
Start Time ,108,15
Stop Time ,125,13
channel ,140,8
tape speed ,150,7
confirmation ,159,5
main menu ,164,5
Select the Program ,169,8
Start Time ,177,18
Stop Time ,196,9
channel ,205,7
tape speed ,212,6
confirmation ,221,2
main menu ,223,4
Select the Program ,227,6
specific day ,233,2
select the month ,235,3
February 1990 ,242,2
Start Time ,247,20
Stop Time ,268,9
channel ,277,5
tape speed ,283,2
confirmation ,288,3
main menu ,291,11
main menu help ,303,45
main menu ,348,2
confirmation ,350,12
main menu ,362,8
timer ,370,3

Error log:
backround handler Display2 4
backround handler Power Off 319
backround handler 342
TURNS POWER OFF AND SETS TIMER 373

Users Actions:
year set Display2 4
year set 1 9
year set 9 12
year set 9 13
year set 0 16
year set OK 20
select the month June 31
February 1990 February 1990 40
February 1990 6 43
Current Time 9 52
Current Time 0 55
Current Time 0 56
Current Time PM 61
Current Time OK 65
main menu ENTER NEW
RECORDING TIME 72
Select the Program Program Once on ... 88
specific day Any other day 95
select the month June 97
February 1990 10 106
Start Time 8 112
Start Time 0 115
Start Time 0 116
Start Time PM 118
Start Time OK 123
Stop Time 1 128
Stop Time 1 129
Stop Time 0 131
Stop Time 0 132
Stop Time PM 134
Stop Time OK 137
channel 5 145
channel OK 148
tape speed Long Play 157
confirmation OK 163
main menu ENTER NEW RECORDING TIME 168
Select the Program Program Monday - Friday at ... 177
Start Time 3 182
Start Time 0 186
Start Time 0 189
Start Time AM 191
Start Time OK 194
Stop Time 3 198
Stop Time 3 200
Stop Time 0 201
Stop Time AM 203
Stop Time OK 205
channel 7 210
channel OK 212
tape speed Standard Play 218
confirmation OK 223
main menu ENTER NEW RECORDING TIME 225
Select the Program Program Once on ... 232
specific day Any other day 235
select the month June 237
February 1990 13 244
Start Time 1 251
Start Time 0 251
Start Time 0 252
Start Time 0 253
Start Time 0 253
Start Time Clear 258
Start Time 1 259
Start Time 0 261
Start Time 0 261
Start Time 0 263
Start Time PM 265
Start Time OK 267
Stop Time 1 269
Stop Time 1 270
Stop Time 0 272
Stop Time 0 273
Stop Time PM 274
Stop Time OK 276
channel 4 280
channel OK 282
tape speed Extended Play 285
confirmation OK 291
main menu Help 302
main menu help Power Off 319
main menu help 341
main menu help Exit Help 347
main menu REVIEW CURRENT RECORDING TIMES 350
confirmation OK 362
main menu Power Off 365
timer FINISHED 372

Programs set
1 June 10, 1990 8:00 PM 11:00 PM 5 LP
2 Monday-Friday 3:00 AM 3:30 AM 7 SP
3 June 13, 1990 10:00 PM 11:00 PM 4 EP
4 : :

Page summary
main menu,6,37
timer,1,3
main menu help,1,45
HELP,0,0
TAPE STATUS,0,0
Current Time,1,20
Current Time Help,0,0
Select the Program,3,28
specific day,2,8
Select the Program Help,0,0
Select the Day,0,0
select the month,3,22
year set,1,20
channel,3,20
Start Time,3,53
Stop Time,3,31
tape speed,3,15
confirmation,4,22
February 1990,3,9

COUNT:86
WASTED TIME:39
TOTAL TIME = Time - Waste=372

Subject NUMBER 16 Saturday, June 23, 1990 10:39:52 PM

Page time log
year set ,0,69
select the month ,69,26
February 1990 ,99,9
Current Time ,110,66
main menu ,176,58
confirmation ,234,72
main menu ,306,4
confirmation ,311,29
HELP ,341,0
confirmation ,342,24
main menu ,366,10
Current Time ,377,15
main menu ,392,3
year set ,396,13
HELP ,409,18
main menu ,427,5
main menu help ,433,36
main menu ,470,8
Select the Program ,478,10
Select the Day ,489,7
Start Time ,497,33
Stop Time ,531,35
channel ,566,22
tape speed ,589,4
confirmation ,596,20
main menu ,616,5
Select the Program ,621,6
Start Time ,628,27
Stop Time ,656,22
channel ,679,7
tape speed ,686,2
confirmation ,691,11
main menu ,702,4
Select the Program ,706,2
Select the Day ,708,3
Start Time ,711,15
Stop Time ,727,12
channel ,739,5
tape speed ,745,3
confirmation ,751,1

Error log:
Must choose am/pm 154
backround handler 300
backround handler 318
backround handler 320
backround handler 321
backround handler 322
backround handler Missed 397
backround handler Missed 400
backround handler Missed 407
backround handler Missed 418
backround handler 442
backround handler 443
backround handler 445
backround handler 448
backround handler 449
backround handler 452
backround handler 454

E-41 backround handler 454
backround handler 455
backround handler 456
backround handler 457
backround handler 458
backround handler 459
backround handler 460
backround handler 463
backround handler 464
backround handler 464
backround handler 465
backround handler 465
backround handler 466
backround handler 467
backround handler Missed 717
SET PROGRAM 1 FOR SUNDAYS AND FOR 8:80 PM 752
DID NOT TURN POWER OFF, DID NOT SET TIMER 752

Users Actions:
year set 8 13
year set 1 33
year set 9 41
year set 9 45
year set 0 49
year set OK 68
select the month June 80
select the month June 93
February 1990 23 107
Current Time 9 136
Current Time 0 145
Current Time 0 147
Current Time OK 154
Current Time PM 163
Current Time OK 176
main menu REVIEW CURRENT RECORDING TIMES 233
confirmation clear 1 260
confirmation Change 277
confirmation Missed 293
confirmation OK 305
main menu REVIEW CURRENT RECORDING TIMES 310
confirmation headings 318
confirmation headings 319
confirmation headings 321
confirmation Missed 322
confirmation Main Menu 327
confirmation Help 340
HELP EXIT HELP 341
confirmation Main Menu 362
main menu SET CURRENT TIME 376
Current Time Main Menu 386
main menu SET CURRENT DATE 395
year set Missed 397
year set Missed 399
year set Missed 406
year set Missed 407
year set Help 409
HELP Missed 415
HELP Main Menu 423
main menu Help 432
main menu help 441 main menu help 442
main menu help 446
main menu help 446
main menu help 448
main menu help 452
main menu help 453
main menu help 454
main menu help 454
main menu help 455
main menu help 456
main menu help 457
main menu help 458
main menu help 458
main menu help 459
main menu help 462
main menu help 463
main menu help 464
main menu help 465
main menu help 465
main menu help 466
main menu help 466
main menu help Exit Help 469
main menu ENTER NEW RECORDING TIME 477
Select the Program Program Once a Week on ... 488
Select the Day Sundays 495
Start Time 8 502
Start Time 8 503
Start Time 0 505
Start Time PM 518
Start Time OK 525
Start Time OK 529
Stop Time 1 535
Stop Time 1 537
Stop Time 0 542
Stop Time 0 543
Stop Time PM 548
Stop Time OK 565
channel 5 576
channel OK 588
tape speed Long Play 593
confirmation OK 615
main menu ENTER NEW RECORDING TIME 619
Select the Program Program Monday - Friday at ... 627
Start Time 3 636
Start Time 0 639
Start Time 0 640
Start Time AM 646
Start Time OK 654
Stop Time 3 665
Stop Time 3 668
Stop Time 0 670
Stop Time AM 674
Stop Time OK 678
channel 7 682
channel OK 686
tape speed Long Play 688
confirmation OK 702
main menu ENTER NEW RECORDING TIME 704
Select the Program Program Once a Week on ... 708
Select the Day Thursdays 710
Start Time 1 714
Start Time 0 716
Start Time Missed 717
Start Time 0 719
Start Time 0 720
Start Time PM 723
Start Time OK 726
Stop Time 1 729
Stop Time 1 730
Stop Time 0 732
Stop Time 0 732
Stop Time PM 736
Stop Time OK 738
channel 4 742
channel OK 744
tape speed Standard Play 747

Programs set
1 : :
1 Sundays 8:80 PM 11:00 PM 5 LP
2 Monday-Friday 3:00 AM 3:30 AM 7 LP
3 Thursdays 10:00 PM 11:00 PM 4 SP
4 : :

Page summary
main menu,8,97
timer,0,0
main menu help,1,36
HELP,2,18
TAPE STATUS,0,0
Current Time,2,81
Current Time Help,0,0
Select the Program,3,18
specific day,0,0
Select the Program Help,0,0
Select the Day,2,10
select the month,1,26
year set,2,82
channel,3,34
Start Time,3,75
Stop Time,3,69
tape speed,3,9
confirmation,6,157
February 1990,1,9

COUNT:118
WASTED TIME:31
TOTAL TIME = Time - Waste=747

Subject number 17
Wednesday, June 27, 1990
6:08:35 PM

Page time log
year set ,1,23
select the month ,24,8
February 1990 ,35,2
Current Time ,39,16
main menu ,56,4
Select the Program ,60,5
specific day ,65,6
Start Time ,73,10
Stop Time ,84,8
channel ,93,4
tape speed ,98,3
confirmation ,103,2
main menu ,105,3
Select the Program ,108,3
Start Time ,112,8
Stop Time ,120,7
channel ,127,4
tape speed ,131,2
confirmation ,135,0
main menu ,136,2
Select the Program ,138,5
Start Time ,144,13
Stop Time ,156,8
channel ,167,3
tape speed ,170,3
confirmation ,175,1
main menu ,177,18
timer ,195,0

Error log:
backround handler Display2 4
Must choose a year 11
Must choose a year 14
SET PROGRAM 1 FOR THE WRONG DATE 195
NO TIMER BUT DID TURN POWER OFF 195

Users Actions:
year set Display2 4
year set 9 6
year set 0 9
year set OK 11
year set OK 14
year set Clear 18
year set 1 20
year set 9 21
year set 9 22
year set 0 22
year set OK 23
select the month June 30
February 1990 6 37
Current Time 9 46
Current Time 0 48
Current Time 0 48
Current Time PM 52
Current Time OK 55
main menu ENTER NEW RECORDING TIME 59
Select the Program Program Once on ... 65

```
specific day Today 71          Page summary                 Subject number 18                Current Time 0 173
Start Time 8 77                main menu,4,37               Wednesday, June 27, 1990         Current Time Clear 157
Start Time 0 78                timer,1,0                    7:31:41 PM                       Current Time 9 189
Start Time 0 79                main menu help,0,0                                            Current Time 0 191
Start Time PM 79               HELP,0,0                     Page time log                    Current Time 0 191
Start Time OK 83               TAPE STATUS,0,0              year set ,0,55                   Current Time PM 199
Stop Time 1 88                 Current Time,1,16            select the month ,56,33          Current Time OK 207
Stop Time 1 89                 Current Time Help,0,0        February 1990 ,94,59             main menu ENTER NEW
Stop Time 0 90                 Select the Program,3,13      Current Time ,156,51               RECORDING TIME 259
Stop Time 0 90                 specific day,1,6             main menu ,206,52                Select the Program Program
Stop Time PM 91                Select the Program Help,0,0  Select the Program ,263,13         Once on ... 273
Stop Time OK 92                Select the Day,0,0           specific day ,274,4              specific day Any other day
channel 5 96                   select the month,1,8         select the month ,279,15           278
channel OK 97                  year set,1,23                February 1990 ,297,6             select the month June 293
tape speed Standard Play       channel,3,11                 Start Time ,305,26               February 1990 10 303
  101                          Start Time,3,31              Stop Time ,333,56                Start Time 8 317
confirmation OK 105            Stop Time,3,23               channel ,390,22                  Start Time 0 319
main menu ENTER NEW            tape speed,3,8               tape speed ,412,11               Start Time 9 320
  RECORDING TIME 106           confirmation,3,3             confirmation ,425,89             Start Time PM 324
Select the Program Program     February 1990,1,2            Select the Program ,514,3        Start Time OK 330
  Monday - Friday at ...                                    specific day ,517,2              Stop Time 1 337
  111                          COUNT:72                     select the month ,519,3          Stop Time 1 337
Start Time 3 115               WASTED TIME:23               February 1990 ,525,1             Stop Time 0 341
Start Time 0 116               TOTAL TIME = Time -          Start Time ,527,7                Stop Time 0 341
Start Time 0 117                 Waste=180                  Stop Time ,535,8                 Stop Time PM 366
Start Time AM 117                                           channel ,544,3                   Stop Time Clear 378
Start Time OK 119                                           tape speed ,547,6                Stop Time 1 383
Stop Time 3 122                                             confirmation ,555,6              Stop Time 1 384
Stop Time 3 123                                             main menu ,561,24                Stop Time 0 385
Stop Time 0 124                                             Select the Program ,585,6        Stop Time 0 386
Stop Time AM 126                                            Start Time ,591,18               Stop Time PM 387
Stop Time OK 126                                            Stop Time ,603,8                 Stop Time OK 389
channel 7 130                                               channel ,618,2                   channel 5 409
channel OK 131                                              tape speed ,621,39               channel OK 411
tape speed Long Play 132                                    confirmation ,662,25             tape speed Long Play 423
confirmation OK 135                                         main menu ,687,14                confirmation Change 455
main menu ENTER NEW                                         Select the Program ,701,5        confirmation Change 481
  RECORDING TIME 137                                        Select the Day ,706,5            confirmation clear 1 513
Select the Program Program                                  Start Time ,712,23               Select the Program Program
  EveryDay at ... 143                                       Stop Time ,737,7                   Once on ... 517
Start Time 9 149                                            channel ,745,2                   specific day Any other day
Start Time 0 150                                            tape speed ,748,1                  519
Start Time 0 151                                            confirmation ,752,3              select the month June 521
Start Time PM 152                                           main menu ,755,40                February 1990 10 526
Start Time AM 154                                           main menu help ,796,21           Start Time 8 528
Start Time OK 157                                           main menu ,817,3                 Start Time 0 529
Stop Time 1 159                                             timer ,821,2                     Start Time 0 530
Stop Time 0 160                                                                              Start Time PM 532
Stop Time 0 161                                             Error log:                       Start Time OK 534
Stop Time 0 163                                             Must choose am/pm 598            Stop Time 1 536
Stop Time AM 165                                            backround handler Missed         Stop Time 1 536
Stop Time OK 166                                              617                            Stop Time 1 537
channel 4 168                                               backround handler Power Off      Stop Time 0 538
channel OK 170                                                812                            Stop Time 0 538
tape speed Standard Play                                    SETS TIMER AND TURNS POWER       Stop Time PM 541
  173                                                         OFF 823                        Stop Time OK 543
confirmation OK 176                                                                          channel 5 545
main menu Power Off 180                                     Users Actions:                   channel OK 547
                                                            year set 1 29                    tape speed Extended Play
Programs set                                                year set 9 32                      553
1 June 6, 1990   9:00:16 PM                                 year set 9 32                    confirmation OK 560
  8:00 PM 11:00 PM 5  SP                                    year set 0 34                    main menu ENTER NEW
2 Monday-Friday  3:00 AM                                    year set OK 55                     RECORDING TIME 584
  3:30 AM 7  LP                                             select the month June 88         Select the Program Program
3 Everyday  9:00 AM 10:00                                   February 1990 6 153                Monday - Friday at ...
  AM 4  SP                                                  Current Time 2 173                 591
4   :    :                                                  Current Time 1 175               Start Time 3 594
                                                            Current Time 0 179               Start Time 0 595
```

Start Time 0 596
Start Time OK 598
Start Time AM 605
Start Time OK 608
Stop Time 3 612
Stop Time 3 612
Stop Time 0 613
Stop Time AM 615
Stop Time Missed 616
Stop Time OK 617
channel 7 619
channel OK 620
tape speed Extended Play 660
confirmation OK 687
main menu ENTER NEW RECORDING TIME 699
Select the Program Program Once a Week on ... 705
Select the Day Thursdays 711
Start Time 1 713
Start Time 0 714
Start Time 0 714
Start Time 0 715
Start Time 0 715
Start Time Clear 723
Start Time 1 724
Start Time 0 725
Start Time 0 726
Start Time 0 727
Start Time PM 734
Start Time OK 735
Stop Time 1 737
Stop Time 1 738
Stop Time 0 739
Stop Time 0 740
Stop Time PM 742
Stop Time OK 744
channel 4 746
channel OK 747
tape speed Extended Play 749
confirmation OK 754
main menu Help 795
main menu help Power Off 812
main menu help Exit Help 817
main menu Power Off 818
timer FINISHED 823

Programs set
1 June 10, 1990 8:00 PM 11:00 PM 5 LP
1 June 10, 1990 8:00 PM 11:00 PM 5 EP
2 Monday-Friday 3:00 AM 3:30 AM 7 EP
3 Thursdays 10:00 PM 11:00 PM 4 EP
4 : :

Page summary
main menu,5,133
timer,1,2
main menu help,1,21
HELP,0,0

TAPE STATUS,0,0
Current Time,1,51
Current Time Help,0,0
Select the Program,4,27
specific day,2,6
Select the Program Help,0,0
Select the Day,1,5
select the month,3,53
year set,1,55
channel,4,28
Start Time,4,74
Stop Time,4,79
tape speed,4,57
confirmation,4,123
February 1990,3,66

COUNT:114
WASTED TIME:43
TOTAL TIME = Time − Waste=823

Subject number 19
Wednesday, June 27, 1990
11:15:04 PM

Page time log
year set ,1,23
select the month ,25,16
February 1990 ,44,9
Current Time ,56,27
main menu ,83,16
Select the Program ,99,8
specific day ,107,6
select the month ,113,8
February 1990 ,124,36
HELP ,160,12
main menu ,172,5
year set ,177,10
select the month ,188,7
February 1990 ,198,4
main menu ,202,10
Select the Program ,212,3
specific day ,215,3
select the month ,218,8
February 1990 ,229,4
Start Time ,234,25
Stop Time ,259,15
channel ,275,9
tape speed ,285,4
confirmation ,291,10
main menu ,301,4
Select the Program ,305,6
Start Time ,312,12
Stop Time ,325,11
channel ,337,7
tape speed ,344,2
confirmation ,349,9
main menu ,358,5
Select the Program ,364,3
Select the Day ,368,3
Start Time ,372,8
Stop Time ,381,7
channel ,389,7
tape speed ,397,2
confirmation ,401,3
main menu ,405,12
confirmation ,418,15
main menu ,434,22
timer ,457,5

Error log:
backround handler Missed 184
TURNS POWER OFF AND SETS TIMER 462

Users Actions:
year set 1 14
year set 9 16
year set 9 19
year set 0 21
year set OK 24
select the month June 36
February 1990 6 53
Current Time 9 64
Current Time 0 70
Current Time 0 70
Current Time PM 77

Current Time OK 83
main menu ENTER NEW RECORDING TIME 98
Select the Program Program Once on ... 107
specific day Any other day 113
select the month June 120
February 1990 Help 160
HELP Main Menu 168
main menu SET CURRENT DATE 177
year set 1 180
year set 9 182
year set 9 182
year set Missed 184
year set 0 185
year set OK 187
select the month June 194
February 1990 6 201
main menu ENTER NEW RECORDING TIME 211
Select the Program Program Once on ... 215
specific day Any other day 218
select the month June 225
February 1990 10 233
Start Time 8 248
Start Time 0 249
Start Time 0 250
Start Time PM 252
Start Time OK 255
Stop Time 1 263
Stop Time 1 263
Stop Time 0 266
Stop Time 0 265
Stop Time PM 270
Stop Time OK 274
channel 5 281
channel OK 284
tape speed Long Play 288
confirmation OK 301
main menu ENTER NEW RECORDING TIME 304
Select the Program Program Monday - Friday at ... 311
Start Time 3 317
Start Time 0 318
Start Time 0 319
Start Time AM 321
Start Time OK 324
Stop Time 3 326
Stop Time 3 327
Stop Time 0 329
Stop Time AM 332
Stop Time OK 336
channel 7 341
channel OK 344
tape speed Extended Play 346
confirmation OK 358
main menu ENTER NEW RECORDING TIME 362
Select the Program Program Once a Week on ... 367
Select the Day Saturdays

```
                                    Subject number 20 Sunday,    Stop Time 1 78         TAPE STATUS,0,0
Start Time 5 375                       July 1, 1990 1:28:06 PM   Stop Time 1 79         Current Time,1,8
Start Time 0 377                                                 Stop Time 0 80         Current Time Help,0,0
Start Time 0 377                    Page time log                Stop Time 0 80         Select the Program,1,19
Start Time PM 379                      year set ,1,15            Stop Time PM 81        specific day,1,4
Start Time OK 380                      select the month ,17,6    Stop Time OK 85        Select the Program Help,0,0
Stop Time 6 384                        February 1990 ,25,5       channel 5 89           Select the Day,1,7
Stop Time 0 386                        Current Time ,31,8        channel OK 90          select the month,2,10
Stop Time 0 386                        main menu ,39,10          tape speed Long Play 99 year set,1,15
Stop Time PM 387                       Select the Program ,49,4  confirmation OK 107    channel,3,13
Stop Time OK 388                       specific day ,53,4        main menu ENTER NEW    Start Time,3,31
channel 6 393                          select the month ,57,4      RECORDING TIME 111   Stop Time,3,18
channel 8 394                          February 1990 ,64,1       Select the Program Program tape speed,3,12
channel OK 396                         Start Time ,66,8             Monday - Friday at ... confirmation,3,11
tape speed Extended Play               Stop Time ,76,9              122                 February 1990,2,6
  398                                  channel ,86,4             Start Time 3 130
confirmation OK 404                    tape speed ,91,8          Start Time 0 131       COUNT:71
main menu REVIEW CURRENT               confirmation ,102,5       Start Time 0 132       WASTED TIME:24
  RECORDING TIMES 417                  main menu ,107,5          Start Time AM 133      TOTAL TIME = Time -
confirmation OK 432                    Select the Program ,112,11 Start Time OK 136       Waste=239
main menu Power Off 452                Start Time ,123,13        Stop Time 3 138
timer FINISHED 461                     Stop Time ,137,5          Stop Time 3 138
                                       channel ,142,4            Stop Time 0 139
Programs set                           tape speed ,146,2         Stop Time AM 140
1 June 10, 1990  8:00 PM               confirmation ,150,4       Stop Time OK 141
   11:00 PM 5  LP                      main menu ,154,12         channel 7 145
2 Monday-Friday  3:00 AM               Select the Program ,166,4 channel OK 146
   3:30 AM 7  EP                       Select the Day ,170,7     tape speed Long Play 148
3 Saturdays  5:00 PM  6:00             Start Time ,177,10        confirmation OK 154
   PM 58  EP                           Stop Time ,188,4          main menu ENTER NEW
4   :   :                              channel ,193,5              RECORDING TIME 164
                                       tape speed ,199,2         Select the Program Program
Page summary                           confirmation ,203,2          Once a Week on ... 170
main menu,7,74                         main menu ,205,29         Select the Day Fridays 176
timer,1,5                              timer ,235,5              Start Time 1 179
main menu help,0,0                                               Start Time 0 180
HELP,1,12                           Error log:                   Start Time 0 181
TAPE STATUS,0,0                        backround handler Missed  Start Time 0 182
Current Time,1,27                        192                     Start Time PM 184
Current Time Help,0,0                  POWERS OFF, SETS TIMER 240 Start Time OK 187
Select the Program,4,20                                          Stop Time 1 188
specific day,2,9                    Users Actions:               Stop Time 1 189
Select the Program Help,0,0            year set 1 11             Stop Time 0 189
Select the Day,1,3                     year set 9 12             Stop Time 0 190
select the month,4,39                  year set 9 13             Stop Time PM 191
year set,2,33                          year set 0 14             Stop Time Missed 191
channel,3,23                           year set OK 16            Stop Time OK 192
Start Time,3,43                        select the month June 21  channel 4 197
Stop Time,3,33                         February 1990 6 30        channel OK 198
tape speed,3,8                         Current Time 9 34         tape speed Long Play 200
confirmation,4,37                      Current Time 0 35         confirmation OK 205
February 1990,4,53                     Current Time 0 35         main menu Power Off 231
                                       Current Time PM 37        timer FINISHED 239
COUNT:86                               Current Time OK 39
WASTED TIME:42                         main menu ENTER NEW       Programs set
TOTAL TIME = Time -                      RECORDING TIME 48       1 June 10, 1990  8:00 PM
  Waste=461                            Select the Program Program   11:00 PM 5  LP
                                         Once on ... 52          2 Monday-Friday  3:00 AM
                                       specific day Any other day   3:30 AM 7  LP
                                         57                      3 Fridays 10:00 PM 11:00 PM
                                       select the month June 60     4  LP
                                       February 1990 10 65       4   :   :
                                       Start Time 8 71
                                       Start Time 0 72           Page summary
                                       Start Time 0 72           main menu,4,56
                                       Start Time PM 73          timer,1,5
                                       Start Time OK 74          main menu help,0,0
                                                                 HELP,0,0
```

Subject number 21 Sunday,
July 1, 1990 2:33:57 PM

Page time log
year set ,..22
select the month ,24.11
February 1990 ,41,3
Current Time ,47,31
main menu ,78,12
Select the Program ,91,8
specific day ,99,5
select the month ,105,7
February 1990 ,118,2
Start Time ,122,26
Stop Time ,151,10
channel ,161,8
tape speed ,171,3
confirmation ,177,3
main menu ,180,5
Select the Program ,185,4
Start Time ,190,28
Stop Time ,219,7
channel ,225,5
tape speed ,231,4
confirmation ,238,4
main menu ,243,4
Select the Program ,247,4
Select the Day ,251,5
Start Time ,257,9
Stop Time ,267,6
channel ,273,7
tape speed ,280,3
confirmation ,286,6
HELP ,292,5
confirmation ,297,2
main menu ,300,9
year set ,309,9
select the month ,319,4
February 1990 ,327,2
main menu ,329,23
main menu help ,353,9
main menu ,363,3
timer ,366,3

Error log:
POWERS OFF, SETS TIMER 369

Users Actions:
year set 1 15
year set 9 17
year set 9 19
year set 0 21
year set OK 23
select the month July 30
February 1990 1 44
Current Time 9 64
Current Time 0 66
Current Time 0 67
Current Time PM 73
Current Time OK 77
main menu ENTER NEW
    RECORDING TIME 89
Select the Program Program
    Once on ... 98
specific day Any other day
    104
select the month June 111

February 1990 10 120
Start Time 8 134
Start Time 9 136
Start Time 0 136
Start Time PM 138
Start Time OK 146
Stop Time 1 154
Stop Time 1 155
Stop Time 0 157
Stop Time 0 157
Stop Time PM 158
Stop Time OK 161
channel 5 166
channel OK 169
tape speed Standard Play
    174
confirmation OK 179
main menu ENTER NEW
    RECORDING TIME 183
Select the Program Program
    Monday - Friday at ...
    189
Start Time 9 192
Start Time Clear 196
Start Time 3 198
Start Time 0 199
Start Time 0 200
Start Time AM 201
Start Time 3 202
Start Time 3 203
Start Time 0 204
Start Time AM 208
Start Time 3 212
Start Time 0 213
Start Time 0 214
Start Time OK 217
Stop Time 3 220
Stop Time 3 221
Stop Time 0 221
Stop Time AM 224
Stop Time OK 225
channel 7 229
channel OK 231
tape speed Standard Play
    234
confirmation OK 242
main menu ENTER NEW
    RECORDING TIME 245
Select the Program Program
    Once a Week on ... 250
Select the Day Sundays 256
Start Time 8 261
Start Time 3 261
Start Time 0 263
Start Time PM 265
Start Time OK 266
Stop Time 9 268
Stop Time 0 270
Stop Time 0 270
Stop Time PM 271
Stop Time OK 272
channel 6 277
channel 1 277
channel OK 279
tape speed Long Play 282
confirmation Help 291
HELP EXIT HELP 296
confirmation OK 299 main menu SET CURRENT DATE
    309
year set 1 314
year set 9 315
year set 9 315
year set 0 316
year set OK 316
select the month June 322
February 1990 6 329
main menu Help 352
main menu help Exit Help
    362
main menu Power Off 364
timer FINISHED 368

Programs set
1 June 10, 1990  8:00 PM
    11:00 PM 5  SP
2 Monday-Friday 03:00 AM
    3:30 AM 7  SP
3 Sundays  8:30 PM  9:00 PM
    61  LP
4   :   :

Page summary
main menu,6,56
timer,1,3
main menu help,1,9
HELP,1,5
TAPE STATUS,0,0
Current Time,1,31
Current Time Help,0,0
Select the Program,3,16
specific day,1,5
Select the Program Help,0,0
Select the Day,1,5
select the month,3,22
year set,2,31
channel,3,20
Start Time,3,63
Stop Time,3,23
tape speed,3,10
confirmation,4,15
February 1990,3,7

COUNT:90
WASTED TIME:47
**TOTAL TIME = Time -
    Waste=**368

Subject number 22 Sunday,
July 1, 1990 3:59:17 PM

Page time log
year set ,1,54
select the month ,56,18
February 1990 ,74,6
Current Time ,81,23
main menu ,105,9
confirmation ,114,4
main menu ,119,11
Select the Program ,130,20
specific day ,150,7
select the month ,157,14
February 1990 ,173,4
Start Time ,177,13
Stop Time ,192,20
channel ,212,7
tape speed ,219,5
confirmation ,226,17
main menu ,243,10
Select the Program ,253,6
Start Time ,259,17
Stop Time ,276,21
channel ,297,6
tape speed ,303,2
confirmation ,307,13
main menu ,321,6
Select the Program ,328,7
Select the Day ,335,2
Start Time ,338,16
Stop Time ,354,9
channel ,363,6
tape speed ,369,6
confirmation ,377,8
main menu ,385,69
timer ,454,2

Error log:
backround handler Missed 67
backround handler 320
POWERS OFF, SETS TIMER 534

Users Actions:
year set 1 41
year set 9 47
year set 9 48
year set 0 50
year set OK 55
select the month Missed 67
select the month June 70
February 1990 6 80
Current Time PM 88
Current Time 9 93
Current Time 0 94
Current Time 0 96
Current Time 0 100
Current Time OK 104
main menu REVIEW CURRENT
    RECORDING TIMES 113
confirmation OK 118
main menu ENTER NEW
    RECORDING TIME 130
Select the Program Program
    Once on ... 150
specific day Any other day
    156 select the month June 170
February 1990 10 173
Start Time PM 184
Start Time 8 186
Start Time 0 187
Start Time 0 188
Start Time OK 190
Stop Time PM 196
Stop Time 1 198
Stop Time 0 200
Stop Time Clear 203
Stop Time PM 205
Stop Time 1 207
Stop Time 1 207
Stop Time 0 209
Stop Time 0 209
Stop Time OK 211
channel 5 217
channel OK 218
tape speed Standard Play 223
confirmation OK 242
main menu ENTER NEW RECORDING TIME 252
Select the Program Program Monday - Friday at ... 258
Start Time AM 265
Start Time 3 268
Start Time 0 269
Start Time 0 269
Start Time OK 275
Stop Time AM 279
Stop Time 3 288
Stop Time 3 289
Stop Time 0 291
Stop Time OK 296
channel 7 301
channel OK 302
tape speed Standard Play 305
confirmation Missed 319
confirmation OK 320
main menu ENTER NEW RECORDING TIME 326
Select the Program Program Once a Week on ... 334
Select the Day Thursdays 337
Start Time PM 345
Start Time 1 348
Start Time 0 350
Start Time 0 350
Start Time 0 351
Start Time OK 353
Stop Time PM 356
Stop Time 1 357
Stop Time 1 359
Stop Time 0 360
Stop Time 0 361
Stop Time OK 363
channel 4 367
channel OK 369
tape speed Standard Play 375
confirmation OK 385
main menu Power Off 454
timer FINISHED 456

Programs set
1 June 10, 1990 8:00 PM
   10:00 PM 5 SP
2 Monday-Friday 3:00 AM
   3:30 AM 7 SP
3 Thursdays 10:00 PM 11:00
   PM 4 SP

Page summary
main menu,5,105
timer,1,2
main menu help,0,0
HELP,0,0
TAPE STATUS,0,0
Current Time,1,23
Current Time Help,0,0
Select the Program,3,33
specific day,1,7
Select the Program Help,0,0
Select the Day,1,2
select the month,2,30
year set,1,54
channel,3,19
Start Time,3,46
Stop Time,3,50
tape speed,3,13
confirmation,4,42
February 1990,2,10

COUNT: 79
WASTED TIME: 19
TOTAL TIME = Time - Waste= 456

Subject number 23 Sunday, July 1, 1990 5:02:00 PM

Page time log
year set ,1,36
select the month ,38,16
February 1990 ,58,3
Current Time ,64,21
main menu ,85,22
confirmation ,108,32
main menu ,140,3
Select the Program ,143,11
specific day ,155,11
select the month ,167,3
February 1990 ,174,2
Start Time ,177,14
Stop Time ,193,9
channel ,203,5
tape speed ,209,7
confirmation ,219,3
main menu ,222,4
Select the Program ,226,10
Start Time ,237,12
Stop Time ,250,8
channel ,258,4
tape speed ,262,2
confirmation ,267,7
main menu ,274,5
Select the Program ,279,5
Start Time ,285,19
Stop Time ,305,3
channel ,309,6
tape speed ,315,1
confirmation ,319,1
main menu ,321,15
main menu help ,336,7
main menu ,344,5
timer ,349,3

Error log:
backround handler Missed 29
backround handler Missed 82
backround handler Missed 215
POWERS OFF, SETS TIMER 352

Users Actions:
year set 1 13
year set 9 15
year set 9 18
year set 0 19
year set 0 24
year set Missed 29
year set Clear 29
year set 1 32
year set 9 32
year set 9 34
year set 0 35
year set OK 36
select the month June 50
February 1990 6 61
Current Time 9 71
Current Time 0 73
Current Time 0 75
Current Time PM 80
Current Time Missed 82
Current Time OK 84 main menu REVIEW CURRENT RECORDING TIMES 106
confirmation Change 118
confirmation Main Menu 136
main menu ENTER NEW RECORDING TIME 142
Select the Program Program Once on ... 154
specific day Any other day 166
select the month June 169
February 1990 10 176
Start Time 8 185
Start Time 0 187
Start Time 0 187
Start Time PM 189
Start Time OK 191
Stop Time 1 196
Stop Time 1 197
Stop Time 0 198
Stop Time 0 198
Stop Time PM 201
Stop Time OK 201
channel 5 207
channel OK 208
tape speed Missed 215
tape speed Standard Play 216
confirmation OK 222
main menu ENTER NEW RECORDING TIME 225
Select the Program Program Monday - Friday at ... 236
Start Time 3 244
Start Time 0 245
Start Time 0 246
Start Time AM 247
Start Time OK 249
Stop Time 3 252
Stop Time 3 253
Stop Time 0 254
Stop Time AM 255
Stop Time OK 257
channel 7 261
channel OK 262
tape speed Standard Play 264
confirmation OK 273
main menu ENTER NEW RECORDING TIME 277
Select the Program Program EveryDay at ... 284
Start Time 7 288
Start Time 0 289
Start Time 0 290
Start Time PM 291
Start Time 8 293
Start Time Clear 298
Start Time 7 300
Start Time 0 301
Start Time 0 301
Start Time PM 302
Start Time OK 303
Stop Time 8 305
Stop Time 0 306
Stop Time 0 307
Stop Time PM 307

E-47

```
Stop Time OF 308
channel 6 312
channel 4 313
channel CK 315
tape speed Standard Play
   316
confirmation OF 320
main menu Help 335
main menu help Exit Help
   343
main menu Power Off 345
timer FINISHED 352
```

Programs set
```
1 June 10, 1990  8:00 PM
   11:00 PM 5  SP
2 Monday-Friday  3:00 AM
   3:30 AM 7  SP
3 Everyday  7:00 PM  8:00
   PM 64  SP
4   :    :
```

Page summary
```
main menu,6,54
timer,1,3
main menu help,1,7
HELP,0,0
TAPE STATUS,0,0
Current Time,1,21
Current Time Help,0,0
Select the Program,3,26
specific day,1,11
Select the Program Help,0,0
Select the Day,0,0
select the month,2,19
year set,1,36
channel,3,15
Start Time,3,45
Stop Time,3,20
tape speed,3,10
confirmation,4,43
February 1990,2,5
```

COUNT:88
WASTED TIME:36
**TOTAL TIME = Time -
   Waste=352**

E-48

What is claimed is:

1. A programmable control, having a status, responsive to an user input and a signal received from a signal source, comprising:
- a controller, for receiving the user input and the signal and producing a control output;
- a memory for storing data relating to an activity of the user;
- a memory for storing data relating to a plurality of user profiles;
- a processor for characterizing said user input to produce a characterized user input;
- means for comparing said characterized user input with at least a portion of said stored data to produce a comparison index;
- a data processing system for adaptively predicting a most probable intended action of the user based on said stored data relating to said activity of the user and derived weighting of at least a subset of possible choices, said derivation being based on a history of use, a context of a respective choice and said status of the control; and
- a user feedback data presenting system comprising an output device for presentation of a variable sequence of programming options to the user, including said most probable intended action of the user, in a plurality of output messages, said output messages differing in available programming options,
- said variable sequence of programming options being determined on the basis of said comparison index.

2. The programmable control according to claim 1, being for performing an action based on user input and an information content of a signal received from a signal source, wherein said output device includes a display device, further comprising:
- a user controlled direct manipulation-type input device, associated with said display device, having a device output, said device output being the user input;
- a plant capable of performing the action, being responsive to an actuator signal; and
- said controller, being for receiving data from said device output of said input device and the signal, and displaying user feedback data on said display device,
- said logical sequence of said user feedback data including at least one sequence of options sufficient to define an operable control program, and a presentation of additional programming options if said control program is not operable.

3. The programmable control according to claim 1 wherein said signal comprises a time-code signal, and said direct manipulation-type input device and associated data display device present programming options to the user comprising time-based programming options having associated relative positions on said display image, said time based programming options comprising an absolute time programming option and a relative time programming option, said controller producing said actuator signal based on said predetermined program, said control program, and said time-code signal.

4. The system according to claim 1, further comprising:
- a user input processing system for adaptively determining a viewer preference based on the user input received by said controller;
- a program material processing system for characterizing the program material based on its content;
- a correlator for correlating said characterized content of the program material with said determined viewer preference to produce a correlation index; and
- a processor, selectively processing the program material based on said correlation index,
- said data processing system receiving an input from said processor.

5. The system according to claim 4, wherein said program material is encrypted, further comprising:
- a decryption system for decrypting the program material if it is selected to produce unencrypted program material and optionally an associated decryption event;
- a memory for storing data relating to the occurrence of said decryption event; and
- a central database for storing data relating to the occurrence of said decryption event in association with data relating to the viewer.

6. The system according to claim 4, wherein:
- said user input processign system monitors a pattern of user activity and predicts a viewer preference;
- said program material processing system comprises:
- a processor for preprocessing the program material to produce a reduced data flow information signal substantially retaining information relating to said abstract information content of the program material and selectively eliminating data not relating to said abstract information content of the program material and for characterizing said information signal based on said abstract information content; and
- a comparing system for determining if said correlation index is indicative of a probable high correlation between said characterization of said information signal and said viewer preference and causing said stored program material to be processed by said processing means based on said determination.

7. The system according to claim 4, wherein said processor comprises an image program material storage and retrieval system.

8. The system according to claim 4, further comprising a memory for storing a characterization of the program material; an input for receiving a feedback signal from the viewer indicating a degree of agreement with said correlation index determination, wherein said feedback signal and said stored characterization are used by said viewer preference predicting means to predict a new viewer preference.

9. The programmable according to claim 1, wherein:
- said data relating to a plurality of stored profiles comprises a plurality of stored profiles; and
- said means for comparing compares said characterized user input with at least one of said plurality of stored profiles to produce said comparison index.

10. The programmable controller according to claim 1, further comprising:
- a plurality of stored profiles;
- a processor for characterizing the signal to produce a characterized signal;
- means for comparing said characterized signal to said plurality of stored profiles to produce a comparison index,
- wherein said processor for characterizing performs an algorithm on said signal comprising a transform selected from the group consisting of an Affine transformation, a Fourier transformation, a discrete cosine transformation and a wavelet transformation and said status of the control includes said comparison index.

11. The programmable controller according to claim 1, said controller being for controlling a recording device for recording an analog signal sequentially on a recording medium having a plurality of uniquely identifiable storage locations, further comprising a sequential recording device for recording the analog signal, and a memory for storing, in a directory location on the recording medium which is separate from the storage location of the analog signal, information relating to said signal, processed to selectively retain characterizing information, and an identifier of a storage location on the recording medium in which said analog signal is recorded.

12. The programmable control according to claim 1, wherein said user feedback data presenting device comprises a display having a plurality of display images, said display images differing in available programming options.

13. An adaptive programmable apparatus having a plurality of states, being programmable by a programmer and operating in an environment in which a plurality of possible events occur, each of the events being associated with different data, comprising:
   an data input for receiving data;
   an programmer input, producing an input signal from the programmer;
   a memory for storing data relating to said data input or said input signal;
   a feedback device for adaptively providing information relating to said input signal and a current status of the apparatus to the programmer, based on said data input or said programmer input, said stored data, and derived weighting of at least a subset of possible choices, said derived weighting being based on a history of use, a context of a respective choice and said current status of the apparatus;
   a memory for storing programming data associated with said input signal; and
   a processor, having a control output, for controlling the response of said apparatus relating to the detection of said input signal or said data in accordance with said stored programming data,
   said processor:
      processing said at least one of said input signal or said data to reduce an amount of information while substantially retaining an abstract portion of said information,
      storing a quantity of said abstracted information,
      processing said abstract portion of said information in conjunction with said stored quantity of abstracted information,
      and providing said control output based on said processed abstract portion of said information and said stored programming data.

14. The apparatus according to claim 13, further comprising:
   an input for receiving a programming preference from the programmer indicating a plurality of possible desired events;
   said processor further including a correlator for correlating said programming preference with said data based on an adaptive algorithm and for determining a likelihood of occurrence of at least one of said desired events, producing said control output.

15. The apparatus according to claim 13 further comprising:
   an input for receiving feedback from the programmer indicating a concurrence with said control output of said processor, and modifying said response control based on said received feedback to increase a likelihood of concurrence.

16. The programmable apparatus according to claim 13, wherein said processor verifies said programming data to ensure that said programming data comprise a complete and consistent set of instructions; and
   includes a feedback system for interactively modifying said programming data.

17. The programmable apparatus according to claim 13, further comprising a chronological database and an accessing system for accessing said chronological database on the basis of said programming data stored in said memory.

18. The programmable apparatus according to claim 13, wherein said processor receives information from said input signal.

19. The programmable apparatus according to claim 13, wherein said processor receives information from said data.

20. The programmable apparatus according to claim 13, further comprising an input signal memory for storing at least a portion of said input signal or said data, a profile generator for selectively generating a profile of said input signal or said data, and an input signal profile memory for storing said profile of said input signal or said data separately from said input signal or said data in said input signal memory.

21. The programmable apparatus according to claim 20, further comprising a processor for comparing said input signal or said data with said stored profile of said input signal or said data to determine the occurrence of an event.

22. The programmable information storage apparatus according to claim 21, wherein said data comprises image data and said processor for comparing performs image analysis.

23. The programmable control according to claim 1, said signal source being an image signal source, further comprising:
   means for storing characterization data representing a plurality of image types, having an output; and
   an image processor, receiving an input from said image signal source and said output from said characterization data storage means, and producing a signal corresponding to a relation between at least one of said plurality of image types and said image signal source,
   said programming options controlling an operation of said image processor.

24. The programmable control according to claim 1, said signal source comprising means for simultaneously transmitting data representing a plurality of programs, said control further comprising:
   means for selecting at least one of said plurality of programs, being responsive to an input;
   a program database containing information relating to said plurality of programs and including data relating to said subset of possible choices;
   said programming options defining an operation to be conducted with respect to a program.

25. The programmable control according to claim 1, wherein said user feedback data presenting system includes a graphical user interface for defining commands, comprising:
   (a) an image display device having at least two dimensions of display, being for providing visual image feedback; and
   (b) a multidimensional input device having at least two dimensions of operability, adapted to correspond to said two dimensions of said display device, and having an output, so that the user may cause said input device to produce a corresponding change in an image of said display device by translating an indicator segment of said display in said at least two dimensions of display, based an said visual feedback received from said display device, said indicator segment being moved to a translated location of said display device corresponding to a user command.

26. The programmable control according to claim 1, said user feedback data presenting system comprising a visual display device, having an alterable type, further comprising:

means for detecting one or more temporal-spatial user characteristics of the input signal, independent of said programming options, selected from the group consisting of a velocity component, an efficiency of input, an accuracy of input, an interruption of input and a high frequency component of input;

means for storing data related to said user characteristics in a memory; and means for altering said image type based on the user characteristics.

27. The programmable control according to claim 26, wherein said means for altering said image type alters said image type based on an output of detection means and said stored data so that said display device an image type which corresponds to said detected user characteristics.

28. The programmable control according to claim 26, being for controlling the causation of an action on the occurrence of an event, further comprising:

control means for receiving and storing a said programming option, said programming option directing an aspect of performance of an action on the occurrence of an event; and means for monitoring an environment of said apparatus to determine the occurrence of the event, and causing the performance of the action on the occurrence of the event.

29. The apparatus according to claim 28, wherein said means for altering said image type alters said image type based on an output of detection means and said stored data so that said display means displays an image type which corresponds to said detected user characteristics.

30. The apparatus according to claim 1, wherein at least one programming option defines a pattern characteristic, further comprising a pattern recognition engine for determining a correspondence of said defined pattern characteristic and the signal received from the signal source, and wherein at least one programming option defines an operation to be performed on the signal received from the signal source, contingent on said correspondence.

31. The programmable control according to claim 1, further comprising an input for receiving data relating to the signal received from the signal source, said data relating to the signal received from the signal source defining the location of events within the signal received from the signal source, said data relating to the signal received from the signal source being comprising said subset of possible choices.

32. The programmable control according to claim 1, wherein the signal received from the signal source includes data relating to real or synthetic processes, further comprising means for modeling said real or synthetic processes based on the signal received from the signal source to define at least one model, at least one of said possible choices corresponding to a function relating to said model.

33. The programmable control according to claim 1, wherein said means for comparing said characterized user input with at least a portion of said stored data to produce a comparison index comprises a neural network.

34. The programmable control according to claim 1, wherein said data processing system comprises a neural network.

35. The programmable control according to claim 1, wherein said context of a respective choice is evaluated by a neural network.

36. The programmable control according to clam 1, wherein said context of a respective choice is evaluated based on an analysis of the signal received from the signal source.

37. The programmable control according to claim 1, wherein said context of a respective choice is evaluated based on a pattern recognition analysis of the signal received from the signal source.

* * * * *